US006908942B2

(12) United States Patent
Gong et al.

(10) Patent No.: US 6,908,942 B2
(45) Date of Patent: Jun. 21, 2005

(54) 6-AMINO-2,2-DIMETHYL-3,4,6-TRISUBSTITUTED BENZOPYRAN DERIVATIVES AND THEIR CONSTRUCTION BY PARALLEL SYNTHESIS ON SOLID-PHASE

(75) Inventors: Young-Dae Gong, Daejeon (KR); Jin-Soo Seo, Daejeon (KR); Jong Yeon Hwang, Jeonrabuk-do (KR); Sung-eun Yoo, Chuncheongnam-do (KR)

(73) Assignee: Korea Research Institute of Chemical Technology, Daejon (KR)

( * ) Notice: Subject to any disclaimer, the term of this patent is extended or adjusted under 35 U.S.C. 154(b) by 0 days.

(21) Appl. No.: 10/461,433

(22) Filed: Jun. 16, 2003

(65) Prior Publication Data

US 2004/0097580 A1 May 20, 2004

(30) Foreign Application Priority Data

Jun. 17, 2002 (KR) ................................ 10-2002-0033755
Jun. 19, 2002 (KR) ................................ 10-2002-0034211
Sep. 6, 2002 (KR) ................................ 10-2002-0053955

(51) Int. Cl.[7] ....................... A61K 31/35; C07D 311/76
(52) U.S. Cl. ....................... 514/456; 514/457; 549/400
(58) Field of Search .......................... 549/400; 514/456, 514/457

(56) References Cited

U.S. PATENT DOCUMENTS 6,555,574 B1 * 4/2003 Tanikawa et al. ........... 514/456

OTHER PUBLICATIONS

I. Sziráki et al., "Manganese: A Transition Metal Protects Nigrostriatal Neurons From Oxidative Stress In The Iron–Induced Animal Model Of Parkinsonism," Neurosci. 85, 1998, pp. 1101–1111.

Y. Goodman, et al., "K+ channel openers protect hippocampal neurons against oxidative injury and amyloid β–peptide toxicity," Brain Research 706, 1996, pp. 328–332.

* cited by examiner

*Primary Examiner*—Rita Desai
*Assistant Examiner*—Raymond Convington
(74) *Attorney, Agent, or Firm*—Finnegan, Henderson, Farabow, Garrett & Dunner, LLP

(57) ABSTRACT

The present invention provides (i) 6-amino-2,2-dimethyl-3,4,6-trisubstituted benzopyran derivatives; (ii) a process for synthesizing benzopyran derivatives with high efficiency by parallel synthesis on a solid-phase as one of combinatorial chemical synthesis technologies; and (iii) a use of the benzopyran derivatives for preventing and treating diseases or disorders induced by promotion of lipid peroxidation or accumulation of oxidized products.

4 Claims, No Drawings

6-AMINO-2,2-DIMETHYL-3,4,6-TRISUBSTITUTED BENZOPYRAN DERIVATIVES AND THEIR CONSTRUCTION BY PARALLEL SYNTHESIS ON SOLID-PHASE

BACKGROUND OF THE INVENTION

1. Field of the Invention

The present invention relates to (i) 6-amino-2,2-dimethyl-3,4,6-trisubstituted benzopyran derivatives; (ii) a process for synthesizing the novel benzopyran derivatives with high efficiency by parallel synthesis on solid-phase as one of combinatorial chemical synthesis technologies; and (iii) a use of the novel benzopyran derivatives for preventing and treating diseases or disorders induced by promotion of lipid peroxidation or accumulation of oxidized products.

2. Description of the Related Art

It has been suggested that the injury or death (e.g., apoptosis) of nerve cells is mainly responsible for several neurologic diseases or disorders such as apoplexy, brain trauma, Alzheimer's disease and Parkinson's disease (G. J. Zoppo et al., *Drugs* 54, 9 (1997); and I. Sziraki et al., *Neurosci.* 85, 1101 (1998)). The factors involved in the injury of nerve cells have been known, which include the elevation of the levels of iron, activated oxygen species and oxidized molecules in nerve cells (M. P. Mattson et al., *Methods Cell Biol.* 46, 187 (1995); and Y. Goodman et al., *Brain Res.* 706, 328 (1996)).

The elevated level of iron in nerve cells leads to the formation of oxygen free radicals such as NO and then promotion of lipid peroxidation, which results in the accumulation of oxidized molecules in cells. The oxidized molecules accumulated in cells give rise to inflammatory diseases, cardiac infarction and dementia as well as neurologic diseases described above. In addition, the oxidized molecules have been reported to lead to acute or chronic tissue or organ injury. Such injuries include organ injury by endotoxins from bacteria infection or tissue injury occurring when the reperfusion in ischemic disease is performed.

Therefore, in order to prevent and treat several diseases due to the injury or death of nerve cells, many researchers have made extensive study to develop novel substances capable of preventing injury of nerve cells due to elevated irons in nerve cells, lipid peroxidation and generation of NO due to endotoxins. The antioxidants have been reported to alleviate injury and death of nerve cells due to irons, and the endeavor to develop novel drugs for preventing injury of nerve cells due to oxidative stress is under way (Y. Zhang et al., *J. Cereb. Blood Flow Metab.* 13, 378 (1993)).

Natural and synthetic products having benzopyran skeleton have been widely known and used as a basic skeletal structure for developing compounds exhibiting therapeutical efficacy in several diseases such as nerve-related diseases, hypertension and diabetes owing to their antioxidation activity.

Construction of benzopyran library having a wide variety of derivatives by means of the technology of combinatorial chemical synthesis is very useful in exploiting hit or lead compounds at the initial stage for developing new drugs.

In particular, it is very important that the library of small organic molecular compounds, wherein various substituents can be introduced and Lipinsky's Rule of 5 can be largely applied, is constructed in a massive and effective manner, in view of the strategy for obtaining molecular diversity useful in screening lead compounds.

The combinatorial chemical synthesis has been focused as a new technology for developing novel substances. Compared to conventional methods where a single compound is synthesized by a single reaction, the technology of combinatorial chemical synthesis allows to synthesize more diverse and abundant compounds simultaneously and to automate a multi-step synthesis, so that it is considered as a highly effective process of synthesizing compounds. The introduction of combinatorial chemical synthesis makes it easier to screen and optimize biological hit and lead compounds having novel structures.

Since the technology of combinatorial chemical synthesis is generally carried out on a solid support, a continuous multi-step process can be automated. In addition, because the isolation and purification of products in this technology is very simple, the high throughput screening for pharmacological efficacy is also made possible.

Although the approach of the combinatorial chemical synthesis appears to overcome the shortcomings of conventional synthesis methods as being uneconomical and ineffective, several bottlenecks still prevents it from being applied to the field of organic synthesis. One such reason is that undesired side reactions occur because most of chemical reactions on a solid support employ excess reagents. Another reason is that the selection of reaction conditions is very restricted because solvents that can be used depend on physical properties of a solid support. In the art of combinatorial chemical synthesis on a solid support, Merrifield resin and Wang resin have been often used as a solid support. However, these supports show negligible swelling effect in a high polar solvent such as alcohol and water, thereby restricting the selection of a solvent for a reaction. Therefore, in order to synthesize diverse derivatives by use of chemical reactions on a solid support, the selection of a solid support and a reaction reagent as well as the screening of reaction conditions become essential.

SUMMARY OF THE INVENTION

The present inventors have carried out intensive researches to develop a novel process for effectively constructing benzopyran library by use of combinatorial chemical synthesis technology on a solid-phase in consideration of the usefulness of benzopyran derivative in synthesis of pharmacologically effective compounds such as an antioxidant and drugs for treating neurologic diseases, hypertension and diabetes, etc. As a result, the present inventors have succeeded in developing a novel parallel synthetic process on a solid-phase by using a combinatorial chemical synthetic method in which 4 steps are performed in a successive manner to effectively produce 6-amino-2,2-dimethyl-3,4,6-trisubstituted benzopyran library with higher yield in a short period of time, whereas the conventional processes performing multi-step reactions in a solution synthesize compounds of interest through steps of a reaction; treatment and purification after the reaction; and an analysis of structure of the synthesized compound per each step.

Accordingly, it is an object of this invention to provide novel 6-amino-2,2-dimethyl-3,4,6-trisubstituted benzopyran derivatives useful in synthesizing drugs.

Another object of this invention to provide a process for preparing 6-amino-2,2-dimethyl-3,4,6-trisubstituted benzopyran derivative by use of parallel synthesis on a solid-phase exhibiting advantages such as high yield and feasibility of automation of multi-step reaction and analysis of chemical structure.

It is still another object of this invention to provide a use of 6-amino-2,2-diethyl-3,4,6-trisubstituted benzopyran derivatives for preventing and eating diseases or disorders induced by promotion of lipid peroxidation and accumulation of oxidized molecules.

DETAILED DESCRIPTION OF THE INVENTION

In one aspect of this invention, there is provided a 6-amino-2,2-dimethyl-3,4,6-trisubstituted benzopyran derivative represented by the following formula (5):

(5)

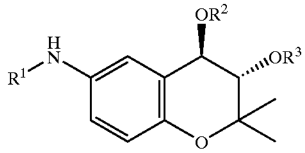

wherein $R^1$ represents a $C_1$–$C_{10}$ alkyl, aryl, benzyl or substituted benzyl, or phenethyl group; $R^2$ represents a $C_1$–$C_{10}$ alkyl, benzyl or substituted benzyl, or phenethyl group; $R^3$ represents a hydrogen atom, a $C_1$–$C_{10}$ alkyl group, a $C_2$–$C_{10}$ alkenyl group, a $C_2$–$C_{10}$ alkynyl, benzyl or substituted benzyl, naphthylmethyl group, or —C(O)$R^4$; $R^4$ represents a $C_1$–$C_{10}$ alkyl, phenyl or substituted phenyl groups or five-or seven-membered heterocyclic ring containing a heteroatom selected from the group consisting of oxygen and sulfur, and the substituted phenyl or benzyl group may be substituted with 1–4 substituents selected from the group consisting of a halogen atom, a nitro group, a $C_1$–$C_{10}$ alkoxy group and a $C_1$–$C_{10}$ haloalkyl group; and $R^1$ is not a $C_1$–$C_{10}$ alkyl group with the proviso that $R^3$ is a hydrogen atom.

In addition, the 6-amino-2,2-dimethyl-3,4,6-trisubstituted benzopyran derivative represented by the formula (5) has several chiral centers, and therefore, its optical isomers in synthesizing process can be obtained and included within the scope of the present compounds.

The present invention will be described in more detail hereunder.

The present invention provides (i) a 6-amino-2,2-dimethyl-3,4,6-trisubstituted benzopyran derivative represented by the formula (5); (ii) a process according to parallel synthesis on solid-phase as one of combinatorial chemical synthesis technologies for permitting to effectively synthesize the novel benzopyran derivatives described above by use of parallel synthesis on solid-phase instead of chemical reaction in liquid-phase; and (iii) use of the novel benzopyran derivatives described above for preventing and treating diseases or disorders induced by lipid peroxidation promotion or accumulation of oxidized products.

The process for preparing a 6-amino-2,2-dimethyl-3,4,6-trisubstituted benzopyran derivative represented by the formula (5) according to the technology of combinatorial chemical synthesis is illustrated in Scheme 1.

Scheme 1

Scheme 1

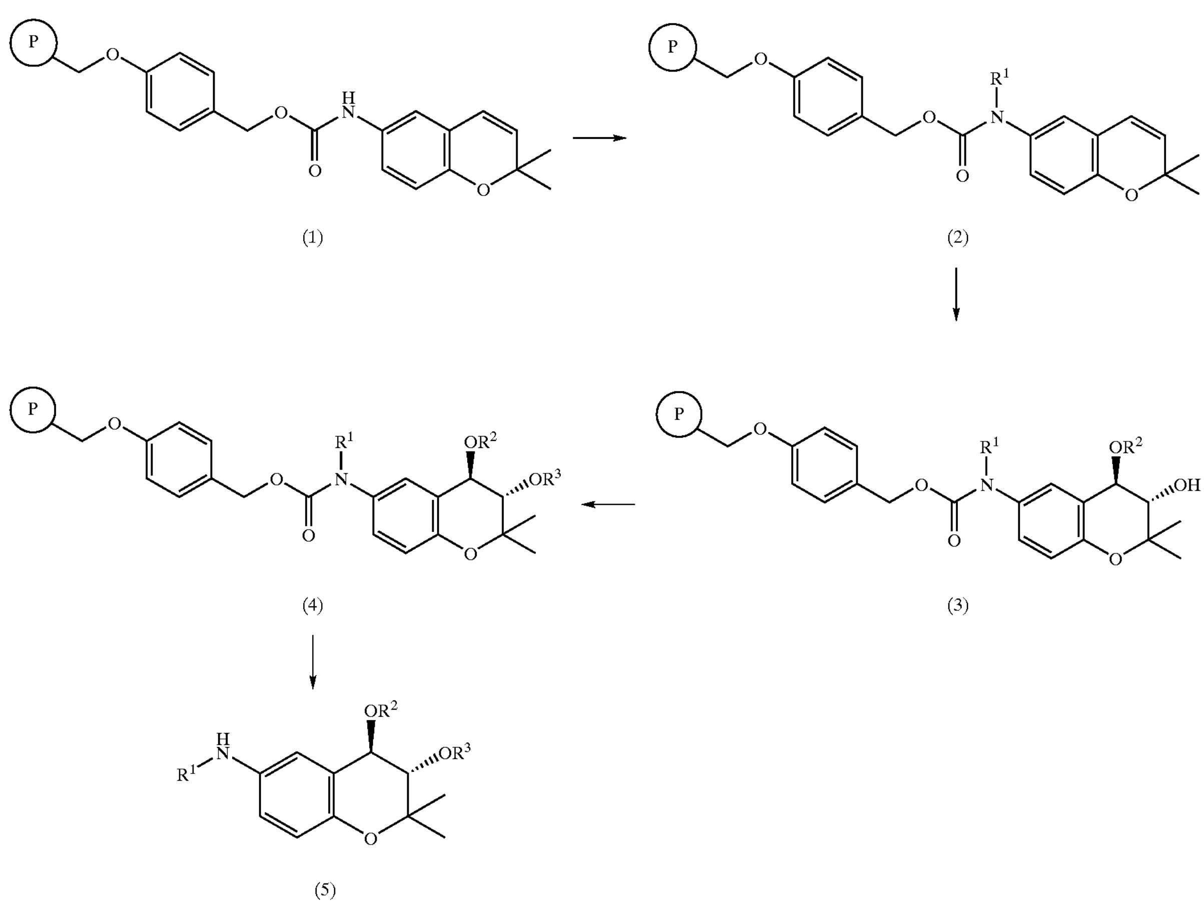

wherein $R^1$, $R^2$ and $R^3$ are the same as above; and $\hat{p}$ is a polymeric solid support selected from the group consisting of polystyrene-divinylbenzene, methacrylic acid-dimethylacrylamide and hydroxyl methacrylic acid.

In the process according to the present invention, the intermediates including 2,2-dimethyl-3-hydroxy-6-alkyl amino benzopyran resin of the formula (3) and 2,2-dimethyl-3-substituted-4-alkoxy-6-alkyl amino benzopyran resin of the formula (4) also have several chiral centers, and if necessary, each optical isomer can be isolated.

The present process represented by the Scheme 1 comprises the following steps:

(a) synthesizing a N-alkyl substituted carbamate resin of the formula (2) by introducing an alkyl substituent selectively to a nitrogen atom of benzopyran linked to a carbamate linker represented by the formula (1);

(b) synthesizing a 2,2-dimethyl-3-hydroxy-6-alkyl amino benzopyran resin of the formula (3) by performing epoxidation and alkoxy addition simultaneously by adding metachloroperbenzoic acid (m-CPBA) and alcohol to the compound of the formula (2); (c) synthesizing a 2,2-dimethyl-3-substituted-4-alkoxy-6-alkyl amino benzopyran derivative of the formula (4) by introducing a substituent $R^3$ to 3-hydroxyl group of the compound of the formula (3); and (d) synthesizing said 6-amino-2,2-dimethyl-3,4,6-trisubstituted benzopyran derivative of the formula (5) by departing the compound of the formula (4) with a dichloromethane solution containing trifluoroacetic acid (TFA) or an organic solvent containing organic acid.

According to the findings of the present inventors, when N-alkylation and hydroxy alkoxylation are successively carried out by use of benzopyran resin having a carbamate linker on a solid support of the formula (1), the number of times for purification can be reduced to one from four in conventional reaction in a solution. Such advantage allows to synthesize a wide variety of 6-amino-2,2-dimethyl-3,4,6-trisubstituted benzopyran derivatives in a short period of time.

In the present process, the necessary steps, compositions of solvent systems and reaction conditions will be described in more detail hereunder:

The organic solvent showing excellent swelling effect on Wang resin or Merrifield resin is useful as solvent for the present process.

In step (a), dimethylsulfoxide (DMSO) or tetrahydrofuran (THF) may be used. Preferably, each of base and $R^1$ substituent is used in the amount of 3 equivalents, and more preferably, about 2 equivalents. As a base, lithium t-butoxide (LiOtBu) is preferred and as $R_1$ substituent, the halides such as alkyl halide or benzyl halide is preferred.

In step (b), to inhibit the occurrence of 3-chlorobenzoic acid as a by-product in oxidation, metachloroperbenzoic acid (m-CPBA) is introduced in the amount of less than 3 equivalents. In particular, it is preferred that prior to addition of m-CPBA, alcohols as alkoxy precursor is excessively added and mixed by agitating for above 15 min followed by addition of an oxidant. The reason is that an alkoxy group predominant over 3-chlorobenzoic acid makes it possible to inhibit the production of a by-product. The alcohols as alkoxy precursor refers to aliphatic alcohols, for example, includes methanol, ethanol, iso-propyl alcohol, benzyl alcohol, and amino acids having aliphatic alcohol at its side chain and protection group at its amine and carboxyl groups.

In step (c), the 3-hydroxy group generated is reacted with halogenated alkyls or carbonyl derivatives as electrophile to introduce $R^3$ group, thereby converting to 2,2-dimethyl-3-substituted form. For example, for converting to 3-alkylether form, halogenated alkyl may be used as electophile and the reaction is performed in the presence of lithium t-butoxide and a solvent of dimethylformamide (DMF). The halogenated alkyls include, but not limited to, halogenated methane, ethane, propane, iso-propane and butane, benzyl halide and substituted benzyl halide. For example, for converting to 3-ester form, carbonyl halide compound containing $R^4$ group may be used as electophile and the reaction is performed in the presence of base and a solvent of dichloromethane. The carbonyl derivative used includes, but not limited to, acetyl halide, t-butylacetyl halide, cyclohexanecarbonyl halide, 3,3 dimethylacryloyl halide, benzoyl halide, p-toluyl halide, 4-anisoyl chloride, 4-halobenzoyl halide, 2-thiopencarbonyl halide and 2-furoyl halide.

In step (d), the departure reaction is carried out using dichloromethane solution containing trifluoroacetic acid (TFA) or an organic solvent containing organic acid in order to produce 6-amino-2,2-dimethyl-3,4,6-trisubstituted benzopyran library of interest represented by the formula (5).

For elucidating the production of 6-amino-2,2-dimethyl-3,4,6-trisubstituted benzopyran library of the formula (5), the compound of interest departed from 2,2-dimethyl-3-substituted-4-alkoxy-6-alkyl amino benzopyran resin of the formula (4) may be purified and isolated in the final step by use of flash column chromatography having multiple columns and its structure is analyzed with NMR and/or Mass spectroscopy. The progress of reaction may be monitored with ATR-FFIR for detecting the intermediates, the resins of the formulae (1), (2), (3) and (4).

Furthermore, the compound of this invention can be used as an inhibitor against lipid peroxidation owing to its inhibitory potency to lipid peroxidation induced iron. Therefore, the present compound is very useful as a drug for preventing and treating several diseases or disorders elicited by promotion of lipid peroxidation and accumulation of oxidized molecules. That is, the present compound can be used as a drug for preventing and treating diseases or disorders such as cancer, arteriosclerosis, diabetes, apoplexy, dementia, Parkinson's disease and senescence that is induced by production of peroxidized lipid with cytotoxicity or destruction of cell membrane due to attack to lipid in cell membrane.

Therefore, in another aspect of this invention, there is provided a pharmaceutical composition for inhibiting lipid peroxidation, i.e., treating or preventing diseases induced by promotion of lipid peroxidation and accumulation of oxidized molecules, which comprises 6-amino-2,2-dimethyl-3,4,6-trisubstituted benzopyran derivative or its pharmaceutically acceptable salt as an active ingredient.

The pharmaceutically acceptable salts of this invention may be prepared according to the conventional process known in the art, for example, by use of an inorganic acid such as hydrochloric acid, hydrogen bromide, sulfuric acid, sodium bisulfate, phosphoric acid and carbonic acid or an organic acid such as formic acid, acetic acid, oxalic acid, benzoic acid, citric acid, tartaric acid, gluconic acid, fumaric acid, lactobionic acid, salicylic acid and acetylsalicylic acid. In addition to this, pharmaceutically acceptable salts may be prepared in a form of metal salt with alkali metal ion such as sodium and potassium and other forms with ammonium ion.

Furthermore, the pharmaceutical composition of this invention may be formulated by using 6-amino-2,2-dimethyl-3,4,6-trisubstituted benzopyran derivative or its pharmaceutically acceptable salt together with a pharmaceutically acceptable carrier, additive, vehicle, diluent and so on. Non-limiting examples of the formulations include, but not limited to, a solution, a suspension or an emulsion, a tablet, a capsule and troches. The pharmaceutical compositions of this invention may be administered orally or parenterally, and the parenteral administration comprises intravenous injection, subcutaneous injection and intramuscular injection. The dosage of pharmaceutical compositions of the present invention to be administered to humans can vary according to various factors such as the type of formulation, the mode of administration, age, body weight, sex, diet, sensitivities to drugs, severity of a disease and physical condition of a patient as well as the type of administration, etc. It is understood that the ordinary skilled physician will readily be able to determine and prescribe a correct dosage of the pharmaceutical compositions. In an embodiment of the present invention, a preferred dosage of the present composition is 0.01–1000 mg/day with reference to the application to an adult patient with a body weight of 70 kg. The present pharmaceutical composition may be administered at regular time intervals according to the instruction of a physician ranging from one to several times per day.

The following specific examples are intended to be illustrative of the invention and should not be construed as limiting the scope of the invention.

EXAMPLE I

Synthesis of 2,2-dimethyl-3-(4-fluorobenzyl)ether-4-methoxy-6-(4-methoxybenzyl)amino Benzopyran (I-1) N-4-methoxybenzylation of Olefin Resin 1

(1)

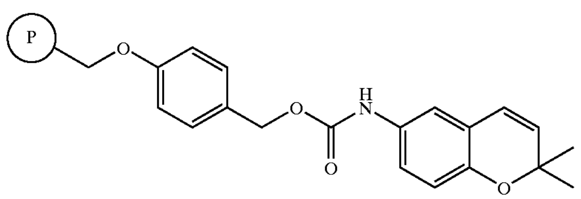

(2a)

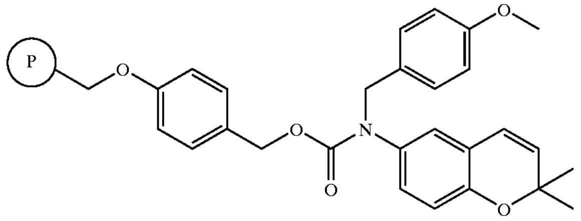

Carbamate resin having a benzopyran structure of the formula (1) (200.00 mg, 0.11 mmol) was added to dimethylsulfoxide (DMSO; 3 ml) and agitated for 10 min at room temperature, followed by adding lithium t-butoxide (LiOtBu)(0.33 ml, 0.33 $\mu$mmol) in 1 M of tetrahydrofuran (THF) and agitating for 20 min at the same temperature. To the mixture, 4-methoxybenzylchloride (4-MeOBnCl; 0.045 ml, 0.33 mmol) was added and agitated to proceed with a reaction for 15 hr at 35 C. Upon completion of the reaction, the reactant mixture was filtered and washed repeatedly with DMF, MC, MC/MeOH and MeOH, thereby yielding N4-methoxybenzyl-substituted carbamate resin of the formula (2a) as a light brown solid (ATR-FTIR analysis result: N-4-methoxy benzylation carbamate, 1700 $cm^{-1}$).

(I-2) Addition of Hydroxy Methoxy to N-methoxybenzyl-substituted Olefin Resin (2a)

(2a)

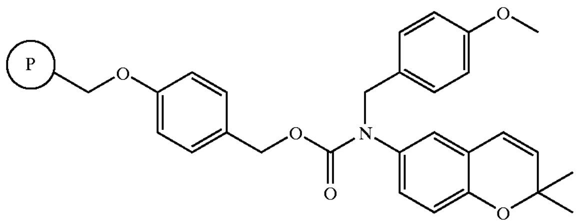

(3a-1

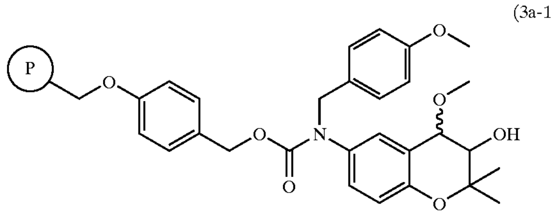

N-4-methoxybenzyl-substituted carbamate resin (200 mg, 0.11 mmol) of the formula (2a) was added to the mixed solution of dichloromethane (3 ml) and methanol (3 ml) and agitated for 30 min, after which metachloroperbenzoic acid (m-CPBA, 81 mg, 0.55 mmol) was added at room temperature and agitated to proceed with a reaction for 12 hr at room temperature. After the completion of the reaction, the reactant mixture was filtered and washed repeatedly with DMF, MC, MC/MeOH and MEOH, thereby yielding the resin of the formula (3a-1) as a light yellow solid.

(I-3) Etherification of N-4-methoxybenzyl-substituted Hydroxy Methoxy Resin (3a-1)

(3a-1)

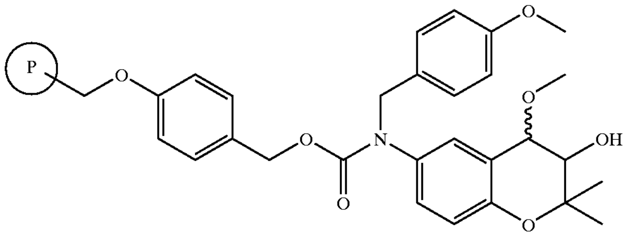

-continued (4a-1)

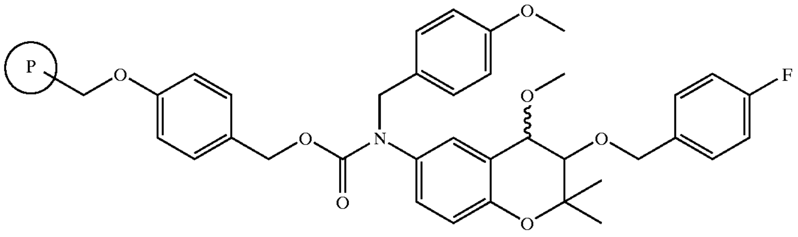

2,2-dimethyl-3-hydroxy-6-(4-methoxybenzyl)-ammo benzopyran resin (200.0 mg, 0.11 mmol) linked to a carbamate linker represented by the formula (3a-1) was added to a solution of dimethylformamide (3 ml) and agitated for 30 min at room temperature, followed by addition of lithium t-butoxide (LiOtBu)(1.1 ml, 1.1 mmol) in 1 M of tetrahydrofuran (THF) and agitation for 30 min at room temperature. To the mixture, 4-fluorobenzylbromide (0.274 ml, 0.22 mmol) was added and agitated to proceed with a reaction for 6 hr at room temperature. After completion of the reaction, the reactant mixture was filtered and washed repeatedly with DMF, MC, MC/MeOH and MeOH, thereby yielding the resin of the formula (4a-1) as a light brown solid.

(I-4) Departure Reaction of 2,2-dimethyl-3(4-fluorobenzyl) ether-4-methoxy-6-(4-methoxybenzyl)amino Benzopyran (4a-1)

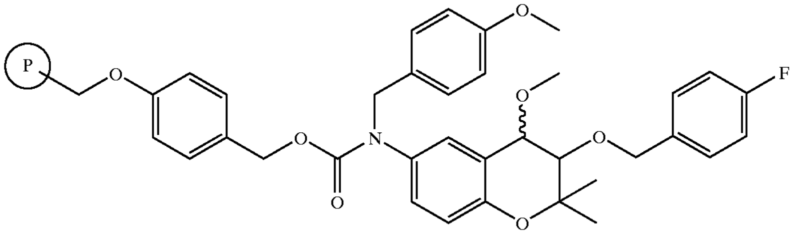

(5-338)

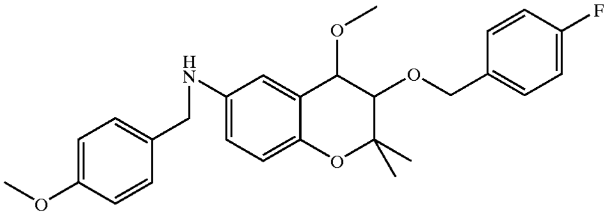

The resin (200 mg) of the formula (4a-1) was added to a solution of dichloromethane (5 ml) and agitated, followed by addition of trifluoroacetic acid (TFA, 1 ml) and agitation for 3 hr at room temperature. After completion of the reaction, the reactant mixture was filtered and the filtrate was washed repeatedly with dichloromethane and methyl alcohol. The filtrates were combined and concentrated. To the concentrates, ethylacetate (3 ml) was added, filtered thorough strong anion exchange resin (SAX) and washed repeatedly with ethylacetate to remove residual TFA. Following concentration of the filtrate under reduced pressure, the concentrate was purified with silica gel column chromatography in the presence of hexane/ethylacetate (4/1, v/v), thereby yielding the compound of the formula (5-338) as a light-yellow oil (22.75 mg, yield=45.8%; 4 step overall yield from resin 1; loading capacity of resin 1=0.55 mmol/g): $^1H$ NMR(200 MHz, $CDCl_3$) δ(PPM) 6.95–7.40 (m, 8H), 6.75 (m, 3H), 4.83(d, 1H, J=11.4 Hz), 4.65 (d, 1H, J=11.4 Hz), 4.15 (s, 2H), 4.28 (d, J=7.3 Hz), 3.67 (s, 3H), 3.53 (d, 1H, J=7.3 Hz), 3.50 (s, 3H), 1.40 (s, 3H), 1.23 (s, 3H); Mass, m/z: 451.54.

The 6-amino-2,2-dimethyl-3,4,6-trisubstituted benzopyran derivatives synthesized according to the method of parallel synthesis on the solid-phase as Example I are summarized in Table 1.

In construction of the library in Table I, the following precursors were employed to prepare combinations of each substituent: for example, $R_1$ precursor includes $CH_3I$, $C_2H_5I$, tBuI, 4-BuI, 4-F—$C_4H_9I$, 4-Me-$C_4H_9I$, 2-$CH_3$-$C_4H_9I$, 3-Cl—$C_4H_9I$, 4-tBu-$C_4H_9I$ and 3-F—$C_4H_9I$; $R^2$ precursor includes $CH_3OH$, $C_2H_5OH$, iPrOH, tBuOH, $C_4H_9OH$, 2-Ph-EtOH and 2-cyclohexyl-EtOH; $R^3$ precursor includes $C_4H_9Br$, 4-F—$C_4H_9Br$, 4-tBu-$C_4H_9Br$, 3-F—$C_4H_9Br$, 2-$CH_3$-$C_4H_9Br$, 2-Cl—$C_4H_9Br$, 3-Cl—$C_4H_9Br$, 4-$CH_3$-$C_4H_9Br$, 4-Br-2-F—$C_4H_9Br$, β-$CH_3Br$—NaOH, 3,5-$CF_3$-$C_4H_9Br$, $CH_3OH$, $C_5H_{11}I$, 1-bromo-2-butene, 3-bromopropene and 3-bromoprophine (Propargyl Br).

TABLE 1

| | Compound No. NMR/MS Data |
|---|---|
| 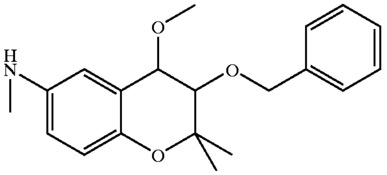 5-1 | $^1$H NMR(200 MHz, $CDCl_3$) δ 7.42~7.29(m, 5H), 6.70~6.50(m, 3H), 4.93(d, 1H, J=11.6 Hz), 4.73(1H, d, J=11.6 Hz), 4.45(d, 1H, J=7.3 Hz), 3.63(d, 1H, J=7.3 Hz), 3.51(s, 3H), 3.63(s, 3H), 1.42(s, 3H), 1.24(s, 3H); MS, m/z: 327.43 |
| 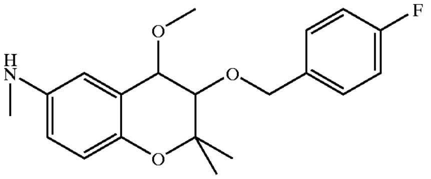 5-2 | $^1$H NMR(200 MHz, $CDCl_3$) δ 7.39~7.32(m, 2H), 7.08~6.99(m, 2H), 6.69~6.52(m, 3H), 4.87(d, 1H, J=11.5 Hz), 4.68(d, 1H, J=11.3 Hz), 4.43(d, 1H, J=7.2 Hz), 4.60(s, 1H, J=7.2 Hz), 3.49(s, 3H), 2.81 (s, 3H), 1.40(s, 3H), 1.25(s, 3H); MS, m/z: 345.42 |
| 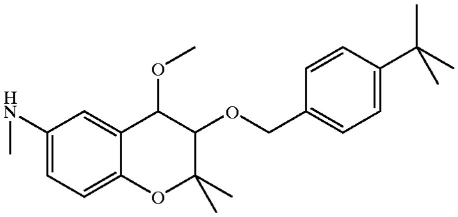 5-3 | $^1$H NMR(200 MHz, $CDCl_3$) δ 7.41~7.16(m, 4H), 6.74~6.52(m, 3H), 4.88(d, 1H, J=11.4 Hz), 4.70(d, 1H, J=11.4 Hz), 4.42(d, 1H, J=7.4 Hz), 3.61(d, 1H, J=7.3 Hz), 3.51(s, 3H), 2.82(s, 3H), 1.42(s, 3H), 1.32(m, 9H), 1.24(s, 3H); MS, m/z: 383.54 |
| 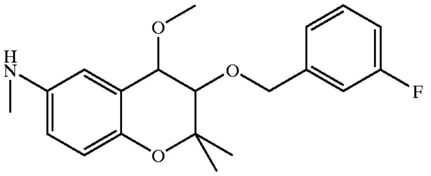 5-4 | $^1$H NMR(200 MHz, $CDCl_3$) δ .31(m, 1H), 7.16~7.0(m, 2H), 6.99(m, 1H), 6.70~6.50(m, 3H), 4.93(d, 1H, J=11.9 Hz), 4.72(d, 1H, J=11.8 Hz), 4.46(d, 1H, J=7.4 Hz), 3.62(d, 1H, J=7.5 Hz), 3.50(s, 3H), 2.81 (s, 3H), 1.43(s, 3H), 1.24(s, 3H); MS, m/z: 345.42 |
| 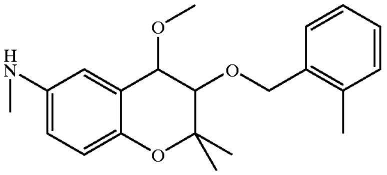 5-5 | $^1$H NMR(200 MHz, $CDCl_3$) δ .31(m, 1H), 7.16~7.0(m, 2H), 6.99(m, 1H), 6.70~6.50(m, 3H), 4.93(d, 1H, J=11.9 Hz), 4.72(d, 1H, J=11.8 Hz), 4.46(d, 1H, J=7.4 Hz), 3.62(d, 1H, J=7.5 Hz), 3.50(s, 3H), 2.81 (s, 3H), 1.43(s, 3H), 1.24(s, 3H); MS, m/z: 345.42 |
| 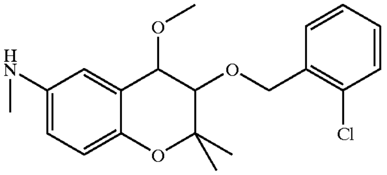 5-6 | $^1$H NMR(200 MHz, $CDCl_3$) δ 7.55(m, 1H), 7.39~7.22(m, 3H), 6.71~6.50(m, 3H), 5.03(d, 1H, J=12.8 Hz), 4.82(d, 1H, J=12.8 Hz), 4.47(d, 1H, J=7.3 Hz), 3.68(d, 1H, J=7.3 Hz), 3.52(s, 3H), 2.81 (s, 3H), 1.43(s, 3H), 1.27(s, 3H); MS, m/z: 361.87 |
| 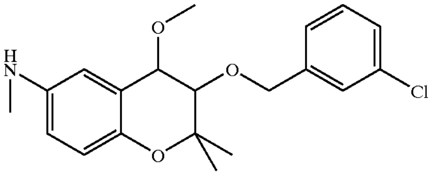 5-7 | $^1$H NMR(200 MHz, $CDCl_3$) δ 7.41(m, 1H), 7.28(m, 3H), 6.70~6.50(m, 3H), 4.90(d, 1H, J=12.0 Hz), 4.70(d, 1H, J=12.0 Hz), 4.46(d, 1H, J=7.5 Hz), 3.61(d, 1H, J=7.5 Hz), 3.50(s, 3H), 2.81 (s, 3H), 1.43(s, 3H), 1.24(s, 3H); MS, m/z: 361.87 |

TABLE 1-continued
| | Compound No. NMR/MS Data |
|---|---|
| 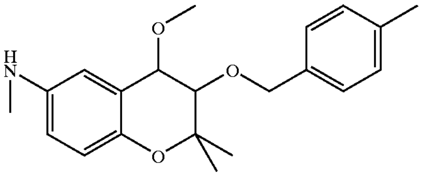 5-8 | $^{1}H$ NMR(200 MHz, $CDCl_3$) δ 7.28(d, 2H, J=7.9 Hz), 7.16(d, 2H, J=7.9 Hz), 6.74~6.49(m, 3H), 4.87(d, 1H, J=11.2 Hz), 4.68(d, 1h, J=11.2 Hz), 4.42(d, 1H, J=7.4 Hz), 4.34(d, 1H, J=7.5 Hz), 3.51(s, 3H), 2.81(s, 3H), 2.81(s, 3H), 1.40(s, 3H), 1.23(s, 3H); MS, m/z: 341.45 |
| 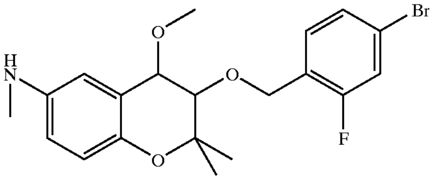 5-9 | $^{1}H$ NMR(200 MHz, $CDCl_3$) δ 7.40~7.22(m, 3H), 6.69~6.50(m, 3H), 4.90(d, 1H, J=11.8 Hz), 4.73(d, 1H, 1=11.8 Hz), 4.42(d, 1H, J=7.5 Hz), 3.61(d, 1H, J=7.5 Hz), 3.51(s, 3H), 2.81(s, 3H), 1.40(s, 3H), 1.21 (s, 3H); MS, m/z: 424.31 |
| 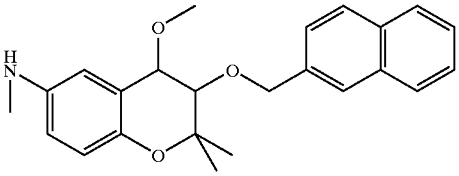 5-10 | $^{1}H$ NMR(200 MHz, $CDCl_3$) δ 7.85(m, 4H), 7.50(m, 3H), 6.71~6.51 (m, 3H), 5.08(d, 1H, J=11.6 Hz), 4.89(d, 1H, J=11.6 Hz), 4.49(d, 1H, J=7.2 Hz), 3.69(d, 1H, J=7.2 Hz), 3.51(s, 3H), 2.82(s, 3H), 1.43(s. 3H), 1.27(s, 3H) ; MS, m/z: 377.49 |
| 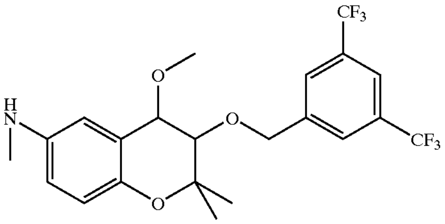 5-11 | MS, m/z: 355.48 |
| 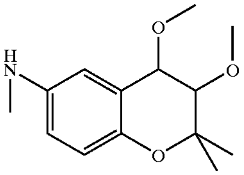 5-12 | MS, m/z: 251.33 |
| 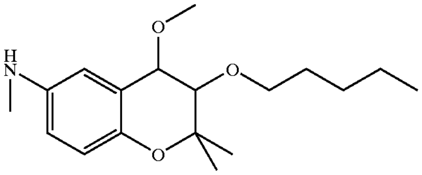 5-13 | MS, m/z: 307.44 |
| 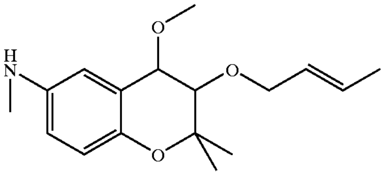 5-14 | MS, m/z: 291.39 |

TABLE 1-continued

| | Compound No. NMR/MS Data |
|---|---|
| 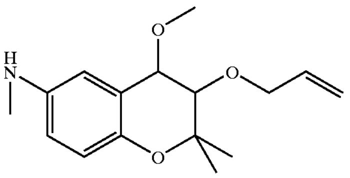 5-15 | MS, m/z: 277.37 |
| 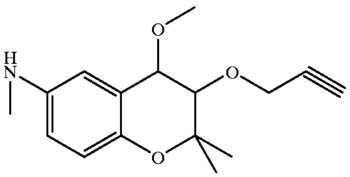 5-16 | MS, m/z: 275.35 |
| 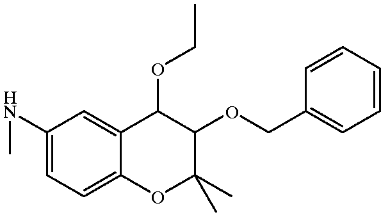 5-17 | $^{1}$H NMR(200 MHz, $CDCl_3$) δ 7.41~7.27(m, 5H), 6.69~6.52(m, 3H), 4.92(d, 1H, J=11.4H), 4.72(d, 1H, J=11.4 Hz), 4.47(d, 1H, J=7.6 Hz), 3.76(q, 2H, J=6.9 Hz), 3.61(d, 1H, J=7.6 Hz), 2.81(s, 3H), 1.41(s, 3H), 1.29(m, 3H), 1.24(s, 3H); MS, m/z: 341.45 |
| 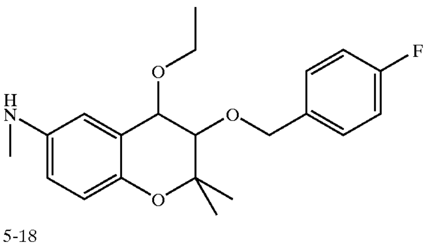 5-18 | $^{1}$H NMR(200 MHz, $CDCl_3$) δ 7.40~7.31(m, 2H), 7.10~6.69(m, 2H), 6.67~6.53(m, 3H), 4.87(d, 1H, J=11.5 Hz), 4.68(d, 1H, J=11.5 Hz), 4.46(d, 1H, J=7.4 Hz), 3.75(q, 2H, J=7.0 Hz), 3.59(d, 1H, J=5.4 Hz), 2.82(s, 3H), 1.40(s, 3H), 1.28(t, 3H, J=J=7.0 Hz), 1.22(s, 3H); MS, m/z: 359.44 |
| 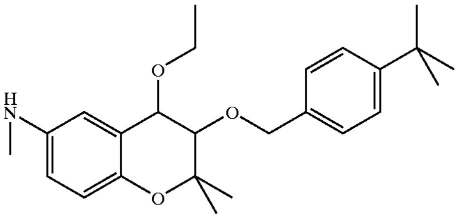 5-19 | $^{1}$H NMR(200 MHz, $CDCl_3$) δ 7.41~7.29(m, 4H), 6.69~6.56(m, 3H), 4.87(d, 1H, J=11.1 Hz), 4.69(s, 1H, J=11.1 Hz), 4.45(d, 1H, J=7.3 Hz), 3.75(m, 2H), 3.60(d, 1H, J=7.5 Hz), 1.41(s, 3H), 1.32(s, 9H), 1.32(m, 3H), 1.24(s, 3H); MS, m/z: 397.56 |
| 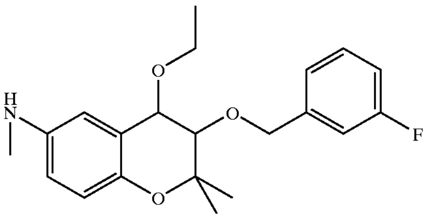 5-20 | $^{1}$H NMR(200 MHz, $CDCl_3$) δ 7.37~7.26(m, 1H), 7.15~6.99(m, 3H), 6.70~6.62(m, 3H), 4.91(d, 1H, J=11.8 Hz), 4.71(d, 1H, J=11.8 Hz), 4.48(d, 1H, J=7.5 Hz), 3.76(q, 2H, J=6.9 Hz), 3.60(d, 1H, J=7.5 Hz), 2.82(s, 3H), 1.42(s, 3H), 1.28(m, 3H), 1.25(s, 3H); MS, m/z: 359.44 |

TABLE 1-continued

| Compound No. | NMR/MS Data |
|---|---|
| 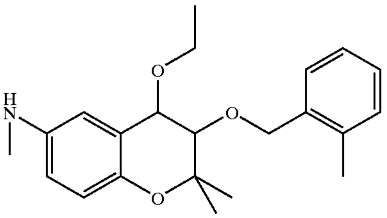 5-21 | $^1$H NMR(200 MHz, $CDCl_3$) δ 7.39(m, 1H), 7.26~7.19(m, 3H), 6.69~6.58(m, 3H), 4.94(d, 1H, J=11.7 Hz), 4.70(d, 1H, J=11.7 Hz), 4.48(d, 1H, J=7.7 Hz), 3.74(q, 2H, J=7.1 Hz), 3.63(d, 1H, J=7.7 Hz), 2.82(s, 3H), 2.36(s, 3H), 1.39(s, 3H), 1.27(m, 3H), 1.23(s, 3H); MS, m/z: 355.48 |
| 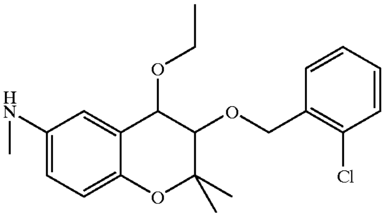 5-22 | $^1$H NMR(200 MHz, $CDCl_3$) δ 7.55(m, 1H), 7.39~7.18(m, 3H), 6.70~6.52(m, 3H), 5.04(d, 1H, J12.7 Hz), 4.81(d, 1H, J=12.7 Hz), 4.50(d, 1H, J=7.5 Hz), 3.77(q, 2H, J=7.0 Hz), 3.67(d, 1H, J=7.6 Hz), 2.81 (s, 3H), 1.42(s, 3H), 1.27(m, 3H), 1.26(s, 3H) MS, m/z: 375.90 |
| 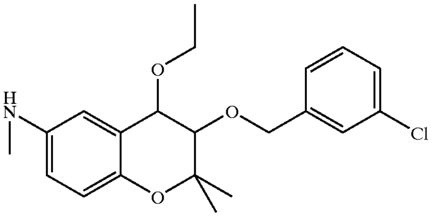 5-23 | $^1$H NMR(200 MHz, $CDCl_3$) δ 7.38~7.17(m, 4H), 6.72~6.50(m, 3H), 4.90(d, 1H, J=12.1 Hz), 4.69(d, 1H, J=12.1 Hz), 4.48(d, 1H, J=7.6 Hz), 3.75(q, 2H, J=7.0 Hz), 3.60(d, 1H, J=7.6 Hz), 1.42(s, 3H), 1.28(s, 3H), 1.28(t, 3H, J=7.0 Hz), 1.24(s, 3H); MS, m/z: 375.90 |
| 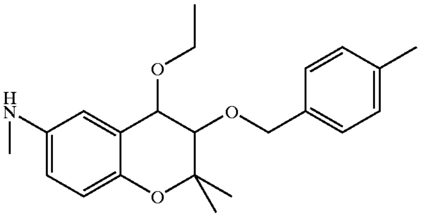 5-24 | $^1$H NMR(200 MHz, $CDCl_3$) δ 7.36~7.06(m, 4H), 6.68~6.49(mm, 3H), 4.8(d, 1H, J=11.4 Hz), 4.67(d, 1H, J=11.4 Hz), 4.45 (d, 1H, J=7.4 Hz), 3.78(m, 2H), 3.59(d, 1H, J=7.4 Hz), 2.81(s, 1H), 2.35(s, 3H), 1.40(s, 3H), 1.28(m, 3H), 1.22(s, 3H); MS, m/z: 355.48 |
| 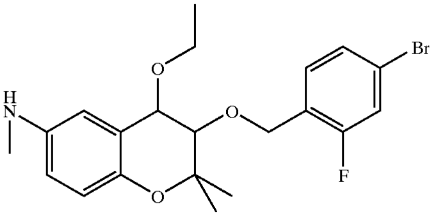 5-25 | $^1$H NMR(200 MHz, $CDCl_3$) δ 7.39~7.23(m, 3H), 6.75~6.49(m, 3H), 4.91 (d, 1H, J=12.5 Hz), 4.72(d, 1H, J=12.5 Hz), 4.46(d, 1H, J=7.4 Hz), 3.7(q, 2H, J=7.0 Hz), 3.60(d, 1H, J=7.4 Hz), 2.80(s, 3H), 1.40(s, 3H), 1.28(t, 3H, J=7.0 Hz), 1.21 (s, 3H); MS, m/z: 438.34 |
| 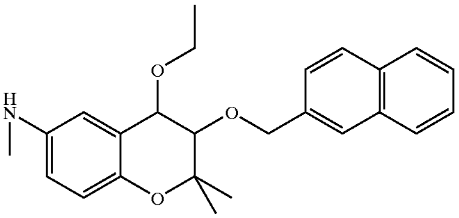 5-26 | $^1$H NMR(200 MHz, $CDCl_3$) δ 7.86~7.82(m, 4H), 7.54~7.46(m, 3H), 6.69~6.50(m, 3H), 5.07(d, 1H, J=12.0 Hz), 4.8(d, 1H, J=12.0 Hz), 4.51(d, 1H, J=7.5 Hz), 3.76(q, 2H, J=6.9 Hz), 3.67(d, 1H, J=7.5 Hz), 2.81(s, 3H), 1.429(s, 3H), 1.28(m, 3H), 1.27(s, 3H); MS, m/z: 391.51 |

TABLE 1-continued

| Compound No. | NMR/MS Data |
|---|---|
| 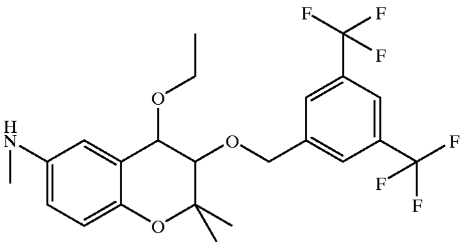 5-27 | $^1$H NMR(200 MHz, $CDCl_3$) δ 7.83(m, 3H), 6.72~6.50(m, 3H), 5.06(d, 1H, J=12.4 Hz), 4.85(d, 1H, J=12.4 Hz), 4.54(d, 1H, J=7.9 Hz), 3.79~3.65(m, 2H), 3.65(d, 1H, J=7.9 Hz), 2.81(s, 3H), 1.44(s, 3H), 1.26(m, 3H), 1.26(s, 3H); MS, m/z: 477.45 |
| 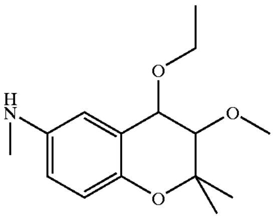 5-28 | $^1$H NMR(200 MHz, $CDCl_3$) δ 6.67~6.48(m, 3H), 4.36(d, 1H, J=7.4 Hz), 3.80(q, 2H, J=6.9 Hz), 3.32(d, 1H, J=7.4 Hz), 2.80(s, 3H), 1.42(s, 3H), 1.31 (t, 3H, J=6.9 Hz), 1.20(s, 3H); MS, m/z: 265.36 |
| 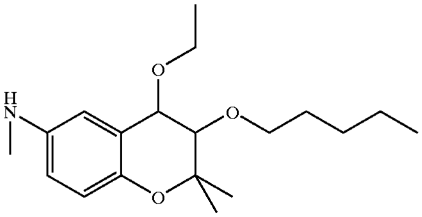 5-29 | $^1$H NMR(200 MHz, $CDCl_3$) δ 6.67~6.50(m, 3H), 4.36(d, 1H, J=7.6 Hz), 3.85~3.75(m, 3H), 3.62~3.58(m, 1H), 3.39(d, 1H, J=7.6 Hz), 2.80(s, 3H), 1.72~1.51(m, 2H), 1.41(s, 3H), 1.33(m, 2H), 1.29(m, 3H), 1.20(s, 3H), 0.91 (m, 3H); MS, m/z: 321.46 |
| 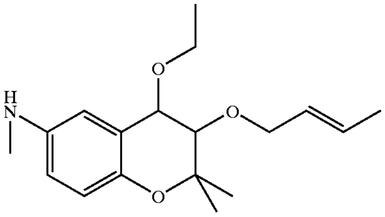 5-30 | $^1$H NMR(200 MHz, $CDCl_3$) δ 6.67~6.48(m, 3H), 5.80~5.58(m, 2H), 4.44~4.08(m, 3H), 3.87~3.74(m, 2H), 3.48(d, 1H, J=7.5 Hz), 2.80(s, 3H), 1.72(d, 3H, J=4.9 Hz), 1.41(s, 3H), 1.30(m, 3H), 1.21(s, 3H); MS, m/z: 305.42 |
| 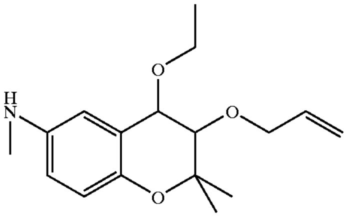 5-31 | $^1$H NMR(200 MHz, $CDCl_3$) δ 6.75~6.49(m, 3H), 6.04~5.87(m, 1H), 5.29(dd, 1H, 1=17.1 Hz, J=1.6 Hz), 5.18(dd, 1H, J=10.2 Hz, J=1.6 Hz), 4.40(d, 1H, J=7.7 Hz), 4.35~4.14(m, 2H), 3.80(q, 2H, J=7.1 Hz), 3.49(d, 1H, 1=7.7 Hz), 2.81(s, 3H), 1.41(s, 3H), 1.30(t, 3H, J=7.1~Hz), 1.22(s, 3H); MS, m/z: 291.39 |
| 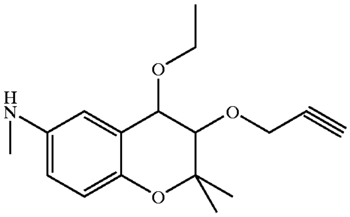 5-32 | $^1$H NMR(200 MHz, $CDCl_3$) δ 6.87~6.49(m, 3H), 4.61~4.35(m, 3H), 3.83~3.30(m, 3H), 2.80(s, 3H), 2.46(m, 1H), 1.44(s, 3H), 1.29(m, 3H), 1.22(s, 3H); MS, m/z: 289.38 |

TABLE 1-continued
| | Compound No. NMR/MS Data |
|---|---|
| 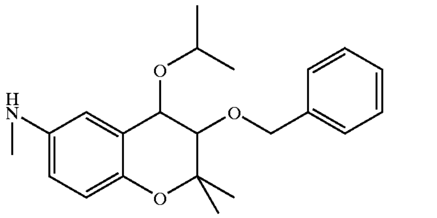 5-33 | MS, m/z: 355.48 |
| 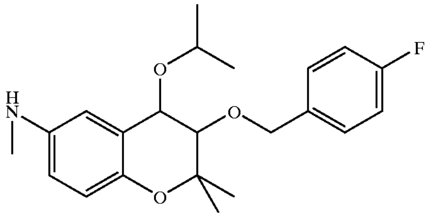 5-34 | MS, m/z: 373.47 |
| 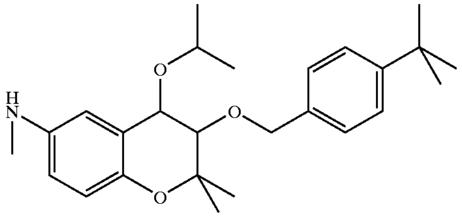 5-35 | MS, m/z: 411.59 |
| 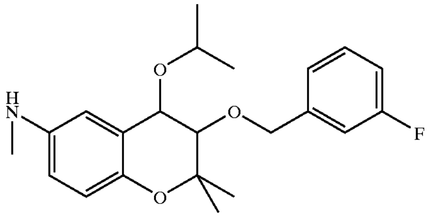 5-36 | MS, m/z: 373.47 |
| 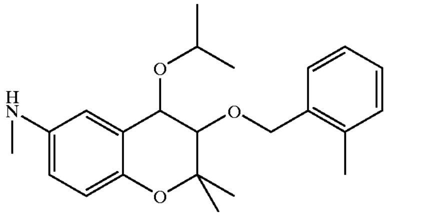 5-37 | MS, m/z: 369.51 |
| 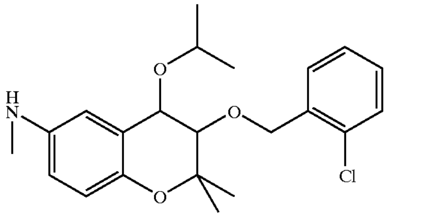 5-38 | MS, m/z: 389.93 |

TABLE 1-continued
| | Compound No. NMR/MS Data |
|---|---|
| 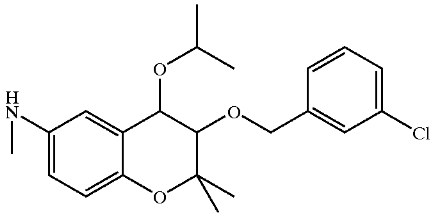 5-39 | MS, m/z: 389.93 |
| 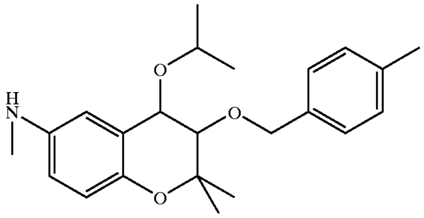 5-40 | MS, m/z: 369.51 |
| 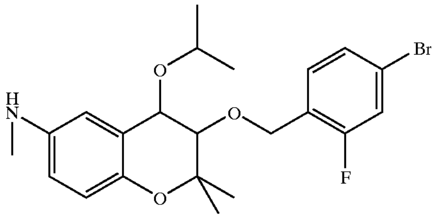 5-41 | MS, m/z: 452.37 |
| 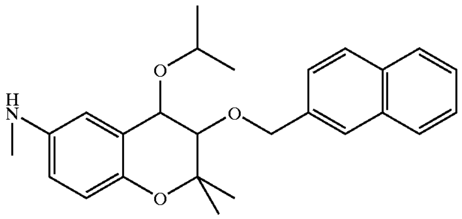 5-42 | MS, m/z: 405.54 |
| 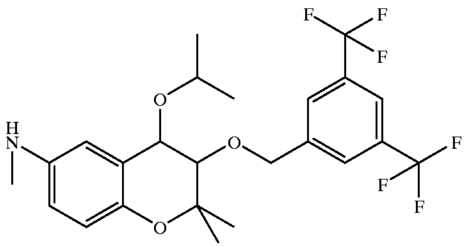 5-43 | MS, m/z: 491.48 |
| 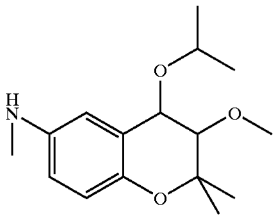 5-44 | MS, m/z: 279.38 |

TABLE 1-continued
| | Compound No. NMR/MS Data |
|---|---|
| 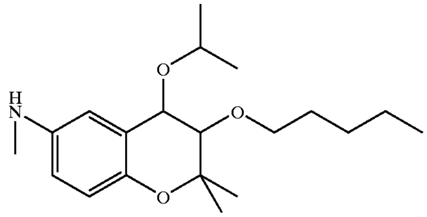 5-45 | MS, m/z: 335.49 |
| 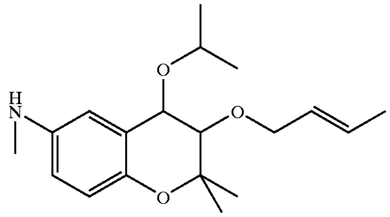 5-46 | MS, m/z: 319.45 |
| 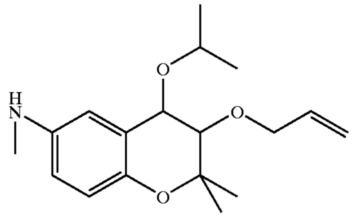 5-47 | MS, m/z: 305.42 |
| 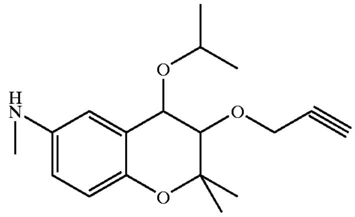 5-48 | MS, m/z: 303.40 |
| 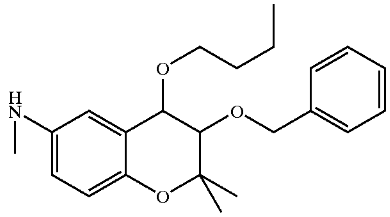 5-49 | $^1$H NMR(200 MHz, $CDCl_3$) δ 7.41~7.26(m, 5H), 6.68~6.49(m, 3H), 4.91(d, 1H, J=11.6 Hz), 4.71(d, 1H, J=11.6 Hz), 4.45(d, 1H, J=7.3 Hz), 3.71(m, 2H), 3.61(d, 1H, J=7.3 Hz), 2.81(s, 3H), 1.60(m, 2H), 1.45(m, 2H), 1.40(s, 3H), 1.24(s, 3H), 0.93(t, 3H, J=7.2 Hz); MS, m/z: 369.51 |
| 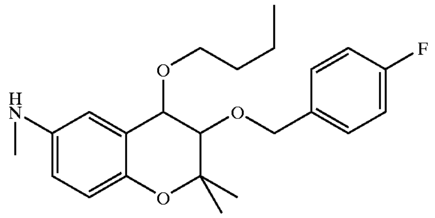 5-50 | $^1$H NMR(200 MHz, $CDCl_3$) δ 7.38~7.26(m, 2H), 7.08~6.99(m, 2H), 6.68~6.50(m, 3H), 4.86(d, 1H, J=11.6 Hz), 4.67(d, 1H, r=1.6 Hz), 4.45(d, 1H, J=7.3 Hz), 3.67(m, 2H), 3.59(d, 1H, J=7.3 Hz), 2.81(s, 3H), 1.62(m, 2H), 1.41(m, 2H), 1.39(s, 3H), 1.23(s, 3H), 0.93(t, 3H, J=7.2 Hz); MS, m/z: 387.50 |

TABLE 1-continued

| Compound No. | NMR/MS Data |
|---|---|
| 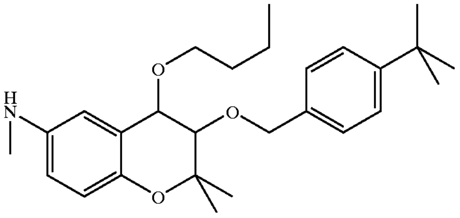 5-51 | $^1$H NMR(200 MHz, $CDCl_3$) δ 7.41~7.26(m, 4H), 6.76~6.48(m, 3H), 4.86(d, 1H, J=11.0 Hz), 4.68(d, 1H, J=11.0 Hz), 4.44(d, 1H, J=7.4 Hz), 3.70(m, 2H), 3.60(d, 1H, J=7.4 Hz), 2.81(s, 3H), 1.61(m, 2H), 1.43(m, 2H), 1.41(s, 3H), 1.32(m, 9H), 1.24(s, 3H), 0.94(m, 3H); MS, m/z: 425.62 |
| 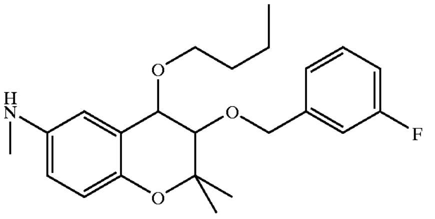 5-52 | $^1$H NMR(200 MHz, $CDCl_3$) δ 7.37~7.29(m, 1H), 7.15~6.99(m, 3H), 6.69~6.49(m, 3H), 4.91(d, 1H, J=11.9 Hz), 4.71(d, 1H, J=12.0 Hz), 4.48(d, 1H, J=7.4 Hz), 3.69(t, 2H, J=6.5 Hz), 3.60(d, 1H, J=7.4 Hz), 2.81(s, 3H), 1.61((m, 2H), 1.45(m, 2H), 1.41(s, 3H), 1.24(s, 3H), 0.93(t, 3H, J=7.2 Hz); MS, m/z: 387.50 |
| 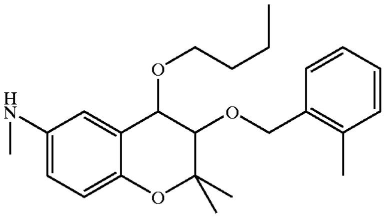 5-53 | $^1$H NMR(200 MHz, $CDCl_3$) δ 7.38(m, 1H), 7.23~7.19(m, 3H), 6.68~6.49(m, 3H), 4.93(d, 1H, J=11.7 Hz), 4.69(d, 1H, J=11.7 Hz), 4.47(d, 1H, J=7.3 Hz), 3.71~3.61 (m, 3H), 2.81(s, 3H), 2.36(s, 3H), 1.62(m, 2H), 1.42m, 2H), 1.38(s, 3H), 1.24(s, 3H), 0.92(t, 3H, J=7.2 Hz); MS, m/z: 383.54 |
| 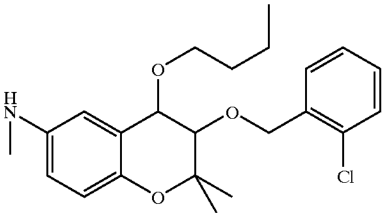 5-54 | MS, m/z: 403.95 |
| 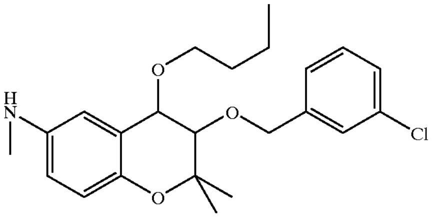 5-55 | $^1$H NMR(200 MHz, $CDCl_3$) δ 7.38~7.24(m, 4H), 6.69~6.49(m, 3H), 4.89(d, 1H, J=11.7 Hz), 4.69(d, 1H, J=11.7 Hz), 4.47(d, 1H, J=7.4 Hz), 3.68(t, 2H, J=6.4 Hz), 3.59(d, 1H, J=7.4 Hz), 2.81(s, 3H), 1.63(m, 2H), 1.45(m, 2H), 1.41(s, 3H), 1.25(s, 3H), 0.93(t, 3H, J=7.2 Hz); MS, m/z: 403.95 |
| 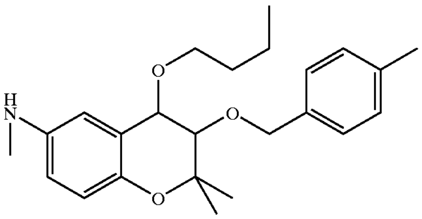 5-56 | MS, m/z 383.54 |

TABLE 1-continued
| | Compound No. NMR/MS Data |
|---|---|
| 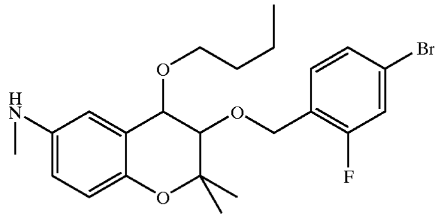 5-57 | $^1H$ NMR(200 MHz, $CDCl_3$) δ 7.34~7.21(m, 3H), 6.69~6.50(m, 3H), 4.90(d, 1H, J=11.8 Hz), 4.71 (d, 1H, J=11.8 Hz), 4.44(d, 1H, J=7.2 Hz), 3.73~3.67(m, 2H), 3.60(d, 1H, J=7.2 Hz), 2.81(s, 3H), 1.60(m, 2H), 1.43(m, 2H), 1.39(m, 3H), 1.22(m, 3H), 0.93(t, 3H, J=7.2 Hz); MS, m/z: 466.39 |
| 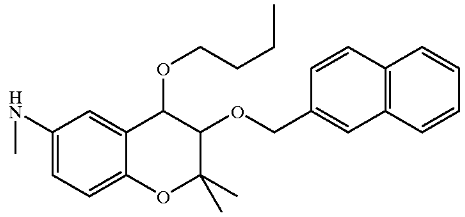 5-58 | MS, m/z: 419.57 |
| 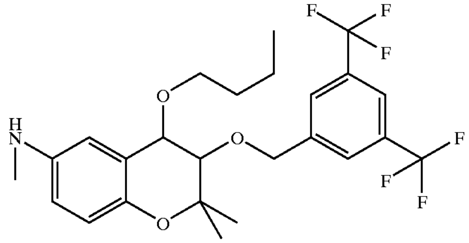 5-59 | MS, m/z: 505.51 |
| 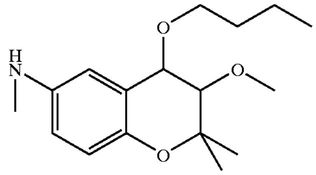 5-60 | MS, m/z: 293.41 |
| 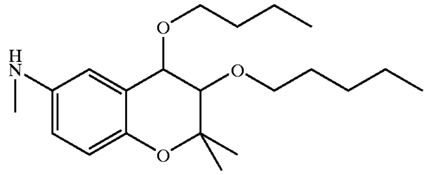 5-61 | MS, m/z: 349.52 |
| 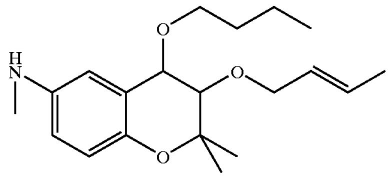 5-62 | MS, m/z: 333.47 |

TABLE 1-continued

| | Compound No. NMR/MS Data |
|---|---|
| 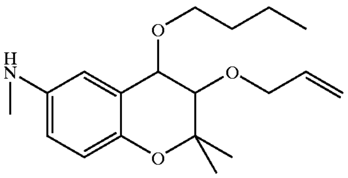 5-63 | $^1$H NMR(200 MHz, $CDCl_3$) δ 6.67~6.48(m, 3H), 6.07~5.87(m, 1H), 5.30(dd, 1H, J=17.1 Hz, J=1.6 Hz), 5.18(dd, 1H, J=10.1 Hz, J=1.6 Hz), 4.39(d, 1H, J=7.5 Hz), 4.35(m, 1H), 4.23(m, 1H), 3.75(m, 2H), 3.59(d, 1H, J=7.5 Hz), 2.80(s, 3H), 1.62(m, 2H), 1.43(m, 2H), 1.41(s, 3H), 1.23(s, 3H), 0.95(t, 3H, J=7.2 Hz); MS, m/z 319.45 |
| 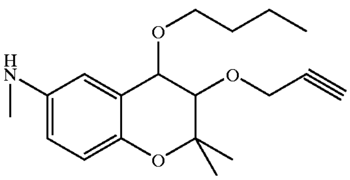 5-64 | $^1$H NMR(200 MHz, $CDCl_3$) δ 6.84(m, 3H), 4.45(d, 2H, J=2.5 Hz), 4.45(m, 1H), 3.72(m, 3H), 2.80(s, 3H), 2.45(t, 1H, J=2.5 Hz), 1.62(m, 2H), 1.47(m, 2H), 1.44(s, 3H), 1.23(s, 3H), 0.95(t, 3H, J=7.2 Hz); MS, m/z: 317.43 |
| 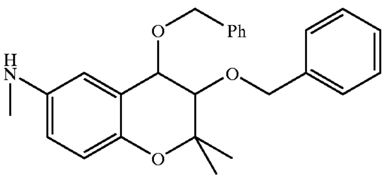 5-65 | $^1$H NMR(200 MHz, $CDCl_3$) δ 7.42~7.29(m, 5H), 6.70~6.49(m, 3H), 4.91 (d, 1H, J=11.4 Hz), 4.83~4.68(m, 3H), 3.71(d, 1H J=7.1 Hz), 2.74(s, 3H), 1.44(s, 3H), 1.27(s, 3H); MS, m/z: 403.53 |
| 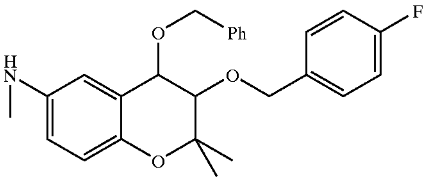 5-66 | MS, m/z: 421.52 |
| 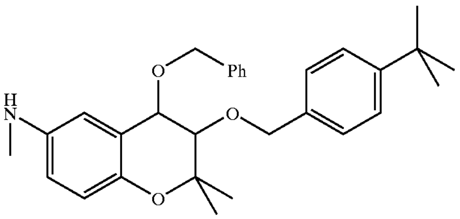 5-67 | $^1$H NMR(200 MHz, $CDCl_3$) δ 7.42~7.14(m, 9H), 6.72~6.51(m, 3H), 4.87(d, 1H, J=11.2 Hz), 4.83~4.67(m, 3H), 4.63(d, 1H, J=7.0 Hz), 3.70(d, 1H, J=7.0 Hz), 2.74(s, 3H), 1.45(s, 3H), 1.33~1.29(m, 9H), 1.27(s, 3H); MS, m/z: 459.63 |
| 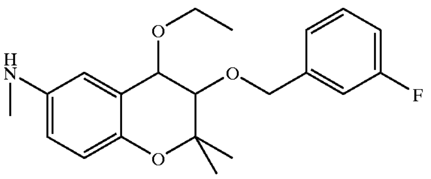 5-68 | $^1$H NMR(200 MHz, $CDCl_3$) δ 7.41~7.25(m, 5H), 7.12~6.71(m, 4H), 6.68(d, 1H, J=8.1 Hz), 6.55~6.49(m, 2H), 4.90(d, 1H, J=12.0 Hz), 4.85~4.64(m, 4H), 3.70(d, 1H, J=7.3 Hz), 2.75(s, 3H), 1.45(s, 3H), 1.28(s, 3H); MS, m/z: 359.44 |
| 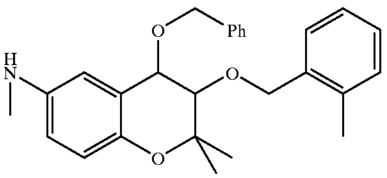 5-69 | $^1$H NMR(200 MHz, $CDCl_3$) δ 7.40~7.28(m, 5H), 7.24~7.17(m, 4H), 6.68(d, 1H, J=8.2 Hz), 6.55~6.49(m, 2H), 4.93(d, 1H, J=11.6 Hz), 4.88~4.63(m, 4H), 3.74(d, 1H, J=7.1 Hz), 2.75(s, 3H), 2.32(s, 3H), 1.42(s, 3H), 1.27(s, 3H) MS, m/z: 417.55 |

TABLE 1-continued

| Compound No. | NMR/MS Data |
|---|---|
| 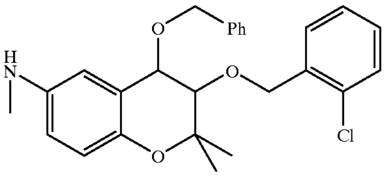 5-70 | $^1$H NMR(200 MHz, $CDCl_3$) δ 7.56~7.20(m, 9H), 6.71~6.49(m, 3H), 5.04(d, 1H, J=12.6 Hz), 4.98~4.669m, 4H), 3.78(d, 1H, J=7.1 Hz), 2.75(s, 3H), 1.45(s, 3H), 1.30(s, 3H); MS, m/z: 437.97 |
| 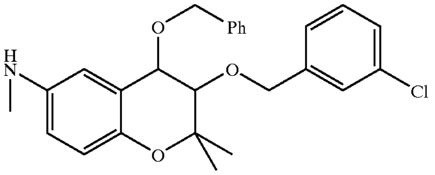 5-71 | $^1$H NMR(200 MHz, $CDCl_3$) δ 7.39~7.21(m, 9H), 6.71~6.49(m, 3H), 4.88(d, 1H, J=12.0 Hz), 4.81~4.64(m, 4H), 3.70(d, 1H, J=7.4 Hz), 2.75(s, 3H), 1.45(s, 3H), 1.28(s, 3H); MS, m/z: 437.97 |
| 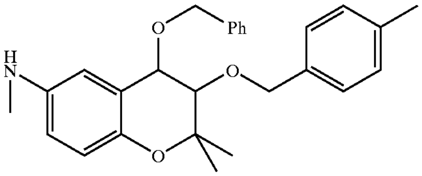 5-72 | $^1$H NMR(200 MHz, $CDCl_3$) δ 7.39~7.06(m, 9H), 6.85~6.51(m, 3H), 4.86(d, 1H, J=11.8 Hz), 4.77~4.34(m, 4H), 3.69(d, 1H, J=7.1 Hz), 2.74(s, 3H), 2.35(s, 3H), 1.43(s, 3H), 1.26(s, 3H); MS, m/z: 417.55 |
| 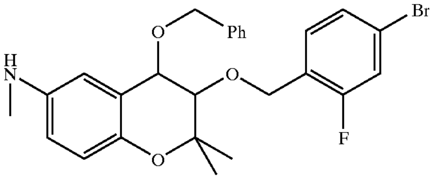 5-73 | $^1$H NMR(200 MHz, $CDCl_3$) δ 7.40~7.15(m, 8H), 6.75~6.48(m, 3H), 4.88(d, 1H, J=12.0 Hz), 4.83~4.61(m, 4H), 3.70(d, 1H, J=7.3 Hz), 2.74(s, 3H), 1.43(s, 3H), 1.24(s, 3H); MS, m/z: 500.41 |
| 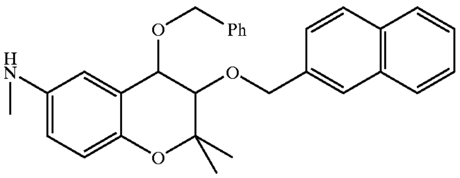 5-74 | $^1$H NMR(200 MHz, $CDCl_3$) δ 7.85~7.81(m, 4H), 7.79~7.40(m, 3H), 7.40~7.219m, 5H), 6.71~6.50(m, 3H), 5.05(d, 1H, J=11.7 Hz), 4.89(d, 1H, J=11.7 Hz), 4.84~4.68(m, 2H), 4.68(d, 1H, J=7.2 Hz), 3.77(d, 1H, J=7.2 Hz), 2.75s, 3H), 1.50(s, 3H), 1.30(s, 3H); MS, m/z: 453.59 |
| 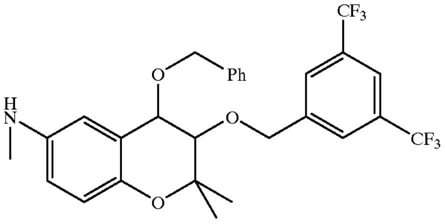 5-75 | MS, m/z: 431.58 |
| 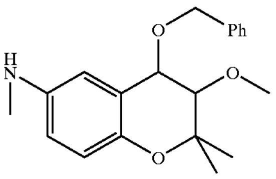 5-76 | MS, m/z: 327.43 |

TABLE 1-continued
| | Compound No. NMR/MS Data |
|---|---|
| 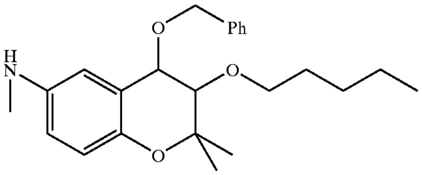 5-77 | MS, m/z: 383.54 |
| 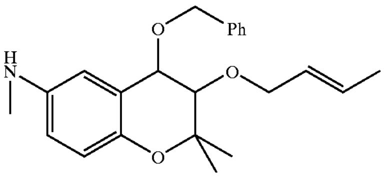 5-78 | $^{1}H$ NMR(200 MHz, $CDCl_3$) δ 7.46~7.29(m, 5H), 6.68~6.46(m, 3H), 5.78~5.63(m, 2H), 4.89~4.72(m, 2H), 4.56(d, 1H, J=7.1 Hz), 4.45~4.10(m, 2H), 3.59(d, 1H, J=7.1 Hz), 2.73(s, 3H), 1.72(m, 3H), 1.44(s, 3H), 1.25(s, 3H); MS, m/z: 357.49 |
| 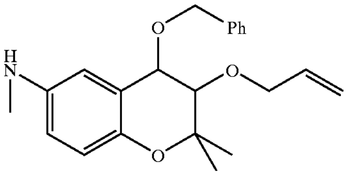 5-79 | $^{1}H$ NMR(200 MHz, $CDCl_3$) δ 7.47~7.26(m, 5H), 7.18~6.72(m, 3H), 6.05~5.86(m, 1H), 5.29(dd, 1H, J=17.1 Hz, J=1.4 Hz), 5.19(dd, 1H, J=10.4 Hz, J=1.4 Hz), 4.82(m, 2H), 4.55~4.12(m, 3H), 3.56(d, 1H, J=7.1 Hz), 2.81(s, 3H), 1.44(s, 3H), 1.28(s, 3H); MS, m/z: 353.47 |
| 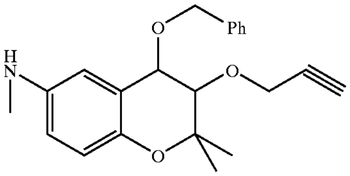 5-80 | $^{1}H$ NMR(200 MHz, $CDCl_3$) δ 7.46~7.30(m, 5H), 6.70~6.48(m, 3H), 4.78(s, 2H), 4.62(d, 1H, J=7.1 Hz), 4.45(d, 1H, J=2.5 Hz), 4.83(d, 1H, J=6.9 Hz), 2.73(s, 3H), 2.47(t, 1H, J=2.4 Hz), 1.47(s, 3H), 1.26(s, 3H); MS, m/z: 351.45 |
| 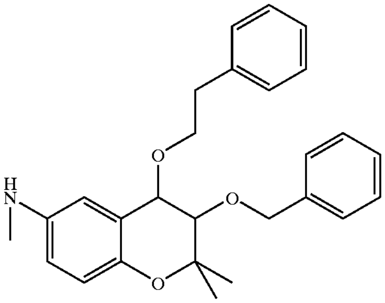 5-81 | MS, m/z: 417.55 |
| 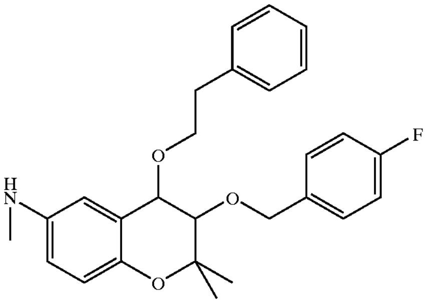 5-82 | MS, m/z: 435.54 |

TABLE 1-continued
| | Compound No. NMR/MS Data |
|---|---|
| 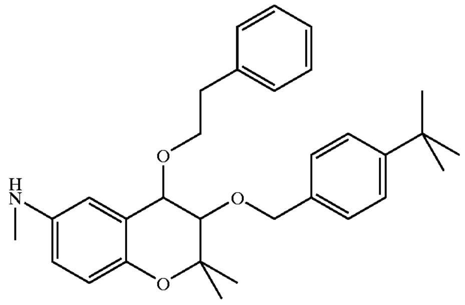 5-83 | MS, m/z: 473.66 |
| 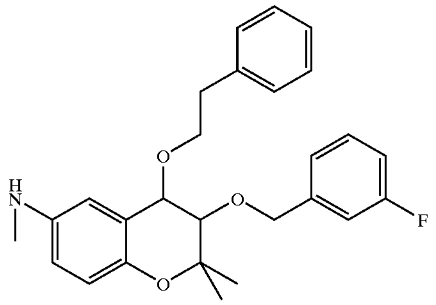 5-84 | MS, m/z: 435.54 |
| 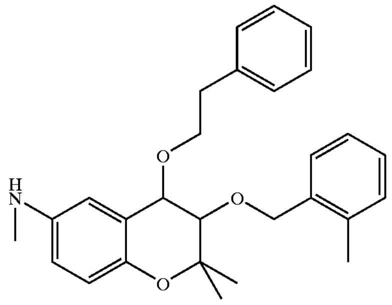 5-85 | MS, m/z: 431.58 |
| 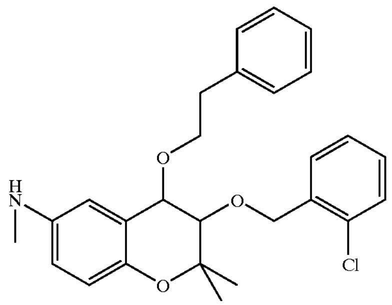 5-86 | MS, m/z: 452.00 |

TABLE 1-continued
| | Compound No. NMR/MS Data |
|---|---|
| 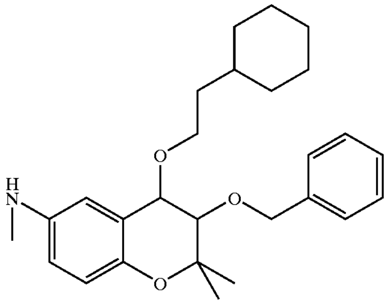 5-87 | MS, m/z: 452.00 |
| 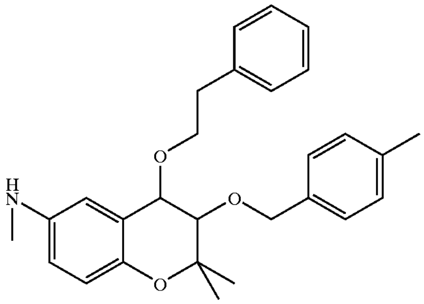 5-88 | MS, m/z: 431.58 |
| 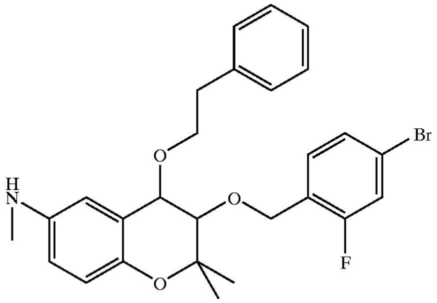 5-89 | MS, m/z: 514.44 |
| 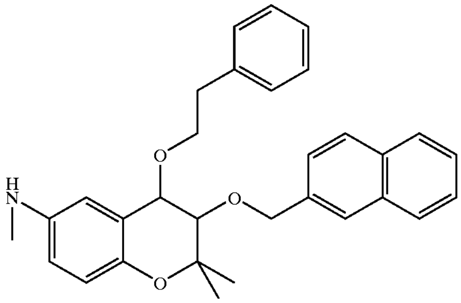 5-90 | MS, m/z: 467.61 |

TABLE 1-continued
| | Compound No. NMR/MS Data |
|---|---|
| 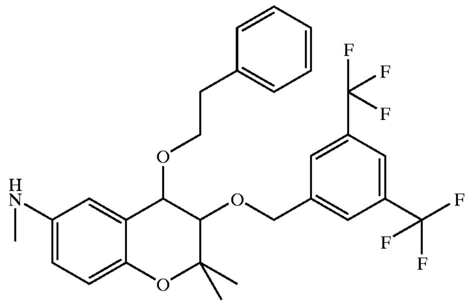 5-91 | MS, m/z: 553.55 |
| 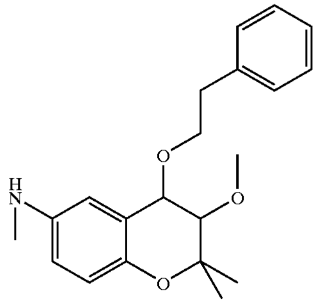 5-92 | MS, m/z: 341.45 |
| 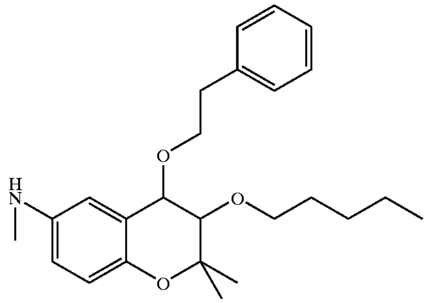 5-93 | MS, m/z: 397.56 |
| 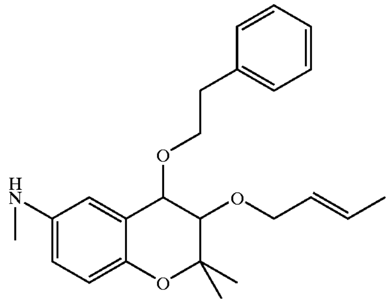 5-94 | MS, m/z: 381.52 |

TABLE 1-continued
| | Compound No. NMR/MS Data |
|---|---|
| 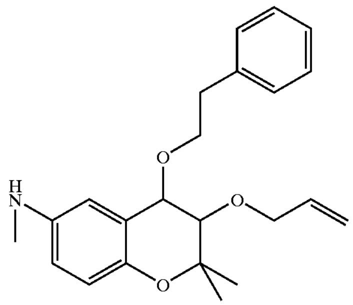 5-95 | MS, m/z: 367.49 |
| 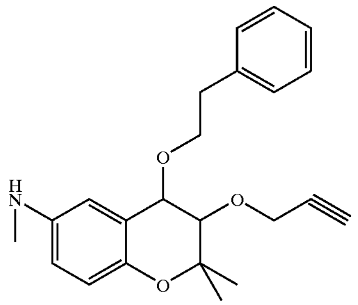 5-96 | MS, m/z: 365.48 |
| 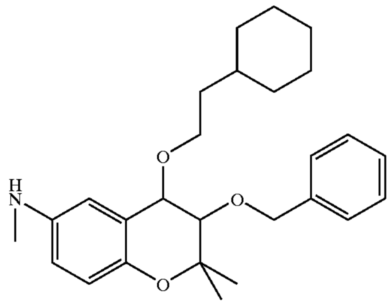 5-97 | MS, m/z: 423.60 |
| 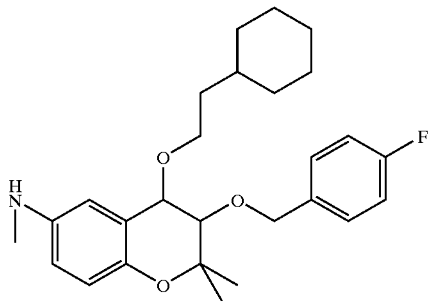 5-98 | MS, m/z: 441 59 |

TABLE 1-continued
| | Compound No. NMR/MS Data |
|---|---|
| 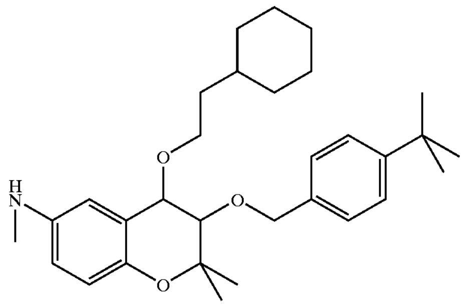 5-99 | MS, m/z: 479.71 |
| 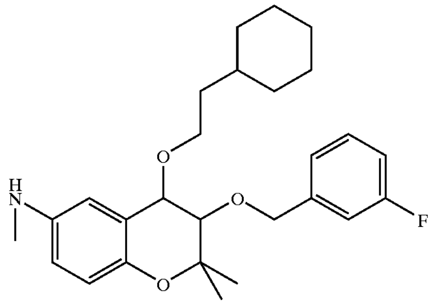 5-100 | MS, m/z: 441.59 |
| 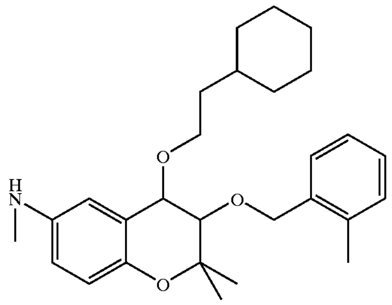 5-101 | MS, m/z: 437.63 |
| 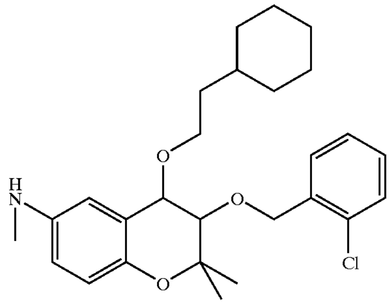 5-102 | MS, m/z: 458.05 |

TABLE 1-continued
| | Compound No. NMR/MS Data |
|---|---|
| 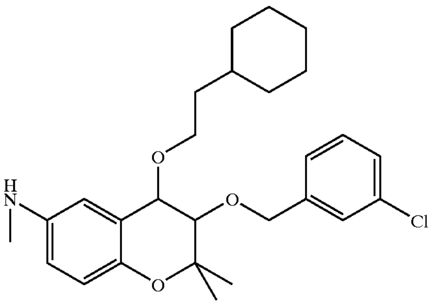 | MS, m/z: 458.05 |
| 5-103 | |
| 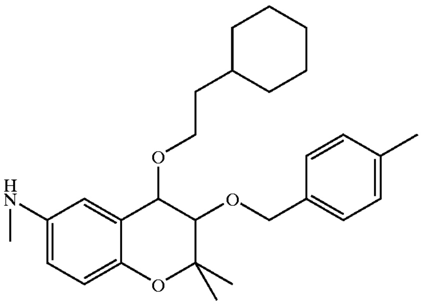 | MS, m/z: 437.63 |
| 5-104 | |
| 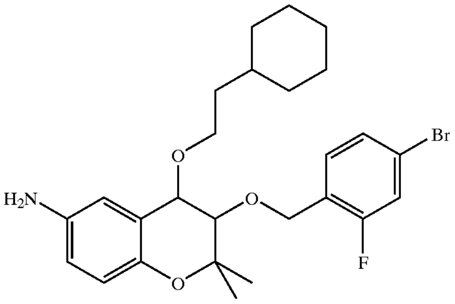 | MS, m/z: 506.46 |
| 5-105 | |
| 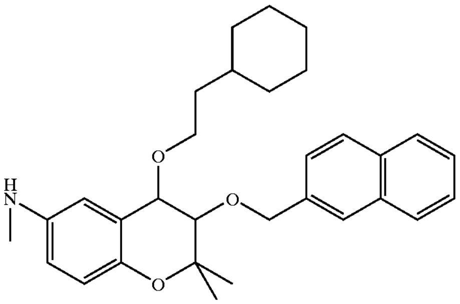 | MS, m/z: 473.66 |
| 5-106 | |

TABLE 1-continued
| | Compound No. NMR/MS Data |
|---|---|
| 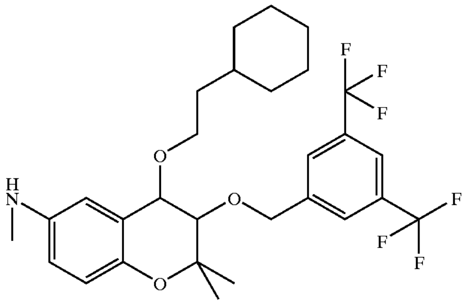 5-107 | MS, m/z: 559.60 |
| 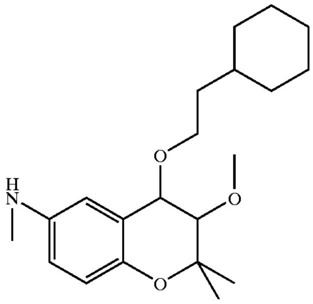 5-108 | MS, m/z: 347.50 |
| 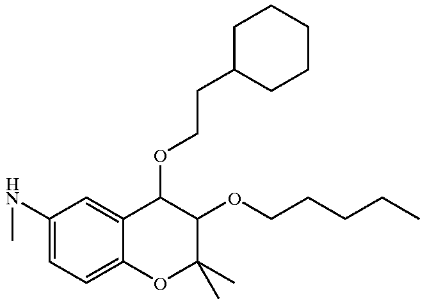 5-109 | MS, m/z: 403.61 |
| 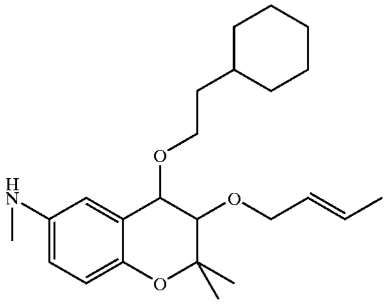 5-110 | MS, m/z: 387.57 |

TABLE 1-continued
| | Compound No. NMR/MS Data |
|---|---|
| 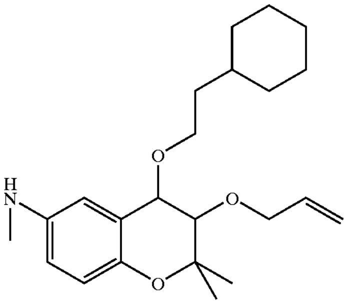 5-111 | MS, m/z: 373.54 |
| 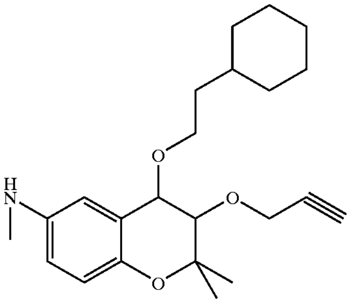 5-112 | MS, m/z: 371.52 |
| 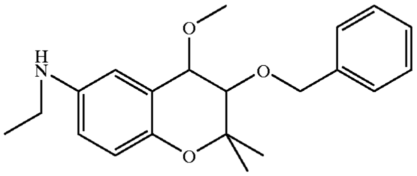 5-113 | $^1$H NMR(200 MHz, $CDCl_3$) δ 7.41~7.26(m, 5H), 6.73~6.59(m, 3H), 4.92(d, 1H, J=11.5 Hz), 4.72(d, 1H, J=11.5 Hz), 4.42(d, 1H, J=7.3 Hz), 3.50(s, 3H), 3.14(q, 2H, J=7.1Hz), 1.41(s, 3H), 1.30~1.20(m, 6H); MS, m/z: 341.45 |
| 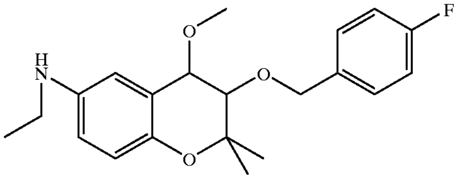 5-114 | $^1$H NMR(200 MHz, $CDCl_3$) δ 7.39~7.32(m, 2H), 7.26~6.99(m, 2H), 6.85(s, 1H), 6.71 (m, 2H), 4.86(d, 1H, J=11.3 Hz), 4.87(d, 1H, J=11.3 Hz), 4.40(d, 1H, J=7.3 Hz), 3.58(d, 1H, J=7.3 Hz), 3.51(s, 3H), 3.15(q, 2H, J=7.1 Hz), 1.40(s, 3H), 1.29~1.20(m, 6H); MS, m/z 359.44 |
| 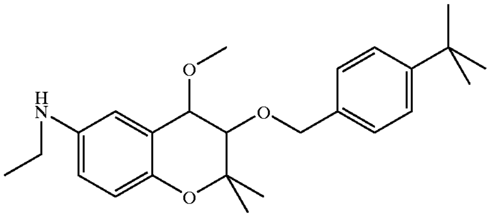 5-115 | $^1$H NMR(200 MHz, $CDCl_3$) δ 7.41~7.15(m, 4H), 6.99~6.68(m, 3H), 4.86(d, 1H, J=11.2 Hz), 4.68(d, 1H, J=11.2 Hz), 3.58(d, 1H, J=7.2 Hz), 3.53(s, 3H). 3.18(q, 2H, J=7.1 Hz), 1.41(s, 3H), 1.32~1.13(m, 15H); MS, m/z: 397.56 |
| 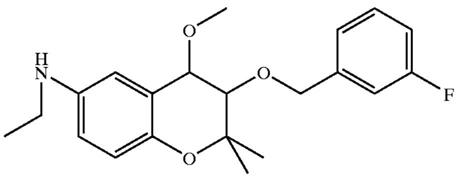 5-116 | $^1$H NMR(200 MHz, $CDCl_3$) δ 7.37~6.99(m, 6H), 6.74(d, 1H, J=8.7 Hz), 4.90(d, 1H, J=12.0 Hz), 4.69(d, 1H, J=12.0 Hz), 4.37(d, 1H, J=.7 Hz), 3.57(m, 1H), 3.56(s, 3H), 3.22(q, 2H, J=7.1 Hz), 1.42(s, 3H), 1.38~1.21(m, 6H); MS, m/z: 359.44 |

TABLE 1-continued

| | Compound No. NMR/MS Data |
|---|---|
| 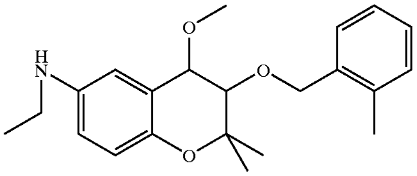 5-117 | $^1$H NMR(200 MHz, $CDCl_3$) δ 7.40~7.14(m, h), 6.78~6.67(m, 3H), 4.92(d, 1H, J=11.7 Hz), 4.70(d, 1H, J=11.7 Hz), 4.41(d, 1H, J=7.4 Hz), 3.63(d, 1H, J=7.3 Hz), 3.50(s, 3H), 3,14(q, 2H, J=7.2 Hz), 2.37(s, 3H), 1.39(s, 3H), 1.28~1.17(m, 6H), 7.55~7.23(m, 4H), 7.06(s, 1H), 6.94~6.88(m, 1H), 6.73(d, 1H, J=8.7 Hz), 5.00(d, 1H, J=12.5 Hz), 4.80(d, 1H, J=12.5 Hz),4.40(d, 1H,, J=7.3 Hz), 3.64(d, 1H, J=7.3 Hz), 3.56(s, 3H), 3.20(q, 2H, J=7.1 Hz), 1.42(s, 3H), 1.32~1.17(m, 6H); MS, m/z: 355.48 |
| 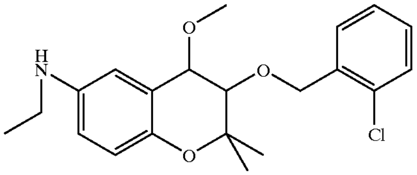 5-118 | MS, m/z: 375.90 |
| 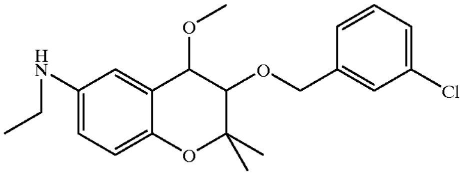 5-119 | $^1$H NMR(200 MHz, $CDCl_3$) δ 7.38~7.25(m, 4H), 6.73~6.59(m, 3H), 4.90(d, 1H, J=11.9 Hz), 4.69(d, 1H, J=11.9 Hz), 4.44(d, 1H, J=7.4 Hz), 3.60(d, 1H, J=7.4 Hz), 3.50(s, 3H), 3.14(q, 2H, J=7.1 Hz), 1.42(s, 3H), 1.28~1.21(m, 6H); MS, m/z: 375.90 |
| 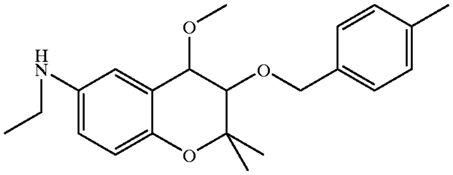 5-120 | $^1$H NMR(200 MHz, $CDCl_3$) δ 7.36~7.02(m, 5H), 6.94~6.88(m, 2H), 6.72(d, 1H, J=8.9 Hz), 4.84(d, 1H, J=11.9 Hz), 4.65(d, 1H, J=11.9 Hz), 4.35(d, 1H, J=7.3 Hz), 3.57(d, 1H, J=7.3 Hz), 3.55(s, 3H), 3.29(q, 2H, J=7.1 Hz), 2.35(s, 3H), 1.39(s, 3H), 1.30~1.15(m, 6H); MS, m/z: 355.48 |
| 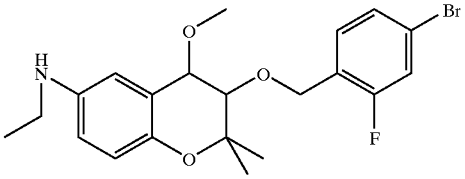 5-121 | $^1$H NMR(200 MHz, $CDCl_3$) δ 7.39~7.23(m, 3H), 6.73~6.58(m, 3H), 4.89(d, 1H, J=11.8 Hz), 4.72(d, 1H, J=11.8 Hz), 4.41(d, 1H, J=7.3 Hz), 4.15(d, 1H, J=7.3 Hz), 3.51(s, 3H), 3.13(q, 2H, J=7.1 Hz), 1.40(s, 3H), 1.29~1.20(m, 6H); MS, m/z: 438.34 |
| 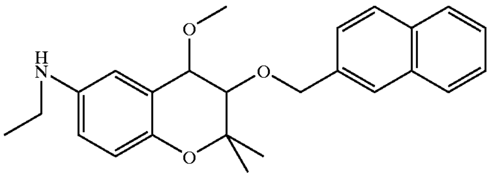 5-122 | $^1$H NMR(200 MHz, $CDCl_3$) δ 7.86~7.81(m, 4H), 7.53~7.46(m, 3H), 7.01(d, 1H, J=3.2 Hz), 6.84(m, 1H), 6.72(d, 1H, J=8.7 Hz), 5.05(d, 1H, J=11.6 Hz), 4.87(d, 1H, J=11.6 Hz), 4.43(d, 1H, J=7.2 Hz), 3.65(d, 1H, J=7.2 Hz), 3.55(s, 3H), 4.19(q, 2H, J=7.2 Hz), 2.04(s, 3H), 1.41(s, 3H), 1.29~1.22(m, 6H); MS, m/z: 391.51 |
| 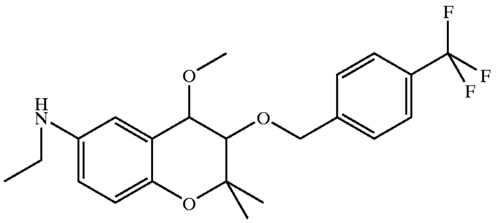 5-123 | $^1$H NMR(200 MHz, $CDCl_3$) δ 7.62(d, 2H, J=8.1 Hz), 7.50(d, 2H, J=8.1 Hz), 6.70~6.54(m, 3H), 5.00(d, 1H, J=12.1 Hz), 5.78(d, 1H, J=12.1 Hz), 4.47(d, 1H, J=7.6 Hz), 3.63(d, 1H, =7.6 Hz), 3.48(s, 3H), 3.13(q, 2H, J=7.1 Hz), 1.43(s, 3H), 1.28~1.21(m, 6H); MS, m/z: 409.45 |

TABLE 1-continued

| Compound No. | NMR/MS Data |
|---|---|
| 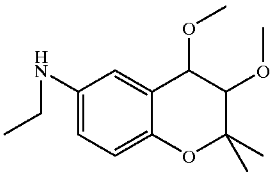 5-124 | $^1H$ NMR(200 MHz, $CDCl_3$) δ 6.68~6.53(m, 3H), 4.32(d, 1H, J=7.3 Hz), 3.61(s, 3H), 3.55(s, 3H), 3.34(d, 1H, J=7.3 Hz), 3.12(q, 2H, J=7.1 Hz), 1.41(s, 3H), 1.27~1.20(m, 6H); MS, m/z: 265.36 |
| 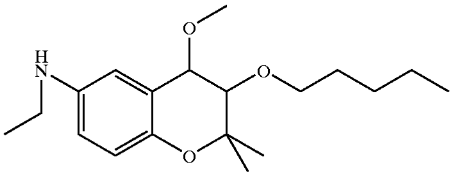 5-125 | $^1H$ NMR(200 MHz, $CDCl_3$) δ 6.92~6.66(m, 3H), 4.28(d, 1H, J=7.3 Hz), 3.88~3.74(m, 2H), 3.70~3.53(m, 2H), 3.61 (s, 3H), 3.39(d, 1H, J=7.3 Hz), 3.16(q, 2H, J=7.2 Hz), 1.80~1.10(m, 13H), 0.91(m, 3H); MS, m/z: 321.46 |
| 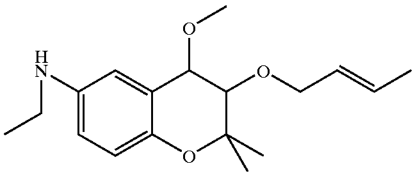 5-126 | $^1H$ NMR(200 MHz, $CDCl_3$) δ 6.91~6.74(m, 2H), 6.68(d, 1H, J=8.4 Hz), 5.73~5.63(m, 2H), 4.33~4.23(m, 2H), 4.16~4.05(m, 1H), 3.56(s, 3H), 3.48(d, 1H, J=7.1 Hz), 3.16(q, 2H, J=7.1 Hz), 1.72(d, 3H, J=6.9 Hz), 1.40(s, 3H), 1.32~1.23(m, 6H); MS, m/z: 35.42 |
| 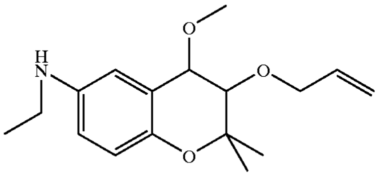 5-127 | $^1H$ NMR(200 MHz, $CDCl_3$) δ 6.67~6.04(m, 3H), 5.99~5.90(m, 1H), 5.30(dd, 1H, J=17.3 Hz, J=1.5 Hz), 5.18(dd, 1H, J=10.4 Hz, J=1.5 Hz), 4.42~4.33(m, 2H), 4.23~4.14(m, 1H), 3.53(s, 3H), 3.52(m, 1H), 3.12(q, 2H, J=7.1 Hz), 1.41(s, 3H), 1.30~1.20(m, 6H); MS, m/z: 291.39 |
| 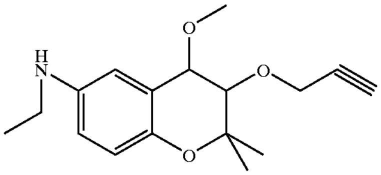 5-128 | $^1H$ NMR(200 MHz, $CDCl_3$) δ 6.71~6.58(m, 3H), 4.46(d, 2H, J=2.4 Hz), 4.41(d, 1H, J=7.1 Hz), 3.74(d, 1H, J=7.1 Hz), 3.52(s, 3H), 3.13(q, 2H, J=7.2 Hz), 2.46(t, 1H, J=2.4 Hz), 1.44(s, 3H), 1.28~1.20(m, 6h); MS, m/z: 289.38 |
| 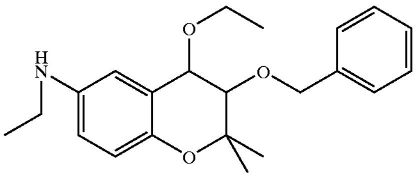 5-129 | MS, m/z: 355.48 |
| 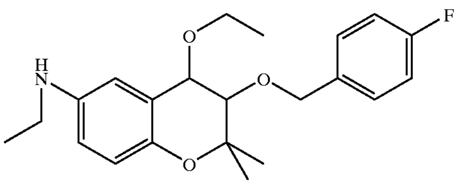 5-130 | MS, m/z: 373.47 |

TABLE 1-continued
| | Compound No. NMR/MS Data |
|---|---|
| 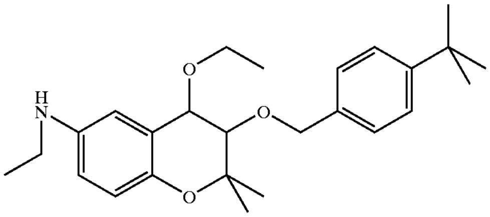 5-131 | MS, m/z: 411.59 |
| 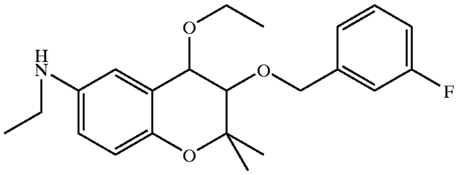 5-132 | MS, m/z: 373.47 |
| 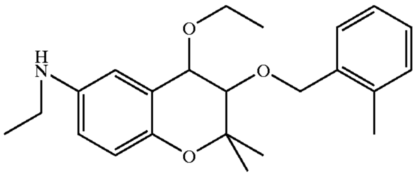 5-133 | MS, m/z: 369.51 |
| 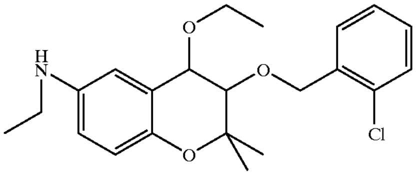 5-134 | MS, m/z: 389.93 |
| 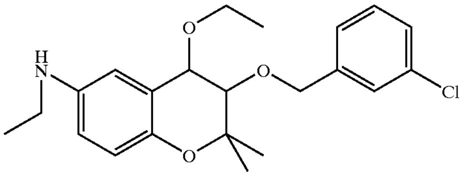 5-135 | MS, m/z: 389.93 |
| 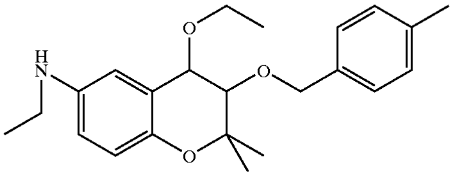 5-136 | MS, m/z: 369.51 |
| 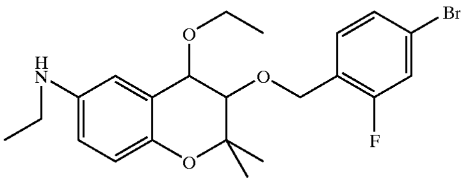 5-137 | MS, m/z: 452.37 |

TABLE 1-continued
| | Compound No. NMR/MS Data |
|---|---|
| 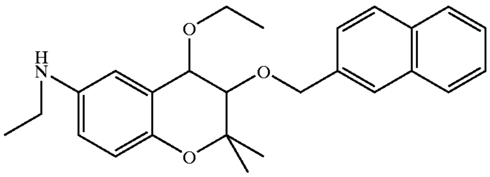 5-138 | MS, m/z: 405.54 |
| 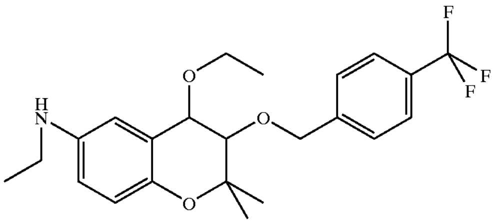 5-139 | MS, m/z: 423.48 |
| 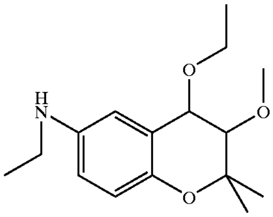 5-140 | MS, m/z: 279.38 |
| 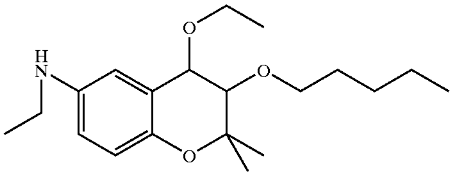 5-141 | MS, m/z: 335.49 |
| 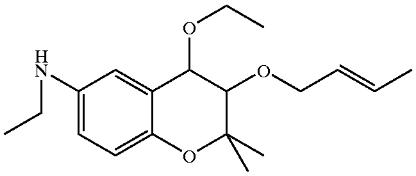 5-142 | MS, m/z: 319.45 |
| 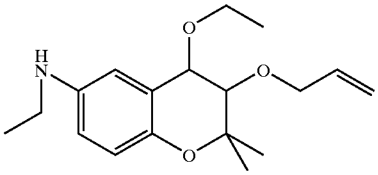 5-143 | MS, m/z: 305.42 |
| 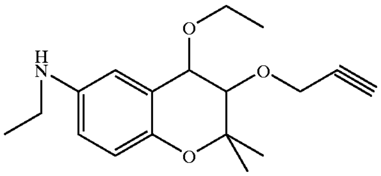 5-144 | MS, m/z: 303.40 |

TABLE 1-continued
| | Compound No. NMR/MS Data |
|---|---|
| 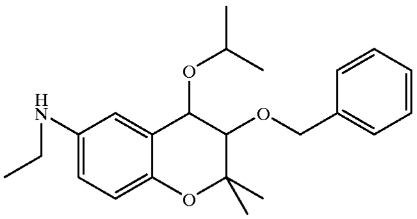<br>5-145 | MS, m/z: 369.51 |
| 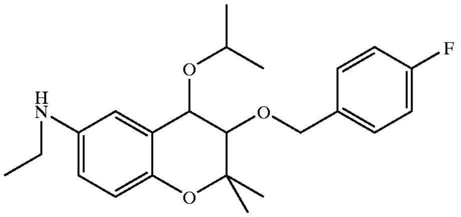<br>5-146 | MS, m/z: 387.50 |
| 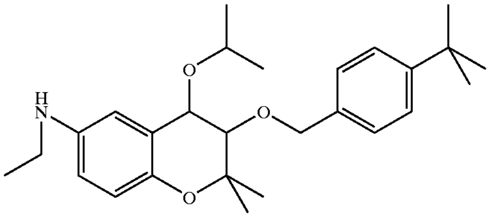<br>5-147 | MS, m/z: 425.62 |
| 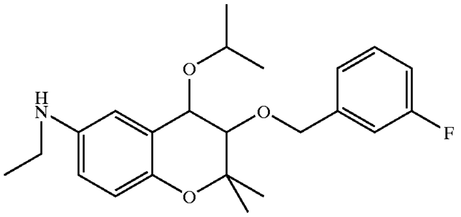<br>5-148 | MS, m/z: 387.50 |
| 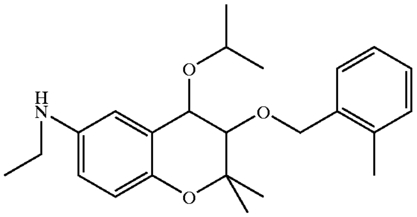<br>5-149 | MS, m/z: 383.54 |
| 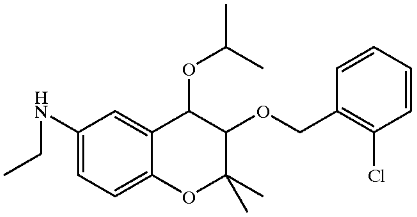<br>5-150 | MS, m/z: 403.95 |

TABLE 1-continued
| | Compound No. NMR/MS Data |
|---|---|
| 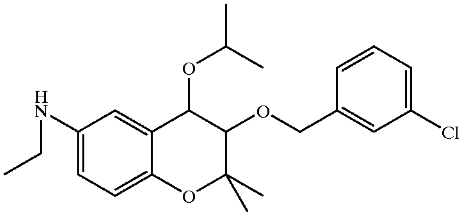<br>5-151 | MS, m/z: 403.95 |
| 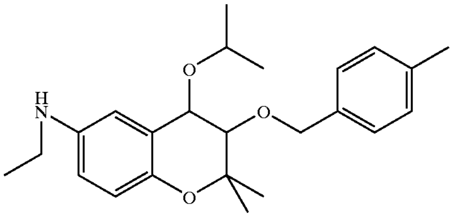<br>5-152 | MS, m/z: 383.54 |
| 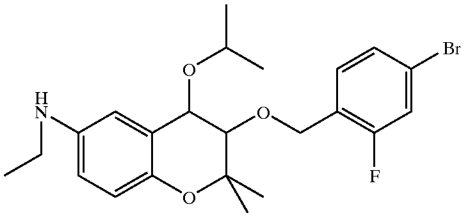<br>5-153 | MS, m/z: 466.39 |
| 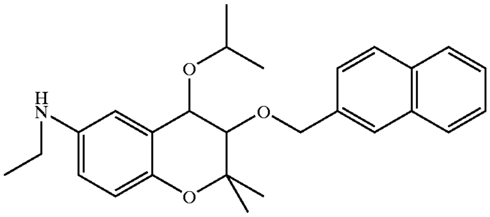<br>5-154 | MS, m/z: 419.54 |
| 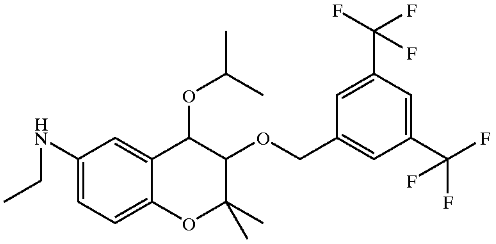<br>5-155 | MS, m/z: 505.51 |
| 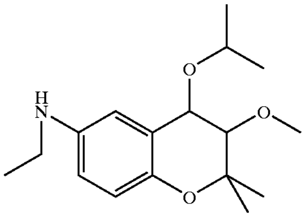<br>5-156 | MS, m/z: 293.41 |

TABLE 1-continued
| | Compound No. NMR/MS Data |
|---|---|
| 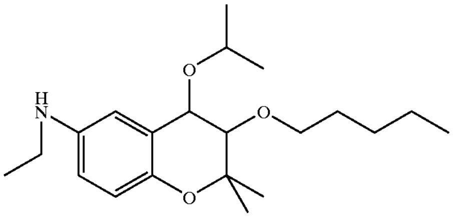 5-157 | MS, m/z: 349.52 |
| 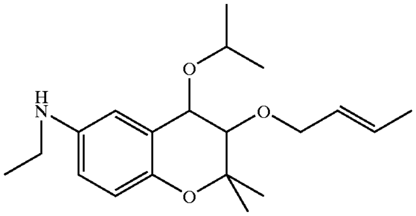 5-158 | MS, m/z: 333.47 |
| 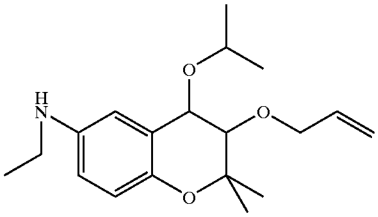 5-159 | MS, m/z: 319.45 |
| 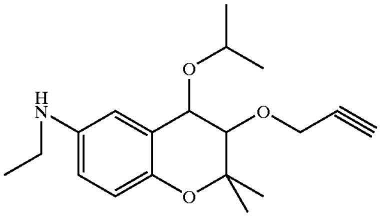 5-160 | MS, m/z: 317.43 |
| 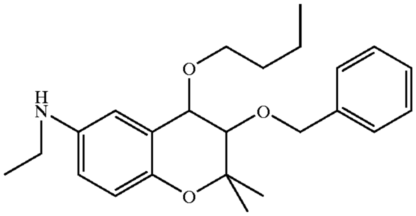 5-161 | MS, m/z: 383.54 |
| 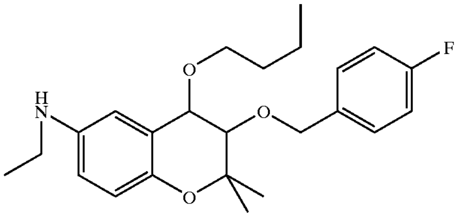 5-162 | MS, m/z: 401.53 |

TABLE 1-continued
| | Compound No. NMR/MS Data |
|---|---|
| 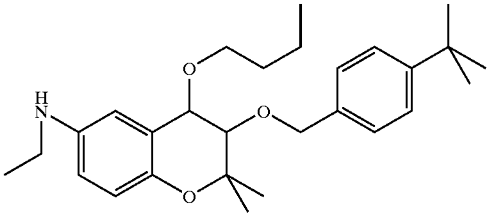 5-163 | MS, m/z: 439.64 |
| 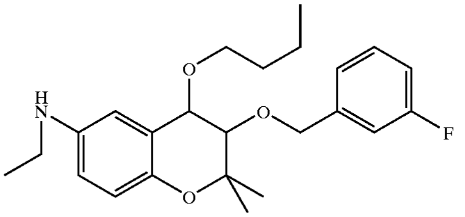 5-164 | MS, m/z: 401.53 |
| 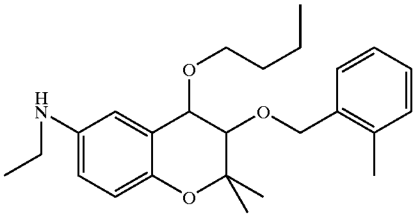 5-165 | MS, m/z: 397.56 |
| 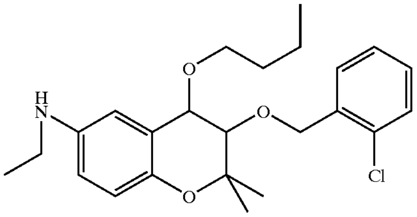 5-166 | MS, m/z: 417.98 |
| 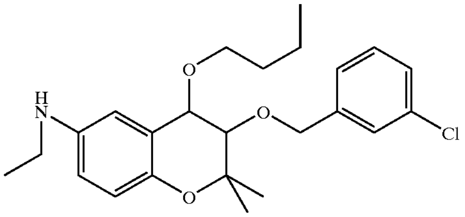 5-167 | MS, m/z: 417.98 |
| 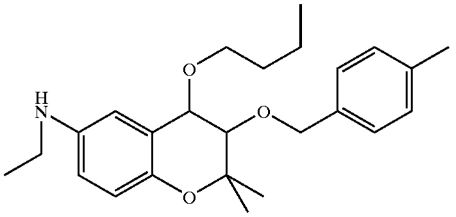 5-168 | MS, m/z: 397.56 |

TABLE 1-continued
| | Compound No. NMR/MS Data |
|---|---|
| 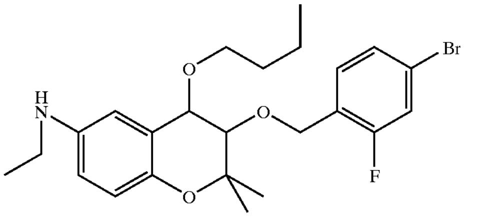 5-169 | MS, m/z: 480.42 |
| 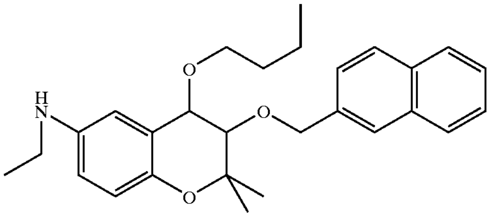 5-170 | MS, m/z: 433.60 |
| 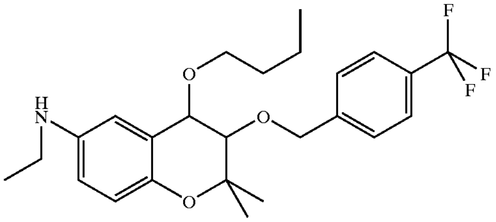 5-171 | MS, m/z: 451.53 |
| 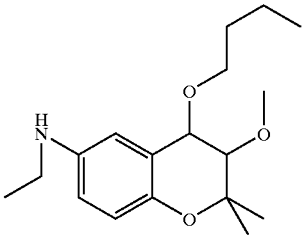 5-172 | MS, m/z: 307.44 |
| 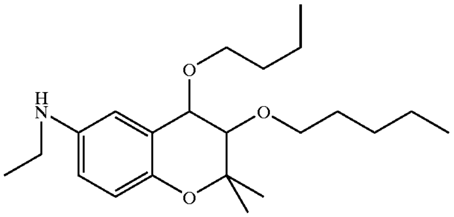 5-173 | MS, m/z: 363.55 |
| 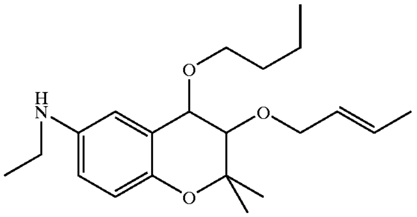 5-174 | MS, m/z: 347.50 |

TABLE 1-continued
| | Compound No. NMR/MS Data |
|---|---|
| 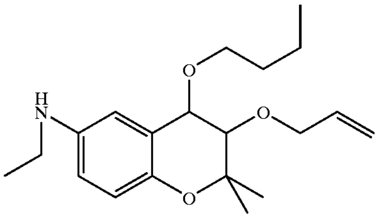 5-175 | MS, m/z: 333.47 |
| 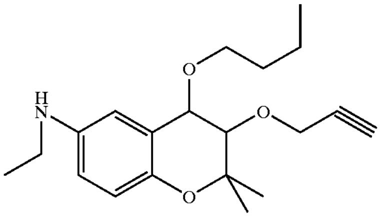 5-176 | MS, m/z: 331.46 |
| 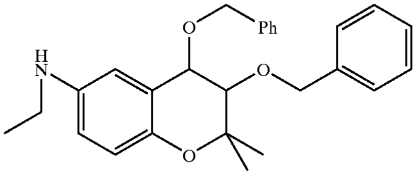 5-177 | MS, m/z: 417.55 |
| 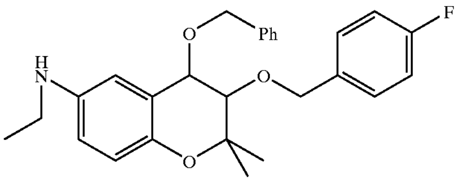 5-178 | MS, m/z: 435.54 |
| 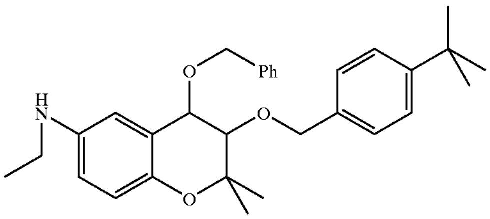 5-179 | MS, m/z: 473.66 |
| 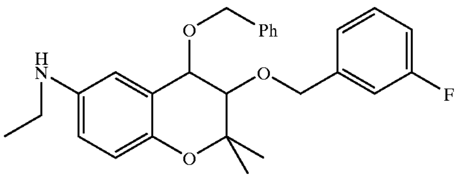 5-180 | MS, m/z: 435.54 |
| 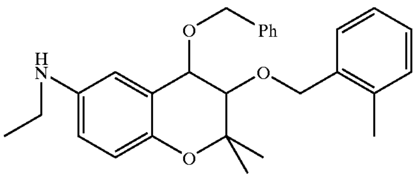 5-181 | MS, m/z: 431.58 |

TABLE 1-continued
| | Compound No. NMR/MS Data |
|---|---|
| 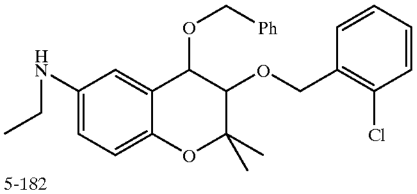 5-182 | MS, m/z: 452.00 |
| 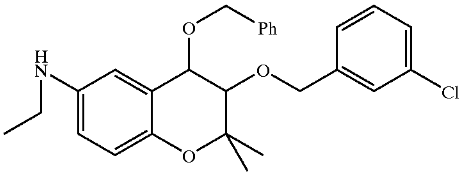 5-183 | MS, m/z: 452.00 |
| 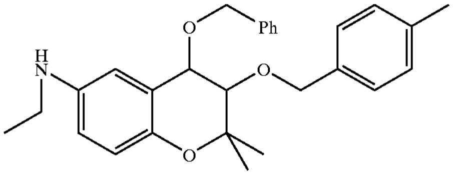 5-184 | MS, m/z: 431.58 |
| 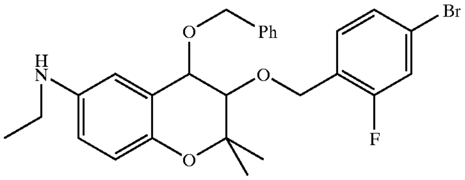 5-185 | MS, m/z: 514.44 |
| 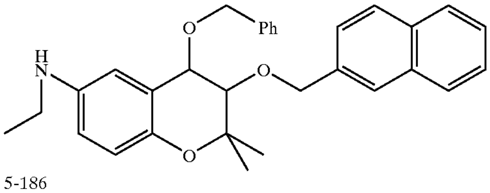 5-186 | MS, m/z: 467.61 |
| 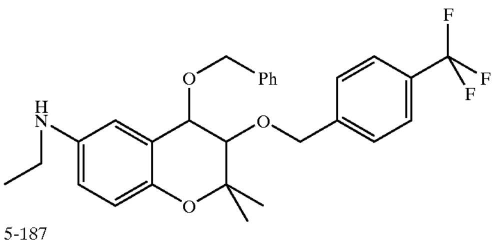 5-187 | MS, m/z: 485.55 |
| 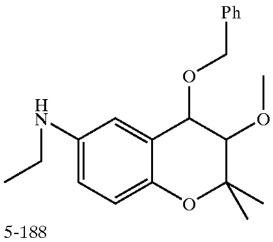 5-188 | MS, m/z: 341.45 |

TABLE 1-continued
| | Compound No. NMR/MS Data |
|---|---|
| 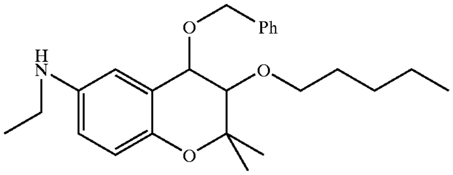 5-189 | MS, m/z: 397.56 |
| 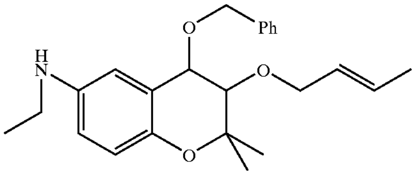 5-190 | MS, m/z: 381.52 |
| 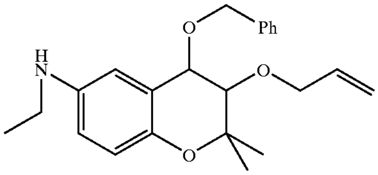 5-191 | MS, m/z: 367.47 |
| 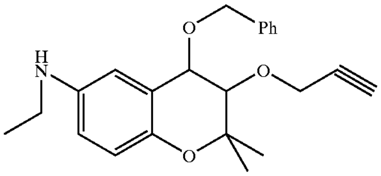 5-192 | MS, m/z: 365.48 |
| 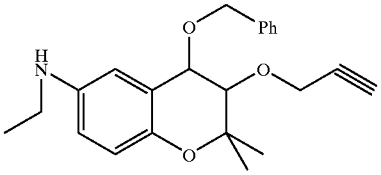 5-193 | MS, m/z: 431.58 |
| 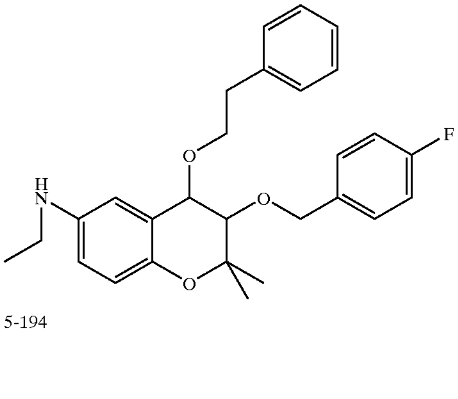 5-194 | MS, m/z: 449.57 |

TABLE 1-continued
| | Compound No. NMR/MS Data |
|---|---|
| 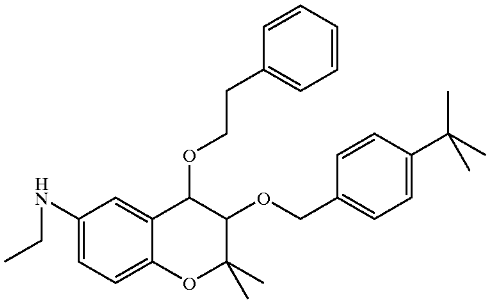 5-195 | MS, m/z: 487.693 |
| 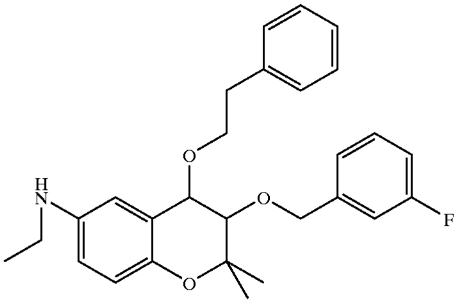 5-196 | MS, m/z: 449.57 |
| 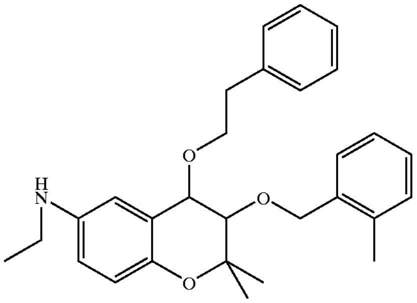 5-197 | MS, m/z: 445.61 |
| 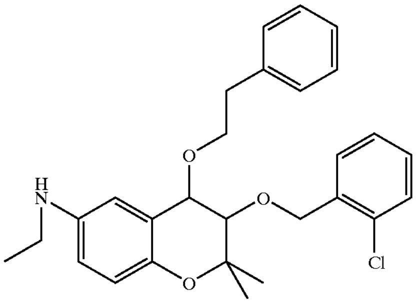 5-198 | MS, m/z: 466.03 |

TABLE 1-continued
| | Compound No. NMR/MS Data |
|---|---|
| 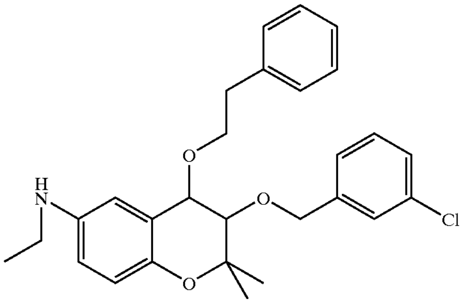 5-199 | MS, m/z: 466.03 |
| 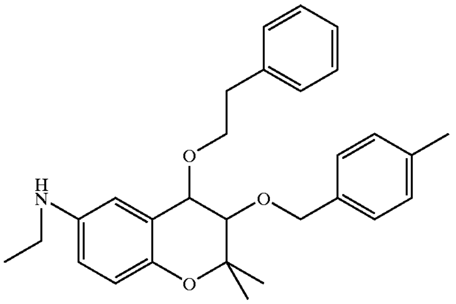 5-200 | MS, m/z: 445.61 |
| 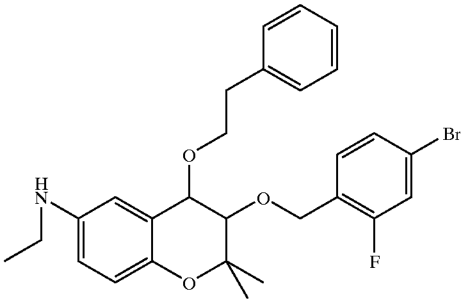 5-201 | MS, m/z: 528.47 |
| 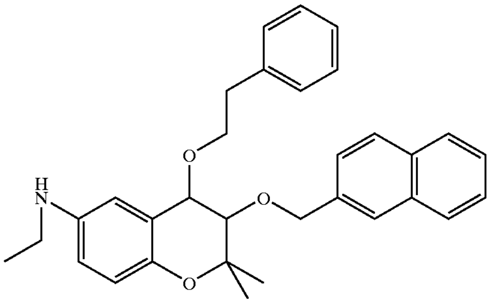 5-202 | MS, m/z: 481.64 |

TABLE 1-continued
| | Compound No. NMR/MS Data |
|---|---|
| 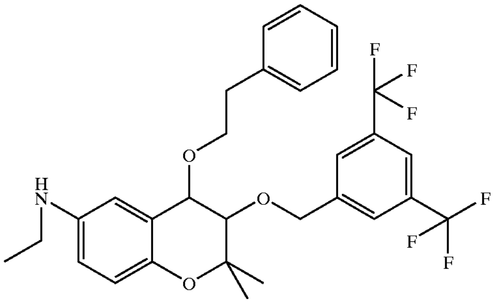 5-203 | MS, m/z: 567.58 |
| 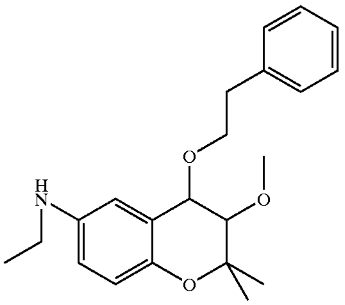 5-204 | MS, m/z: 355.48 |
| 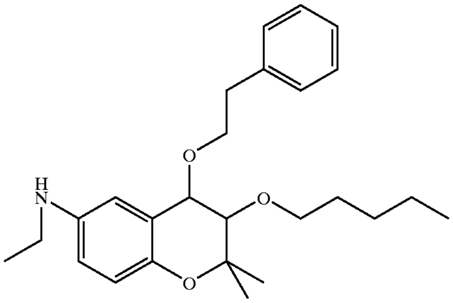 5-205 | MS, m/z: 411.59 |
| 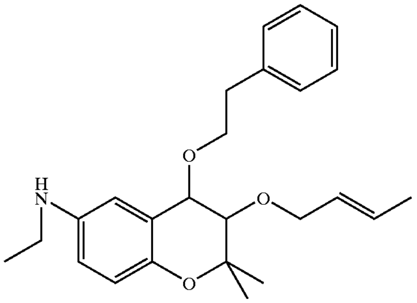 5-206 | MS, m/z: 395.55 |

TABLE 1-continued
| | Compound No. NMR/MS Data |
|---|---|
| 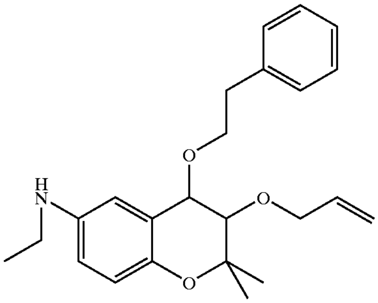 5-207 | MS, m/z: 381.52 |
| 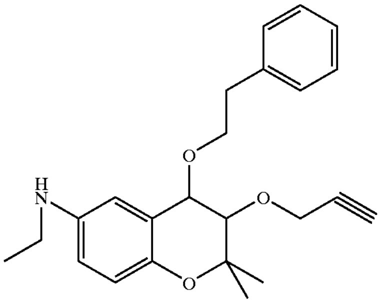 5-208 | MS, m/z: 379.50 |
| 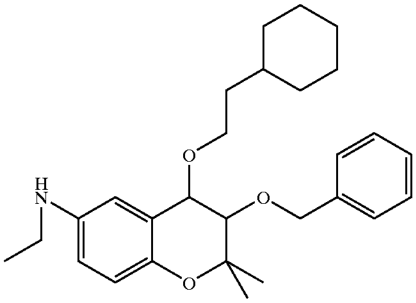 5-209 | MS, m/z: 437.633 |
| 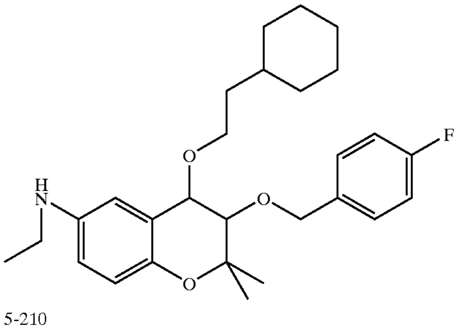 5-210 | MS, m/z: 455.62 |

TABLE 1-continued
| | Compound No. NMR/MS Data |
|---|---|
| 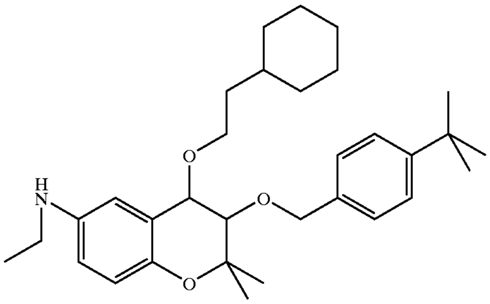 5-211 | MS, m/z: 493.47 |
| 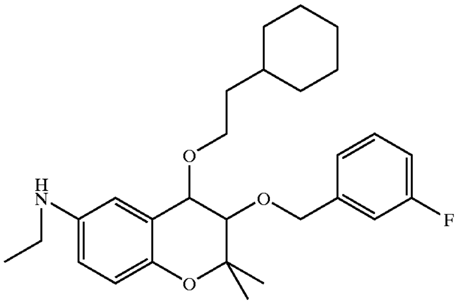 5-212 | MS, m/z: 455.62 |
| 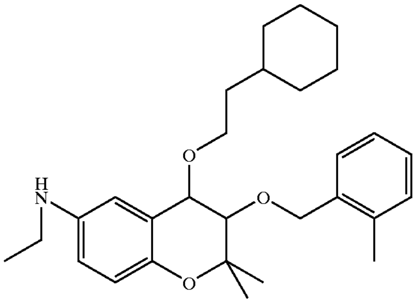 5-213 | MS, m/z: 451.66 |
| 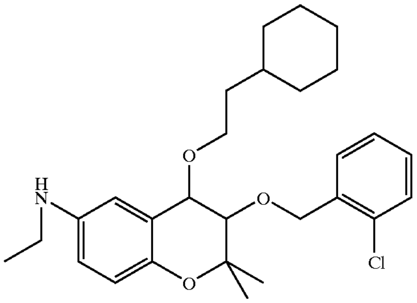 5-214 | MS, m/z: 472.07 |

TABLE 1-continued
| | Compound No. | NMR/MS Data |
|---|---|---|
| 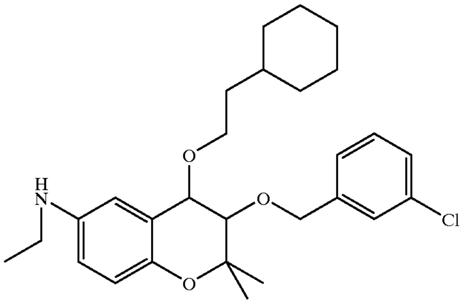 | 5-215 | MS, m/z: 472.07 |
| 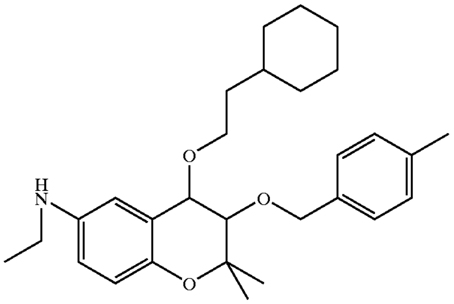 | 5-216 | MS, m/z: 451.66 |
| 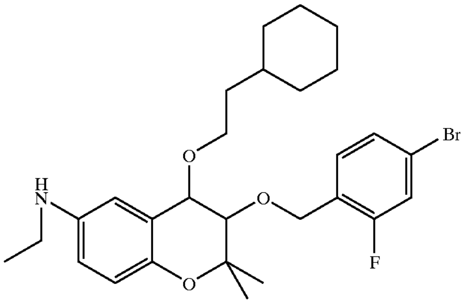 | 5-217 | MS, m/z: 534.51 |
| 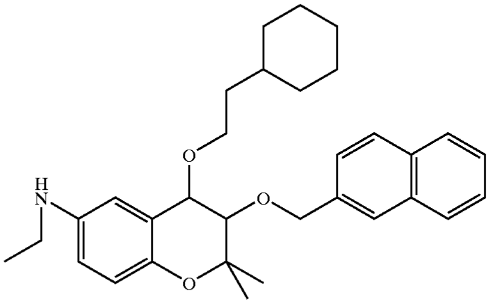 | 5-218 | MS, m/z: 487.69 |

TABLE 1-continued
| | Compound No. | NMR/MS Data |
|---|---|---|
| 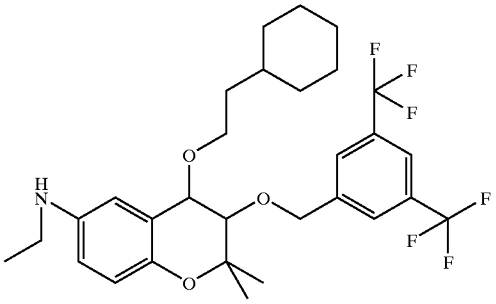 | 5-219 | MS, m/z: 873.62 |
| 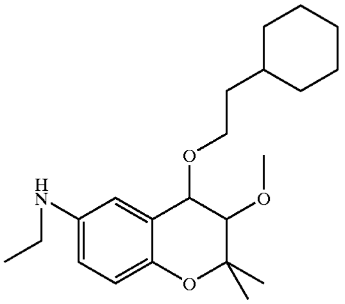 | 5-220 | MS, m/z: 361.53 |
| 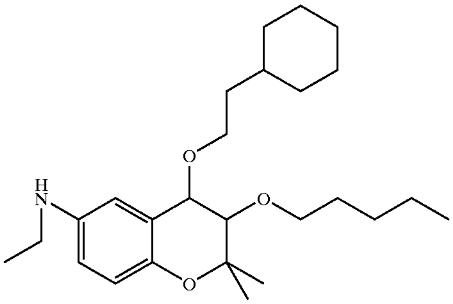 | 5-221 | MS, m/z: 417.64 |
| 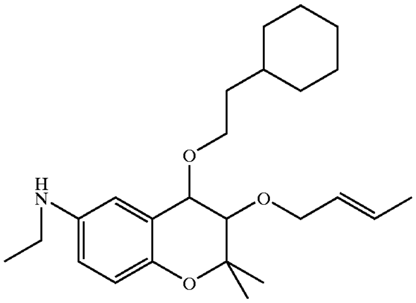 | 5-222 | MS, m/z: 401.59 |

TABLE 1-continued
| | Compound No. NMR/MS Data |
|---|---|
| 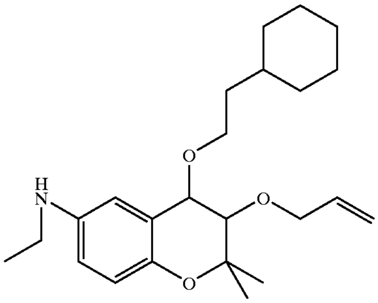 5-223 | MS, m/z: 387.57 |
| 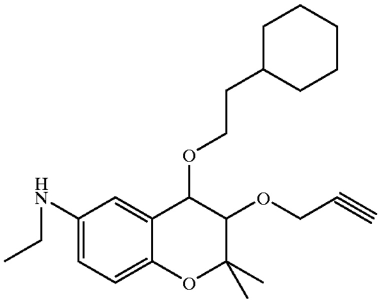 5-224 | MS, m/z: 385.55 |
| 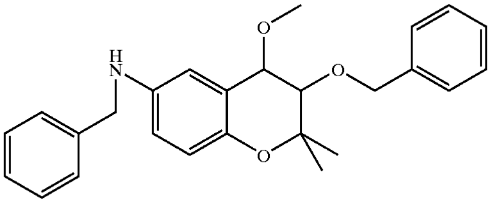 5-225 | MS, m/z: 403.53 |
| 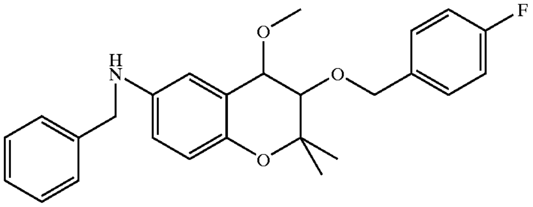 5-226 | $^{1}H$ NMR(500 MHz, $CDCl_3$) δ 7.34~7.10(m, 9H), 7.06~7.03(m, 2H), 6.73(d, 1H, J=8.8 Hz), 4.82(d, 1H, J=11.4 Hz), 4.63(d, 1H, J=11.4 Hz), 4.25(d, 1H, J=6.9 Hz), 4.21(s, 3H), 3.51(d, 1H, J=6.9 Hz), 3.49(s, 3H), 1.40(s, 3H), 1.26(s, 3H); MS, m/z: 421.52~ |
| 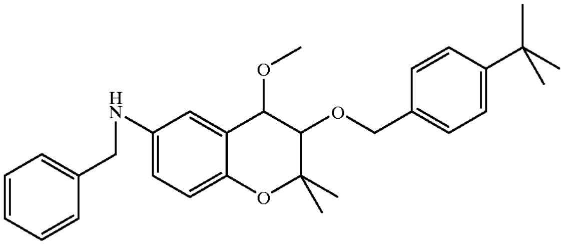 5-227 | $^{1}H$ NMR(500 MHz, $CDCl_3$) δ 7.39~7.26(m, 9H), 6.69~6.56(m, 3H), 4.87(d, 1H, J=11.2 Hz), 4.53(d, 1H J=11.2 Hz), 4.40(d, 1H, J=7.3 Hz), 4.28(s, 2H), 3.60(d, 1H, J=7.3 Hz), 3.45(s, 3H), 1.41(s, 3H), 1.32(s, 9H), 1.23(s, 3H); MS, m/z: 459.63 |

TABLE 1-continued

| | Compound No. NMR/MS Data |
|---|---|
| 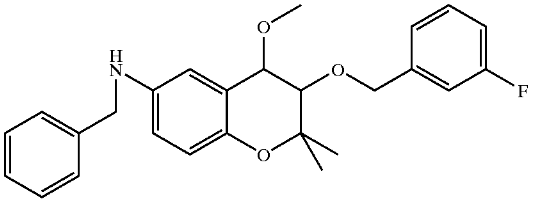 5-228 | $^1$H NMR(500 MHz, $CDCl_3$) δ 7.38~7.26(m, 6H), 7.14~7.10(m, 2H), 7.00(m, 1H), 6.72~6.60(m, 3H), 4.91(d, 1H, J=11.9 Hz), 4.71(d, 1H, J=11.7 Hz), 4.42(d, H, J=7.4 Hz), 4.27(s, 2H), 3.55(d, 1H, J=7.45 Hz), 3.44(s, 3H), 1.42(s, 3H), 1.24(s, 3H); MS, m/z: 421.52 |
| 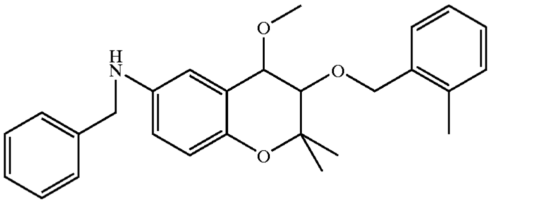 5-229 | $^1$H NMR(200 MHz, $CDCl_3$) δ 7.37~7.18(m, 9H), 6.68~6.51(m, 3H), 4.92(d, 1H, J=11.8 Hz), 4.69(d, 1H, J=11.8 Hz), 4.41(d, 1H, J=7.2 Hz), 4.27(s, 2H), 3.62(d, 1H, J=7.2 Hz), 3.42(s, 3H), 2.37(s, 3H), 1.39(s, 3H), 1.22(s, 3H); MS, m/z: 417.55 |
| 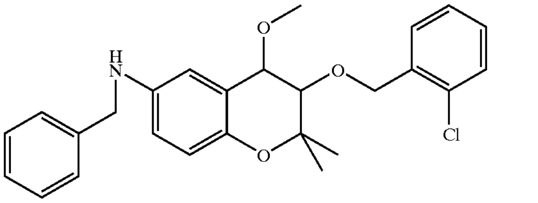 5-230 | MS, m/z: 437.97 |
| 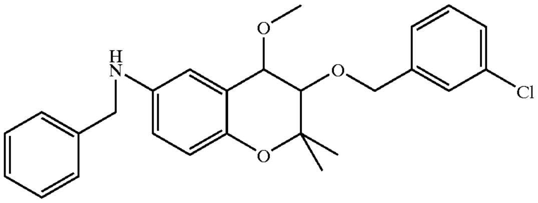 5-231 | $^1$H NMR(200 MHz, $CDCl_3$) δ 7.38~7.23 (m, 9H), 6.98~6.51(m, 3H), 4.92(d, 1H, J=11.3 Hz), 4.73 (d, 1H, J=11.3 Hz), 4.36(d, 1H, J=7.3 Hz), 4.25(s, 2H), 3.58(d, 1H, J=7.3 Hz), 3.42(m, 3H), 1.57~1.23 (m, 9H); MS, m/z: 437.97 |
| 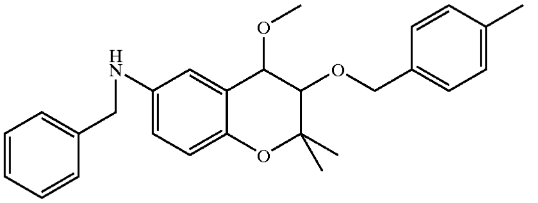 5-232 | $^1$H NMR(500 MHz, $CDCl_3$) δ 7.34~7.26(7H), 7.16(d, 2H, J=7.8 Hz), 6.94(s, 1H), 6.78(m, 1H), 6.67(d, 1H, J=8.7 Hz), 4.84(d, 1H, J=11.3 Hz), 4.65(d, 1H, J=11.3 Hz), 4.33(d, 1H, J=7.1 Hz), 4.25(s, 2H), 3.56(d, 1H, J=7.1 Hz), 3.47(s, 3H), 2.35(s, 3H), 1.38(s, 3H), 1.22(s, 3H); MS, m/z: 417.55 |
| 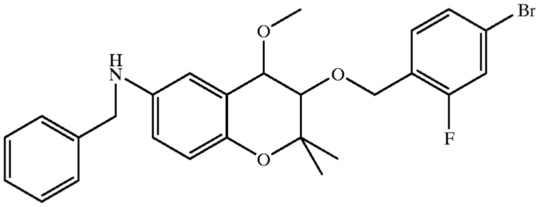 5-233 | $^1$H NMR(500 MHz, $CDCl_3$) δ 7.38~7.23(m, 8H), 6.66~6.57(m, 3H), 4.89(d, 1H, J=11.9 Hz), 4.72(d, 1H, J=11.9 Hz), 4.40(d, 1H, J=7.4 Hz), 4.27(s, 2H), 3.59(d, 1H, J=7.4 Hz), 3.45(s, 3H), 1.39(s, 3H), 1.20(s, 3H); MS, m/z: 500.41 |

TABLE 1-continued
| | Compound No. NMR/MS Data |
|---|---|
| 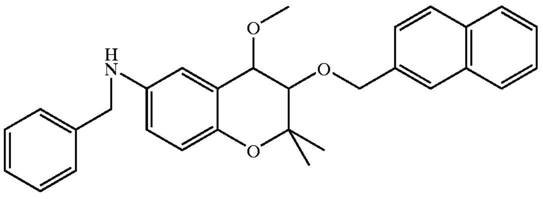 5-234 | MS, m/z: 453.59 |
| 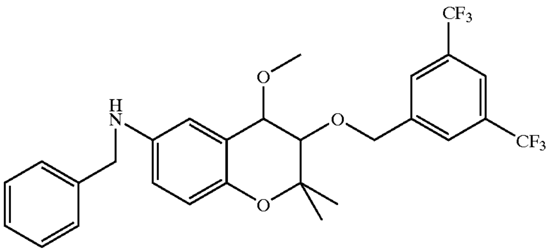 5-235 | MS, m/z: 431.58 |
| 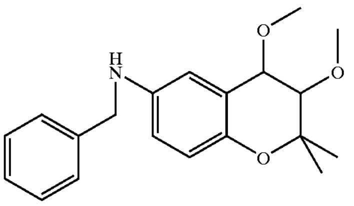 5-236 | MS, m/z: 327.43 |
| 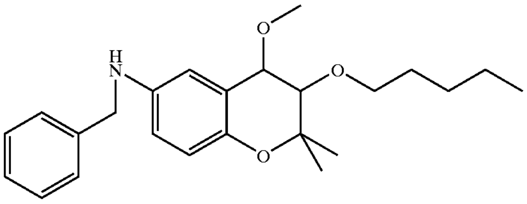 5-237 | MS, m/z: 383.54 |
| 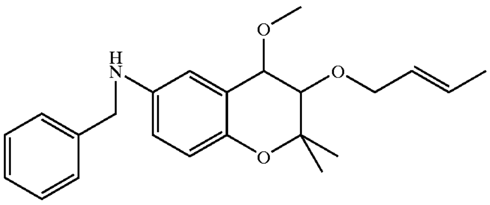 5-238 | MS, m/z: 367.49 |
| 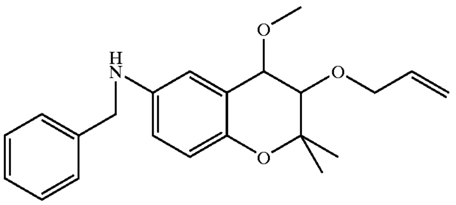 5-239 | MS, m/z: 353.47 |

TABLE 1-continued
| | Compound No. NMR/MS Data |
|---|---|
| 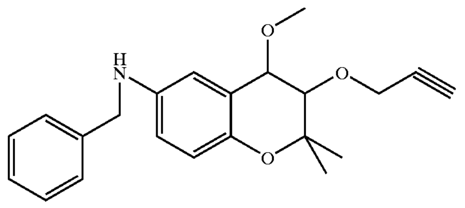 5-240 | MS, m/z: 351.45 |
| 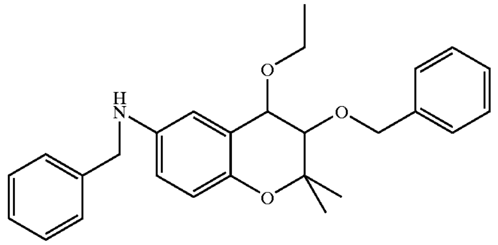 5-241 | MS, m/z: 417.55 |
| 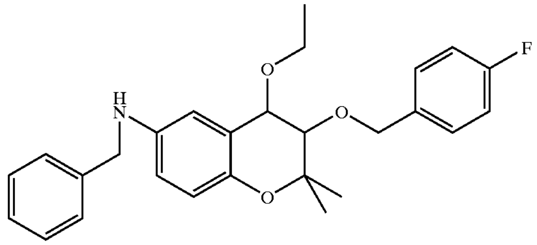 5-242 | MS, m/z: 435.54 |
| 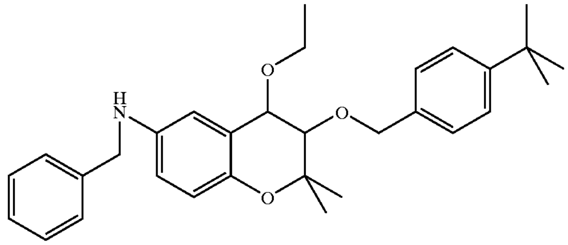 5-243 | MS, m/z: |
| 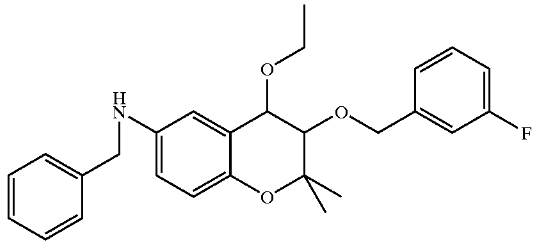 5-244 | MS, m/z: 473.66 |

TABLE 1-continued
| | Compound No. NMR/MS Data |
|---|---|
| 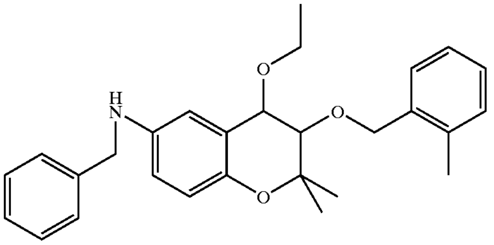 5-245 | MS, m/z: 435.54 |
| 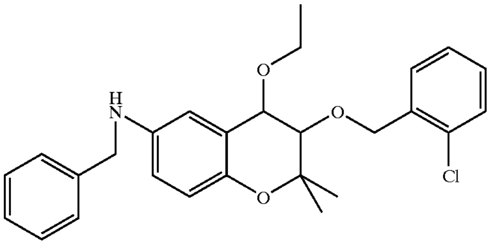 5-246 | MS, m/z: 431.58 |
| 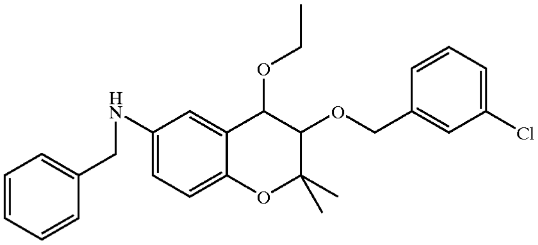 5-247 | MS, m/z: 452.00 |
| 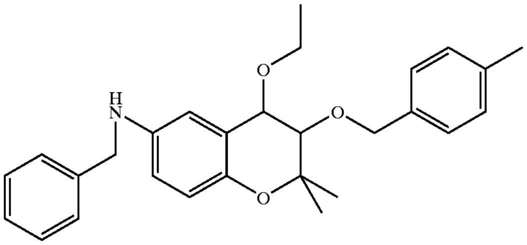 5-248 | MS, m/z: 452.00 |
| 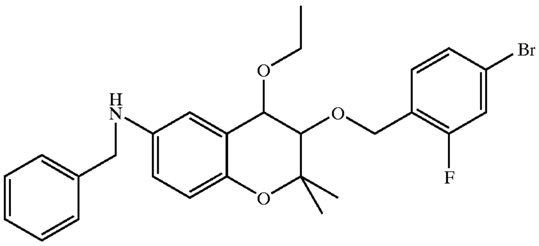 5-249 | MS, m/z: 431.58 |

TABLE 1-continued
| Compound No. | NMR/MS Data |
| --- | --- |
| 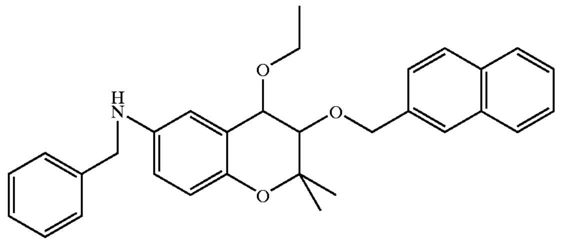 5-250 | MS, m/z: 514.44 |
| 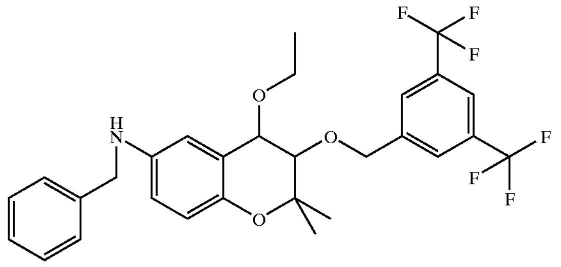 5-251 | MS, m/z: 467.61 |
| 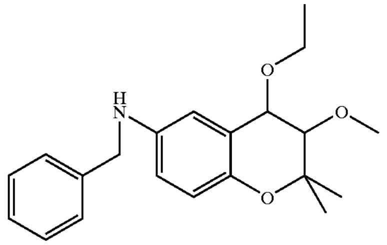 5-252 | MS, m/z: 553.55 |
| 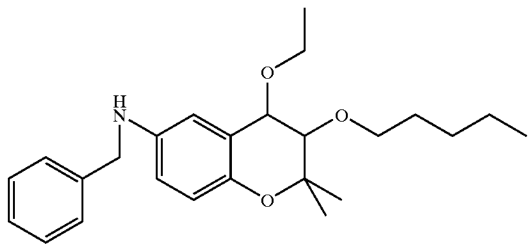 5-253 | MS, m/z: 341.45 |
| 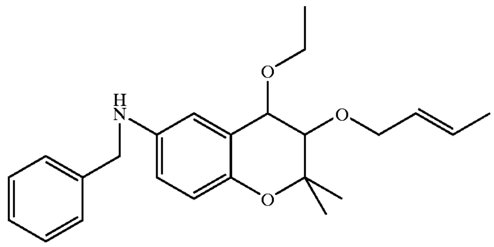 5-254 | MS, m/z: 397.56 |

TABLE 1-continued
| | Compound No. NMR/MS Data |
|---|---|
| 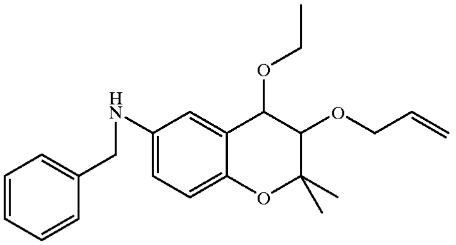 5-255 | MS, m/z: 381.52 |
| 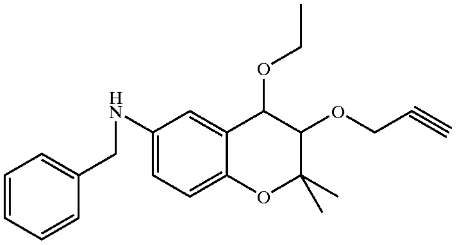 5-256 | MS, m/z: 367.49 |
| 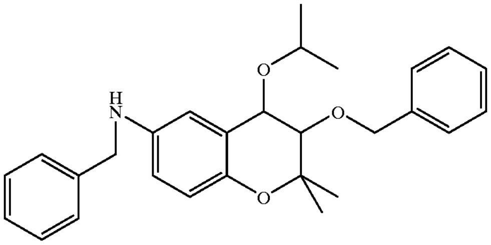 5-257 | MS, m/z: 365.48 |
| 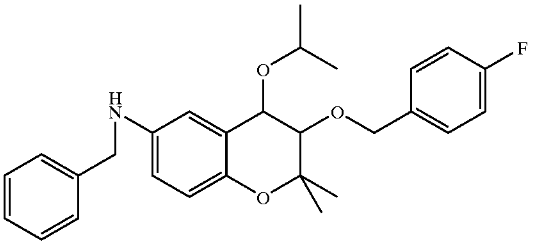 5-258 | MS, m/z: 431.58 |
| 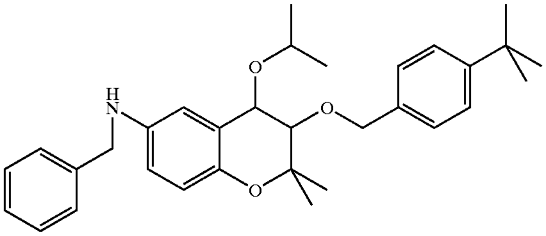 5-259 | MS, m/z: 449.57 |

TABLE 1-continued
| | Compound No. NMR/MS Data |
|---|---|
| 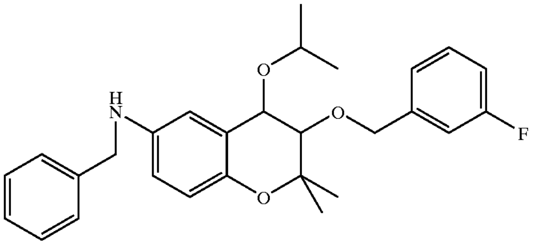 5-260 | MS, m/z: 487.69 |
| 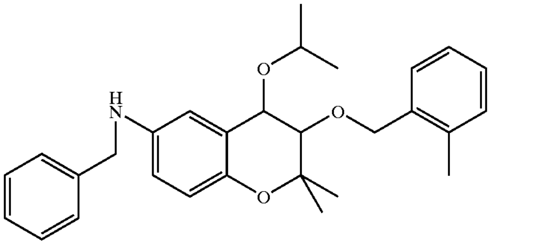 5-261 | MS, m/z: 449.57 |
| 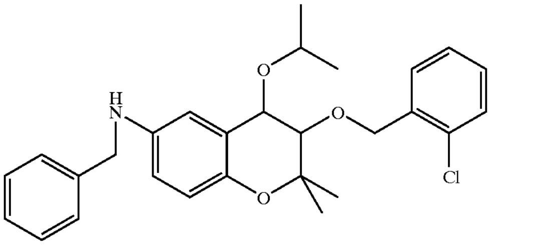 5-262 | MS, m/z: 445.61 |
| 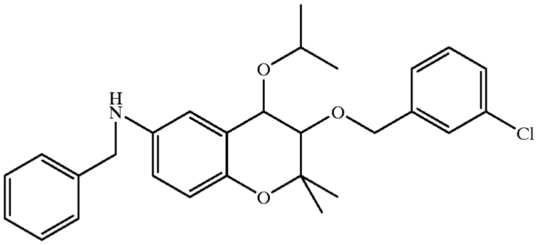 5-263 | MS, m/z: 466.03 |
| 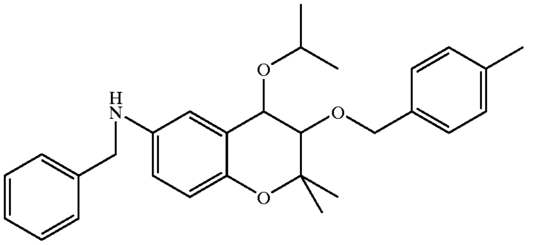 5-264 | MS, m/z: 466.03 |

TABLE 1-continued
| | Compound No. NMR/MS Data |
|---|---|
| 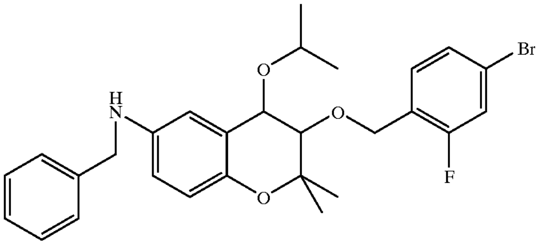 5-265 | MS, m/z: 445.61 |
| 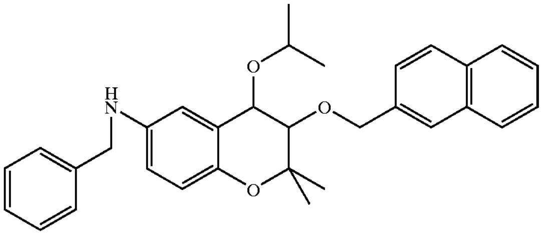 5-266 | MS, m/z: 528.47 |
| 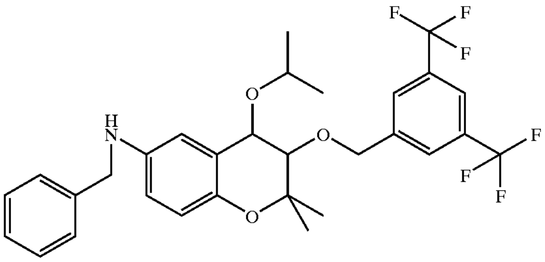 5-267 | MS, m/z: 481.64 |
| 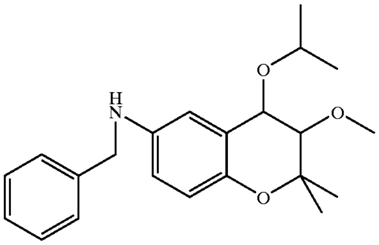 5-268 | MS, m/z: 567.59 |
| 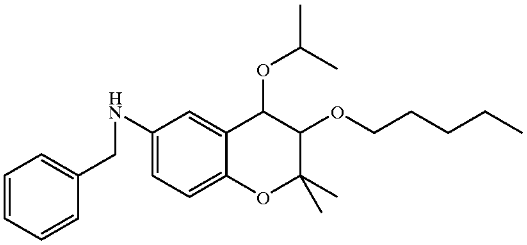 5-269 | MS, m/z: 355.48 |

TABLE 1-continued
| | Compound No. NMR/MS Data |
|---|---|
| 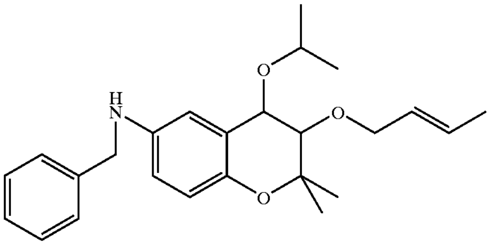<br>5-270 | MS, m/z: 411.59 |
| 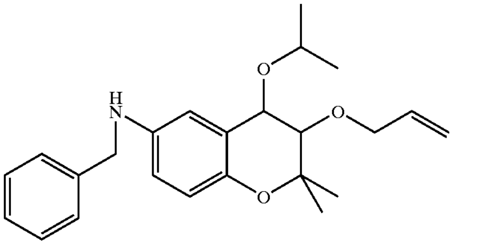<br>5-271 | MS, m/z: 395.55 |
| 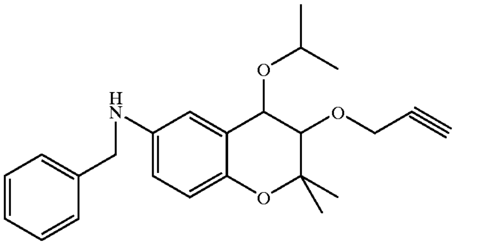<br>5-272 | MS, m/z: 381.52 |
| 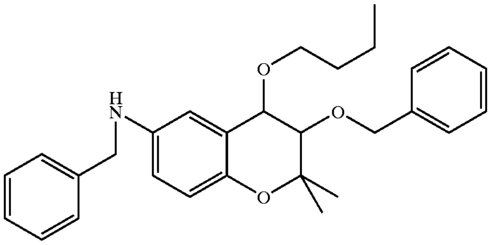<br>5-273 | MS, m/z: 445.61 |
| 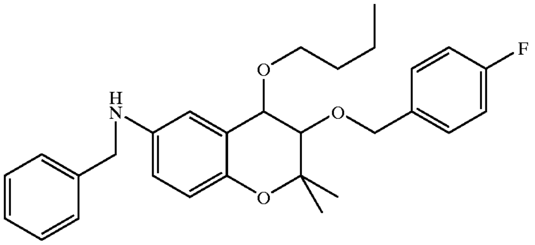<br>5-274 | MS, m/z: 463.60 |

TABLE 1-continued
| | Compound No. NMR/MS Data |
|---|---|
| 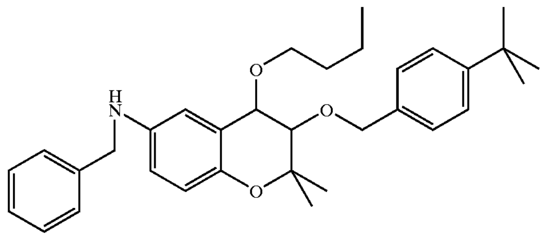 5-275 | MS, m/z: 501.72 |
| 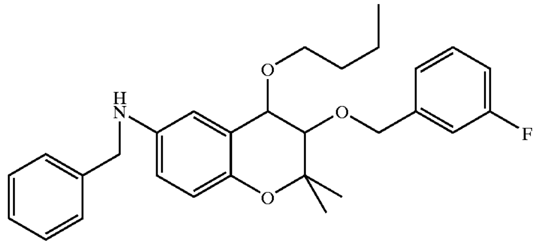 5-276 | MS, m/z: 463.60 |
| 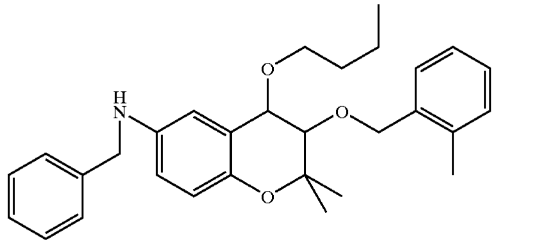 5-277 | MS, m/z: 459.63 |
| 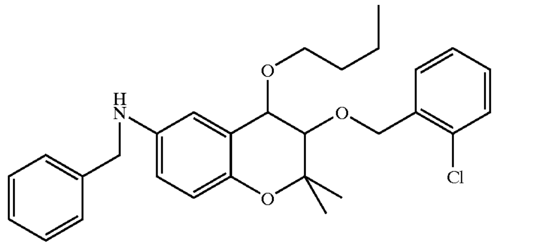 5-278 | MS, m/z: 480.05 |
| 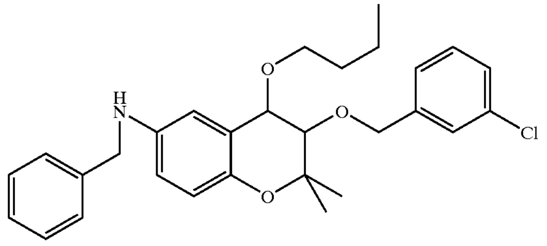 5-279 | MS, m/z: 480.05 |

TABLE 1-continued
| Compound No. | NMR/MS Data |
|---|---|
| 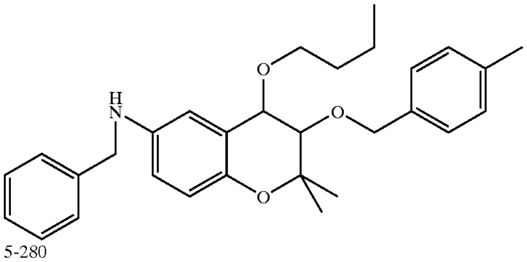 5-280 | MS, m/z: 459.63 |
| 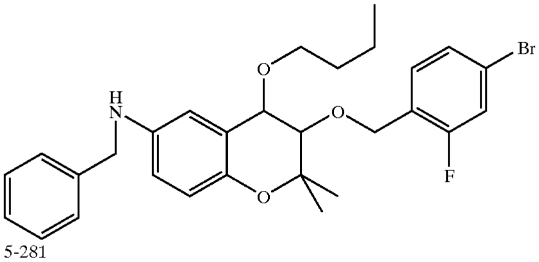 5-281 | MS, m/z: 542.49 |
| 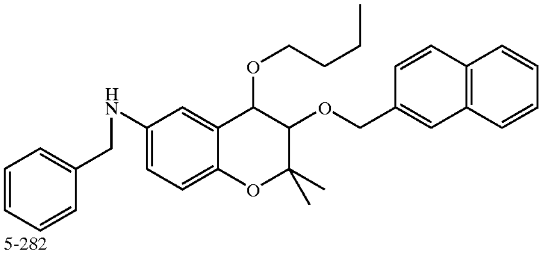 5-282 | MS, m/z: 495.67 |
| 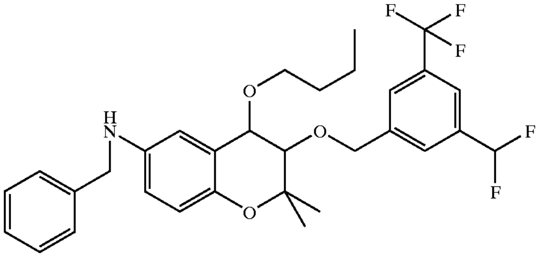 5-283 | MS, m/z: 581.60 |
| 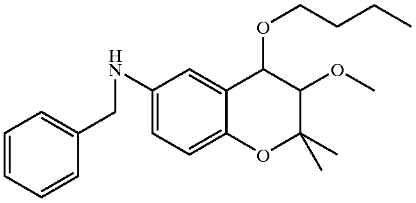 5-284 | MS, m/z: 369.51 |
| 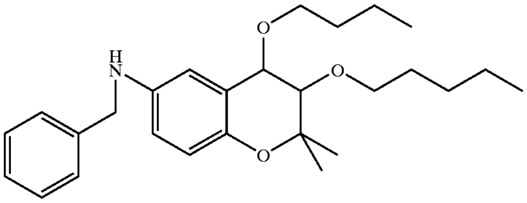 5-285 | MS, m/z: 425.62 |

TABLE 1-continued
| | Compound No. NMR/MS Data |
|---|---|
| 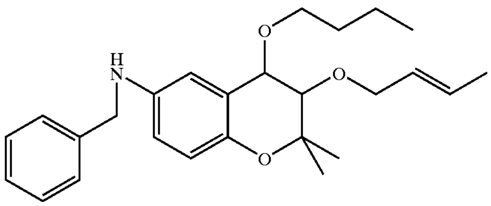 5-286 | MS, m/z: 409.57 |
| 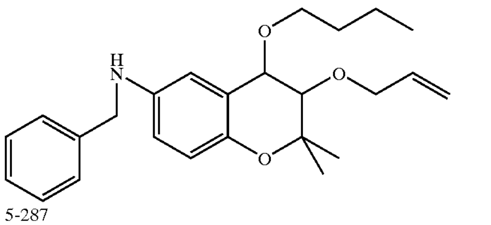 5-287 | MS, m/z: 395.55 |
| 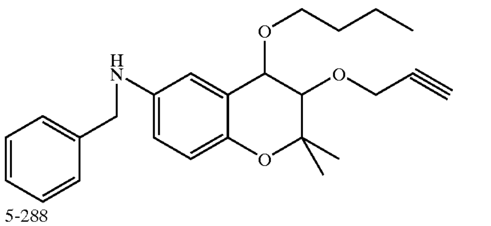 5-288 | MS, m/z: 393.53 |
| 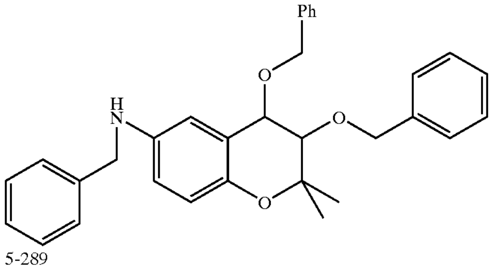 5-289 | $^1$H NMR(200 MHz, $CDCl_3$) δ 7.34~7.25 (m, 15H), 6.68~6.52 (m, 3H), 4.89 (d, 1H, J=11.4 Hz), 4.78~4.60 (m, 3H), 4.20 (s, 2H), 3.69 (d, 1H, J=7.2 Hz), 1.43 (s, 3H), 1.27 (s, 3H); MS, m/z: 479.62 |
| 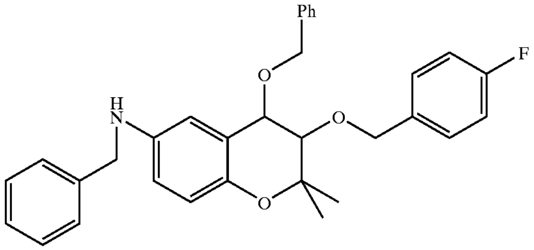 5-290 | $^1$H NMR(200 MHz, $CDCl_3$) δ 7.35~7.24 (m, 10H), 7.06~6.97 (m, 4H), 6.98~6.57 (m, 3H), 4.85 (d, 1H, J=11.5 Hz), 4.70 (m, 4H), 4.21 (s, 2H), 3.68 (d, 1H, J=7.0 Hz), 1.43 (s, 3H), 1.26 (s, 3H); MS, m/z: 497.62 |
| 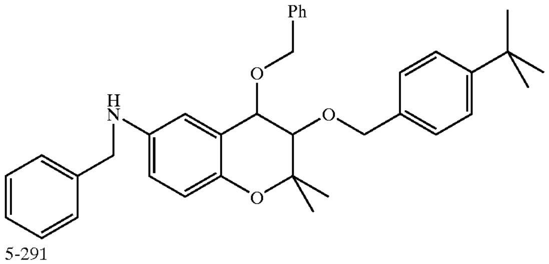 5-291 | $^1$H NMR(200 MHz, $CDCl_3$) δ 7.42~7.25 (m, 14H), 6.68~6.55 (m, 3H), 4.85 (d, 1H, J=11.2 Hz), 4.73~4.58 (m, 4H), 4.12 (s, 2H), 3.69 (d, 1H, J=7.2 Hz), 1.33 (s, 3H), 1.32 (s, 9H), 1.26 (s, 3H); MS, m/z: 535.73 |

TABLE 1-continued
| | Compound No. NMR/MS Data |
|---|---|
| 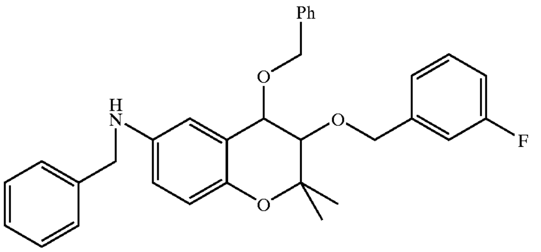 5-292 | $^1$H NMR(200 MHz, $CDCl_3$) δ 7.35~7.25 (m, 10H), 7.11~6.94 (m, 4H), 6.65~6.52 (m, 3H), 4.87 (d, 1H, J=12.2 Hz), 4.70 (m, 2H), 4.21 (s, 2H), 3.69 (d, 1H, J=7.2 Hz), 1.45 (s, 3H), 1.28 (s, 3H); MS, m/z: 497.62 |
| 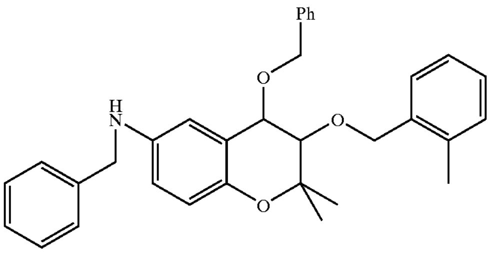 5-293 | $^1$H NMR(200 MHz, $CDCl_3$) δ 7.40~7.18 (m, 13H), 6.65~6.56 (m, 3H), 4.92 (d, 1H, J=11.6 Hz), 4.73~4.61 (m, 2H), 4.21 (s, 2H), 3.73 (d, 1H, J=7.2 Hz), 2.31 (s, 3H), 1.42 (s, 9H), 1.28 (s, 3H); MS, m/z: 493.65 |
| 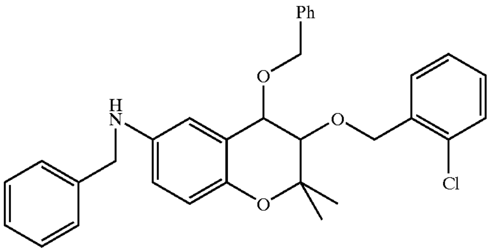 5-294 | MS, m/z: 393.65 |
| 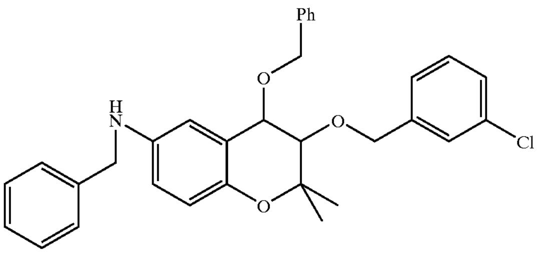 5-295 | $^1$H NMR(200 MHz, $CDCl_3$) δ 7.35~7.19 (m, 14H), 6.68~6.55 (m, 3H), 4.80 (d, 1H, J=11.2 Hz), 4.69~4.61 (m, 3H), 4.20 (s, 2H), 3.67 (d, 1H, J=7.2 Hz), 1.44 (s, 3H), 1.27 (s, 3H); MS, m/z: 514.07 |
| 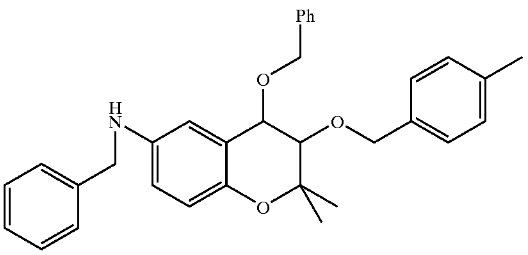 5-296 | $^1$H NMR(200 MHz, $CDCl_3$) δ 7.34~7.12 (m, 13H), 6.63~6.58 (m, 3H), 4.90 (d, 1H, J=11.6 Hz), 4.73~4.61 (m, 2H), 4.19 (s, 2H), 3.67 (d, 1H, J=7.0 Hz), 2.34 (s, 3H), 1.42 (s, 9H), 1.25 (s, 3H); MS, m/z: 493.65 |

TABLE 1-continued
| | Compound No. NMR/MS Data |
|---|---|
| 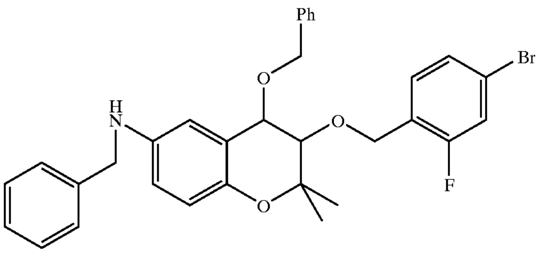 5-297 | $^{1}$H NMR(200 MHz, $CDCl_3$) δ 7.35~7.20 (m, 13H), 6.63~6.56 (m, 3H), 4.78 (d, 1H, J=11.4 Hz), 4.72~4.69 (m, 3H), 4.59 (d, 1H, J=7.2 Hz), 4.20 (s, 2H), 3.68 (d, 1H, J=7.2 Hz), 1.42 (s, 3H), 1.24 (s, 3H); MS, m/z: 576.51 |
| 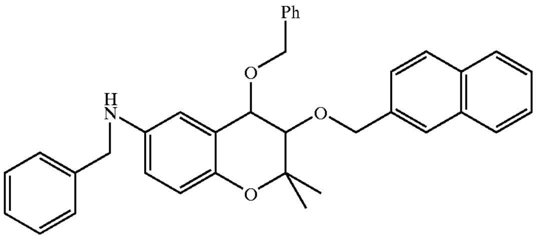 5-298 | $^{1}$H NMR(200 MHz, $CDCl_3$) δ 7.84~7.76 (m, 14H), 7.50~7.45 (m, 3H), 7.32~7.25 (m, 10H), 6.70~6.55 (m, 3H), 5.03 (d, 1H, J=11.6 Hz), 4.86 (d, 1H, J=11.6 Hz), 4.70 (m, 2H), 4.20 (s, 2H), 3.74 (d, 1H, J=7.0 Hz), 1.44 (s, 3H), 1.29 (s, 3H); MS, m/z: 529.69 |
| 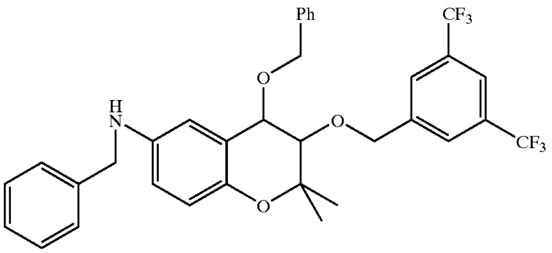 5-299 | $^{1}$H NMR(200 MHz, $CDCl_3$) δ 7.79~7.74 (m, 3H), 7.37~7.22 (m, 10H), 6.70~6.55 (m, 3H), 4.96 (d, 1H, J=12.6 Hz), 4.77 (d, 1H, J=12.6 Hz), 4.70 (m, 4H), 4.22 (s, 2H), 3.71 (d, 1H, J=7.6 Hz), 1.46 (s, 3H), 1.28 (s, 3H); MS, m/z: 507.68 |
| 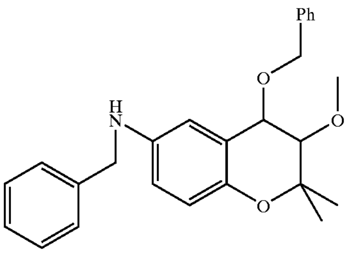 5-300 | $^{1}$H NMR(200 MHz, $CDCl_3$) δ 7.39~7.26 (m, 10H), 6.67~6.50 (m, 3H), 4.81 (d, 1H, J=11.4 Hz), 4.72 (d, 1H, J=11.4 Hz), 4.50 (d, 1H, J=7.0 Hz), 4.20 (s, 2H), 3.60 (s, 2H), 3.41 (d, 1H, J=7.0 Hz), 1.44 (s, 3H), 1.23~(s, 3H); MS, m/z: 403.53 |
| 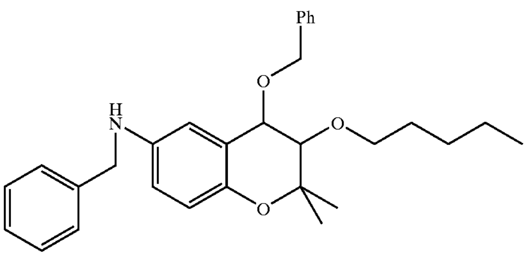 5-301 | MS, m/z: 459.63 |

TABLE 1-continued
| | Compound No. NMR/MS Data |
|---|---|
| 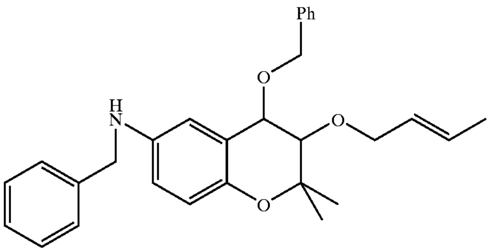 5-302 | MS, m/z: 443.59 |
| 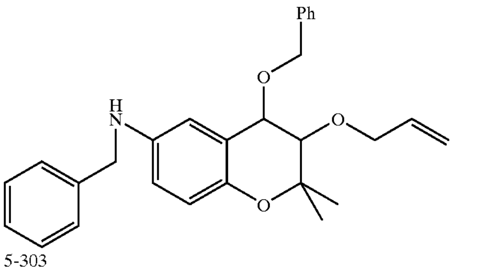 5-303 | MS, m/z: 429.56 |
| 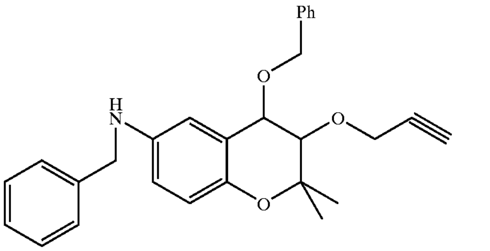 5-304 | MS, m/z: 427.55 |
| 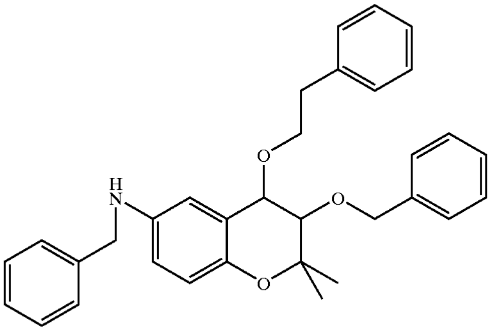 5-305 | MS, m/z: 493.65 |
| 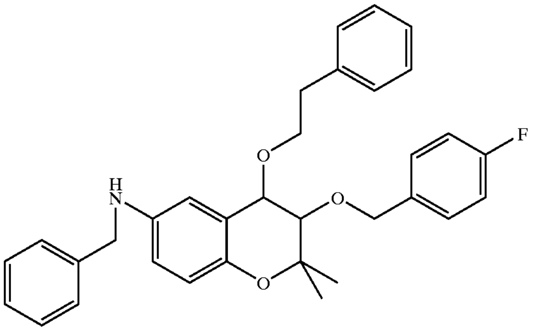 5-306 | $^1$H NMR(200 MHz, $CDCl_3$) δ 7.30~6.91 (m, 14H), 6.57~6.30 (m, 3H), 4.62 (d, 1H, J=11.2 Hz), 4.48 (d, 1H, J=11.2 Hz), 4.35 (d, 1H, J=8.0 Hz), 4.12 (s, 2H), 3.80~3.74 (m, 2H), 3.46 (d, (d, 1H, J=8.0 Hz), 2.79 (t, 2H, J=6.2 Hz), 1.28 (s, 3H), 1.12 (s, 3H); MS, m/z: 511.64 |

TABLE 1-continued

| | Compound No. NMR/MS Data |
|---|---|
| 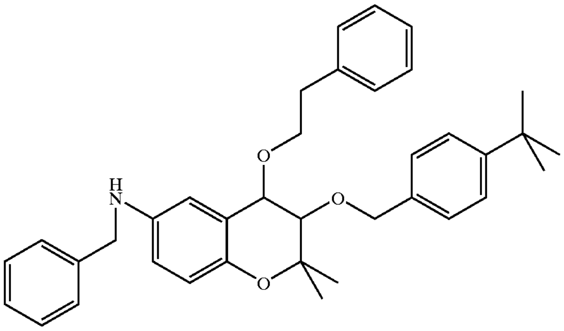 5-307 | $^1H$ NMR(200 MHz, $CDCl_3$) δ 7.32~7.27 (m, 14H), 6.57~6.30 (m, 3H), 4.64 (d, 1H, J=11.2 Hz), 4.50 (d, 1H, J=11.2 Hz), 4.36 (d, 1H, J=8.0 Hz), 4.11 (s, 2H), 3.80~3.74 (m, 2H), 4.46 (d, 1H, J=8.0 Hz), 2.80 (t, 2H, J=6.2 Hz), 1.34 (s, 3H), 1.25 (s, 3H); MS, m/z: 549.76 |
| 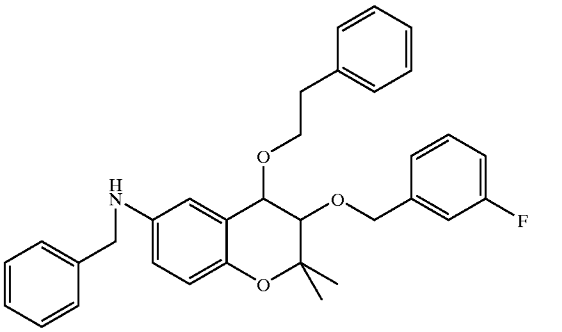 5-308 | $^1H$ NMR(300 MHz, $CDCl_3$) δ 7.30~7.19 (m, 11H), 7.13(m, 1H), 7.04(m, 2H), 6.98(m, 1H), 6.62 (d, 1H, J=5.2 Hz), 6.52 (dd, 1H, J=5.2 Hz, J=1.5 Hz), 6.36 (d, 1H, J=1.5 Hz), 4.72 (d, 1H, J=7.1 Hz), 4.58 (d, 1H, J=7.1 Hz), 4.44 (d, 1H, J=4.6 Hz), 4.19 (s, 2H), 3.55 (m, 2H), 3.85 (d, 1H, J=4.6 Hz), 2.86 (t, 2H, J=4.0 Hz), 1.38 (s, 3H), 1.21 (s, 3H); MS, m/z: 511.64 |
| 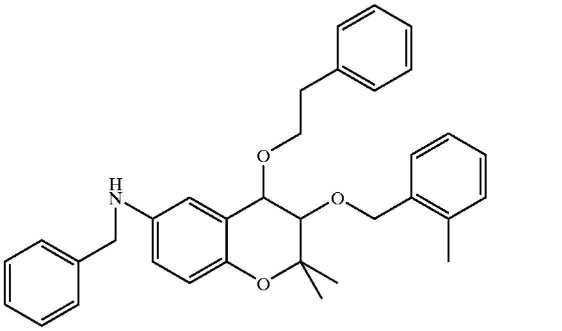 5-309 | $^1H$ NMR(200 MHz, $CDCl_3$) δ 7.30~7.04 (m, 14H), 6.55(d, 1H, J=8.6 Hz), 6.45 (dd, 1H, J=8.6 Hz, J=2.4 Hz), 6.29 (d, 1H, J=2.4 Hz), 4.75 (d, H, J=11.8 Hz), 4.56 (d, 1H, J=11.8 Hz), 4.36 (d, 1H, J=7.8 Hz), 4.11 (s, 2H), 3.78 (m, 2H), 3.52 (d, 1H, J=7.8 Hz), 2.79 (t, 2H, J=6.6 Hz), 2.25 (s, 3H), 1.28 (s, 3H), 1.13 (s, 3H); MS, m/z: 507.68 |
| 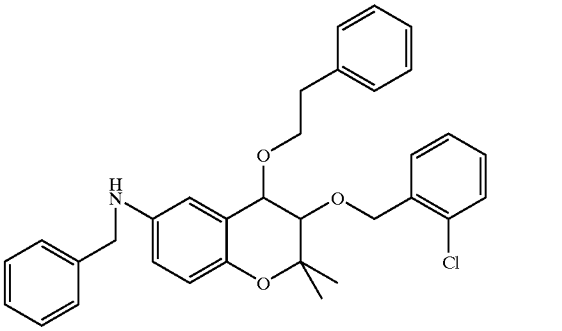 5-310 | $^1H$ NMR(200 MHz, $CDCl_3$) δ 7.42~7.03 (m, 14H), 6.60~6.29 (m, 3H), 4.85 (d, 1H, J=12.8 Hz), 4.72 (d, 1H, J=12.8 Hz), 4.38 (d, 1H, J=7.6 Hz), 4.12 (s, 2H), 3.82~3.76 (m, 2H), 3.55 (d, 1H, J=7.6 Hz), 2.79 (t, 2H, J=6.2 Hz), 1.28 (s, 3H), 1.12 (s, 3H); MS, m/z: 528.10 |

TABLE 1-continued
| | Compound No. NMR/MS Data |
|---|---|
| 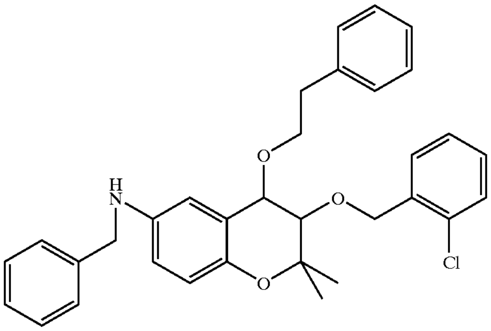 5-311 | $^1$H NMR(200 MHz, $CDCl_3$) δ 7.30~7.05 (m, 14H), 6.57~6.28 (m, 3H), 4.63 (d, 1H, J=12.0 Hz), 4.47 (d, 1H, J=12.0 Hz), 4.36 (d, 1H, J=7.8 Hz), 4.12 (s, 2H), 3.80~3.73 (m, 2H), 3.46 (d, 1H, J=7.8 Hz), 2.78 (t, 2H, J=6.4 Hz), 1.30 (s, 3H), 1.13 (s, 3H); MS, m/z: 528.10 |
| 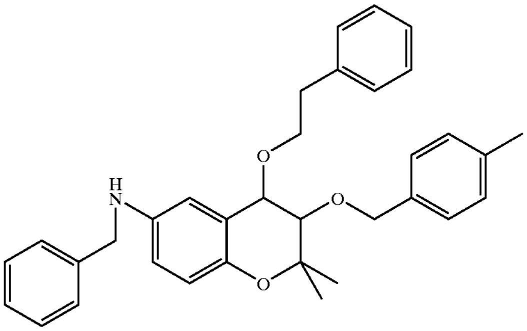 5-312 | $^1$H NMR(200 MHz, $CDCl_3$) δ 7.28~7.04 (m, 14H), 6.60~6.27 (m, 3H), 4.63 (d, 1H, J=11.2 Hz), 4.39 (d, 1H, J=11.2 Hz), 4.42 (d, 1H, J=7.6 Hz), 4.12 (s, 2H), 3.80~3.75 (m, 2H), 3.46 (d, 1H, J=7.6 Hz), 2.78 (t, 2H, J=6.4 Hz), 2.27 (s, 3H), 1.28 (s, 3H), 1.15 (s, 3H); MS, m/z: 507.68 |
| 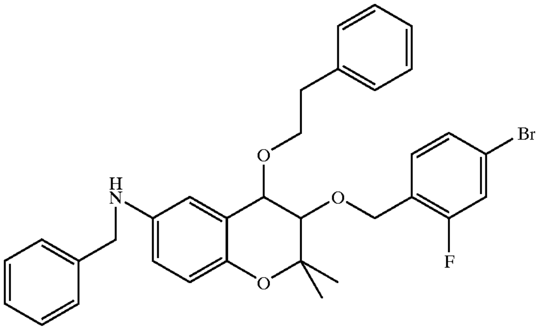 5-313 | $^1$H NMR(300 MHz, $CDCl_3$) δ 7.38~7.19 (m, 12H), 6.98~6.62 (m, 3H), 4.47 (d, 1H, J=5.5 Hz), 4.60 (d, 1H, J=5.5 Hz), 4.40 (d, 1H, J=4.6 Hz), 4.18 (s, 2H), 3.90~3.84 (m, 2H), 3.54 (d, 1H, J=4.6 Hz), 2.87 (t, 2H, J=4.0 Hz), 1.33 (s, 3H), 1.18 (s, 3H); MS, m/z: 590.54 |
| 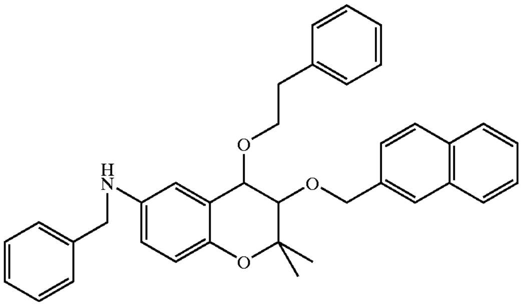 5-314 | MS, m/z: 543.71 |

TABLE 1-continued
| Compound No. | NMR/MS Data |
|---|---|
| 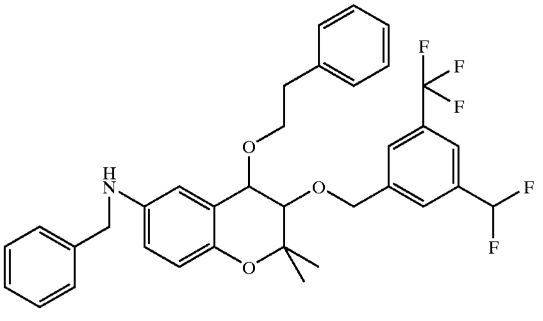 5-315 | MS, m/z: 629.65 |
| 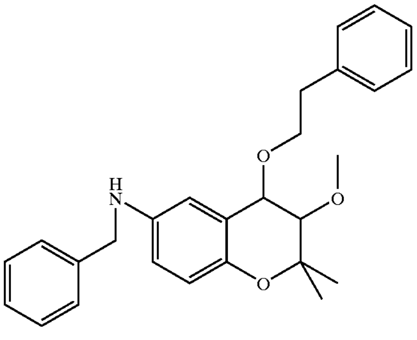 5-316 | $^1$H NMR(300 MHz, $CDCl_3$) δ 7.37~7.13 (m, 10H), 6.98~6.62 (m, 3H), 4.31 (d, 1H, J=4.6 Hz), 4.17 (s, 2H), 3.98~3.88 (m, 2H), 3.51 (s, 3H), 3.27 (d, 1H, J=4.6 Hz), 2.87 (t, 2H, J=4.1 Hz), 1.38 (s, 3H), 1.18 (s, 3H); MS, m/z: 417.55 |
| 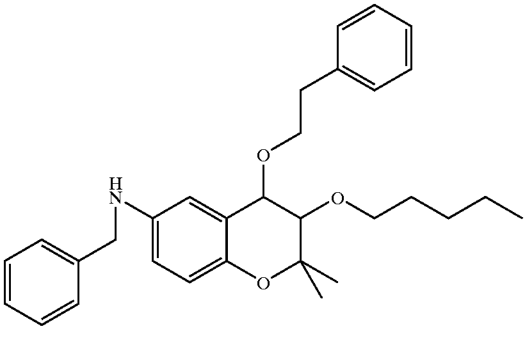 5-317 | MS, m/z: 473.66 |
| 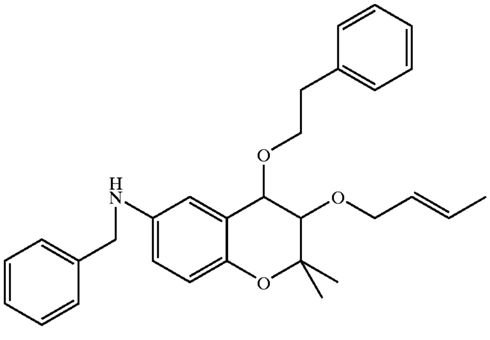 5-318 | MS, m/z: 457.62 |

TABLE 1-continued
| | Compound No. NMR/MS Data |
|---|---|
| 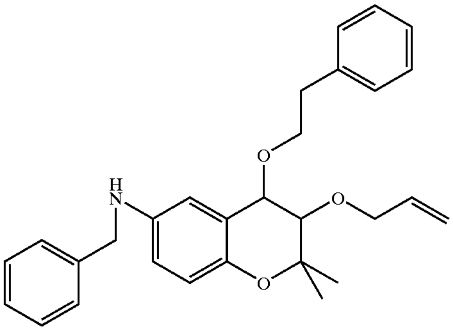<br>5-319 | MS, m/z: 443.59 |
| 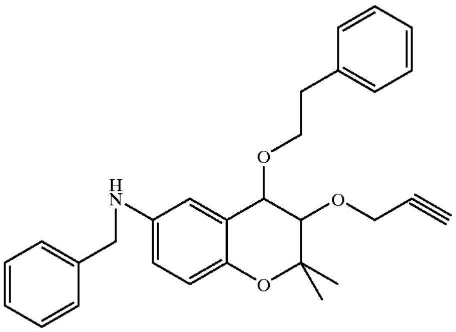<br>5-320 | MS, m/z: 441.58 |
| 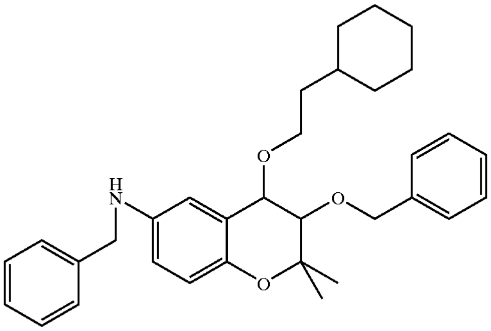<br>5-321 | MS, m/z: 499.70 |
| 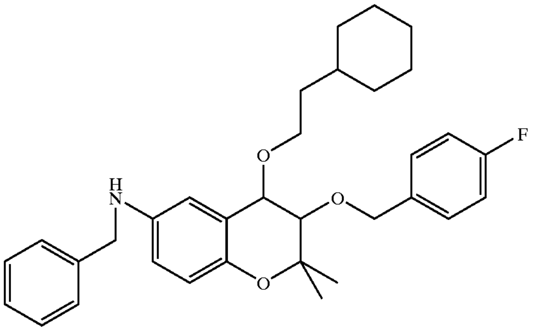<br>5-322 | $^1H$ NMR(300 MHz, $CDCl_3$) δ 7.35~7.23 (m, 9H), 7.07~6.67 (m, 3H), 4.82 (d, 1H, J=11.4 Hz), 4.64 (d, 1H, J=11.4 Hz), 4.34 (d, 1H, J=7.0 Hz), 3.70~3.64 (m, 2H), 3.53 (d, 1H, J=7.0 Hz), 1.70~1.15 (m, 19H); MS, m/z: 517.69 |

TABLE 1-continued
| | Compound No. NMR/MS Data |
|---|---|
| 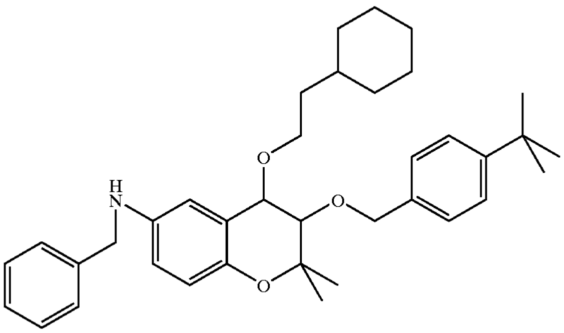 5-323 | $^1$H NMR(300 MHz, $CDCl_3$) δ 7.40~7.15 (m, 9H), 6.73~6.68 (m, 3H), 4.81 (d, 1H, J=11.3 Hz), 4.64 (d, 1H, J=11.3 Hz), 4.30 (d, 1H, J=6.7 Hz), 4.22 (s, 2H), 3.72~3.68 (m, 2H), 3.52 (d, 1H, J=76.7 Hz), 1.71~0.92 (m, 33H); MS, m/z: 555.81 |
| 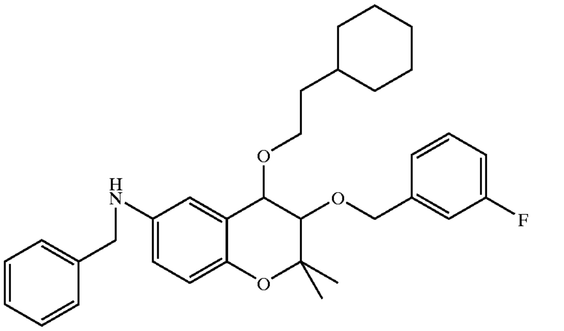 5-324 | $^1$H NMR(300 MHz, $CDCl_3$) δ 7.32~7.25 (m, 6H), 7.12~6.67 (m, 6H), 4.87 (d, 1H, J=11.9 Hz), 4.68 (d, 1H, J=11.9 Hz), 4.36 (d, 1H, J=7.1 Hz), 4.23 (s, 2H), 3.68 (t, 2H, J=6.9 Hz), 3.54 (d, 1H, J=7.1 Hz), 1.68~0.87 (m, 19H); MS, m/z: 517.69 |
| 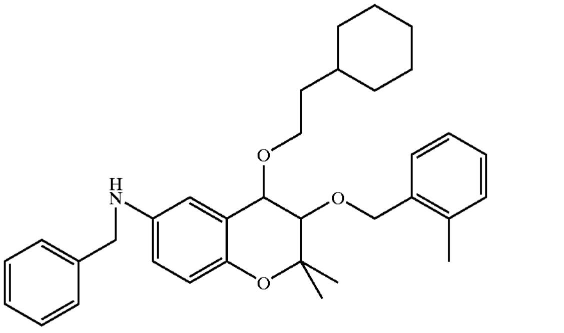 5-325 | $^1$H NMR(300 MHz, $CDCl_3$) δ 7.35~7.10 (m, 9H), 6.93~6.68 (m, 3H), 4.86 (d, H, J=11.7 Hz), 4.67 (d, 1H, J=11.7 Hz), 4.33 (d, 1H, J=6.8 Hz), 4.23 (s, 2H), 3.69~3.63 (m, 2H), 3.56 (d, 1H, J=6.8 Hz), 1.53~0.90 (m, 19H): MS, m/z: 513.73 |
| 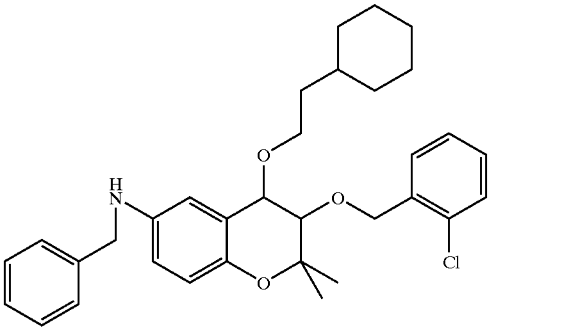 5-326 | $^1$H NMR(300 MHz, $CDCl_3$) δ 7.39~7.25 (m, 9H), 6.70~6.64 (m, 3H), 5.00 (d, 1H, J=12.8 Hz), 4.79 (d, 1H, J=12.8 Hz), 4.35 (d, 1H, J=7.4 Hz), 4.27 (s, 2H), 3.70~3.64 (m, 2H), 1.66~0.84 (m, 19H); MS, m/z: 534.14 |

TABLE 1-continued
| | Compound No. NMR/MS Data |
|---|---|
| 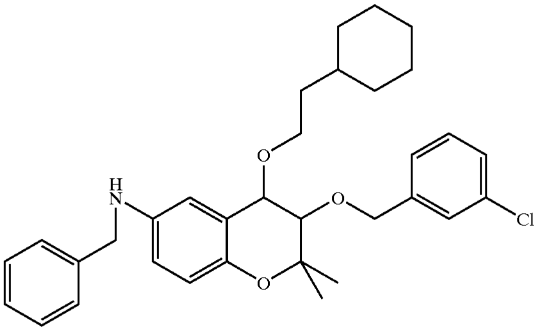 5-327 | $^1H$ NMR(200 MHz, $CDCl_3$) δ 7.36~7.26 (m, 9H), 6.68~6.54 (m, 3H), 4.87 (d, 1H, J=12.0 Hz), 4.68 (d, 1H, J=12.0 Hz), 4.40 (d, 1H, J=6.7 Hz), 4.28 (s, 2H), 3.70~3.56 (m, 3H), 1.65~1.24 (m, 19H); MS, m/z: 596.59 |
| 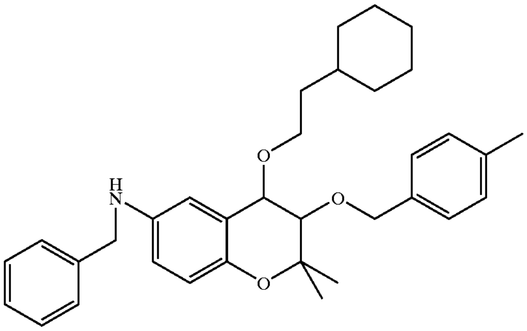 5-328 | MS, m/z: 513.73 |
| 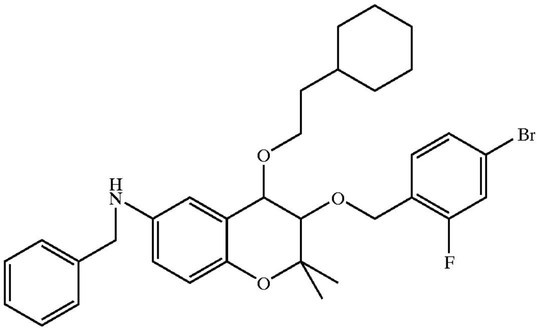 5-329 | MS, m/z: 596.59 |
| 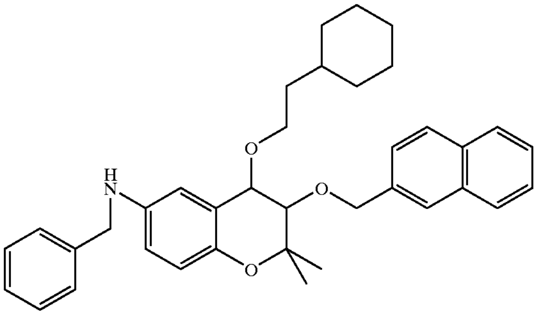 5-330 | MS, m/z: 549.76 |

TABLE 1-continued
| | Compound No. NMR/MS Data |
|---|---|
| 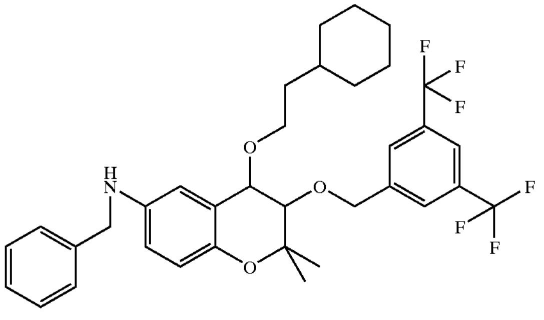 5-331 | MS, m/z: 635.70 |
| 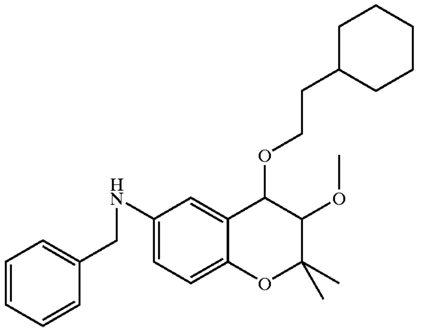 5-332 | $^1$H NMR(200 MHz, $CDCl_3$) δ 7.36~6.97 (m, 7H), 6.75~6.67 (m, 1H), 4.25 (d, 1H, J=6.4 Hz), 4.21 (m, 2H), 3.83~3.62 (m, 4H), 3.32 (d, 1H, J=6.4 Hz), 1.70~0.95 (m, 28H); MS, m/z: 479.71 |
| 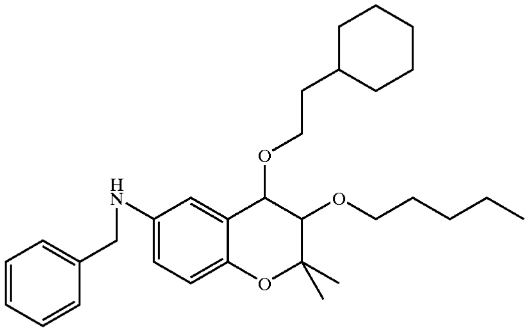 5-333 | MS, m/z: 479.71 |
| 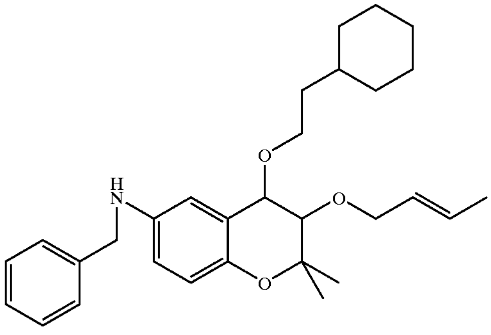 5-334 | MS, m/z: 463.67 |

TABLE 1-continued
| | Compound No. NMR/MS Data |
|---|---|
| 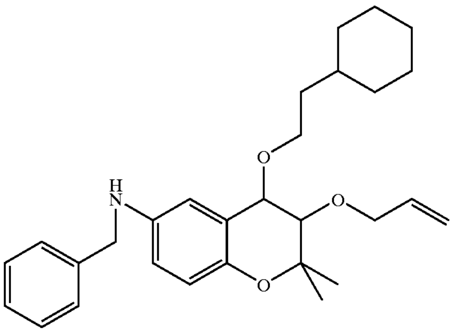 5-335 | MS, m/z: 449.64 |
| 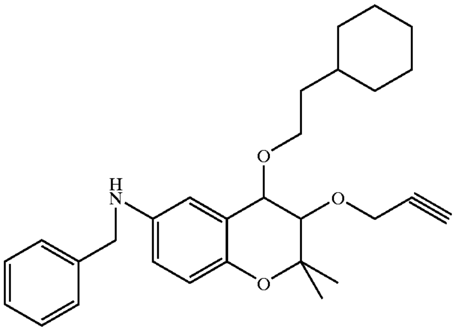 5-336 | MS, m/z: 447.62 |
| 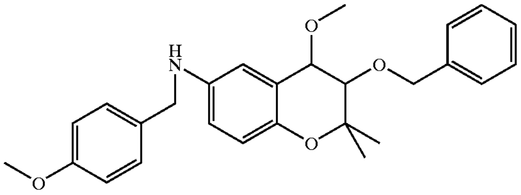 5-337 | $^1$H NMR(200 MHz, $CDCl_3$) δ 7.30(m 4.90(d, 1H, J=11.1Hz), 4.72(d, 1H, J=11.1 Hz), 4.40(d, J=7.3 Hz), 4.20(s, 2H), 3.79(s, 3H) 3.60(d, 1H, J=7.3 Hz), 3.45(s, 3H), 1.40(s, 3H), 1.23(s, 3H); MS, m/z: 433.55 5-337 |
| 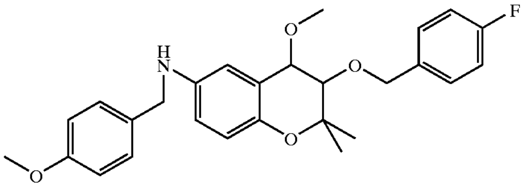 5-338 | $^1$H NMR(200 MHz, $CDCl_3$) δ 6.95~7.40(m, 8H), 6.75(m, 3H), 4.83(d, 1H, J=11.4 Hz), 4.65(d, 1H, J=11.4 Hz), 4.15(s, 2H), 4.2 3.50(s, 3H), 1.40(s, 3H), 1.23(s, 3H); MS, m/z: 451.54 |
| 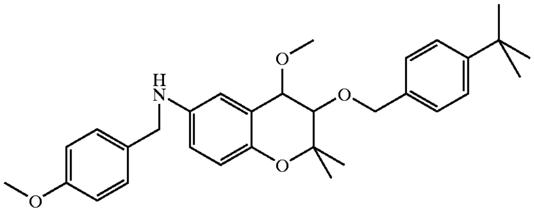 5-339 | $^1$H NMR(200 MHz, $CDCl_3$) δ 7.10~7.40(m, 7H), 6.90(d, 1H, J=8.6 Hz), 6.75(m, 3H), 4.83(d, 1H, J=11.3 Hz), 4.65(d, 1H, J=11 3.53(d, 1H, J=6.9 Hz), 3.50(s, 3H), 1.32(m, 15H) MS, m/z: 489.66 |

TABLE 1-continued

| | Compound No. NMR/MS Data |
|---|---|
| 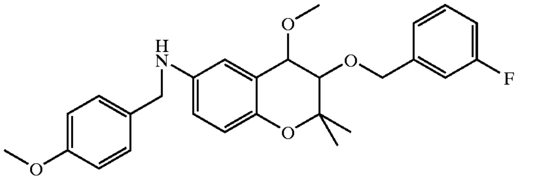 5-340 | $^1$H NMR(200 MHz, $CDCl_3$) δ 7.30(m 6.75(m, 3H), 4.90(d, 1H, J=11.3 Hz), 4.70(d, 1H, J=11.3 Hz), 4.40(d, J=6.9 Hz), 4.20(s, 2H), 3.79(s, 3H), 3.61(d, 1H, J=6.9 Hz), 3.45(s, 3H), 1.41(s, 3H), 1.23(s, 3H); MS, m/z: 451.54 |
| 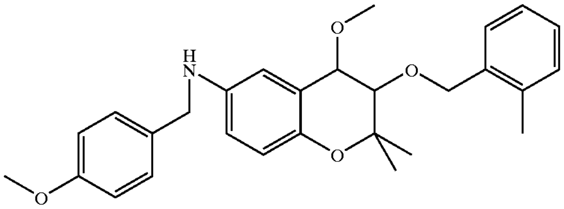 5-341 | $^1$H NMR(200 MHz, $CDCl_3$) δ 7.18~7.42(m, 6H)6.87(d, 2H, J=8.5 Hz), 6.65(m, 2H), 6.56(dd, 1H, J=9.0 Hz, J=2.6 Hz), 4.90(d, 1H, J=11.6 Hz), 4.70(d, 1H, J=11.6 Hz), 4.41 (d, J=7.5 Hz), 4.20(s, 2H), 3.79(s, 3H), 3.63(d, 1H, J=7.5 Hz), 3.45(s, 3H), 2.38(s, 3H), 1.40(s, 3H), 1.23(s, 3H); MS, m/z: 447.58 |
| 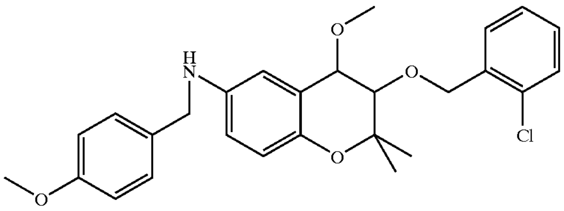 5-342 | $^1$H NMR(200 MHz, $CDCl_3$) δ 7.84(m, 2H), 7.26(m, 2H), 6.88(d, 2H, J=8.5 Hz), 6.70~6.59(m, 3H), 5.06(d, 1H, J=12.5 Hz), 4.84(d, 1H, J=12.5 Hz), 4.50(d, 1H, J=7.7 Hz), 4.22(s, 2H), 3.81(s, 3H), 3.65(d, 1H, J=7.7 Hz), 3.43(s, 3H), 1.46(s, 3H), 1.26(s, 3H); MS, m/z: 468.00 |
| 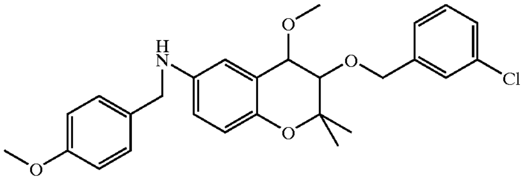 5-343 | $^1$H NMR(200 MHz, $CDCl_3$) δ 7.20~7.42(m, 6H), 6.87(d, 2H, J=8.5 Hz), 6.65(m, 2H), 6.56(dd, 1H, J=9.1 Hz, J=2.2 Hz), 4.88(d, 1H, J=12.5 Hz), 4.69(d, 1H, J=12.5 Hz), 4.20(s, 2H), 4.40(d, J=7.7 Hz), 3.60(d, 1H, J=7.7 Hz), 3.80(s, 3H), 3.46(s, 3H), 1.30(m, 6H); MS, m/z: 468.00 |
| 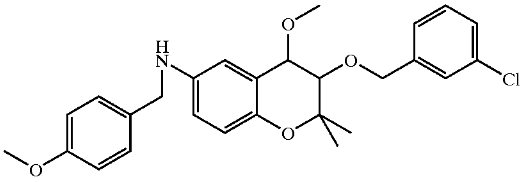 5-344 | $^1$H NMR(200 MHz, $CDCl_3$) δ 7.10~7.42(m, 6H)677(d, 2H, J=8.5 Hz), 6.56~6.70(m, 3H), 4.86(d, 1H, J=11.4 Hz), 4.66(d, 1H, J=11.4 Hz), 4.39(d, J=7.3 Hz), 4.20(s, 2H), 3.80(s, 3H), 3.58(d, 1H, J=7.3 Hz), 3.47(s, 3H), 2.35(s, 3H), 1.30(m, 6H); MS, m/z: 447.58 |
| 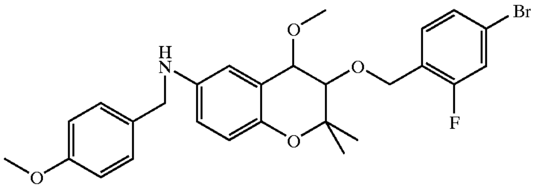 5-345 | $^1$H NMR(200 MHz, $CDCl_3$) d 7.34~7.22(m, 5H), 6.86(d, 2H), 6.71~6.60(m, 3H), 4.90(d, 1H, J=11.9 Hz), 4.72(d, 1H, J=11.9 Hz), 4.39(d, 1H, J=7.2 Hz), 4.20(s, 2H), 3.80(s, 3H), 3.59(d, 1H, J=7.2 Hz), 3.47(s, 3H), 1.40(s, 3H), 1.21 (s, 3H); MS, m/z: 530.44 |
| 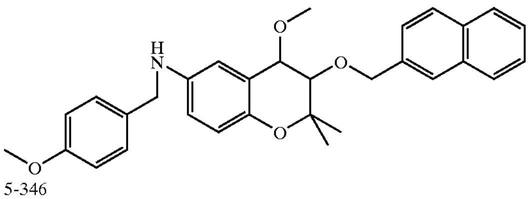 5-346 | $^1$H NMR(200 MHz, $CDCl_3$) δ 7.57(m, 1H), 7.39~7.19(m, 8H), 6.86(d, 2H, J=10.2 Hz), 6.73~6.56(m, 3H), 5.02(d, 1H, J=12.5 Hz), 4.71(d, 1H, J=12.5 Hz), 4.44(d, 1H, J=7.2 Hz), 3.80(s, 3H), 3.66(d, 1H. J=7.3 Hz0, 3.48(s, 3H), 1.42(s, 3H), 1.26(s, 3H); MS, m/z: 483.61 |

TABLE 1-continued

| | Compound No. NMR/MS Data |
|---|---|
| 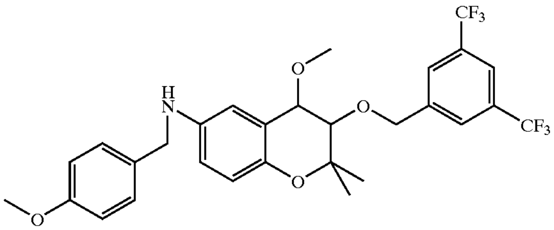 5-347 | $^1$H NMR(200 MHz, $CDCl_3$) δ 7.82(m, 3H), 7.21(m, 2H), 6.87(d, 2H, J=9.5 Hz), 6.50~6.70(m, 3H), 5.06(d, 1H,. J=12.4 Hz), 4.84(d, 1H, J=12.4 Hz), 4.49(d, J=7.7 Hz), 4.20(s, 2H), 3.80(s, 3H), 3.64(d, 1H, J=7.7 Hz), 3.42(s, 3H), 1.45(s, 3H), 1.25(s, 3H); MS, m/z: 461.61 |
| 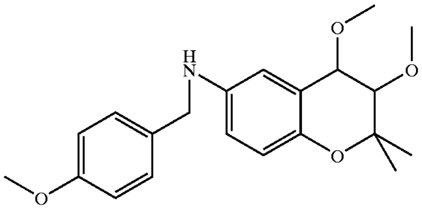 5-348 | $^1$H NMR(200 MHz, $CDCl_3$) δ 7.28(m, 2H), 6.87(d, 2H, J=9.0 Hz), 6.65(d, 1H, J=2.5 Hz), 6.62(s, 1H), 6.54(dd, 1H, J=9.0 Hz, J=2.5 Hz), 4.31(d, 1H, J=7.3 Hz), 4.20(s, 2H), 3.80(s, 3H), 3.61(s, 3H), 3.52(s, 3H), 3.34(d, 1H, J=7.3 Hz), 1.41(s, 3H), 1.20(s, 3H); MS, m/z: 357.45 |
| 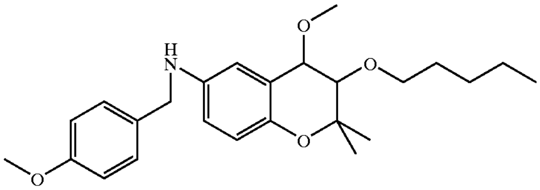 5-349 | $^1$H NMR(200 MHz, $CDCl_3$) δ 7.28(d, 2H, J=8.4 Hz), 6.87(d, 2H, J=8.4 Hz), 6.65(d, 1H, J=2.8 Hz), 6.61(s, 1H), 6.52(dd, 1H, J=8.6 Hz, J=2.8 Hz), 4.30(d, J=7.3 Hz), 4.20(s, 2H), 3.80(s, 3H), 3.50(s, 3H), 3.40(d, 1H, J=7.3 Hz), 1.60(br, 2H), 1.40(s, 3H), 1.21~1.45(m, 4H), 1.20(s, 3H), 0.91 (br, 3H); MS, m/z: 413.61 |
| 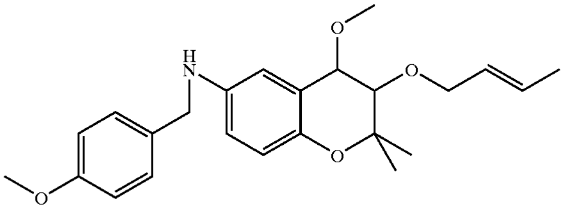 5-350 | $^1$H NMR(200 MHz, $CDCl_3$) δ 7.28(d, 2H, J=9.5 Hz), 6.87(d, 2H, J=9.5 Hz), 6.65(m, 2H), 6.52(dd, 1H, J=8.6 Hz, J=2.7 Hz), 5.70(m, 2H), 4.00~4.40(m, 2H), 4.19(s, 2H), 3.80(s, 3H), 3.50(s, 3H), 1.71 (d, 3H, J=6 Hz), 1.40(s, 3H), 1.21 (s, 3H); MS, m/z: 357.45 |
| 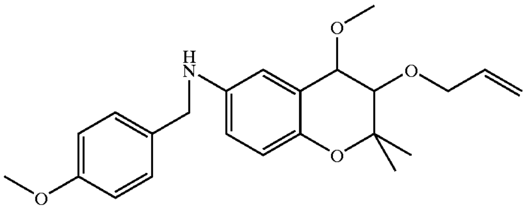 5-351 | $^1$H NMR(200 MHz, $CDCl_3$) δ 7.34(d, 1H, J=2.6 Hz), 7.16~7.16(m, 3H), 6.70(m, 3H), 5.92(m, 1H), 5.34~5.17(m, 2H), 5.30(dd, 1H, J=17.3 Hz, J=1.6 Hz), 5.19(dd, 1H, J=10.3 Hz, J=1.6 Hz), 4.20(s, 2H), 3.68(s, 3H), 3.54(s, 3H), 4.43(d, 1H, J=7.1 Hz), 1.40(s, 3H), 1.24(s, 3H); MS, m/z: 383.49 |
| 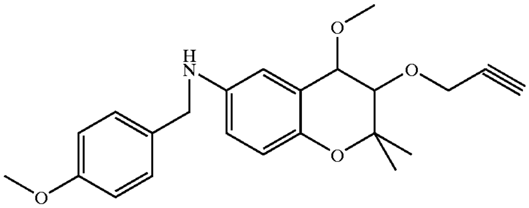 5-352 | $^1$H NMR(200 MHz, $CDCl_3$) δ 7.26(d, 2H, J=8.6 Hz), 6.86(d, 2H, J=8.6 Hz), 6.67~6.55(m, 3H), 4.46~4.38(m, 3H), 4.19(s, 2H), 3.79(s, 3H), 3.73(d, 1H, J=7.3 Hz), 3.47(s, 3H), 2.54(t, 1H, J=2.4 Hz), 1.43(s, 3H), 1.21 (s, 3H); MS, m/z: 381.48 |

TABLE 1-continued

| | Compound No. NMR/MS Data |
|---|---|
| 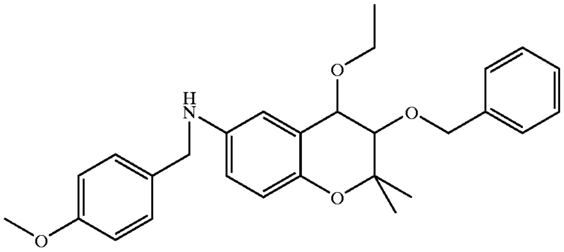 5-353 | $^1$H NMR(200 MHz, $CDCl_3$) δ 7.41~7.25(m, 7H), 6.88(d, 2H, J=8.7 Hz), 6.69~6.51(m, 3H), 4.91(d, 1H, J=11.4 Hz), 4.71(d, 1H, J=11.4 Hz), 4.45(d, 1H, J=7.5 Hz), 4.21(s, 2H), 3.81(s, 3H), 3.74(m, 2H), 3.61(d, 1H, J=7.5 Hz), 1.41(s, 3H), 1.26(s, 3H), 1.26(t, 3H, J=7.0 Hz); MS, m/z: 447.58 |
| 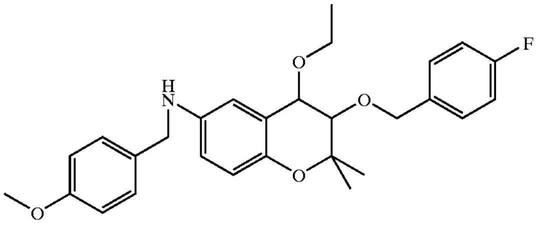 5-354 | $^1$H NMR(200 MHz, $CDCl_3$) δ 7.36~7.25(m, 4H), 7.06(d, 2H, J=8.6 Hz), 6.87(d, 2H, J=8.6 Hz), 4.86(d, 1H, J=11.5 Hz), 4.67(d, 1H, J=11.5 Hz), 4.43(d, 1H, J=7.6 Hz), 4.20(s, 2H), 3.80(s, 3H), 3.70(q, 2H, J=7.1), 3.58(d, 1H, J=7.6 Hz), 1.39(s, 3H), 1.25(s, 3H), 1.21(m, 3H); MS, m/z: 465.57 |
| 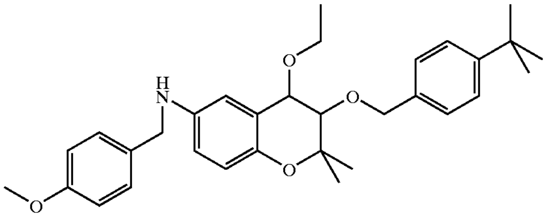 5-355 | $^1$H NMR(200 MHz, $CDCl_3$) δ 7.40~7.28(m, 6H), 6.87(d, 2H, J=8.6 Hz), 6.68~6.57(m, 3H), 4.86(d, 1H, J=11.2 Hz), 4.68(d, 1H, J=11.2 Hz), 4.429d, 1H, J=7.5 Hz), 4.20(s, 2H), 3.80(s, 3H), 3.71(q, 1H, J=7.1 Hz), 3.59(d, 1H, J=7.5 Hz), 1.41(s, 3H), 1.32(m, 9H), 1.26(s, 3H), 1.27(m, 3H); MS, m/z: 503.69 |
| 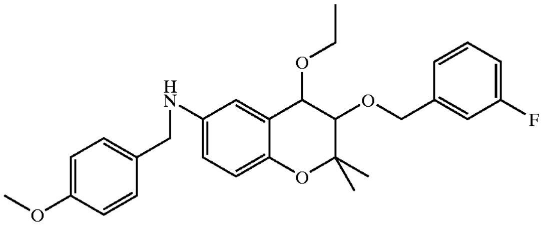 5-356 | $^1$H NMR(200 MHz, $CDCl_3$) δ 7.37~7.24(m, 4H), 7.08~6.91(m, 4H), 6.88(d, 2H, J=8.7 Hz), 6.68~6.51(m, 3H), 4.92(d, 1H, J=11.7 Hz), 4.71 (d, 1H, J=11.7 Hz), 4.46(d, 1H, J=7.5 Hz), 4.219(s, 2H), 3.81(s, 3H), 3.69(q, 2H, J=7.0 Hz), 3.59(d, 1H, J=7.5 Hz), 1.42(s, 3H), 1.24(s, 3H), 1.23(m, 3H); MS, m/z: 465.57 |
| 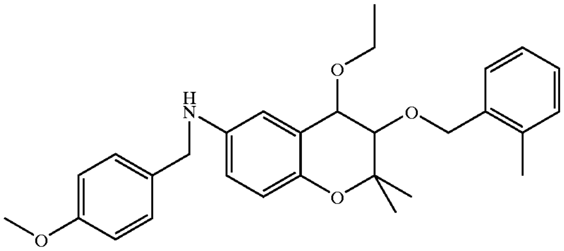 5-357 | $^1$H NMR(200 MHz, $CDCl_3$) δ 7.41~7.14(m, 6H), 6.87(d, 2H, J=8.8 Hz), 6.69~6.54(m, 3H), 4.93(d, 1H, J=11.7 Hz), 4.70(d, 1H, J=11.7 Hz), 4.459(d, 1H, J=7.7 Hz), 3.80(s, 3H), 3.70(q, 2H, J=7.0 Hz), 3.62(d, 1H, J=7.7 Hz), 1.39(s, 3H), 1.23(s, 3H), 1.23(t, 3H, J=7.7 Hz); MS, m/z: 461.61 |

TABLE 1-continued

| Compound No. | NMR/MS Data |
|---|---|
| 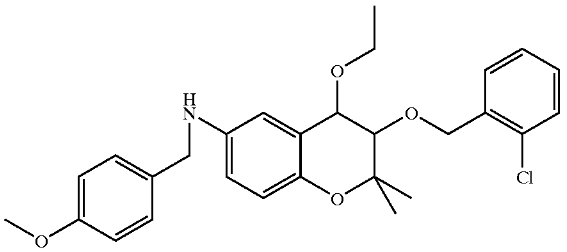 5-358 | $^1$H NMR(200 MHz, $CDCl_3$) δ 7.56~7.52(m, 1H), 7.39~7.9(m, 5H), 6.87(d, 2H, J=8.7 Hz), 6.70~6.54(m, 3H), 5.04(d, 1H, J=12.9 Hz), 4.80(d, 1H, J=12.9 Hz), 4.47(d, 1H, J=7.3 Hz), 4.21(s, 2H), 3.80(s, 3H), 3.70(m, 3H), 1.42(s, 3H), 1.26~1.17(m, 6H); MS, m/z: 482.02 |
| 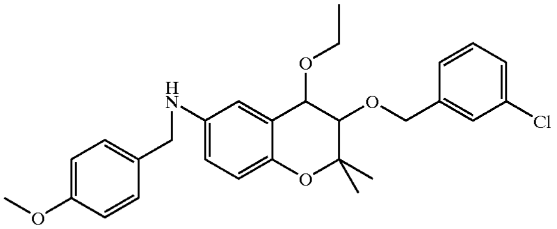 5-359 | 1$^1$H NMR(200 MHz, $CDCl_3$) δ 7.38~7.17(m, 6H), 6.88(d, 2H, J=8.7 Hz), 6.68~6.51(m, 3H), 4.89(d, 1H, J=11.9 Hz), 4.69(d, 1H, J=11.9 Hz), 4.46(d, H, J=7.6 Hz), 4.21(s, 2H), 3.81(s, 3H), 3.78(m, 2H), 3.59(d, 1H, J=7.6 Hz), 1.42(s, 3H), 1.24(s, 3H), 1.23(m, 3H); MS, m/z: 482.02 |
| 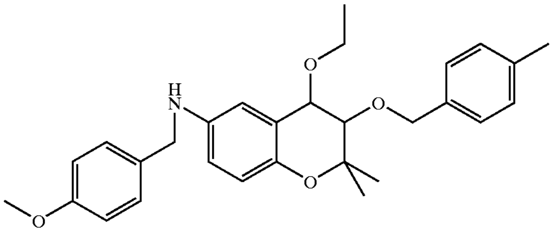 5-360 | $^1$H NMR(200 MHz, $CDCl_3$) δ 7.37~7.08(m, 6H), 6.87(d, 2H, J=8.6 Hz), 6.676.51(m, 3H), 4.86(d, 1H, J=11.2 Hz), 4.65(d, 1H, J=11.2 Hz), 4.42(d, 1H, J=7.5 Hz), 4.20(s, 2H), 3.80(s, 3H), 3.71 (m, 2H), 3.58(d, 1H, J=7.5 Hz), 2.35(s, 3H), 1.40(s, 3H), 1.23(s, 3H), 1.22(m, 3H); MS, m/z: 461.61 |
| 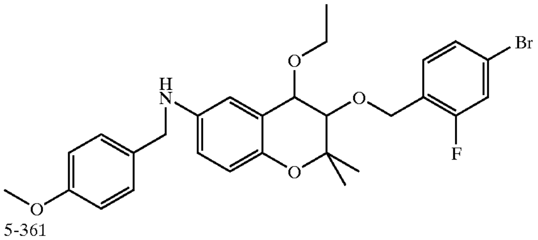 5-361 | $^1$H NMR(200 MHz, $CDCl_3$) δ 7.38~7.22(m, 5H), 6.87(d, 2H, J=8.4 Hz), 6.67~6.51(m, 3H), 4.90(d, 1H, J=12.1 Hz), 4.71(d, 1H, J=12.1 Hz), 4.43(d, 1H, J=7.5 Hz), 4.20(s, 2H), 3.80(s, 3H), 3.70(m, 2H), 3.59(d, 1H, J=7.5 Hz), 1.40(s, 3H), 1.23(m, 3H), 1.21 (s, 3H); MS, m/z: 544.47 |
| 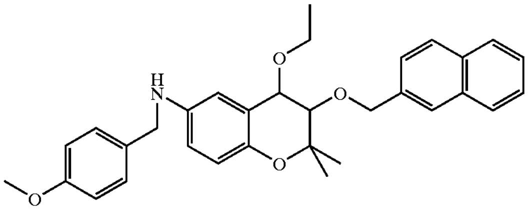 5-362 | $^1$H NMR(200 MHz, $CDCl_3$) δ 7.82(m, 4H), 7.53~7.46(m, 3H), 7.30(d, 2H, J=8.7Hz), 6.88(d, 2H, J=8.7 Hz), 6.68~6.52(m, 3H), 5.07(d, 1H, J=11.4 Hz)m, 4.88(d, 1H, J=11.4 Hz), 4.48(d, 1H, J=7.4 Hz), 4.21(s, 2H), 3.80(s, 3H), 3.74(m, 2H), 3.66(d, 1H, J=7.4 Hz), 1.42(s, 3H), 1.26(m, 3H), 1.23(s, 3H); MS, m/z: 497.64 |
| 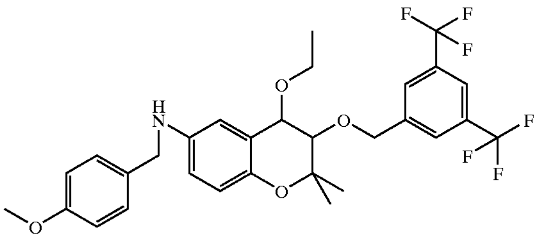 5-363 | $^1$H NMR(200 MHz, $CDCl_3$) δ 7.82(m, 3H), 7.30(d, 2H, J=8.4 Hz), 6.88(d, 2H, J=8.4 Hz), 6.68~6.52(m, 3H), 5.05(d, 1H, J=12.4 Hz), 4.84(d, 1H, J=12.4 Hz), 4.52(d, 1H, J=7.7 Hz), 4.21(s, 2H), 3.80(s, 3H), 3.74(m, 3H), 1.44(s, 3H), 1.26(m, 3H), 1.20(s, 3H); MS, m/z: 583.58 |

TABLE 1-continued

| Compound No. | NMR/MS Data |
|---|---|
| 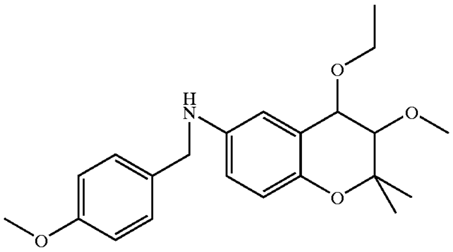 5-364 | $^1$H NMR(200 MHz, $CDCl_3$) δ 7.29(d, 2H, J=8.4 Hz), 6.87(d, 2H, J=8.4 Hz), 6.66~6.49(m, 3H), 4.33(d, 1H), 4.20(s, 2H), 3.80(s, 3H), 3.76(m, 2H), 3.60(s, 3H), 3.31(d, 1H, J=7.3 Hz), 1.41(s, 3H), 1.25(t, 3H, J=70 Hz), 1.20(s, 3H); MS, m/z: 371.48 |
| 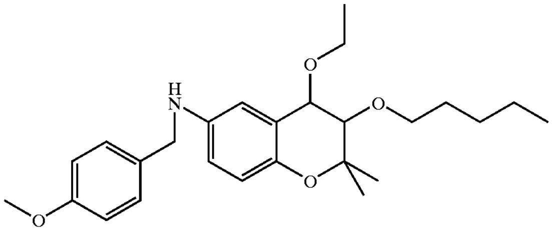 5-365 | $^1$H NMR(200 MHz, $CDCl_3$) δ 7.29(d, 2H, J=8.5 Hz), 6.87(d, 2H, J=8.5 Hz), 6.65~6.49(m, 3H), 4.33(d, 1H, J=7.8 Hz, 3.80(s, 3H), 3.81(m, 2H), 3.61(m, 2H), 3.38(d, 1H, J=7.8 Hz), 1.61(m, 2H), 1.40(s, 3H), 1.20(s, 3H), 1.50~1.16(m, 9H), 0.91(m, 3H); MS, m/z: 427.59 |
| 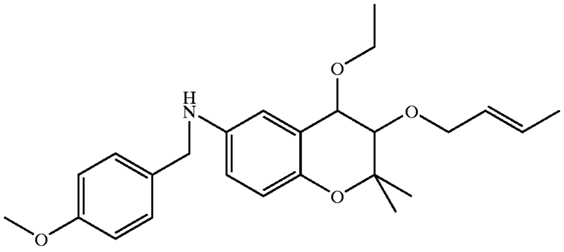 5-366 | $^1$H NMR(200 MHz, $CDCl_3$) δ 7.29(d, 2H, J=8.7 Hz), 6.87(d, 2H, J=8.7 Hz), 6.65~6.49(m ,3H), 5.68(m, 2H), 4.40~4.10(m, 2H), 4.19(s, 2H), 3.80(s, 3H), 3.76(m, 2H), 3.47(d, 1H, J=7.7 Hz), 1.72(d, 3H, J=5.1 Hz), 1.40(s, 3H), 1.29(m, 3H), 1.20(s, 3H); MS, m/z: 411.55 |
| 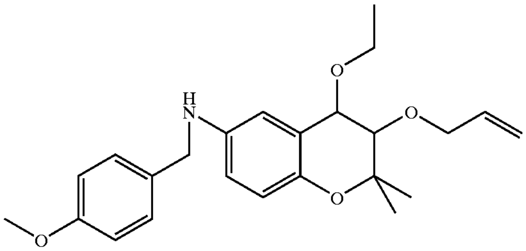 5-367 | $^1$H NMR(200 MHz, $CDCl_3$) δ 7.29(d, 2H, J=8.7 Hz), 6.87(d, 2H, J=8.7 Hz), 6.60~6.50(m, 3H), 6.94(m, 2H), 5.29(dd, 1H, J=17.1 Hz, J=1.6 Hz), 5.18(dd, 1H, J=10.3 Hz, J=1.8 Hz), 4.38(m, 2H), 4.19(s, 2H), 4.18(m, 1H), 3.80(s, 3H), 3.76(m, 2H), 3.48(d, 1H, J=7.7 Hz); MS, m/z: 397.52 |
| 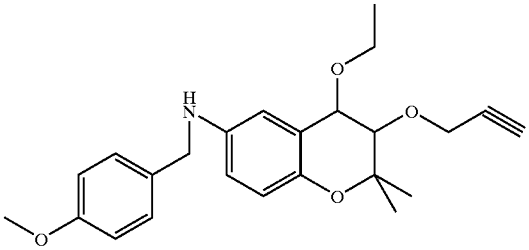 5-368 | $^1$H NMR(200 MHz, $CDCl_3$) δ 7.28(d, 2H, J=8.7 Hz), 6.86(d, 2H, J=8.7 Hz), 6.67~6.57(m, 3H), 4.45(d, 2H, J=2.2 Hz), 4.19(s, 2H), 3.80(s, 3H), 3.70(m, 2H), 2.45(t, 1H, J=2.3 Hz), 1.44s, 3H), 1.24(m, 3H), 1.22(s, 3H); MS, m/z: 395.50 |

TABLE 1-continued
| | Compound No. NMR/MS Data |
|---|---|
| 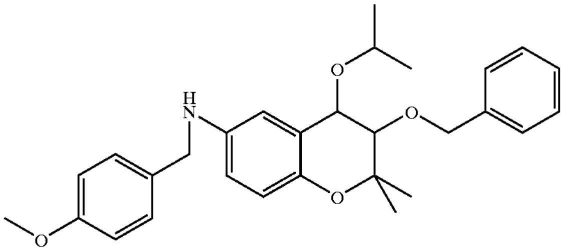 5-369 | MS, m/z: 461.61 |
| 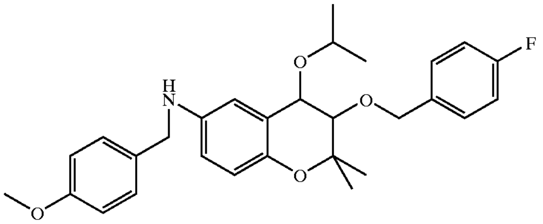 5-370 | MS, m/z: 479.60 |
| 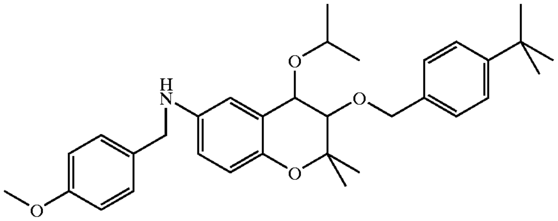 5-371 | MS, m/z: 517.71 |
| 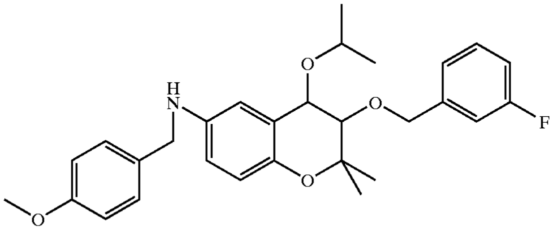 5-372 | MS, m/z 479.60 |
| 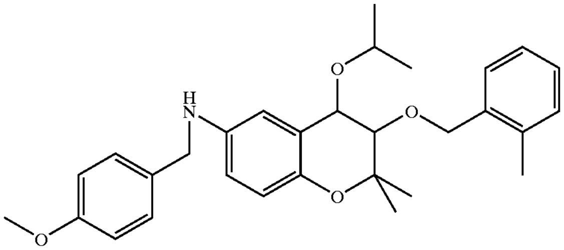 5-373 | MS, m/z: 475.63 |

TABLE 1-continued
| | Compound No. NMR/MS Data |
|---|---|
| 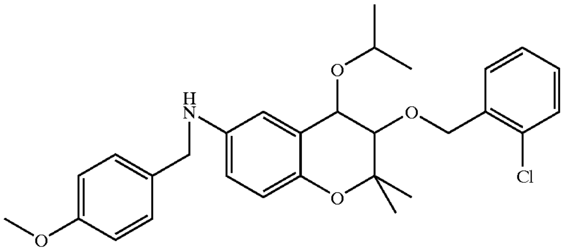 5-374 | MS, m/z: 496.05 |
| 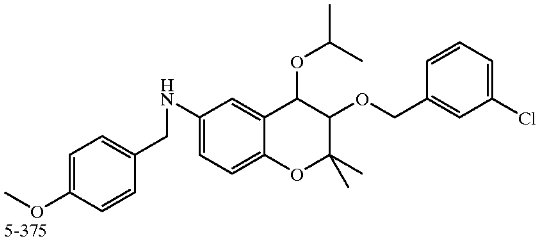 5-375 | MS, m/z: 496.05 |
| 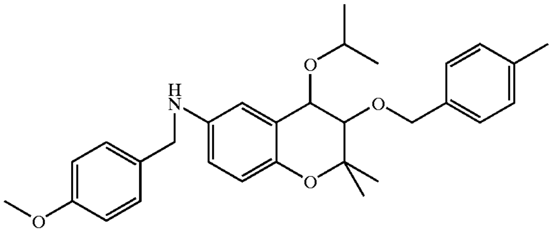 5-376 | MS, m/z: 475.63 |
| 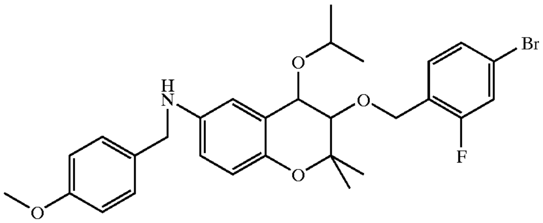 5-377 | MS, m/z: 558.49 |
| 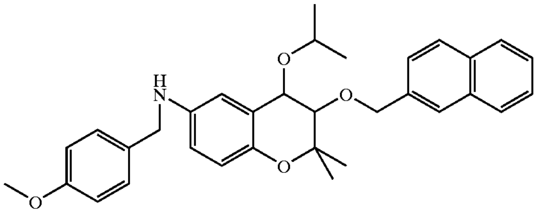 5-378 | MS, m/z: 511.67 |
| 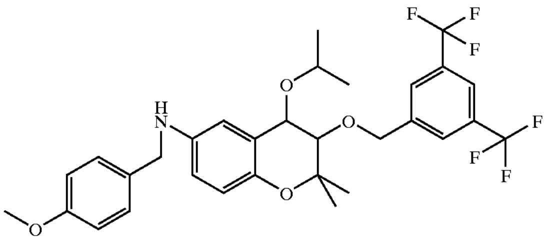 5-379 | MS, m/z: 597.60 |

TABLE 1-continued
| | Compound No. NMR/MS Data |
|---|---|
| 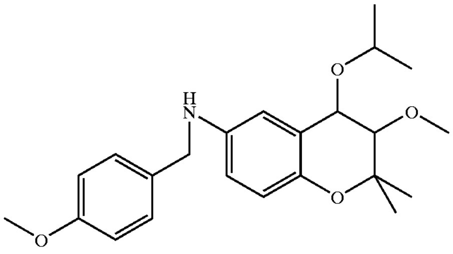 5-380 | MS, m/z: 385.51 |
| 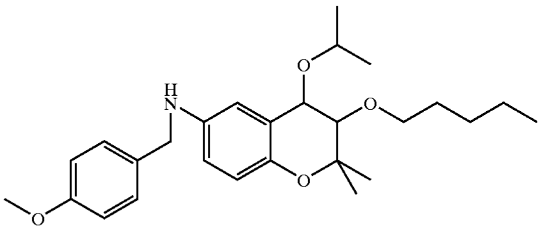 5-381 | MS, m/z: 441.62 |
| 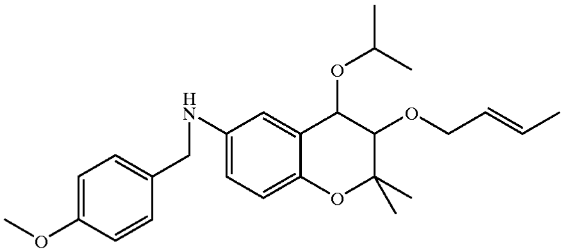 5-382 | MS, m/z: 425.57 |
| 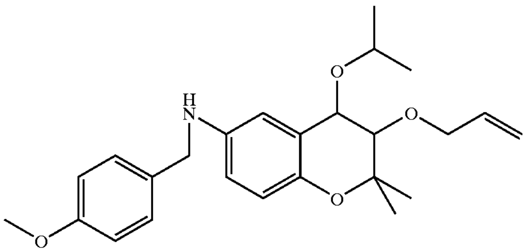 5-383 | MS, m/z: 597.60 |
| 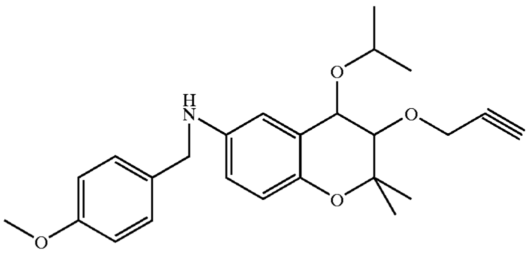 5-384 | MS, m/z: 409.53 |

TABLE 1-continued

| | Compound No. NMR/MS Data |
|---|---|
| 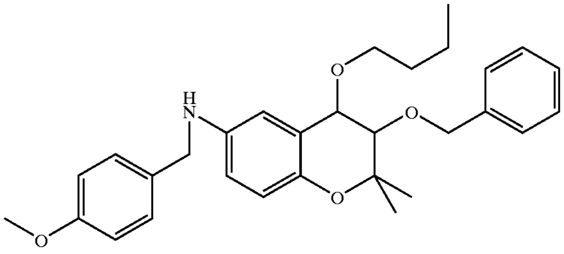 5-385 | $^1$H NMR(200 MHz, $CDCl_3$) δ 7.36~7.25(m, 7H), 6.86(d, 2H, J=8.5 Hz), 6.69~6.58(m, 3H), 4.89(d, 1H, J=11.4 Hz), 4.69(d, 1H, J=11.4 Hz), 4.42(d, 1H, J=7.1 Hz), 4.20(s, 2H), 3.79(s, 3H), 3.70(m, 2H), 3.58(d, 1H, J=7.1 Hz), 1.60(m, 2H), 1.50(m, 2H), 1.40(s, 3H), 1.23(s, 3H), 0.91(t, 3H, J=7.3 Hz); MS, m/z: 475.63 |
| 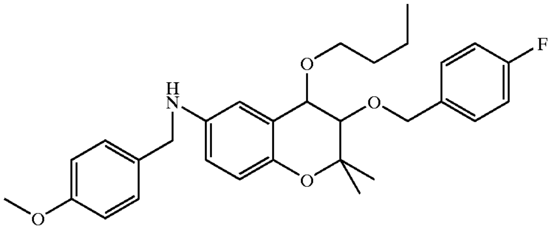 5-386 | $^1$H NMR(200 MHz, $CDCl_3$) δ 7.37~7.23(m, 4H), 7.09~6.99(m, 2H), 6.86(d, 2H, J=8.6 Hz), 6.70~6.57(m, 3H), 4.85(d, 1H, J=11.4 Hz), 4.66(d, 1H, J=11.4 Hz), 4.40(d, 1H, J=7.3 Hz), 4.19(s, 2H), 3.79(s, 3H), 3.68~3.60(m, 2H), 3.57(d, 1H, J= 7.3 Hz), 1.58(m, 2H), 1.38(s, 3H), 1.42~1.25(m, 2H), 1.22(s, 3H), 0.92(t, 3H, J=7.2 Hz); MS, m/z: 493.62 |
| 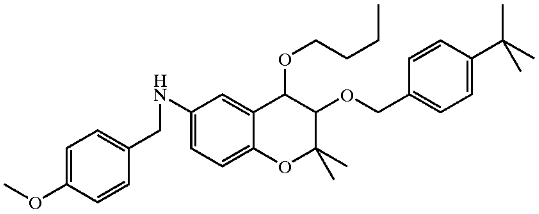 5-387 | $^1$H NMR(200 MHz, $CDCl_3$) δ 7.32~7.22(m, 3H), 7.18~6.99(m, 3H), 6.87(d, 2H, J=8.5 Hz), 6.67~6.56(m, 3H), 4.90(d, 1H, J=12.0 Hz), 4.69(d, 1H, J=12.0 Hz), 4.43(d, 1H, J=7.3z), 4.20(s, 2H), 3.79(s, 3H), 3.64(m, 2H), 3.58(d, 1H, J=7.3 Hz), 1.57(m, 2H), 1.41(s, 3H), 1.41(m, 2H), 1.24(s, 3H), 0.91(t, 3H, J=7.1 Hz); MS, m/z: 531.74 |
| 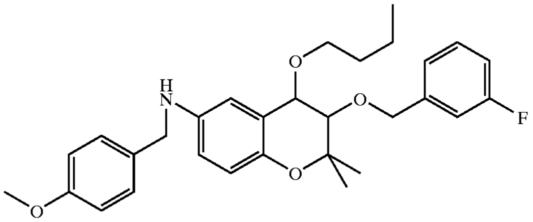 5-388 | $^1$H NMR(200 MHz, $CDCl_3$) δ 7.32~7.25(m, 3H), 7.20~6.99(m, 3H), 6.87(d, 2H, J=8.5 Hz), 6.67~6.56(m, 3H), 4.90(d, 1H, J=12.0 Hz), 4.69(d, 1H), 4.44(d, 1H, J=7.3 Hz), 4.20(s, 2H), 3.79(s, 3H), 3.61(q, 2H, J=7.5 Hz), 1.58(m, 2H), 1.41(s, 3H), 1.43~1.24(m, 2H), 1.24(s, 3H), 0.91(t, 3H, J=7.3 Hz): MS, m/z: 493.62 |
| 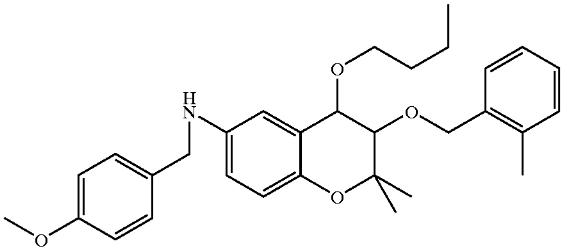 5-389 | $^1$H NMR(200 MHz, $CDCl_3$) δ 7.36~7.16(m, 6H), 6.86(d, 2H, J=8.7 Hz), 6.67~6.56(m, 3H), 4.93(d, 1H, J=11.8 Hz), 4.68(d, 1H, J=11.8 Hz), 4.43(d, 1H, J=7.3 Hz), 4.20(s, 2H), 3.79(s, 3H), 3.64~3.55(m, 3H), 2.35(s, 3H), 1.57(m, 2H), 1.42~1.30(m, 2H), 1.37(s, 3H), 1.23(s, 3H), 0.90(t, 3H, J=7.2 Hz); MS, m/z: 489.66 |

TABLE 1-continued

| Compound No. | NMR/MS Data |
|---|---|
| 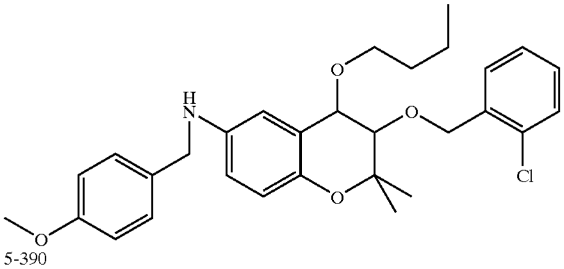 5-390 | $^1$H NMR(200 MHz, $CDCl_3$) δ 7.90~7.73(m, 4H), 7.29(d, 2H, J=8.5 Hz), 6.86(d, 2H, J=8.5 Hz), 5.04(d, 1HJ=12.3 Hz), 4.84(d, 1H, J=12.3 Hz), 4.49(d, 1H, J=7.7 Hz), 4.21(s, 2H), 3.80(s, 3H), 3.70~3.58(m, 3H), 1.62~1.20(m, 4H), 1.44(s, 3H), 1.25(s, 3H), 0.89(t, 3H, J=7.1 Hz); MS, m/z: 510.08 |
| 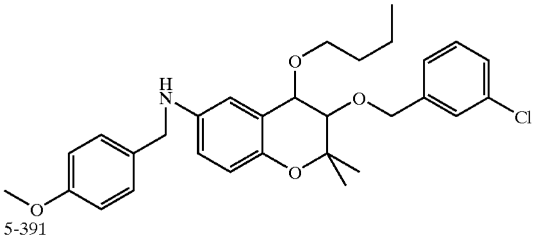 5-391 | $^1$H NMR(200 MHz, $CDCl_3$) δ 7.40~7.25(m, 6H), 7.87(d, 2H, J=6.7 Hz), 6.68~6.57(m, 3H), 4.87(d, 1H, J=11.8 Hz), 4.68(d, 1H, J=11.8 Hz), 4.43(d, 1H, J=7.4 Hz), 4.20(s, 2fH), 3.79(s, 3H), 3.61 (m, 2H), 4.43(d, 1H, J=7.4H), 1.58(m, 2H), 1.41(3, 3H), 1.41 (m, 2H), 1.24(s, 3H), 0.91(t, 3H, J=7.2 Hz); MS, m/z: 510.08 |
| 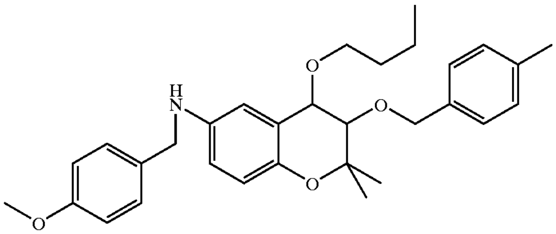 5-392 | $^1$H NMR(200 MHz, $CDCl_3$) δ 7.32~7.14(m, 6H), 6.85(d, 2H, J=8.6 Hz), 6.80~6.60(m, 3H), 4.84(d, 1H, J=11.3 Hz), 4.65(d, 1H, J=11.3 Hz), 4.39(d, 1H, J=7.3 Hz), 4.19(s, 2H), 3.79(s, 3H), 3.76~3.55(m, 3H), 2.35(s, 3H), 1.59(m, 2H), 1.38(s, 3H), 1.39(m, 2H), 1.22(s, 3H), 0/92(t, 3H, J=7.2 Hz); MS, m/z: 489.66 |
| 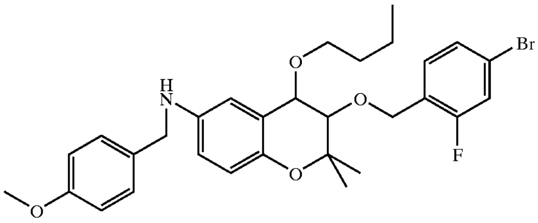 5-393 | $^1$H NMR(200 MHz, $CDCl_3$) δ 7.38~7.20(m, 5H), 6.86(d, 2H, J=7.6 Hz), 6.67~6.55(m, 3H), 4.86(d, 1H, J=11.2 Hz), 4.73(d, 1H, J=11.2 Hz), 4.39(d, 1H, J=7.4 Hz), 4.20(s, 2H), 3.79(s, 3H), 3.64(m, 2H), 3.58(d, 1H, J=7.4H), 1.59(m, 3H), 1.38(s, 3H), 1.39(m, 2H), 1.21(s, 3H), 0.92(t, 3H, J=7.2 Hz); MS, m/z: 572.52 |
| 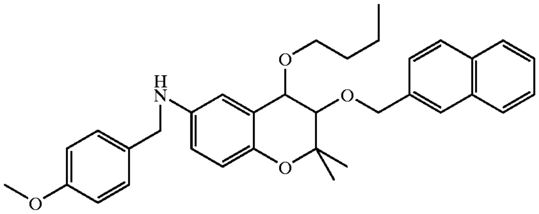 5-394 | $^1$H NMR(200 MHz, $CDCl_3$) δ 7.81(m, 4H), 7.49(m, 3H), 7.2((d, 2H, J=8.7 Hz), 6.87(d, 2H, J=8.7 Hz), 6.68~6.50(m, 3H), 5.02(d, 1H, J=11.2 Hz), 4.89(d, 1H, J=11.2 Hz), 4.44(d, 1H, J=7.1 Hz), 4.20(s, 2H), 3.79(s, 3H), 3.95(d, 1H, J=7.1 Hz), 3.95(m, 2H), 1.59(m, 2H), 1.41(s, 3H), 1.45(m, 2H), 1.26(s, 3H), 0.89(t, 3H, J=7.2 Hz); MS, m/z: 525.69 |
| 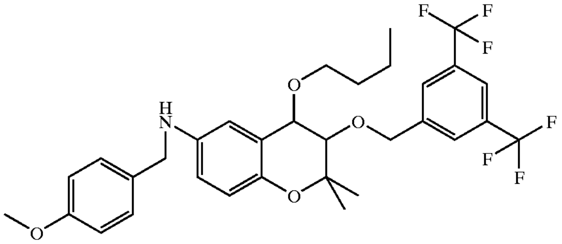 5-395 | $^1$H NMR(200 MHz, $CDCl_3$) δ 7.54(m, 1H), 7.41~7.20(m, 4H), 6.85(d, 2H, J=8.6 Hz), 6.80~6.60(m, 3H), 5.50(d, 1H, J= 11.4 Hz), 4.81(d, 1H, J=11.4 Hz), 4.20(d, 1H, J=7.3 Hz), 3.78(s, 3H), 3.62(m, 3H), 1.58(m, 2H), 1.41(s, 3H), 1.42(m, 2H), 1.26(s, 3H), 0.89(t, 3H, J=7.2 Hz); MS, m/z: 611.63 |

TABLE 1-continued

| | Compound No. NMR/MS Data |
|---|---|
| 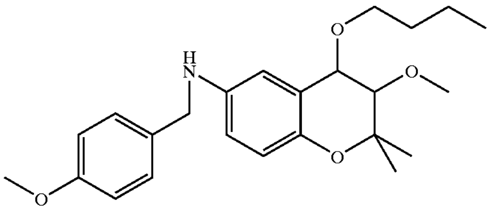 5-396 | $^1$H NMR(200 MHz, $CDCl_3$) δ 7.27(d, 2H, J=8.6 Hz), 6.86(d, 2H, J=8.6 Hz), 6.67~6.57(m, 3H), 4.31(d, 1H, J=7.3 Hz), 419(s, 2H), 3.79(s, 3H), 3.33(m, 3H), 3.60(s, 3H), 6.31(d, 1H, J=7.3 Hz), 1.60(m, 2H), 1.42(m, 2H), 1.41(s, 3H), 1.20(s, 3H), 0.94(t, 3H, J=7.2 Hz); MS, m/z: 399.53 |
| 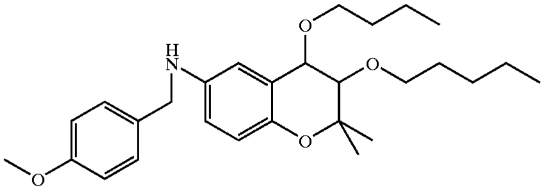 5-397 | $^1$H NMR(200 MHz, $CDCl_3$) δ 7.27(d, 2H, J=9.0 Hz), 6.86(d, 2H, J=9.0 Hz), 6.78~6.50(m, 3H), 4.32(d, 1H, J=7.3 Hz), 4.19(s, 2H), 3.79(s, 3H), 3.84~3.50(m, 4H), 3.38(d, 1H, J=7.3 Hz), 1.60(m, 4H), 1.40(s, 3H), 1.41(m, 6H), 1.20(s, 3H), 0.94(m, 6H); MS, m/z: 455.64 |
| 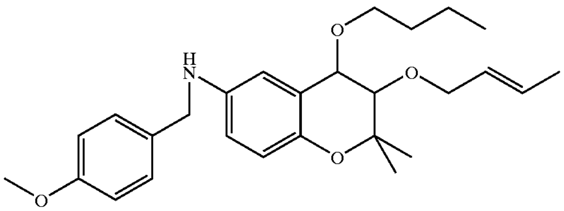 5-398 | $^1$H NMR(200 MHz, $CDCl_3$) δ 7.28(d, 2H, J=8.5 Hz), 6.86(d, 2H, J=8.5 Hz), 5.80~5.51(m, 2H), 4.35(d, 1H, J=7.3 Hz), 4.19(s, 2H), 4.21(m, 2H), 3.79(s, 3H), 3.75(m, 2H), 3.46(d, 1H, J=7.3H), 1.72(d, 3H, J=5.0 Hz), 1.65(m, 2H), 1.39(s, 3H), 1.40(m, 2H), 1.21(s, 3H), 0.94(t, 3H, J=7.2 Hz); MS, m/z: 439.60 |
| 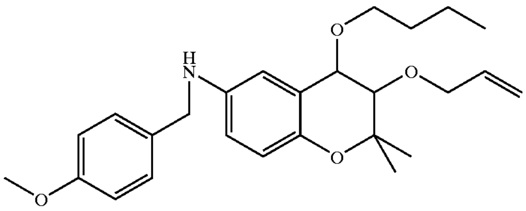 5-399 | $^1$H NMR(200 MHz, $CDCl_3$) δ 7.28(d, 2H, J=8.5 Hz), 6.86(d, 2H, J=8.5 Hz), 6.67~6.57(m, 3H), 5.97(m, 1H), 5.28(d, 1H, J=18.9 Hz), 5.20(d, 1H, J=10.4~Hz), 4.35(d, 1H, J=7.2 Hz), 4.19(s, 2H), .20(m, 2H), 3.79(s, 3H), 3.69(m, 2H), 3.48(d, 1H, J=7.2H), 1.60(m, 2H), 1.40(s, 3H), 1.41(m, 2H), 1.22(s, 3H), 0.93(t, 3H, J=7.1 Hz); MS, m/z: 425.57 |
| 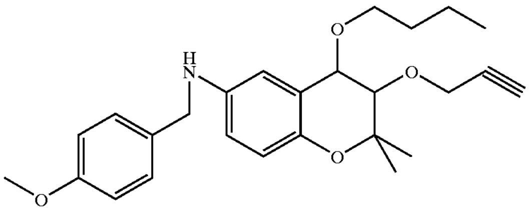 5-400 | $^1$H NMR(200 MHz, $CDCl_3$) δ 7.28(d, 2H, J=8.7 Hz), 6.86(d, 2H, J=8.7), 6.70~6.50(m, 3H), 4.43(m, 3H), 4.19(s, 2H), 3.79(s, 3H), 3.67(m, 3H), 2.45(m, 1H), 1.58(m, H), 1.43(s, 3H), 1.44(m, 2H), 1.23(s, 3H), 0.93(t, 3H, J=7.2 Hz); MS, m/z: 423.56 |
| 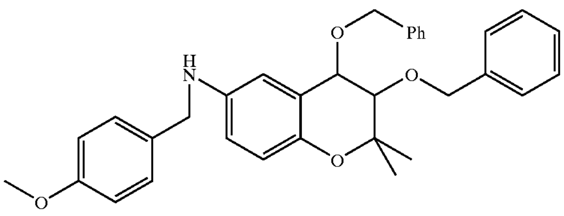 5-401 | $^1$H NMR(200 MHz, $CDCl_3$) δ 7.37~7.28(m, 12H), 6.86(d, 2H), J=8.5 Hz), 6.69~6.56(m, 3H), 4.91(d, 1H, J=11.4 Hz), 4.75~4.61(m, 4H), 4.14(s, 2H), 3.80(s, 3H), 3.71(d, 1H, J=8.1 Hz), 1.45(s, 3H), 1.28(s, 3H); MS, m/z: 509.65 |

TABLE 1-continued

| | Compound No. NMR/MS Data |
|---|---|
| 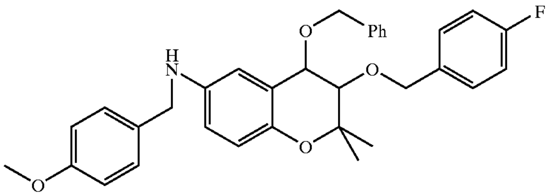 5-402 | $^1$H NMR(200 MHz, $CDCl_3$) δ 7.36~7.24(m, 9H), 7.02(m, 2H), 6.84(d, 2H, J=8.8 Hz), 6.70~6.56(m, 3H), 4.84(d, 1H, J=11.2 Hz), 4.72~4.59(m, 2H), 4.70(s, 2H), 4.13(s, 2H), 3.77(s, 3H), 3.68(d, 1H, J=7.1 Hz), 1.43(s, 3H), 1.26(s, 3H); MS, m/z: 527.64 |
| 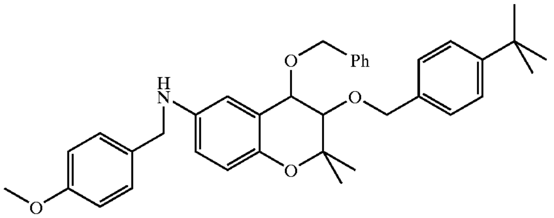 5-403 | $^1$H NMR(200 MHz, $CDCl_3$) δ 7.41~7.24(m, 11H), 6.86(d, 2H, J=8.7 Hz), 6.69~6.58(m, 3H), 4.86(d, 1H, J=11.4 Hz), 4.79~4.58(m, 4H), 4.13(s, 2H), 3.78(s, 3H), 1.44(s, 3H), 1.32(m, 9H), 1.27(s, 3H); MS, m/z: 565.76 |
| 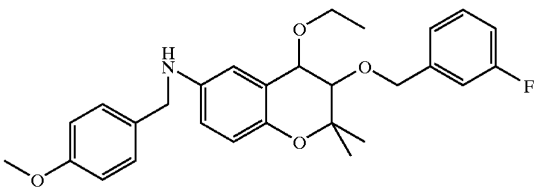 5-404 | $^1$H NMR(200 MHz, $CDCl_3$) δ 7.35~7.25(m, 7H), 7.11~6.89(m, 4H), 6.86(d, 2H, 8.8 Hz), 6.61~6.57(m, 3H), 4.88(d, 1H, J=11.4 Hz), 4.71~4.62(m, 4H), 4.14(s, 2H), 3.79(s, 3H), 3.70(d, 1H, J=7.1 Hz), 1.45(s, 3H), 1.28(s, 3H); MS, m/z: 465.57 |
| 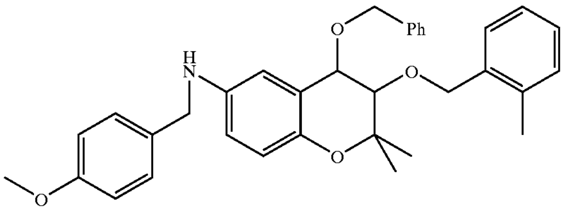 5-405 | $^1$H NMR(200 MHz, $CDCl_3$) δ 7.38~7.17(m, 11H), 6.83(d, 2H, J=8.5 8.5 Hz), 6.70~6.63(m, 3H), 4.90(d, 1H, J=11.6 Hz), 4.71~4.59(m, 4H), 4.10(s, 2H), 3.76(s, 3H), 3.71(d, 1H, J= 7.1 Hz), 2.30(s, 3H), 1.41(s, 3H), 1.27(s, 3H); MS, m/z: 523.68 |
| 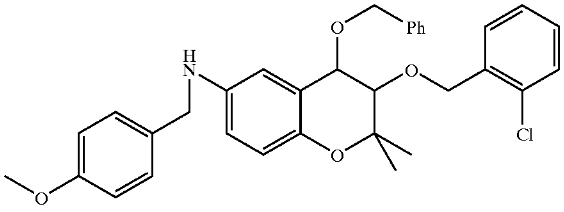 5-406 | $^1$H NMR(200 MHz, $CDCl_3$) δ 7.49~7.09(m, 11H), 6.94~6.87(m, 2H), 6.79~6.69(m, 3H), 4.95(d, 1H, J=12 Hz), 4.91~4.72(m, 3H), 4.58(d, 1H, J=6.7 Hz), 4.12(s, 2H), 3.67(s, 3H), 3.67(m, 1H), 1.43(s, 3H), 1.31(s, 3H); MS, m/z: 544.10 |
| 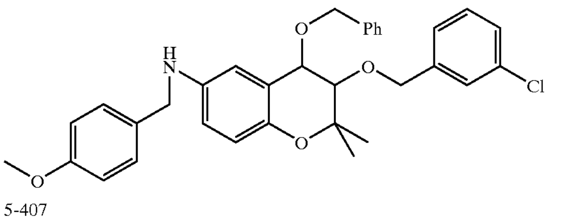 5-407 | $^1$H NMR(200 MHz, $CDCl_3$) δ 7.35~7.19(m, 11H), 6.84(d, 2H, J=8.7 Hz), 6.71~6.63(m, 3H), 4.85(d, 1H, J=12.0 Hz), 4.70(s, 2H), 4.70~4.60(M, 2H), 4.13(s, 2H), 3.76(s, 3H), 3.67(d, 1H, J=7.3 Hz), 1.44(s, 3H), 1.28(s, 3H); MS, m/z: 544.10 |

TABLE 1-continued
| | Compound No. NMR/MS Data |
|---|---|
| 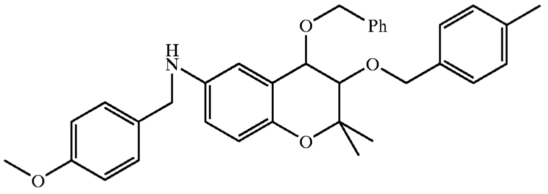 5-408 | $^1$H NMR(200 MHz, $CDCl_3$) δ 7.36~7.13(m, 11H), 6.84~6.67(m, 5H), 4.83(d, 1H, J=11.4 Hz), 4.72~4.56(m, 2H), 4.12(s, 2H), 3.75(s, 3H), 3.66(d, 1H, J=6.9 Hz), 2.35(s, 3H), 1.42(s, 3H), 1.26(s, 3H); MS, m/z: 523.68 |
| 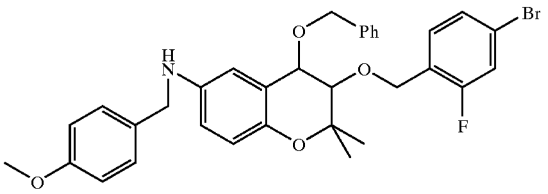 5-409 | $^1$H NMR(200 MHz, $CDCl_3$) δ 7.36~7.21 (m, 10H), 6.85(d, 2H, J=8.7 Hz), 6.69~6.59(m, 3H), 4.84~4.58(m, 5H), 4.12(s, 2H), 3.78(s, 3H), 3.69(d, 1H, J=7.1 Hz), 1.42(s, 3H), 1.24(s, 3H); MS, m/z 606.54 |
| 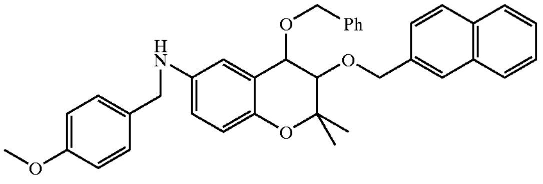 5-410 | $^1$H NMR(200 MHz, $CDCl_3$) δ 7.82(m, 4H), 7.47(m, 3H), 7.34~7.24(m, 7H), 6.85(d, 2H, J=8.5 Hz), 6.72~6.59(m, 3H), 5.04(d, 1H, J=11.5 Hz), 4.87(d, 1H, J=11.5 Hz), 4.74~4.64(m, 3H), 4.149s, 2H), 3.78(s, 3H), 3.74(d, 1H, J=7.1 Hz), 1.46(s, 3H), 1.31(s, 3H); MS, m/z: 559.71 |
| 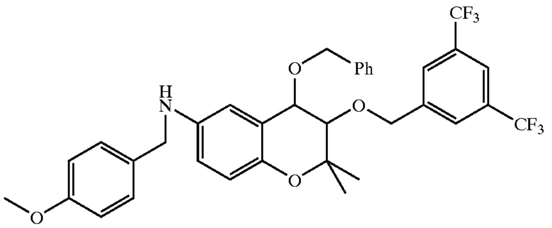 5-411 | MS, m/z: 537.71 |
| 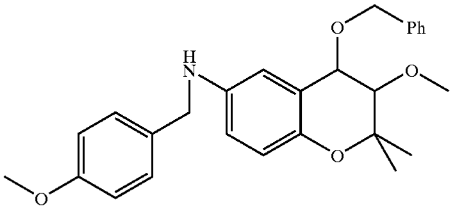 5-412 | MS, m/z: 433.55 |
| 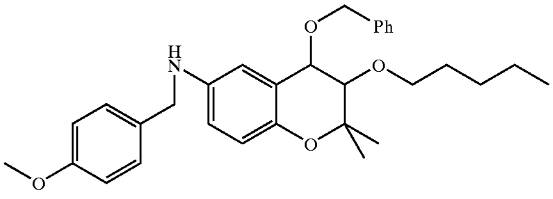 5-413 | $^1$H NMR(200 MHz, $CDCl_3$) δ 7.41~7.20(m, 7H), 6.84~6.65(m, 5H), 4.76(d, 2H, J=4.0 Hz), 4.49(q, 1H, J=17.4 Hz), 4.16(s, 2H), 3.76(m, 1H), 3.75(s, 3H), 3.66(m, 1H), 3.59(d, 1H, J=7.2 Hz), 1.60(br, 2H), 1.43(s, 3H), 1.44~1.23(m, 4H), 1.24(s, 3H), 0.90(m, 3H); MS, m/z: 489.66 |

TABLE 1-continued
| | Compound No. NMR/MS Data |
|---|---|
| 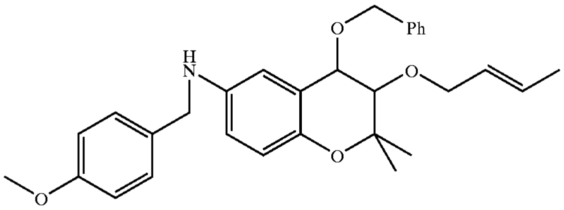 5-414 | $^1$H NMR(200 MHz, $CDCl_3$) δ 7.42~7.25(m, 7H), 6.86(m, 2H), 6.67~6.48(m, 3H), 5.68(m, 2H), 4.77(m, 2H), 4.54(d, 1H, J=7.2 Hz), 4.40~4.15(m, 2H), 4.13(s, 2H), 3.79(s, 3H), 3.58(d, 1H, J=7.2 Hz), 1.73(m, 3H), 1.44(s, 3H), 1.25(s, 3H); MS, m/z: 473.62 |
| 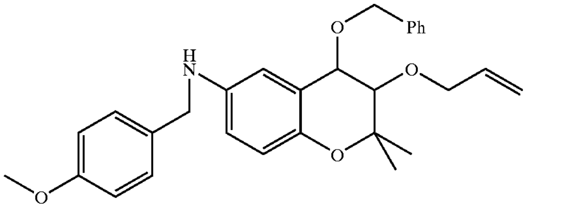 5-415 | $^1$H NMR(200 MHz, $CDCl_3$) δ 7.41~7.23(m, 7H), 6.85(d, 2H, J=8.7 Hz), 6.68~6.55(m, 3H), 5.98(m, 1H), 5.30(d, 1H, J=18.9 Hz), 5.19(d, 1H, J=10.4 Hz), 4.75(q, 2H, J=17.4 Hz), 4.55(d, 1H, J=7.2 Hz), 4.42~4.16(m, 2H), 4.13(s, 2H), 3.79(s, 3H), 3.59(d, 1H, J=7.2 Hz), 1.44(s, 3H), 1.26(s, 3H); MS, m/z: 459.59 |
| 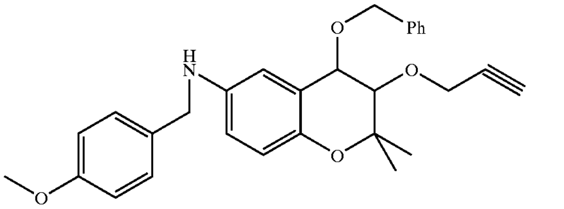 5-416 | MS, m/z: 457.57 |
| 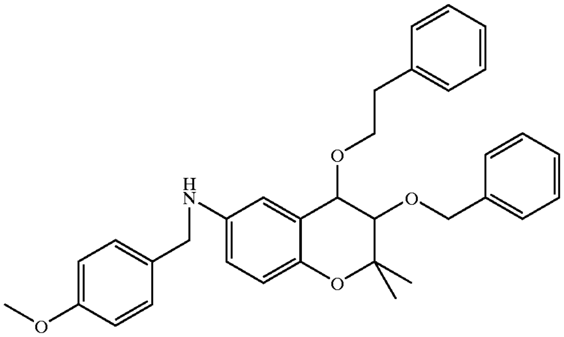 5-417 | MS, m/z: 523.68 |
| 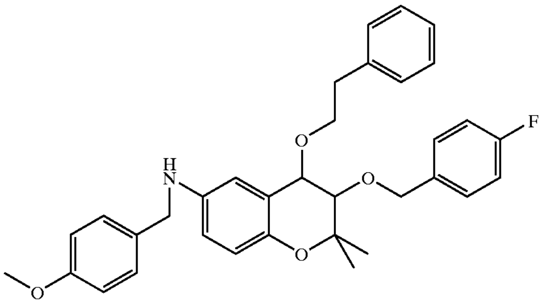 5-418 | MS, m/z: 541.67 |

TABLE 1-continued
| | Compound No. NMR/MS Data |
|---|---|
| 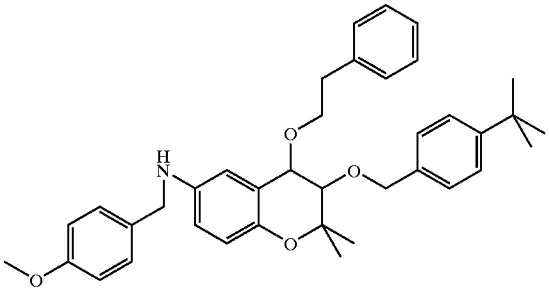 5-419 | MS, m/z: 579.79 |
| 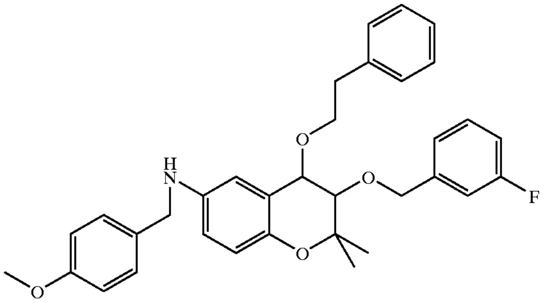 5-420 | MS, m/z: 541.67 |
| 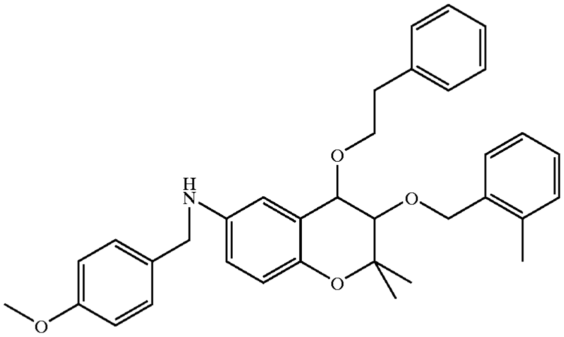 5-421 | MS, m/z: 537.71 |
| 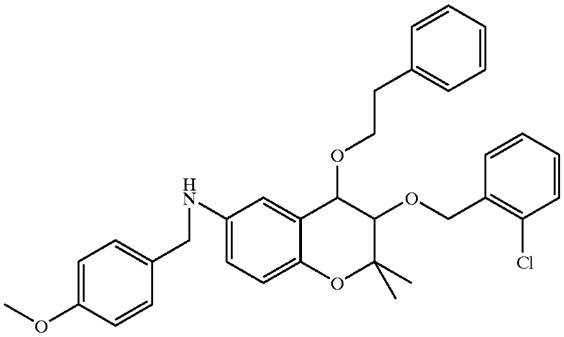 5-422 | MS, m/z: 558.12 |

TABLE 1-continued
| Compound No. | NMR/MS Data |
|---|---|
| 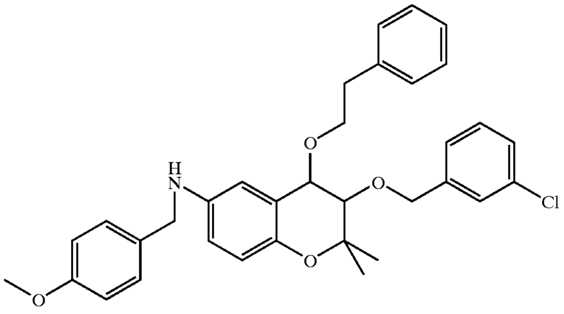 5-423 | MS, m/z: 558.12 |
| 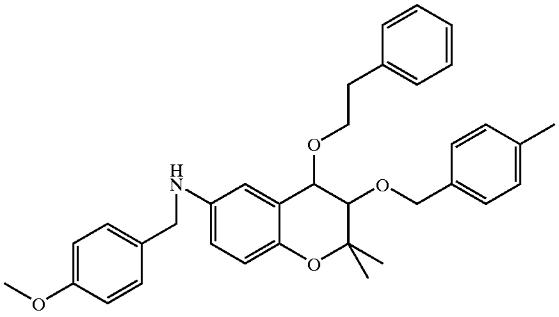 5-424 | MS, m/z: 537.71 |
| 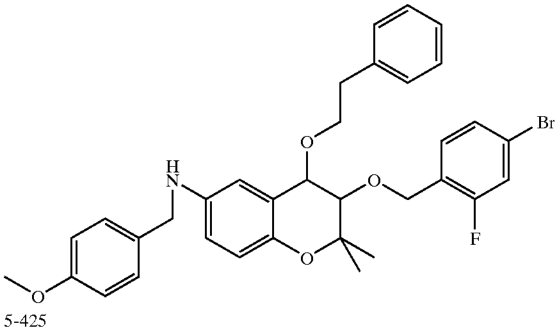 5-425 | MS, m/z: 620.56 |
| 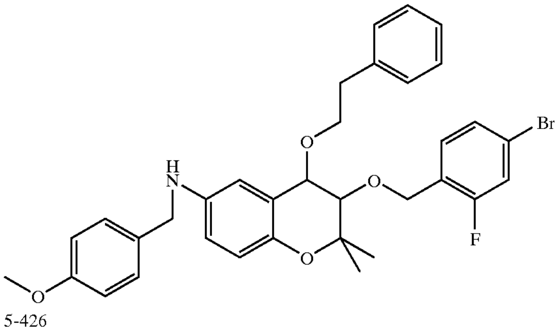 5-426 | MS, m/z: 573.74 |

TABLE 1-continued
| | Compound No. NMR/MS Data |
|---|---|
| 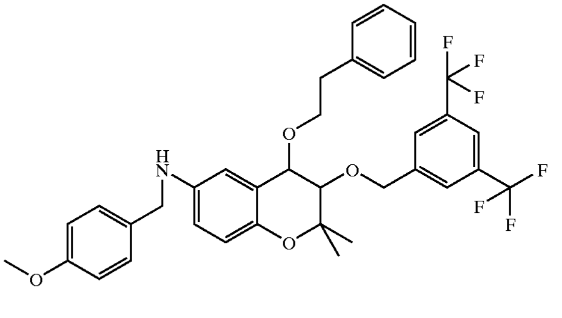 5-527 | MS, m/z: 659.68 |
| 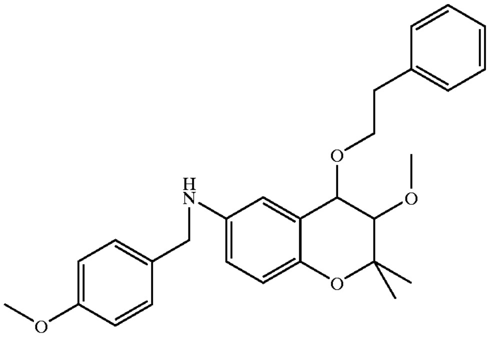 5-428 | MS, m/z: 447.58 |
| 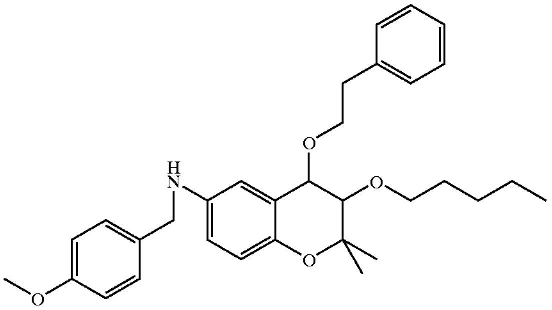 5-429 | MS, m/z: 503.69 |
| 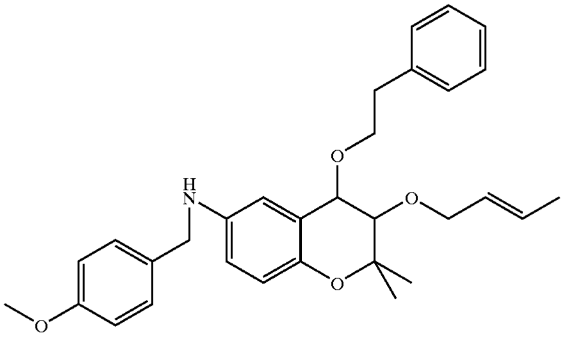 5-430 | MS, m/z: 487.64 |

TABLE 1-continued
| | Compound No. NMR/MS Data |
|---|---|
| 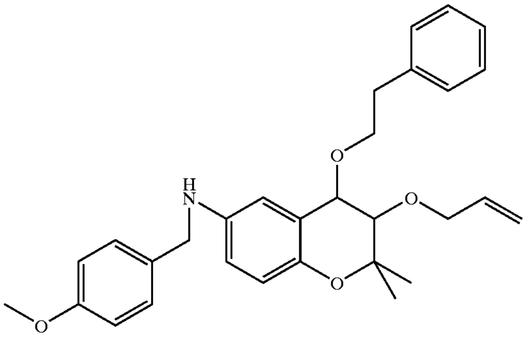 5-431 | MS, m/z: 473.62 |
| 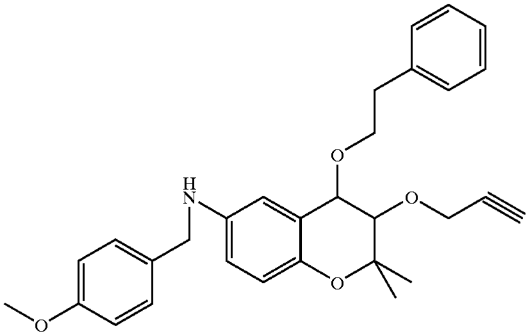 5-432 | MS, m/z: 471.60 |
| 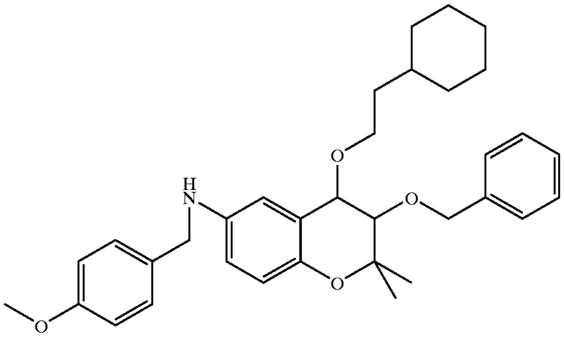 5-433 | $^{1}H$ NMR(200 MHz, $CDCl_3$) δ 7.88~7.26(m, 7H), 6.87(d, 2H, J=8.8 Hz), 6.71~6.589m, 3H), 4.90(d, 1H, J=11.4 Hz), 4.70(d, 1H, J=11.4 Hz), 4.42(d, 1H, J=7.3 Hz), 4.20(s, 2H), 3.80(s, 3H), 3.69(m, 2H), 3.59(d, 1H, J=7.3 Hz), 1.80~1.19(m, 11H), 1.39(s, 3H), 1.24(s, 3H), 0.91(m, 2H); MS, m/z: 529.73 |
| 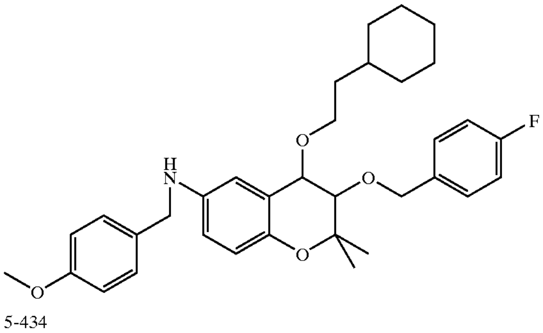 5-434 | $^{1}H$ NMR(200 MHz, $CDCl_3$) δ 7.40~7.20(m, 4H), 7.14~6.96(m, 4H) 6.87(d, 1H, J=8.7 Hz), 6.70~6.55(m, 3H), 4.85(d, 1H, J=11.5 Hz), 4.67(d, 1H, J=11.5 Hz), 4.41 (d, 1H, J=7.3 Hz), 4.20(s, 2H), 3.80(s, 3H), 3.67(m, 2H), 3.57(d, 1H, J=7.3 Hz0, 1.80~1.10(m, 11H), 1.39(s, 3H), 1.23(s, 3H), 0.92(m, 2H); MS, m/z: 547.72 |

TABLE 1-continued
| | Compound No. NMR/MS Data |
|---|---|
| 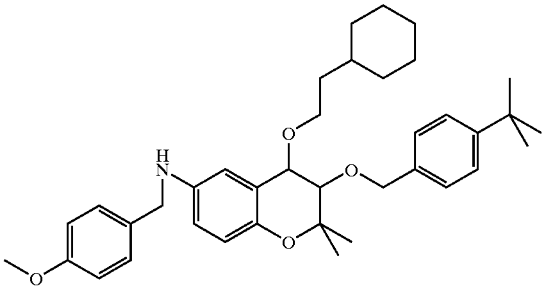 5-435 | $^1$H NMR(200 MHz, $CDCl_3$) δ 7.41~7.26(m, 6H), 6.86(d, 2H, J=8.5 Hz), 6.71~6.55(m, 3H), 4.85(d, 1H, J=11.2 Hz), 4.68(d, 1H, J=11.2 Hz), 4.40(d, 1H, J=7.5 Hz), 4.20(s, 2H), 3.79(s, 3H), 3.70(m, 2H), 3.58(d, 1H, J=7.5 Hz), 1.80~1.05(m, 11h)1.41(s, 3H), 1.32(m, 9H), 1.23(s, 3H), 0.91(m, 2H); MS, m/z: 585.83 |
| 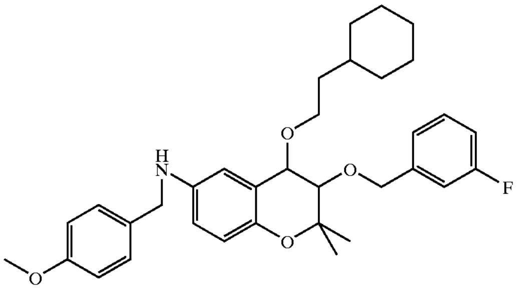 5-436 | $^1$H NMR(200 MHz, $CDCl_3$) δ 7.33~7.26(m, 4H), 7.14~6.98(m, 2H), 6.88(d, 2H, J=8.7 Hz), 6.67~6.56(m ,3H), 4.90(d, 1H, J=11.9 Hz), 4.70(d, 1H, J=11.9 Hz), 4.44(d, 1H, K=7.5 Hz), 4.20(s, 2H), 3.80(s, 3H), 3.68(t, 2H, J=6.6 Hz), 3.59(d, 1H, J=7.5 Hz), 1.80~1.05(m, 11H), 1.40(s, 3H), 1.24(s, 3H), 0.91 (2H); MS, m/z: 547.72 |
| 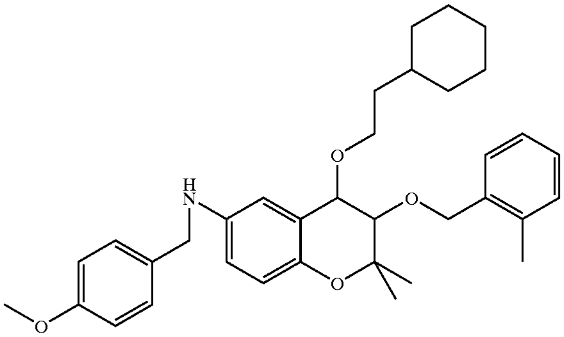 5-437 | MS, m/z: 543.75 |
| 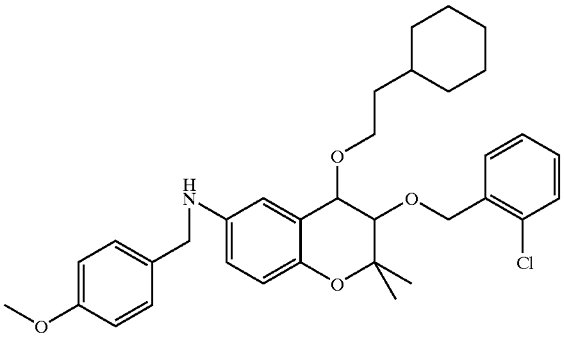 5-438 | $^1$H NMR(200 MHz, $CDCl_3$) δ 7.82(m, 4H), 7.29(d, 2H, J=8.6 Hz), 6.87(d, 2H, J=8.6 Hz), 5.04(d, 1H, J=12.7 Hz), 4.83(d, 1H, J=12.7 Hz), 4.48(d, 1H, J=7.6 Hz), 4.20(s, 2H), 3.80(s, 3H), 3.64(m, 2H), 3.63(d, 1H, J=7.6 Hz), 1.80~1.05(m, 11H), 1.43(s, 3H), 1.25(s, 3H), 0.88(m, 2h); MS, m/z: 564.17 |

TABLE 1-continued

| | Compound No. NMR/MS Data |
|---|---|
| 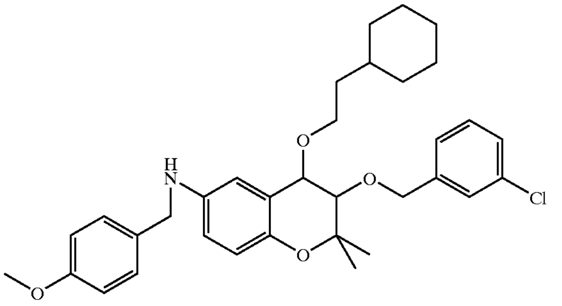 5-439 | $^1$H NMR(200 MHz, $CDCl_3$) δ 7.37~7.20(m, 6H), 6.86(d, 2H, J=8.6 Hz), 6.73~6.62(m, 3H), 4.87(d, 1H, J=11.8 Hz), 4.68(d, 1H, J=11.8 Hz), 4.41 (d, 1H, J=7.7 Hz), 4.20(s, 2H), 3.79(s, 3H), 3.68(t, 2H, J=6.6 Hz), 3.57(d, 1H, J=7.7 Hz), 1.80~1.05(m, 11H), 1.41(s, 3H), 1.24(s, 3H), 0.90(m, 2H); MS, m/z: 564.17 |
| 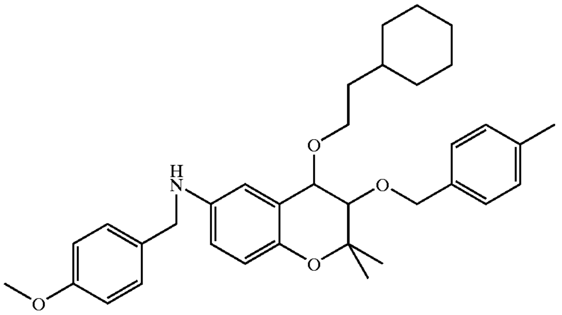 5-440 | $^1$H NMR(200 MHz, $CDCl_3$) δ 7.29~7.14(m, 6H), 6.87~6.78(m, 3H), 6.65(s, 2H), 4.83(d, 1H, J=11.3 Hz), 4.65(d, 1H, J=11.3 Hz), 4.38(d, 1H, J=7.0 Hz), 4.19(s, 2H), 3.78(s, 3H), 3.66(m, 2H), 3.56(d, 1H, J=7.1 Hz), 1.38(s, 3H), 1.80~1.04(m, 11H), 1.38(s, 3H), 1.23(s, 3H), 0.94(m, 2H)543.75 |
| 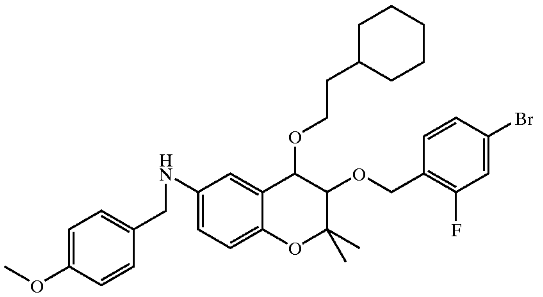 5-441 | $^1$H NMR(200 MHz, $CDCl_3$) δ 7.38~7.22(m, 5H), 6.87(d, 2H, J=8.6 Hz), 6.67~6.51(m, 3H), 4.87(d, 1H, J=12.0 Hz), 4.71(d, 1H, J=12.0 Hz), 3.80(s, 2H), 2.17(s, 3H), 1.80~1.05(m, 11H), 1.39(s, 3H), 1.21(s, 3H), 0.93(m, 2H); MS, m/z: 626.61 |
| 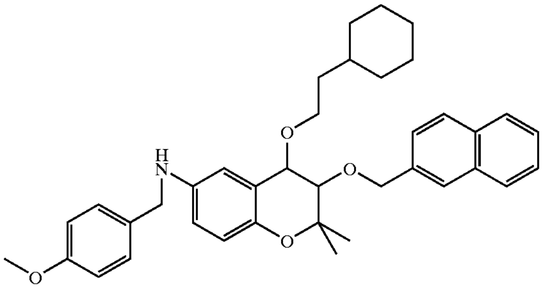 5-442 | $^1$H NMR(200 MHz, $CDCl_3$) δ 7.86~7.80(m, 4H), 7.51~7.46(m, 3H), 7.27~7.23(d, 2H, J=8.1 Hz), 7.01~6.65(m, 5H), 5.03(d, 1H, J=11.7 Hz), 4.36(d, 1H, J=11.7 Hz), 4.41(d, 1H, J=7.0 Hz), 4.18(s, 2H), 3.75(s, 3H), 3.68(m, 2H), 3.62(d, 1H, J=7.0 Hz), 1.78~0.76(m, 13 Hz), 1.39(s, 3H), 1.27(s, 3H); MS, m/z: 579.79 |

TABLE 1-continued
| Compound No. | | NMR/MS Data |
|---|---|---|
| 5-443 | 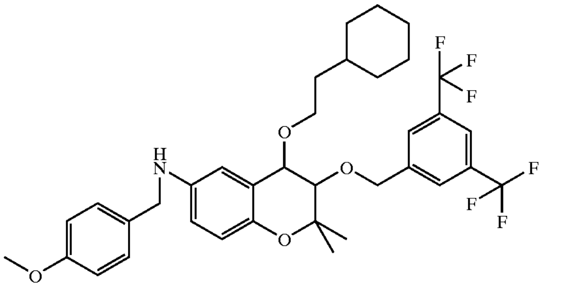 | $^1$H NMR(200 MHz, $CDCl_3$) δ 7.54(m, 1H), 7.38~7.23(m, 4H), 6.86(d, 2H, J=8.7 Hz), 6.79~6.60(m, 3H), 5.01(d, 1H, J=12.8 Hz), 4.80(d, 1H, J=12.8 Hz), 4.4(d, 1H, J=7.3 Hz), 4.20(s, 2H), 3.79(s, 3H), 3.77~3.63(m, 3H), 1.80~1.05(m, 11H), 1.41(s, 3H), 1.26(s, 3H), 0.88(m, 2H); MS, m/z: 665.72 |
| 5-444 | 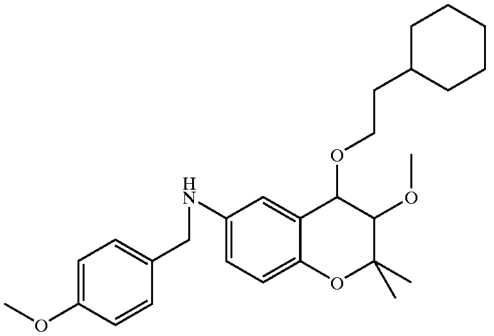 | $^1$H NMR(200 MHz, $CDCl_3$) δ 7.27(d, 2H, J=8.5 Hz), 6.85(d, 2H, J=8.5 Hz), 6.73~6.59(m, 3H), 4.30(d, 1H, J=7.5 Hz), 4.19(s ,2H), 3.79(s, 3H), 3.77(m, 2H), 3.59(m, 2H), 3.98(d, 1H, J=7.5 Hz), 1.80~1.05(m, 17H), 0.90(m, 5H); MS, m/z: 509.74 |
| 5-445 | 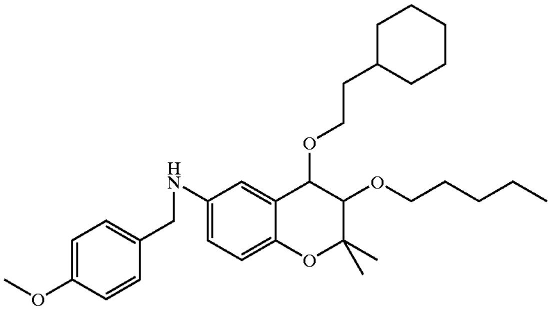 | $^1$H NMR(200 MHz, $CDCl_3$) δ 7.27(d, 2H, J=8.5 Hz), 6.85(d, 2H, J=8.5 Hz), 6.73~6.59(m, 3H), 4.30(d, 1H, J=7.5 Hz), 4.19(s ,2H), 3.79(s, 3H), 3.77(m, 2H), 3.59(m, 2H), 3.98(d, 1H, J=7.5 Hz), 1.80~1.05(m, 17H), 0.90(m, 5H); MS, m/z: 509.74 |
| 5-446 | 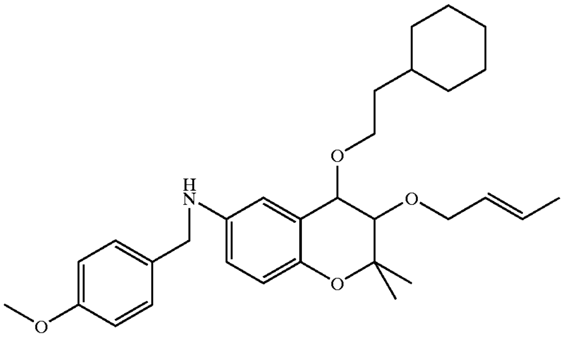 | $^1$H NMR(200 MHz, $CDCl_3$) δ 7.25(d, 2H, J=8.7 Hz), 6.93~6.23(m, 5H), 5.80~5.50(m, 2H), 4.28(d, 1H, J=6.9 Hz), 4.17(s, 2H), 4.13(m, 2H), 3.75(s, 3H), 3.73(m, 2H), 3.43(d, 1H, J=7.1 Hz), 1.80~1.05(m, 11H), 1.72(d, 3H, J=5.9 Hz), 1.39(s, 3H), 1.22(s, 3H), 0.94(m, 2H); MS, m/z: 493.69 |

TABLE 1-continued

| | Compound No. NMR/MS Data |
|---|---|
| 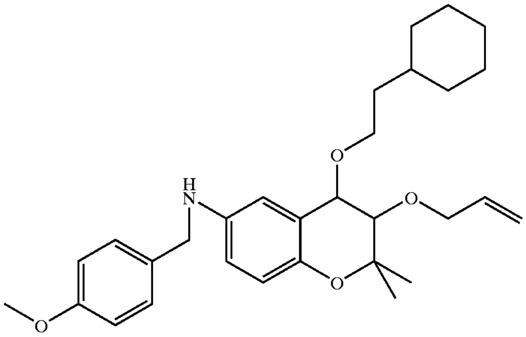 5-447 | $^1$H NMR(200 MHz, $CDCl_3$) δ 7.25(d, 2H, J=8.5 Hz), 6.88~6.62(m, 5 Hz), 5.84(m, 1H), 5.29(dd, 1H, J=17.1 Hz, J=1.5 Hz), 5.18(dd, 1H, J=10.2 Hz, J=1.4 Hz), 4.32(d, 1h, J=7.3 Hz), 4.17(s, 2H), 3.76(s, 3H), 3.74(m, 2H), 3.46(d, 1H, J=7.3 Hz), 1.80~1.05(m, 11H), 1.40(s, 3H), 1.23(s, 3H), 0.90(m, 2H); MS, m/z: 479.67 |
| 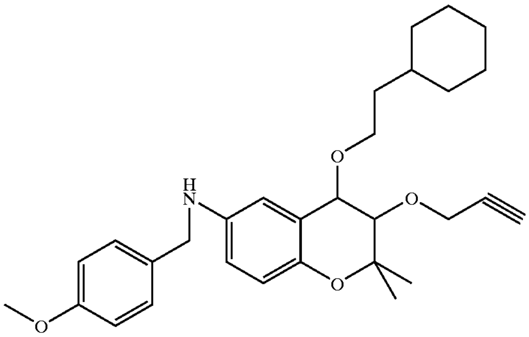 5-448 | $^1$H NMR(200 MHz, $CDCl_3$) δ 7.25(d, 2H, J=8.5 Hz), 6.85~6.68(m, 5H), 4.42(d, 2H, J=2.4 Hz), 4.37(d, 1H, J=7.1 Hz), 4.17(s, 2H), 3.76(s, 3H), 3.75~3.65(m, 3H), 2.46(t, 1H, J=2.3 Hz), 1.80~1.05(m, 11H), 1.43(s, 3H), 1.23(s, 3H), 0.95(m, 2H); MS, m/z: 477.65 |
| 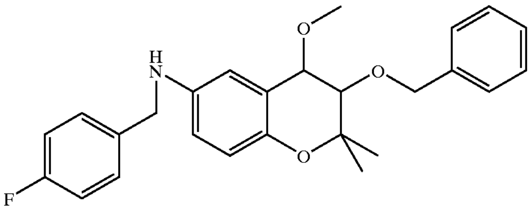 5-449 | $^1$H NMR(200 MHz, $CDCl_3$) δ 7.03~7.41(m, 7H), 6.98~7.06(m, 2H), 6.64(s, 1H), 6.67(d, 1H, J=6.3 Hz), 6.53(dd, 1H, J=2.8 Hz, J=8.7 Hz), 4.92(d, 1H, J=11.4 Hz), 4.72(d, 1H, J=11.5 Hz), 4.41(d, 1H, J=7.3 Hz), 4.25(s, 2H), 3.61(d, 1H, J=7.3 Hz), 3.45(s, 3H), 1.41(s, 3H), 1.24(s, 3H); MS, m/z: 421.52 |
| 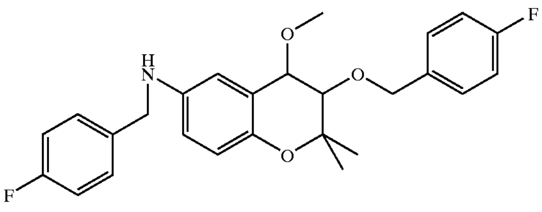 5-450 | $^1$H NMR(200 MHz, $CDCl_3$) δ 7.30~7.39(m, 4H), 6.97~7.08(m, 4H), 6.64(s, 1H), 6.50~6.68(m, 2H), 4.87(d, 1H, J=11.4 Hz), 4.68(d, 1H, J=11.4 Hz), 4.41 (d, 1H, J=7.3 Hz), 4.25(s, 2H), 3.59(d, 1H, J=7.3 Hz), 3.44(s, 3H), 1.40(s, 3H), 1.22(s, 3H); MS, m/z: 439.51 |
| 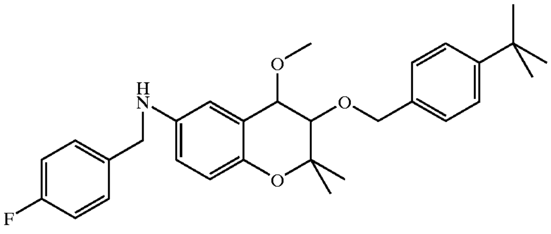 5-451 | MS, m/z: 477.63 |

TABLE 1-continued

| Compound No. | NMR/MS Data |
|---|---|
| 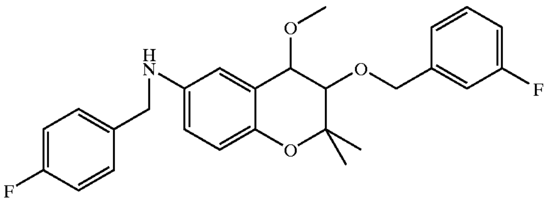 5-452 | $^1$H NMR(200 MHz, $CDCl_3$) δ 7.29~7.37(m, 3H), 6.97~7.14(m, 5H), 6.64(s, 1H), 6.51~6.69(m, 2H), 4.92(d, 1H, J=11.9 Hz), 4.71(d, 1H, J=11.9 Hz), 4.43(d, 1H, J=7.5 Hz), 4.25(s, 2H), 3.60(d, 1H, J=7.5 Hz), 3.44(s, 3H), 1.42(s, 3H), 1.24(s, 3H); MS, m/z: 439.51 |
| 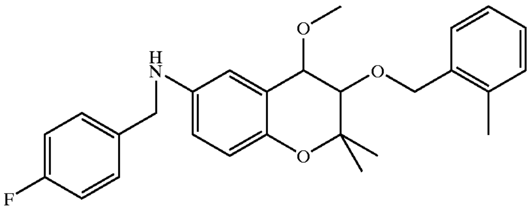 5-453 | $^1$H NMR(200 MHz, $CDCl_3$) δ 7.30~7.41(m, 4H), 7.19~7.24(m, 2H), 6.97~7.06(m, 2H), 6.69(s, 1H), 6.66(d, 1H, J=7.1 Hz), 6.57(dd, 1H, J=2.6 Hz, J=8.7 Hz), 4.92(d, 1H, J=11.6 Hz), 4.70(d, 1H, J=11.6 Hz), 4.40(d, 1H, J=7.3 Hz), 4.25(s, 2H), 3.62(d, 1H, J=7.3 Hz), 3.44(s, 3H), 2.37(s, 3H), 1.39(s, 3H), 1.23(s, 3H); MS, m/z: 435.54 |
| 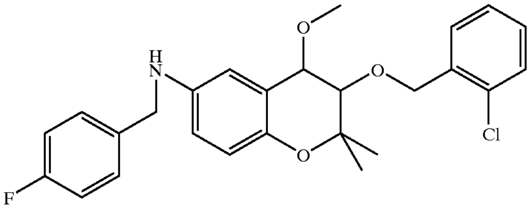 5-454 | MS, m/z: 455.96 |
| 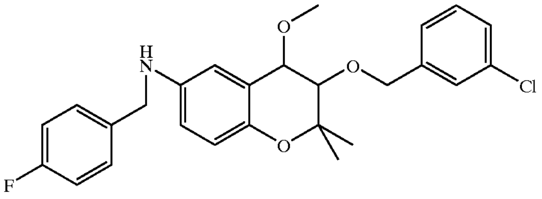 5-455 | $^1$H NMR(200 MHz, $CDCl_3$) δ 7.26~7.38(m, 6H), 6.95~7.04(m, 2H), 6.63~6.74(m, 3H), 4.92(d, 1H, J=11.6 Hz), 4.70(d, 1H, J=11.6 Hz), 4.40(d, 1H, J=7.3 Hz), 4.24(s, 2H), 3.58(d, 1H, J=7.3 Hz), 1.41(s, 3H), 1.24(s, 3H); MS, m/z: 455.96 |
| 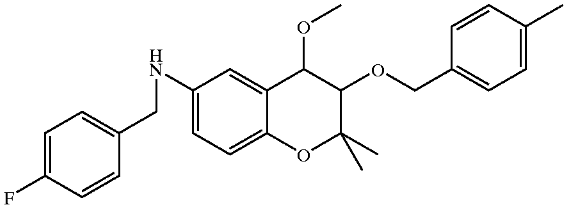 4-456 | $^1$H NMR(200 MHz, $CDCl_3$) δ 7.82~7.86(m, 2H), 7.31~7.54(m, 2H), 7.31~7.26(m, 2H), 6.96~7.05(m, 2H), 6.92~6.73(m, 3H), 5.06(d, 1H, J=11.6 Hz), 4.87(d, 1H, J=11.6 Hz), 4.44(d, 1H, J=7.1 Hz), 4.26(s, 2H), 3.66(d, 1H, J=7.1 Hz), 3.46(s, 3H), 1.42(s, 3H), 1.26(s, 3H); MS, m/z: 435.54 |
| 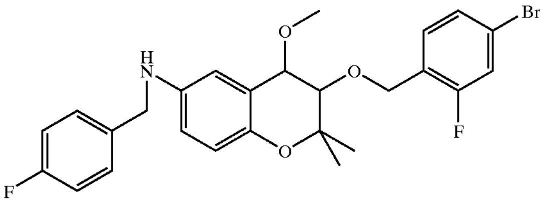 5-457 | $^1$H NMR(200 MHz, $CDCl_3$) δ 7.22~7.38(m, 5H), 6.97~7.06(m, 2H), 6.66(d, 1H, J=6.7 Hz), 6.63(s, 1H), 6.53(dd, 1H, J=2.8, J=8.5 Hz), 4.89(d, 1H, J=12.0 Hz), 4.72(d, 1H, J=12.0 Hz), 4.39(d, 1H, J=7.3 Hz), 4.25(s, 2H), 3.60(d, 1H, J=7.3 Hz), 3.45(s, 3H), 1.39(s, 3H), 1.20(s, 3H); MS, m/z: 518.40 |

TABLE 1-continued

| | Compound No. NMR/MS Data |
|---|---|
| 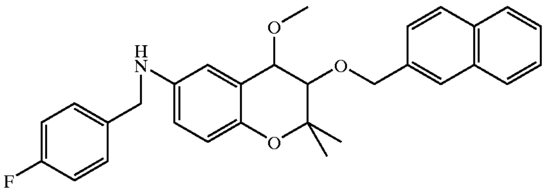 5-458 | MS, m/z: 471.58 |
| 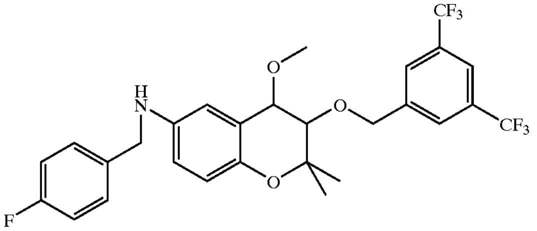 5-459 | $^1$H NMR(200 MHz, $CDCl_3$) δ 7.83(s, 3H), 7.29~7.36(m, 2H), 6.96~7.05(m, 2H), 6.63~6.73(m, 3H), 5.05(d, 1H, J=12.6 Hz), 4.83(d, 1H, J=12.6 Hz), 4.46(d, 1H, J=7.5 Hz), 4.25(s, 2H), 3.63(d, 1H, J=7.5 Hz), 3.42(s, 3H), 1.45(s, 3H), 1.25(s, 3H); MS, m/z: 557.51 |
| 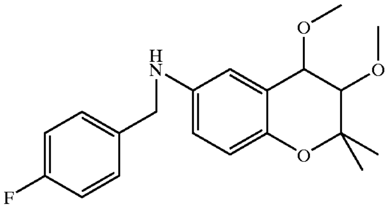 5-460 | $^1$H NMR(200 MHz, $CDCl_3$) δ 7.26~7.36(m, 2H), 6.97~7.05(m, 2H), 6.62~6.68(m, 2H), 6.53(dd, 1H, J=2.8, J=8.7 Hz), 4.29(d, 1H, J=7.1 Hz), 4.24(s, 2H), 3.60(s, 3H), 3.50(s, 3H), 1.41(s, 3H), 1.20(s, 3H); MS, m/z: 345.42 |
| 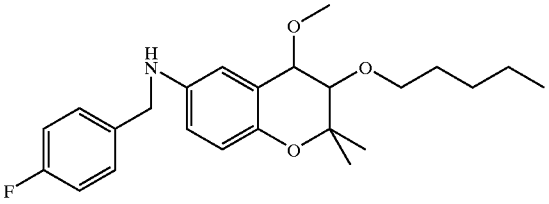 5-461 | $^1$H NMR(200 MHz, $CDCl_3$) δ 7.27~7.36(m, 2H), 6.96~7.04(m, 2H), 6.54~6.69(m, 3H), 4.27(d, 1H, J=7,5 Hz), 4.24(s, 2H), 3.51~3.88(m, 2H), 3.50(s, 3H), 3.39(d, 1H, J=7.5 Hz), 1.57~1.61(m, 2H), 1.40(s, 3H), 1.25~1.36(m, 4H), 1.20(s, 3H), 0.90~0.94(m, 3H); MS, m/z: 401.53 |
| 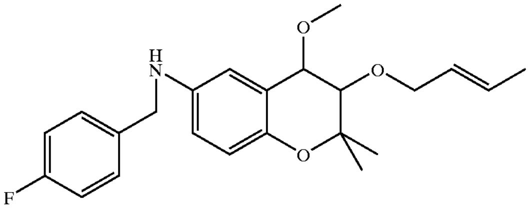 5-462 | $^1$H NMR(200 MHz, $CDCl_3$) δ 7.30~7.37(m, 2H), 6.97~7.05(m, 2H), 6.65(d, 1H, J=4.1 Hz), 6.62(s, 1H), 6.65(dd, 1H, J=2.6 Hz, J=8.7 Hz), 5.58~5.73(m, 2H), 4.31(d, 1H, J=7.1 Hz), 4.07~4.26(m, 2H), 4.24(s, 2H), 3.48(d, 1H, J=7.1 Hz), 3.49(s, 3H), 1.72(d, 3H, J=6.1), 1.40(s, 3H), 1.21(s, 3H); MS, m/z: 385.48 |
| 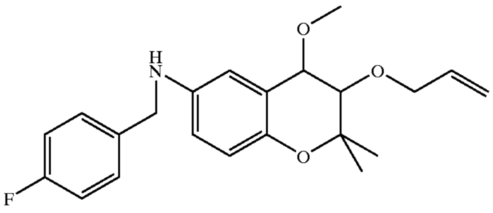 5-463 | $^1$H NMH(200 MHz, $CDCl_3$) δ 7.29~7.38(m, 2H), 6.96~7.04(m, 2H), 6.59~6.71(m, 3H), 5.87~6.01 (m, 1H), 5.16~5.34(m, 2H), 4.18~4.43(m, 2H), 4.24(s, 2H), 3.49(s, 3H), 1.41(s, 3H), 1.22(s, 3H); MS, m/z: 371.46 |

TABLE 1-continued

| | Compound No. NMR/MS Data |
|---|---|
| 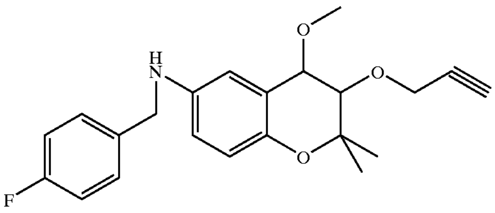 5-464 | MS, m/z: 369.44 |
| 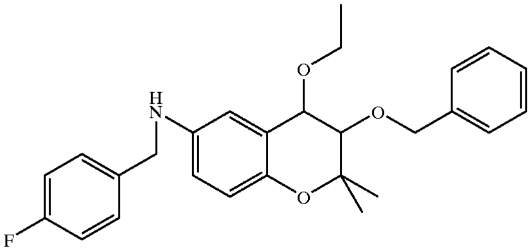 5-465 | $^1$H NMR(200 MHz, $CDCl_3$) δ 7.26~7.38(m, 7H), 6.95~6.04(m, 2H), 6.51~6.68(m, 3H), 4.90(d, 1H, J=12.0 Hz), 4.71(d, 1H, J=12.0 Hz), 4.43(d, 1H, J=7.5 Hz), 4.25(s, 2H), 3.64~3.23(m, 2H), 3.59(d, 1H, J=7.5 Hz), 1.40(s, 3H), 1.23(s, 3H), 1.18~1.21(m, 3H); MS, m/z: 435.54 |
| 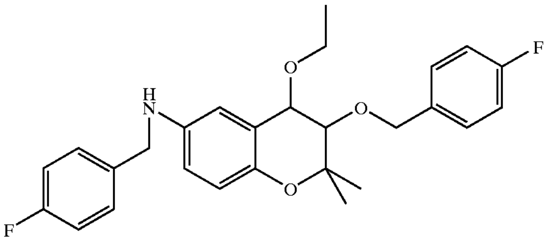 5-466 | $^1$H NMR(200 MHz, $CDCl_3$) δ 7.22~7.38(m, 4H), 6.96~7.08(m, 4H), 6.49~6.69(m, 3H), 4.87(d, 1H, J=11.4 Hz), 4.67(d, 1H, J=11.4 Hz), 4.43(d, 1H, J=7.5 Hz), 4.25(s, 2H), 3.64~3.75(m, 2H), 3.58(d, 1H, J=7.5 Hz), 1.40(s, 3H), 1.22(s, 3H), 1.18~1.25(m, 3H); MS, m/z: 453.53 |
| 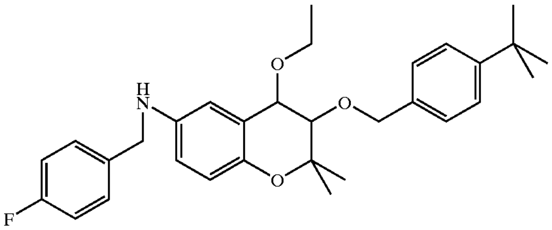 5-467 | $^1$H NMR(200 MHz, $CDCl_3$) δ 7.26~7.41(m, 6H), 6.95~7.04(m, 2H), 6.65~6.75(m, 3H), 4.86(d, 1H, J=11.4 Hz), 4.68(d, 1H, J=11.4 Hz), 4.39(d, 1H, J=7.5 Hz), 4.24(s, 2H), 3.64~3.74(m, 2H), 3.58(d, 1H, J=7.5 Hz), 1.41(s, 3H), 1.33(s, 9H), 1.31(s, 3H), 1.18~1.25(m, 3H); MS, m/z: 491.65 |
| 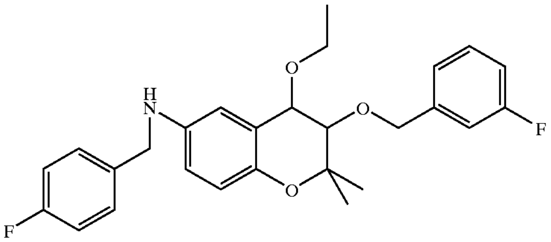 5-468 | $^1$H NMR(200 MHz, $CDCl_3$) δ 7.24~7.38(m, 3H), 6.95~7.14(m, 5H), 6.50~6.70(m, 3H), 4.90(d, 1H, J=11.6 Hz), 4.70(d, 1H, J=11.6 Hz), 4.44(d, 1H, J=7.7 Hz), 4.25(s, 2H), 3.63~3.74(m, 2H), 3.58(d, 1H, J=7.7 Hz), 1.41(s, 3H), 1.23(s, 3H), 1.17~1.27(m, 3H); MS, m/z: 453.53 |

TABLE 1-continued

| | Compound No. NMR/MS Data |
|---|---|
| 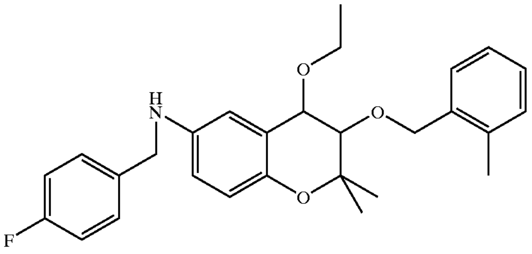 5-469 | $^1$H NMR(200 MHz, $CDCl_3$) δ 7.16~7.40(m, 6H), 6.98~7.06(m, 2H), 4.50~6.67(m, 3H), 4.92(d, 1H, J=11.8 Hz), 4.69(d, 1H, J=11.8 Hz), 4.43(d, 1H, J=7.7 Hz), 4.25(s, 2H), 3.63~3.74(m, 2H), 3.62(d, 1H, J=7.7 Hz), 2.35(s, 3H), 1.38(s, 3H), 1.22(s, 3H), 1.17~1.20(m, 3H); MS, m/z: 449.57 |
| 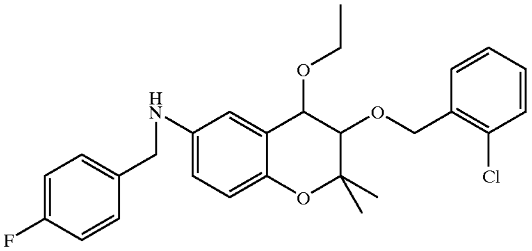 5-470 | $^1$H NMR(200 MHz, $CDCl_3$) δ 7.18~7.38(m, 5H), 6.97~7.06(m, 2H), 6.50~6.68(m, 3H), 4.02(d, 1H, J=12.4 Hz), 4.79(d, 1H, J=12.4 Hz), 4.46(d, 1H, J=7.5 hz), 4.25(s, 2H), 3.63~3.75(m, 3H0, 1.41(s, 3H), 1.25(s, 3H), 1.17~1.24(m, 3H); MS, m/z: 469.99 |
| 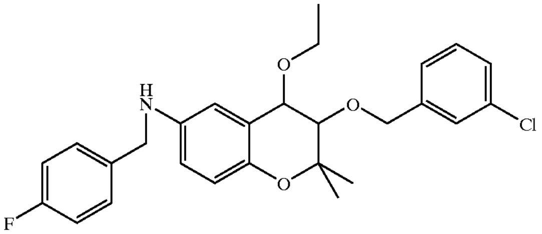 5-471 | $^1$H NMR(200 MHz, $CDCl_3$) δ 7.14~7.38(m, 6H), 6.95~7.06(m, 2H), 6.50~6.67(m, 3H), 4.88(d, 1H, J=11.8 Hz), 4.64(d, 1H, J=11.8 Hz), 4.43(d, 1H, J=7.9 Hz), 4.25(s, 2H), 3.63~3.73(m, 2H), 3.58(d, 1H, J=7.9 Hz), 1.41(s, 3H), 1.23(s, 3H), 1.17~1.21(m, 3H); MS, m/z: 469.99 |
| 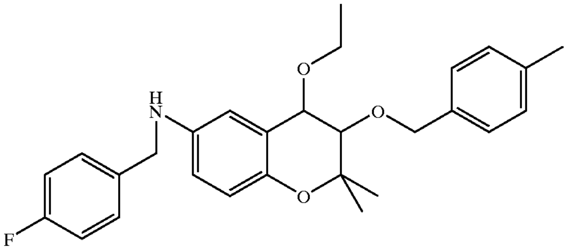 5-472 | $^1$H NMR(200 MHz, $CDCl_3$) δ 7.14~7.37(m, 6H), 6.96~7.05(m, 2H), 6.53~6.67(m, 3H), 4.85(d, 1H, J=11.2 Hz), 4.65(d, 1H, J=11.2 Hz), 4.40(d, 1H, J=7.5 Hz), 4.25(s, 2H), 3.60~3.75(m, 2H0, 3.57(d, 1H, J=7.5 Hz), 2.35(s, 3H), 1.39(s, 3h), 1.22(s, 3H), 1.18~1.25(m, 3H); MS, m/z: 449.57 |
| 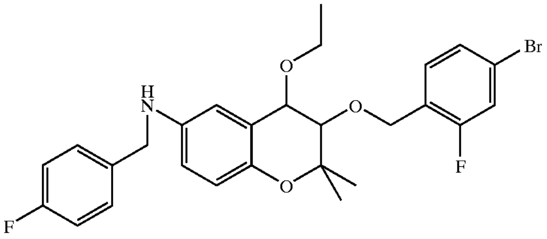 5-473 | $^1$H NMR(200 MHz, $CDCl_3$) δ 7.20~7.38(m, 5H), 6.95~7.03(m, 2H), 6.49~6.68(m, 3H), 4.89(d, 1H, J=11.0 Hz), 4.71(d, 1H, J=11.0 Hz), 4.41(d, 1H, J=7.5 Hz), 4.25(s, 2H), 3.65~3.75(m, 2H), 3.59(d, 1H, J=7.5 Hz), 1.39(s, 3H), 1.20(s, s. 3H), 1.18~1.21(m, 3H); MS, m/z: 532.43 |

TABLE 1-continued
| | Compound No. NMR/MS Data |
|---|---|
| 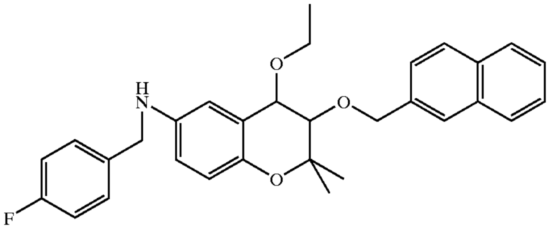 5-474 | $^1$H NMR(200 MHz, $CDCl_3$) δ 7.76~7.87(m, 4H), 7.44~7.53(m, 3H), 7.32~7.43(m, 2H), 6.96~7.31(m, 2H), 6.59~6.69(m, 3H), 5.06(d, 1H, J=11.8 Hz), 4.88(d, 1H, J=11.8 Hz), 4.47(d, 1H, J=7.5 Hz), 4.25(s, 2H), 3.69~3.77(m, 2H), 3.66(d, 1H, J=7.5 Hz), 1.42(s, 3H), 1.27(s, 3H), 1.19~1.26(m, 3H); MS, m/z: 485.60 |
| 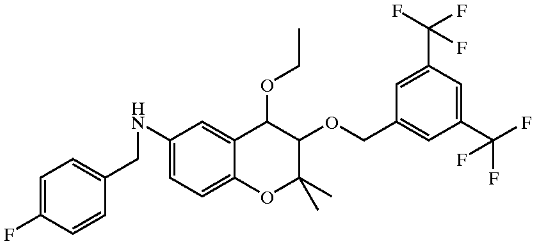 5-475 | MS, m/z: 571.54 |
| 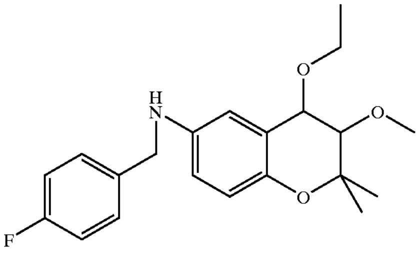 5-476 | MS, m/z: 359.44 |
| 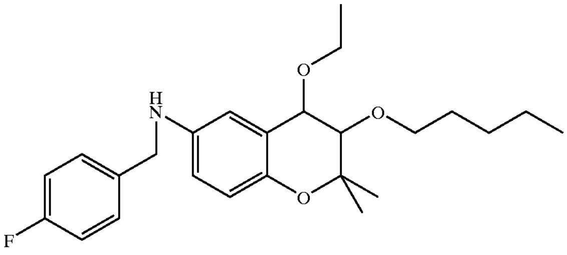 5-477 | $^1$H NMR(200 MHz, $CDCl_3$) δ 7.26~7.37(m, 2H), 6.96~7.05(m, 2H), 6.50~6.65(m, 3H), 4.31(d, 1H, J=7.5 Hz), 4.24(s, 2H), 3.57~3.84(m, 4H), 3.38(d, 1H, J=7.5 Hz), 1.57~1.63(m, 2H), 1.40(s, 3H), 1.21~1.37(m, 7H), 1.19(s, 3H), 0.88~0.94(m, 3H); MS, m/z: 415.55 |
| 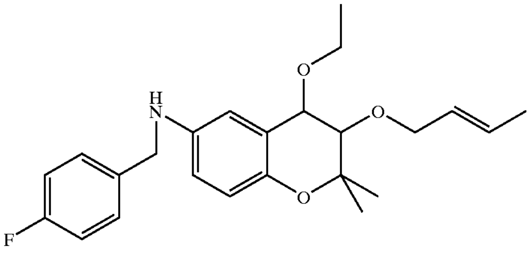 5-478 | $^1$H NMR(200 MHz, $CDCl_3$) δ 7.26~7.37(m, 2H), 6.97~7.06(m, 2H), 6.47~6.65(m, 3H), 5.63~5.71(m, 2H), 4.34(d, 1H, J=7.9 Hz), 4.24(s, 2H), 4.12~4.31(m, 2H), 3.70~3.78(m, 2H), 3.46(d, 1H, J=7.5 hz), 1.72(d, 3H, J=5.3 Hz), 1.40(s, 3H), 1.23~1.27(m, 3H), 3H), 1.20(s, 3H); MS, m/z: 399.51 |

TABLE 1-continued
| | Compound No. NMR/MS Data |
|---|---|
| 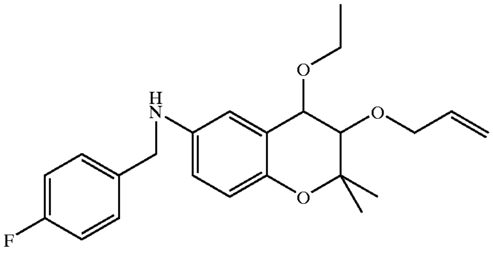 5-479 | $^1$H NMR(200 MHz, $CDCl_3$) δ 7.30~7.37(m, 2H), 6.97~7.06(m, 2H), 6.01~6.66(m, 3H), 5.87~5.98(m, 1H), 5.14~5.35(m, 2H), 4.36(d, 1H, J=7.5 Hz), 4.24(s, 2H), 4.12~4.32(m, 2H), 3.66~3.79(m, 2H), 3.48(d, 1H, J=7.5 Hz), 1.41(s, 3H), 1.23(s, 3H), 1.19~1.22(m, 3H); MS, m/z: 385.48 |
| 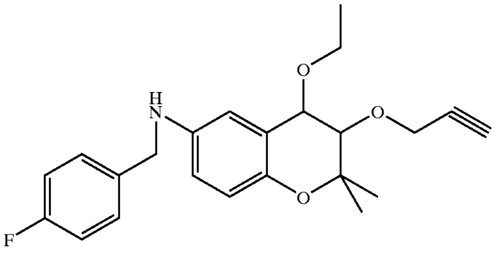 5-480 | MS, m/z: 383.47 |
| 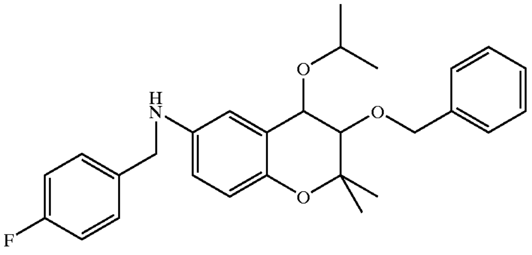 5-481 | $^1$H NMR(200 MHz, $CDCl_3$) δ 0.76~0.38(m, 7H), 6.96~7.07(m, 2H), 6.48~6.68((m, 3H), 4.88(d, 1H, J=11.4 Hz), 4.69(d, 1H, J=11.4 Hz), 4.37(d, 1H, J=7.1 Hz), 4.25(s, 2H), 3.96~4.02(m, 1H), 3.52(d, 1H, J=7.1 Hz), 1.38(s, 3H), 1.27(s, 3H), 1.24(d, 3H, J=1.6 Hz), 1.20(d, 3H, J=1.2 Hz); MS, m/z: 449.57 |
| 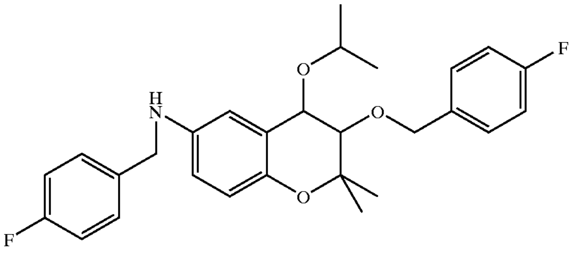 5-482 | $^1$H NMR(200 MHz, $CDCl_3$) δ 7.21~7.38(m, 4H), 6.94~7.08(m, 4H), 6.48~6.69(m, 3H), 4.56~4.86(m, 2H), 4.36(d, 1H, J=7.3 Hz), 4.25(s, 2H), 3.95~4.01(m, 1H), 3.50(d, 1H, J=7.2 Hz), 1.37(s, 3H), 1.26(2, 3H), 1.21~1.25(m, 6H); MS, m/z: 467.56 |
| 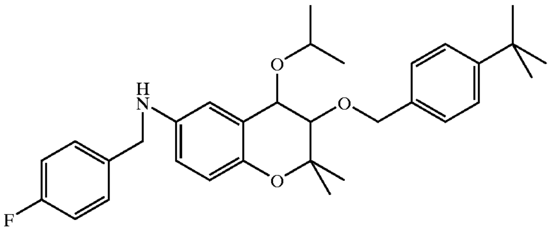 5-483 | MS, m/z: 505.68 |

TABLE 1-continued

| | Compound No. NMR/MS Data |
|---|---|
| 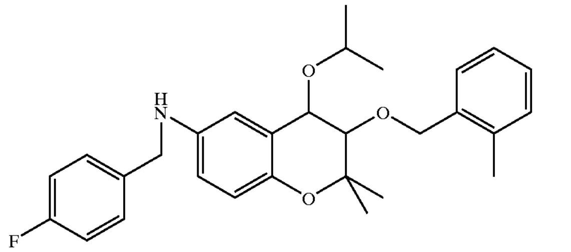<br>5-484 | $^1$H NMR(200 MHz, $CDCl_3$) δ 7.23~7.38(m, 3H), 6.95~7.09(m, 5H), 6.48~6.62(m, 3H), 4.88(d, 1H, J=11.8 Hz), 4.68(d, 1H, J=12.2 Hz), 4.38(d, 1H, J=7.3 Hz), 4.25(s, 2H), 3.95~4.01(m, 1H), 3.51 (d, 1H, J=7.3 Hz), 1.39(s, 3H), 1.28(s, 3H), 1.23(d, 3H, J=2.4 Hz), 1.20(d, 3H, J=2.6 Hz); MS, m/z: 467.56 |
| 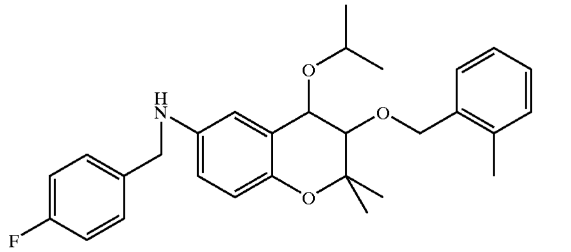<br>5-485 | $^1$H NMR(200 MHz, $CDCl_3$) δ 7.16~7.40(m, 6H), 6.97~7.06(m, 2H), 6.48~6.66(m, 3H), 4.87(d, 1H, J=12.0 Hz), 4.70(d, 1H, J=12.0 Hz), 4.36(d, 1H, J=7.3 Hz), 4.25(s, 2H), 3.92~3.99(m, 1H), 3.54(d, 1H, J=7.3 Hz), 2.32(s, 3H), 1.34(s, 3H), 1.28(s, 3H), 1.18~1.26(m, 6H); MS, m/z: 463.60 |
| 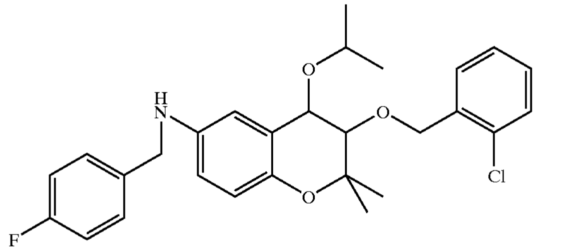<br>5-486 | $^1$H NMR(200 MHz, $CDCl_3$) δ 7.15~7.48(m, 6H), 6.92~7.05(m, 2H), 6.54~6.70(m, 3H), 4.99(d, 1H, J=12.9 Hz), 4.78(d, 1H, J=12.8 Hz), 4.40(d, 1H, J=7.3 Hz), 4.24(s, 2H), 3.82~4.02(m, 1H), 3.58(d, 1H, J=7.3 Hz), 1.39(s, 3H), 1.30(s, 3H), 1.18~1.26(m, 6H); MS, m/z: 484.02 |
| 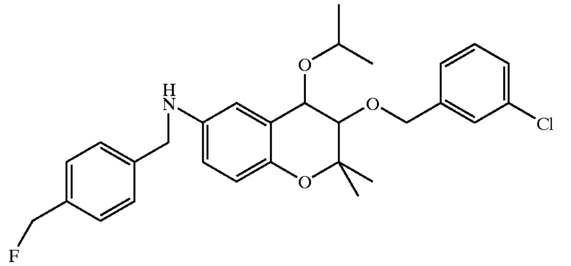<br>5-487 | $^1$H NMR(200 MHz, $CDCl_3$) δ 7.16~7.37(m, 6H), 6.93~7.03(m, 2H), 6.66~6.75(m, 3H), 4.85(d, 1H, J=12.0 Hz), 4.67(d, 1H, J=12.0 Hz), 4.36(d, 1H, J=7.1 Hz), 4.24(s, 2H), 3.94~4.03(m, 1H), 3.49(d, 1H, J=7.1 Hz), 1.39(s, 3H), 1.28(s, 3H), 1.19~1.25(m, 6H); MS, m/z: 484.02 |
| 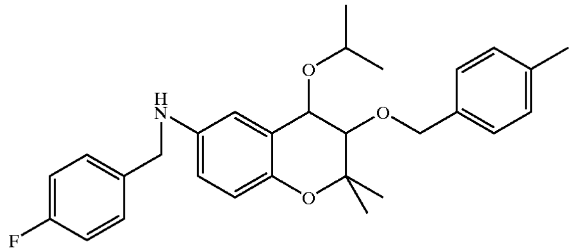<br>5-488 | $^1$H NMR(200 MHz, $CDCl_3$) δ 7.13~7.38(m, 6H), 6.79~7.10(m, 2H), 6.49~6.65(m, 3H), 4.83(d, 1H, J=11.4 Hz), 4.65(d, 1H, J=11.4 Hz), 4.35(d, 1H, J=7.1 Hz), 4.24(s, 2H), 3.96~4.02(m, 1H), 3.50(d, 1H, J=7.1 Hz), 2.30(s, 3H), 1.37(s, 3H), 1.25(s, 3H), 1.23(d, 3H, J=3.9 Hz), .1.20(o 3H, J=3.9 Hz); MS, m/z: 463.60 |

TABLE 1-continued

| | Compound No. NMR/MS Data |
|---|---|
| 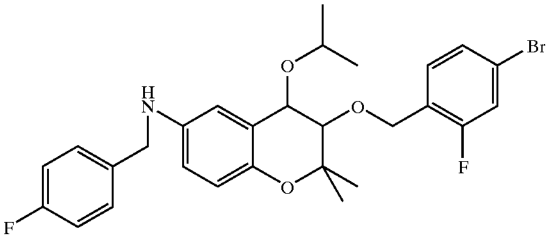 5-489 | $^{1}$H NMR(200 MHz, $CDCl_3$) δ 7.20~7.37(m, 5H), 6.94~7.05(m, 2H), 6.53~6.69(m, 3H), 4.87(d, 1H, J=11.6 Hz), 4.68(d, 1H, J=12.0 Hz), 4.35(d, 1H, J=7.1 Hz), 4.24(s, 2H), 3.96~4.02(m, 1H), 3.51(d, 1H, J=7.1 Hz), 1.37(s, 3H), 1.24(s, 3H), 1.20~1.22(m, 6H); MS, m/z: 546.46 |
| 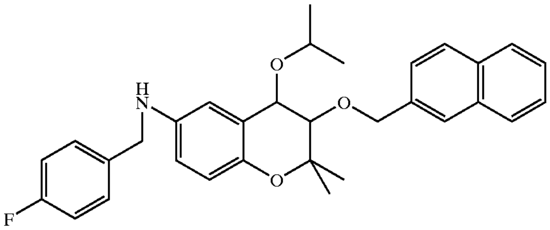 5-490 | $^{1}$H NMR(200 MHz, $CDCl_3$) δ 7.75~7.86(m, 4H), 7.46~7.51(m, 3H), 7.20~7.37(m, 2H), 6.96~7.05(m, 2H), 6.57~6.69(m, 3H), 5.03(d, 1H, J=11.6 Hz), 4.85(d, 1H, J=11.6 Hz), 4.39(d, 1H, J=7.1 Hz), 4.25(s, 2H), 3.96~4.03(m, 1H), 3.57(d, 1H, J=7.1 Hz), 1.39(s, 3H), 1.31 (s, 3H), 1.24(d, 3H, J=3.7 Hz), 1.19(d, 3H, J=3.5 Hz); MS, m/z: 499.63 |
| 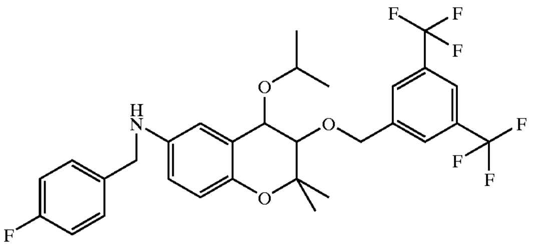 5-491 | $^{1}$H NMR(200 MHz, $CDCl_3$) δ 7.80(b, 3H), 7.26~7.38(m, 2H), 6.97~6.06(m, 2H), 6.53~6.68(m, 3H), 5.02(d, 1H, J=12.8 Hz), 4.81(d, 1H, J=12.8 Hz), 4.41(d, 1H, J=7.5 Hz), 4.25(s, 2H), 3.92~3.98(m, 1H), 3.54(d, 1H, J=7.5 Hz), 1.45(s, 3H), 1.30(s, 3H), 1.23(d, 3H, J=6.1 Hz), 1.17(d, 3H, J=6.3 Hz); MS, m/z: 585.57 |
| 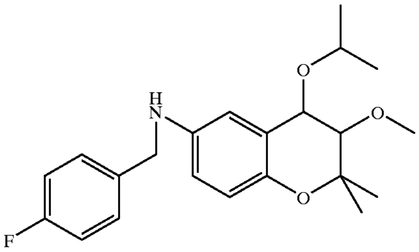 5-492 | $^{1}$H NMR(200 MHz, $CDCl_3$) δ 7.26~7.38(m, 2H), 6.97~7.05(m, 2H), 6.48~6.64(m, 3H), 4.28(d, 1H, J=7.1 Hz), 4.24(s, 2H), 3.98~4.10(m, 1H), 3.58(s, 3H), 3.22(d, 1H, J=7.1 Hz), 1.40(s, 3H), 1.28(s, 3H), 1.26(d, 3H, J=2.2 Hz), 1.23(d, 3H, J=2.2 Hz); MS, m/z: 373.47 |
| 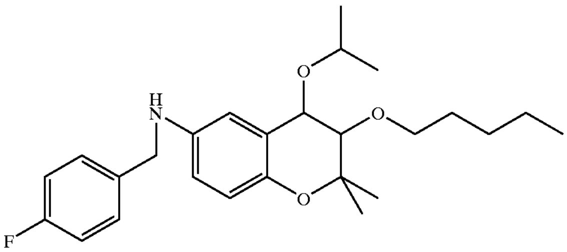 5-493 | $^{1}$H NMR(200 MHz, $CDCl_3$) δ 7.31~7.38(m, 2H), 6.96~7.07(m, 2H), 6.49~6.64(m, 3H), 4.28(d, 1H, J=7.1 Hz), 4.24(s, 2H), 3.99~4.11(m, 1H), 3.78~3.86(m, 1H), 3.58~3.76(m, 1H), 3.52~3.56(m, 1H), 3.31(d, 1H, J=7.1 Hz), 1.44~1.62(m, 2H), 1.39(s, 3H), 1.30~1.35(m, 4h), 1.25~1.26(m, 6H), 1.23(s, 3H); MS, m/z: 429.58 |

TABLE 1-continued
| | Compound No. NMR/MS Data |
|---|---|
| 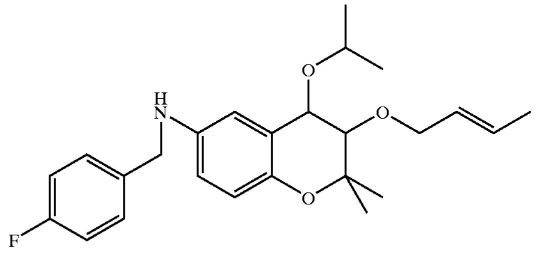 5-494 | MS, m/z: 413.54 |
| 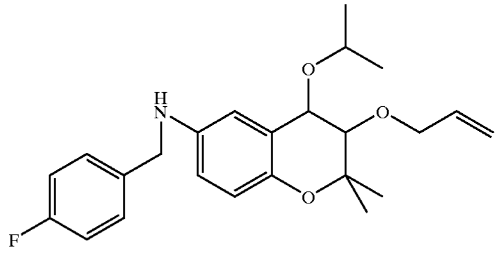 5-495 | $^1$H NMR(200 MHz, $CDCl_3$) δ 7.11~7.36(m, 2H), 6.86~7.06(m, 2H), 6.72~6.76(m, 3H), 5.86~5.99(m, 1H), 5.17~5.33(m, 2H), 4.23(s, 2H), 4.12~4.34(m, 3H), 3.98~4.09(m, 1H), 3.35(d, 1H, J=6.9 Hz), 1.40(s, 3H), 1.23~1.26(m, 9H); MS, m/z: 399.51 |
| 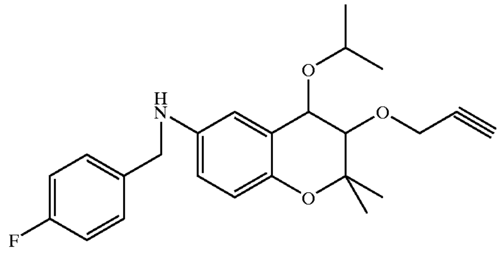 5-496 | $^1$H NMR(200 MHz, $CDCl_3$) δ 7.22~7.29(m, 2H), 6.89~6.98(m, 2H), 6.67~6.88(m, 3H), 4.38~4.40(m, 2H), 4.34(d, 1H, J=6.7 Hz), 4.21(s, 2H), 3.99~4.06(m, 1H), 3.51(d, 1H, J=6.7 Hz), 2.45~2.47(m, 1H), 1.45(s, 3H), 1.28(b, 6H0, 1.25(s, 3H); MS, m/z: 397.49 |
| 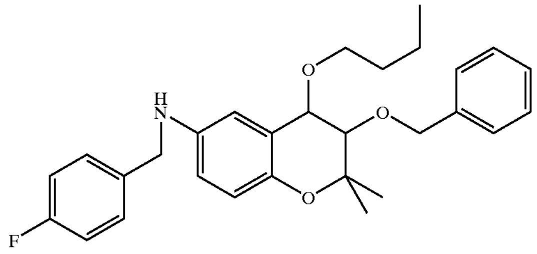 5-497 | $^1$H NMR(200 MHz, $CDCl_3$) δ 7.27~7.38(m, 7H), 6.97~7.06(m, 2H), 6.54~6.68(m, 3H), 4.71(d, 1h, J=11.5 Hz), 4.40(d, 1H, J=11.5 Hz), 4.40(d, 1H, J=11.1), 3.57~4.25(m, 3H), 1.54~2.17(m, 2H), 1.24~1.43(m, 2H), 1.40(s, 3H), 1.24(s, 3H), 0.91(t, 3H, J=7.2 Hz); MS, m/z: 463.60 |
| 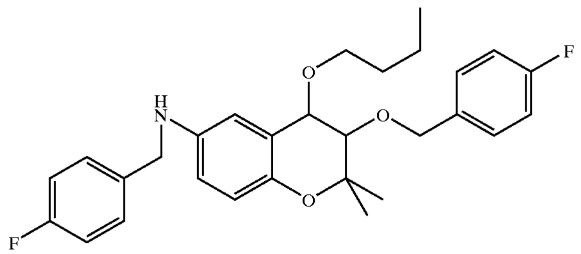 5-498 | $^1$H NMR(200 MHz, $CDCl_3$) δ 7.23~7.37(m, 4H), 6.92~7.09(m, 4H), 6.59~6.73(m, 3h), 4.84(d, 1H, J=11.4 Hz), 4.65(d, 1H, J=11.4 Hz), 4.38(d, 1H, J=7.3 Hz), 4.24(s, 2H), 3.58~3.69(m, 2H), 3.56(d, 1H, J=7.3 Hz), 1.46~1.61(m, 2H), 1.25~1.42(m, 2H), 1.38(s, 3H), 1.25(s, 3H), 0.92(t, 3H, J=7.1 Hz); MS, m/z: 481.59 |

TABLE 1-continued

| | Compound No. NMR/MS Data |
|---|---|
| 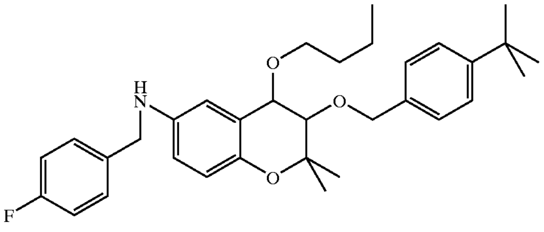 5-499 | $^1$H NMR(200 MHz, $CDCl_3$) δ 7.27~7.40(m, 6H), 6.93~7.26(m, 2H), 6.66~6.82(m, 3H), 4.83(d, 1H, J=11.2 Hz), 4.65(d, 1H, J=11.2 Hz), 4.36(d, 1H, J=6.0 Hz), 4.24(s, 2H0, 3.59~1.61(m, 2H), 1.24~1.39(m, 2H), 1.39(s, 3H), 1.32(s, 9H), 1.24(s, 3H), 0.92(t, 3H, J=7.2 Hz); MS, m/z: 519.71 |
| 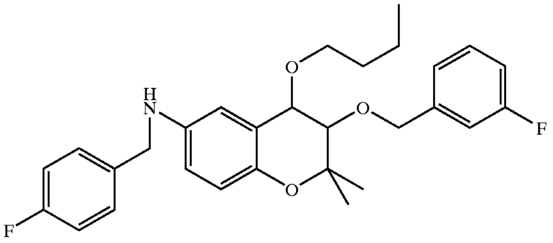 5-500 | $^1$H NMR(200 MHz, $CDCl_3$) δ 7.26~7.36(m, 3H), 6.94~7.13(m, 5H), 6.34~6.73(m, 3H), 4.89(d, 1H, J=12.0 Hz), 4.69(d, 1H, J=12.0 Hz), 4.40(d, 1H, J=7.3 Hz), 4.24(s, 2H), 3.63~4.19(m, 2H), 3.57(d, 1H, J=7.3 Hz), 1.50~1.60(m, 2H), 1.27~1.45(m, 2H), 1.40(s, 3H), 1.24(s, 3H), 0.91(t, 3H, J=7.1 Hz); MS, m/z: 481.59 |
| 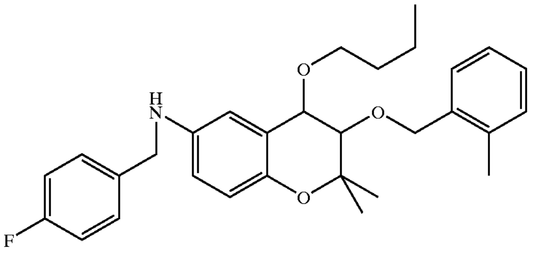 5-501 | $^1$H NMR(200 MHz, $CDCl_3$) δ 7.16~7.39(m, 6H), 6.92~7.05(m, 2H), 6.61~6.73(m, 3H), 4.91 (d, 1H, J=11.4 Hz), 4.69(d, 1H, J=11.4), 4.40(d, 1H, J=7.1 Hz), 4.24(s, 2H), 3.56~3.73(m, 3H), 2.35(s, 3H), 1.49~1.60(m, 2H), 1.26~1.45(m, 2H), 1.40(s, 3H), 1.24(s, 3H), 0.90(t, 3H, J=7.2); MS, m/z: 477.62 |
| 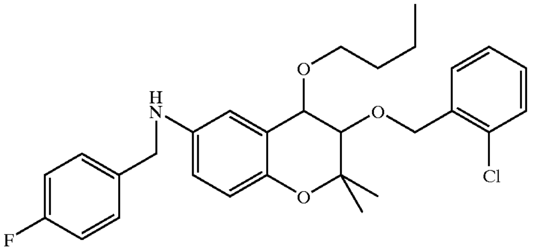 5-502 | MS, m/z: 498.04 |
| 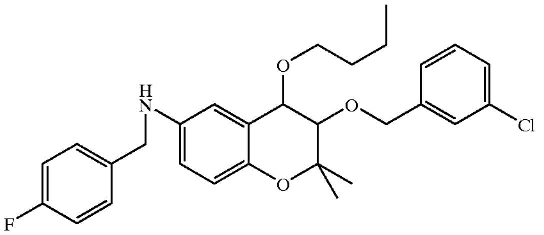 5-503 | $^1$H NMR(200 MHz, $CDCl_3$) δ 7.16~7.36(m, 6H), 6.92~7.04(m, 2H), 6.78(s, 1H), 6.67(d, 2H, J=1.4 Hz), 4.86(d, 1H, J=11.8 Hz), 4.67(d, 1H, J=11.0 Hz), 4.39(d, 1H, J=7.3 Hz), 3.60~4.18(m, 2H), 3.56(d, 1H, J=7.3 Hz), 1.50~1.61(m, 2H), 1.24~1.44(m, 2H), 1.40(s, 3H), 1.24(s, 3H), 0.91(t, 3H, J=7.1 Hz); MS, m/z 498.04 |

TABLE 1-continued

| | Compound No. NMR/MS Data |
|---|---|
| 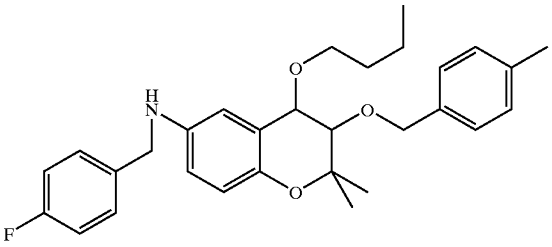 5-504 | $^1$H NMR(200 MHz, $CDCl_3$) δ 7.14~7.35(m, 6H), 6.94~6.99(m, 2H), 6.78(s, 1H), 6.66(d, 2H, J=1.4 Hz), 4.83(d, 1H, J=11.2 Hz), 4.64(d, 1H, J=11.2), 4.37(d, 1H, J=7.7), 4.24(s, 2H), 3.57~3.70(m, 2H), 3.55(d, 1H, J=7.7), 3.54~3.70(m, 2H), 2.35(s, 3H), 1.54~1.61(m, 2H), 1.25~1.51(m, 2H), 1.38(s, 3H), 1.22(s, 3H), 0.92(t, 3H, J=7.1 Hz); MS, m/z: 477.62 |
| 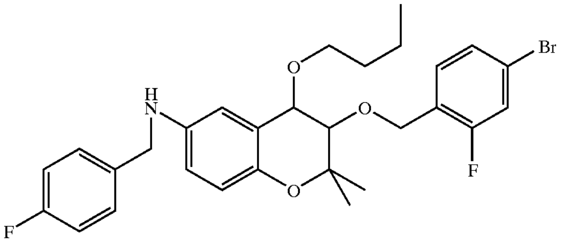 5-505 | MS, m/z: 560.48 |
| 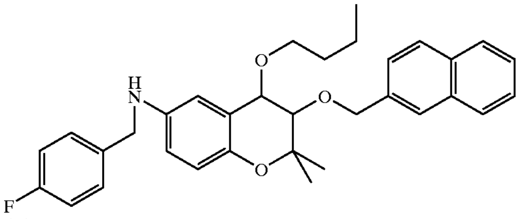 5-506 | $^1$H NMR(200 MHz, $CDCl_3$) δ 7.80~7.86(m, 4H), 7.45~7.50(m, 3H), 7.25~7.34(m, 2H), 6.93~6.80(m, 2H), 6.80(s, 1H), 6.67(d, 2H, J=2.0 Hz), 5.03(d, 1H, J=11.6), 4.86(d, 1H, J=11.6 Hz), 4.42(d, 1H, J=7.1 Hz), 4.23(s, 2H), 3.63~3.76(m, 2H), 3.28(d, 1H, J=7.1 Hz), 1.50~1.64(m, 2H), 1.27~1.46(m, 2H), 1.40(s, 3H), 1.21(s, 3H), 0.85~0.98(m 3H); MS, m/z: 513.66 |
| 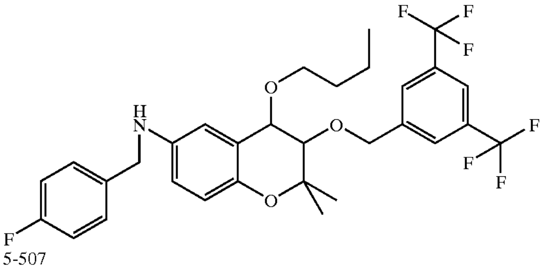 5-507 | MS, m/z: 599.59 |
| 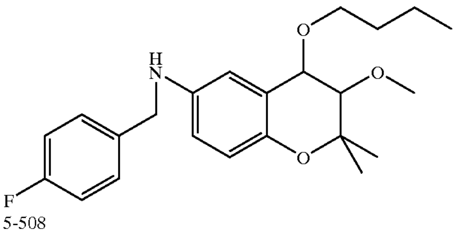 5-508 | $^1$H NMR(200 MHz, $CDCl_3$) δ 7.14~7.30(m, 4H), 6.87~7.01(m, 3H), 4.24(d, 1H, J=6.9 Hz), 4.22(s, 2H), 3.68~3.78(m, 2H), 3.58(s, 3H), 3.25(d, 1H, J=6.9 Hz), 1.47~1.66(m, 2H), 1.40~1.43(m, 2H0, 1.40(s, 3H), 1.23(s, 3H), 0.90~0.98(m, 3H); MS, m/z: 387.50 |
| 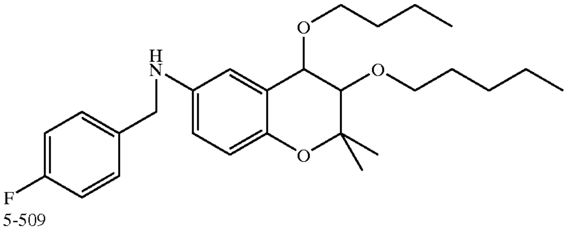 5-509 | $^1$H NMR(200 MHz, $CDCl_3$) δ 7.28~7.36(m, 2H), 6.89~7.03(m, 2H), 6.62~6.81(m, 3H), 4.32(d, 1H, J=7.3 Hz), 4,24(s, 2H), 3.55~3.82(m, 4H), 3.36(d, 1H, J=7.3 Hz), 1.52~1.75(m, 4H), 1.39(s, 3H), 1.26~1.49(m, 6h), 1.21(s, 3H), 0.90~0.98(m, 6H); MS, m/z: 443.61 |

TABLE 1-continued

| Compound No. | NMR/MS Data |
|---|---|
| 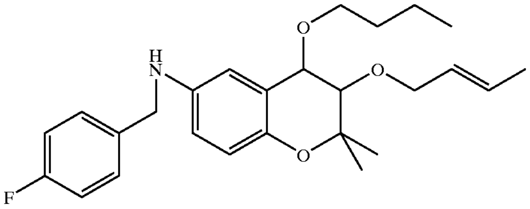 5-510 | $^{1}H$ NMR(200 MHz, $CDCl_3$) δ 7.26~7.37(m, 2H), 6.96~7.04(m, 2H), 6.56~6.70(m, 2H), 5.62~5.71(m, 2H), 4.31(d, 1H, J=7.1 Hz), 4.24(s, 2H), 4.05~4.28(m, 2H), 3.48~3.75(m, 2H), 3.45(d, 1H, J=7.1 Hz), 1.69~1.73(m, 3H), 1.53~1.66(m, 2H), 1.39(s, 3H), 1.21(s, 3H), 1.26~1.45(m, 2H), 0.94(t, 3H, J=7.1 Hz); MS, m/z: 427.56 |
| 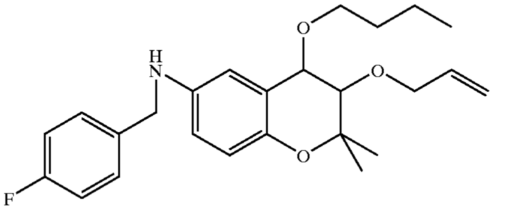 5-511 | $^{1}H$ NMR(200 MHz, $CDCl_3$) δ 7.27~7.37(m, 2H), 6.95~7.06(m, 2H), 6.52~6.66(m, 3H), 5.86~6.05(m, 1H), 5.14~5.35(m, 2H), 4.34(d, 1H, J=7.3 Hz), 4.11~4.40(m, 2H), 4.24(s, 2H), 3.58~3.77(m, 2h), 3.47(d, 1H, J=7.3 Hz), 1.52~1.66(m, 2H), 1.34~1.48(m, 2H), 1.40(s, 3H), 1.22(s, 3H), 0.93(t, 3H, J=7.1 Hz); MS, m/z: 413.54 |
| 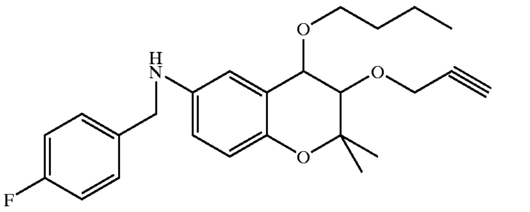 5-512 | $^{1}H$ NMR(200 MHz, $CDCl_3$) δ 7.26~7.37(m, 2H), 6.97~7.06(m, 2H), 6.50~6.67(m, 3H), 4.43(dd, 2H, J=0.81, J=2.7), 4.39(d, 1H, J=7.1 Hz), 4.24(s, 2H), 3.59~3.69(m, 3H), 2.44~2.46(m, 1H), 1.51~1.61(m, 2H), 1.43(s, 3H), 1.29~1.40(m, 2H), 1.22(s, 3H), 0.93(t, 3H, J=7.1 Hz); MS, m/z: 411.52 |
| 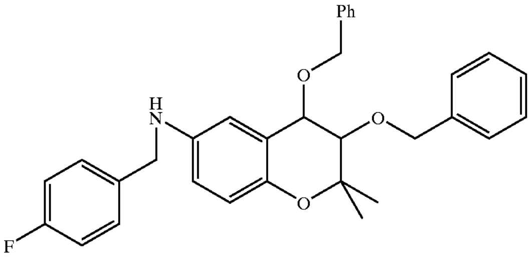 5-513 | $^{1}H$ NMR(200 MHz, $CDCl_3$) δ 7.26~7.37(m, 12H), 6.95~7.04(m, 2H), 6.52~6.68(m, 3H), 4.89(d, 1H, J=11.4 Hz), 4.67(d, 1H, J=11.6 Hz), 4.73(d, 2H, J=2.8 Hz), 4.60(d, 1H, J=7.3 Hz), 4.17(s, 2H), 3.69(d, 1H, J=7.1 Hz), 1.43(s, 3H), 1.27(s, 3H); MS, m/z: 497.61 |
| 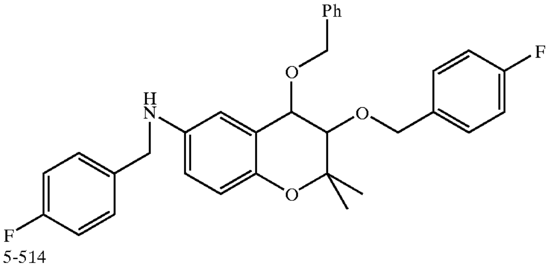 5-514 | $^{1}H$ NMR(200 MHz, $CDCl_3$) δ 7.33~7.56(m, 9H), 6.96~7.06(m, 4H), 6.49~6.68(m, 3H), 4.85(d, 1H, J=11.6 Hz), 4.70(d, 2H, J=4.3 Hz), 7.17(s, 2H), 4.17~4.54(m, 2H), 3.69(d, 1H, J=7.1 Hz), 1.43(s, 3H), 1.26(s, 3H); MS, m/z: 515.61 |
| 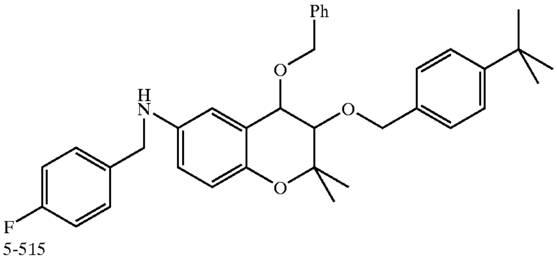 5-515 | $^{1}H$ NMR(200 MHz, $CDCl_3$) δ 7.27~7.40(m, 10H), 6.68~7.04(m, 2H), 6.50~6.63(m, 3h0, 4.86(d, 1H, J=11.0 Hz), 4.63~4.79(m, 3H), 4.59(d, 1H, J=7.5 Hz), 4.17(s, 2H), 3.69(d, 1H, J=7.1 Hz), 1.44(s, 3H), 1.32(s, 9H), 1.26(s, 3H); MS, m/z: 553.72 |

TABLE 1-continued
| | Compound No. NMR/MS Data |
|---|---|
| 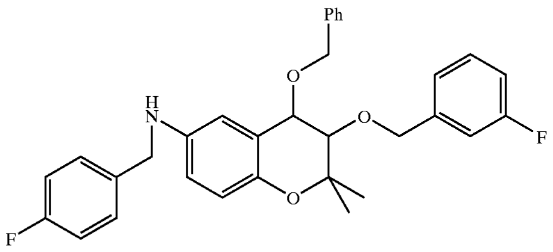<br>5-516 | $^1H$ NMR(200 MHz, $CDCl_3$) δ 7.34~7.56(m, 8H), 6.95~7.11(m, 5H), 6.49~6.69(m, 3H), 4.89(d, 1H, J=11.8 Hz), 4.67~4.83(m, 3H), 4.63(d, 1H, J=7.5 Hz), 4.18(s, 2H), 3.69(d, 1H, J=7.5 Hz), 1.45(s, 3H), 1.28(s, 3H); MS, m/z: 535.68 |
| 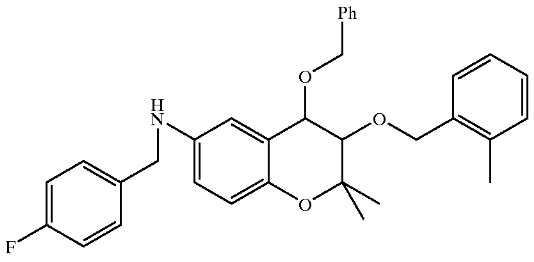<br>5-517 | $^1H$ NMR(200 MHz, $CDCl_3$) δ 7.19~7.39(m, 11H), 6.96~7.17(m, 2H), 6.51~6.69(m, 3H), 4.91 (d, 1H, J=11.6 Hz), 4.67~4.73(m, 3H), 4.62(d, 1H, J=7.1 Hz), 4.18(s, 2H), 3.73(d, 1H, J=7.1 Hz), 2.30(s, 3H), 1.42(s, 3H), 1.27(s, 3H): MS, m/z: 531.72 |
| 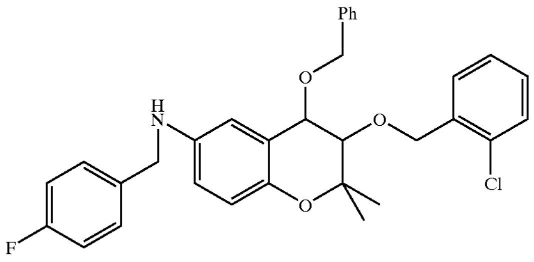<br>5-518 | MS, m/z: 532.06 |
| 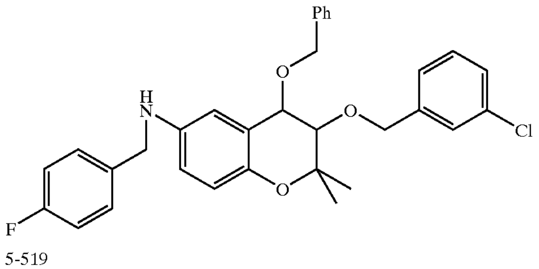<br>5-519 | $^1H$ NMR(200 MHz, $CDCl_3$) δ 7.17~7.34(m, 11H), 6.96~7.04(m, 2H), 6.51~6.69(m, 3H), 4.86(d, 1H, J=12.0 Hz), 4.61~4.71(m, 4H), 4.18(s, 2H), 3.68(d, 1H, J=7.3 Hz), 1.45(s, 3H), 1.28(s, 3H); MS, m/z: 532.06 |
| 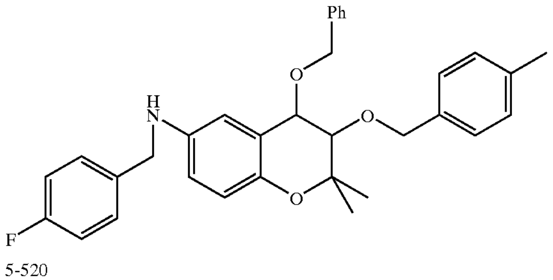<br>5-520 | MS, m/z: 511.64 |

TABLE 1-continued

| | Compound No. NMR/MS Data |
|---|---|
| 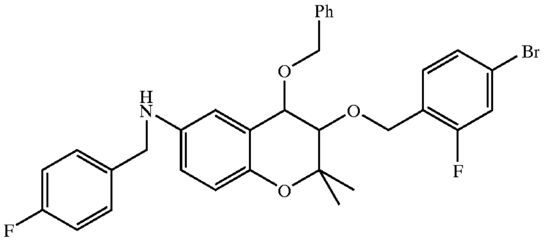 5-521 | $^1$H NMR(200 MHz, $CDCl_3$) δ 7.21~7.33(m, 10H), 6.95~7.04(m, 2H), 6.50~6.68(m, 3H), 4.87(d, 1H, J=12.2), 4.68~4.74(m, 3H), 4.60(d, 1H, J=7.3 Hz), 4.17(s, 2H), 3.69(d, 1H, J=7.3 Hz), 1.42(s, 3H), 1.24(s, 3H); MS, m/z: 594.50 |
| 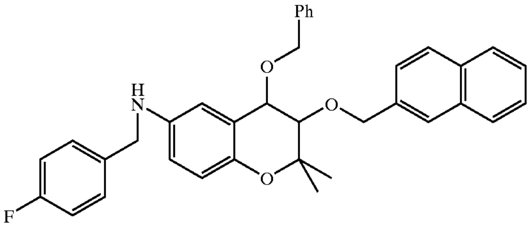 5-522 | $^1$H NMR(200 MHz, $CDCl_3$) δ 7.76~7.86(m, 4H), 7.45~7.50(m, 3H), 7.15~7.34(m, 7H), 6.95~7.04(m, 2h), 6.50~6.69(m, 3H), 5.05(d, 1H, J=11.6 Hz), 4.87(d, 1H, J=11.6 Hz), 4.71(d, 2H, J=7.7 Hz), 4.64(d, 1H, J=6.9 Hz), 4.18(s, 2H), 3.76(d, 1H, J=6.9 Hz), 1.45(s, 3H), 1.30(s, 3H); MS, m/z: 547.68 |
| 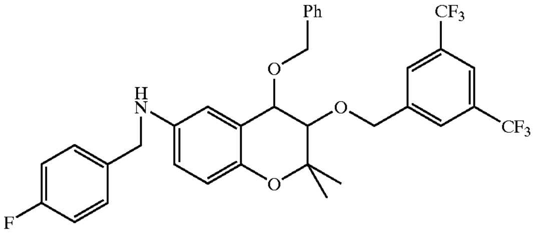 5-523 | $^1$H NMR(200 MHz, $CDCl_3$) δ 7.79(s, 2H), 7.74(s, 1H), 7.27~7.34(m, 7H), 6.95~7.04(m, 2H), 6.51~6.70(m, 3H), 4.97(d, 1H, J=12.4 Hz), 4.78(d, 1H, J=12.4 Hz), 4.69(d, 1H, J=7.5 Hz), 4.68(s, 2H), 4.19(s, 2H), 3.72(d, 1H, J=7.5 Hz), 1.46(s, 3H), 1.28(s, 3H); MS, m/z: 633.61 |
| 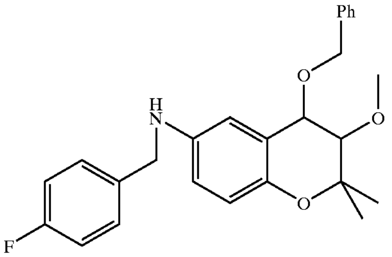 5-524 | $^1$H NMR(200 MHz, $CDCl_3$) δ 7.27~7.39(m, 7H), 6.94~7.26(m, 2H), 6.57~6.68(m, 3H), 4.82(d, 1H, J=12.0 Hz), 4.72(d, 1H, J=12.0 Hz), 4.49(d, 1H, J=7.1 Hz), 4.17(s, 2H), 3.60(s, 3H), 3.41(d, 1H, J=7.1 Hz), 1.44(s, 3H), 1.24(s, 3H); MS, m/z: 421.52 |
| 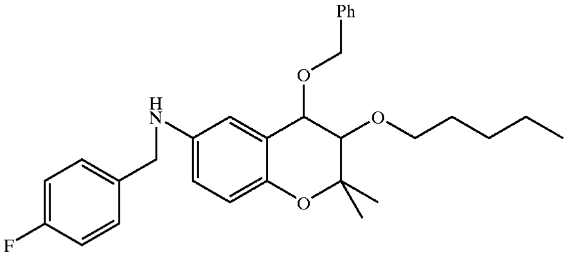 5-525 | $^1$H NMR(200 MHz, $CDCl_3$) δ 7.23~7.38(m, 7H), 6.90~6.98(m, 2H), 6.66~6.77(m, 3h), 4.71(d, 1H, J=12.0 Hz), 4.67(d, 1H, J=12.0 Hz), 4.47(d, 1H, J=7.3 Hz), 4.16(s, 2H), 3.52~3.83(m, 2H), 3.47(d, 1H, J=7.1 Hz), 1.43~1.60(b, 2H), 1.42(s, 3H), 1.24(s, 3H), 1.30~1.42(m, 4H), 0.89~0.93(m, 3H), MS, m/z: 477.62 |

TABLE 1-continued

| | Compound No. NMR/MS Data |
|---|---|
| 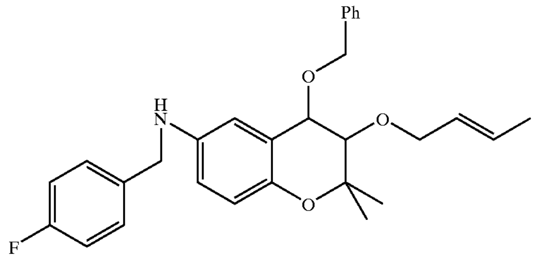<br>5-526 | $^1$H NMR(200 MHz, $CDCl_3$) δ 7.26~7.38(m, 7H), 6.95~7.06(m, 2H), 6.48~6.65(m, 3H), 5.62~5.70(m, 2H), 4.82(d, 1H, J=11.6 Hz), 4.71(d, 1H, J=11.6 Hz), 4.52(d, 1H, J=7.1 Hz), 4.08~4.31(m, 2H), 4.16(s, 2H), 3.57(d, 1H, J=7.1 Hz), 1.63~1.74(m, 3H), 1.43(s, 3H), 1.24(s, 3H); MS, m/z: 461.58 |
| 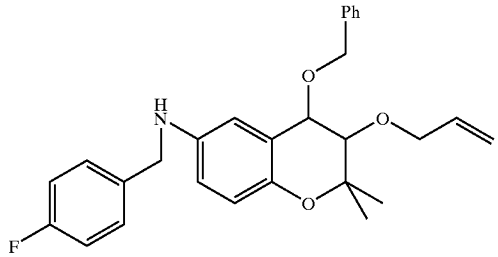<br>5-527 | $^1$H NMR(200 MHz, $CDCl_3$) δ 7.14~7.41(m, 7H), 6.84~7.06(m, 2H), 6.49~6.69(m, 3H), 5.87~6.06(m, 1H), 5.15~5.34(m, 2H), 4.80(d, 1H, J=11.4 Hz), 4.70(d, 1H, J=11.4 Hz), 4.54(d, 1H, J=7.3 Hz), 4.20~4.45(m, 2H), 4.17(s, 2H), 3.59(d, 1H, J=7.3 Hz), 1.44(2, 3H), 1.25(s, 3H); MS, m/z: 447.55 |
| 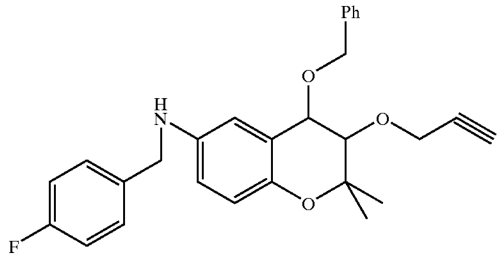<br>5-528 | $^1$H NMR(200 MHz, $CDCl_3$) δ 7.29~7.38(m, 7H), 6.94~7.03(m, 2H), 6.59~6.69(m, 3H), 4.73(b, 2H), 4.42(d, 2H, J=2.4 Hz), 4.17(s, 2H), 3.80(d, 1H, J=6.5 Hz), 2.46(t, 1H, J=2.3 Hz); MS, m/z: 445.54 |
| 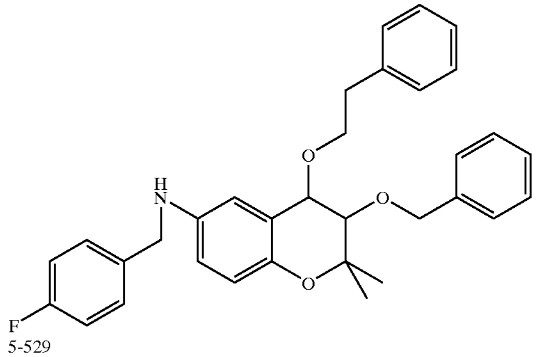<br>5-529 | MS, m/z: 511.64 |
| 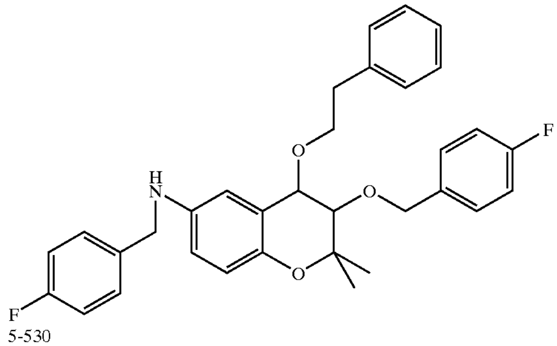<br>5-530 | $^1$H NMR(200 MHz, $CDCl_3$) δ 7.22~7.37(m, 12 H), 6.90~7.11(m, 2H), 6.59~6.84(m, 3H), 4.68(d, 1H, J=11.0 Hz), 4.54(d, 1H, J=11.2 Hz), 4.39(d, 1H, J=7.5 Hz), 4.17(s, 2H), 3.87(t, 2H, J=6.9 Hz), 3.51 (d, 1H, J=7.5 Hz), 2.89(t, 2H, J=6.7 Hz), 1.34(s, 3H), 1.19(s, 3H); MS, m/z: 529.63 |

TABLE 1-continued

| Compound No. | NMR/MS Data |
|---|---|
| 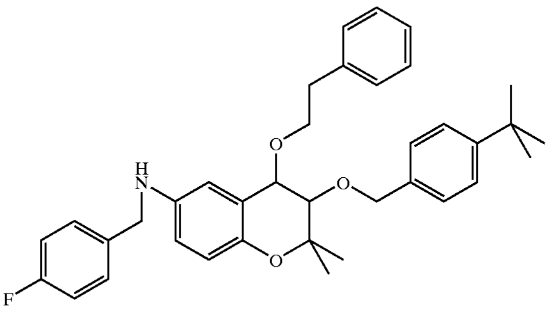 5-531 | $^1$H NMR(200 MHz, $CDCl_3$) δ 7.20~7.35(m, 9H), 6.94~7.06(m, 4H), 6.43~6.60(m, 3H), 4.69(d, 1H, J=11.6 Hz), 4.55(d, 1H, J=11.6 Hz), 4.41(d, 1H, J=7.5 Hz), 4.15(s, 2H), 3.82~3.92(m, 2H), 3.53(d, 1H, J=7.5 Hz), 2.88(t, 2H, J=6.5 Hz), 1.36(s, 3H), 1.19(s, 3H); MS, m/z: 567.75 |
| 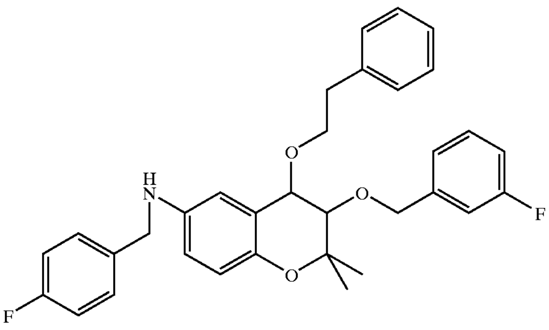 5-532 | $^1$H NMR(200 MHz, $CDCl_3$) δ 7.64~7.84(m, 3H), 7.15~7.39(m, 7H), 6.94~7.02(m, 2H), 6.69~6.79(m, 3H), 4.88(d, 1H, J=11.6 Hz), 4.62(d, 1H, J=11.6 Hz), 4.52(d, 1H, J=9.6 Hz), 4.46(d, 1H, J=7.5 Hz), 4.21(s, 2H), 3.81~3.92(m, 2H), 3.52(d, 1H, J=7.9 Hz), 2.87(t, 2H, J=6.9 Hz), 1.38(s, 3H), 1.21(s, 3H); MS, m/z: 529.63 |
| 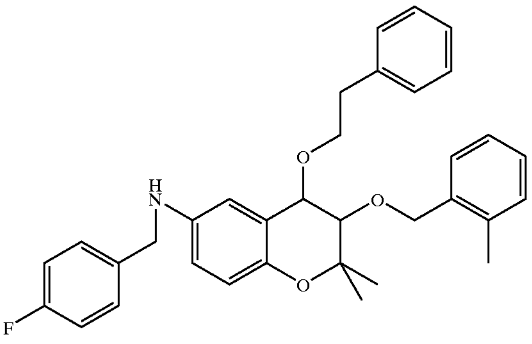 5-533 | $^1$H NMR(200 MHz, $CDCl_3$) δ 7.11~7.36(m, 11H), 7.01~7.06(m, 2H), 6.40~6.97(m, 3H), 4.81(d, 1H, J=11.8 Hz), 4.63(d, 1H, J=11.8 Hz), 4.41(d, 1H, d~7.5 Hz), 4.15(s, 2H), 3.80~3.96(m, 2H), 3.59(d, 1H, J=7.5 Hz), 2.87(t, 2H, J=6.7 Hz), 2.32(s, 3H), 1.34(s, 3H), 1.21(s, 3H); MS, m/z: 525.67 |
| 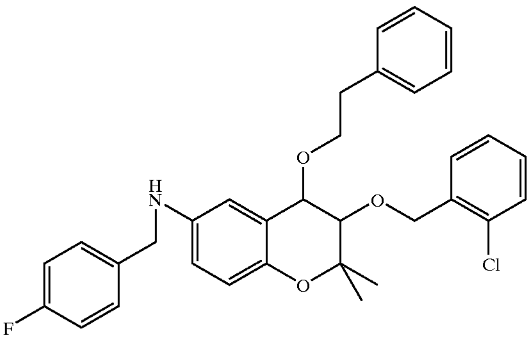 5-534 | $^1$H NMR(200 MHz, $CDCl_3$) δ 7.10~7.37(m, 11H), 6.96~7.04(m, 2H), 6.52~6.67(m, 3H), 4.67(d, 1H, J=11.8 Hz), 4.55(d, 1H, J=11.8 Hz), 4.41(d, 1H, J=7.7 Hz), 4.17(s, 2H), 3.83~3.90(m, 2H), 3.52(d, 1H, J=7.7 Hz), 2.88(t, 2H, J=6.3 Hz), 1.37(s, 3H), 1.21(s, 3H); MS, m/z: 546.09 |

TABLE 1-continued
| | Compound No. NMR/MS Data |
|---|---|
| 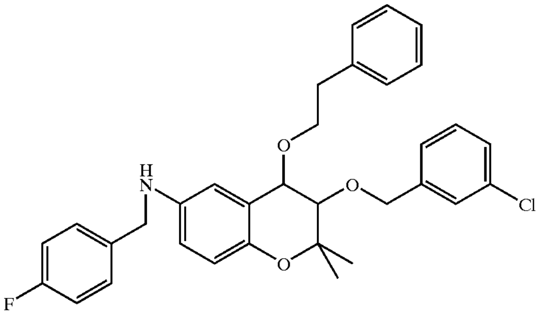 5-535 | $^1$H NMR(200 MHz, $CDCl_3$) δ 7.15~7.35(m, 11H), 6.93~7.10(m, 2H), 6.50~6.67(m, 3H), 4.67(d, 1H, J=12.2 Hz), 4.54(d, 1H, J=12.0 Hz), 4.42(d, 1H, J=7.5 Hz), 4.16(s, 2H), 3.87(t, 2H, J=6.3 Hz), 3.52(d, 1H, J=7.5 Hz), 2.87(t, 2H, J=6.5 Hz), 1.37(s, 3H), 1.21(s, 3H); MS, m/z: 546.09 |
| 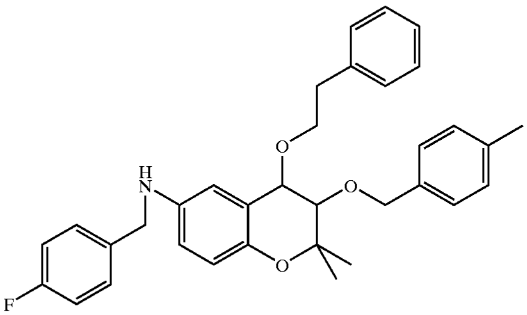 5-536 | MS, m/z: 525.67 |
| 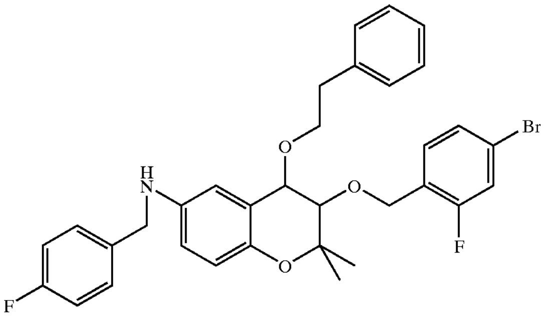 5-537 | $^1$H NMR(200 MHz, $CDCl_3$) δ 7.46~7.51(m, 1H), 7.13~7.39(m, 9H), 6.94~7.06(m, 2H), 6.38~6.76(m, 3H), 4.92(d, 1H, J=12.6 Hz), 4.74(d, 1H, J=12.6 Hz), 4.45(d, 1H, J=7.7 Hz), 4.15(s, 2H), 3.87~3.91(m, 2H), 3.62(d, 1H, J=7.7 Hz), 2.88(t, 2H, J=6.7 Hz), 1.38(s, 3H), 1.23(s, 3H); MS, m/z: 608.53 |
| 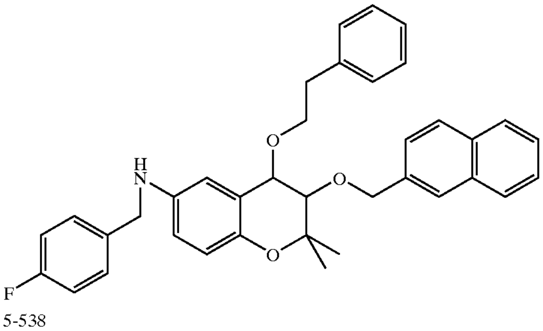 5-538 | $^1$H NMR(200 MHz, $CDCl_3$) δ 7.73~7.86(m, 4H), 7.34~7.50(m, 3H), 7.09~7.32(m, 7H), 6.95~7.04(m, 2H), 6.53~6.63(m, 3H), 4.89(d, 1H, J=11.6 Hz), 4.76(d, 1H, J=11.6 Hz), 4.44(d, 1H, J=7.5 Hz), 4.16(s, 2H), 3.83~3.94(m, 2H), 3.60(d, 1H, J=7.5 Hz), 2.87(t, 2H, J=6.5 Hz), 1.37(s, 3H), 1.24(s, 3H); MS, m/z: 531.70 |

TABLE 1-continued
| Compound No. | NMR/MS Data |
|---|---|
| 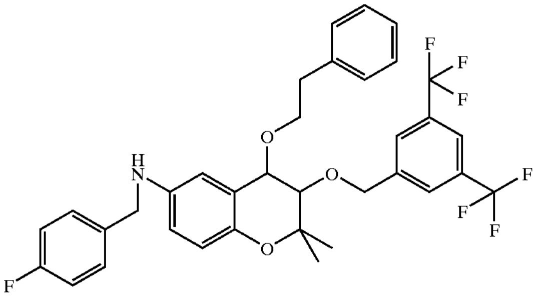 5-539 | $^1$H NMR(200 MHz, $CDCl_3$) δ 7.66~7.79(m, 3H), 7.11~7.37(m, 7H), 6.97~7.06(m, 2H), 6.47~6.68(m, 3H), 4.66(d, 1H, J=12.8 Hz), 4.54(d, 1H, J=12.8 Hz), 4.49(d, 1H, J=8.1 Hz), 4.19(s, 2H), 3.78~3.88(m, 2H), 3.56(d, 1H, J=8.1 Hz), 2.84(t, 2H, J=6.5 Hz), 1.39(s, 3H), 1.21 (s, 3H); MS, m/z: 647.64 |
| 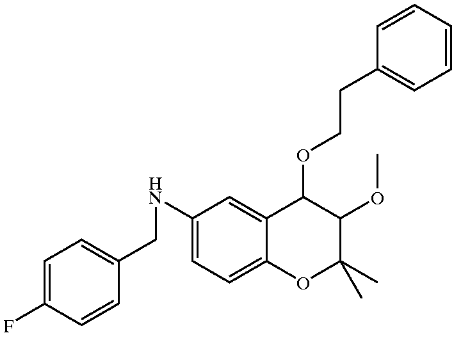 5-540 | MS, m/z: 435.54 |
| 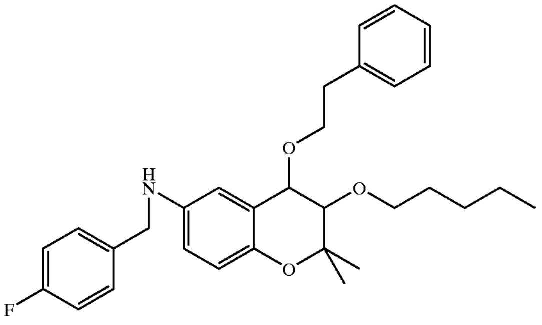 5-541 | MS, m/z: 491.65 |
| 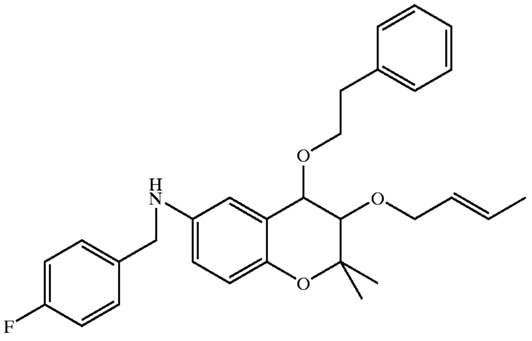 5-542 | $^1$H NMR(200 MHz, $CDCl_3$) δ 7.11~7.35(m, 7H), 6.97~7.06(m, 2H), 6.30~6.62(m 3H) 6.51~5.72(m, 2H) 4.13(s, 2H), 3.86~4.13(m, 5H), 3.44(d, 1H, J=7.5 Hz), 2.91(t, 2H, J=6.7 Hz), 1.64~1.73(m, 3H), 1.37(s, 3H), 1.18(s, 3H); MS, m/z: 475.60 |

TABLE 1-continued
| | Compound No. NMR/MS Data |
|---|---|
| 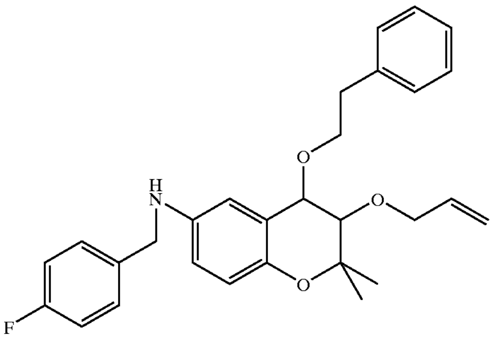 5-543 | $^1$H NMR(200 MHz, $CDCl_3$) δ 7.22~7.37(m, 7H), 6.97~7.06(m, 2H), 6.34~6.66(m, 3H), 5.84~5.98(m, 1H), 5.14~5.34(m, 2H), 4.14(s, 2H), 3.85~4.44(m, 5H), 3.44(o 1H, J=7.7 Hz), 2.91(t, 2H, J=6.7 Hz), 1.38(s, 3H), 1.19(s, 3H); MS, m/z: 461.58 |
| 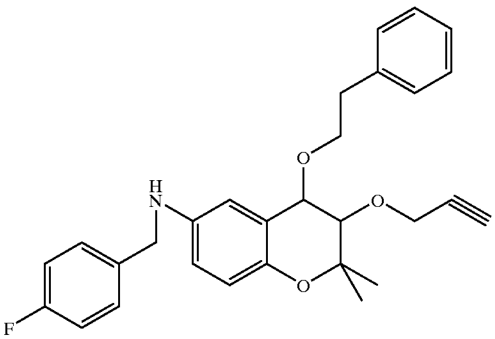 5-544 | $^1$H NMR(200 MHz, $CDCl_3$) δ 7.22~7.35(m, 7H), 6.98~7.06(m, 2H), 6.30~6.64(m, 3H), 4.40(d, 1H, J=7.5 Hz), 4.31(d, 2H, J=2.2 Hz), 4.14(s, 2H), 3.84~3.93(m, 2H), 3.64(d, 1H, J= 7.5 Hz), 2.90(t, 2H, J=6.7 Hz), 2.44(t, 1H, J=2.2 Hz), 1.40(s, 3H), 1.18(s, 3H); MS, m/z: 459.57 |
| 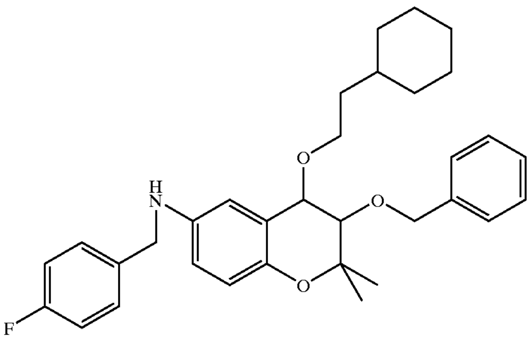 5-545 | $^1$H NMR(200 MHz, $CDCl_3$) δ 7.26~7.38(m. 7H), 6.94~7.03(m, 2H), 6.66~6.78(m, 2H), 4.88(d, 1H, J=11.4 Hz), 4.69(d, 1H, J=11.6 Hz), 4.38(d, 1H, J=7.1 Hz), 1.39(s, 3H), 1.18(s, 3H), 1.14~1.70(m, 11H), 0.86~0.92(m, 2H); MS, m/z: 517.69 |
| 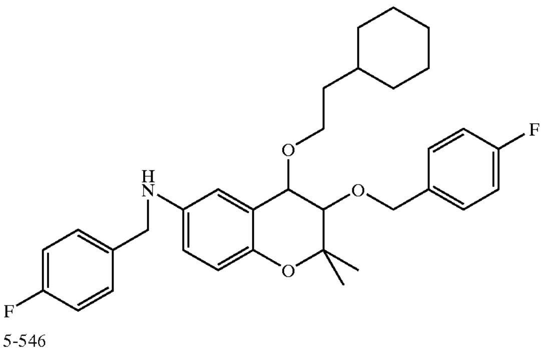 5-546 | $^1$H NMR(200 MHz, $CDCl_3$) δ 7.28~7.37(m, 4h), 6.95~7.08(m, 4H), 6.64~6.74(m, 3H0, 4.84(d, 1H, J=11.4 Hz), 4.66(d, 1H, J=11.2 Hz), 4.38(d, 1H, J=7.3 Hz), 4.24(s, 2H), 3.63~3.70(m, 2H), 3.56(d, 1H, J=7.1 Hz), 1.38(s, 3H0, 1.23(s, 3H), 1.15~1.69(m, 11H), 0.80~0.92(m, 2H); MS, m/z: 535.68 |

TABLE 1-continued
| | Compound No. NMR/MS Data |
|---|---|
| 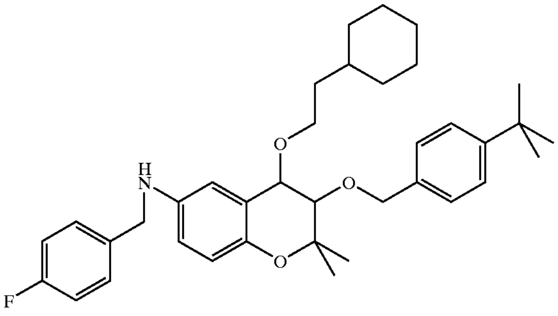 5-547 | MS, m/z: 573.80 |
| 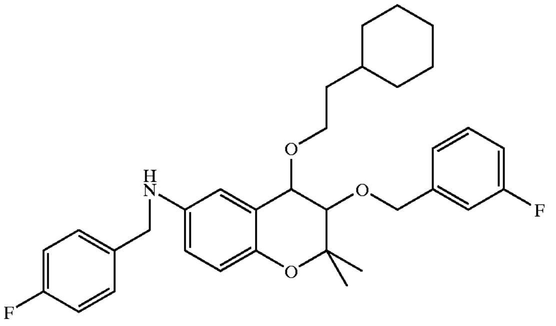 5-548 | $^1$H NMR(200 MHz, $CDCl_3$) δ 7.26~7.38(m, 3H), 6.98~7.13(m, 5H), 6.49~6.67(m, 3H), 4.89(d, 1H, J=12.0 Hz), 4.70(d, 1H, J=12.0 Hz), 4.42(d, 1H, J=7.5 Hz), 4.25(s, 2H), 3.62~3.89(m, 2H0, 3.58(d, 1H, J=7.5 Hz), 1.14~1.68(m, 11H), 0.85~0.90(m, 2H); MS, m/z: 535.68 |
| 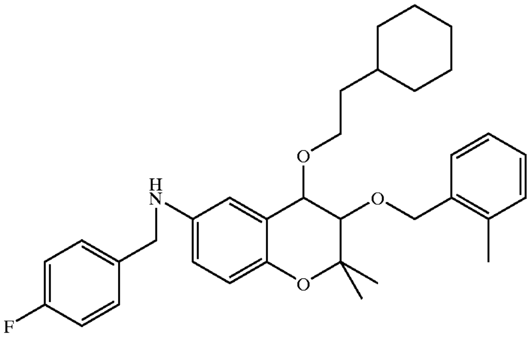 5-549 | $^1$H NMR(200 MHz, $CDCl_3$) δ 7.22~7.39(m, 6H), 6.94~7.02(m, 2H0, 6.66~6.79(m, 3h), 4.90(d, 1H, J=12.0 Hz), 4.69(d, 1H, J=12.0 Hz), 4.39(d, 1H, J=7.3 Hz), 4.24(s, 2H), 3.63~4.19(m, 2H), 3.60(d, 1H, J=7.1 Hz), 2.34(s, 3H), 1.36(s, 3H), 1.24(s, 3H), 1.14~1.69(m, 11H), 0.85~0.91(m, 2H); MS, m/z: 531.71 |
| 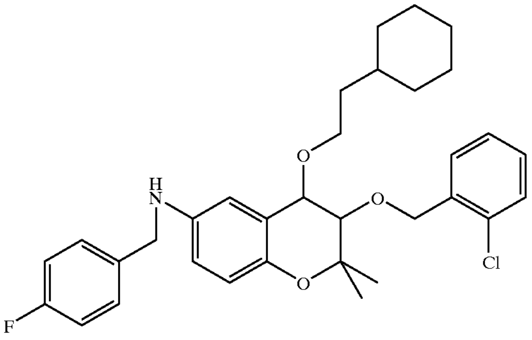 5-550 | MS, m/z: 552.14 |

TABLE 1-continued
| | Compound No. NMR/MS Data |
|---|---|
| 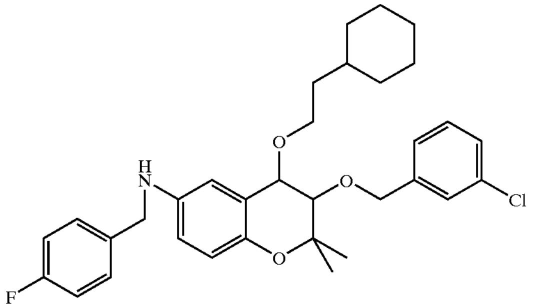 5-551 | $^1$H NMR(200 MHz, $CDCl_3$) δ 7.26~7.37(m, 6H), 6.96~7.05(m, 2H), 6.64~6.72(m, 3H), 4.87(d, 1H, J=12.2 Hz), 4.48(d, 1H, J=12.2 Hz), 4.41(d, 1H, J=7.1 Hz), 4.24(s, 2H), 3.63~3.70(m, 2H), 3.57(d, 1H, J=7.3 Hz), 1.41(s, 3H), 1.25(s, 3H), 1.14~1.50(m, 11H), 0.86~0.92(m, 2H); MS, m/z: 552.14 |
| 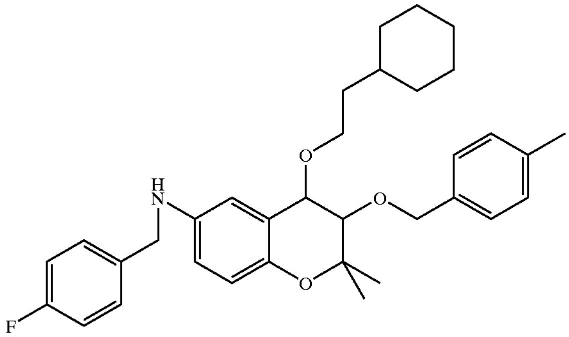 5-552 | MS, m/z: 531.71 |
| 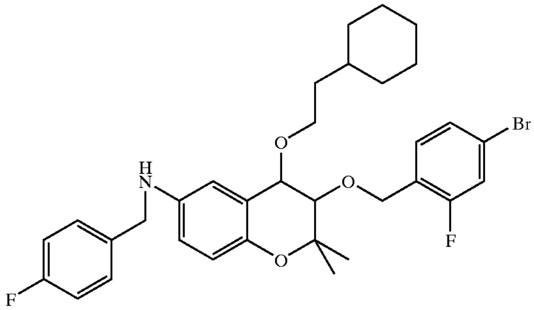 5-553 | $^1$H NMR(200 MHz, $CDCl_3$) δ 7.26~7.37(m, 5H), 6.98~7.08(m, 2H), 6.49~6.66(m, 3H), 4.88(d, 1H, J=12.0 Hz), 4.71(d, 1H, J=12.0 Hz), 4.40(d, 1H, J=7.5 Hz), 4.24(s, 2H), 3.62~3.68(m, 2H), 3.59(d, 1H, J=7.5 Hz), 1.39(s, 3H), 1.21(s, 3H), 1.14~1.65(m, 11H), 0.85~0.96(m, 2H); MS, m/z: 614.58 |
| 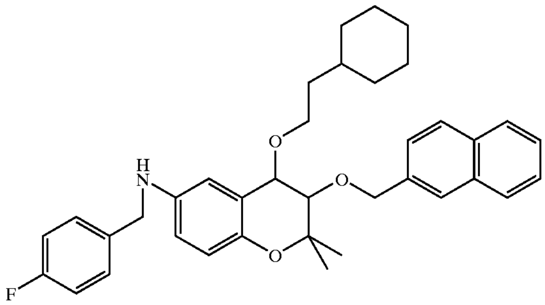 5-554 | MS, m/z: 567.75 |

TABLE 1-continued
| | Compound No. NMR/MS Data |
|---|---|
| 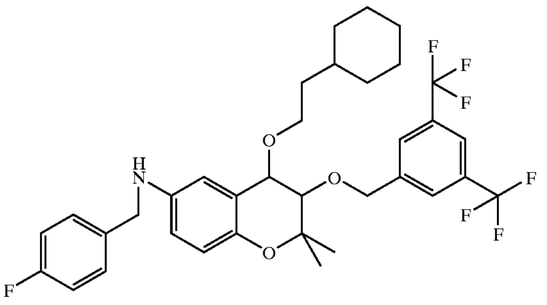 5-555 | $^1$H NMR(200 MHz, $CDCl_3$) δ 7.81(b, 3H). 7.28~7.38(m, 2H), 6.98~7.25(m, 2H), 6.50~6.68(m, 3H), 5.03(d. 1H, J=12.6 Hz), 4.83(d, 1H, J=12.4 Hz), 4.48(d, 1H, J=7.9 Hz), 3.59~3.67(m, 3H), 1.43(s, 3H), 1.25(s, 3H), 1.11~1.65(m, 11H), 0.82~0.88(m, 2H); MS, m/z: 653.69 |
| 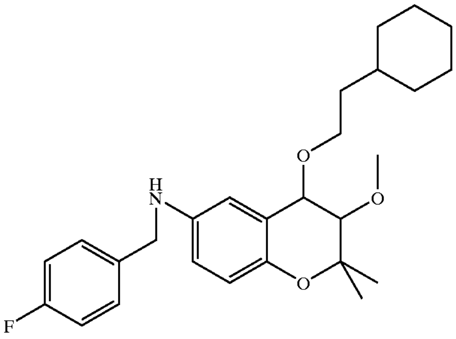 5-556 | $^1$H NMR(200 MHz, $CDCl_3$) δ 7.26~7.35(m, 2H), 6.94~7.02(m, 2H), 6.65~6.77(m, 3H), 4.28(d, 1H, J=6.7 Hz), 4.23(s, 2H), 6.64~6.78(m, 2H), 3.59(s, 3H), 3.29(d, 1H, J=6.7 Hz), 1.40(s, 3H), 1.21(s, 3H), 1.21~1.75(m, 1H), 0.89~0.95(m, 2H); MS, m/z 441.59 |
| 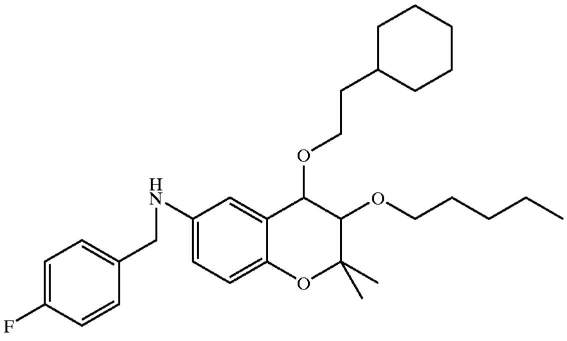 5-557 | MS, m/z: 497.70 |
| 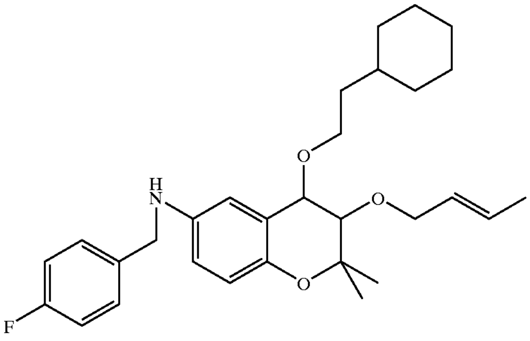 5-558 | $^1$H NMR(200 MHz, $CDCl_3$) δ 7.26~7.33(m, 2H), 6.85~7.01(m, 2H), 6.63~6.70(m, 3H), 5.61~5.72(m, 2H). 4.29(d, 1H, J=6.9 Hz), 4.22(s, 2H), 4.11~4.22(m, 2H), 3.72~3.76(m, 2H), 3.44(d, 1H, J=7.1 Hz), 1.39(s, 3H), 1.23(s, 3H), 1.43~1.74(m, 11H), 0.86~0.92(m, 2H); MS, m/z: 481.66 |

TABLE 1-continued
| | Compound No. NMR/MS Data |
|---|---|
| 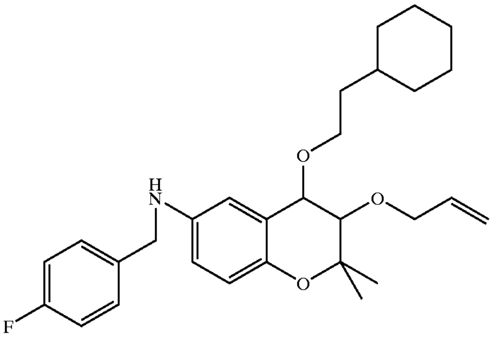 5-559 | $^1$H NMR(200 MHz, $CDCl_3$) δ 7.30~7.37(m, 2H), 6.96~7.05(m, 2H), 6.57~6.66(m, 3H), 6.16~5.34(m, 1H), 5.82~6.02(m, 1H), 4.34(d, 1H, J=7.1 Hz), 4.24(s, 2H), 4.18~4.36(m, 2H), 3.66~3.76(m, 2H), 3.47(d, 1H, J=7.5 Hz), 1.40(s, 3H), 1.22(s, 3H), 1.22~1.69(m, 11H), 0.86~0.92(m, 2H); MS, m/z: 467.63 |
| 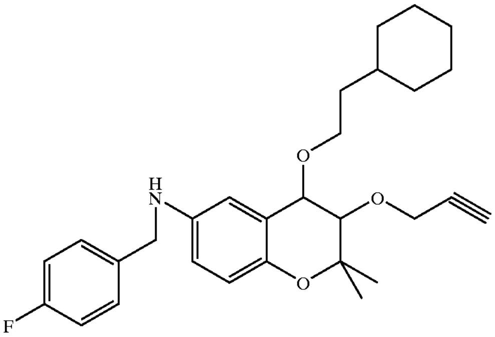 5-560 | $^1$H NMR(200 MHz, $CDCl_3$) δ 7.25~7.36(m, 2H), 6.94~7.02(m, 2H), 6.68~6.82(m, 3H), 4.42(d, 2H, J=2.4 Hz), 4.36(d, 1H, J=7.3 Hz), 4.24(s, 2H), 3.65~3.73(m, 3H), 2.04~2.47(m, 1H), 1.43(s, 3H), 1.23(s, 3H), 1.23~1.69(m, 11H), 0.86~0.96(m, 2H); MS, m/z: 465.61 |
| 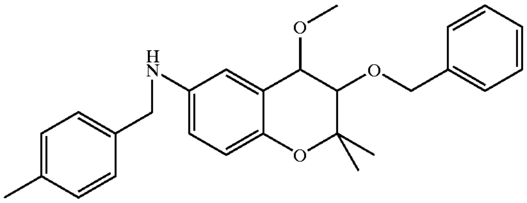 5-561 | $^1$H NMR(200 MHz, $CDCl_3$) δ 7.24~7.38(m, 5H), 7.14(m, 2H), 6.50~6.66(m, 3H), 4.91(d, 1H, J=11.6 Hz), 4.71(d, 1H, J= 11.6 Hz), 4.42(d, 1H, J=7.3 Hz), 4.23(s, 2H), 3.61(d, 1H, J=7.3 Hz), 3.45(s, 3H), 2.34(s, 3H), 1.40(s, 3H), 1.23(s, 3H); MS, m/z: 417.55 |
| 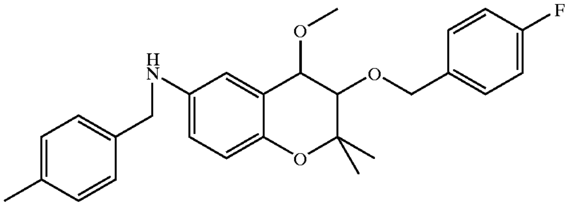 5-562 | $^1$H NMR(200 MHz, $CDCl_3$) δ 7.26~7.40(m, 4H), 7.00~7.25(m, 4H), 6.54~6.68(m, 3H), 4.87(d, 1H, J=11.4 Hz), 4.67(d, 1H, J=11.6 Hz), 4.42(d, 1H, J=7.5 Hz), 4.23(s, 2H), 3.60(d, 1H, J=7.5 Hz), 3.45(s, 3H), 2.34(s, 3H), 1.41(s, 3H), 1.23(s, 3H); MS, m/z: 435.54 |
| 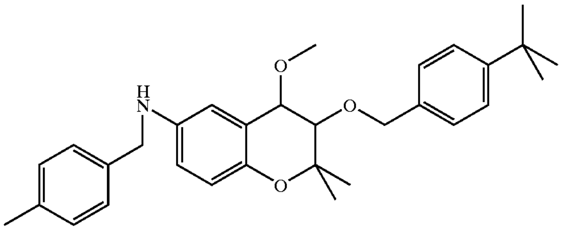 5-563 | MS, m/z: 473.66 |

TABLE 1-continued

| | Compound No. NMR/MS Data |
|---|---|
| 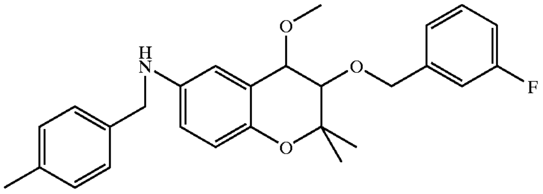 5-564 | $^1$H NMR(200 MHz, $CDCl_3$) δ 7.24~7.33(m, 4H), 7.08~7.16(m, 4H), 6.60~6.72(m, 3H), 4.92(d, 1H, J=12.0 Hz), 4.70(d, 1H, J=12.0 Hz), 4.42(d, 1H, J=7.3 Hz), 4.23(s, 2H), 3.60(d, 1H, J=7.3 Hz), 3.45(s, 3H), 2.33(s, 3H), 1.42(s, 3H), 1.24(s, 3H); MS, m/z: 435.54 |
| 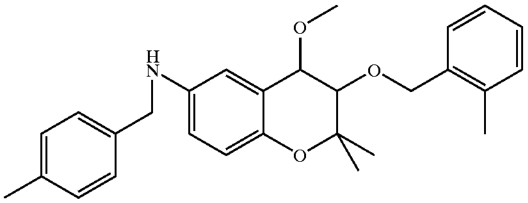 5-565 | $^1$H NMR(200 MHz, $CDCl_3$) δ 7.38~7.41(m, 3H), 7.13~7.29(m, 7H), 6.53~6.69(m, 3H), 4.93(d, 1H, J=11.6 Hz), 4.70(d, 1H, J=11.6 Hz), 4.42(d, 1H, J=7.3 Hz), 4.23(s, 2H), 3.64(d, 1H, J=7.3 Hz), 3.45(s, 3H), 2.37(s, 3H), 2.34(s, 3H), 1.39(s, 3H), 1.23(s, 3H); MS, m/z: 431.58 |
| 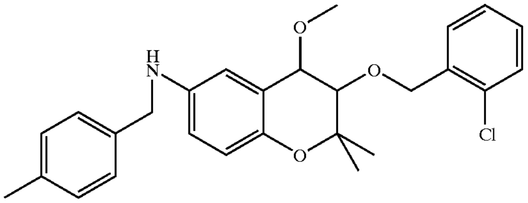 5-566 | $^1$H NMR(200 MHz, $CDCl_3$) δ 7.52~7.57(m, 1H), 7.12~7.39(m, 7H), 6.60~6.73(m, 3H), 5.02(d, 1H, J=12.4 Hz), 4.81(d, 1H, J=12.4 Hz), 4.44(d, 1H, J=7.3 Hz), 4.23(s, 2H), 3.67(d, 1H, J=7.3 Hz), 3.48(s, 3H), 2.33(s, 3H), 1.42(s, 3H), 1.26(s, 3H); MS, m/z: 452.00 |
| 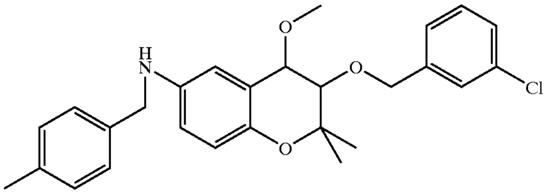 5-567 | $^1$H NMR(200 MHz, $CDCl_3$) δ 7.38~7.39(m, 1H), 7.21~7.30(m, 6H), 7.12~7.16(m, 1H), 6.59~6.70(m, 3H), 4.90(d, 1H, J= 12.0 Hz), 4.69(d, 1H, J=12.0 Hz), 4.43(d, 1H, J=7.5 Hz), 4.23(s, 2H), 3.60(d, 1H, J=7.5 Hz), 3.45(s, 3H), 2.34(s, 3H), 1.42(s, 3H), 1.24(s, 3H); MS, m/z: 452.00 |
| 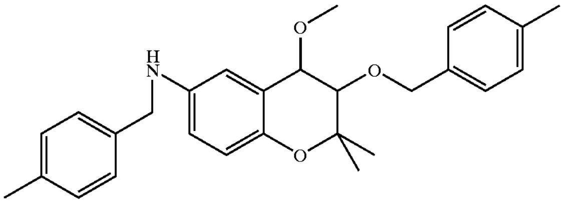 5-568 | $^1$H NMR(200 MHz, $CDCl_3$) δ 7.23~7.30(m, 4H), 7.11~7.18(m, 4H), 6.55~6.72(m, 3H), 4.86(d, 1H, J=11.2 Hz), 4.66(d, 1H, J=11.2 Hz), 4.39(d, 1H, J=6.9 Hz), 4.22(s, 2H), 3.58(d, 1H, J=6.9 Hz), 3.47(s, 3H), 2.35(s, 3H), 2.33(s, 3H), 1.39(s, 3H), 1.22(s, 3H); MS, m/z: 431.58 |
| 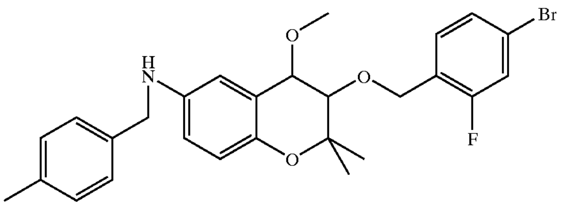 5-569 | $^1$H NMR(200 MHz, $CDCl_3$) δ 7.17~7.39(m, 7H), 6.51~6.68(m, 3H), 4.90(d, 1H, J=12.0 Hz), 4.73(d, 1H, J=12.0 Hz), 4.41(d, 1H, J=7.3 Hz), 4.23(s, 2H), 3.61(d, 1H, J=7.3 Hz), 3.46(s, 3H), 2.35(s, 3H), 1.40(s, 3H), 1.21(s, 3H); MS, m/z: 514.44 |

TABLE 1-continued

| | Compound No. NMR/MS Data |
|---|---|
| 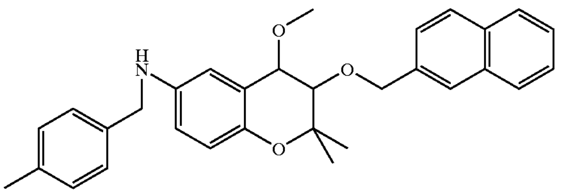 5-570 | MS, m/z: 467.61 |
| 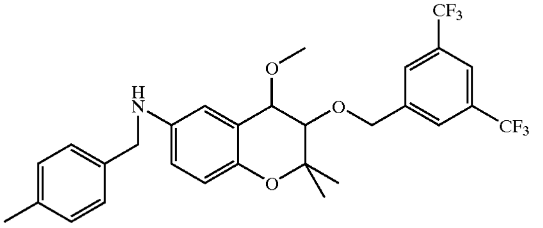 5-571 | $^1$H NMR(200 MHz, $CDCl_3$) δ 7.83(b, 3H), 7.13~7.29(m, 4H), 6.52~6.69(m, 3H), 5.06(d, 1H, J=12.4 Hz), 4.83(d, 1H, J=12.4 Hz), 4.50(d, 1H, J=7.7 Hz), 4.24(s, 2H), 3.65(d, 1H, J=7.7 Hz), 3.41 (s, 3H), 2.34(s, 3H), 1.45(s, 3H), 1.26(s, 3H); MS, m/z: 445.61 |
| 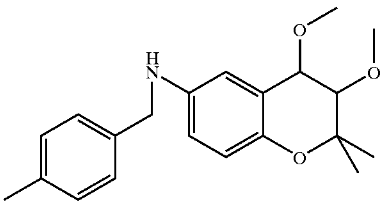 5-572 | MS, m/z: 341.45 |
| 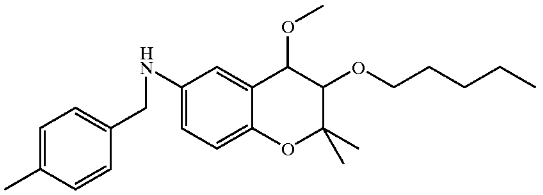 5-573 | $^1$H NMR(200 MHz, $CDCl_3$) δ 7.12~7.28(m, 4H), 6.49~6.66(m, 3H), 4.30(d, 1H, J=7.1 Hz), 4.22(s, 2H), 3.81~3.86(m, 1H), 3.56~3.78(m, 2H), 3.50(s, 3H), 3.40(s, 3H), 2.34(s, 3H), 1.57~1.61(m, 2H), 1.40(s, 3H), 1.26~1.38(m, 4H), 1.20(s, 3H), 0.90~0.94(m 3H); MS, m/z: 397.56 |
| 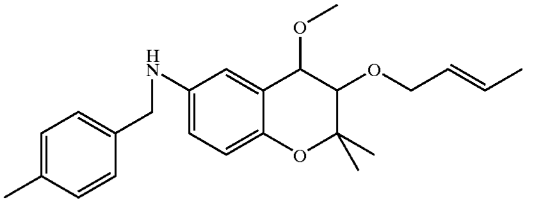 5-574 | $^1$H NMR(200 MHz, $CDCl_3$) δ 7.24~7.28(m, 2H), 7.12~7.24(m, 2H), 6.65(d, 1H, J=3.3 Hz), 6.62(s, 1H), 6.52(dd, 1H, J=2.8 Hz, J=8.9 Hz), 5.63~5.73(m, 2H), 4.33(d, 1H, J=7.3 Hz), 4.22(s, 2H), 4.08~4.27(m, 2H), 3.50(d, 1H, J=7.3 Hz), 3.50(s, 3H), 2.34(s, 3H), 1.71(d, 3H, J=0.8 Hz), 1.40(s, 3H), 1.21(s, 3H); MS, m/z: 381.52 |
| 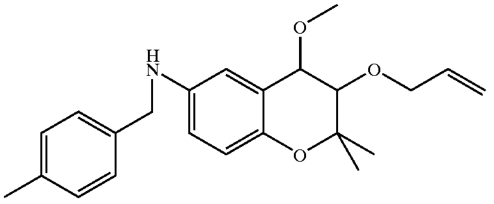 5-575 | $^1$H NMR(200 MHz, $CDCl_3$) δ 7.25~7.29(m, 2H), 7.12~7.16(m, 2H), 6.02~6.67(m, 3H), 5.88~5.99(m, 1H), 5.37(dd, 1H, J=1.6 Hz, J=17.3 Hz), 5.19(dd, 1H, J=1.4 Hz, j=10.4 Hz), 4.35(d, 1H, J=7.5 Hz), 4.23(s, 2H), 4.18~4.36(m, 2H), 3.51(d, 1H, J=7.5 Hz), 3.49(s, 3H), 2.34(s, 3H), 1.42(s, 3H), 1.22(s, 3H); MS, m/z: 367.49 |

TABLE 1-continued
| | Compound No. NMR/MS Data |
|---|---|
| 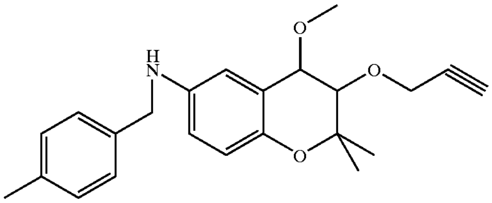 5-576 | $^1$H NMR(200 MHz, $CDCl_3$) δ 7.24~7.28(m, 2H), 7.12~7.16(m, 2H), 6.57~6.68(m, 3H), 4.46(d, 2H, J=2.2 Hz), 4.41(d, 1H, J=7.1 Hz), 4.22(s, 3H), 3.74(d, 1H, J=7.1 Hz), 3.46(s, 3H), 2.46(t, 1H, J=2.4 Hz), 2.34(s, 3H), 1.44(s, 3H), 1.22(s, 3H); MS, m/z: 365.48 |
| 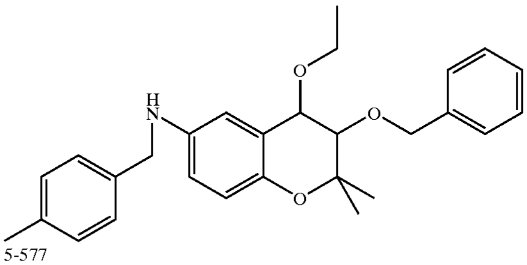 5-577 | MS, m/z: 431.58 |
| 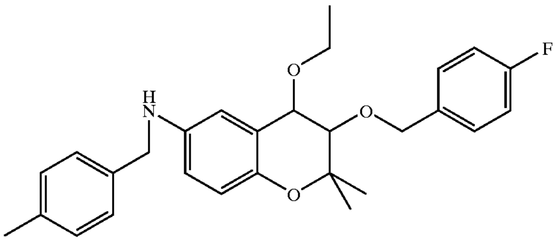 5-578 | MS, m/z: 449.57 |
| 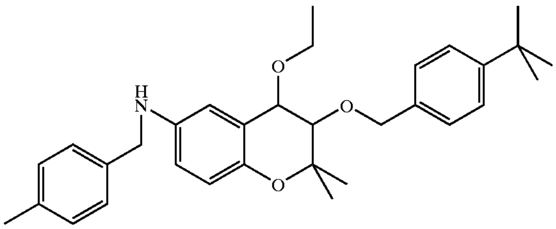 5-579 | MS, m/z: 487.69 |
| 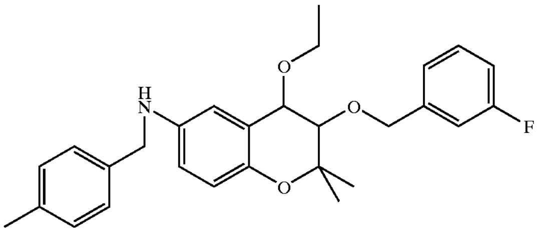 5-580 | MS, m/z: 449.57 |
| 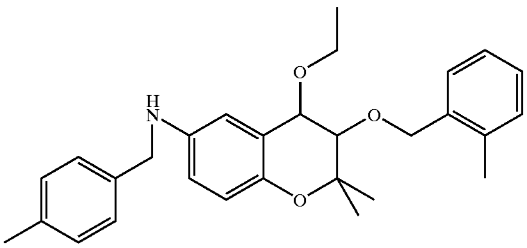 5-581 | MS, m/z: 445.61 |

TABLE 1-continued
| | Compound No. NMR/MS Data |
|---|---|
| 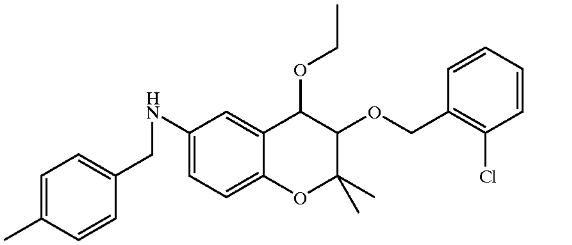<br>5-582 | MS, m/z: 466.03 |
| 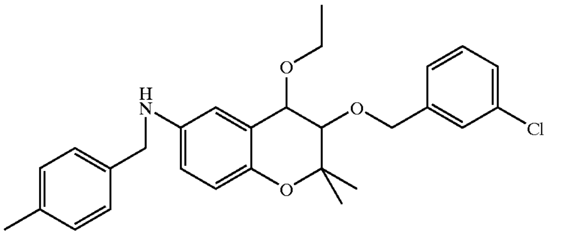<br>5-583 | MS, m/z: 466.03 |
| 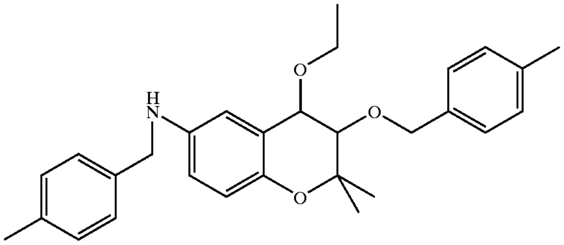<br>5-584 | MS, m/z: 445.61 |
| 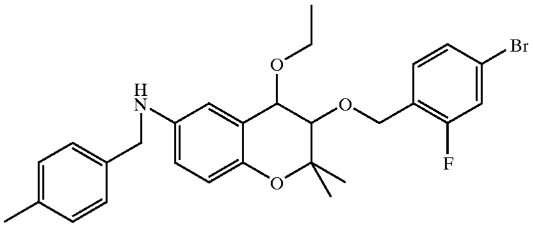<br>5-585 | MS, m/z: 528.47 |
| 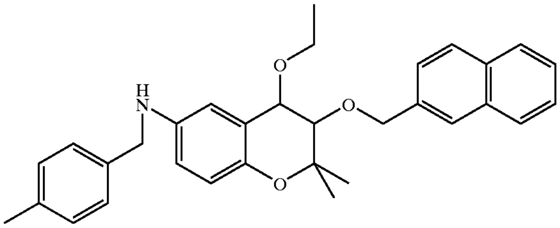<br>5-586 | MS, m/z: 481.64 |

TABLE 1-continued
| | Compound No. NMR/MS Data |
|---|---|
| 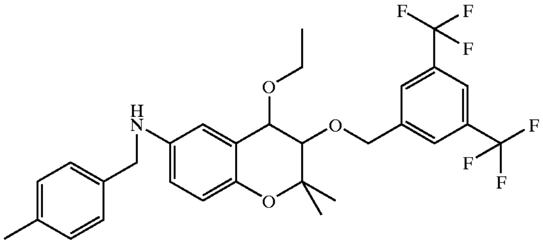 5-587 | MS, m/z: 567.58 |
| 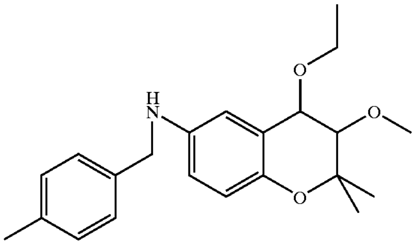 5-588 | MS, m/z: 355.48 |
| 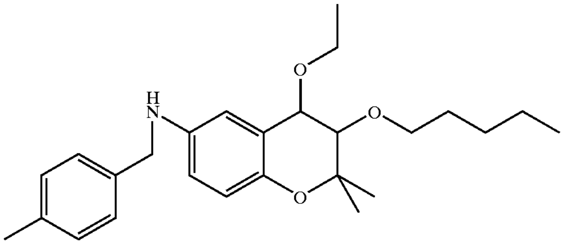 5-589 | MS, m/z: 411.59 |
| 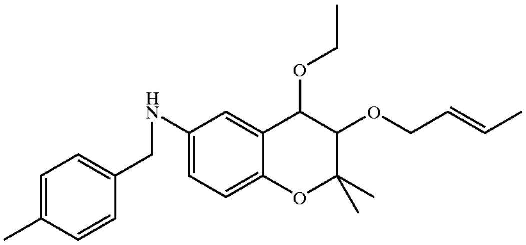 5-590 | MS, m/z: 395.55 |
| 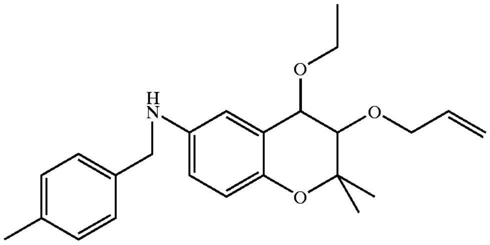 5-591 | MS, m/z: 381.52 |

TABLE 1-continued
| Compound No. | NMR/MS Data |
|---|---|
| 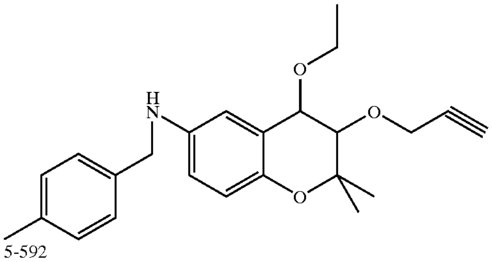 5-592 | MS, m/z: 379.50 |
| 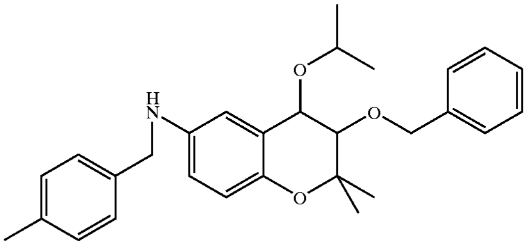 5-593 | MS, m/z 445.61 |
| 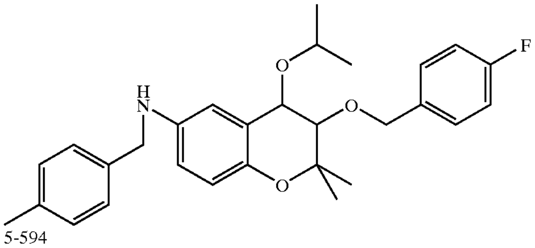 5-594 | MS, m/z: 463.60 |
| 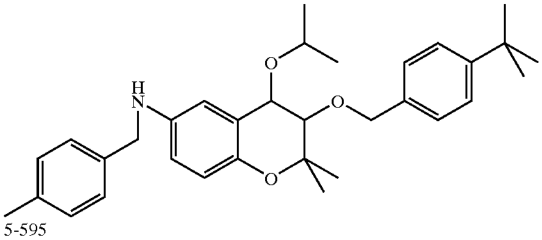 5-595 | MS, m/z: 501.72 |
| 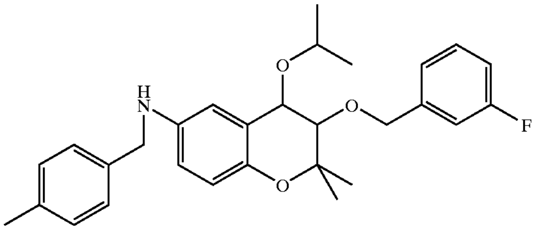 5-596 | MS, m/z: 463.60 |
| 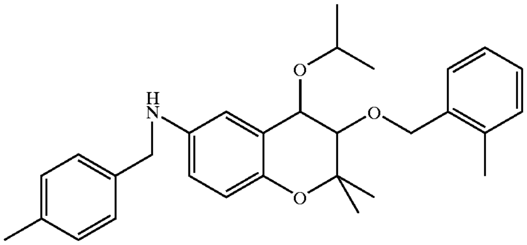 5-597 | MS, m/z: 459.63 |

TABLE 1-continued
| | Compound No. NMR/MS Data |
|---|---|
| 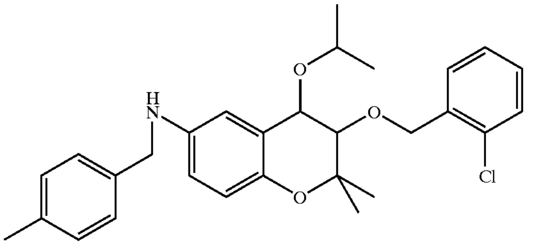 5-598 | MS, m/z: 480.05 |
| 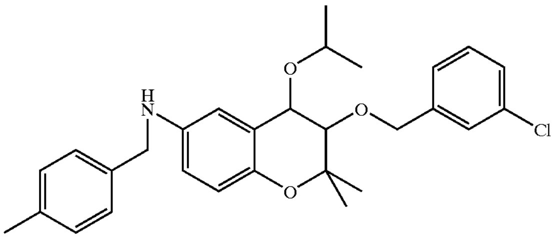 5-599 | MS, m/z: 480.05 |
| 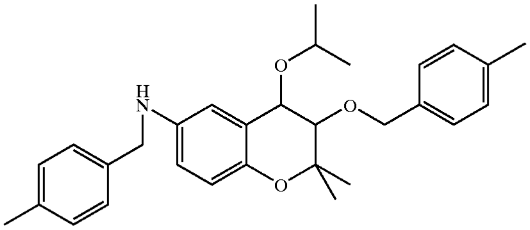 5-600 | MS, m/z: 459.63 |
| 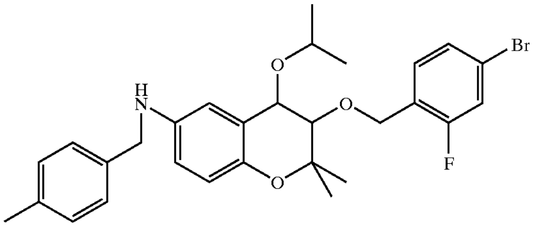 5-601 | MS, m/z: 542.49 |
| 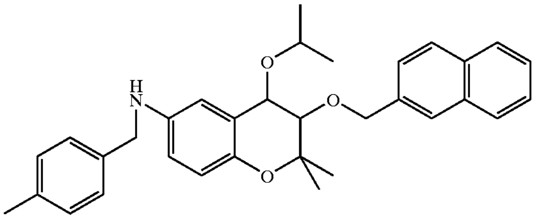 5-602 | MS, m/z: 495.67 |

TABLE 1-continued
| | Compound No. NMR/MS Data |
|---|---|
| 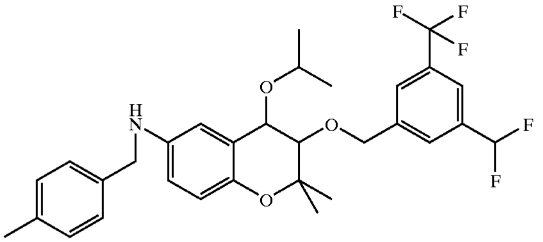 5-603 | MS, m/z: 581.60 |
| 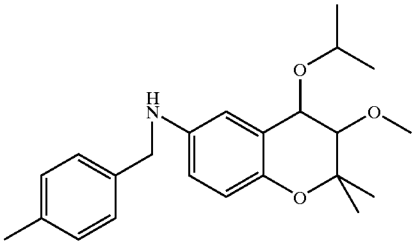 5-604 | MS, m/z: 369.51 |
| 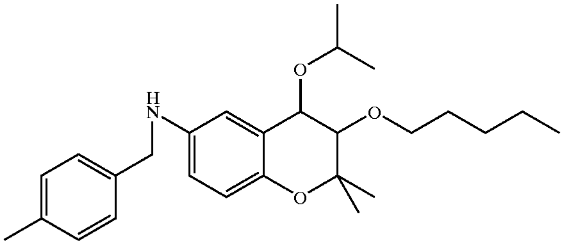 5-605 | MS, m/z: 425.62 |
| 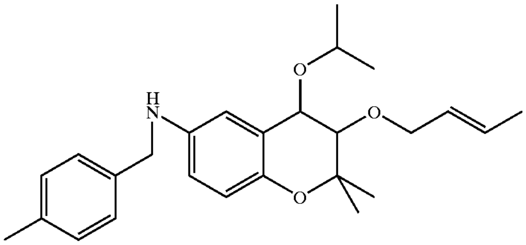 5-606 | MS, m/z: 409.57 |
| 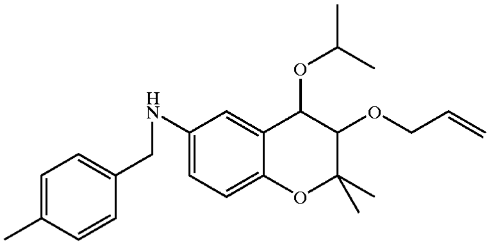 5-607 | MS, m/z: 395.55 |

TABLE 1-continued
| | Compound No. NMR/MS Data |
|---|---|
| 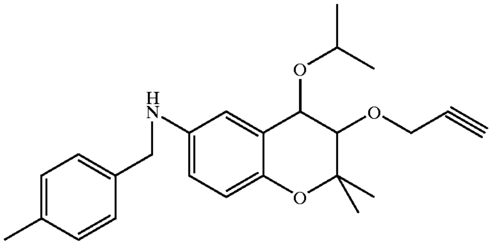 5-608 | MS, m/z: 393.53 |
| 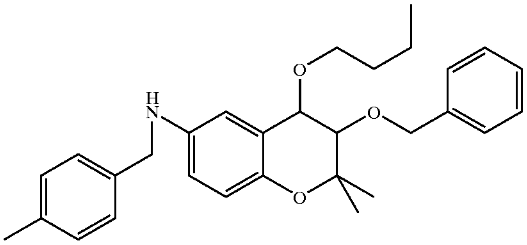 5-609 | MS, m/z: 459.63 |
| 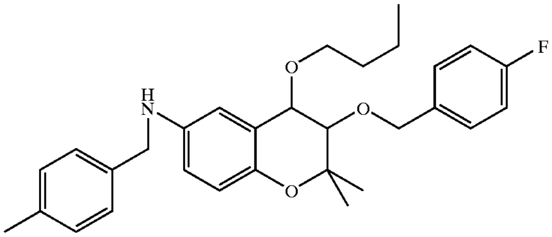 5-610 | MS, m/z: 477.62 |
| 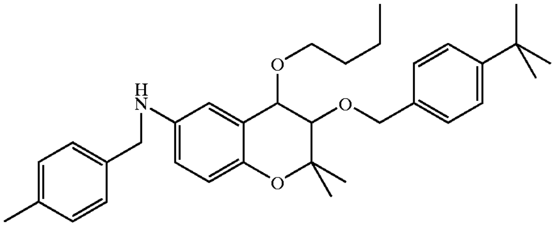 5-611 | MS, m/z: 515.74 |
| 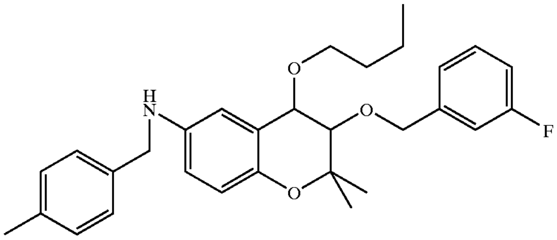 5-612 | MS, m/z: 477.62 |

TABLE 1-continued
| | Compound No. NMR/MS Data |
|---|---|
| 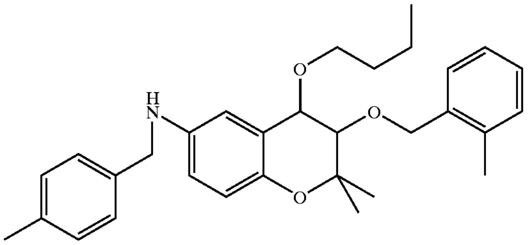 5-613 | MS, m/z: 473.66 |
| 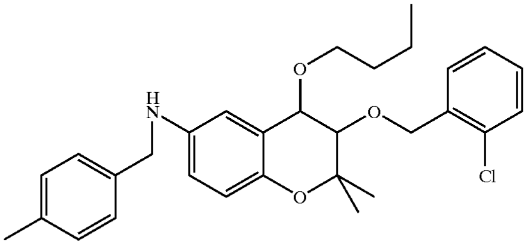 5-614 | MS, m/z: 494.08 |
| 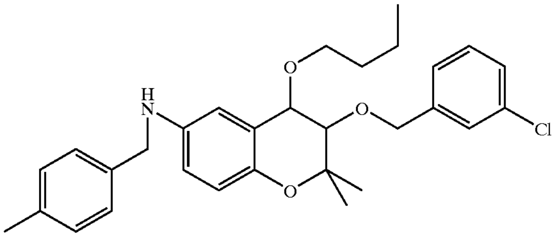 5-615 | MS, m/z: 494.08 |
| 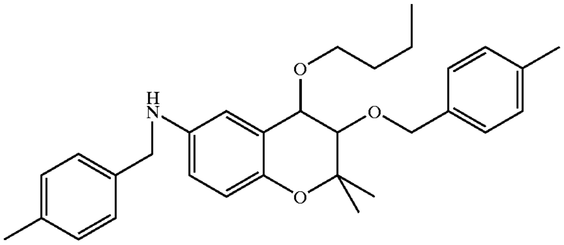 5-616 | MS, m/z: 473.66 |
| 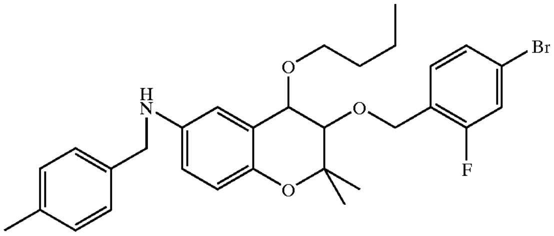 5-617 | MS, m/z: 556.52 |

TABLE 1-continued
| Compound No. | NMR/MS Data |
| --- | --- |
| 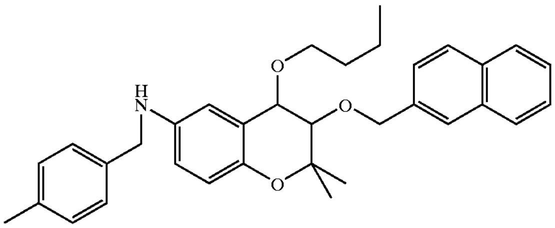 5-618 | MS, m/z: 509.69 |
| 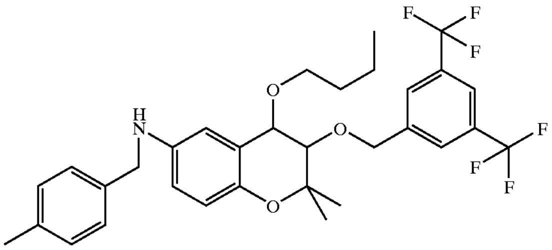 5-619 | MS, m/z: 595.63 |
| 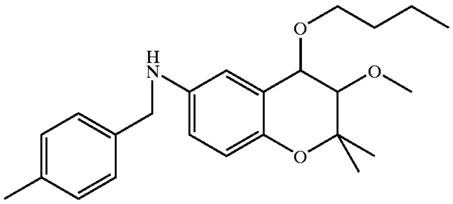 5-620 | MS, m/z: 383.54 |
| 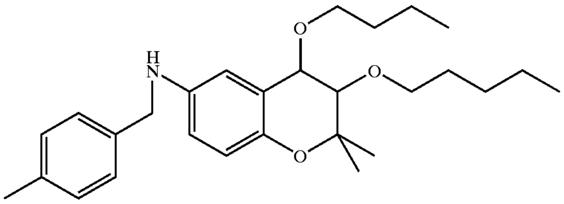 5-621 | MS, m/z: 439.64 |
| 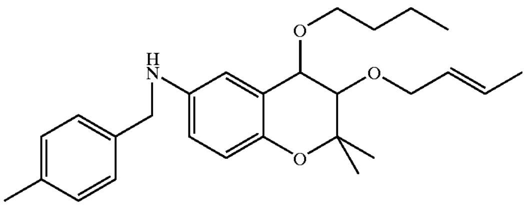 5-622 | MS, m/z: 423.60 |

TABLE 1-continued
| | Compound No. NMR/MS Data |
|---|---|
| 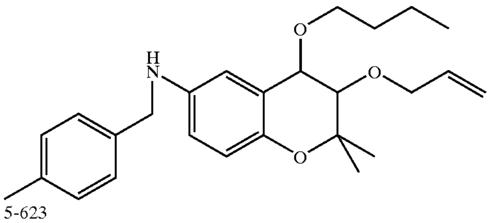 5-623 | MS, m/z: 409.57 |
| 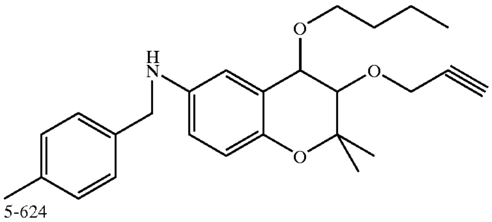 5-624 | MS, m/z: 407.56 |
| 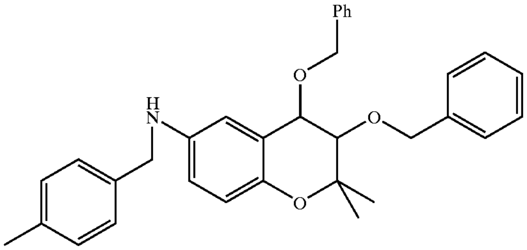 5-625 | MS, m/z: 493.65 |
| 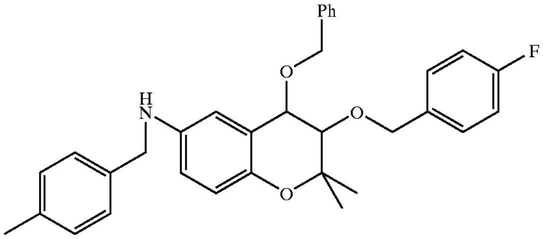 5-626 | MS, m/z: 511.64 |
| 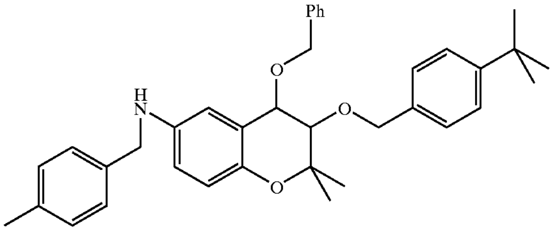 5-627 | MS, m/z: 549.76 |
| 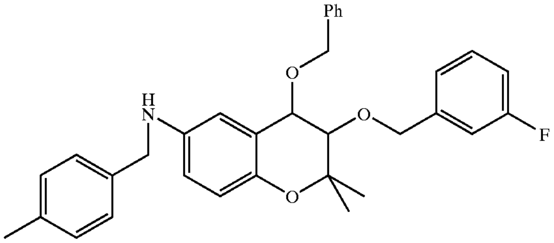 5-628 | MS, m/z: 511.64 |

TABLE 1-continued
| | Compound No. NMR/MS Data |
|---|---|
| 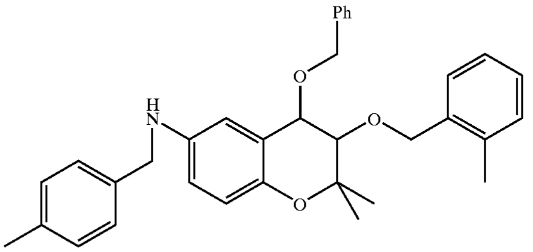 5-629 | MS, m/z: 507.68 |
| 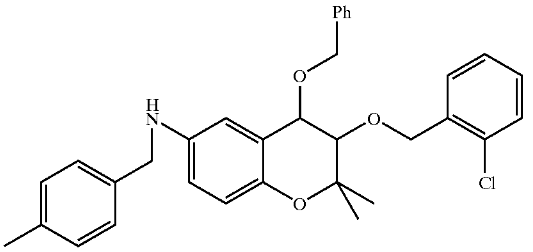 5-630 | MS, m/z: 528.10 |
| 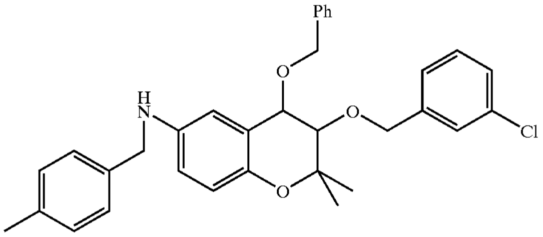 5-631 | MS, m/z: 528.10 |
| 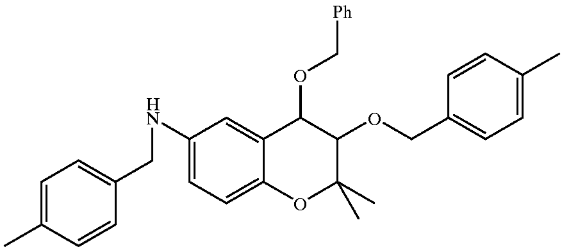 5-632 | MS, m/z: 507.68 |
| 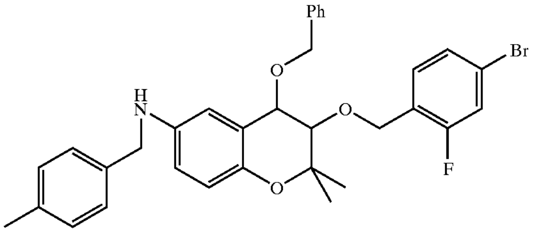 5-633 | MS, m/z: 590.54 |

TABLE 1-continued
| | Compound No. NMR/MS Data |
|---|---|
| 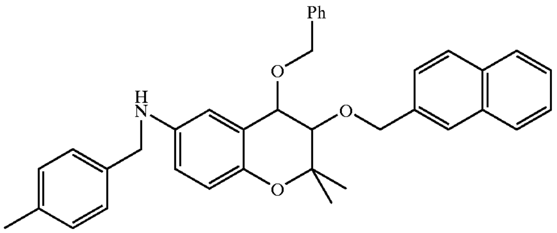 5-634 | MS, m/z: 543.71 |
| 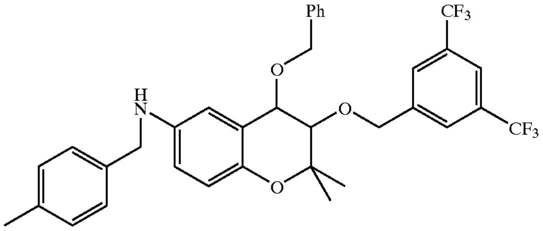 5-635 | MS, m/z: 521.71 |
| 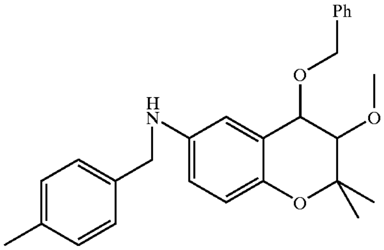 5-636 | MS, m/z: 417.55 |
| 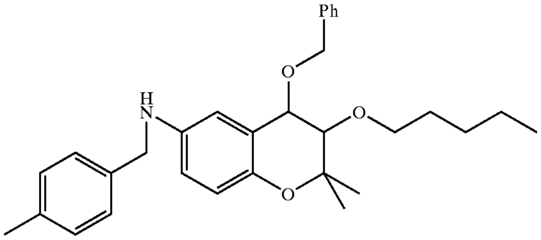 5-637 | MS, m/z: 473.66 |
| 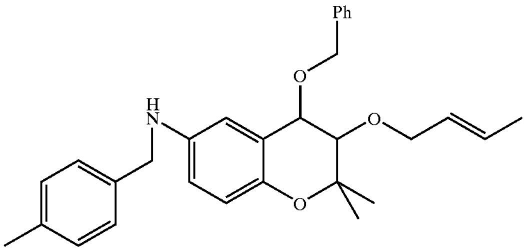 5-638 | MS, m/z: 457.62 |

TABLE 1-continued
| | Compound No. NMR/MS Data |
|---|---|
| 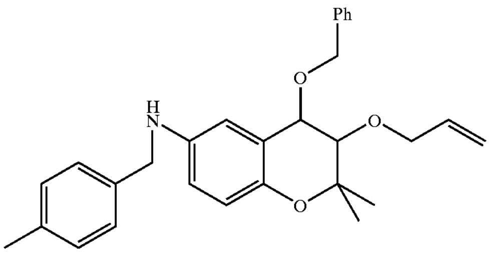 5-639 | MS, m/z: 443.59 |
| 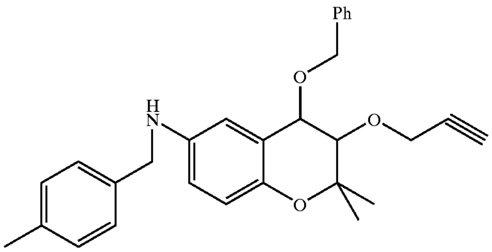 5-640 | MS, m/z: 441.58 |
| 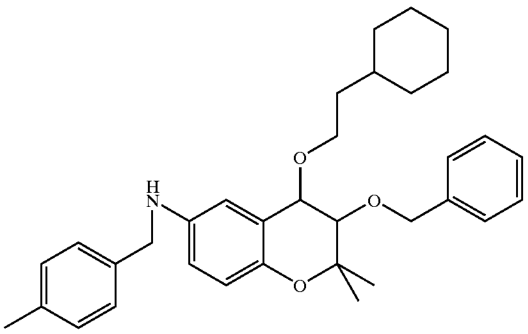 5-641 | MS, m/z: 507.68 |
| 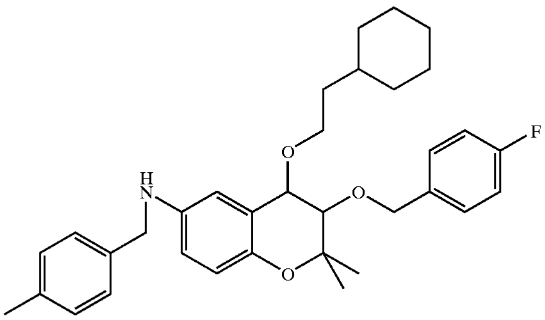 5-642 | MS, m/z: 525.67 |

TABLE 1-continued
| | Compound No. NMR/MS Data |
|---|---|
| 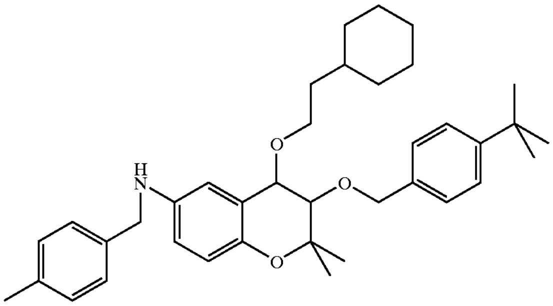 5-643 | MS, m/z: 563.79 |
| 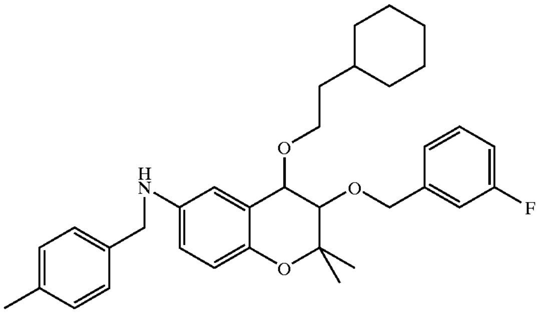 5-644 | MS, m/z: 525.67 |
| 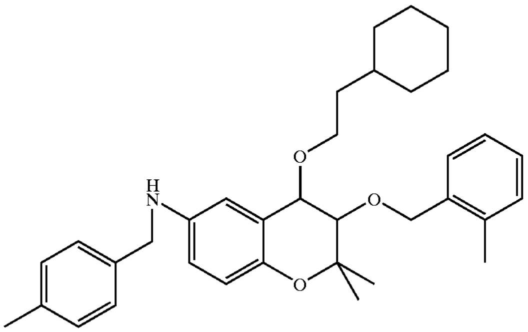 5-645 | MS, m/z: 521.71 |
| 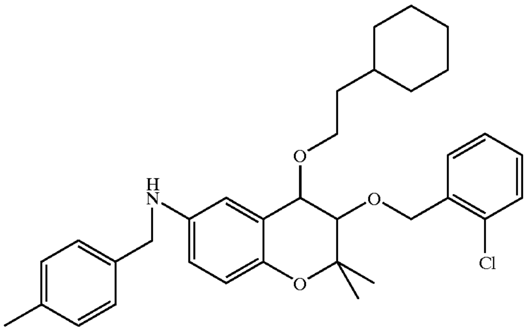 5-646 | MS, m/z: 542.12 |

TABLE 1-continued
| | Compound No. NMR/MS Data |
|---|---|
| 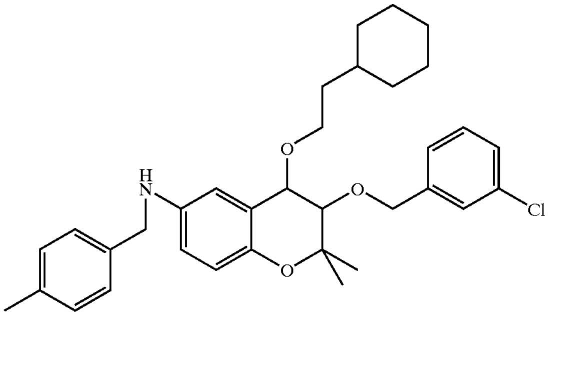 5-647 | MS, m/z: 542.12 |
| 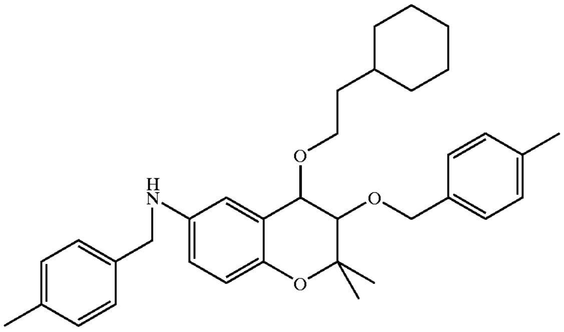 5-648 | MS, m/z: 521.71 |
| 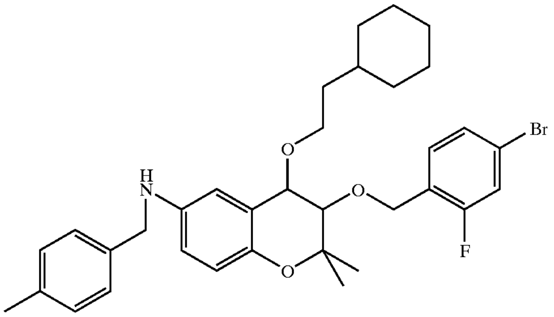 5-649 | MS, m/z: 604.57 |
| 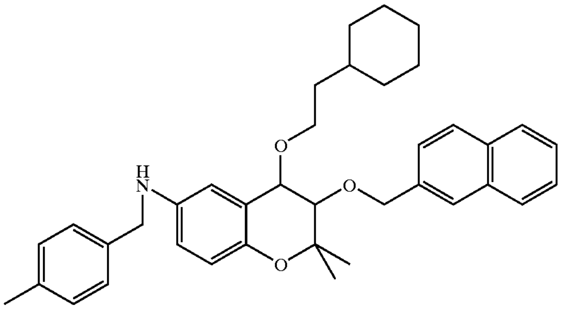 5-650 | MS, m/z: 557.74 |

TABLE 1-continued
| | Compound No. NMR/MS Data |
|---|---|
| 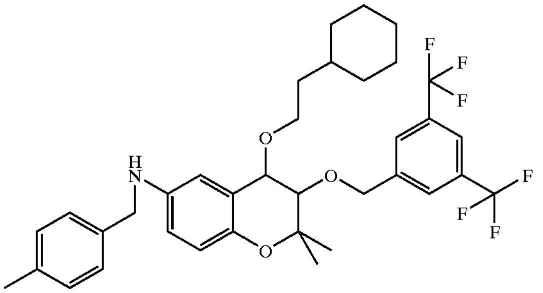 5-651 | MS, m/z: 643.68 |
| 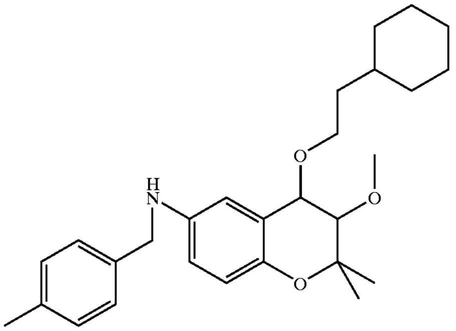 5-652 | MS, m/z: 431.58 |
| 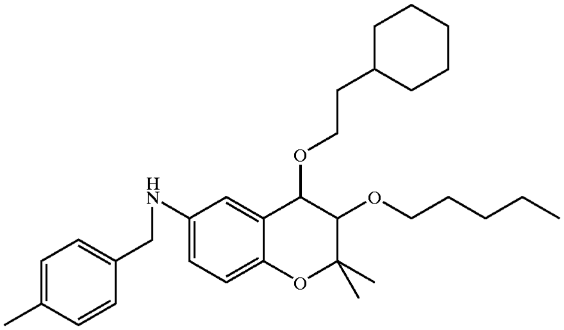 5-653 | MS, m/z: 487.69 |
| 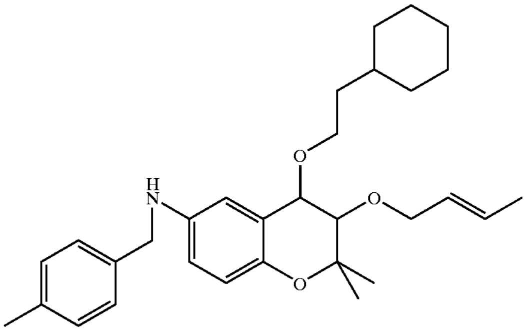 5-654 | MS, m/z: 471.65 |

TABLE 1-continued
| | Compound No. NMR/MS Data |
|---|---|
| 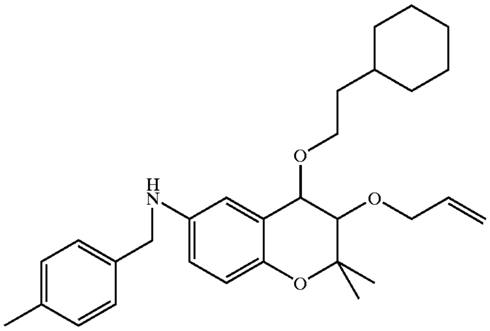 5-655 | MS, m/z: 457.62 |
| 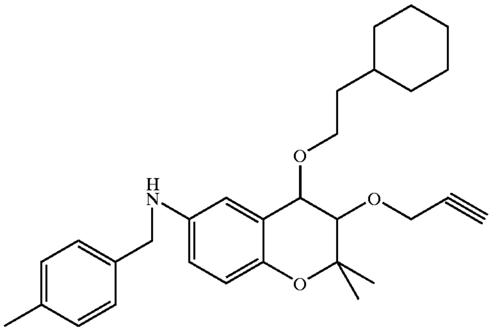 5-656 | MS, m/z: 455.60 |
| 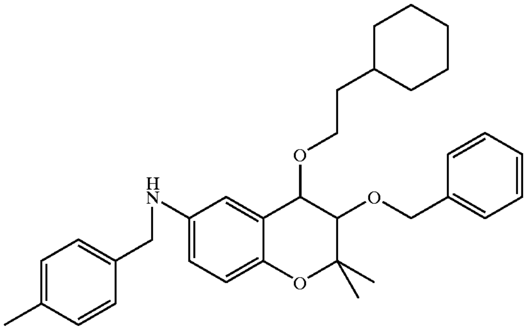 5-657 | MS, m/z: 513.73 |
| 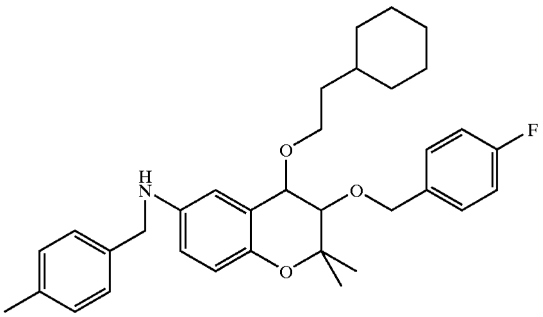 5-658 | MS, m/z: 531.72 |

TABLE 1-continued
| | Compound No. NMR/MS Data |
|---|---|
| 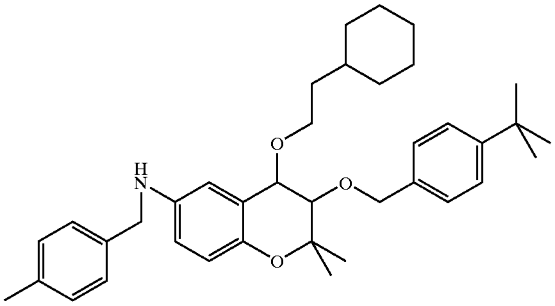 5-659 | MS, m/z: 569.84 |
| 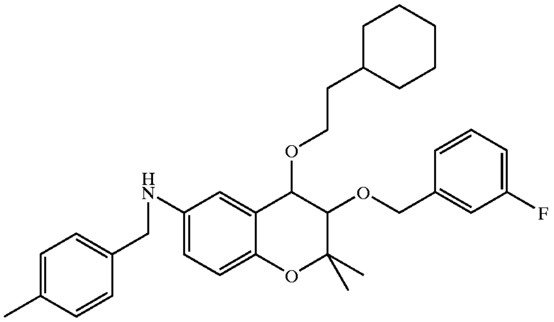 5-660 | MS, m/z: 531.72 |
| 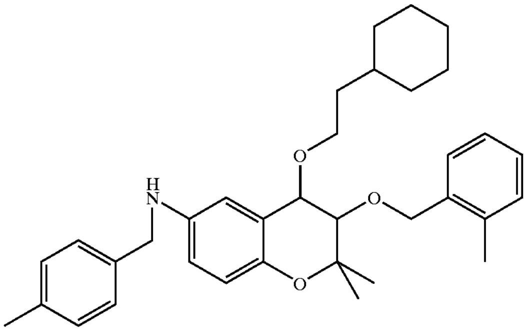 5-661 | MS, m/z: 527.75 |
| 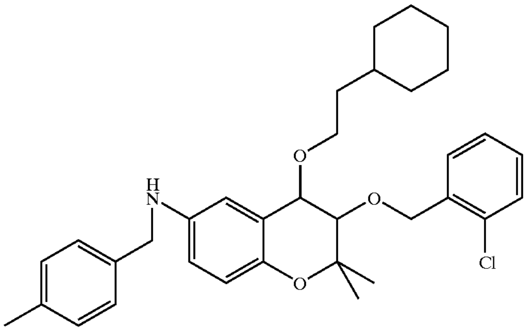 5-662 | MS, m/z: 548.17 |

TABLE 1-continued
| | Compound No. NMR/MS Data |
|---|---|
| 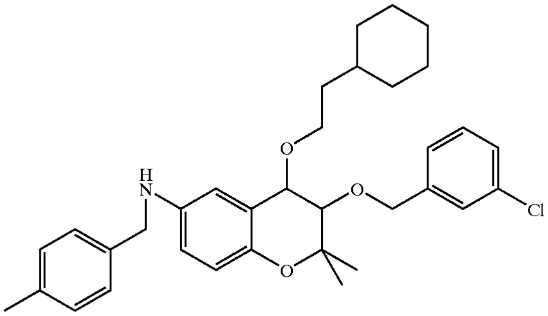 5-663 | MS, m/z: 548.17 |
| 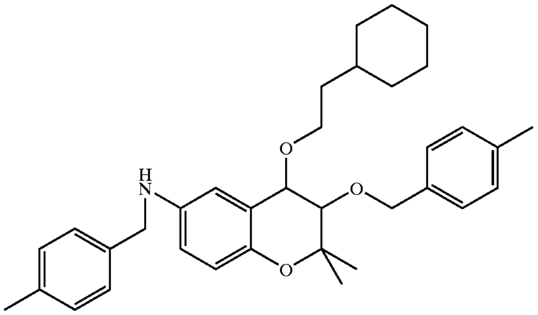 5-664 | MS, m/z: 527.75 |
| 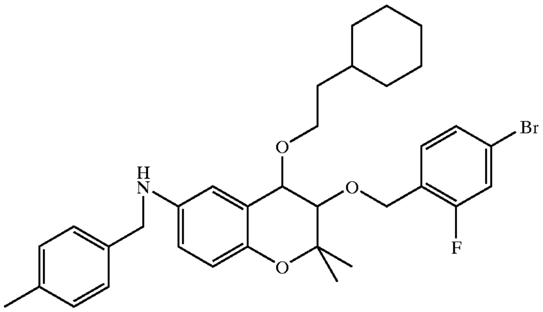 5-665 | MS, m/z: 610.61 |
| 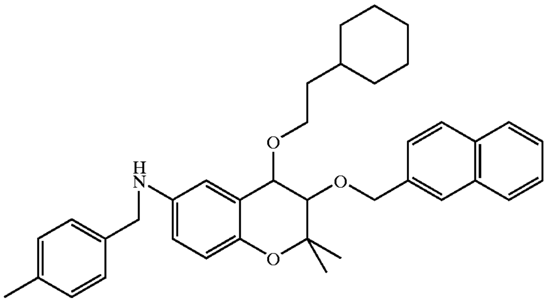 5-666 | MS, m/z: 563.79 |

TABLE 1-continued
| Compound No. | NMR/MS Data |
|---|---|
| 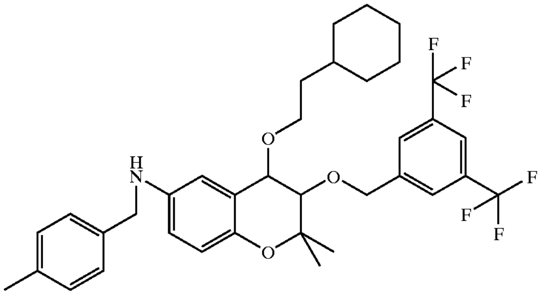 5-667 | MS, m/z: 649.72 |
| 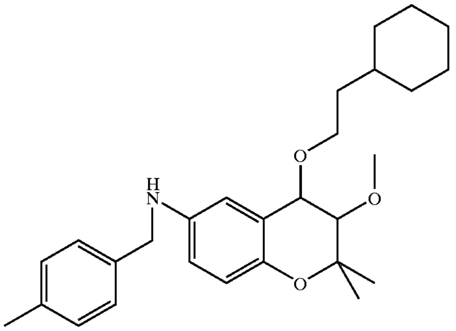 5-668 | MS, m/z: 437.63 |
| 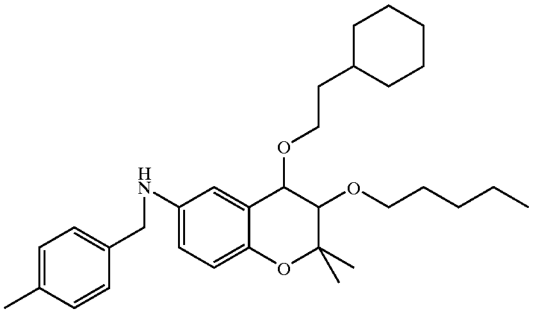 5-669 | MS, m/z: 493.74 |
| 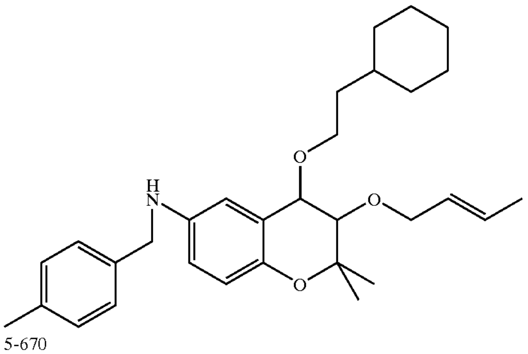 5-670 | MS, m/z: 477.69 |

TABLE 1-continued
| | Compound No. NMR/MS Data |
|---|---|
| 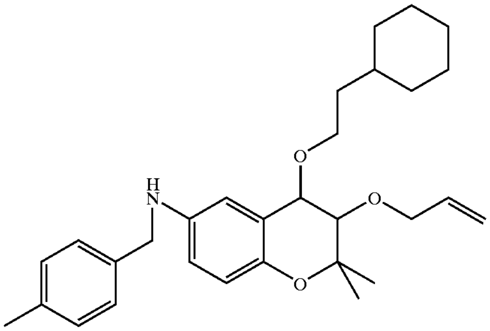 5-671 | MS, m/z: 463.67 |
| 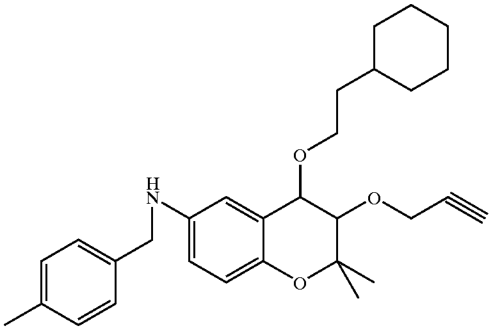 5-672 | MS, m/z: 461.65 |
| 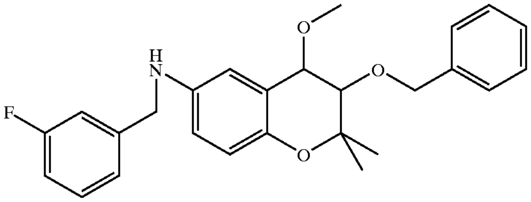 5-673 | MS, m/z: 421.52 |
| 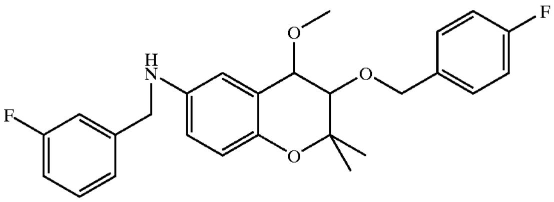 5-674 | MS, m/z: 439.51 |
| 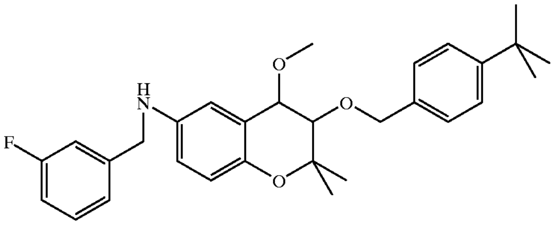 5-675 | MS, m/z: 477.62 |

TABLE 1-continued
| | Compound No. NMR/MS Data |
|---|---|
| 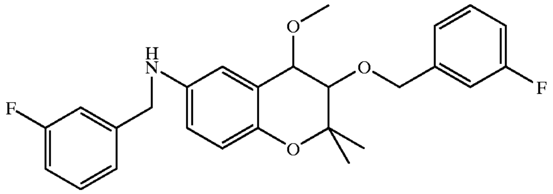 5-676 | MS, m/z: 439.51 |
| 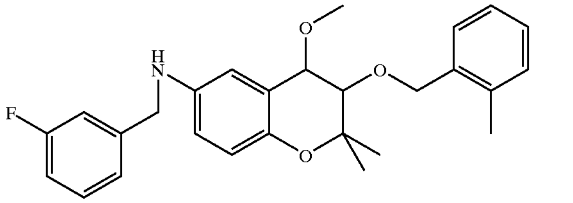 5-677 | MS, m/z: 435.54 |
| 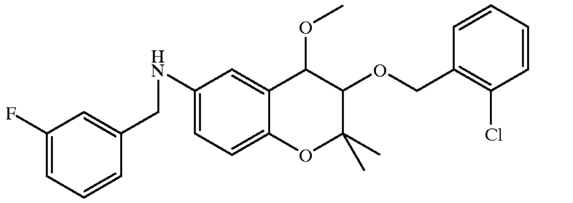 5-678 | MS, m/z: 455.96 |
| 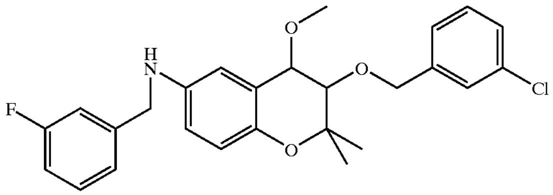 5-679 | MS, m/z: 455.96 |
| 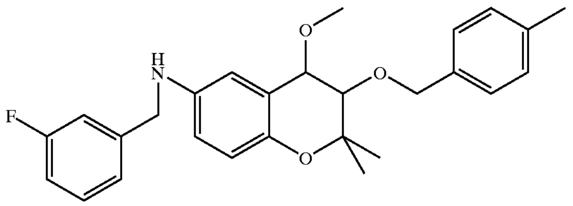 5-680 | MS, m/z: 435.54 |
| 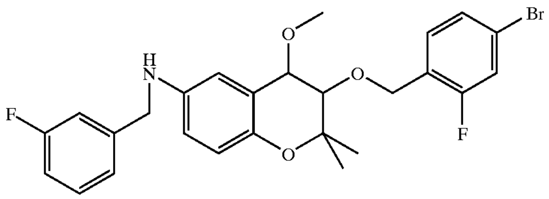 5-681 | MS, m/z: 518.40 |

TABLE 1-continued
| | Compound No. NMR/MS Data |
|---|---|
| 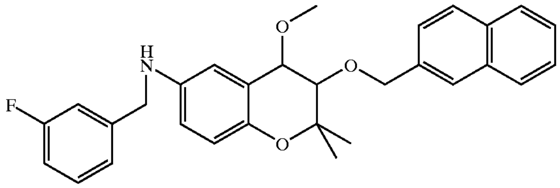 5-682 | MS, m/z: 471.58 |
| 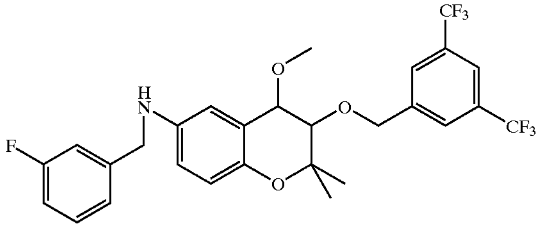 5-683 | MS, m/z: 449.57 |
| 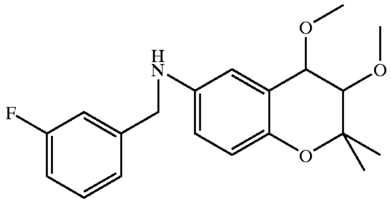 5-684 | MS, m/z: 345.42 |
| 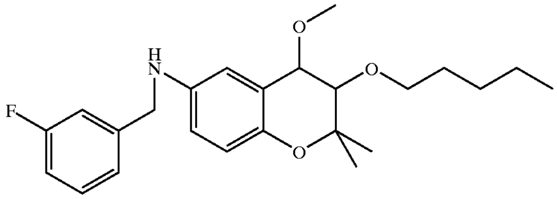 5-685 | MS, m/z: 401.53 |
| 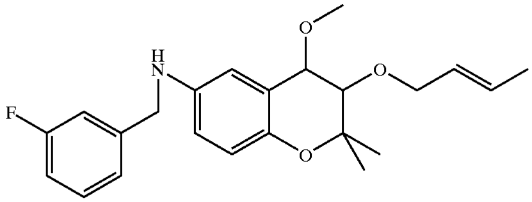 5-686 | MS, m/z: 385.48 |
| 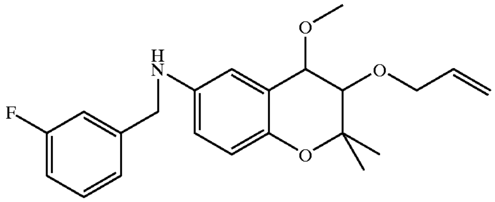 5-687 | MS, m/z: 371.46 |

TABLE 1-continued
| Compound No. | NMR/MS Data |
|---|---|
| 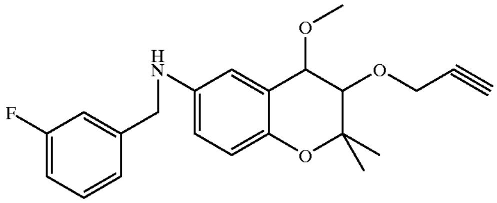 5-688 | MS, m/z: 369.44 |
| 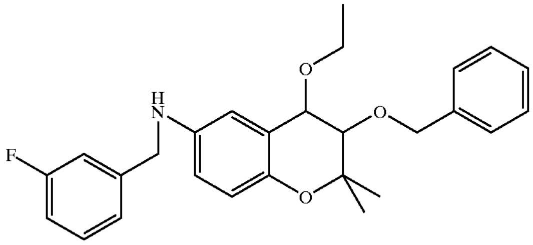 5-689 | MS, m/z: 435.54 |
| 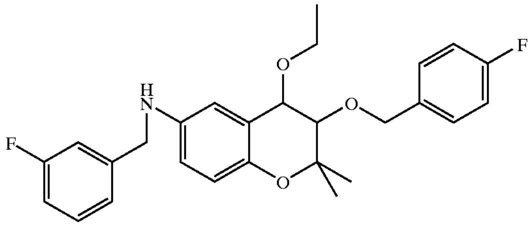 5-690 | MS, m/z: 453.53 |
| 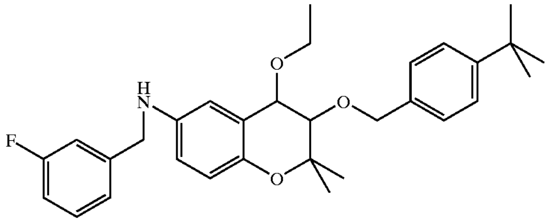 5-691 | MS, m/z: 491.65 |
| 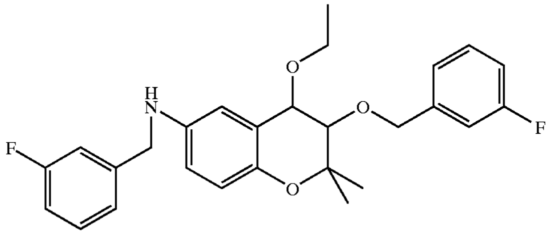 5-692 | MS, m/z: 453.53 |
| 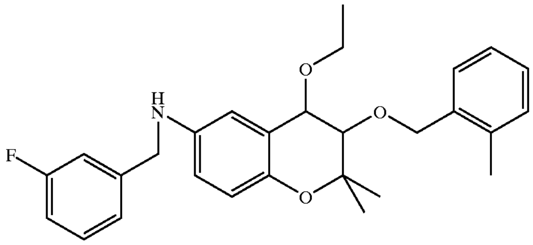 5-693 | MS, m/z: 449.57 |

TABLE 1-continued
| | Compound No. NMR/MS Data |
|---|---|
| 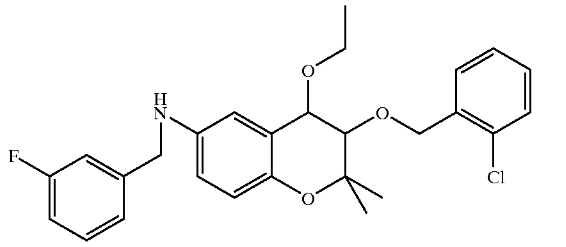 5-694 | MS, m/z: 469.99 |
| 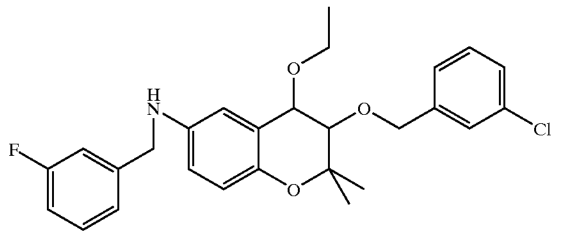 5-695 | MS, m/z: 469.99 |
| 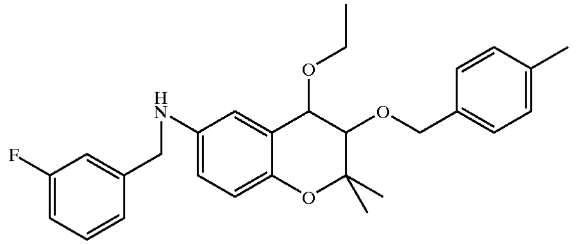 5-696 | MS, m/z: 449.57 |
| 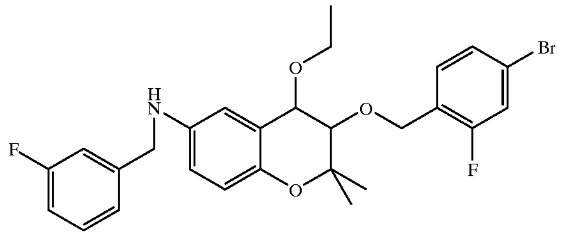 5-697 | MS, m/z: 532.43 |
| 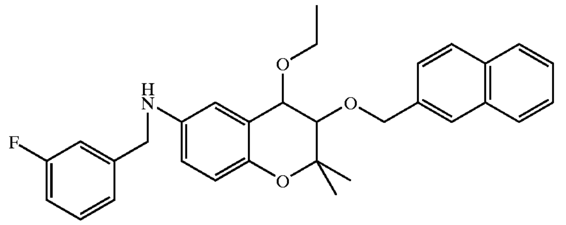 5-698 | MS, m/z: 485.60 |

TABLE 1-continued
| | Compound No. NMR/MS Data |
|---|---|
| 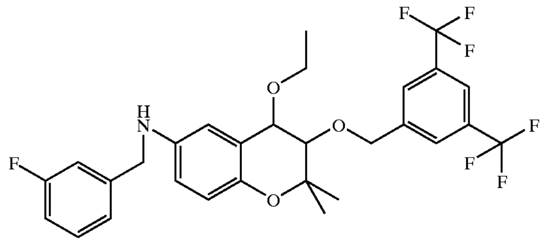 5-699 | MS, m/z: 571.54 |
| 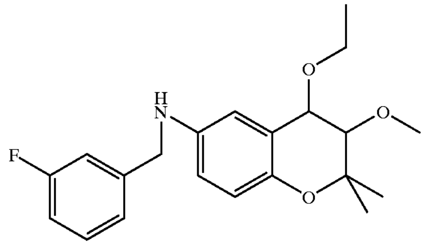 5-700 | MS, m/z: 359.44 |
| 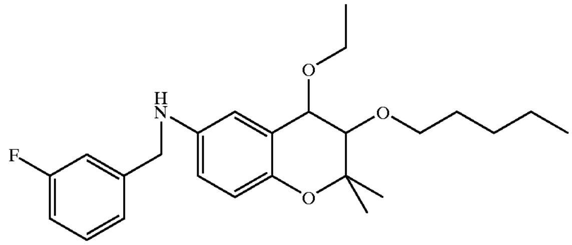 5-701 | MS, m/z: 415.55 |
| 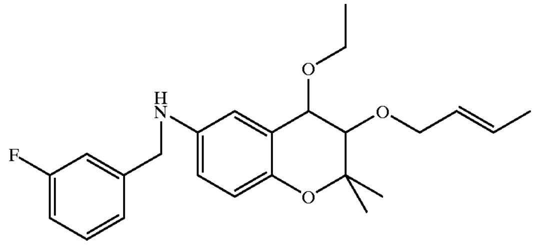 5-702 | MS, m/z: 399.51 |
| 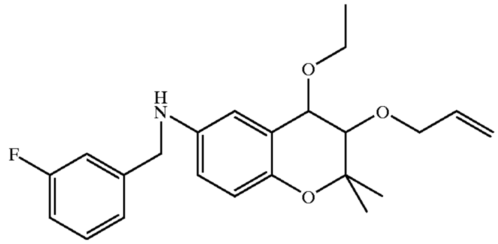 5-703 | MS, m/z: 385.48 |

TABLE 1-continued
| | Compound No. NMR/MS Data |
|---|---|
| 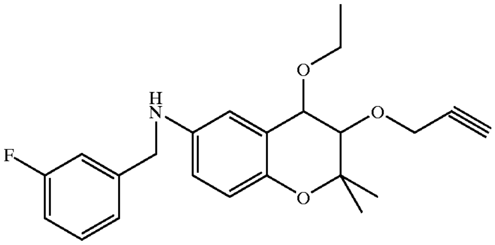 5-704 | MS, m/z: 383.47 |
| 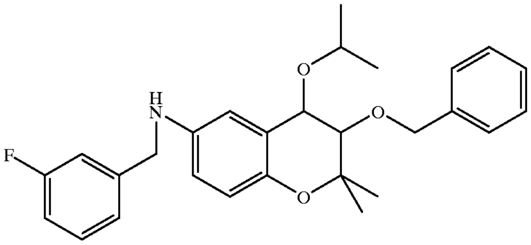 5-705 | MS, m/z: 449.57 |
| 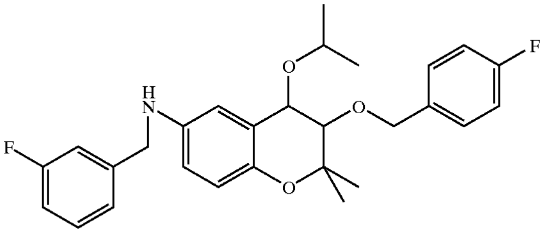 5-706 | MS, m/z: 467.56 |
| 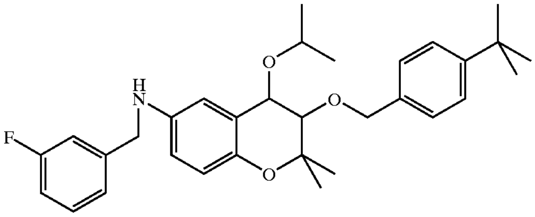 5-707 | MS, m/z: 505.68 |
| 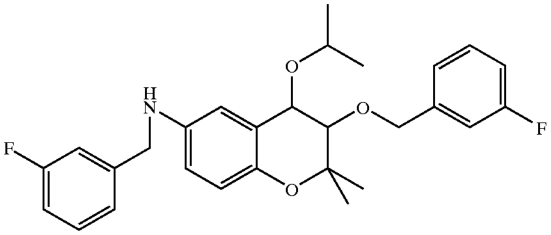 5-708 | MS, m/z: 467.56 |

TABLE 1-continued
| | Compound No. NMR/MS Data |
|---|---|
| 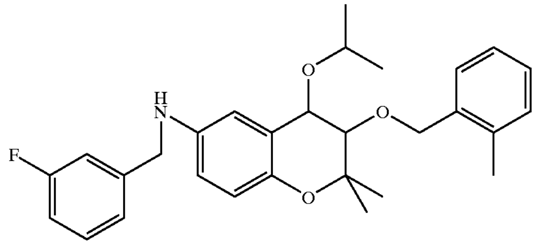 5-709 | MS, m/z: 463.60 |
| 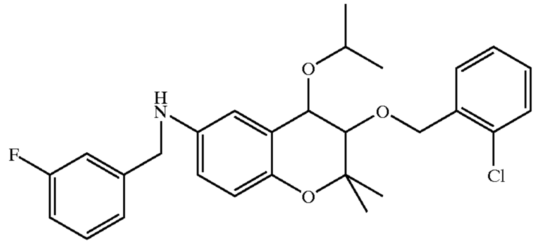 5-710 | MS, m/z: 484.02 |
| 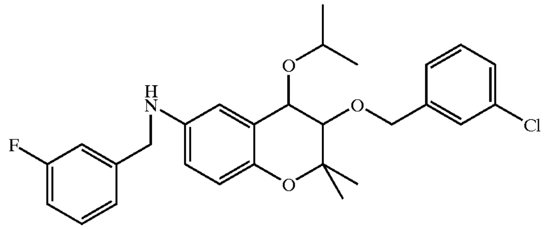 5-711 | MS, m/z: 484.02 |
| 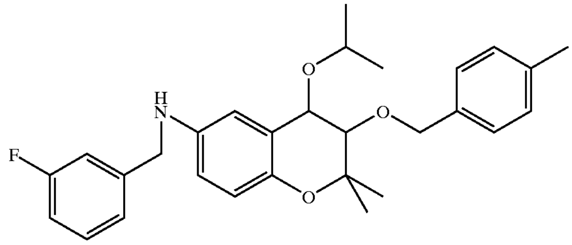 5-712 | MS, m/z: 463.60 |
| 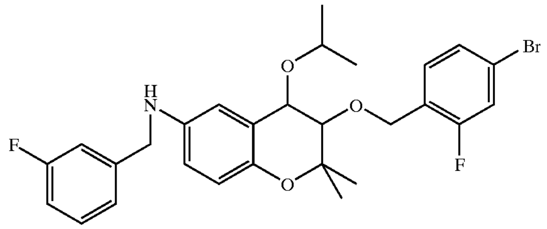 5-713 | MS, m/z: 546.46 |

TABLE 1-continued
| | Compound No. NMR/MS Data |
|---|---|
| 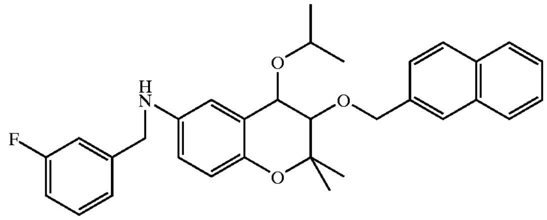 5-714 | MS, m/z: 499.63 |
| 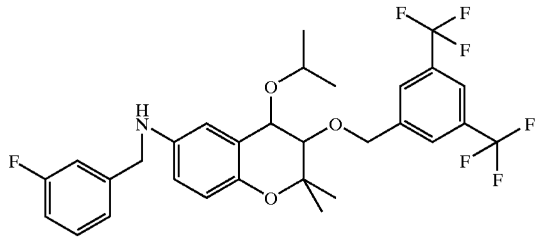 5-715 | MS, m/z: 585.57 |
| 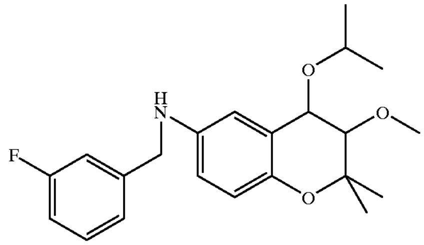 5-716 | MS, m/z: 373.47 |
| 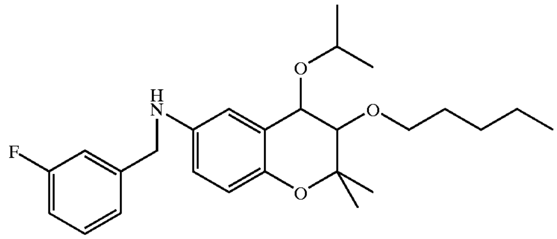 5-717 | MS, m/z: 429.58 |
| 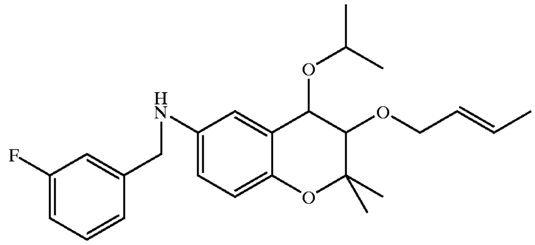 5-718 | MS, m/z: 413.54 |

TABLE 1-continued
| | Compound No. NMR/MS Data |
|---|---|
| 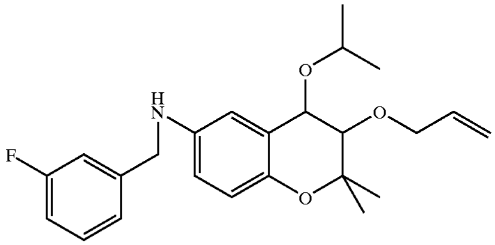 5-719 | MS, m/z: 399.51 |
| 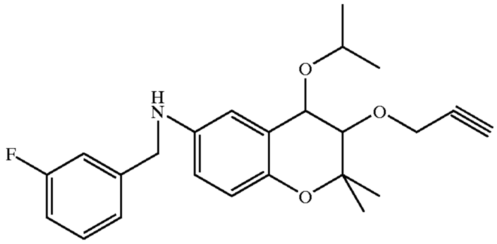 5-720 | MS, m/z: 397.49 |
| 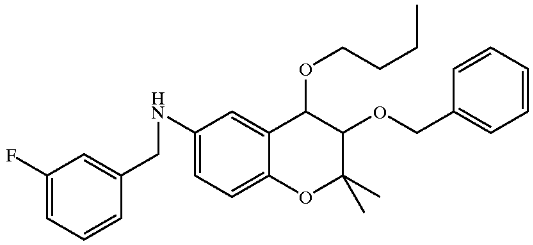 5-721 | MS, m/z: 463.60 |
| 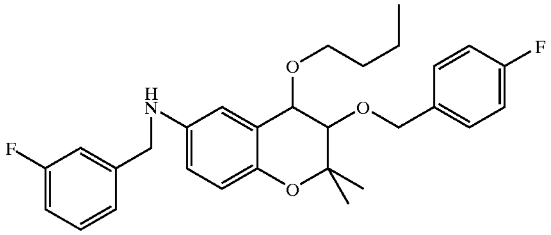 5-722 | MS, m/z: 481.59 |
| 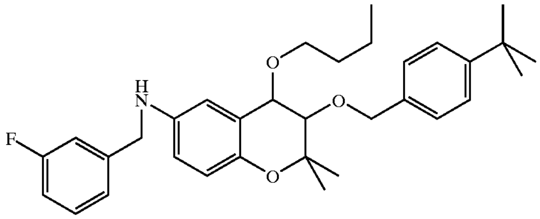 5-723 | MS, m/z: 519.71 |

TABLE 1-continued
| | Compound No. NMR/MS Data |
|---|---|
| 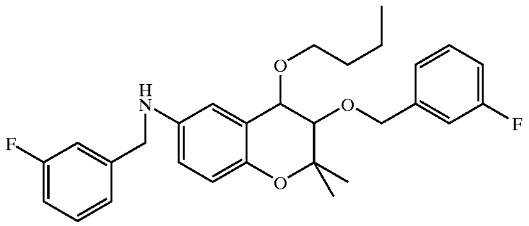 5-724 | MS, m/z: 481.59 |
| 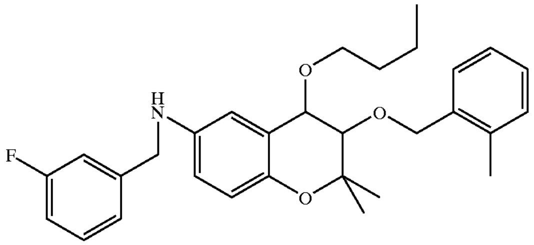 5-725 | MS, m/z: 477.62 |
| 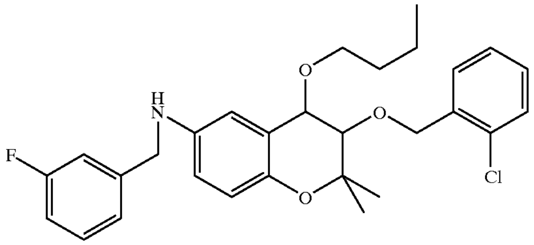 5-726 | MS, m/z: 498.04 |
| 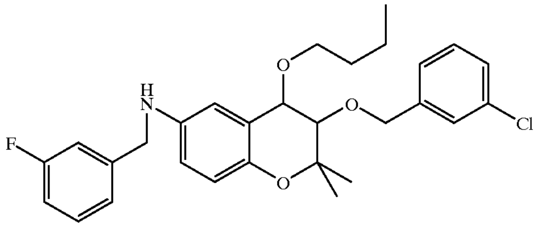 5-727 | MS, m/z: 498.04 |
| 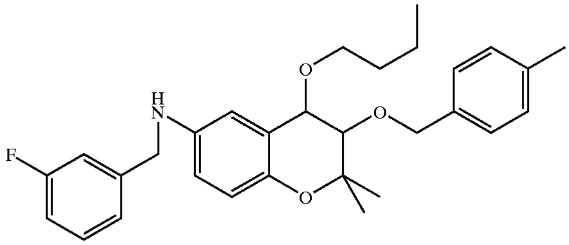 5-728 | MS, m/z: 477.62 |

TABLE 1-continued
| | Compound No. NMR/MS Data |
|---|---|
| 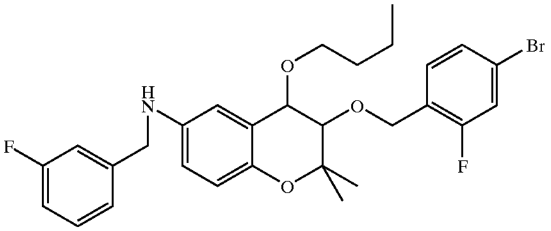 5-729 | MS, m/z: 560.48 |
| 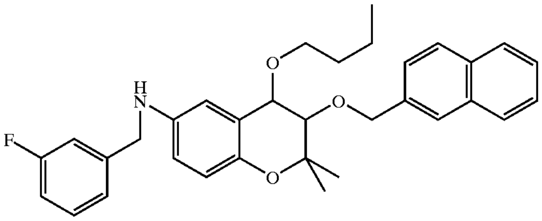 5-730 | MS, m/z: 513.66 |
| 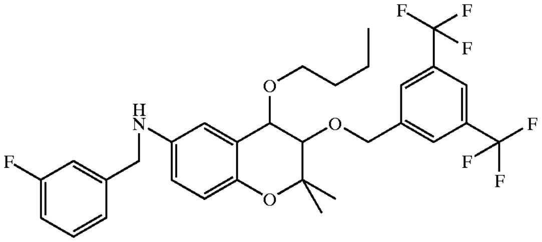 5-731 | MS, m/z: 599.59 |
| 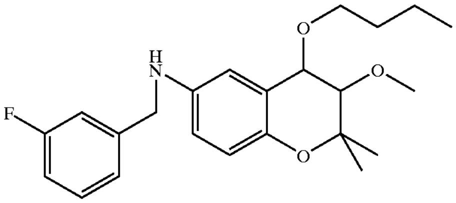 5-732 | MS, m/z: 387.50 |
| 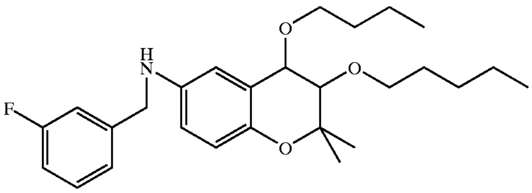 5-733 | MS, m/z: 443.61 |
| 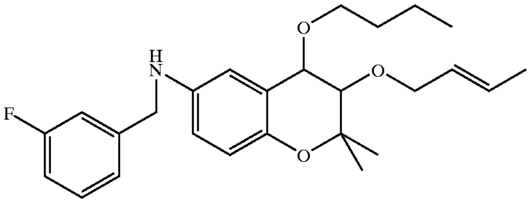 5-734 | MS, m/z: 427.56 |

TABLE 1-continued
| | Compound No. NMR/MS Data |
|---|---|
| 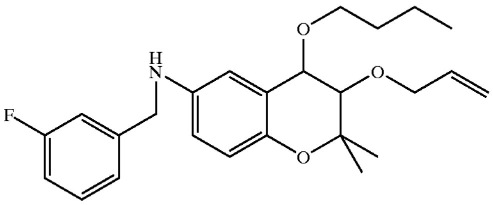<br>5-735 | MS, m/z: 413.54 |
| 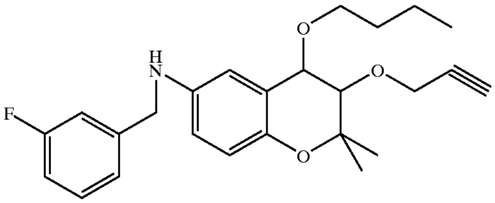<br>5-736 | MS, m/z: 411.52 |
| 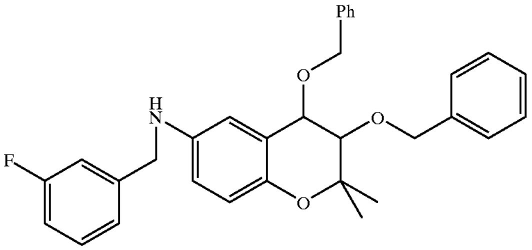<br>5-737 | MS, m/z: 497.62 |
| 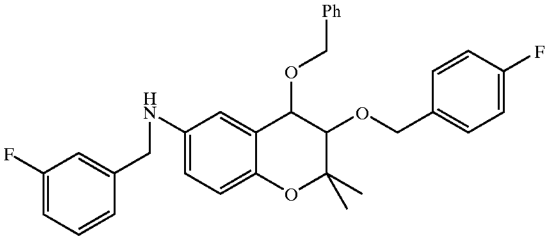<br>5-738 | MS, m/z: 515.61 |
| 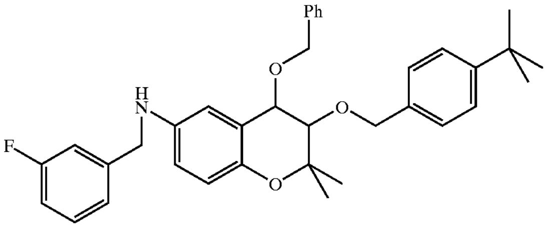<br>5-739 | MS, m/z: 553.72 |
| 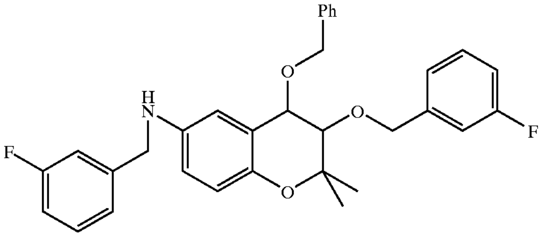<br>5-740 | MS, m/z: 515.61 |

TABLE 1-continued
| | Compound No. NMR/MS Data |
|---|---|
| 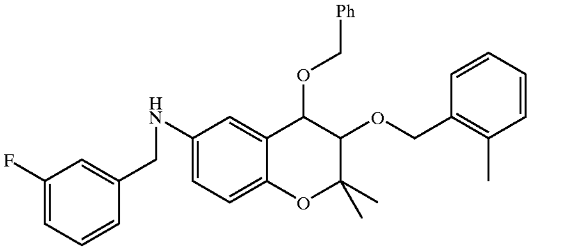 5-741 | MS, m/z: 511.64 |
| 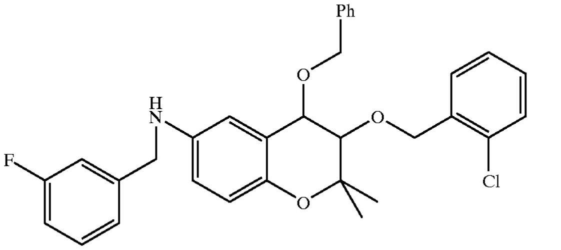 5-742 | MS, m/z: 532.06 |
| 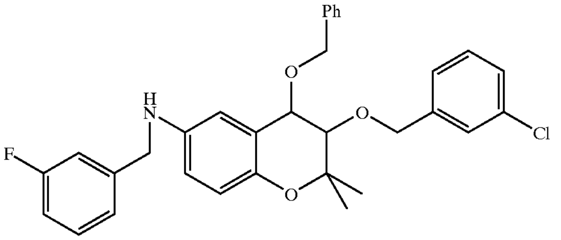 5-743 | MS, m/z: 532.06 |
| 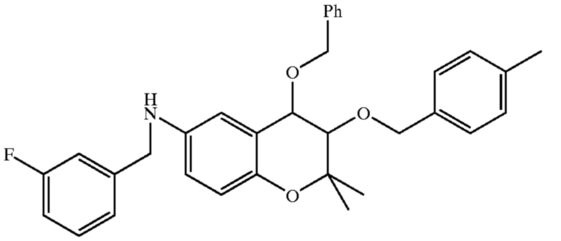 5-744 | MS, m/z: 511.64 |
| 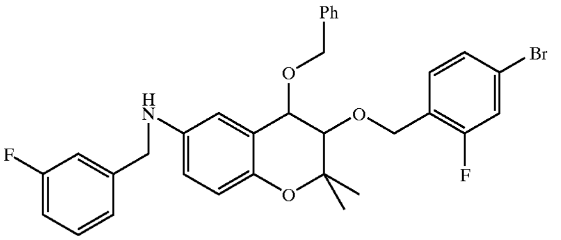 5-745 | MS, m/z: 594.50 |

TABLE 1-continued
| | Compound No. NMR/MS Data |
|---|---|
| 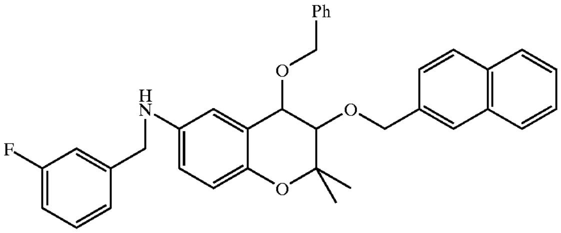 5-746 | MS, m/z: 547.68 |
| 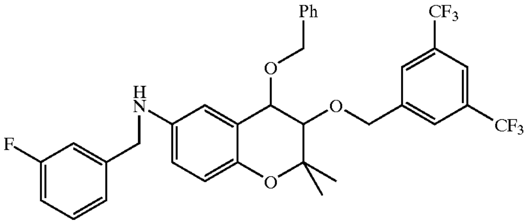 5-747 | MS, m/z: 525.67 |
| 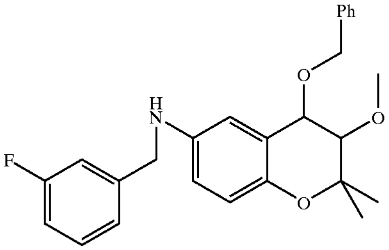 5-748 | MS, m/z: 421.52 |
| 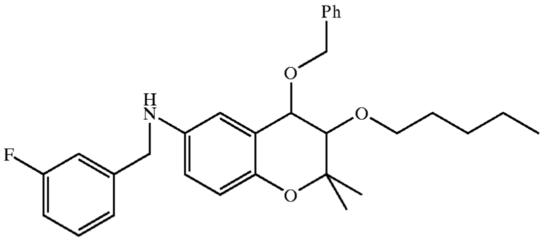 5-749 | MS, m/z: 477.62 |
| 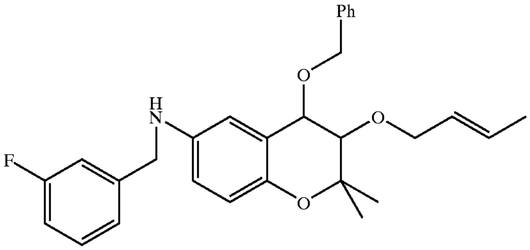 5-750 | MS, m/z: 461.58 |

TABLE 1-continued
| | Compound No. NMR/MS Data |
|---|---|
| 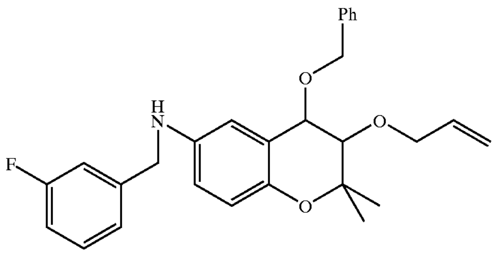 | MS, m/z: 447.55 |
| 5-751 | |
| 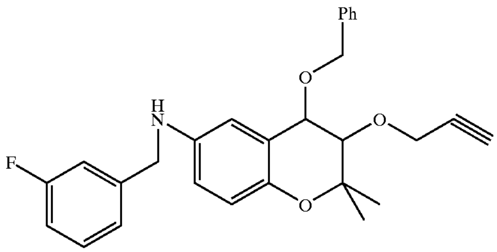 | MS, m/z: 445.54 |
| 5-752 | |
| 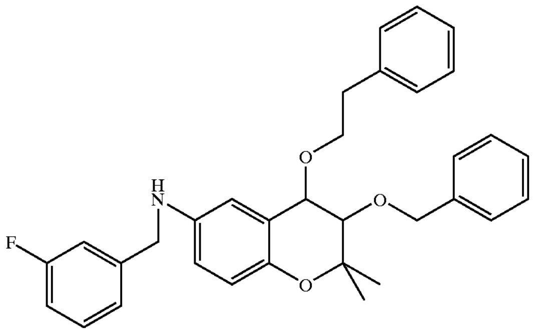 | MS, m/z: 511.64 |
| 5-753 | |
| 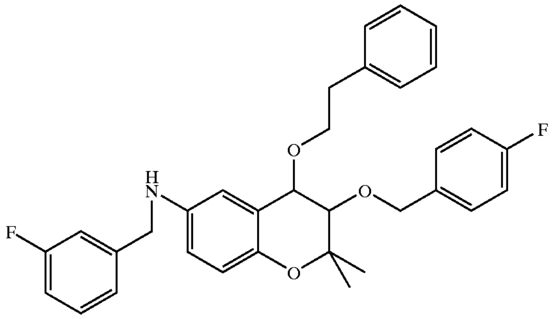 | MS, m/z: 529.63 |
| 5-754 | |

TABLE 1-continued
| | Compound No. NMR/MS Data |
|---|---|
| 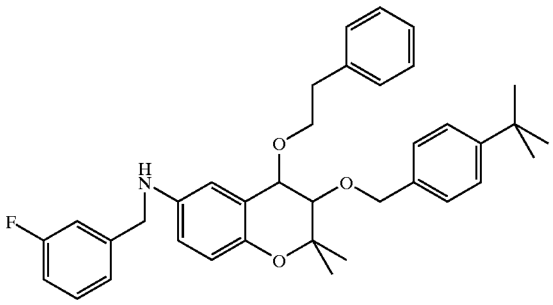<br>5-755 | MS, m/z: 567.75 |
| 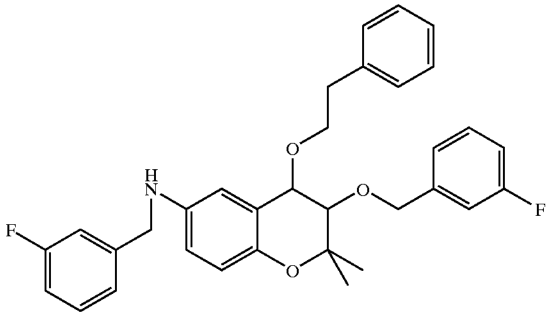<br>5-756 | MS, m/z: 529.63 |
| 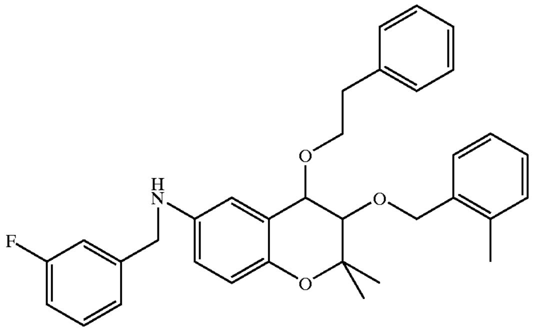<br>5-757 | MS, m/z: 525.67 |
| 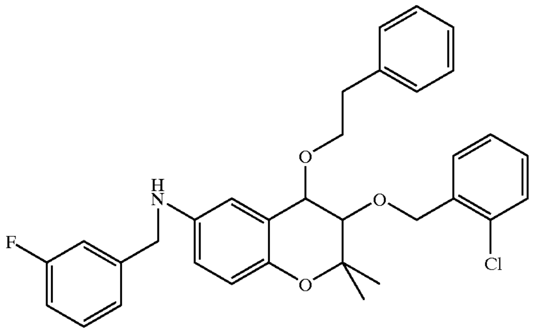<br>5-758 | MS, m/z: 546.09 |

TABLE 1-continued
| | Compound No. NMR/MS Data |
|---|---|
| 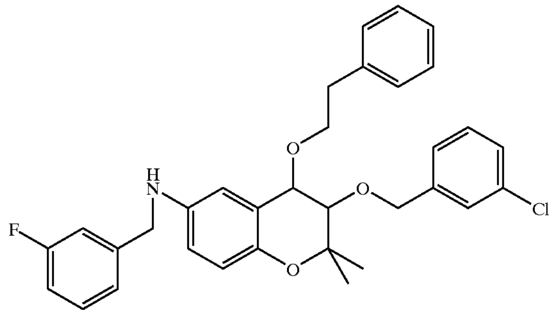 5-759 | MS, m/z: 546.09 |
| 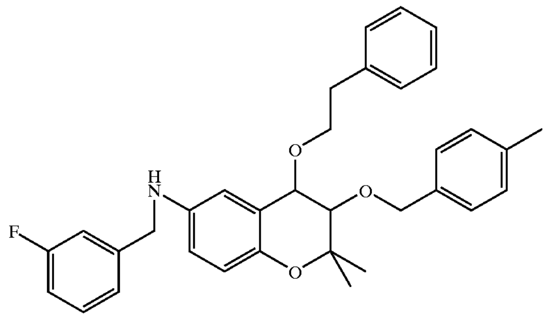 5-760 | MS, m/z: 525.67 |
| 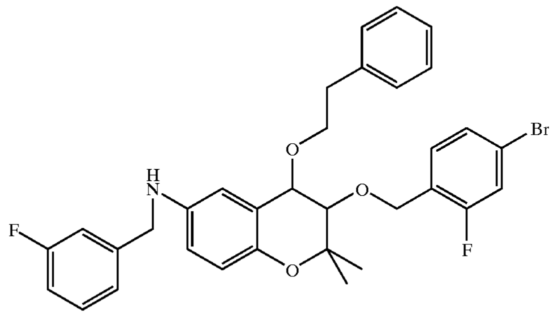 5-761 | MS, m/z: 608.53 |
| 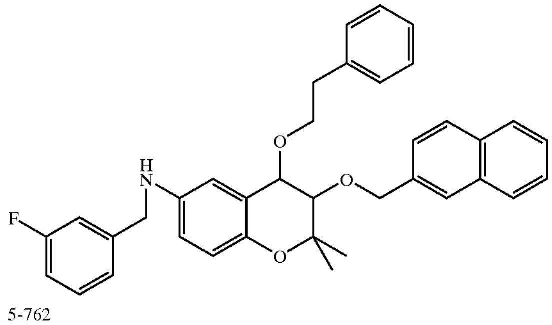 5-762 | MS, m/z: 561.70 |

TABLE 1-continued
| | Compound No. NMR/MS Data |
|---|---|
| 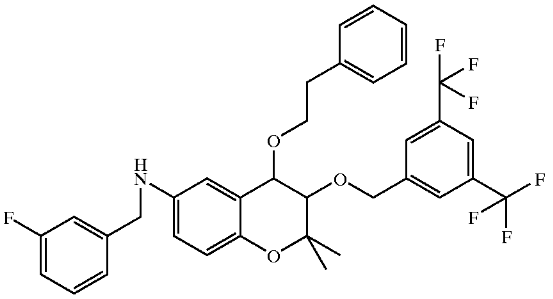 | MS, m/z: 647.64 |
| 5-763 | |
| 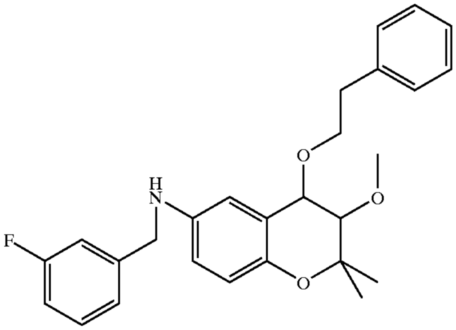 | MS, m/z: 435.54 |
| 5-764 | |
| 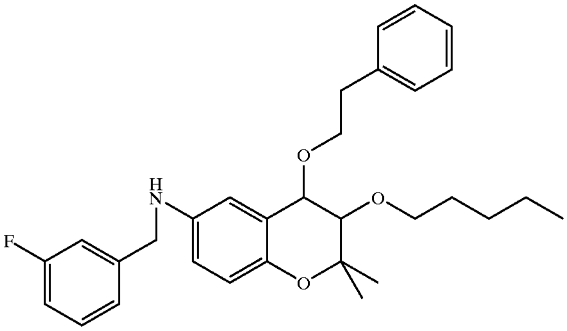 | MS, m/z: 491.65 |
| 5-765 | |
| 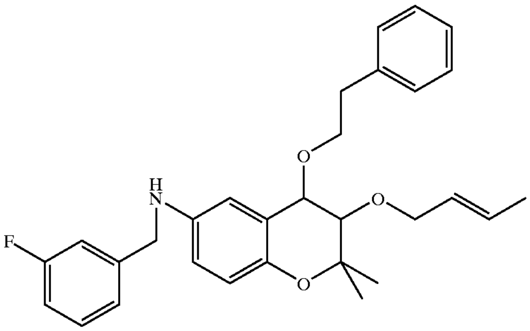 | MS, m/z: 475.61 |
| 5-766 | |

TABLE 1-continued
| | Compound No. NMR/MS Data |
|---|---|
| 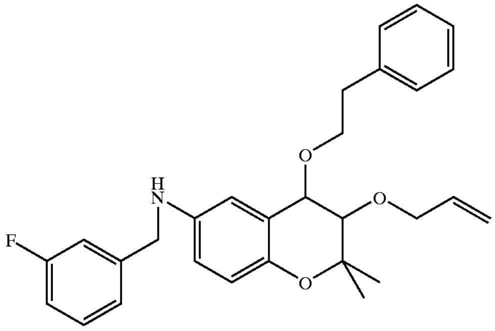 5-767 | MS, m/z: 461.58 |
| 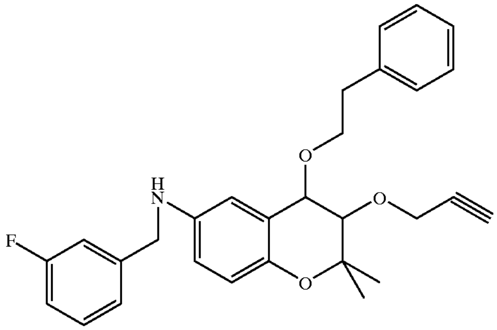 5-768 | MS, m/z: 459.57 |
| 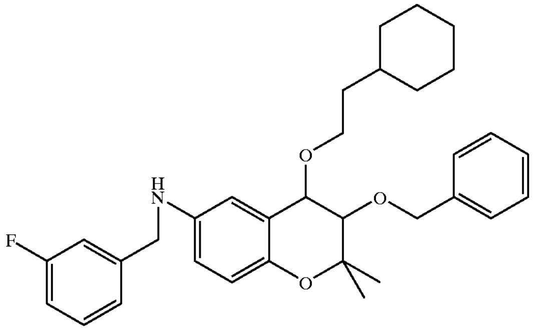 5-769 | MS, m/z: 517.69 |
| 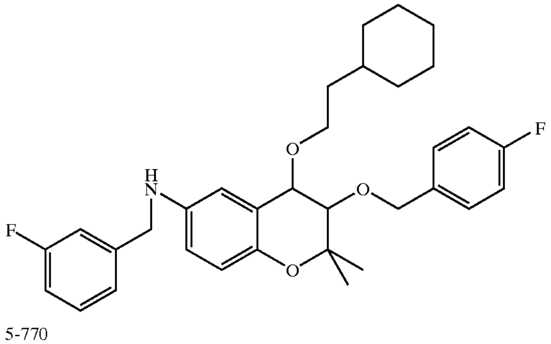 5-770 | MS, m/z: 535.68 |

TABLE 1-continued
| | Compound No. NMR/MS Data |
|---|---|
| 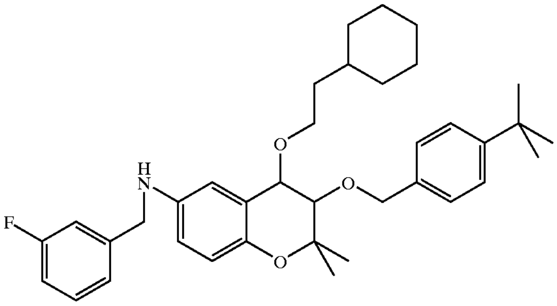 5-771 | MS, m/z: 573.80 |
| 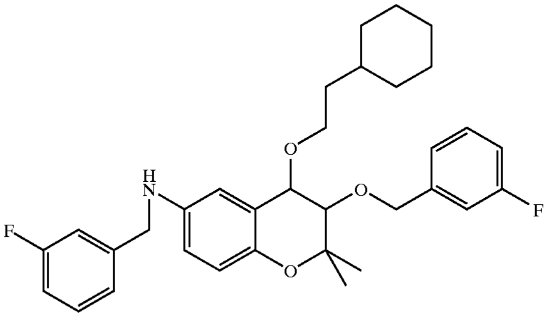 5-772 | MS, m/z: 535.68 |
| 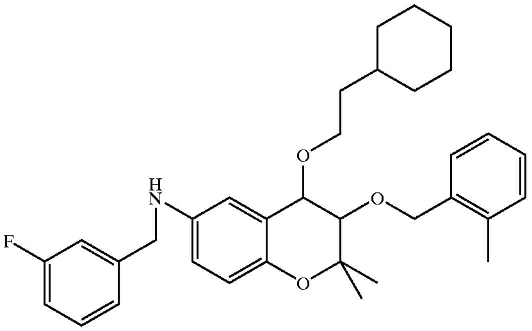 5-773 | MS, m/z: 531.72 |
| 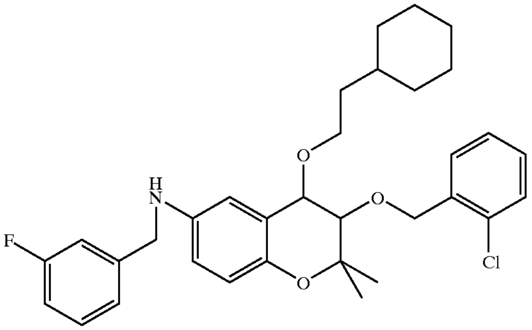 5-774 | MS, m/z: 552.14 |

TABLE 1-continued
| | Compound No. NMR/MS Data |
|---|---|
| 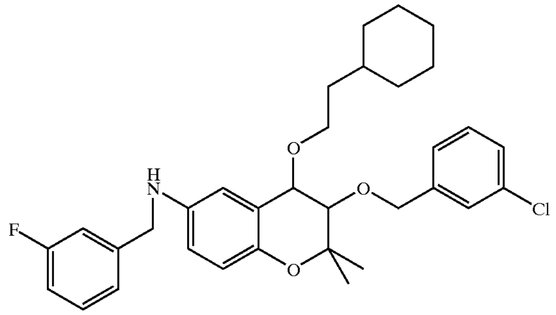 5-775 | MS, m/z: 552.14 |
| 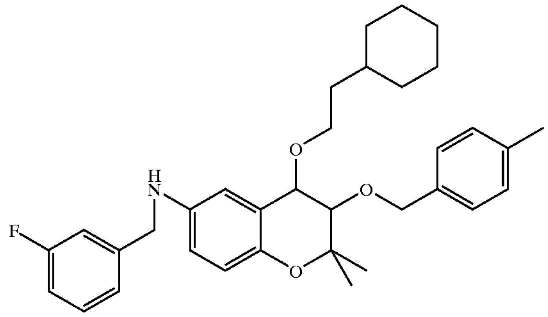 5-776 | MS, m/z: 531.72 |
| 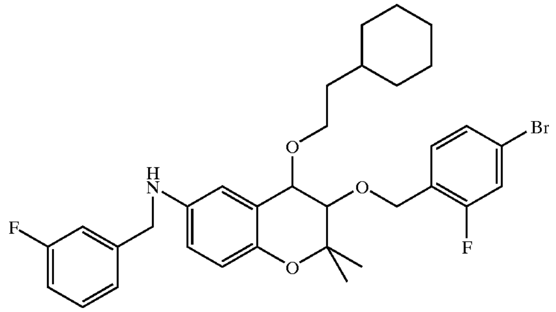 5-777 | MS, m/z: 614.58 |
| 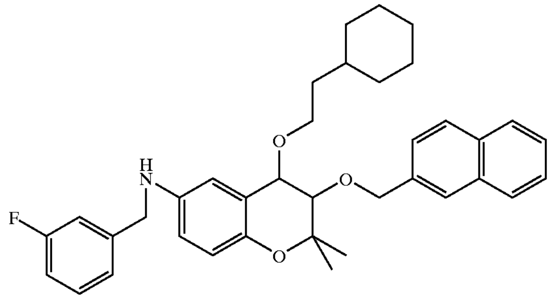 5-778 | MS, m/z: 567.75 |

TABLE 1-continued
| | Compound No. NMR/MS Data |
|---|---|
| 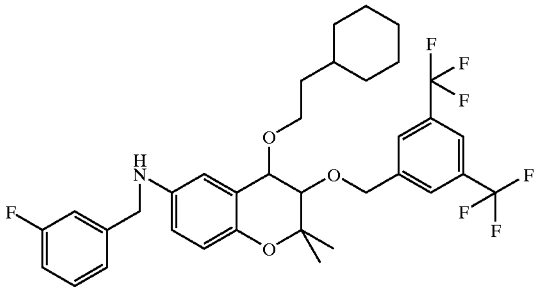 5-779 | MS, m/z: 653.69 |
| 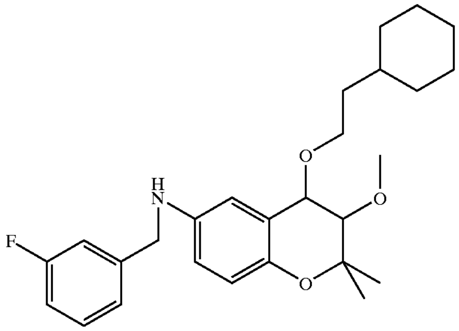 5-780 | MS, m/z: 441.59 |
| 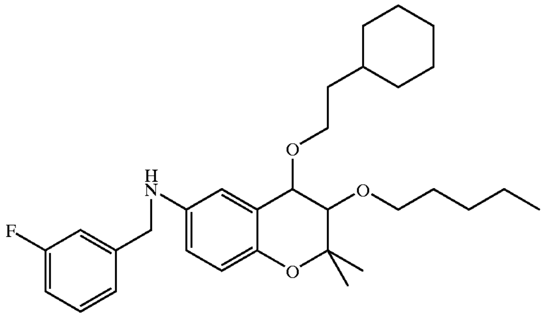 5-781 | MS, m/z: 497.70 |
| 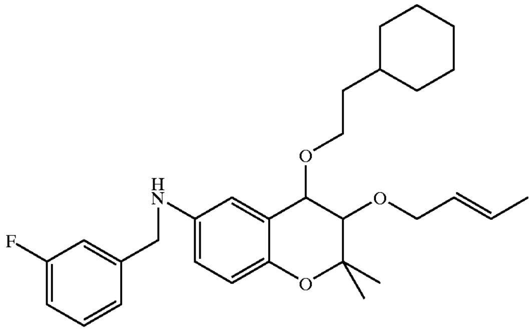 5-782 | MS, m/z: 481.66 |

TABLE 1-continued
| | Compound No. NMR/MS Data |
|---|---|
| 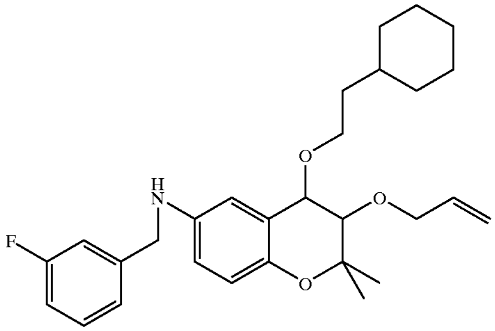 5-783 | MS, m/z: 467.63 |
| 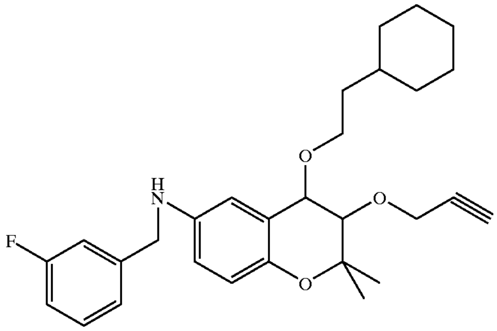 5-784 | MS, m/z: 465.61 |
| 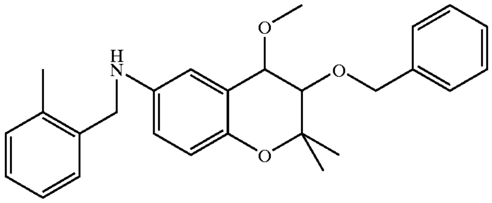 5-785 | MS, m/z: 417.55 |
| 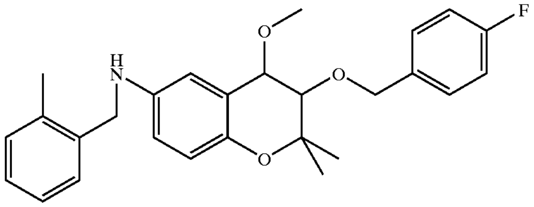 5-786 | MS, m/z: 435.54 |
| 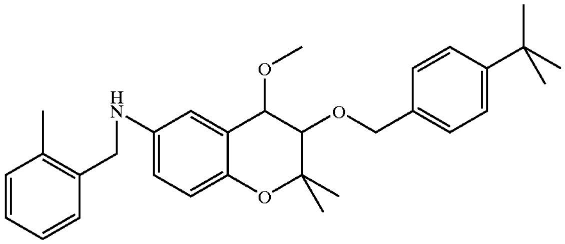 5-787 | MS, m/z: 473.66 |

TABLE 1-continued
| | Compound No. NMR/MS Data |
|---|---|
| 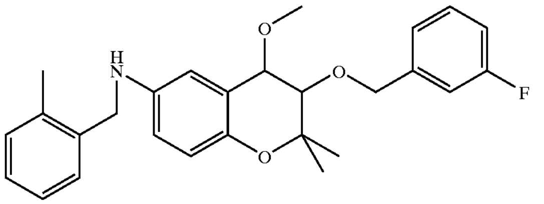 5-788 | MS, m/z: 435.54 |
| 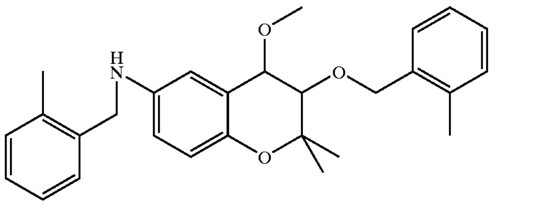 5-789 | MS, m/z: 431.58 |
| 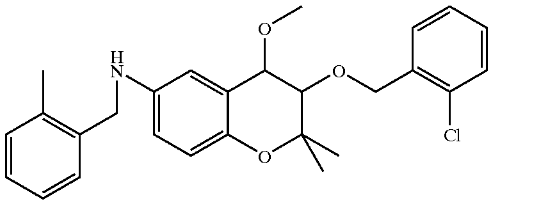 5-790 | MS, m/z: 452.00 |
| 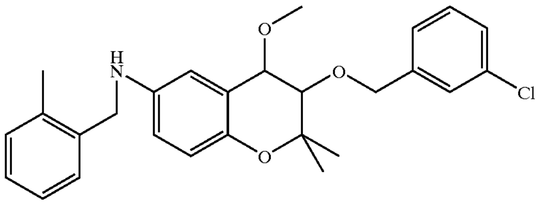 5-791 | MS, m/z: 452.00 |
| 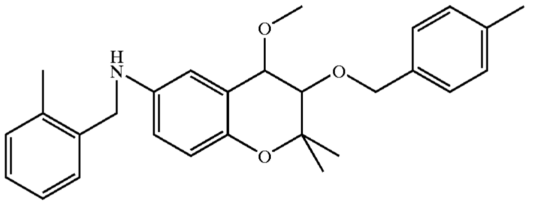 5-792 | MS, m/z: 431.58 |
| 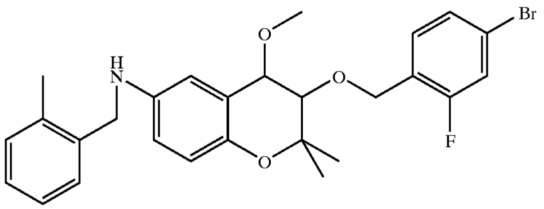 5-793 | MS, m/z: 514.44 |

TABLE 1-continued
| | Compound No. NMR/MS Data |
|---|---|
| 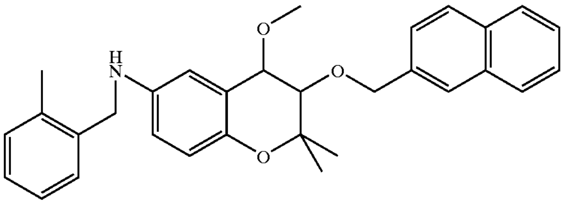 5-794 | MS, m/z: 467.61 |
| 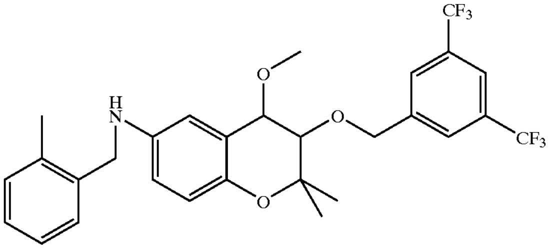 5-795 | MS, m/z: 445.61 |
| 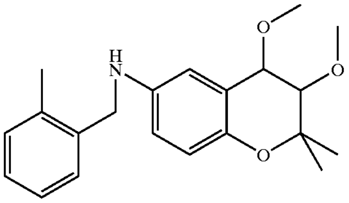 5-796 | MS, m/z: 341.45 |
| 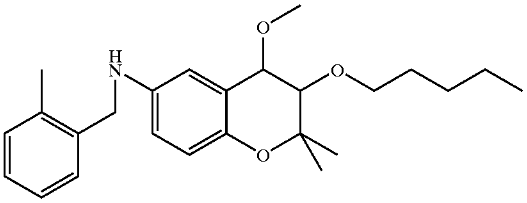 5-797 | MS, m/z: 397.56 |
| 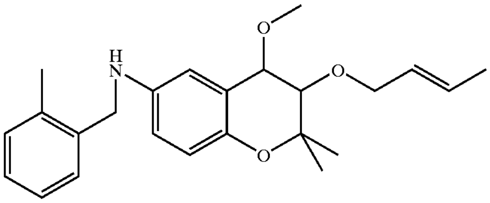 5-798 | MS, m/z: 381.52 |
| 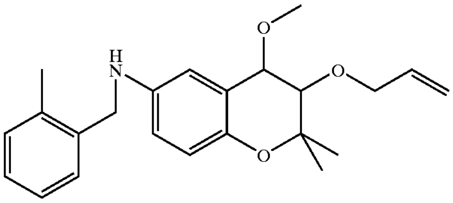 5-799 | MS, m/z: 367.49 |

TABLE 1-continued
| | Compound No. NMR/MS Data |
|---|---|
| 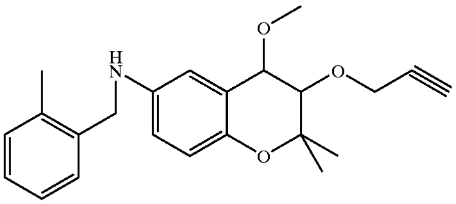 5-800 | MS, m/z: 365.45 |
| 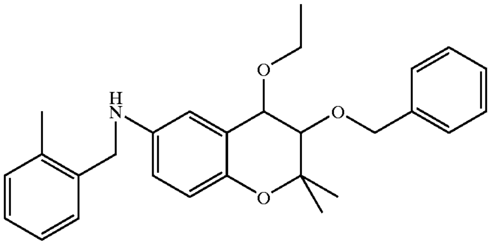 5-801 | MS, m/z: 431.58 |
| 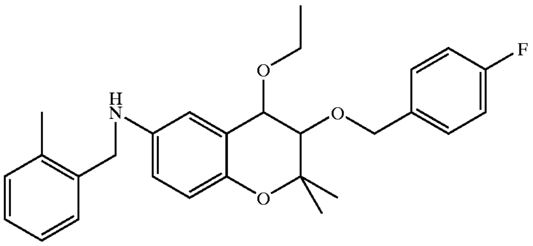 5-802 | MS, m/z: 449.57 |
| 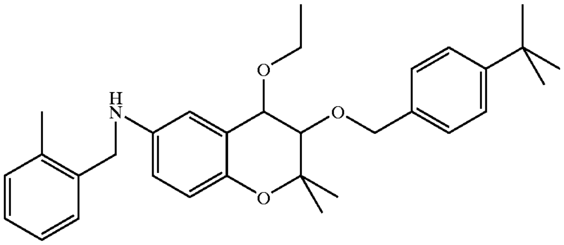 5-803 | MS, m/z: 487.69 |
| 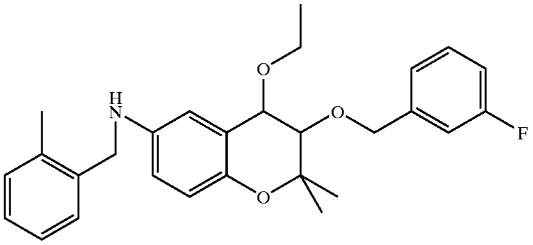 5-804 | MS, m/z: 449.57 |

TABLE 1-continued
| | Compound No. NMR/MS Data |
|---|---|
| 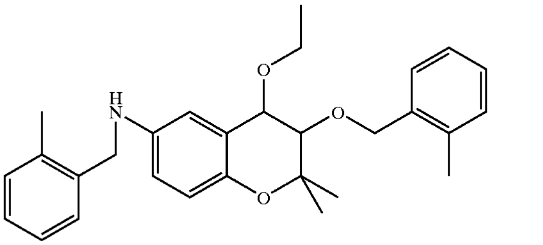 5-805 | MS, m/z: 445.61 |
| 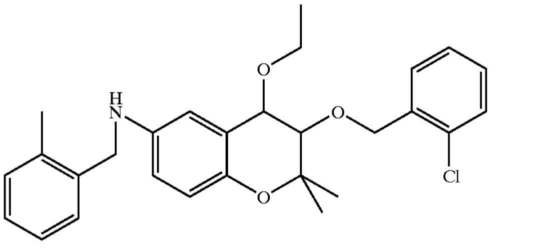 5-806 | MS, m/z: 466.03 |
| 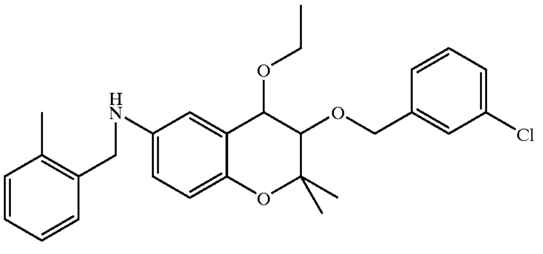 5-807 | MS, m/z: 466.03 |
| 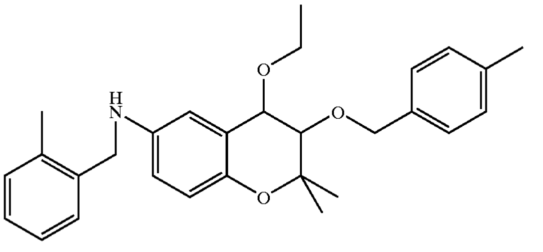 5-808 | MS, m/z: 445.61 |
| 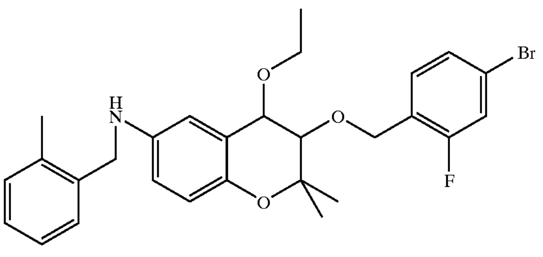 5-809 | MS, m/z: 528.47 |

TABLE 1-continued
| | Compound No. NMR/MS Data |
|---|---|
| 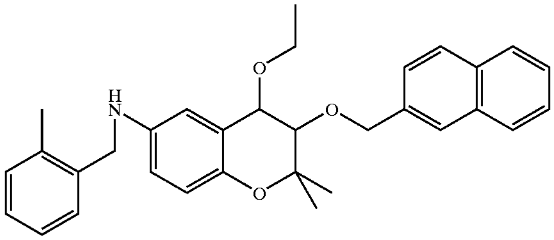 5-810 | MS, m/z: 481.64 |
| 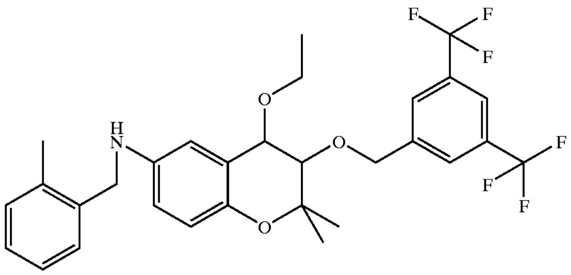 5-811 | MS, m/z: 567.58 |
| 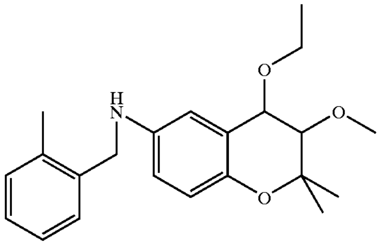 5-812 | MS, m/z: 355.48 |
| 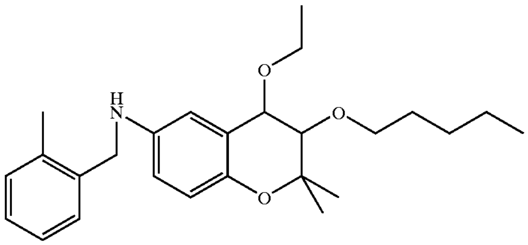 5-813 | MS, m/z: 411.59 |
| 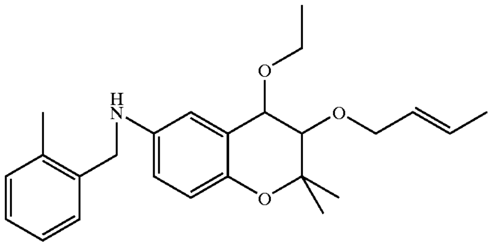 5-814 | MS, m/z: 395.55 |

TABLE 1-continued
| | Compound No. NMR/MS Data |
|---|---|
| 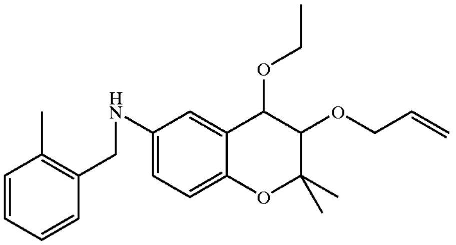 5-815 | MS, m/z: 381.52 |
| 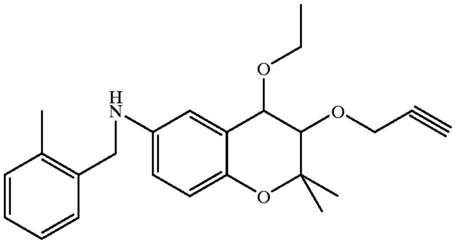 5-816 | MS, m/z: 379.50 |
| 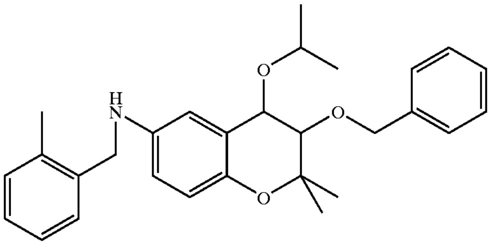 5-817 | MS, m/z: 445.61 |
| 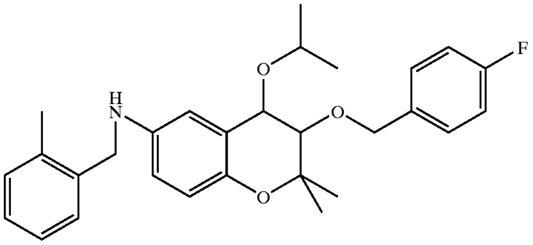 5-818 | MS, m/z: 463.60 |
| 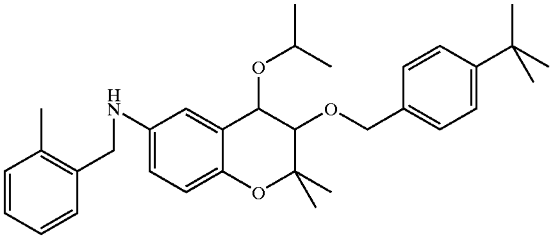 5-819 | MS, m/z: 501.72 |

TABLE 1-continued
| | Compound No. NMR/MS Data |
|---|---|
| 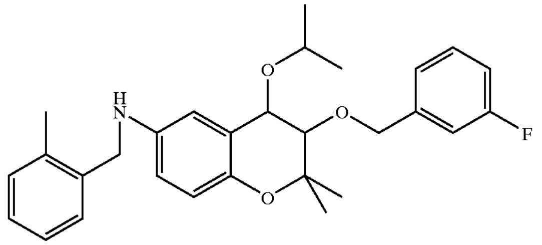 5-820 | MS, m/z: 463.60 |
| 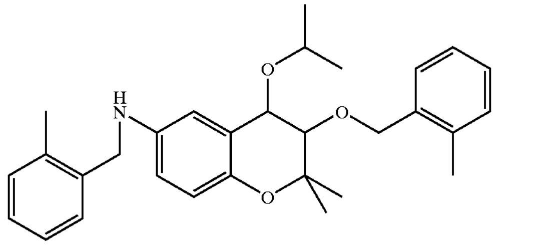 5-821 | MS, m/z: 459.63 |
| 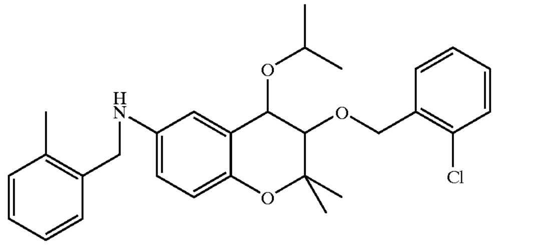 5-822 | MS, m/z: 480.05 |
| 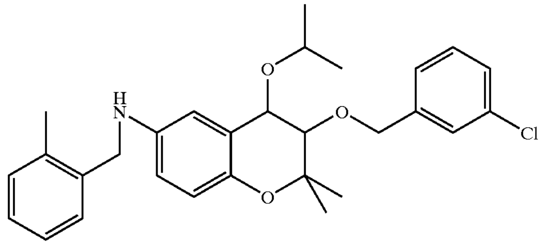 5-823 | MS, m/z: 480.05 |
| 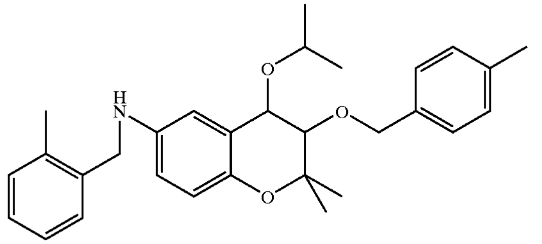 5-824 | MS, m/z: 459.63 |

TABLE 1-continued
| | Compound No. NMR/MS Data |
|---|---|
| 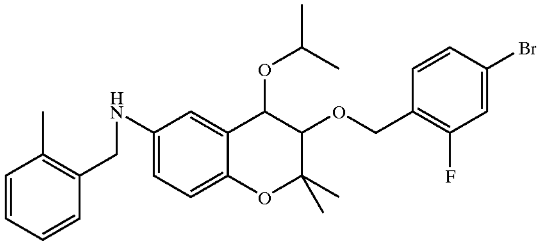 5-825 | MS, m/z: 542.49 |
| 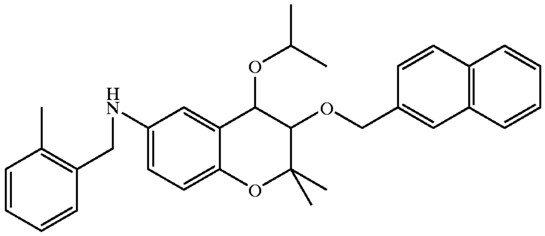 5-826 | MS, m/z: 495.67 |
| 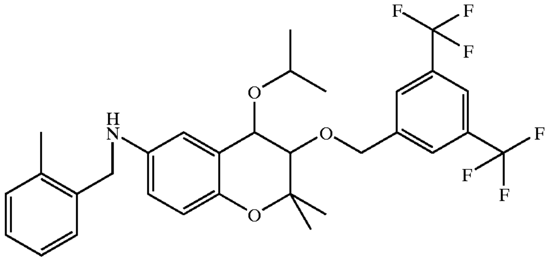 5-827 | MS, m/z: 581.60 |
| 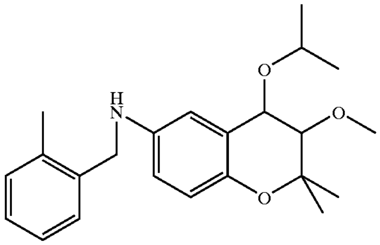 5-828 | MS, m/z: 369.51 |
| 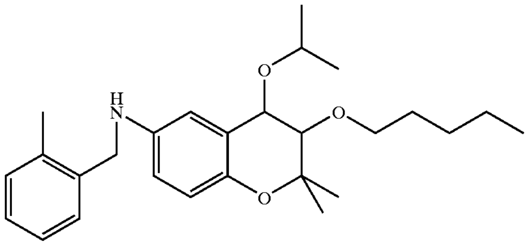 5-829 | MS, m/z: 425.62 |

TABLE 1-continued
| | Compound No. NMR/MS Data |
|---|---|
| 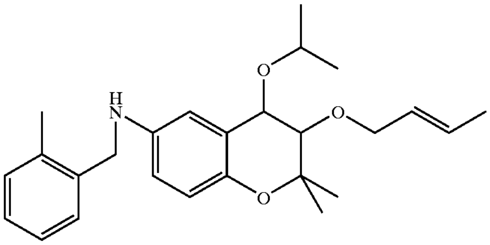 5-830 | MS, m/z: 409.57 |
| 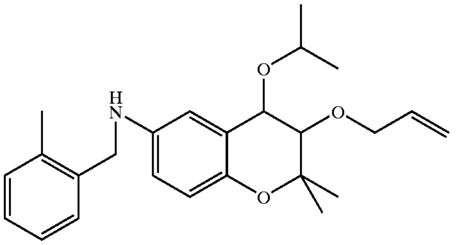 5-831 | MS, m/z: 395.55 |
| 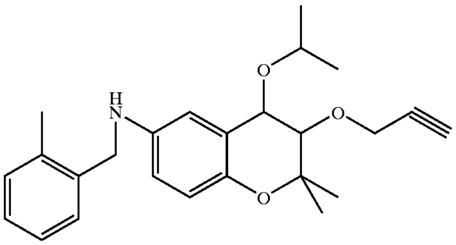 5-832 | MS, m/z: 393.53 |
| 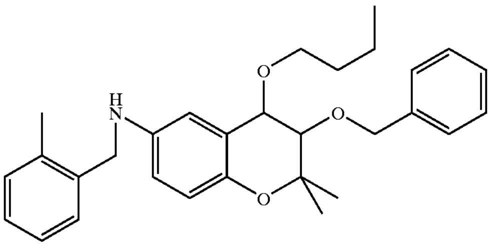 5-833 | MS, m/z: 459.63 |
| 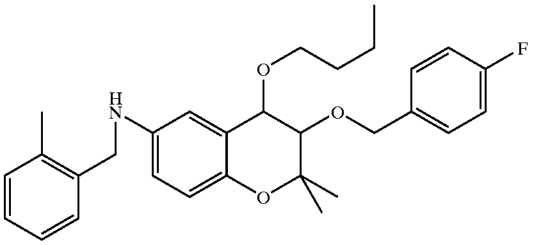 5-834 | MS, m/z: 477.62 |

TABLE 1-continued
| | Compound No. NMR/MS Data |
|---|---|
| 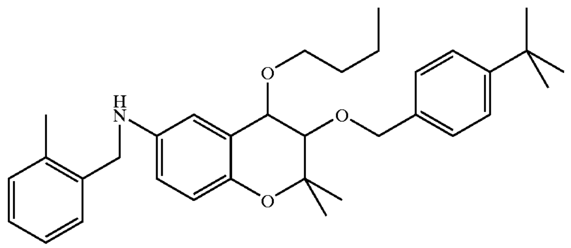 5-835 | MS, m/z: 515.74 |
| 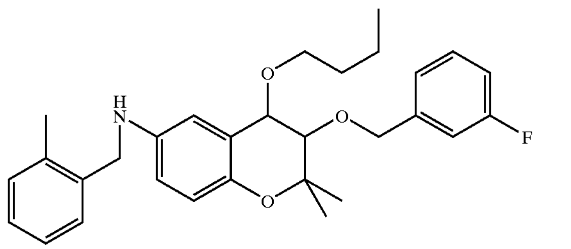 5-836 | MS, m/z: 477.62 |
| 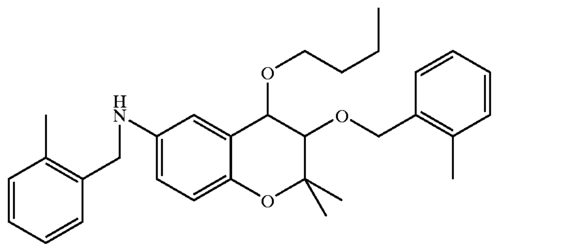 5-837 | MS, m/z: 473.66 |
| 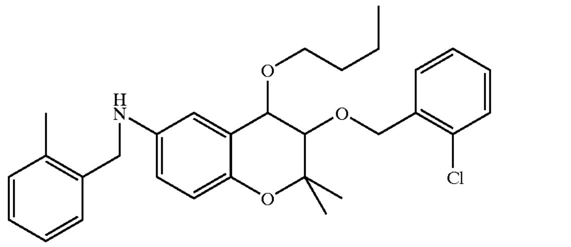 5-838 | MS, m/z: 494.08 |
| 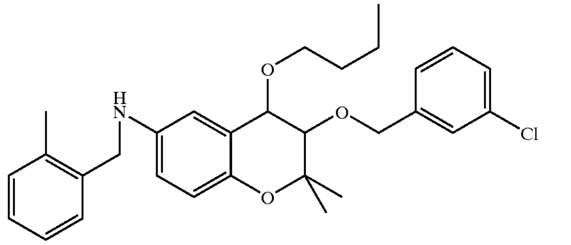 5-839 | MS, m/z: 494.08 |

TABLE 1-continued
| | Compound No. NMR/MS Data |
|---|---|
| 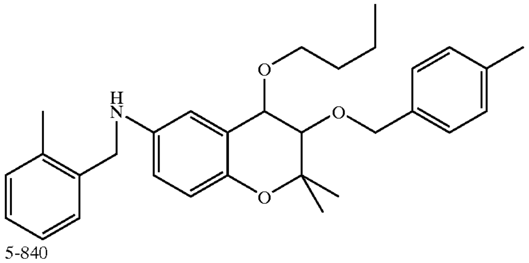 5-840 | MS, m/z: 473.66 |
| 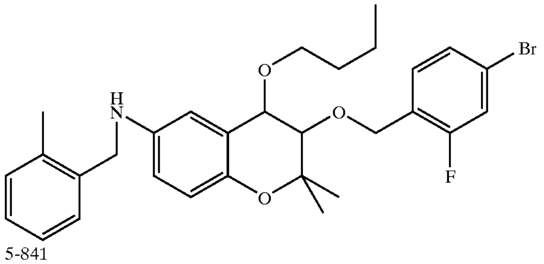 5-841 | MS, m/z: 556.52 |
| 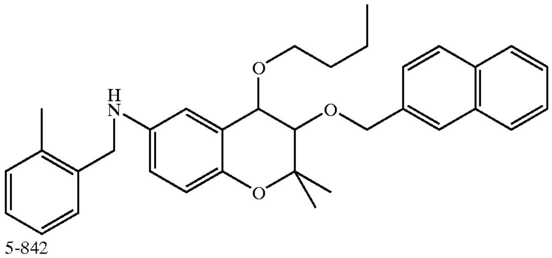 5-842 | MS, m/z: 509.69 |
| 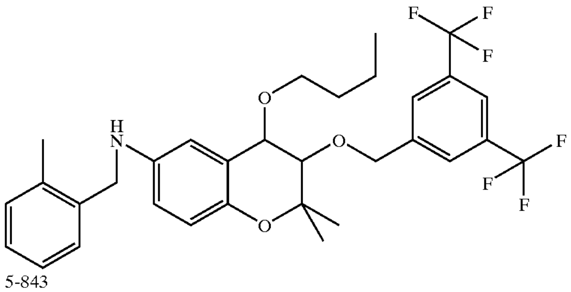 5-843 | MS, m/z: 595.63 |
| 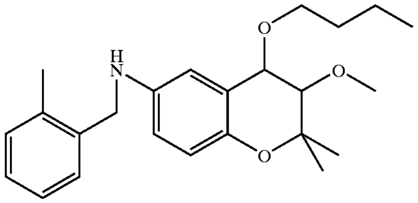 5-844 | MS, m/z: 383.54 |
| 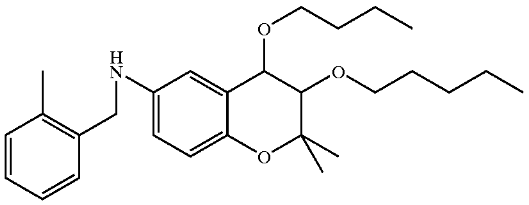 5-845 | MS, m/z: 439.64 |

TABLE 1-continued
| | Compound No. NMR/MS Data |
|---|---|
| 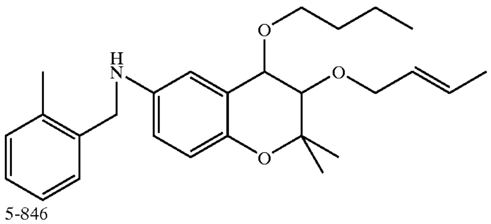 5-846 | MS, m/z: 423.60 |
| 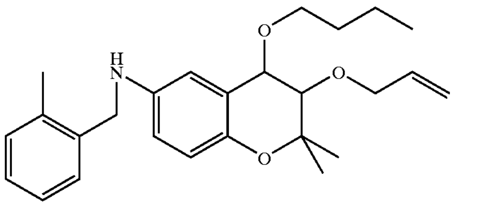 5-847 | MS, m/z: 409.57 |
| 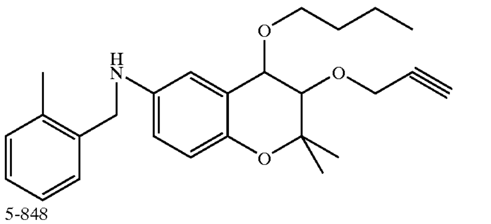 5-848 | MS, m/z: 407.56 |
| 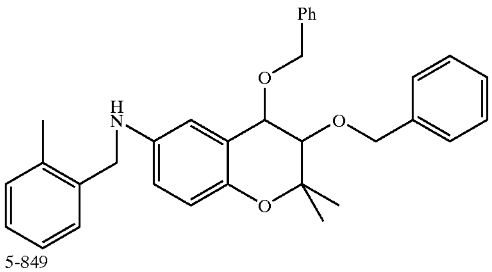 5-849 | MS, m/z: 493.65 |
| 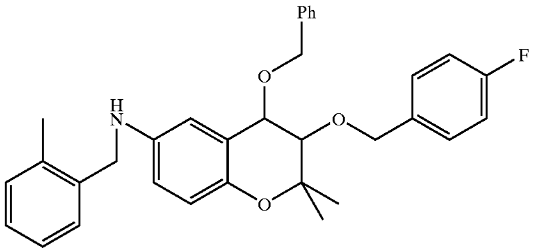 5-850 | MS, m/z: 511.64 |
| 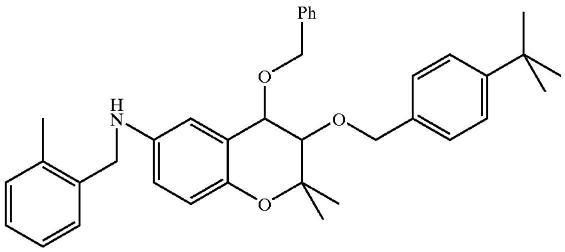 5-851 | MS, m/z: 549.76 |

TABLE 1-continued
| | Compound No. NMR/MS Data |
|---|---|
| 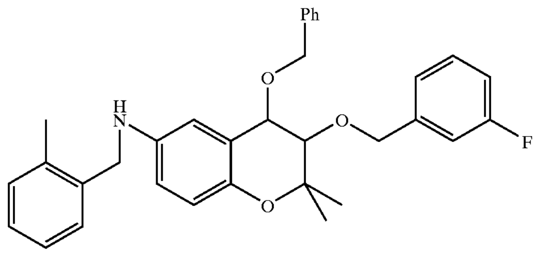 5-852 | MS, m/z: 511.64 |
| 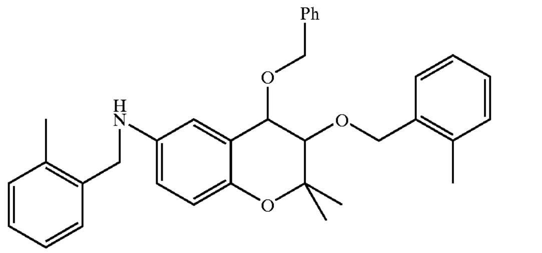 5-853 | MS, m/z: 507.68 |
| 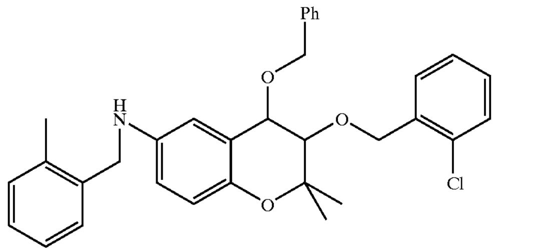 5-854 | MS, m/z: 528.10 |
| 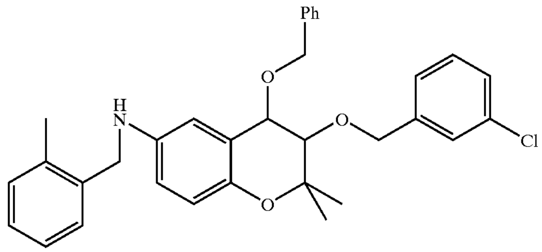 5-855 | MS, m/z: 528.10 |
| 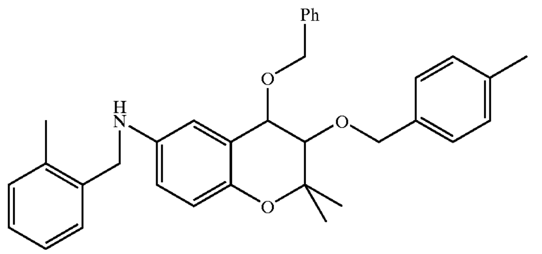 5-856 | MS, m/z: 507.68 |

TABLE 1-continued
| | Compound No. NMR/MS Data |
|---|---|
| 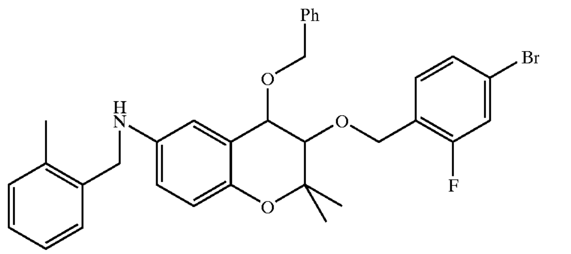 5-857 | MS, m/z: 590.54 |
| 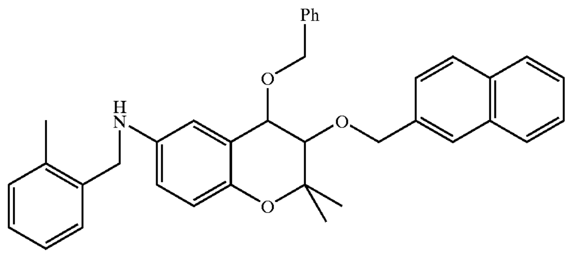 5-858 | MS, m/z: 543.71 |
| 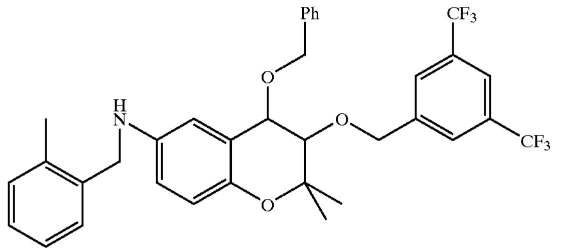 5-859 | MS, m/z: 521.71 |
| 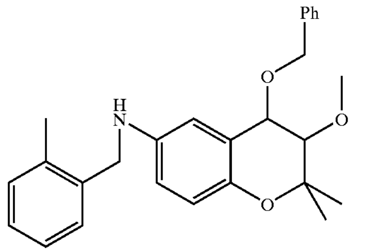 5-860 | MS, m/z: 417.55 |
| 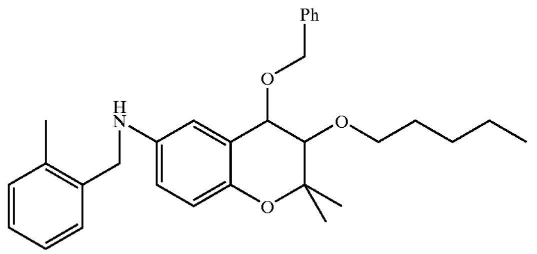 5-861 | MS, m/z: 473.66 |

TABLE 1-continued
| | Compound No. NMR/MS Data |
|---|---|
| 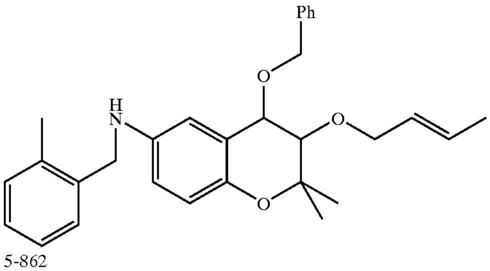 5-862 | MS, m/z: 457.62 |
| 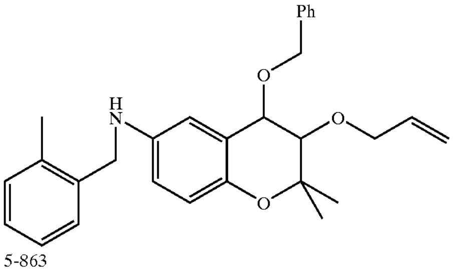 5-863 | MS, m/z: 443.59 |
| 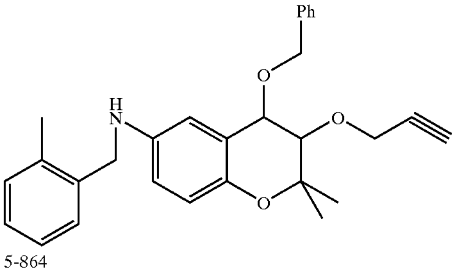 5-864 | MS, m/z: 441.58 |
| 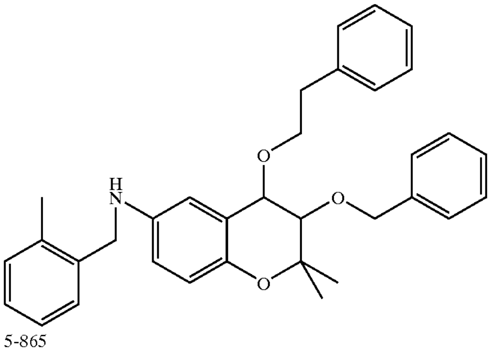 5-865 | MS, m/z: 507.68 |
| 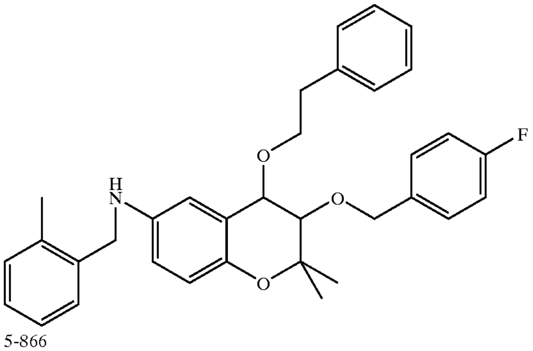 5-866 | MS, m/z: 525.67 |

TABLE 1-continued
| | Compound No. NMR/MS Data |
|---|---|
| 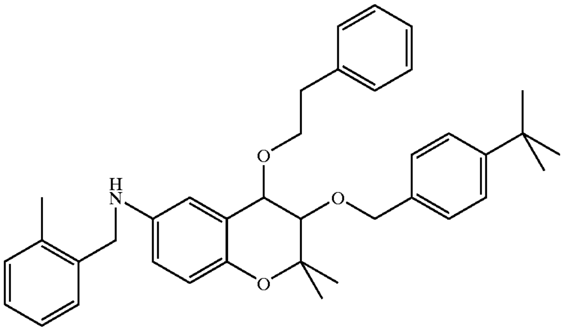 5-867 | MS, m/z: 563.79 |
| 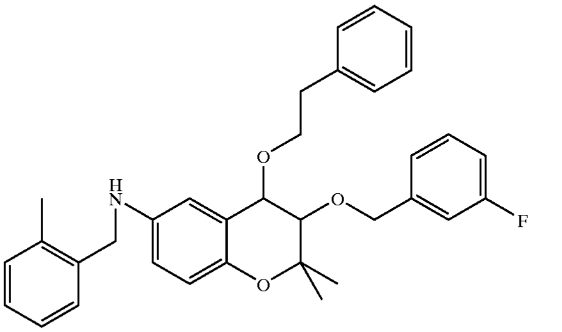 5-868 | MS, m/z: 525.67 |
| 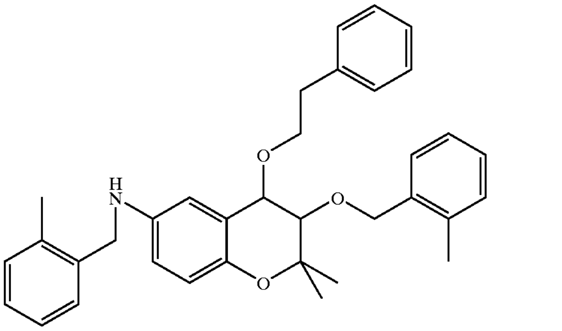 5-869 | MS, m/z: 521.71 |
| 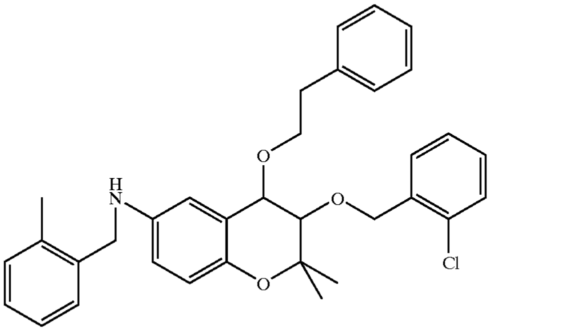 5-870 | MS, m/z: 542.12 |

TABLE 1-continued
| | Compound No. NMR/MS Data |
|---|---|
| 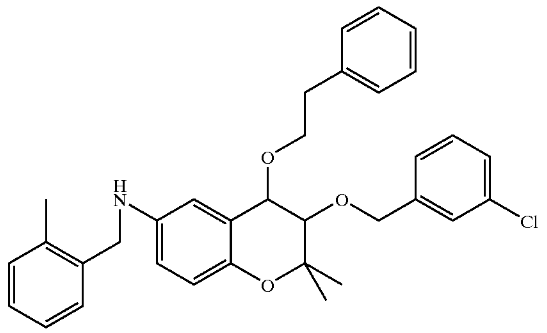 5-871 | MS, m/z: 542.12 |
| 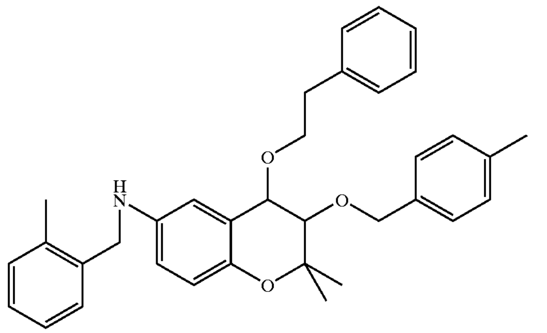 5-872 | MS, m/z: 521.71 |
| 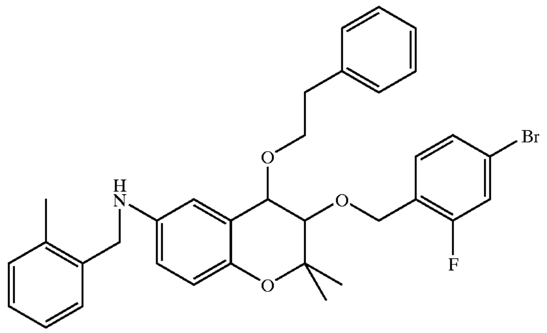 5-873 | MS, m/z: 604.57 |
| 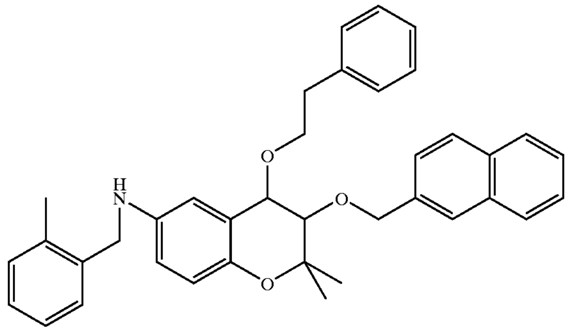 5-874 | MS, m/z: 557.74 |

TABLE 1-continued
| | Compound No. NMR/MS Data |
|---|---|
| 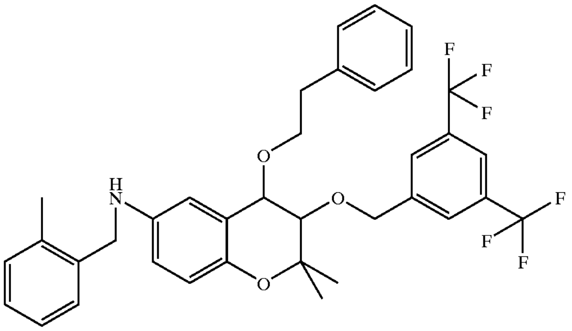 5-875 | MS, m/z: 643.68 |
| 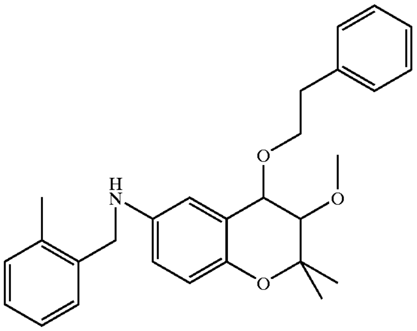 5-876 | MS, m/z: 431.58 |
| 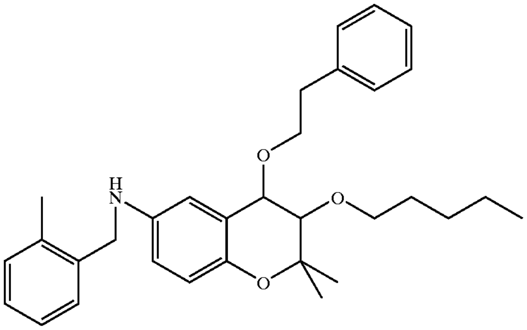 5-877 | MS, m/z: 487.69 |
| 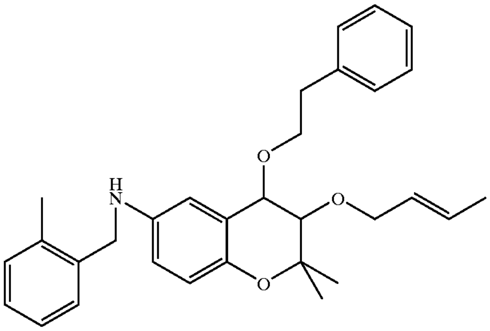 5-878 | MS, m/z: 471.65 |

TABLE 1-continued
| | Compound No. NMR/MS Data |
|---|---|
| 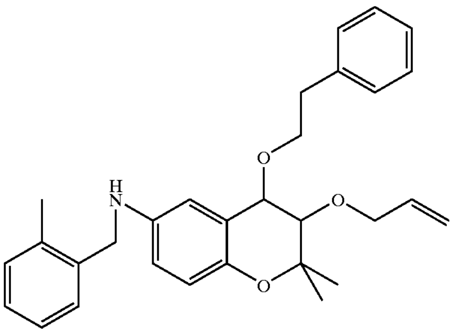 5-879 | MS, m/z: 457.62 |
| 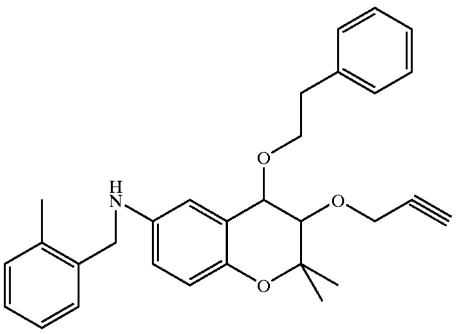 5-880 | MS, m/z: 455.60 |
| 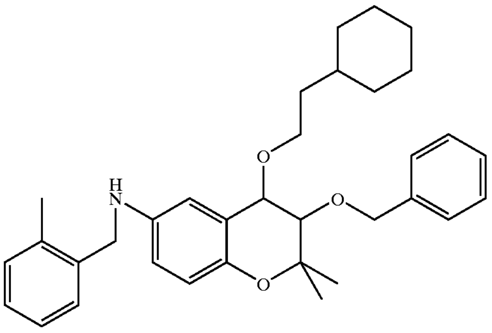 5-881 | MS, m/z: 513.73 |
| 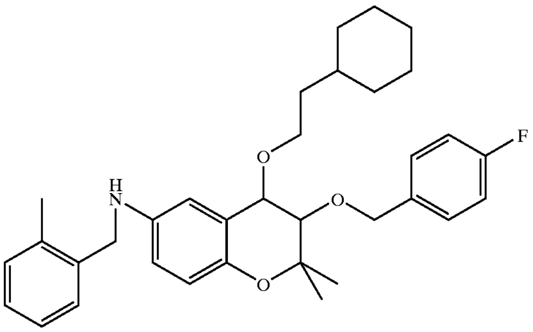 5-882 | MS, m/z: 531.72 |

TABLE 1-continued
| | Compound No. NMR/MS Data |
|---|---|
| 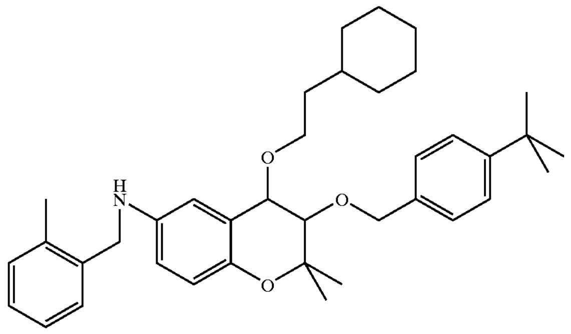 5-883 | MS, m/z: 569.84 |
| 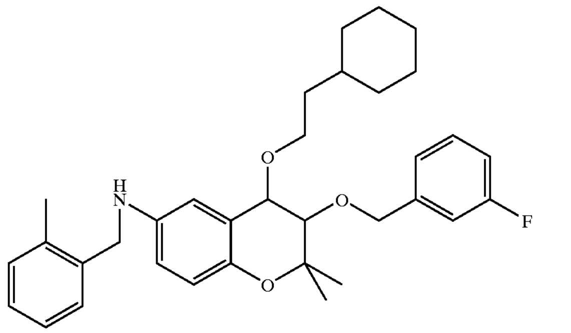 5-884 | MS, m/z: 531.72 |
| 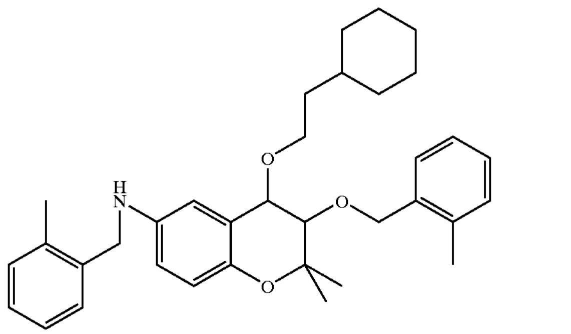 5-885 | MS, m/z: 527.75 |
| 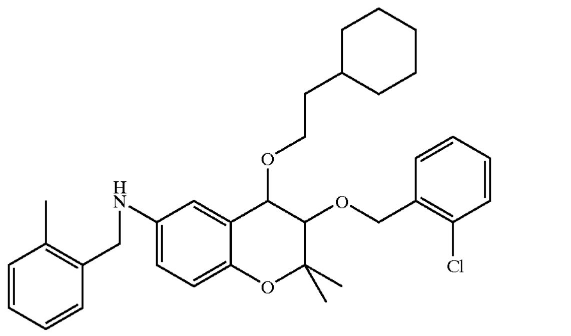 5-886 | MS, m/z: 548.17 |

TABLE 1-continued
| | Compound No. NMR/MS Data |
|---|---|
| 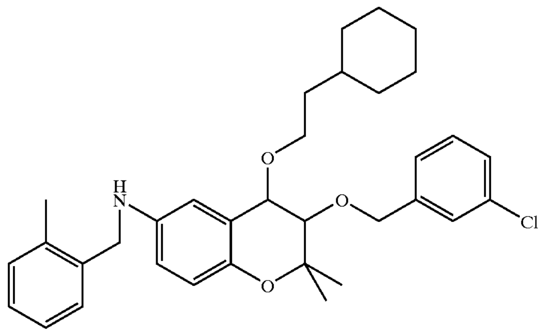<br>5-887 | MS, m/z: 548.17 |
| 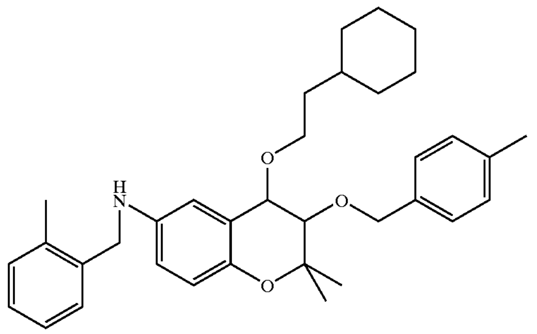<br>5-888 | MS, m/z: 527.75 |
| 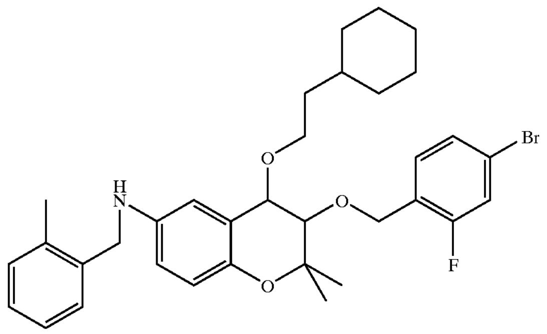<br>5-889 | MS, m/z: 610.61 |
| 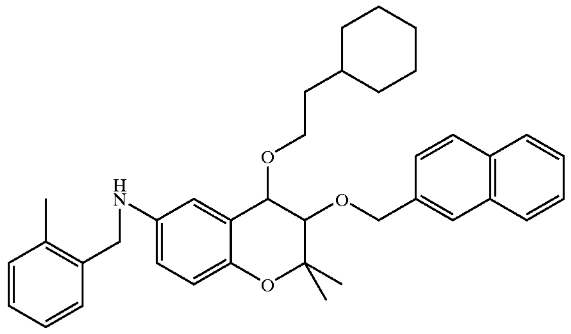<br>5-890 | MS, m/z: 563.79 |

TABLE 1-continued
| | Compound No. NMR/MS Data |
|---|---|
| 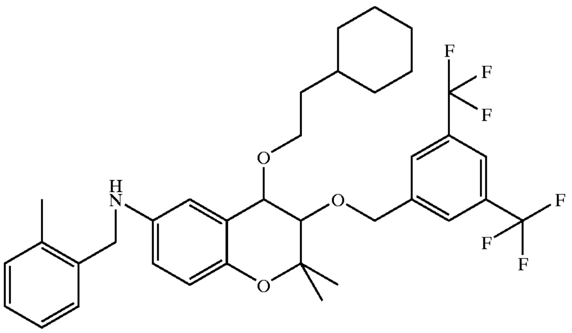 5-891 | MS, m/z: 649.72 |
| 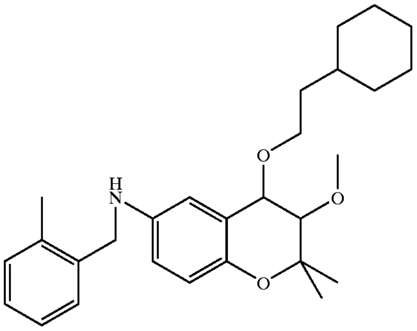 5-892 | MS, m/z: 437.63 |
| 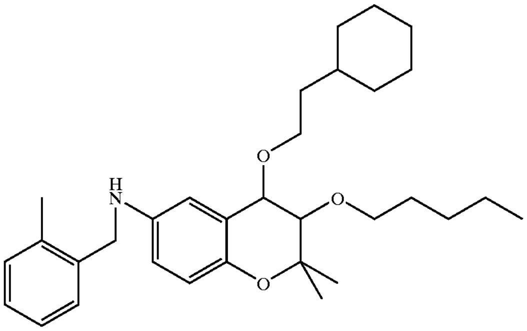 5-893 | MS, m/z: 493.74 |
| 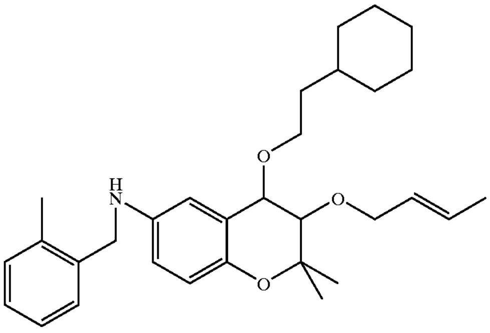 5-894 | MS, m/z: 477.69 |

TABLE 1-continued
| | Compound No. NMR/MS Data |
|---|---|
| 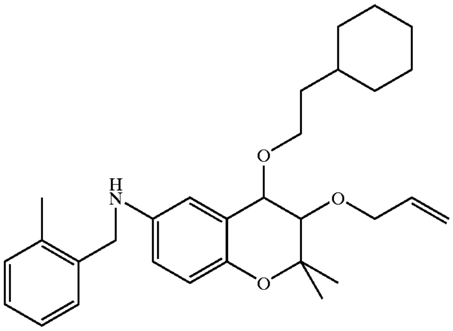<br>5-895 | MS, m/z: 463.67 |
| 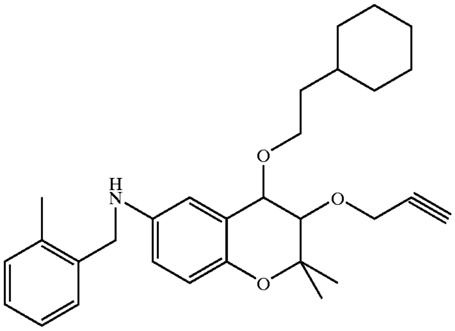<br>5-896 | MS, m/z: 461.65 |
| 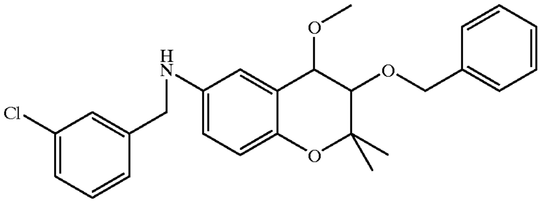<br>5-897 | MS, m/z: 437.97 |
| 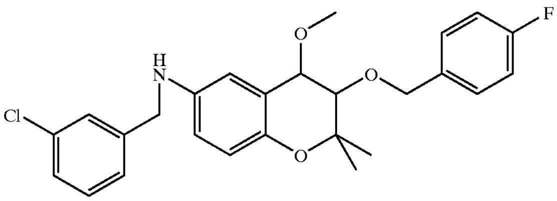<br>5-898 | MS, m/z: 455.96 |
| 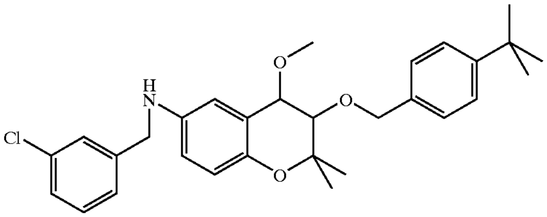<br>5-899 | MS, m/z: 494.08 |

TABLE 1-continued
| | Compound No. NMR/MS Data |
|---|---|
| 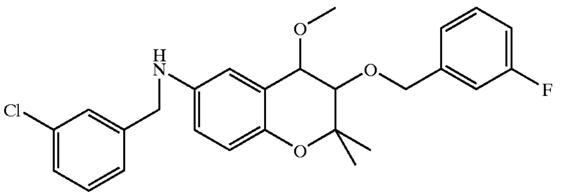 5-900 | MS, m/z: 455.96 |
| 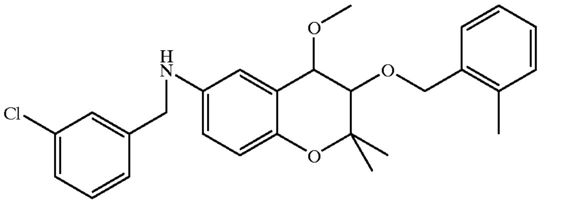 5-901 | MS, m/z: 452.00 |
| 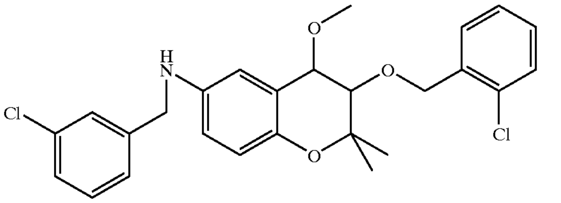 5-902 | MS, m/z: 472.42 |
| 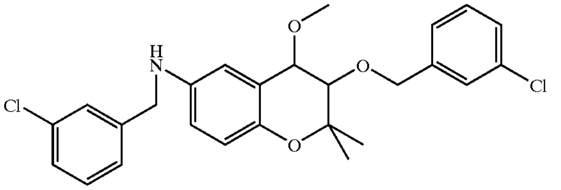 5-903 | MS, m/z: 472.42 |
| 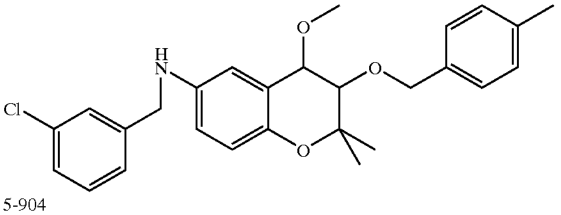 5-904 | MS, m/z: 452.00 |
| 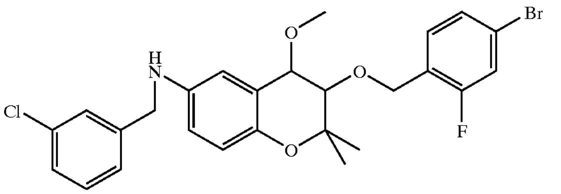 5-905 | MS, m/z: 543.86 |
| 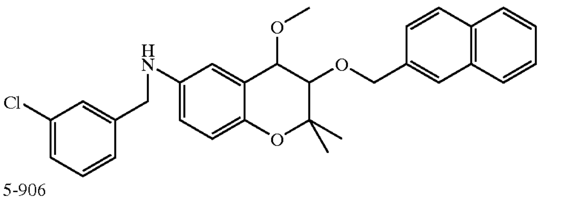 5-906 | MS, m/z: 488.03 |

TABLE 1-continued
| | Compound No. NMR/MS Data |
|---|---|
| 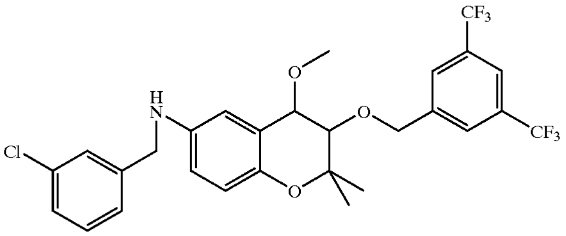 5-907 | MS, m/z: 466.03 |
| 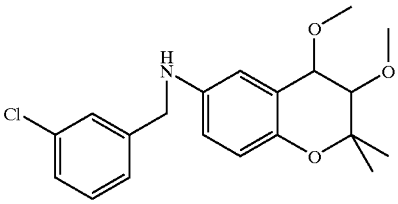 5-908 | MS, m/z: 361.87 |
| 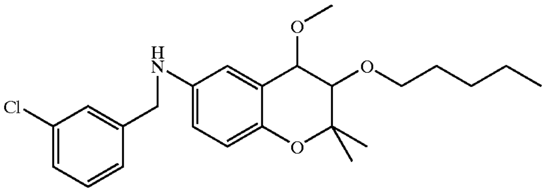 5-909 | MS, m/z: 417.98 |
| 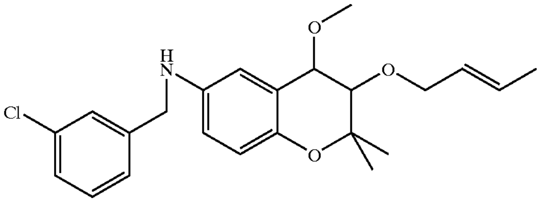 5-910 | MS, m/z: 401.94 |
| 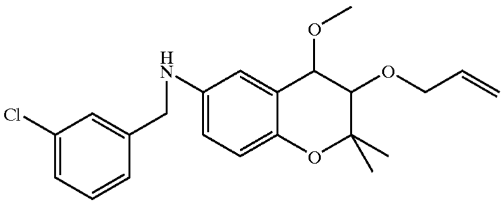 5-911 | MS, m/z: 387.91 |
| 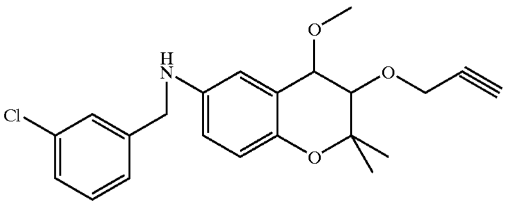 5-912 | MS, m/z: 385.89 |

TABLE 1-continued
| | Compound No. NMR/MS Data |
|---|---|
| 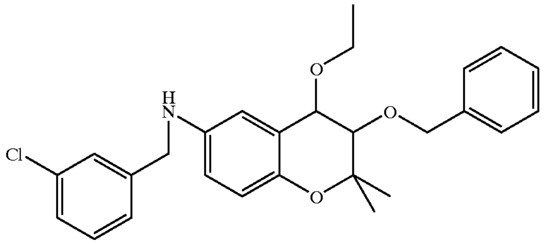 5-913 | MS, m/z: 452.00 |
| 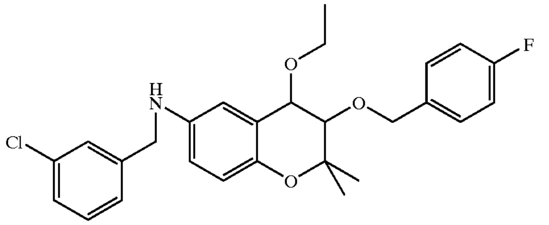 5-914 | MS, m/z: 469.99 |
| 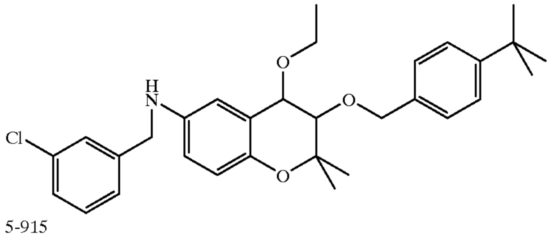 5-915 | MS, m/z: 508.11 |
| 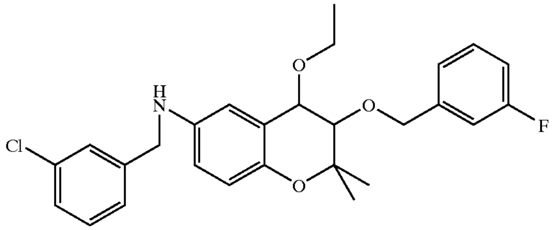 5-916 | MS, m/z: 469.99 |
| 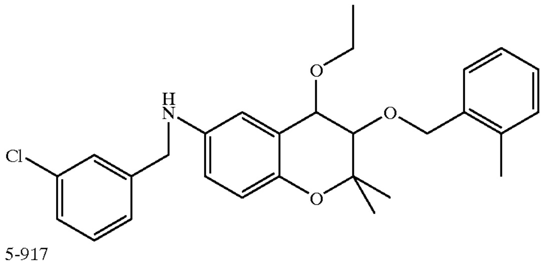 5-917 | MS, m/z: 466.03 |
| 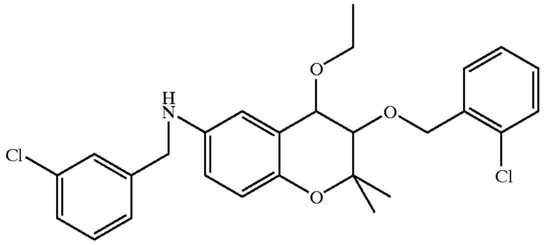 5-918 | MS, m/z: 486.44 |

TABLE 1-continued
| | Compound No. NMR/MS Data |
|---|---|
| 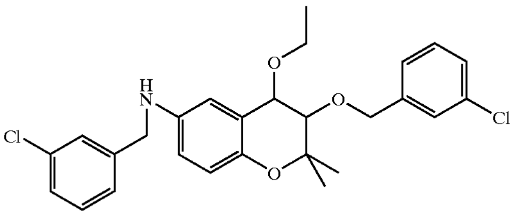 5-919 | MS, m/z: 486.44 |
| 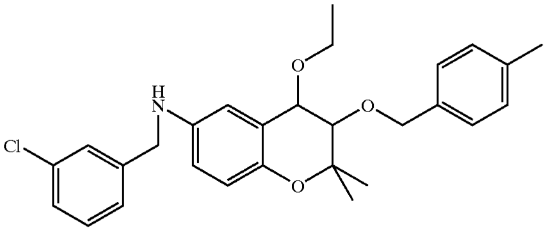 5-920 | MS, m/z: 466.03 |
| 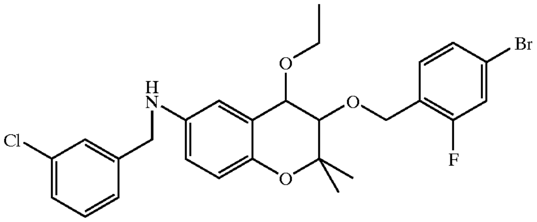 5-921 | MS, m/z: 548.88 |
| 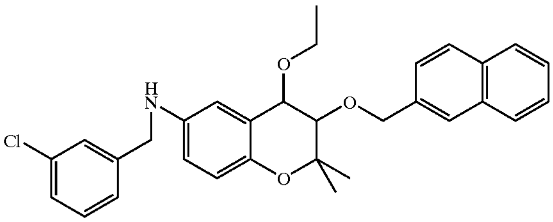 5-922 | MS, m/z: 502.06 |
| 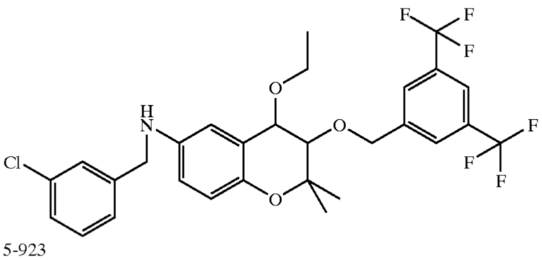 5-923 | MS, m/z: 587.99 |
| 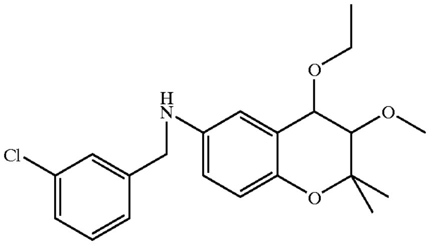 5-924 | MS, m/z: 375.90 |

TABLE 1-continued
| Compound No. | NMR/MS Data |
|---|---|
| 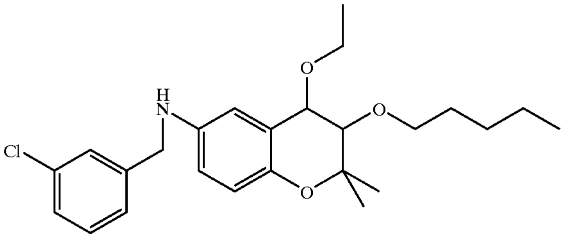 5-925 | MS, m/z: 432.01 |
| 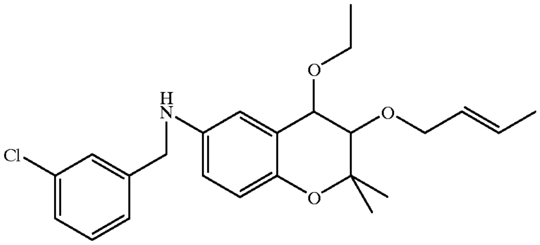 5-926 | MS, m/z: 415.96 |
| 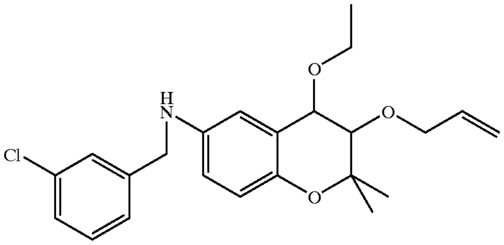 5-927 | MS, m/z: 401.94 |
| 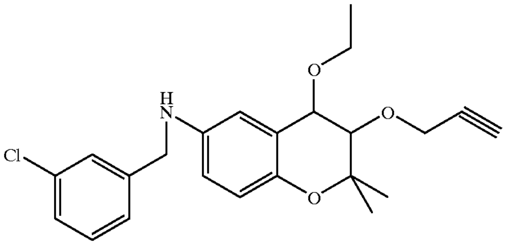 5-928 | MS, m/z: 399.92 |
| 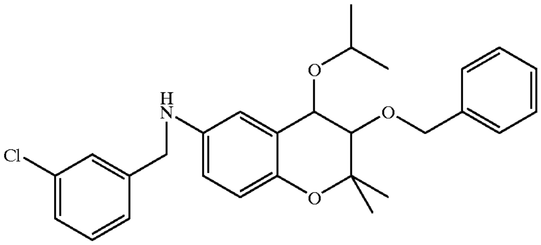 5-929 | MS, m/z: 466.03 |

TABLE 1-continued
| | Compound No. NMR/MS Data |
|---|---|
| 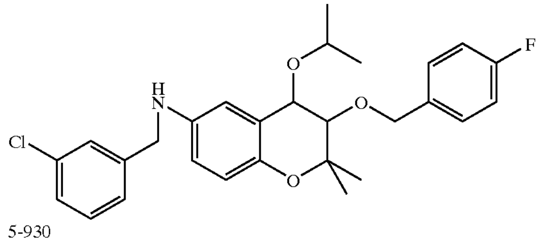<br>5-930 | MS, m/z: 484.02 |
| 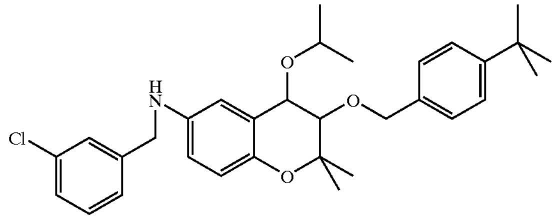<br>5-931 | MS, m/z: 522.13 |
| 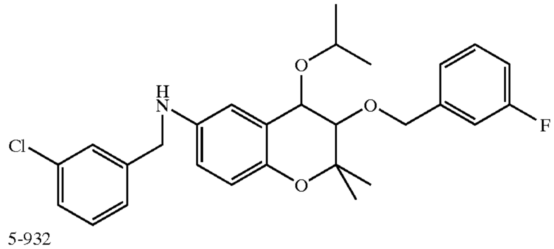<br>5-932 | MS, m/z: 484.02 |
| 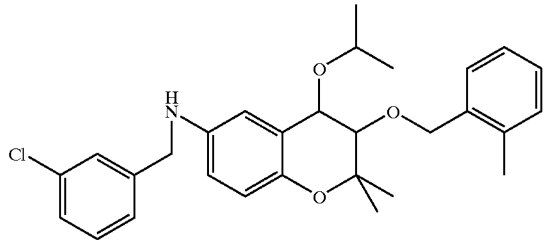<br>5-933 | MS, m/z: 480.05 |
| 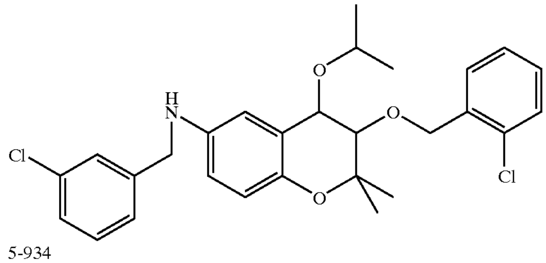<br>5-934 | MS, m/z: 500.47 |
| 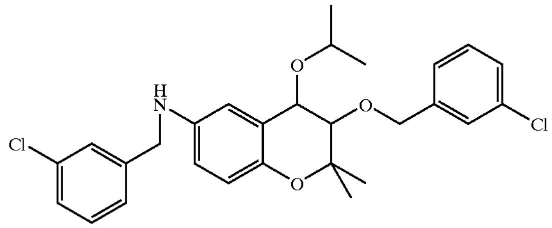<br>5-935 | MS, m/z: 500.47 |

TABLE 1-continued
| | Compound No. NMR/MS Data |
|---|---|
| 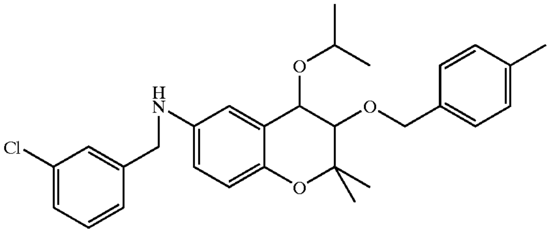 5-936 | MS, m/z: 480.05 |
| 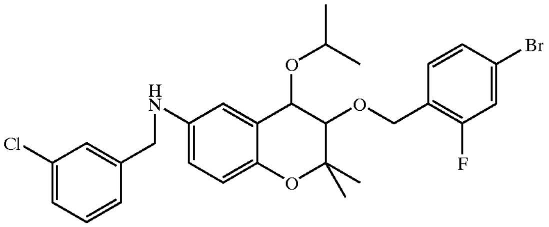 5-937 | MS, m/z: 562.91 |
| 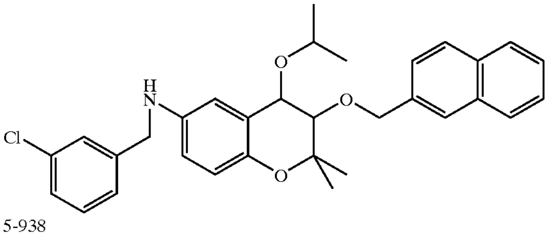 5-938 | MS, m/z: 516.09 |
| 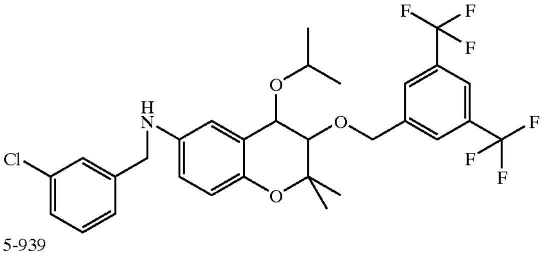 5-939 | MS, m/z: 602.02 |
| 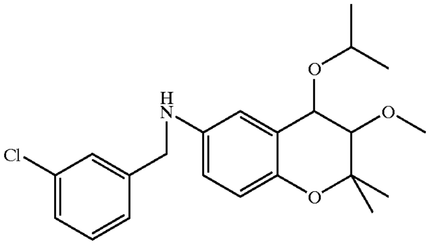 5-940 | MS, m/z: 389.93 |
| 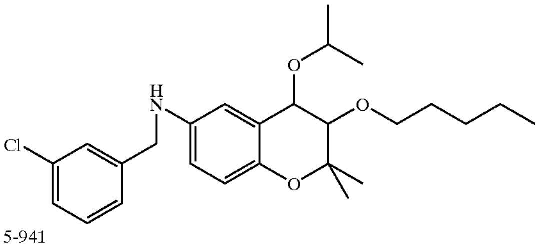 5-941 | MS, m/z: 446.03 |

TABLE 1-continued
| | Compound No. NMR/MS Data |
|---|---|
| 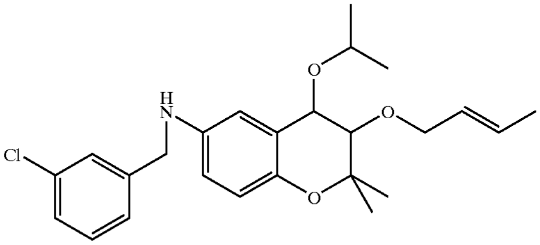<br>5-942 | MS, m/z: 429.99 |
| 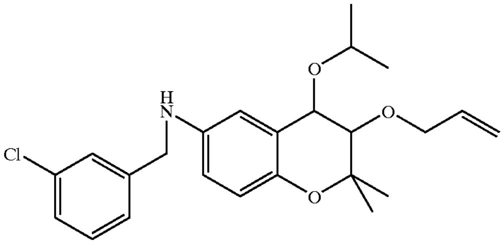<br>5-943 | MS, m/z: 415.96 |
| 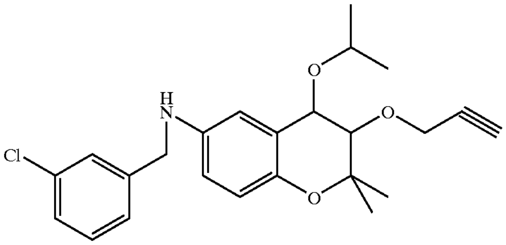<br>5-944 | MS, m/z: 413.95 |
| 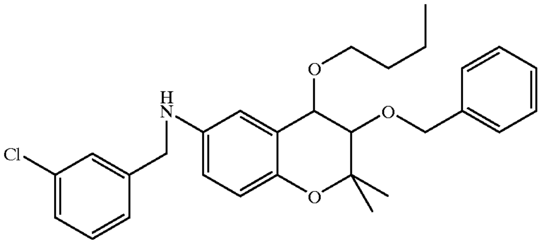<br>5-945 | MS, m/z: 480.05 |
| 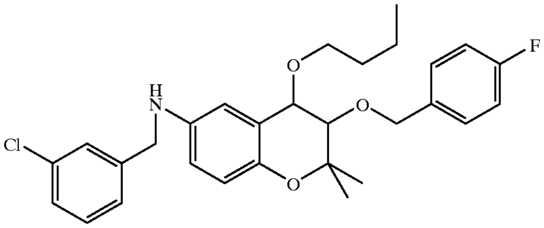<br>5-946 | MS, m/z: 498.04 |

TABLE 1-continued
| | Compound No. NMR/MS Data |
|---|---|
| 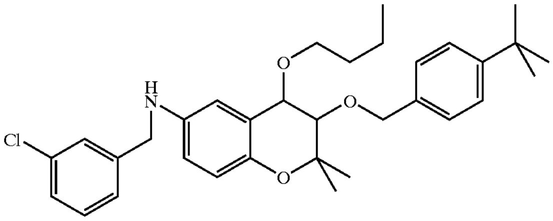 5-947 | MS, m/z: 536.16 |
| 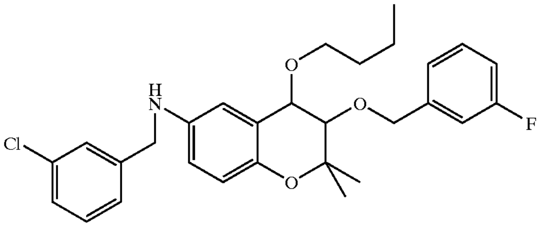 5-948 | MS, m/z: 498.04 |
| 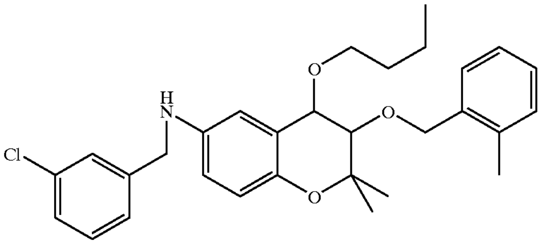 5-949 | MS, m/z: 494.08 |
| 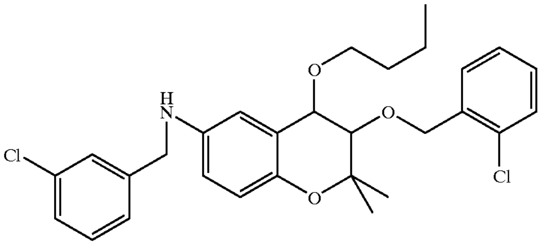 5-950 | MS, m/z: 514.50 |
| 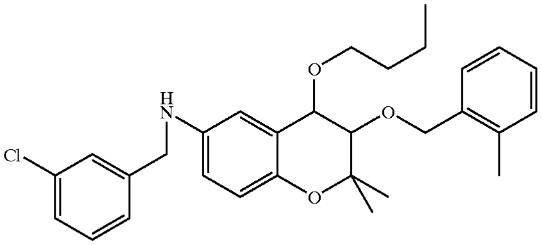 5-949 | MS, m/z: 494.08 |

TABLE 1-continued
| | Compound No. NMR/MS Data |
|---|---|
| 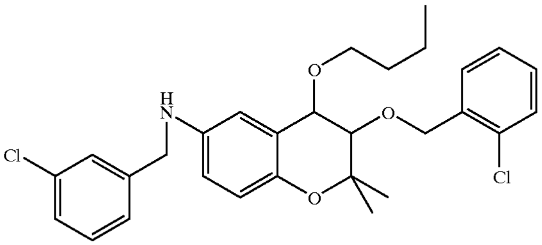 5-950 | MS, m/z: 514.50 |
| 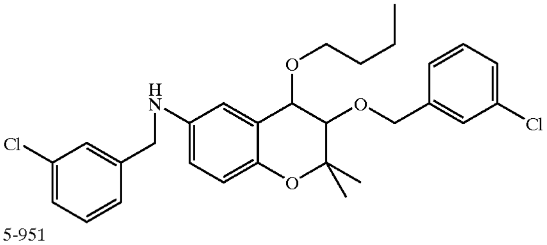 5-951 | MS, m/z: 514.50 |
| 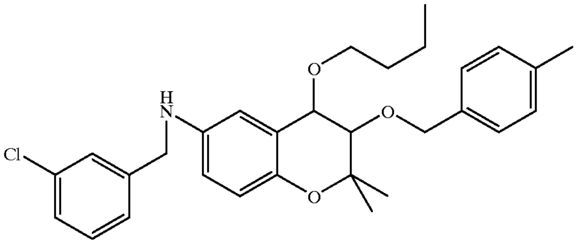 5-952 | MS, m/z: 494.08 |
| 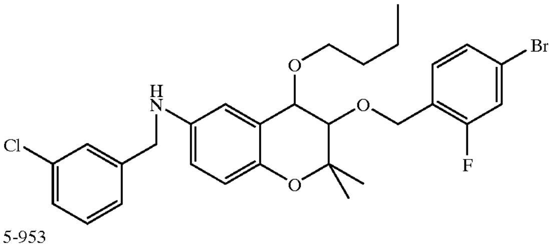 5-953 | MS, m/z: 576.94 |
| 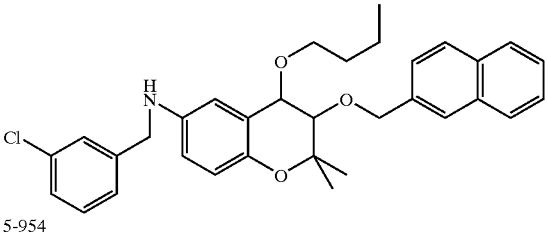 5-954 | MS, m/z: 530.11 |
| 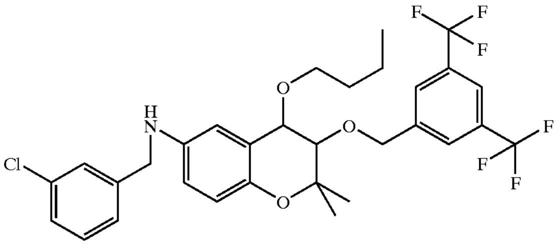 5-955 | MS, m/z: 616.05 |

TABLE 1-continued
| | Compound No. NMR/MS Data |
|---|---|
| 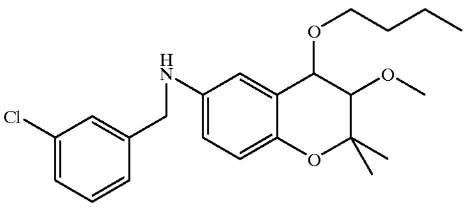 5-956 | MS, m/z: 403.95 |
| 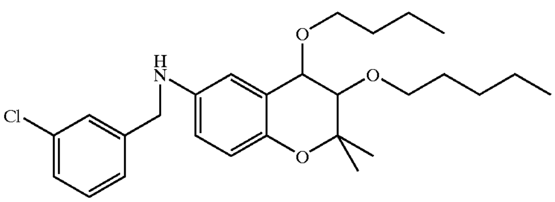 5-957 | MS, m/z: 460.06 |
| 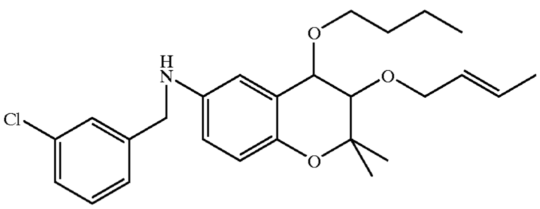 5-958 | MS, m/z: 444.02 |
| 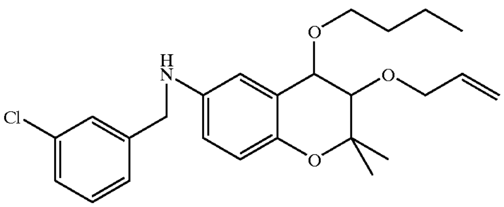 5-959 | MS, m/z: 429.99 |
| 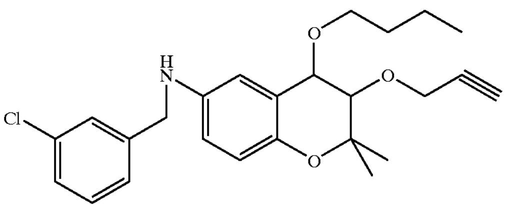 5-960 | MS, m/z: 427.98 |
| 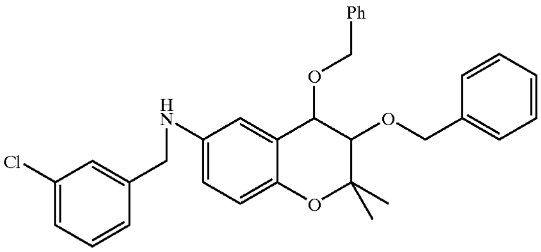 5-961 | MS, m/z: 514.07 |

TABLE 1-continued
| | Compound No. NMR/MS Data |
|---|---|
| 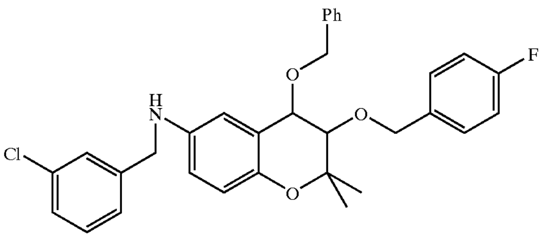 5-962 | MS, m/z: 532.06 |
| 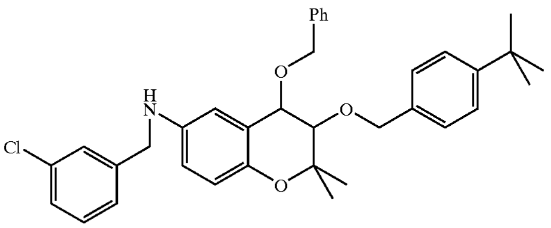 5-963 | MS, m/z: 570.18 |
| 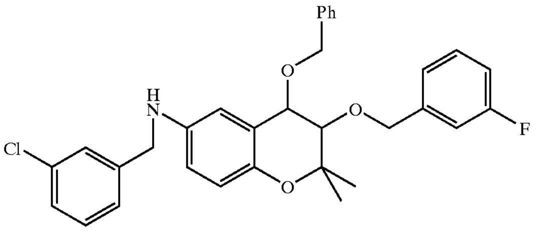 5-964 | MS, m/z: 532.06 |
| 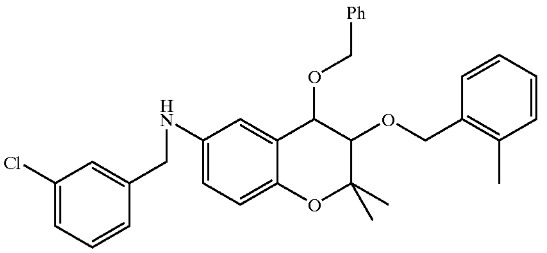 5-965 | MS, m/z: 528.10 |
| 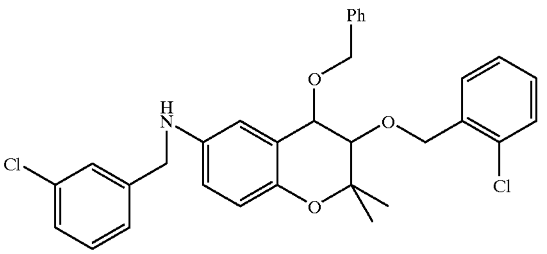 5-966 | MS, m/z: 548.51 |

TABLE 1-continued
| | Compound No. NMR/MS Data |
|---|---|
| 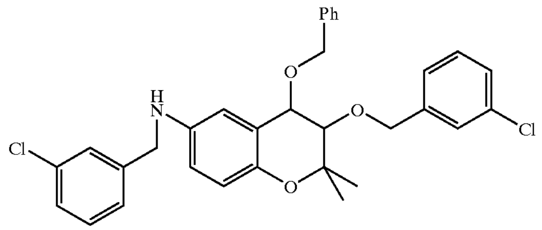 5-967 | MS, m/z: 548.51 |
| 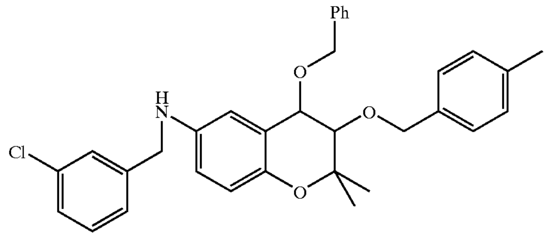 5-968 | MS, m/z: 528.10 |
| 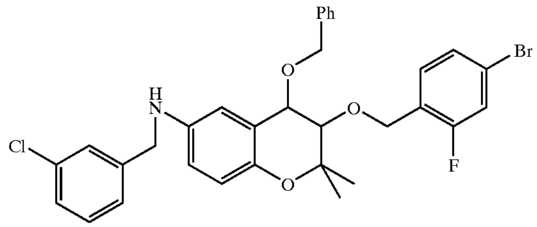 5-969 | MS, m/z: 610.96 |
| 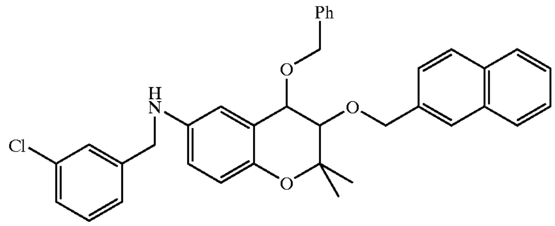 5-970 | MS, m/z: 564.13 |
| 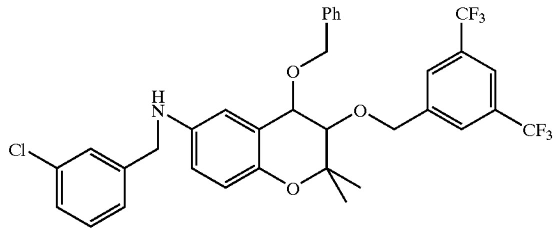 5-971 | MS, m/z: 542.12 |

TABLE 1-continued
| | Compound No. NMR/MS Data |
|---|---|
| 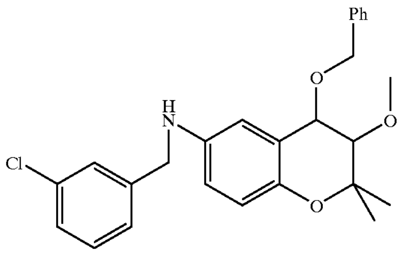 5-972 | MS, m/z: 437.97 |
| 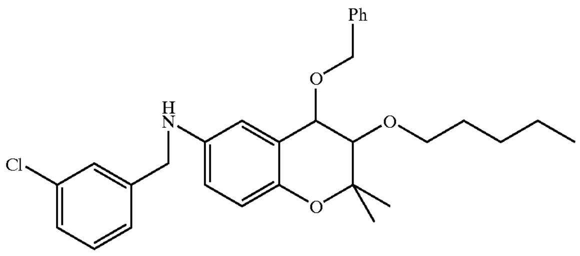 5-973 | MS, m/z: 494.08 |
| 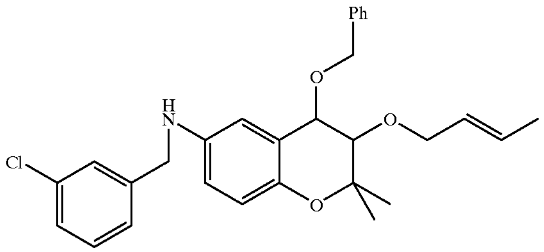 5-974 | MS, m/z: 478.04 |
| 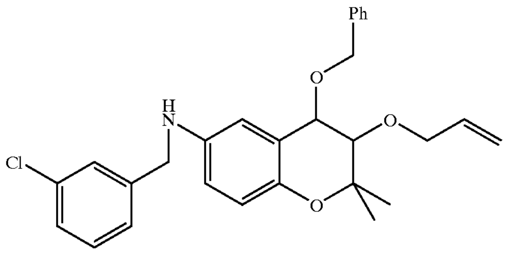 5-975 | MS, m/z: 464.01 |
| 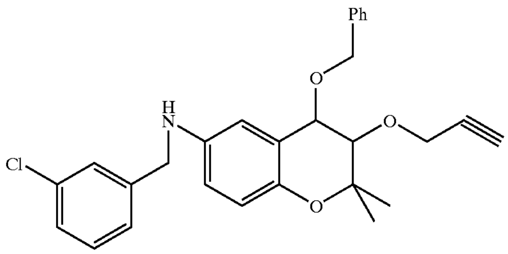 5-976 | MS, m/z: 461.99 |

TABLE 1-continued
| | Compound No. NMR/MS Data |
|---|---|
| 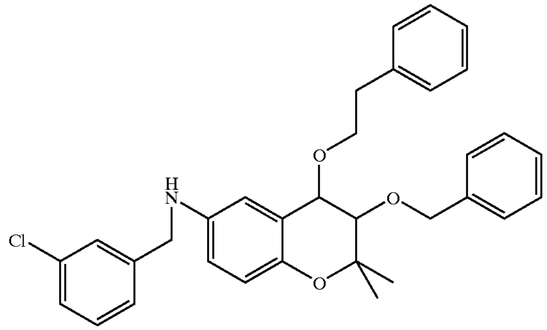 5-977 | MS, m/z: 528.10 |
| 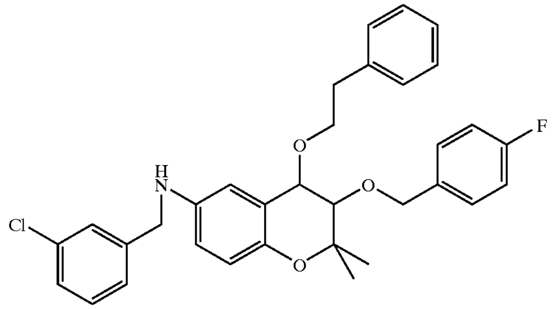 5-978 | MS, m/z: 546.09 |
| 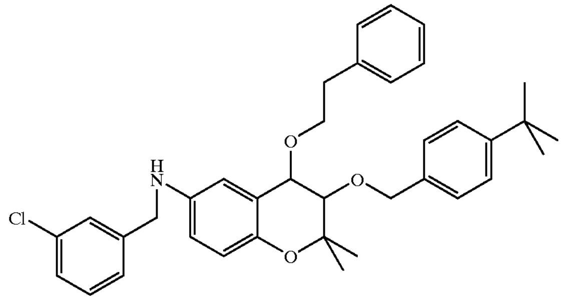 5-979 | MS, m/z: 584.21 |
| 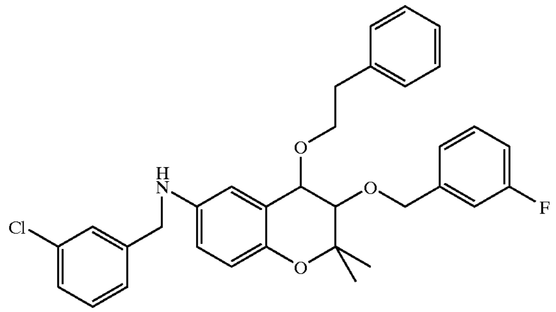 5-980 | MS, m/z: 546.09 |

TABLE 1-continued
| | Compound No. NMR/MS Data |
|---|---|
| 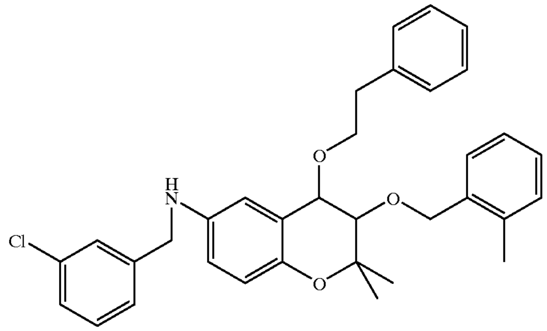 5-981 | MS, m/z: 542.12 |
| 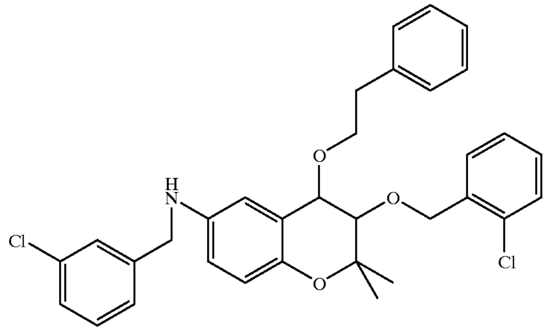 5-982 | MS, m/z: 562.54 |
| 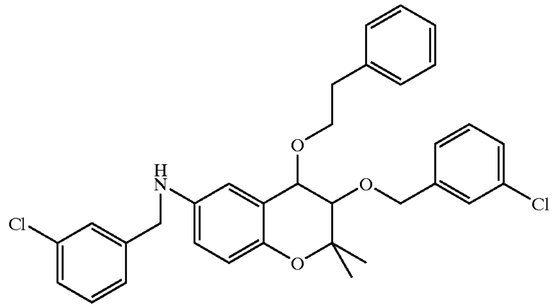 5-983 | MS, m/z: 562.54 |
| 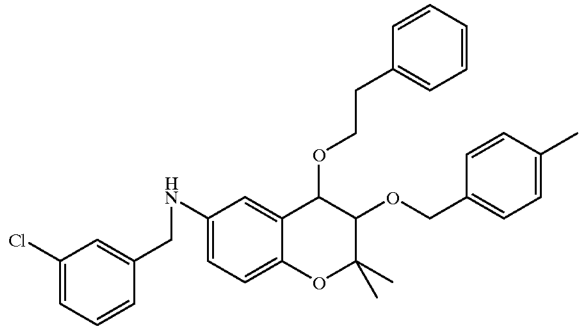 5-984 | MS, m/z: 542.12 |

TABLE 1-continued
| | Compound No. NMR/MS Data |
|---|---|
| 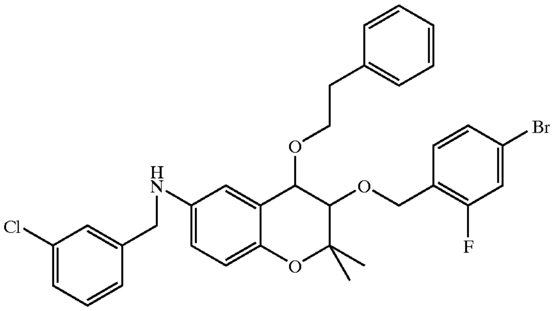 5-985 | MS, m/z: 624.98 |
| 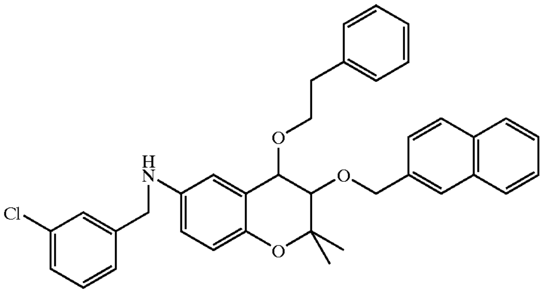 5-986 | MS, m/z: 578.16 |
| 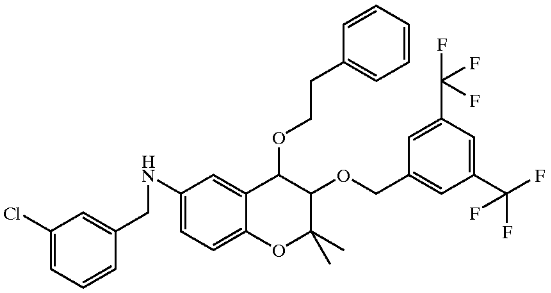 5-987 | MS, m/z: 664.09 |
| 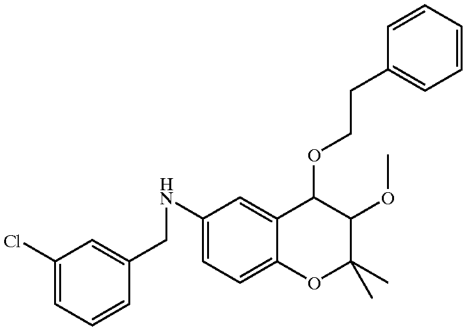 5-988 | MS, m/z: 452.00 |

TABLE 1-continued
| | Compound No. NMR/MS Data |
|---|---|
| 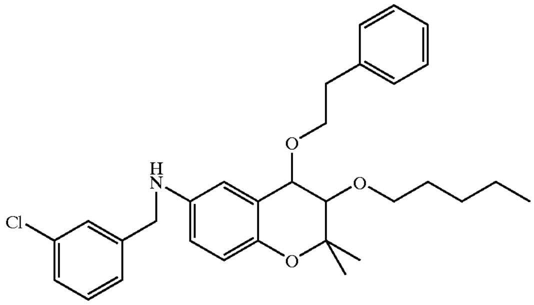 5-989 | MS, m/z: 508.11 |
| 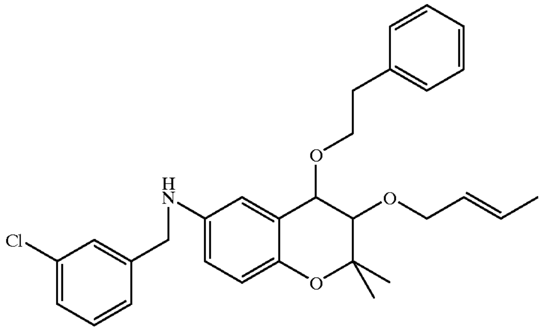 5-990 | MS, m/z: 492.06 |
| 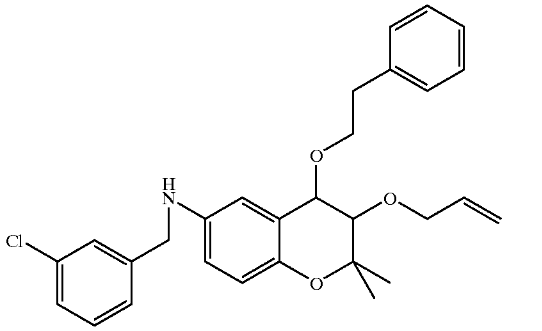 5-991 | MS, m/z: 478.04 |
| 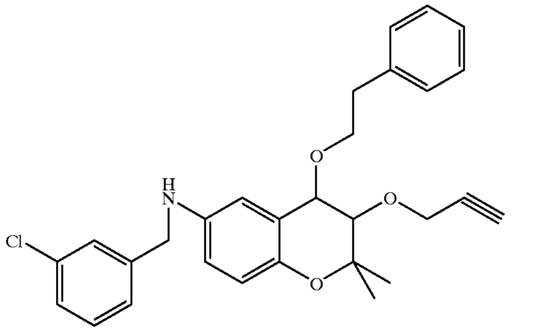 5-992 | MS, m/z: 476.02 |

TABLE 1-continued
| | Compound No. NMR/MS Data |
|---|---|
| 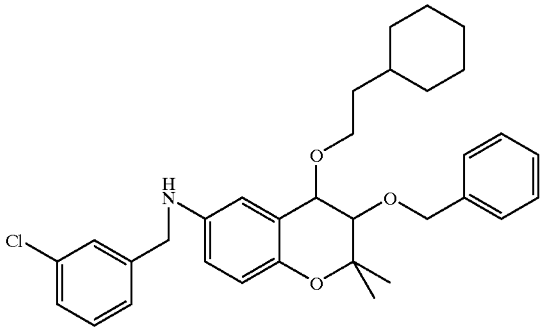 5-993 | MS, m/z: 534.14 |
| 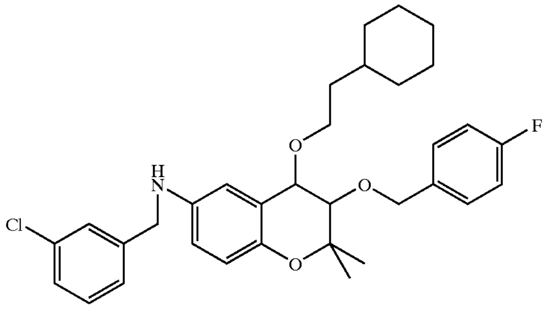 5-994 | MS, m/z: 552.14 |
| 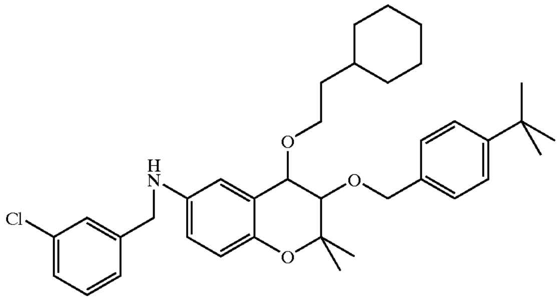 5-995 | MS, m/z: 590.25 |
| 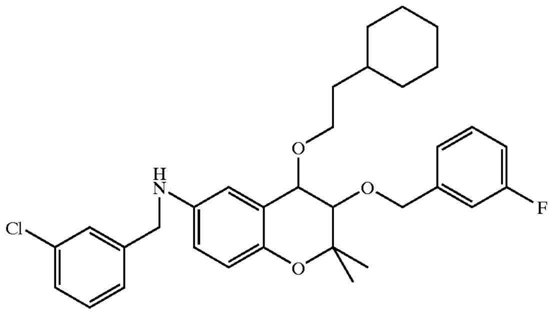 5-996 | MS, m/z: 552.14 |

TABLE 1-continued
| | Compound No. NMR/MS Data |
|---|---|
| 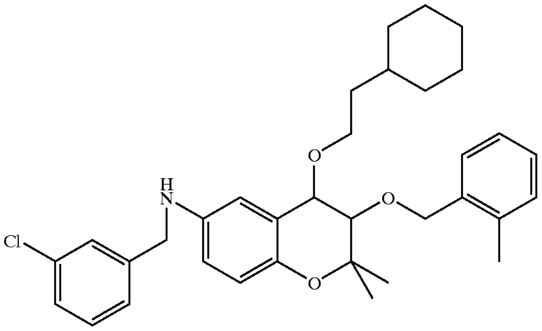 5-997 | MS, m/z: 548.17 |
| 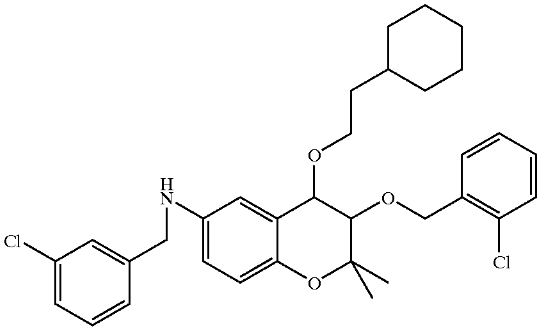 5-998 | MS, m/z: 568.59 |
| 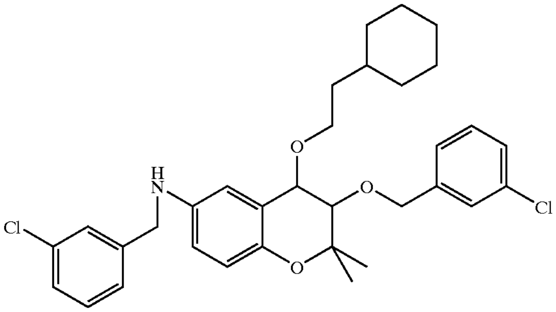 5-999 | MS, m/z: 568.59 |
| 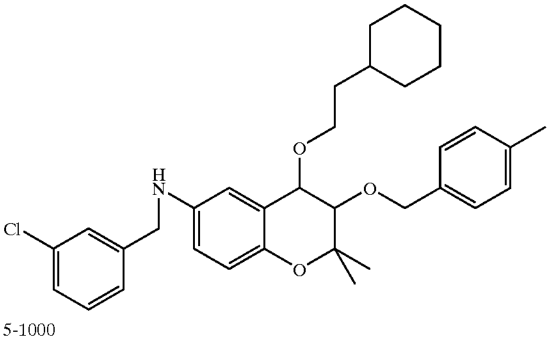 5-1000 | MS, m/z: 548.17 |

TABLE 1-continued
| | Compound No. NMR/MS Data |
|---|---|
| 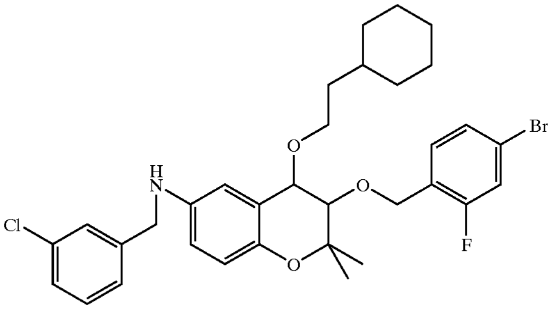 5-1001 | MS, m/z: 631.03 |
| 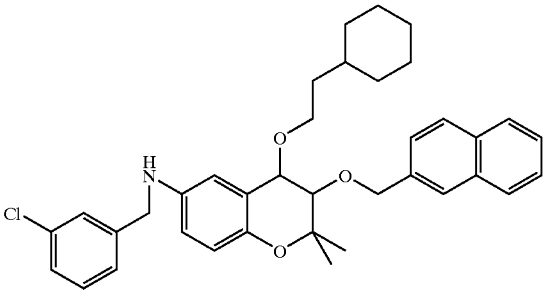 5-1002 | MS, m/z: 584.21 |
| 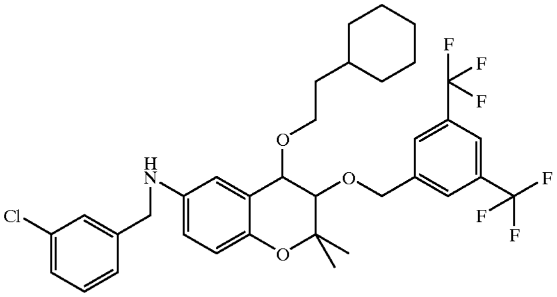 5-1003 | MS, m/z: 670.14 |
| 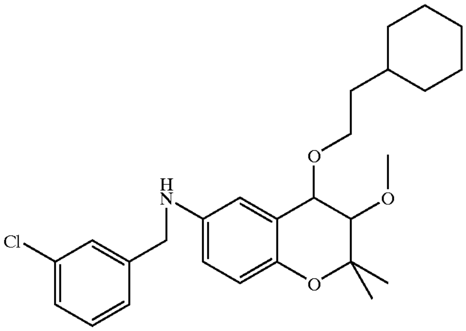 5-1004 | MS, m/z: 458.05 |

TABLE 1-continued
| | Compound No. NMR/MS Data |
|---|---|
| 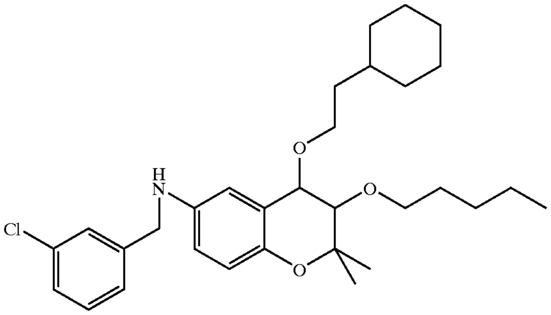 5-1005 | MS, m/z: 514.15 |
| 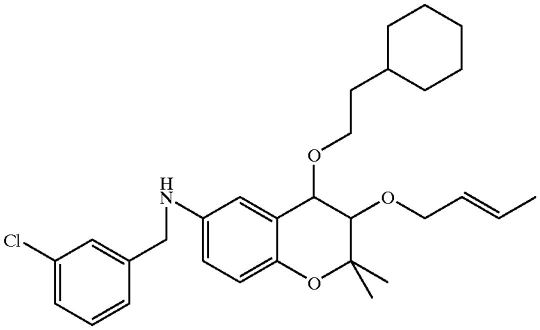 5-1006 | MS, m/z: 498.11 |
| 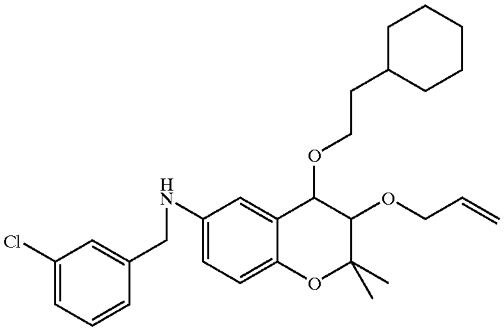 5-1007 | MS, m/z: 484.08 |
| 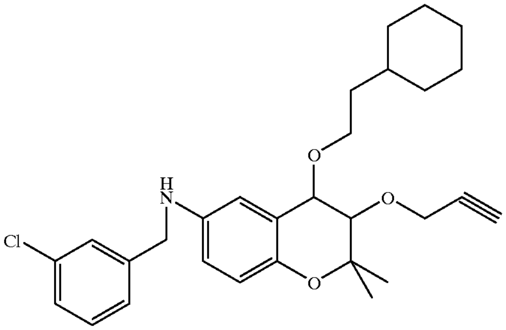 5-1008 | MS, m/z: 482.07 |

TABLE 1-continued
| | Compound No. NMR/MS Data |
|---|---|
| 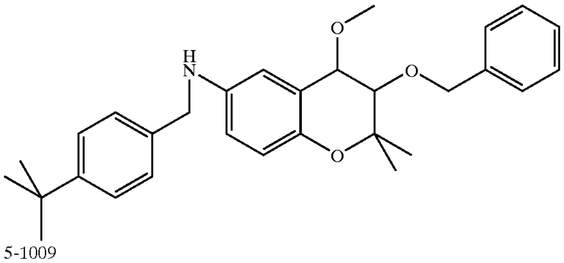 5-1009 | MS, m/z: 459.63 |
| 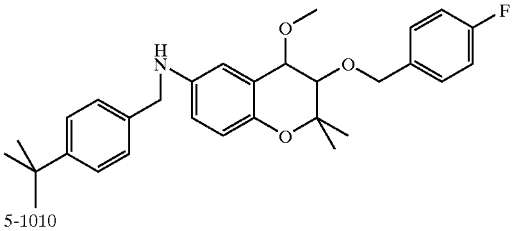 5-1010 | MS, m/z: 477.62 |
| 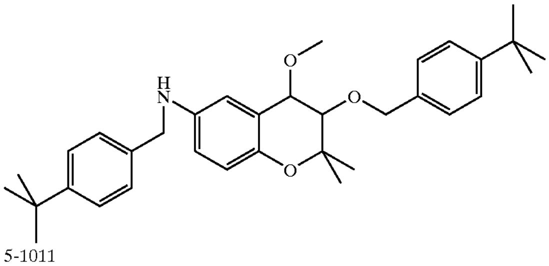 5-1011 | MS, m/z: 515.74 |
| 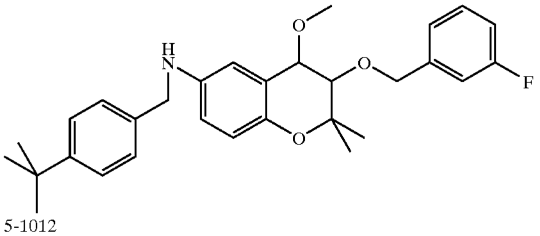 5-1012 | MS, m/z: 477.62 |
| 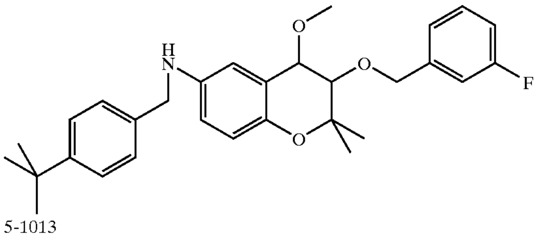 5-1013 | MS, m/z: 473.66 |
| 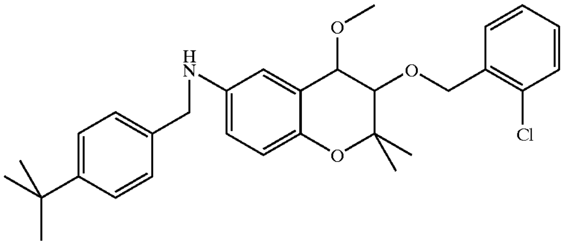 5-1014 | MS, m/z: 494.08 |

TABLE 1-continued
| | Compound No. NMR/MS Data |
|---|---|
| 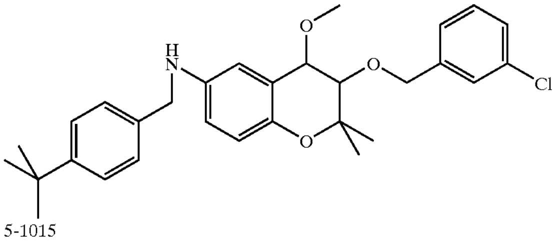 5-1015 | MS, m/z: 494.08 |
| 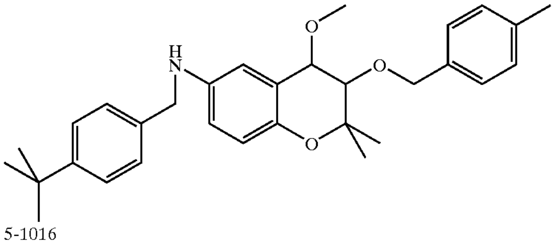 5-1016 | MS, m/z: 473.66 |
| 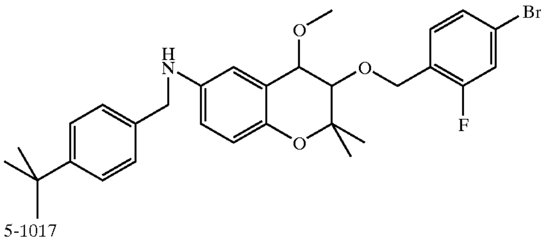 5-1017 | MS, m/z: 556.52 |
| 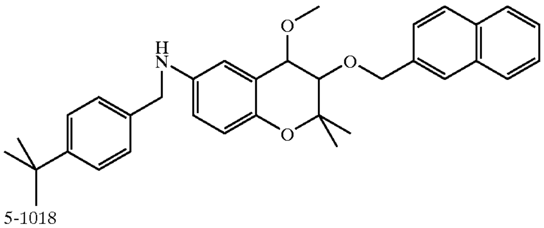 5-1018 | MS, m/z: 509.69 |
| 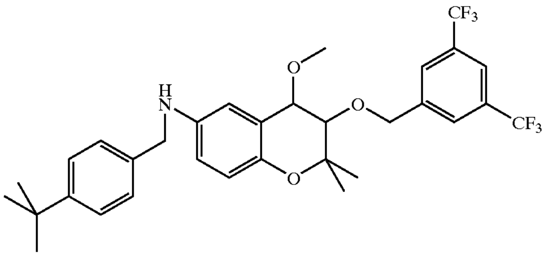 5-1019 | MS, m/z: 487.69 |
| 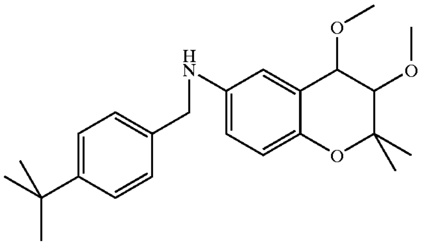 5-1020 | MS, m/z: 383.54 |

TABLE 1-continued
| | Compound No. NMR/MS Data |
|---|---|
| 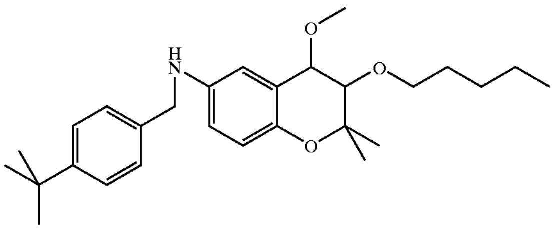 5-1021 | MS, m/z: 439.64 |
| 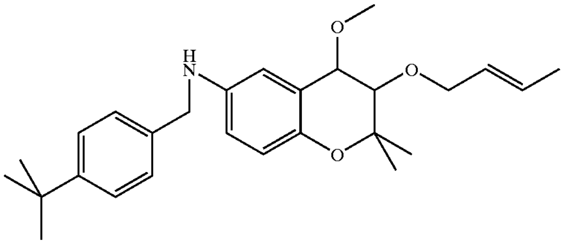 5-1022 | MS, m/z: 423.60 |
| 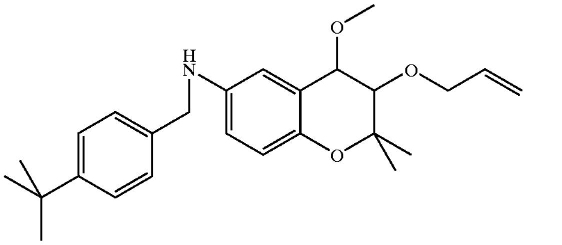 5-1023 | MS, m/z: 409.57 |
| 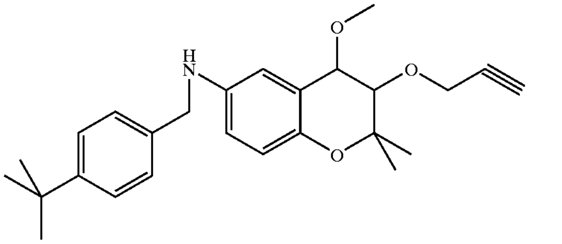 5-1024 | MS, m/z: 407.56 |
| 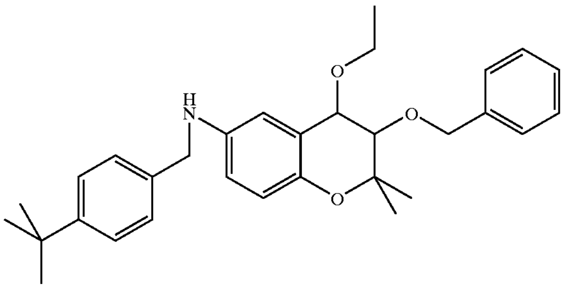 5-1025 | $^1$H NMR(500 MHz, $CDCl_3$) δ 7.39~7.28(m, 9H), 6.67~6.54(m, 3H), 4.89(d, 1H, J=11.4 Hz), 4.71 (d, 1H, J=11.4 Hz), 4.44(d, 1H, J=7.6 Hz), 4.23(s, 2H), 3.74~3.66(m, 2H), 3.60(d, 1H, J=7.6 Hz), 1.40(s, 3H), 1.31(s, 9H), 1.22(s, 3H), 1.19(s, 3H); MS, m/z = 431.58; MS, m/z: 473.66 |

TABLE 1-continued

| | Compound No. NMR/MS Data |
|---|---|
| 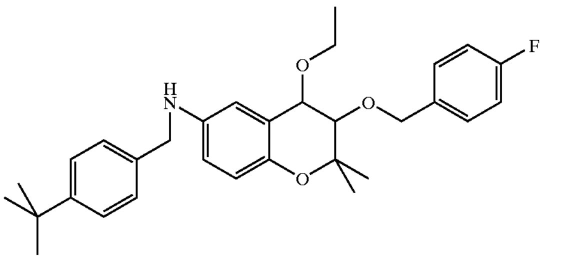 5-1026 | $^1H$ NMR(500 MHz, $CDCl_3$) δ 7.37~7.30(m, 6H), 7.05~7.01(m, 2H), 6.66~6.56(m, 3H), 4.86(d, 1H, J=11.4 Hz), 4.67(d, 1H, J=11.4 Hz), 4.43(d, 1H, J=7.6 Hz), 4.23(s, 2H), 3.70~3.67(m, 2H), 3.58(d, 1H, J=7.6 Hz), 1.39(s, 3H), 1.31~1.30(m, 9H), 1.21~1.19(m, 6H); MS, m/z: 491.65 |
| 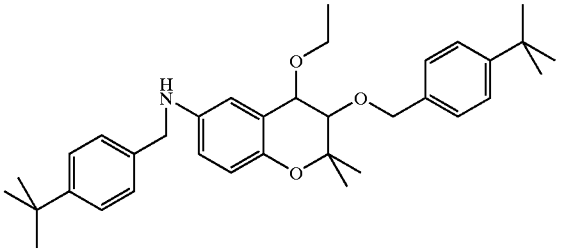 5-1027 | $^1H$ NMR(500 MHz, $CDCl_3$) δ 7.39~7.30(m, 8H), 6.69~6.57(m, 3H), 4.86(d, 1H, J=11.2 Hz), 4.68(d, 1H, J=11.2 Hz), 4.42(d, 1H, J=7.6 Hz), 4.23(s, 2H), 3.74~3.65(d, 2H), 3.59(d, 1H, J= 7.6 Hz), 1.41(s, 3H), 1,32~1.29(m, 18H), 1.21~1.19(m, 6H); MS, m/z: 529.77 |
| 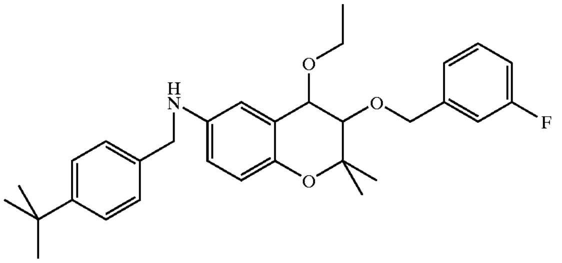 5-1028 | $^1H$ NMR(500 MHz, $CDCl_3$) δ 7.38~7.28(m, 5H), 7.13~7.07(m, 2H), 7.00(m, 1H), 6.69~6.56(m, 3H), 4.91(d, 1H, J=11.8 Hz), 4.71 (d, 1H, J=11.8 Hz), 4.46(d, 1H, J=7.7 Hz), 4.23(s, 2H), 3.72~3.67(m, 2H), 3.59(d, 1H, J=7.7 Hz), 1.42(s, 3H), 1.32(s, 9H), 1.24(s, 3H), 1.21(t, 3H, J=6.95 Hz); MS, m/z: 491.65 |
| 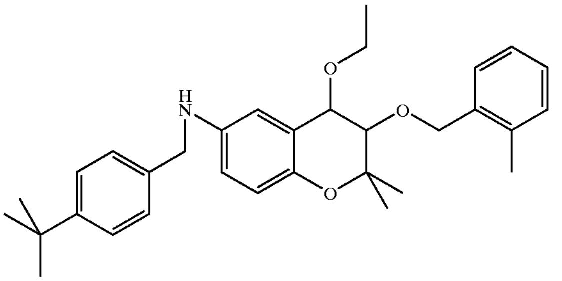 5-1029 | $^1H$ NMR(500 MHz, $CDCl_3$) δ 7.39~7.30(m, 5H), 7.21~7.15(m, 3H), 6.66~6.54(m, 3H), 4.93(d, 1H, J=11.7 Hz), 4.69(d, 1H, J=11.7 Hz), 4.45(d, 1H, J=7.7 Hz), 4.23(s, 2H), 3.71~3.64(m, 2H), 3.62(d, 1H, J=7.7 Hz), 2.35(s, 3H), 1.38(s, 3H), 1.31(s, 9H), 1.22(s, 3H), 1.19(t, 3H, t=7.0 Hz); MS, m/z: 487.69 |
| 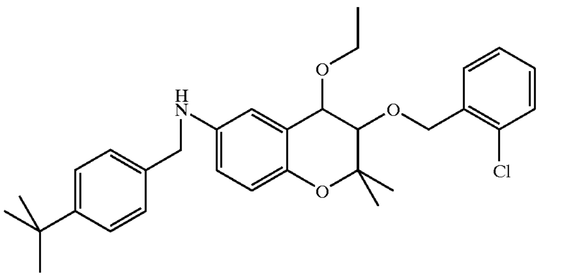 5-1030 | $^1H$ NMR(500 MHz, $CDCl_3$) δ 7.54(m, 1H), 7.38~7.22"(m, 8H), 6.70~6.57(m, 3H), 5.04(d, 1H, J=12.7 Hz), 4.81(d, 1H, J= 12.7 Hz), 4.48(d, 1H, J=7.6 Hz), 4.24(s, 2H), 3.71(q, 2H, J=7.0 Hz), 3.67(d, 1H, J=7.7 Hz), 1.43(s, 3H), 1.33(s, 9H), 1.26(s, 3H), 1.21(t, 3H, J=7.0 Hz); MS, m/z: 508.11 |

TABLE 1-continued
| | Compound No. NMR/MS Data |
|---|---|
| 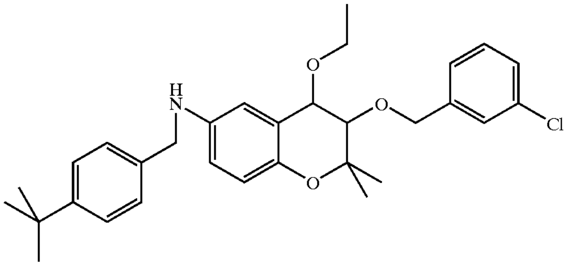 5-1031 | $^1$H NMR(500 MHz, $CDCl_3$) δ 7.38~7.24(m, 8H), 6.69~6.65(m, 2H), 6.58(m, 1H), 4.89(d, 1H, J=11.8 Hz), 4.70(d, 1H, J= 11.8 Hz), 4.46(d, 1H, J=7.8 Hz), 4.24(s, 2H), 3.68(m, 2H), 3.59(d, 1H, J=7.8 Hz), 1.42(s, 3H), 1.31 (s, 9H), 1.24(s, 3H), 1.21 (t, 3H, J=6.95 Hz); MS, m/z: 508.11 |
| 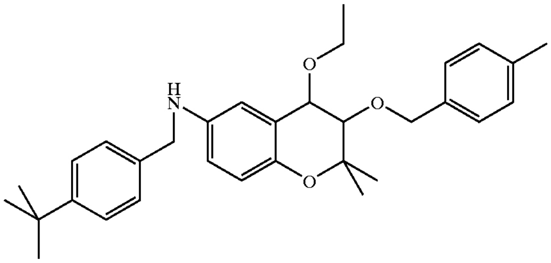 5-1032 | MS, m/z = 487.69 |
| 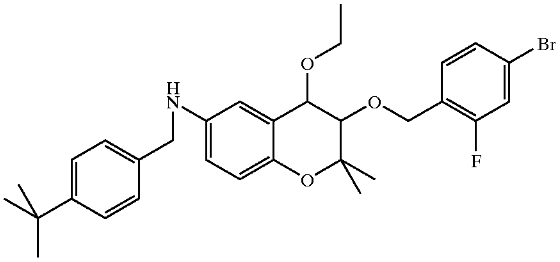 5-1033 | $^1$H NMR(500 MHz, $CDCl_3$) δ 7.37~7.20(m, 7H), 6.70~6.55(m, 3H), 489(d, 1H, J=11.9 Hz), 4.71 (d, 1H, J=11.9 Hz), 4.42(d, 1H, J=7.7 Hz), 4.23(s, 2H), 3.72~3.67(m, 2H), 3.59(d, 1H, J= 7.7 Hz)1.40(s, 3H), 1.30(s, 9H), 1.23~1.19(m, 6H); MS, m/z: 570.55 |
| 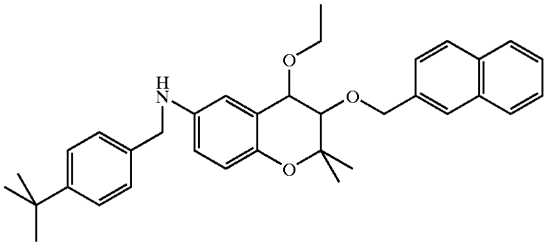 5-1034 | MS, m/z = 523.72 |
| 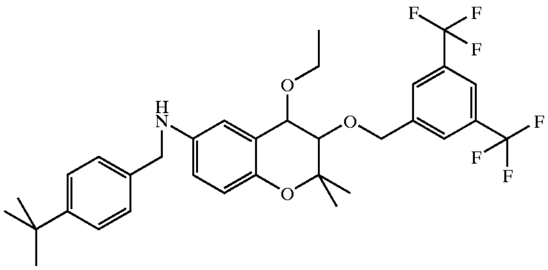 5-1035 | MS, m/z = 609.66 |

TABLE 1-continued

| | Compound No. NMR/MS Data |
|---|---|
| 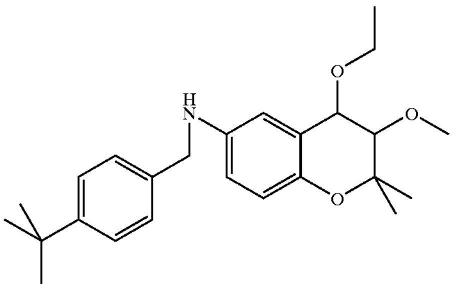 5-1036 | $^1$H NMR(500 MHz, $CDCl_3$) δ 7.37~7.30(m, 4H), 6.70~6.54(m, 3H), 4.33(d, 1H, J=7.5 Hz), 4.23(s, 2H), 3.78~3.70(m, 2H), 3.60(s, 3H), 3.31 (d, 1H, J=7.5 Hz), 1.41 (s, 3H), 1.31(s, 9H), 1.24(t, 3H, J=7.1 Hz), 1.19(s, 3H); MS, m/z: 398.56 |
| 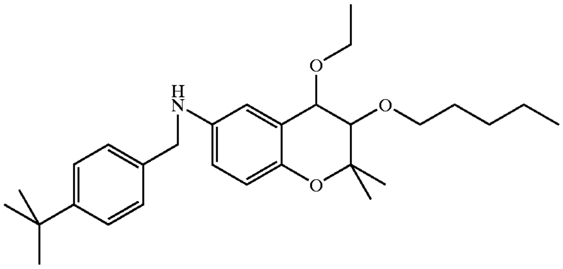 5-1037 | $^1$H NMR(500 MHz, $CDCl_3$) δ 7.36(d, 2H, J=8.3 Hz), 7.31(d, 2H, J=8.3 Hz), 6.70~6.57(m, 3H), 4.32(d, 1H, J=7.7 Hz), 4.22(s, 3H), 3.82~3.819m, 1H), 3.76~3.72(m, 2H), 3.60~3.58(m, 1H), 3.38(d, 1H, J=7.7 Hz), 1.62~1.59(m, 1H), 1.40(s, 3H), 1.37~1.28(m, 13H), 1.23(t, 3H, J=7.0 Hz), 1.19(s, 3H), 0.91(m, 3H); MS, m/z: 453.67 |
| 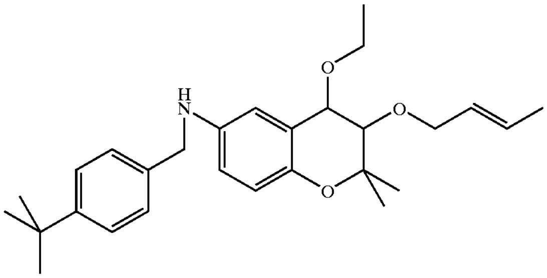 5-1038 | $^1$H NMR(500 MHz, $CDCl_3$) δ 7.36(d, 2H, J=8.3 Hz), 7.31(d, 2H, J=8.3 Hz), 6.68~6.56(m, 3H), 5.75~5.61(m, 2H), 4.40~4.34(m, 1H), 4.30~4.23(m, 1H), 4.22(s, 2H), 4.13~4.09(m, 1H), 3.79~3.70(m, 2H), 3.47(d, 1H, J=7.7 Hz), 1.73~1.68(m, 3H), 1.40(s, 3H), 1.31(s, 9H), 1.25~1.20(m, 6H); MS, m/z = 437.63 |
| 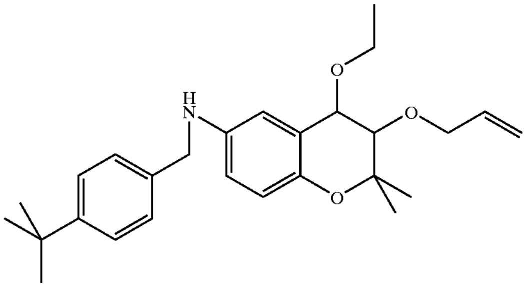 5-1039 | $^1$H NMR(500 MHz, $CDCl_3$) δ 7.36(d, 2H, J=8.4 Hz), 7.31(d, 2H, J=8.4 Hz), 6.68~6.56(m, 3H), 6.00~5.92(m, 1H), 5.32~5.28(m, 1H), 5.17~5.16(m, 1H), 4.36(d, 1H, J=7.6 Hz), 4.35~4.34(m, 1H), 4.23(s, 2H), 4.21~4.16(m, 1H), 3.77~3.70(m, 2H), 3.46(d, 1H, J=7.7 Hz), 1.41(s, 3H), 1.31(s, 9H), 1.24~1.21 (m, 6H); MS, m/z: 423.60 |
| 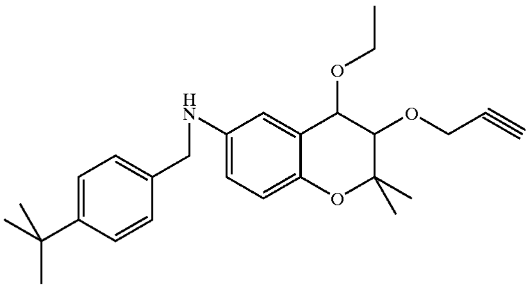 5-1040 | $^1$H NMR(500 MHz, $CDCl_3$) δ 7.34(d, 2H, J=8.3 Hz), 7.30(d, 2H, J=8.3 Hz), 6.66~6.56(m, 3H), 4.44(s, 2H), 4.44(d, 1H, J=7.7 Hz), 4.22(s, 2H), 3.72~3.67(m, 3H), 2.44(t, 1H, J=2.4 Hz), 1.43(s, 3H), 1.30(s, 9H), 1.22~1.20(m, 6H); MS, m/z: 421.58 |

TABLE 1-continued
| | Compound No. NMR/MS Data |
|---|---|
| 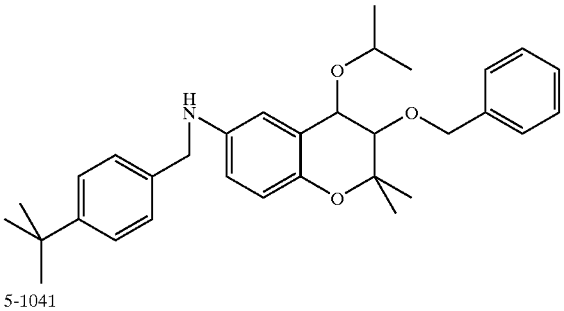 5-1041 | MS, m/z: 487.69 |
| 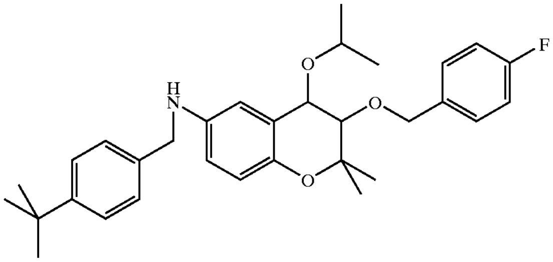 5-1042 | MS, m/z: 505.68 |
| 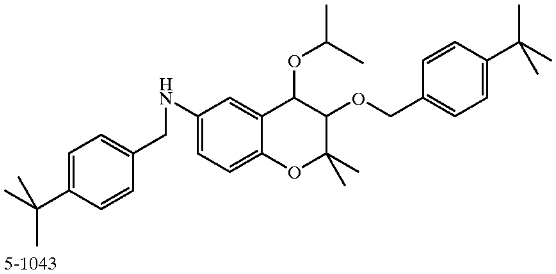 5-1043 | MS, m/z: 543.80 |
| 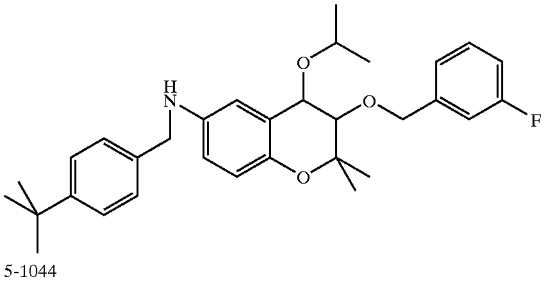 5-1044 | MS, m/z: 505.68 |
| 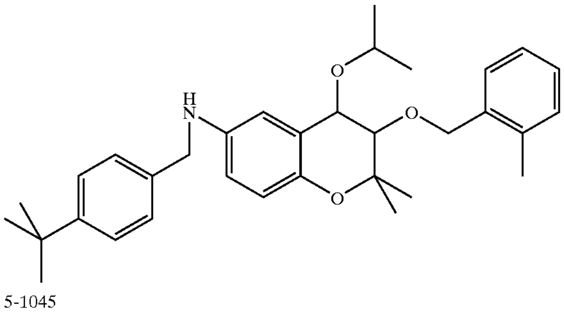 5-1045 | MS, m/z: 501.72 |

TABLE 1-continued
| | Compound No. NMR/MS Data |
|---|---|
| 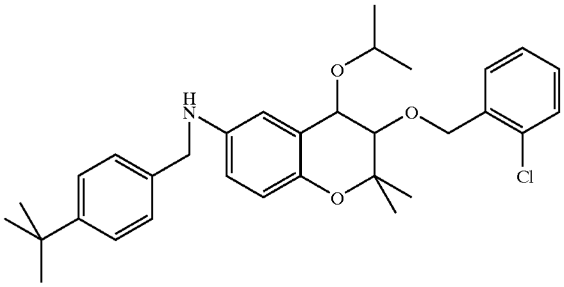 5-1046 | MS, m/z: 522.13 |
| 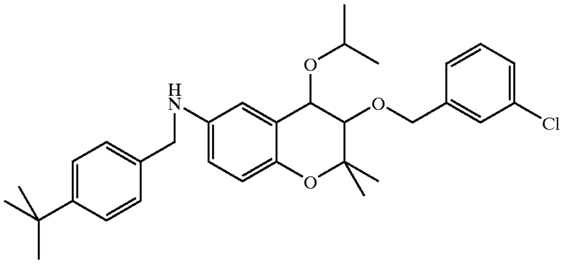 5-1047 | MS, m/z: 522.13 |
| 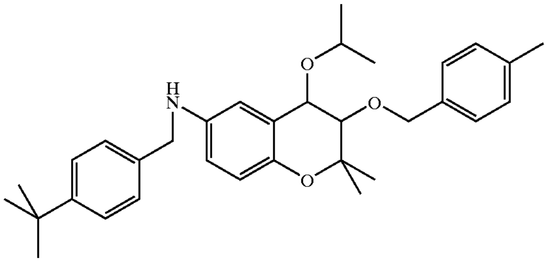 5-1048 | MS, m/z: 501.72 |
| 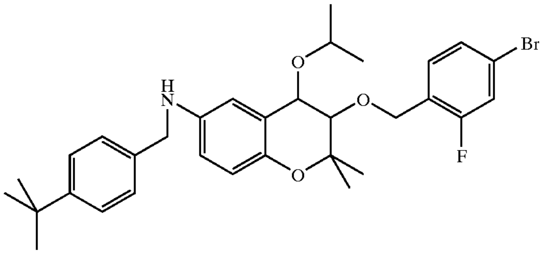 5-1049 | MS, m/z: 584.57 |
| 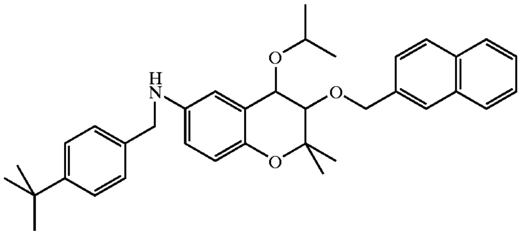 5-1050 | MS, m/z: 537.75 |

TABLE 1-continued
| | Compound No. NMR/MS Data |
|---|---|
| 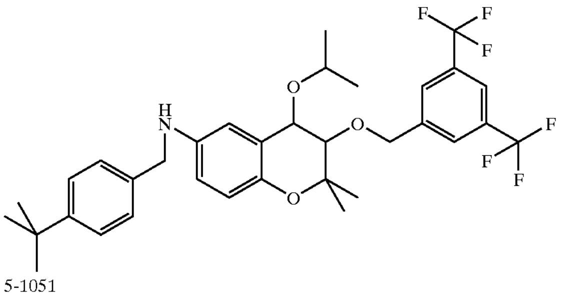 5-1051 | MS, m623.69/z: |
| 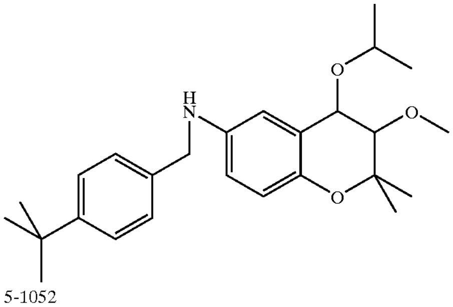 5-1052 | MS, m/z: 411.59 |
| 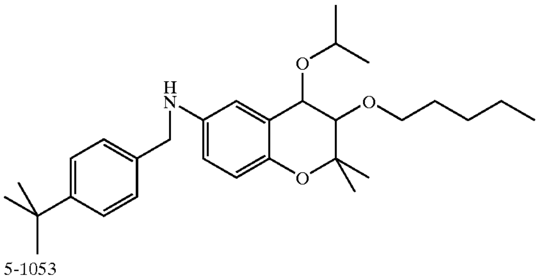 5-1053 | MS, m/z: 467.70 |
| 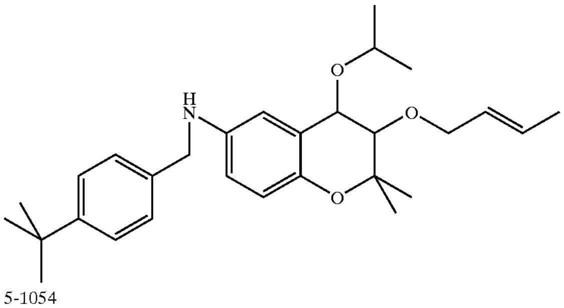 5-1054 | MS, m/z: 451.66 |
| 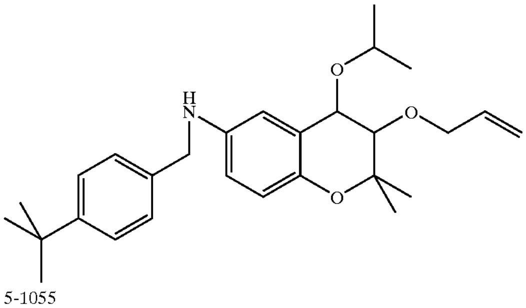 5-1055 | MS, m/z: 437.63 |

TABLE 1-continued
| | Compound No. NMR/MS Data |
|---|---|
| 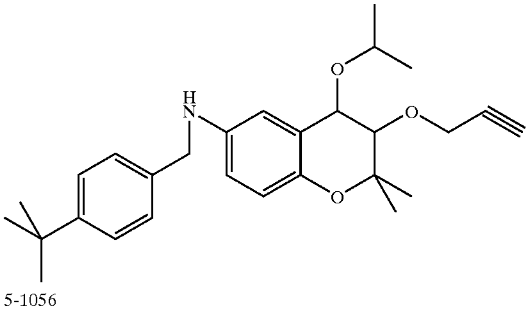 5-1056 | MS, m/z: 435.61 |
| 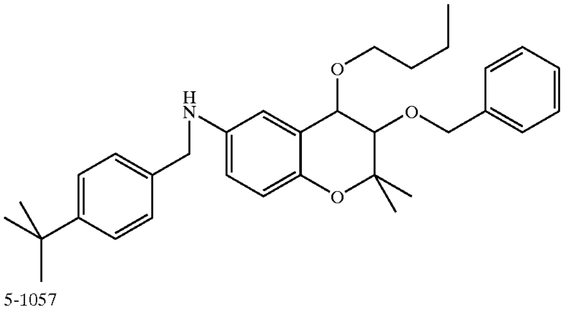 5-1057 | MS, m/z: 501.72 |
| 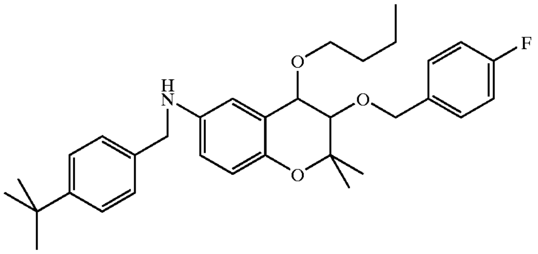 5-1058 | MS, m/z: 519.71 |
| 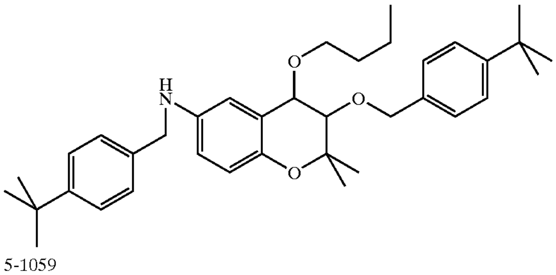 5-1059 | MS, m/z: 557.82 |
| 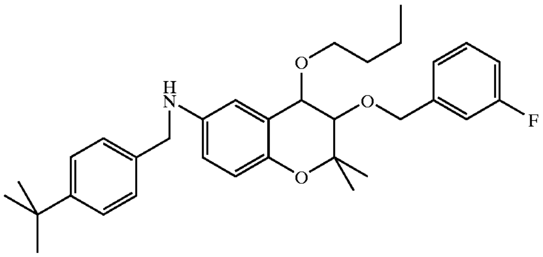 5-1060 | MS, m/z: 519.71 |

TABLE 1-continued
| | Compound No. NMR/MS Data |
|---|---|
| 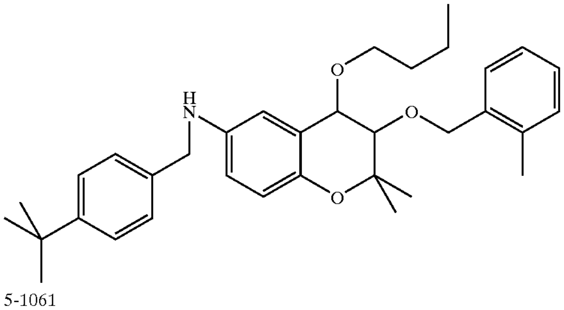 5-1061 | MS, m/z: 515.74 |
| 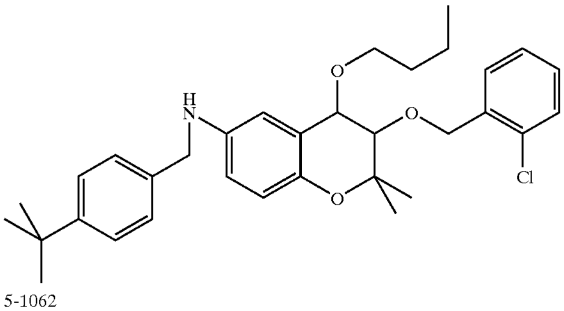 5-1062 | MS, m/z: 536.16 |
| 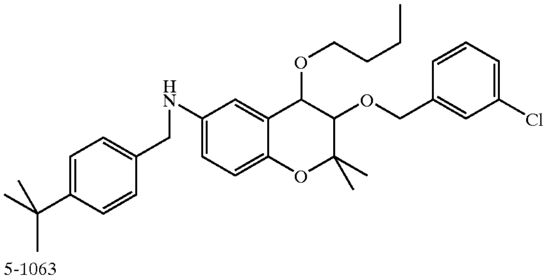 5-1063 | MS, m/z: 536.16 |
| 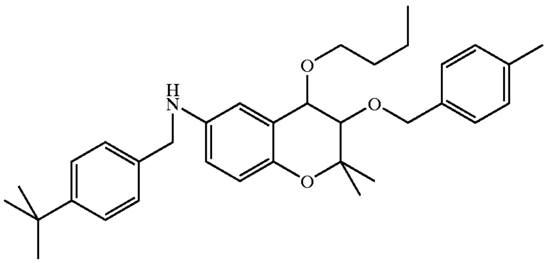 5-1064 | MS, m/z: 515.74 |
| 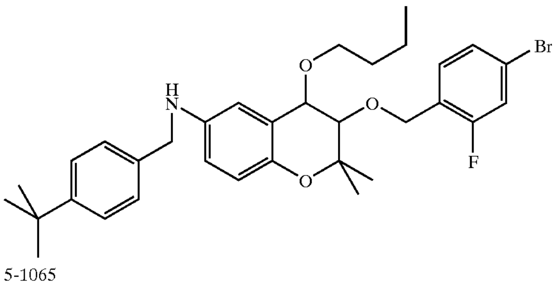 5-1065 | MS, m/z: 598.60 |

TABLE 1-continued
| | Compound No. NMR/MS Data |
|---|---|
| 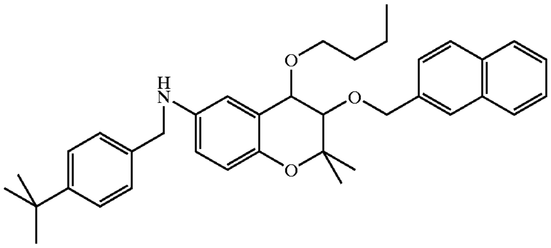 5-1066 | MS, m/z: 551.78 |
| 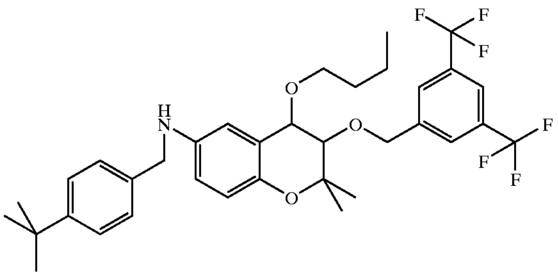 5-1067 | MS, m/z: 637.71 |
| 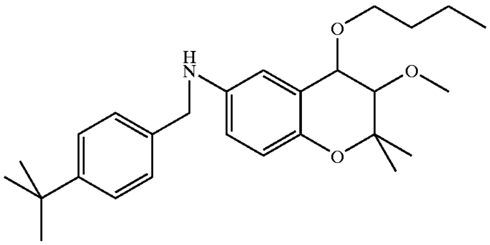 5-1068 | MS, m/z: 425.62 |
| 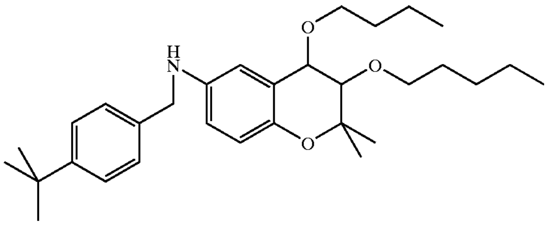 5-1069 | MS, m/z: 481.73 |
| 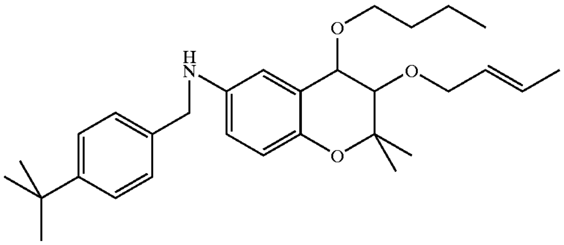 5-1070 | MS, m/z: 465.68 |

TABLE 1-continued
| | Compound No. NMR/MS Data |
|---|---|
| 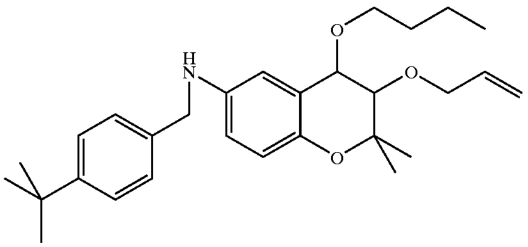 5-1071 | MS, m/z: 451.66 |
| 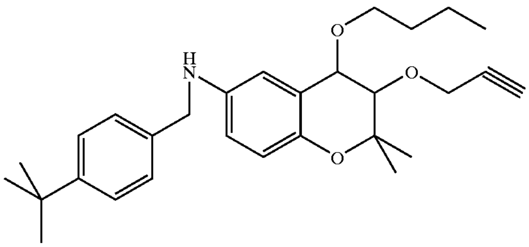 5-1072 | MS, m/z: 449.64 |
| 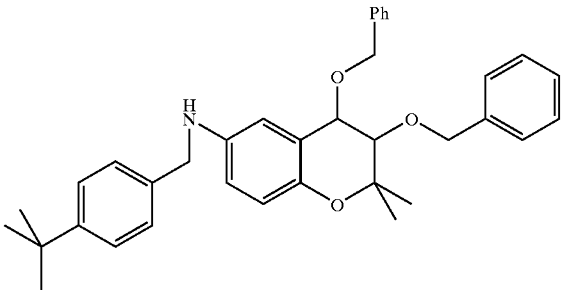 5-1073 | MS, m/z: 535.73 |
| 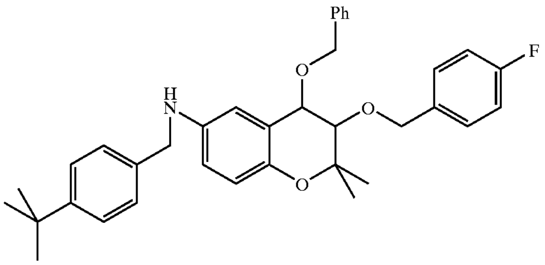 5-1074 | MS, m/z: 553.72 |
| 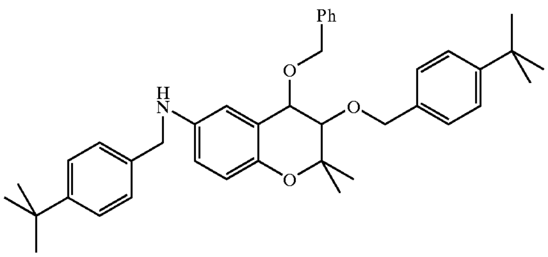 5-1075 | MS, m/z: 591.84 |

TABLE 1-continued
| | Compound No. NMR/MS Data |
|---|---|
| 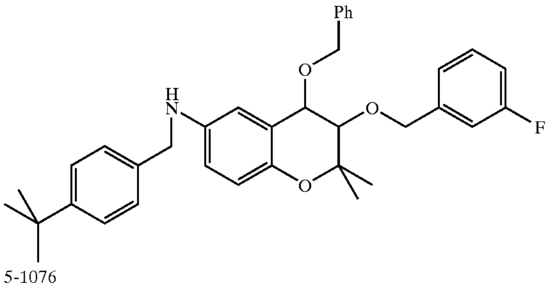 5-1076 | MS, m/z: 553.72 |
| 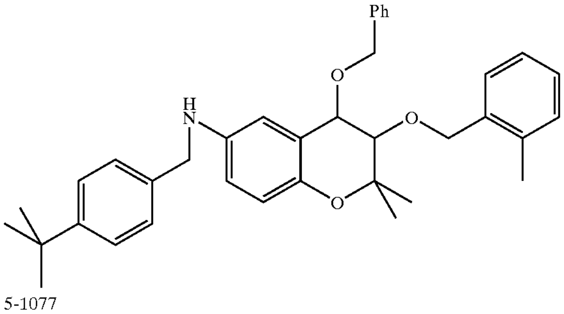 5-1077 | MS, m/z: 549.76 |
| 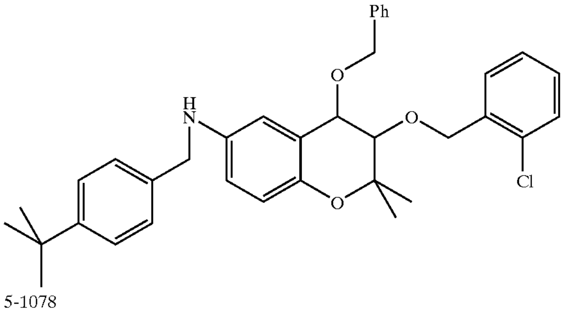 5-1078 | MS, m/z: 570.18 |
| 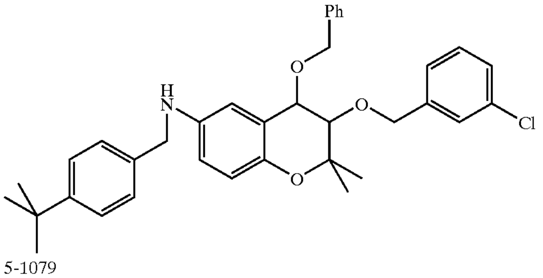 5-1079 | MS, m/z: 570.18 |
| 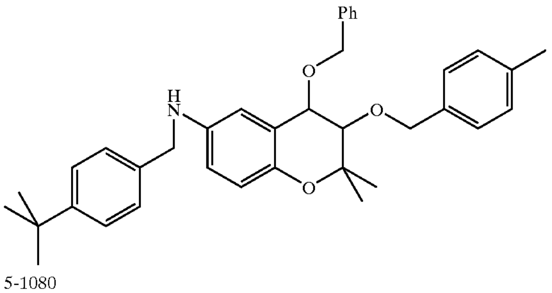 5-1080 | MS, m/z: 549.76 |

TABLE 1-continued
| | Compound No. NMR/MS Data |
|---|---|
| 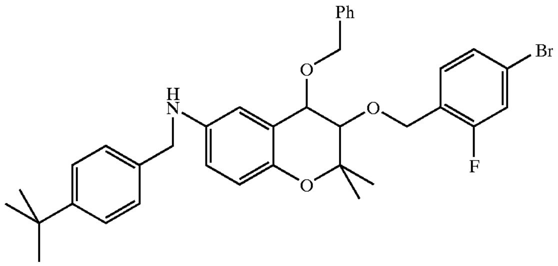 5-1081 | MS, m/z: 632.62 |
| 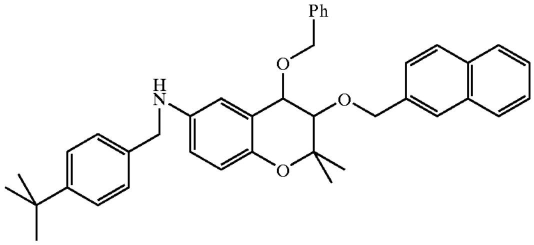 5-1082 | MS, m/z: 585.79 |
| 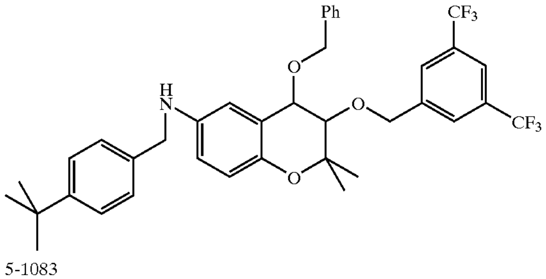 5-1083 | MS, m/z: 563.79 |
| 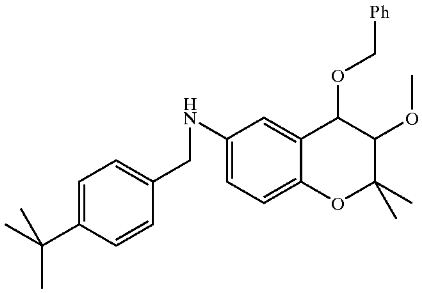 5-1084 | MS, m/z: 459.63 |
| 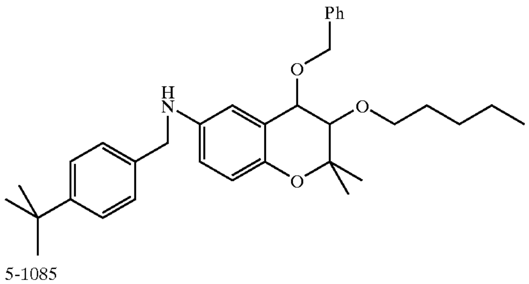 5-1085 | MS, m/z: 515.74 |

TABLE 1-continued
| | Compound No. NMR/MS Data |
|---|---|
| 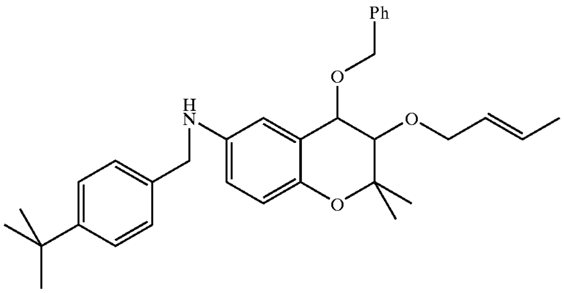 5-1086 | MS, m/z: 499.70 |
| 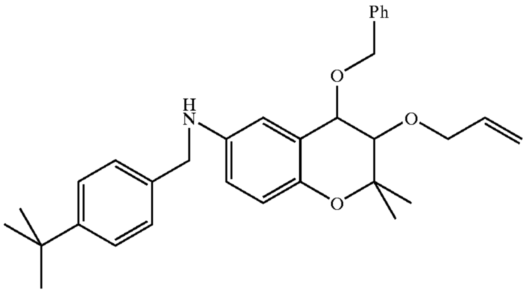 5-1087 | MS, m/z: 485.67 |
| 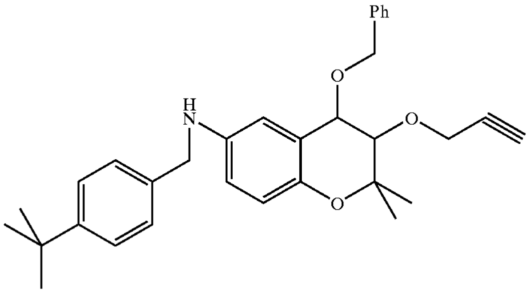 5-1088 | MS, m/z: 483.66 |
| 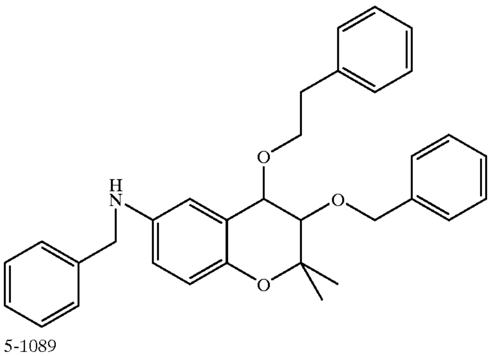 5-1089 | MS, m/z: 493.65 |

TABLE 1-continued
| | Compound No. NMR/MS Data |
|---|---|
| 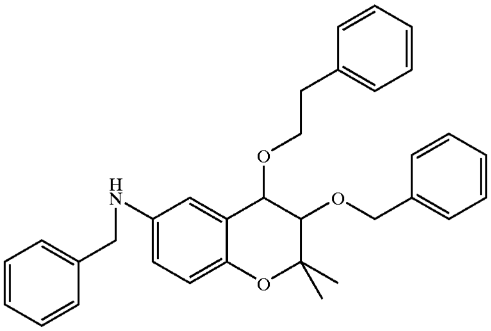 5-1090 | MS, m/z: 511.64 |
| 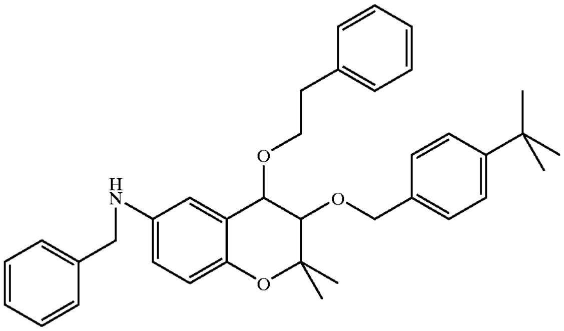 5-1091 | MS, m/z: 549.76 |
| 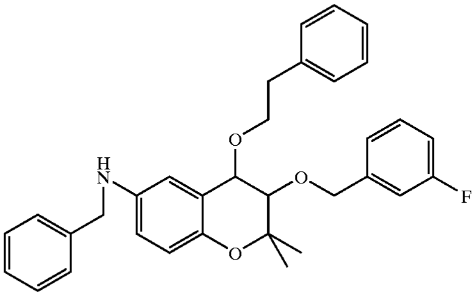 5-1092 | MS, m/z: 511.64 |
| 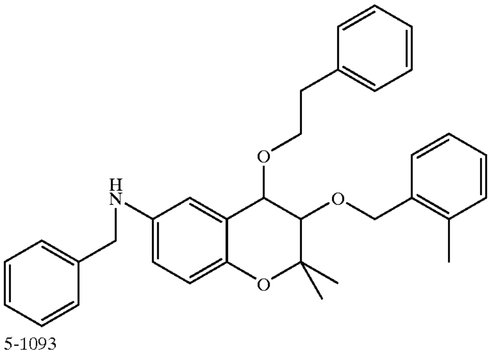 5-1093 | MS, m/z: 507.68 |

TABLE 1-continued
| | Compound No. NMR/MS Data |
|---|---|
| 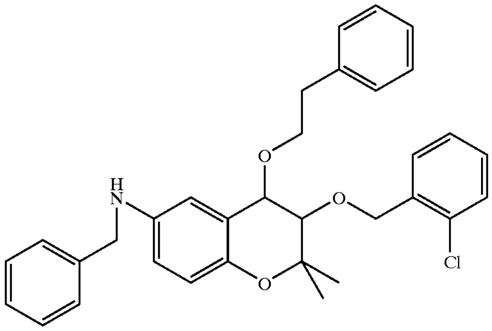 5-1094 | MS, m/z: 528.10 |
| 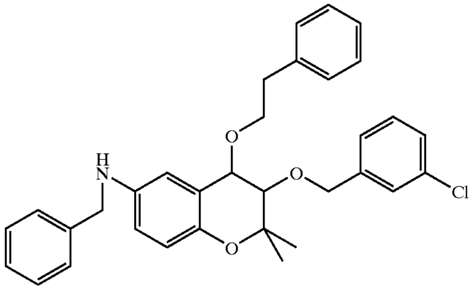 5-1095 | MS, m/z: 528.10 |
| 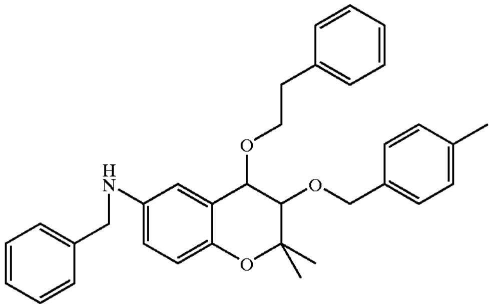 5-1096 | MS, m/z: 507.68 |
| 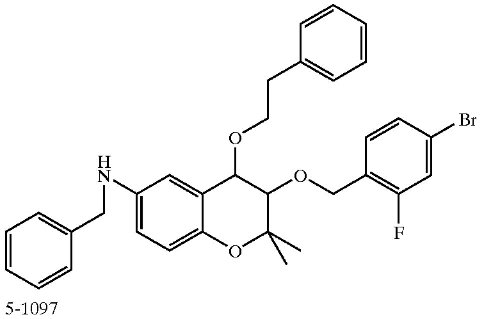 5-1097 | MS, m/z: 590.54 |

TABLE 1-continued
| | Compound No. NMR/MS Data |
|---|---|
| 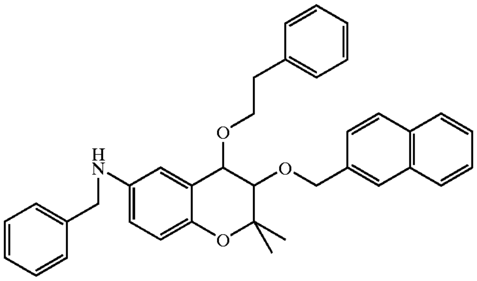 5-1098 | MS, m/z: 543.71 |
| 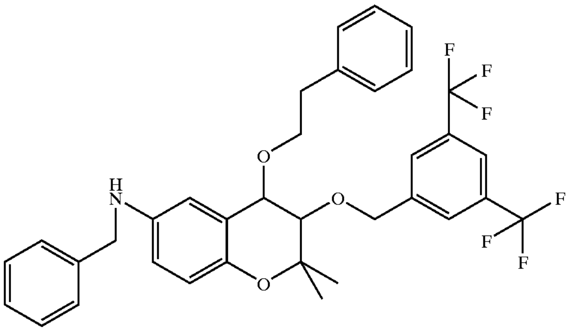 5-1099 | MS, m/z: 629.65 |
| 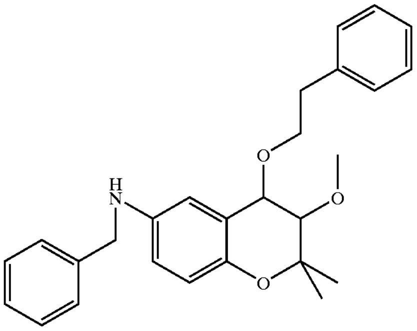 5-1100 | MS, m/z: 417.55 |
| 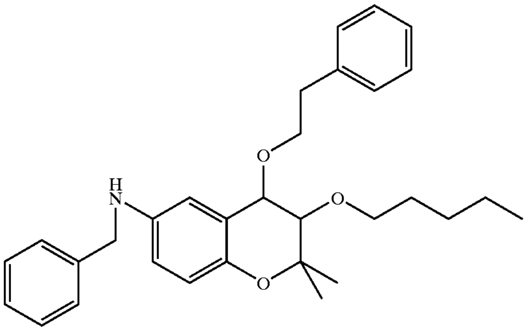 5-1101 | MS, m/z: 473.66 |

TABLE 1-continued
| | Compound No. NMR/MS Data |
|---|---|
| 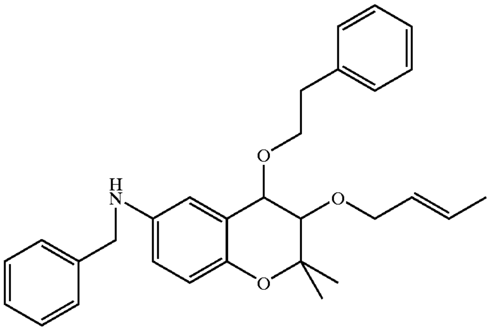 5-1102 | MS, m/z: 457.62 |
| 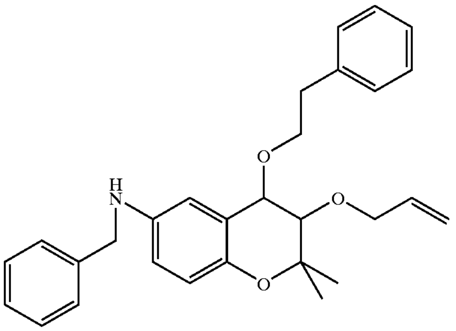 5-1103 | MS, m/z: 443.59 |
| 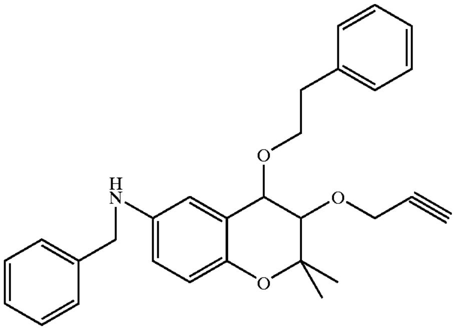 5-1104 | MS, m/z: 441.58 |
| 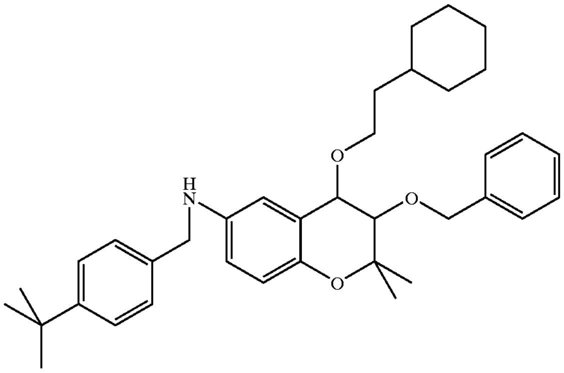 5-1105 | MS, m/z: 555.81 |

TABLE 1-continued
| | Compound No. NMR/MS Data |
|---|---|
| 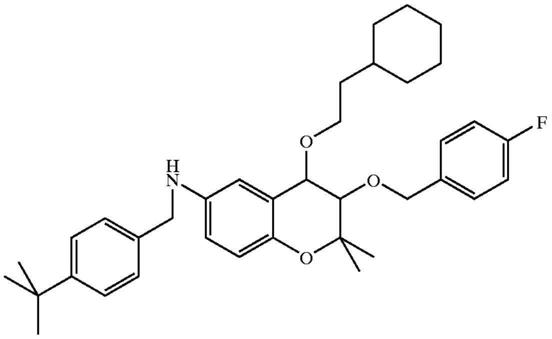 5-1106 | MS, m/z: 573.80 |
| 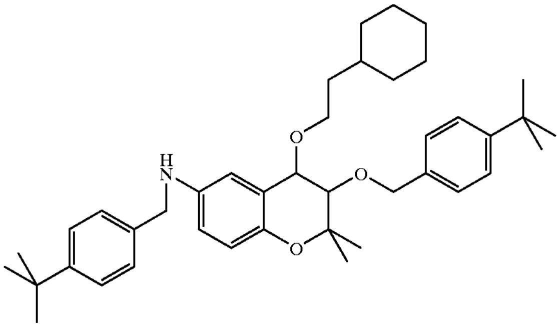 5-1107 | MS, m/z: 611.92 |
| 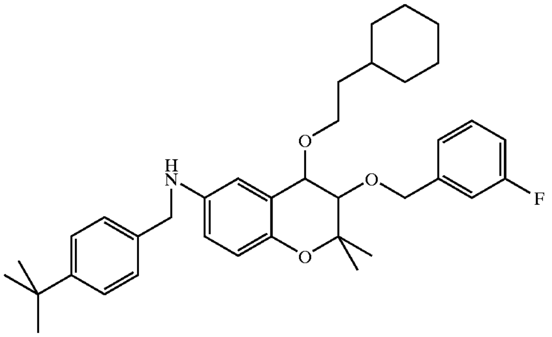 5-1108 | MS, m/z: 573.80 |
| 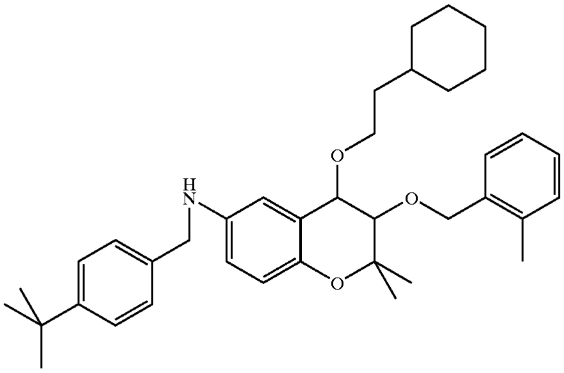 5-1109 | MS, m/z: 569.84 |

TABLE 1-continued
| | Compound No. NMR/MS Data |
|---|---|
| 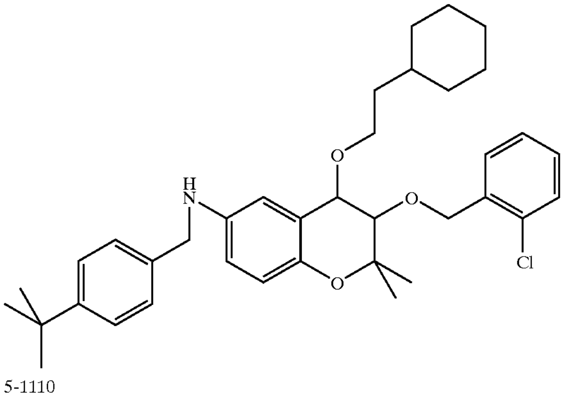 5-1110 | MS, m/z: 590.25 |
| 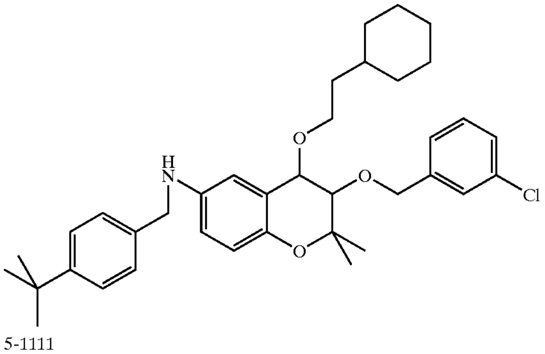 5-1111 | MS, m/z: 590.25 |
| 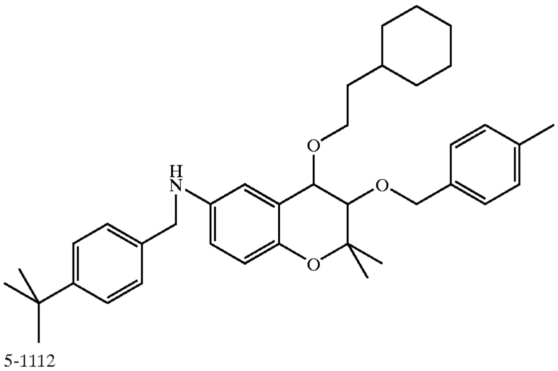 5-1112 | MS, m/z: 569.84 |
| 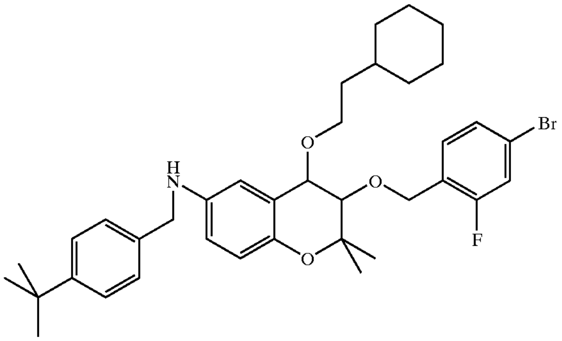 5-1113 | MS, m/z: 652.69 |

TABLE 1-continued
| | Compound No. NMR/MS Data |
|---|---|
| 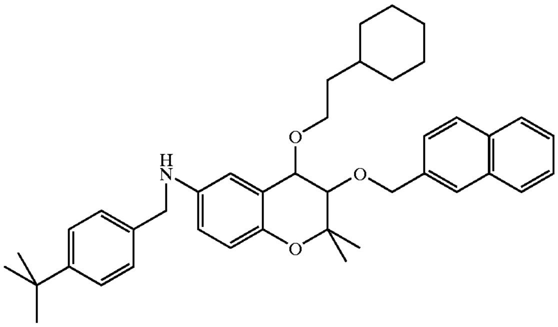 5-1114 | MS, m/z: 605.87 |
| 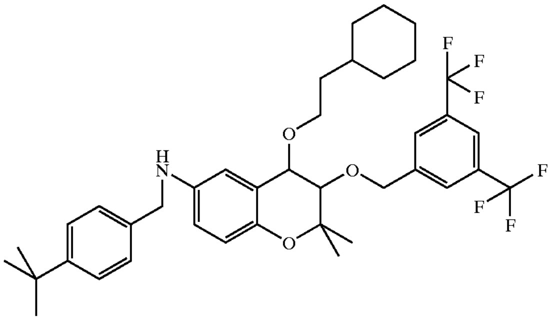 5-1115 | MS, m/z: 691.80 |
| 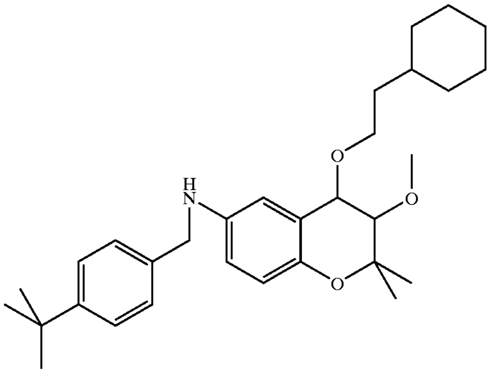 5-1116 | MS, m/z: 479.71 |
| 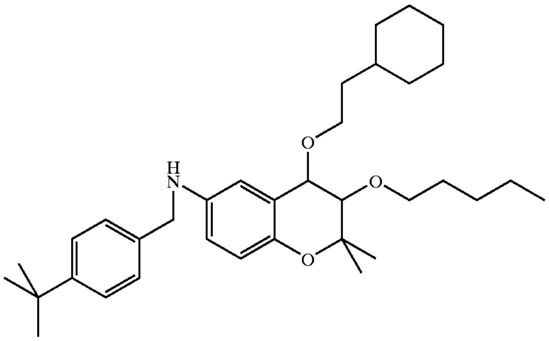 5-1117 | MS, m/z: 535.82 |

TABLE 1-continued
| | Compound No. NMR/MS Data |
| --- | --- |
| 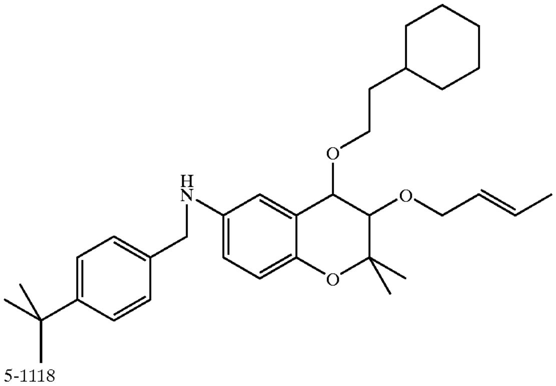 5-1118 | MS, m/z: 519.77 |
| 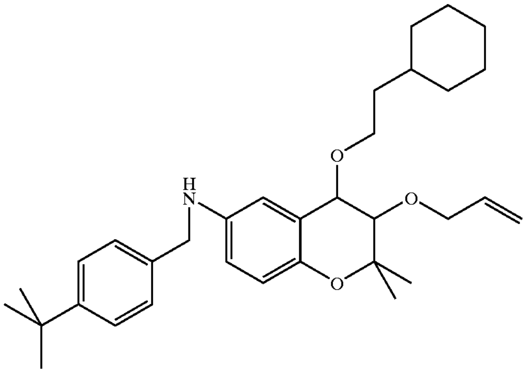 5-1119 | MS, m/z: 505.75 |
| 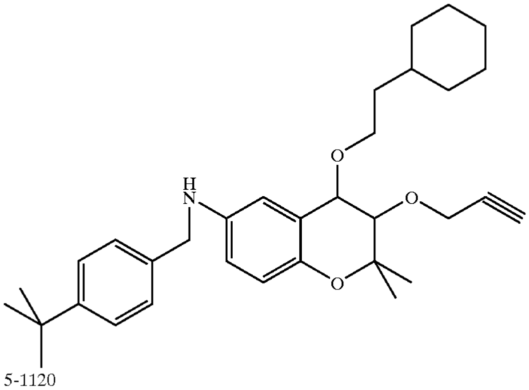 5-1120 | MS, m/z: 503.73 |
EXAMPLE II
Hydroxy Alkoxy Addition and Departure of N-methyl-substituted Olefin Resin (2a)
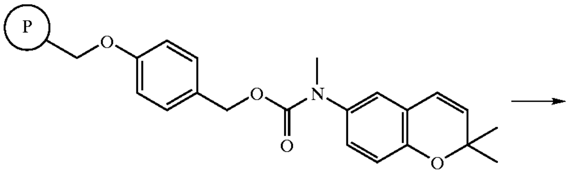
(2a)
-continued
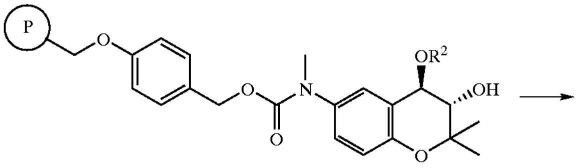
(3)

-continued

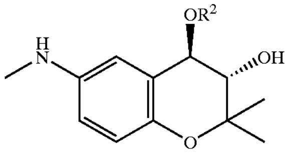

(5a)

(II-1) Hydroxy Methoxy Addition and Departure of N-methylsubstituted Olefin Resin (2a)

(3-1)

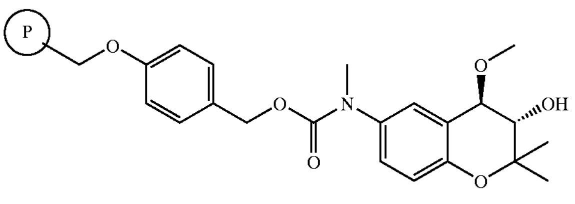

N-methyl-substituted olefin resin (200.00 mg, 0.11 mmol) of the formula (2a) was added to the mixed solution of dichloromethane (3 ml) and methanol (3 ml) and agitated for 30 min, after which metachloroperbenzoic acid (m-CPBA, 81 mg, 0.55 mmol) was added at room temperature and agitated to proceed with a reaction for 15 hr at room temperature. After completion of the reaction, the reactant mixture was filtered and washed repeatedly with DMF, MC, MC/MeOH and MeOH, thereby yielding the resin of the formula (3-1) as a light yellow solid (208.6 mg). Thus obtained resin (3-1) was added to a solution of dichloromethane (5 ml) and agitated, followed by addition of

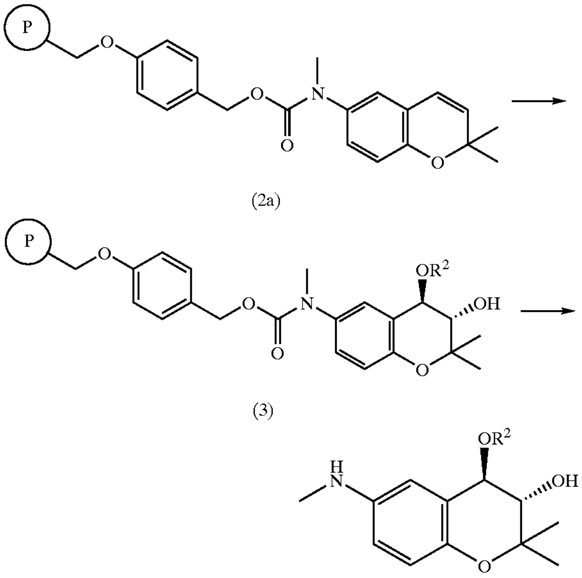

(2a)

(3)

(5a)

filtrate was washed repeatedly with $CH_2Cl_2$ and MeOH. The filtrates were combined and concentrated. To the concentrates, ethylacetate (3 ml) was added, filtered thorough strong anion exchange resin (SAX resin) and washed repeatedly with ethylacetate to remove residual trifluoroacetic acid. Following concentration of the filtrate under reduced pressure, the concentrate was purified with silica gel column chromatography in the presence of hexane/ethylacetate (4/1, v/v), thereby yielding the compound of the formula (5-1121) as a light-yellow oil (16.3 mg, resin 1; from loading capacity 0.55 mmol/g, yield=63%): $^1H$ NMR (300 MHz, $CDCl_3$) δ(PPM) 6.69 (d, 1H, J=5.2 Hz), 6.65 (d, 1H, J=1.7 Hz), 6.58 (dd, 1H, J=5.2 Hz, J=1.7 Hz), 4.34 (d, 1H, J=4.4 Hz), 3.84 (d, 1H, J=4.4 Hz), 3.49 (s, 3H), 2.82 (s, 3H), 1.43 (s, 3H), 1.26 (s, 3H); $^{13}C$ (75 MHz) δ 145.49, 143.00, 121.33, 117.84, 115.50, 111.70, 78.16, 71.99, 55.70, 31.90, 25.68, 20.04; M/S 237.30

(II-2) Hydroxy Ethoxy Addition and Departure of N-methyl-substituted Olefin Resin (2a)

(3-2)

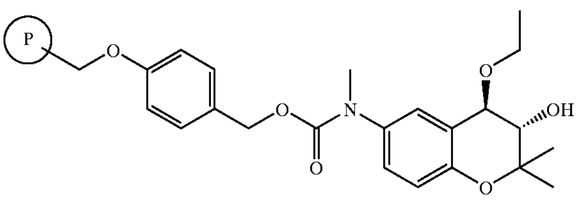

N-methyl-substituted olefin resin (200.00 mg, 0.11 mmol) of the formula (2a) was added to the mixed solution of dichloromethane (3 ml) and ethanol (3 ml) and agitated for 30 min, after which metachloroperbenzoic acid (m-CPBA, 81 mg, 0.55 mmol) was added at room temperature and agitated to proceed with a reaction for 15 hr at room temperature. After completion of the reaction, the reactant mixture was filtered and washed repeatedly with DMF, MC, MC/MeOH and MeOH, thereby yielding the resin of the formula (3-2) as a light yellow solid (207.4 mg). Thus obtained resin (3-2) was added to a solution of dichloromethane (5 ml) and agitated, followed by addition of trifluoroacetic acid (TFA, 1 ml) and agitation for 4 hr at room temperature. After completion of the reaction, the reactant mixture was filtered and the filtrate was washed repeatedly with $CH_2Cl_2$ and MeOH. The filtrates were combined and concentrated. To the concentrates, ethylacetate (3 ml) was added, filtered thorough strong anion exchange resin (SAX resin) and washed repeatedly with ethylacetate to remove residual trifluoroacetic acid. Following concentration of the filtrate under reduced pressure, the concentrate was purified with silica gel column chromatography in the presence of hexane/ethylacetate (4/1, v/v), giving the compound of the formula (5-1121) as a light-yellow oil (16.7 mg, resin 1; from loading capacity 0.55 mmol/g, yield=60%): $^1H$ NMR (200 MHz, $CDCl_3$) δ (PPM) 6.70–6.50 (m, 3H), 4.36 (d, 1H, J=7.4 Hz), 3.82–3.67 (m, 3H), 2.81 (s, 3H), 1.43 (s, 3H), 1.32–1.25 (m, 61); M/S 251.33

(II-3) Hydroxy 2-propoxy Addition and Departure of N-methyl-substituted Olefin Resin (2a)

(3-3)

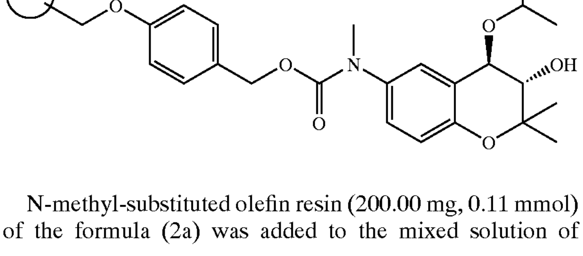

N-methyl-substituted olefin resin (200.00 mg, 0.11 mmol) of the formula (2a) was added to the mixed solution of dichloromethane (3 ml) and 2-propanol (3 ml) and agitated for 30 min, after which metachloroperbenzoic acid (m-CPBA, 81 mg, 0.55 mmol) was added at room temperature and agitated to proceed with a reaction for 15 hr at room temperature. After completion of the reaction, the reactant mixture was filtered and washed repeatedly with DMF, MC, MC/MeOH and MeOH, thereby yielding the resin of the formula (3-3) as a light yellow solid (206.8 mg). Thus obtained resin (3-3) was added to a solution of dichloromethane (5 ml) and agitated, followed by addition of trifluoroacetic acid (TFA, 1 ml) and agitation for 4 hr at room temperature. After completion of the reaction, the reactant mixture was filtered and the filtrate was washed repeatedly with $CH_2Cl_2$ and MeOH. The filtrates were combined and concentrated. To the concentrates, ethylacetate (3 ml) was added, filtered thorough strong anion exchange resin (SAX resin) and washed repeatedly with ethylacetate to remove residual trifluoroacetic acid. Following concentration of the filtrate under reduced pressure, the concentrate was purified with silica gel column chromatography in the presence of hexane/ethylacetate (4/1, v/v), giving the compound of the formula (5-1123) as a light-yellow oil (14.8 mg, resin 1; from loading capacity 0.55 mmol/g, yield=56%): M/S 265.36

(II-4) Hydroxy 2-butoxy Addition and Departure of N-methyl-substituted Olefin Resin (2a)

(3-4)

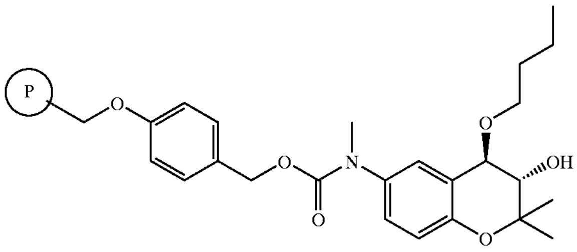

N-methyl-substituted olefin resin (200.00 mg, 0.11 mmol) of the formula (2a) was added to the mixed solution of dichloromethane (3 ml) and butanol (3 ml) and agitated for 30 min, after which metachloroperbenzoic acid (m-CPBA, 81 mg, 0.55 mmol) was added at room temperature and agitated to proceed with a reaction for 15 hr at room temperature. After completion of the reaction, the reactant mixture was filtered and washed repeatedly with DMF, MC, MC/MeOH and MeOH, thereby yielding the resin of the formula (3-4) as a light yellow solid (208.3 mg). Thus obtained resin (3-4) was added to a solution of dichloromethane (5 ml) and agitated, followed by addition of trifluoroacetic acid (TFA, 1 ml) and agitation for 4 hr at room temperature. After completion of the reaction, the reactant mixture was filtered and the filtrate was washed repeatedly with $CH_2Cl_2$ and MeOH. The filtrates were combined and concentrated. To the concentrates, ethylacetate (3 ml) was added, filtered thorough strong anion exchange resin (SAX resin) and washed repeatedly with ethylacetate to remove residual trifluoroacetic acid. Following concentration of the filtrate under reduced pressure, the concentrate was purified with silica gel column chromatography in the presence of hexane/ethylacetate (4/1, v/v), thereby yielding the compound of the formula (5-1124) as a light-yellow oil (19.1 mg, resin 1; from loading capacity 0.55 mmol/g, yield=62%): $^1$H NMR (200 MHz, $CDCl_3$) δ (PPM) 6.70–6.50 (m, 3H), 4.35 (d, 1H, J=7.2 Hz), 3.80 (d, 1H, J=7.2 Hz) 3.67 (t, 2H, J=6.2 Hz), 2.81 (s, 3H), 1.67–1.53 (m, 2H), 1.49–1.30 (m, 2H), 1.42 (s, 3H), 1.25(s, 3H), 0.94 (t, 3H, J=7.2 Hz); M/S 279.38

The 6-amino-2,2-dimethyl-3,4,6-trisubstituted benzopyran derivatives synthesized according to the method of parallel synthesis on the solid-phase as Example II are summarized in Table 2.

In construction of the library in Table 2, the following precursors were employed to preparing combinations of each substituent: for example, $R^1$ precursor includes $CH_3I$, $C_2H_5I$, tBuI, 4-BuI, 4-F—$C_4H_9I$, 4-Me-$C_4H_9I$, 2-$CH_3$-$C_4H_9I$, 3-Cl—$C_4H_9I$, 4-tBu-$C_4H_9I$ and 3-F—$C_4H_9I$; $R^2$ precursor includes $CH_3OH$, $C_2H_5OH$, iPrOH, tBuOH, $C_4H_9OH$, 2-Ph-EtOH and 2-cyclohexyl-EtOH.

TABLE 2

(5)

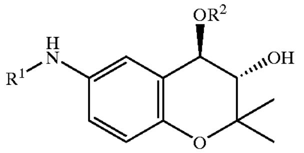

| Compound No. | $R^1$ | $R^2$ | NMR/MS Data |
|---|---|---|---|
| 5-1121 |  |  | |
| 5-1122 |  | 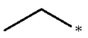 | |
| 5-1123 |  | 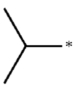 | |
| 5-1124 |  | 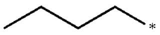 | |

TABLE 2-continued
(5)
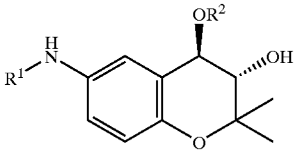
| Compound No. | $R^1$ | $R^2$ | NMR/MS Data |
|---|---|---|---|
| 5-1125 |  | 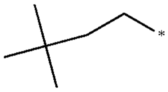 | M/S 307.44 |
| 5-1126 |  | 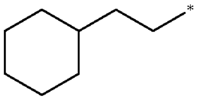 | $^1$H NMR(200MHz, $CDCl_3$) δ 6.70~6.52(m, 3H), 4.34(d, 1H, J=7.0Hz), 3.80(d, 1H, J=7.0Hz), 3.70(t, 2H, J=6.6Hz), 2.81(s, 3H), 1.75~0.94(m, 19H); M/S 333.47 |
| 5-1127 |  | 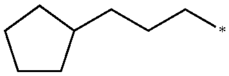 | M/S 333.47 |
| 5-1128 |  | 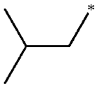 | M/S 279.38 |
| 5-1129 |  | 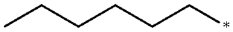 | M/S 307.44 |
| 5-1130 |  | 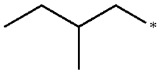 | M/S 293.41 |
| 5-1131 |  | 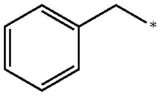 | $^1$H NMR(200MHz, $CDCl_3$) δ 7.44~7.28(m, 5H), 6.78~6.69(m, 3H), 4.76(s, 2H), 4.48(d, 1H, J=7.0Hz), 3.85(d, 1H, J=7.0Hz), 2.78(s, 3H), 1.44(s, 3H), 1.27(s, 3H); M/S 313.40 |
| 5-1132 |  | 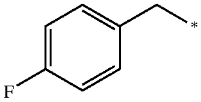 | M/S 331.39 |
| 5-1133 |  | 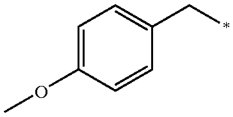 | M/S 343.43 |
| 5-1134 |  | 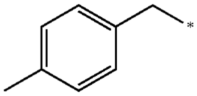 | M/S 327.43 |
| 5-1135 |  | 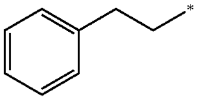 | M/S 327.43 |
| 5-1136 |  | 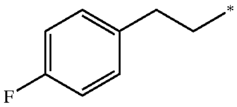 | M/S 345.41 |

TABLE 2-continued
(5)
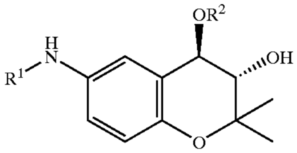
| Compound No. | $R^1$ | $R^2$ | NMR/MS Data |
|---|---|---|---|
| 5-1137 |  | 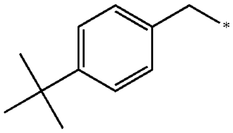 | M/S 369.51 |
| 5-1138 |  | 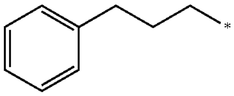 | M/S 341.45 |
| 5-1139 |  | 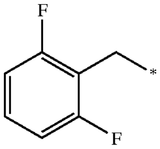 | M/S 349.38 |
| 5-1140 |  | 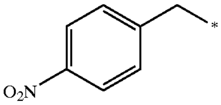 | M/S 358.39 |
| 5-1141 | 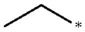 |  | M/S 251.33 |
| 5-1142 | 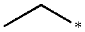 | 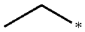 | M/S 265.36 |
| 5-1143 | 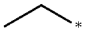 | 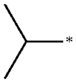 | M/S 279.38 |
| 5-1144 | 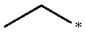 | 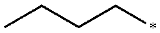 | M/S 293.40 |
| 5-1145 | 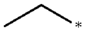 | 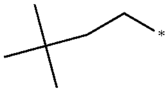 | M/S 321.46 |
| 5-1146 | 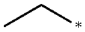 | 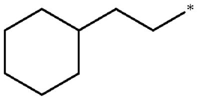 | M/S 347.50 |
| 5-1147 | 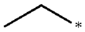 | 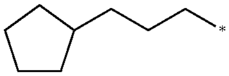 | M/S 347.50 |
| 5-1148 | 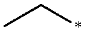 | 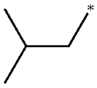 | M/S 293.41 |
| 5-1149 | 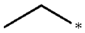 | 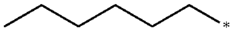 | M/S 321.46 |
| 5-1150 | 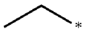 | 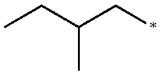 | M/S 307.44 |

TABLE 2-continued
(5)
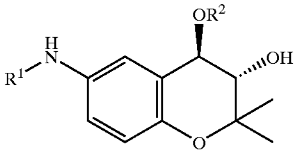
| Compound No. | $R^1$ | $R^2$ | NMR/MS Data |
|---|---|---|---|
| 5-1151 | 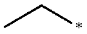 | 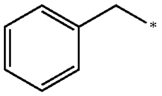 | M/S 327.43 |
| 5-1152 | 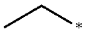 | 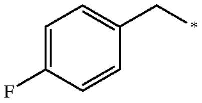 | M/S 345.42 |
| 5-1153 | 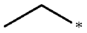 | 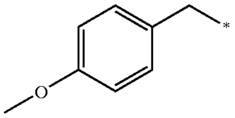 | M/S 357.45 |
| 5-1154 | 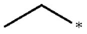 | 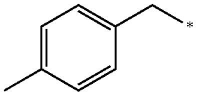 | M/S 341.45 |
| 5-1155 | 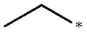 | 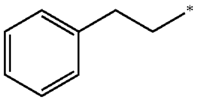 | M/S 341.45 |
| 5-1156 | 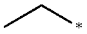 | 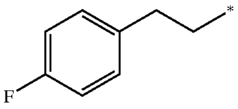 | M/S 359.44 |
| 5-1157 | 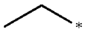 | 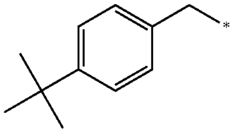 | M/S 383.54 |
| 5-1158 | 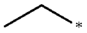 | 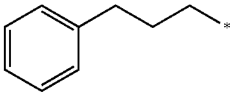 | M/S 355.48 |
| 5-1159 | 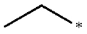 | 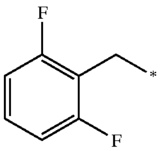 | M/S 363.41 |
| 5-1160 | 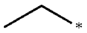 | 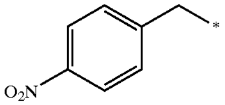 | M/S 372.42 |
| 5-1161 | 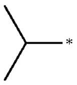 |  | M/S 265.36 |

TABLE 2-continued
(5)
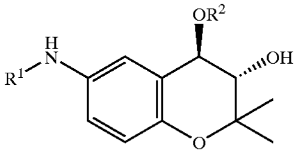
| Compound No. | $R^1$ | $R^2$ | NMR/MS Data |
|---|---|---|---|
| 5-1162 | 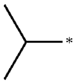 | 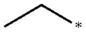 | M/S 279.38 |
| 5-1163 | 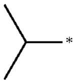 | 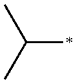 | M/S 293.41 |
| 5-1164 | 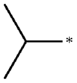 | 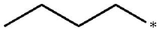 | M/S 307.44 |
| 5-1165 | 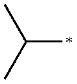 | 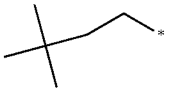 | M/S 335.49 |
| 5-1166 | 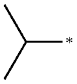 | 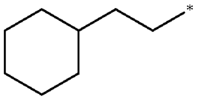 | M/S 361.53 |
| 5-1167 | 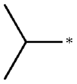 | 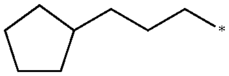 | M/S 361.53 |
| 5-1168 | 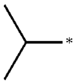 | 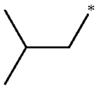 | M/S 307.44 |
| 5-1169 | 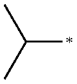 | 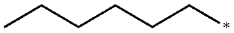 | M/S 335.49 |
| 5-1170 | 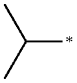 | 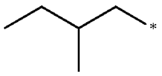 | M/S 321.46 |
| 5-1171 | 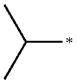 | 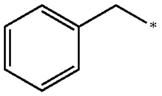 | M/S 341.45 |
| 5-1172 | 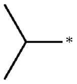 | 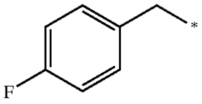 | M/S 359.44 |
| 5-1173 | 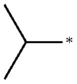 | 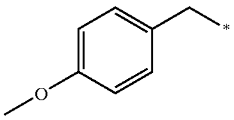 | M/S 371.48 |

TABLE 2-continued
(5)
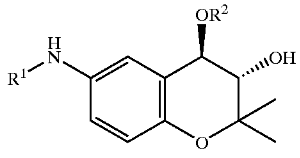
| Compound No. | $R^1$ | $R^2$ | NMR/MS Data |
|---|---|---|---|
| 5-1174 | 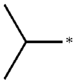 | 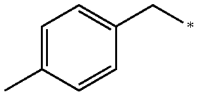 | M/S 355.48 |
| 5-1175 | 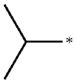 | 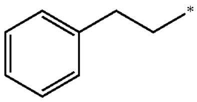 | M/S 355.48 |
| 5-1176 | 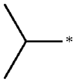 | 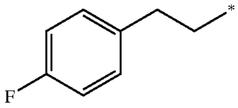 | M/S 373.47 |
| 5-1177 | 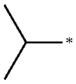 | 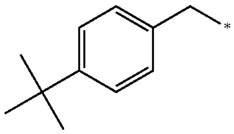 | M/S 397.56 |
| 5-1178 | 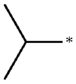 | 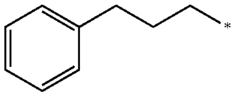 | M/S 369.50 |
| 5-1179 | 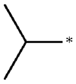 | 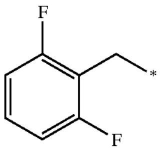 | M/S 377.44 |
| 5-1180 | 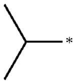 | 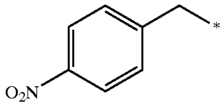 | M/S 386.45 |
| 5-1181 | 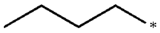 |  | M/S 279.38 |
| 5-1182 | 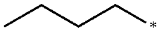 | 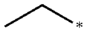 | M/S 293.41 |
| 5-1183 | 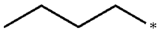 | 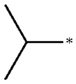 | M/S 307.44 |
| 5-1184 | 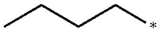 | 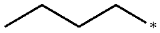 | M/S 321.46 |
| 5-1185 | 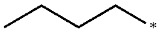 | 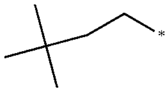 | M/S 349.52 |
| 5-1186 | 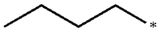 | 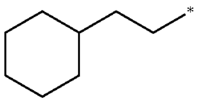 | M/S 375.56 |

TABLE 2-continued
(5)
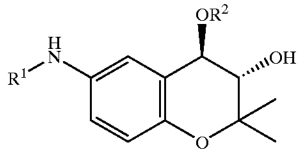
| Compound No. | $R^1$ | $R^2$ | NMR/MS Data |
|---|---|---|---|
| 5-1187 | 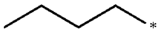 | 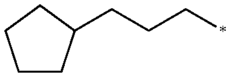 | M/S 375.56 |
| 5-1188 | 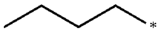 | 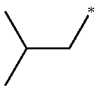 | M/S 321.46 |
| 5-1189 | 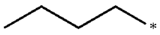 | 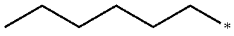 | M/S 349.52 |
| 5-1190 | 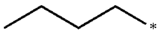 | 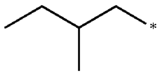 | M/S 335.49 |
| 5-1191 | 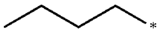 | 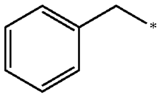 | M/S 335.48 |
| 5-1192 | 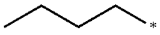 | 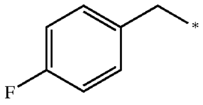 | M/S 373.47 |
| 5-1193 | 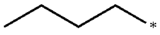 | 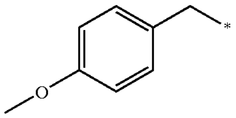 | M/S 385.51 |
| 5-1194 | 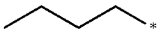 | 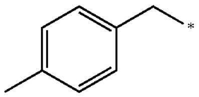 | M/S 369.51 |
| 5-1195 | 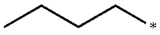 | 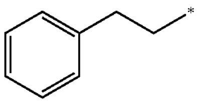 | M/S 369.51 |
| 5-1196 | 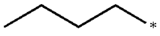 | 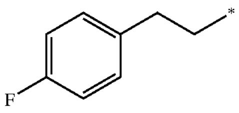 | M/S 387.49 |
| 5-1197 | 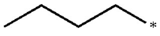 | 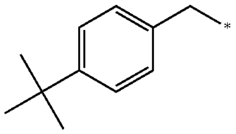 | M/S 411.59 |
| 5-1198 | 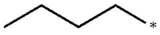 | 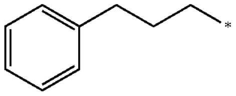 | M/S 383.54 |

TABLE 2-continued
(5)
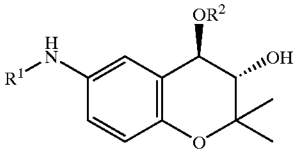
| Compound No. | $R^1$ | $R^2$ | NMR/MS Data |
|---|---|---|---|
| 5-1199 | 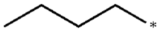 | 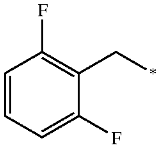 | M/S 391.46 |
| 5-1200 | 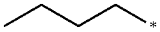 | 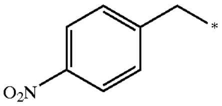 | M/S 400.48 |
| 5-1201 | 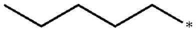 |  | M/S 293.41 |
| 5-1202 | 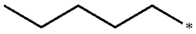 | 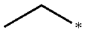 | M/S 307.44 |
| 5-1203 | 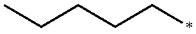 | 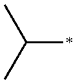 | M/S 321.46 |
| 5-1204 | 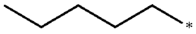 | 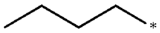 | M/S 335.49 |
| 5-1205 | 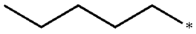 | 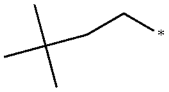 | M/S 363.55 |
| 5-1206 | 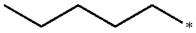 | 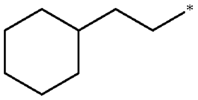 | M/S 389.58 |
| 5-1207 | 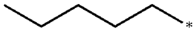 | 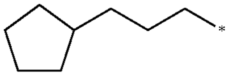 | M/S 389.58 |
| 5-1208 | 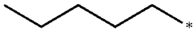 | 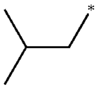 | M/S 335.49 |
| 5-1209 | 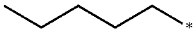 | 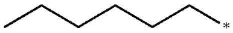 | M/S 363.55 |
| 5-1210 | 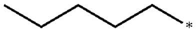 | 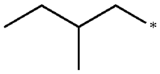 | M/S 349.52 |
| 5-1211 | 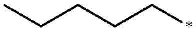 | 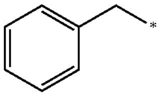 | M/S 369.51 |
| 5-1212 | 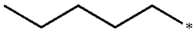 | 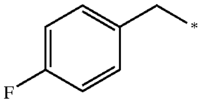 | M/S 387.49 |

TABLE 2-continued
(5)
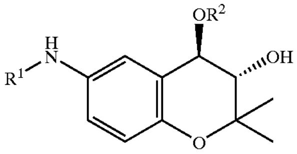
| Compound No. | $R^1$ | $R^2$ | NMR/MS Data |
|---|---|---|---|
| 5-1213 | 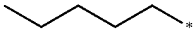 | 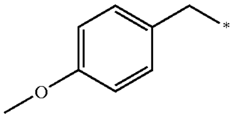 | M/S 399.53 |
| 5-1214 | 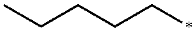 | 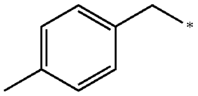 | M/S 383.54 |
| 5-1215 | 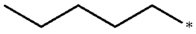 | 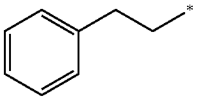 | M/S 383.54 |
| 5-1216 | 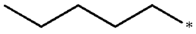 | 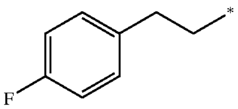 | M/S 401.53 |
| 5-1217 | 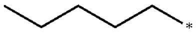 | 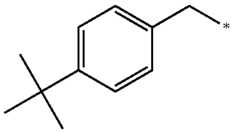 | M/S 425.62 |
| 5-1218 | 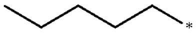 | 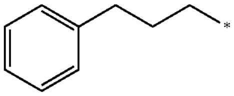 | M/S 397.56 |
| 5-1219 | 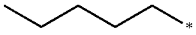 | 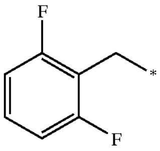 | M/S 405.49 |
| 5-1220 | 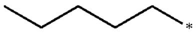 | 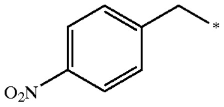 | M/S 414.51 |
| 5-1221 | 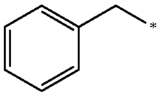 |  | $^1$H NMR(300MHz, CDCl δ 7.36(m, 4H), 7.28(d, 1H, J=4.3Hz), 6.67(m, 2H), 6.57(dd, 1H, J=5.2Hz J=1.7Hz), 4.31(d, 1H, J=4.5Hz), 4.28(s, 2H), 3.82(d, 1H, J=4.5Hz), 3.82(d, 1H, J=4.4Hz), 3.41 (s, 3H), 1.43(s, 3H), 1.25(s, 3H); M/S 313.40 |
| 5-1222 | 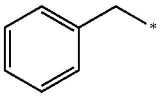 | 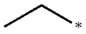 | M/S 327.43 |

TABLE 2-continued
(5)
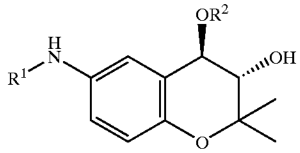
| Compound No. | $R^1$ | $R^2$ | NMR/MS Data |
|---|---|---|---|
| 5-1223 | 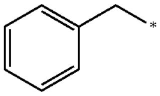 | 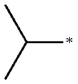 | $^1H$ NMR(200MHz, $CDCl_3$) δ 7.40~7.24(m, 5H), 6.67~6.50(m, 3H), 4.70(s, 2H), 6.27(d, 1H, J=6.6Hz), 4.01~3.95(m, 1H), 3.67(d, 1H, J=6.6Hz), 1.40(s, 2H), 1.29~1.22(m, 10H); M/S 341.45 |
| 5-1224 | 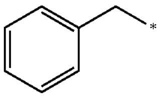 | 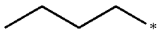 | M/S 355.48 |
| 5-1225 | 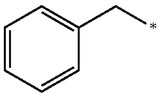 | 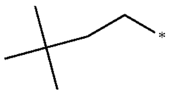 | M/S 383.54 |
| 5-1226 | 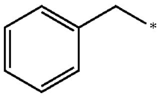 | 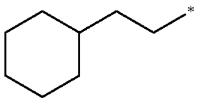 | $^1H$ NMR(300MHz, $CDCl_3$) δ 7.28(m, 5H), 7.00(d, 1H, J=2.5Hz), 6.87(dd, 1H, J=8.7Hz, J=2.5Hz), 6.68(d, 1H, J=8.7Hz), 4.23(d, 1H, J=7.0Hz), 4.23(s, 2H), 3.73(d, 1H, J=7.0Hz), 3.66(td, 2H, J=6.84Hz, J=3.36Hz), 1.72~1.63(m, 5H), 1.50(td, 2H, J=6.84Hz, J=6.77Hz), 1.41 (s, 3H), 1.25(s, 3H), 1.21~1.17(m, 4H), 0.92(m, 2H); M/S 409.57 |
| 5-1227 | 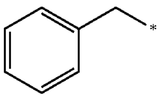 | 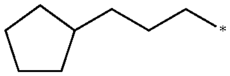 | M/S 409.57 |
| 5-1228 | 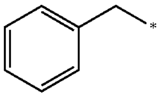 | 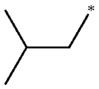 | M/S 355.48 |
| 5-1229 | 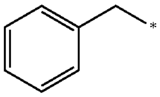 | 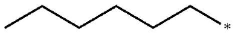 | M/S 383.54 |
| 5-1230 | 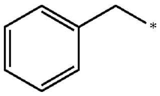 | 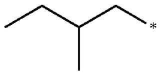 | M/S 369.51 |
| 5-1231 | 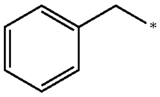 | 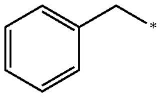 | $^1H$ NMR(200MHz, $CDCl_3$) δ 7.37~7.25(m, 10H), 6.65~6.56(m, 3H), 4.68(s, 2H), 4.48(d, 1H, J=7.4Hz), 4.23(s, 2H), 3.86(d, 1H, J=7.4 Hz), 1.43(s, 3H), 1.25(s, 3H); M/S 389.49 |
| 5-1232 | 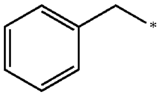 | 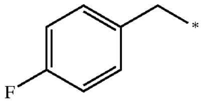 | M/S 407.49 |
| 5-1233 | 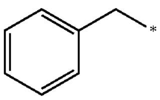 | 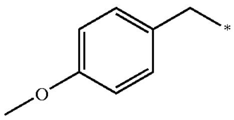 | M/S 419.53 |

TABLE 2-continued
(5)
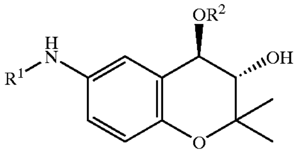
| Compound No. | $R^1$ | $R^2$ | NMR/MS Data |
|---|---|---|---|
| 5-1234 | 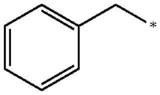 | 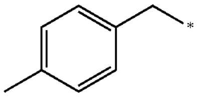 | M/S 403.53 |
| 5-1235 | 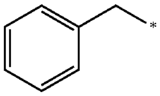 | 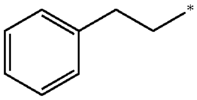 | M/S 403.53 |
| 5-1236 | 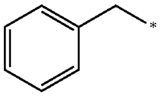 | 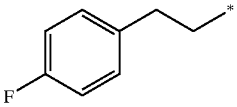 | M/S 421.52 |
| 5-1237 | 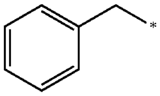 | 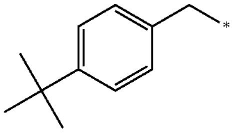 | M/S 445.60 |
| 5-1238 | 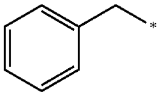 | 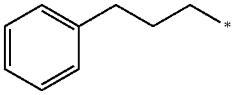 | M/S 417.55 |
| 5-1239 | 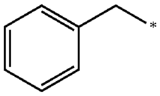 | 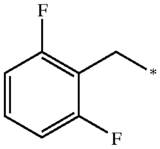 | M/S 425.47 |
| 5-1240 | 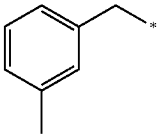 | 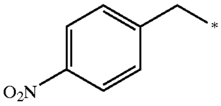 | M/S 434.49 |
| 5-1241 | 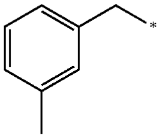 |  | M/S 327.42 |
| 5-1242 | 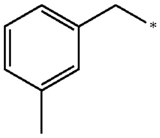 | 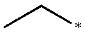 | M/S 341.45 |

TABLE 2-continued
(5)
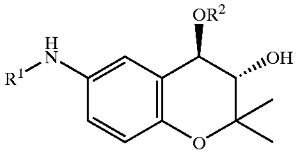
| Compound No. | $R^1$ | $R^2$ | NMR/MS Data |
| --- | --- | --- | --- |
| 5-1243 | 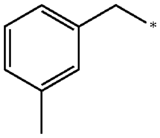 | 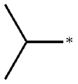 | M/S 355.48 |
| 5-1244 | 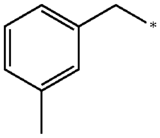 | 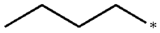 | M/S 369.50 |
| 5-1245 | 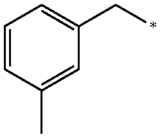 | 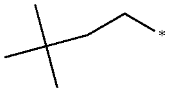 | M/S 397.56 |
| 5-1246 | 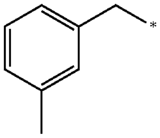 | 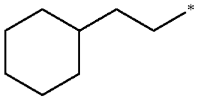 | M/S 423.60 |
| 5-1247 | 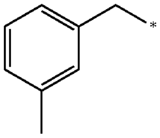 | 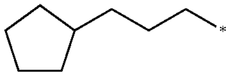 | M/S 423.60 |
| 5-1248 | 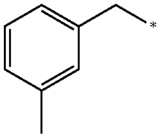 | 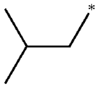 | M/S 369.50 |
| 5-1249 | 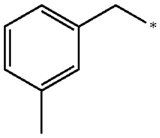 | 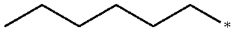 | M/S 397.56 |
| 5-1250 | 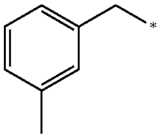 | 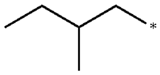 | M/S 383.53 |
| 5-1251 | 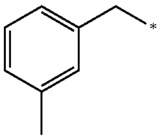 | 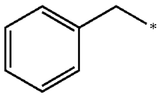 | M/S 403.52 |

TABLE 2-continued
(5)
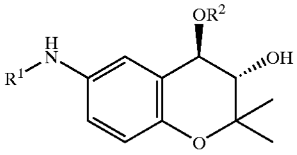
| Compound No. | $R^1$ | $R^2$ | NMR/MS Data |
|---|---|---|---|
| 5-1252 | 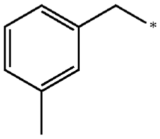 | 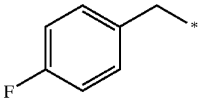 | M/S 421.51 |
| 5-1253 | 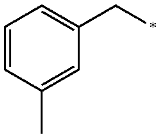 | 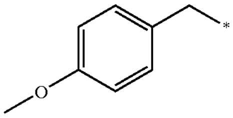 | M/S 433.55 |
| 5-1254 | 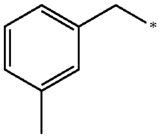 | 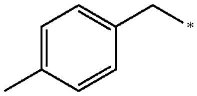 | M/S 431.58 |
| 5-1255 | 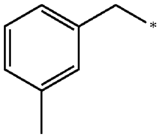 | 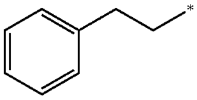 | M/S 417.55 |
| 5-1256 | 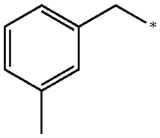 | 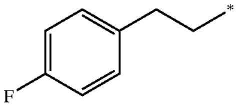 | M/S 435.54 |
| 5-1257 | 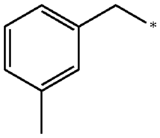 | 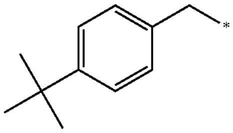 | M/S 459.63 |
| 5-1258 | 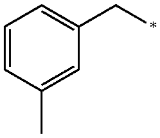 | 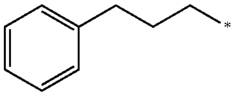 | M/S 431.58 |
| 5-1259 | 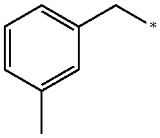 | 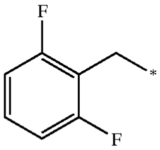 | M/S 439.50 |
| 5-1260 | 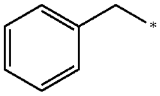 | 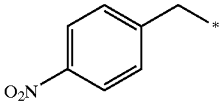 | M/S 448.52 |

TABLE 2-continued
(5)
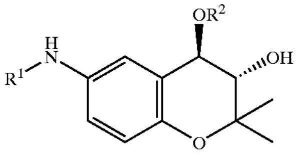
| Compound No. | $R^1$ | $R^2$ | NMR/MS Data |
|---|---|---|---|
| 5-1261 | 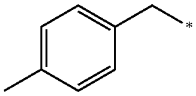 |  | $^1H$ NMR(300MHz, $CDCl_3$) δ 7.26(d, 2H, J=4.8Hz), 7.14(d, 2H, J=4.8Hz), 6.67(d, 1H, J=5.2Hz, J=1.7Hz), 6.65(d, 1H, J=1.7Hz), 6.56(dd, 1H, J=5.2Hz, J=1.7Hz), 4.31(d, 1H, J=4.4Hz), 4.23(s, 2H), 3.82(d, 1H, J=4.4Hz), 3.43(s, 3H), 2.34(s, 3H), 1.43(s, 9H), 1.25(s, 3H); $^{13}C$(75 MHz) δ 145.33, 142.20, 136.89, 136.27, 129.25, 127.71, 121.28, 117.81, 115.56, 111.94, 78.13, 72.00, 55.62, 49.16 25.74, 21.08, 20.00, M/S 327.42 |
| 5-1262 | 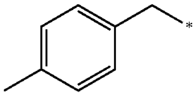 | 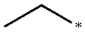 | M/S 341.45 |
| 5-1263 | 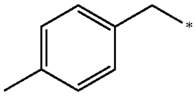 | 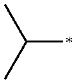 | M/S 355.48 |
| 5-1264 | 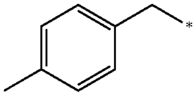 | 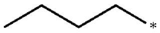 | M/S 369.50 |
| 5-1265 | 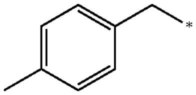 | 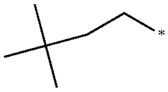 | M/S 397.56 |
| 5-1266 | 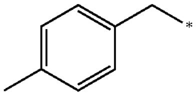 | 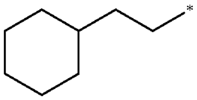 | M/S 423.60 |
| 5-1267 | 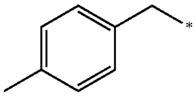 | 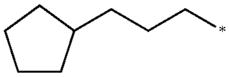 | M/S 423.60 |
| 5-1268 | 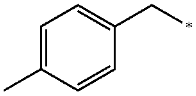 | 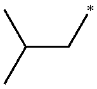 | M/S 369.50 |
| 5-1269 | 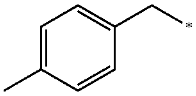 | 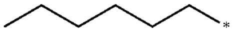 | M/S 397.56 |
| 5-1270 | 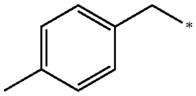 | 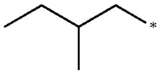 | M/S 383.53 |
| 5-1271 | 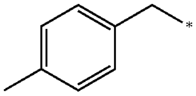 | 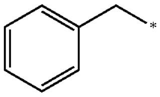 | M/S 403.52 |

TABLE 2-continued
(5)
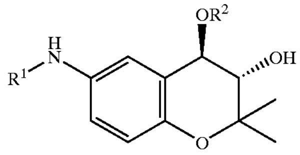
| Compound No. | $R^1$ | $R^2$ | NMR/MS Data |
|---|---|---|---|
| 5-1272 | 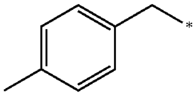 | 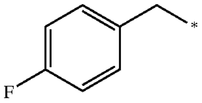 | M/S 421.51 |
| 5-1273 | 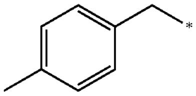 | 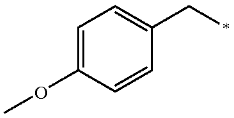 | M/S 433.55 |
| 5-1274 | 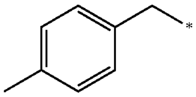 | 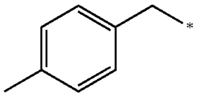 | M/S 431.58 |
| 5-1275 | 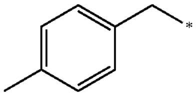 | 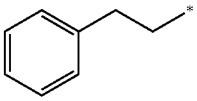 | M/S 417.55 |
| 5-1276 | 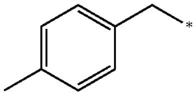 | 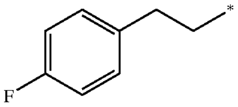 | M/S 435.54 |
| 5-1277 | 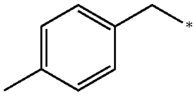 | 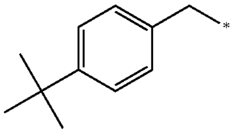 | M/S 459.63 |
| 5-1278 | 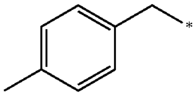 | 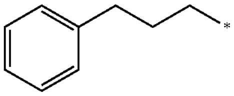 | M/S 431.58 |
| 5-1279 | 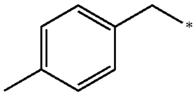 | 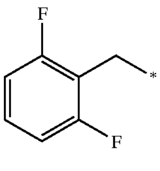 | M/S 439.50 |
| 5-1280 | 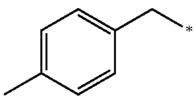 | 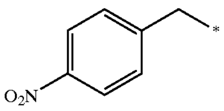 | M/S 448.52 |
| 5-1281 | 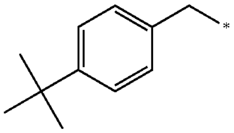 |  | $^1$H NMR(300MHz, $CDCl_3$) δ 7.37(d, 2H, J=5.0Hz), 7.31(d, 2H, J=5.0Hz), 6.67(d, 1H, J=5.2Hz, J=1.7Hz), 6.65(d, 1H, J=1.7Hz), 6.58(dd, 1H, J=5.2Hz, J=1.7Hz), 4.31(d, 1H, J=4.5Hz), 4.24(s, 2H), 3.82(d, 1H, J=4.5), 3.41 (s, 3H), 1.43(s, 3H), 1.32(s, 9H), 1.25(s, 3H); —C(75 MHz) δ 150.26, 145.39, 142.20, 136.21, 127.56, 125.49, 121.24, 117.83, 115.67, 111.98, 78.10, 71.96, 55.51, 49.13, 34.49, 31.35, 25.75, 19.98; M/S 369.50 |

TABLE 2-continued
(5)
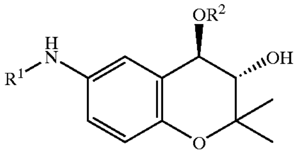
| Compound No. | $R^1$ | $R^2$ | NMR/MS Data |
|---|---|---|---|
| 5-1282 | 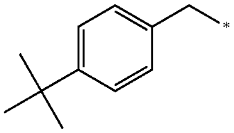 | 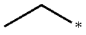 | $^1H$ NMR(300MHz, $CDCl_3$) δ 7.40(d, 1H, J=4.9 Hz), 7.37(d, 2H, J=4.9Hz), 7.31(d, 2H, J=4.9 Hz), 6.66(d, 1H, J=5.2Hz), 6.65(d, 1H, J=1.5 Hz), 6.57(dd, 1H, J=5.2Hz, J=1.5Hz), 4.33(d, 1H, J=4.5Hz), 4.23(s, 2H), 3.78(d, 1H, J=4.5 Hz), 3.65(qd, 2H, J=4.2Hz, J=1.8Hz), 1.43(s, 3H), 1.31 (s, 3H), 1.24(s, 3H), 1.20(t, 3H, J=4.2 Hz); M/S 383.53 |
| 5-1283 | 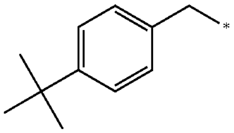 | 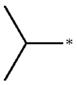 | M/S 397.56 |
| 5-1284 | 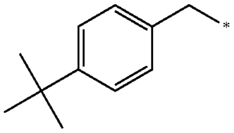 | 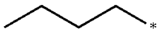 | M/S 411.58 |
| 5-1285 | 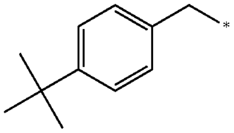 | 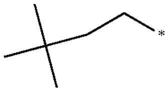 | M/S 439.64 |
| 5-1286 | 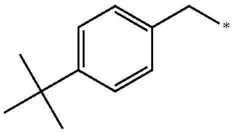 | 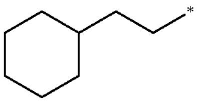 | M/S 465.68 |
| 5-1287 | 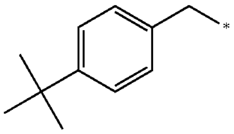 | 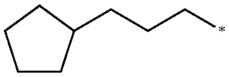 | M/S 465.68 |
| 5-1288 | 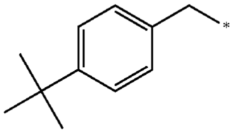 | 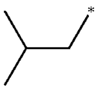 | M/S 411.58 |
| 5-1289 | 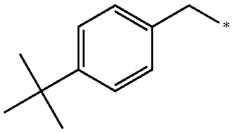 | 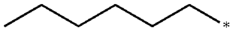 | M/S 439.64 |
| 5-1290 | 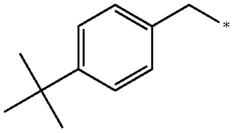 | 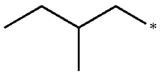 | M/S 425.61 |

TABLE 2-continued
(5)
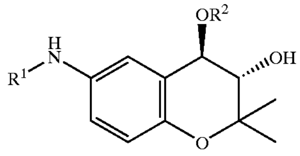
| Compound No. | $R^1$ | $R^2$ | NMR/MS Data |
|---|---|---|---|
| 5-1291 | 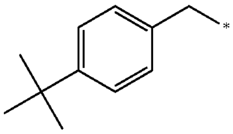 | 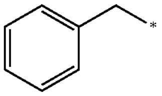 | M/S 445.60 |
| 5-1292 | 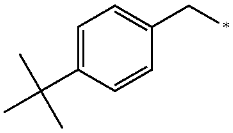 | 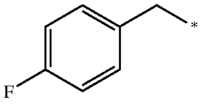 | M/S 463.59 |
| 5-1293 | 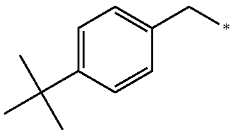 | 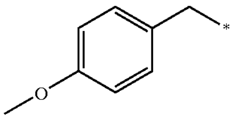 | M/S 475.63 |
| 5-1294 | 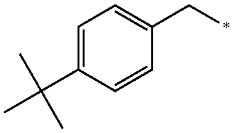 | 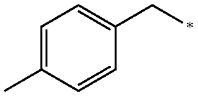 | M/S 473.66 |
| 5-1295 | 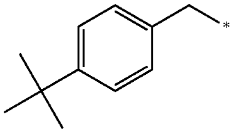 | 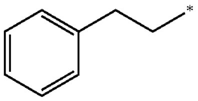 | M/S 459.63 |
| 5-1296 | 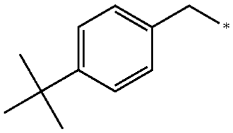 | 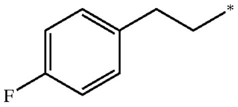 | M/S 477.62 |
| 5-1297 | 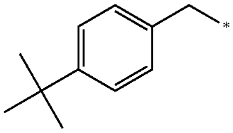 | 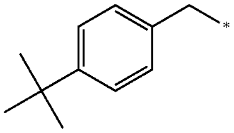 | M/S 501.71 |
| 5-1298 | 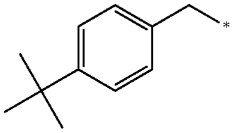 | 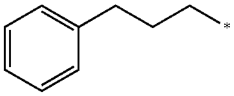 | M/S 473.66 |
| 5-1299 | 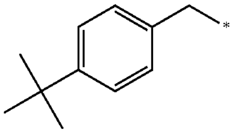 | 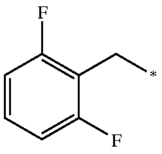 | M/S 481.58 |

TABLE 2-continued (5)

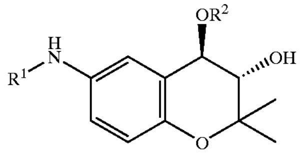

| Compound No. | $R^1$ | $R^2$ | NMR/MS Data |
|---|---|---|---|
| 5-1300 | 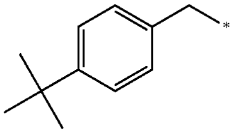 | 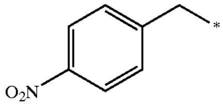 | M/S 490.60 |
| 5-1301 | 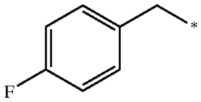 |  | $^1$H NMR(300MHz, $CDCl_3$) δ 7.33(m, 2H), 7.01(m, 2H), 6.67(d, 1H, J=5.1Hz), 6.63(d, 1H, J=1.7Hz), 6.55(dd, 1H, J=5.1Hz, J=1.7Hz), 4.30(d, 1H, J=4.5Hz), 4.25(s, 2H), 3.81(d, 1H, J=4.5Hz), 3.42(s, 3H), 1.43(s, 3H), 1.24(s, 3H); M/S 331.39 |
| 5-1302 | 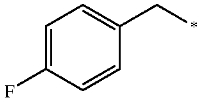 | 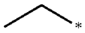 | M/S 345.41 |
| 5-1303 | 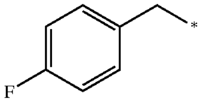 | 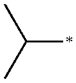 | $^1$H NMR(300MHz, $CDCl_3$) δ 7.34(dd, 2H, J=4.9 Hz, J=3.4Hz), 7.01(t, 2H, J=5.2Hz), 6.65(m, 2H), 6.60(d, 1H, J=5.3Hz), 4.26(d, 1H, J=4.1 Hz), 4.24(s, 2H), 3.97(m, 1H), 3.66(d, 1H, J=4.1Hz), 1.40(s, 3H), 1.28(s, 3H), 1.26(d, 3H, J=3.6Hz), 1.23(d, 3H, J=3.7Hz); M/S 359.44 |
| 5-1304 | 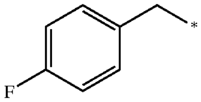 | 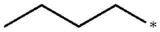 | $^1$H NMR(300MHz, $CDCl_3$) δ 7.30~7.28(m, 2H), 6.98~6.94(m, 2H), 6.90(s, 1H), 6.81(d, 1H, J=5.4Hz), 6.69(d, 1H, J=5.4Hz), 4.25(d, 1H, J=4.3Hz), 4.23(s, 2H), 3.76(d, 1H, J=4.3Hz), 3.62(t, 2H, J=3.2Hz), 1.58(m, 2H), 1.44~1.35(m, 5H), 1.26(s, 3H), 0.94(t, 3H, J=4.4Hz); M/S 373.47 |
| 5-1305 | 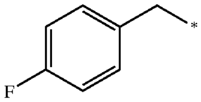 | 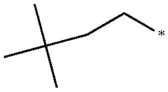 | M/S 401.52 |
| 5-1306 | 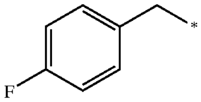 | 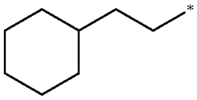 | $^1$H NMR(300MHz, $CDCl_3$) δ 7.33(ddd, 2H, J=8.6Hz, J=2.1Hz), 7.01(ddd, 2H, J=8.6Hz, J=2.1Hz), 6.66(d, 1H, J=8.7Hz), 6.64(d, 1H, J=2.8Hz), 6.56(dd, 1H, J=8.7Hz, J=2.8), 4.29(d, 1H, J=7.4Hz), 4.24(s, 2H), 3.84(d, 1H, J=7.4Hz), 3.63(t, 2H, J=6.7Hz), 1.71~1.67(m, 4H), 1.52~1.18(m, 8H), 1.42(s, 3H), 1.24(s, 3H), 0.92(m, 1H); M/S 427.56 |
| 5-1307 | 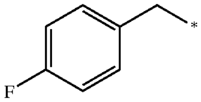 | 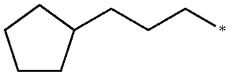 | M/S 427.56 |
| 5-1308 | 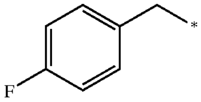 | 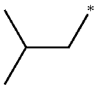 | M/S 373.47 |
| 5-1309 | 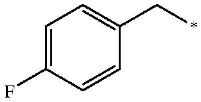 | 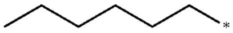 | M/S 401.52 |

TABLE 2-continued
(5)
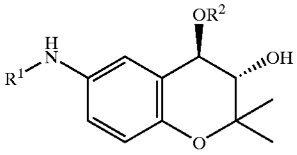
| Compound No. | $R^1$ | $R^2$ | NMR/MS Data |
|---|---|---|---|
| 5-1310 | 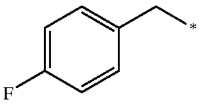 | 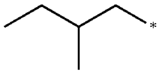 | M/S 387.49 |
| 5-1311 | 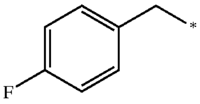 | 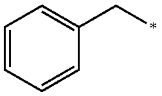 | M/S 407.48 |
| 5-1312 | 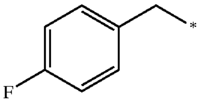 | 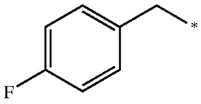 | M/S 425.47 |
| 5-1313 | 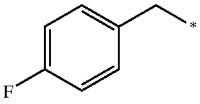 | 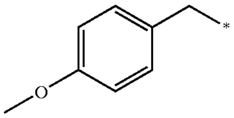 | M/S 437.51 |
| 5-1314 | 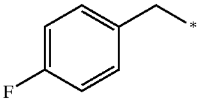 | 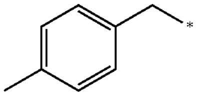 | M/S 435.54 |
| 5-1315 | 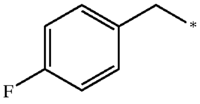 | 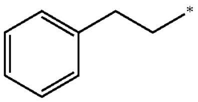 | $^1$H NMR(300MHz, $CDCl_3$) $\delta$ 7.39~7.17(m, 7H), 7.00(t, 2H, J=8.7Hz), 6.62(d, 1H, J=8.7Hz), 6.54(dd, 1H, J=8.7Hz, J=2.7Hz), 6.31(d, 1H, J=2.7Hz), 4.27(d, 1H, J=7.8Hz), 4.15(s, 2H), 3.89~3.76(m, 2H), 3.65(d, 1H, J=7.8Hz), 2.88(dd, 2H, 6.6??), 1.35(s, 3H), 1.16(s, 3H); M/S 421.51 |
| 5-1316 | 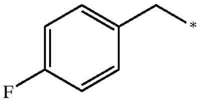 | 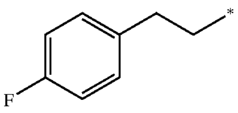 | M/S 439.50 |
| 5-1317 | 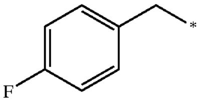 | 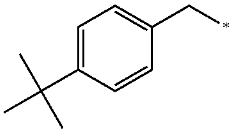 | M/S 463.59 |
| 5-1318 | 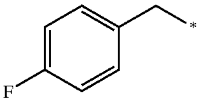 | 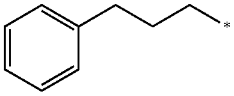 | M/S 435.54 |
| 5-1319 | 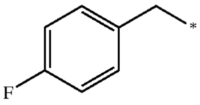 | 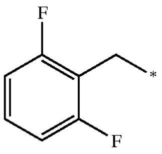 | M/S 443.47 |

TABLE 2-continued
(5)
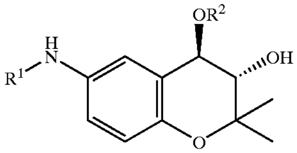
| Compound No. | R¹ | R² | NMR/MS Data |
|---|---|---|---|
| 5-1320 | 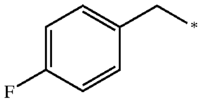 | 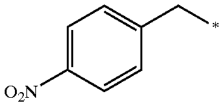 | M/S 452.48 |
| 5-1321 | 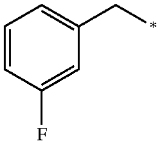 |  | $^1$H NMR(300MHz, $CDCl_3$) δ 7.29(m, 1H), 7.15(d, 1H, J=4.6Hz), 7.09(m, 1H), 6.95(ddd, 1H, J=5.0Hz, J=1.5Hz), 6.67(d, 1H, J=5.2Hz), 6.65(d, 1H, J=1.7Hz), 6.57(dd, 1H, J=5.2Hz, J=1.7Hz), 4.30(d, 1H, J=4.5Hz), 4.29(s, 2H), 3.81 (d, 1H, J=4.5Hz), 3.41(s, 3H), 1.43(s, 3H), 1.25(s, 3H); M/S 345.41 |
| 5-1322 | 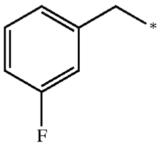 | 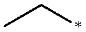 | M/S 331.39 |
| 5-1323 | 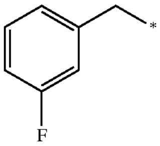 | 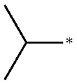 | $^1$H NMR(300MHz, $CDCl_3$) δ 7.34(dd, 2H, J=4.9, J=3.4Hz), 7.01(t, 2H, J=5.2Hz), 6.65(m, 2H), 6.60(d, 1H, J=5.3Hz), 4.26(d, 1H, J=4.1Hz), 4.24(s, 2H), 3.97(m, 1H), 3.66(d, 1H, J=4.1Hz), 1.40(s, 3H), 1.28(s, 3H), 1.26(d, 3H, J=3.6Hz), 1.23(d, 3H, J=3.7Hz), M/S 359.44 |
| 5-1324 | 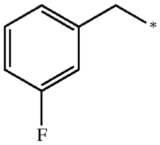 | 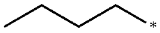 | M/S 373.47 |
| 5-1325 | 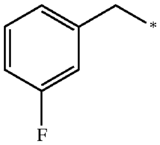 | 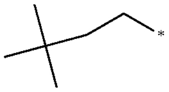 | M/S 401.52 |
| 5-1326 | 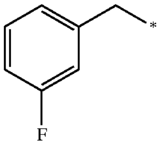 | 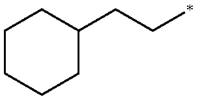 | M/S 427.56 |
| 5-1327 | 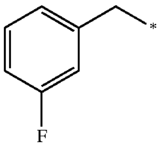 | 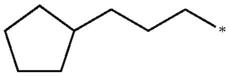 | M/S 427.56 |

TABLE 2-continued
(5)
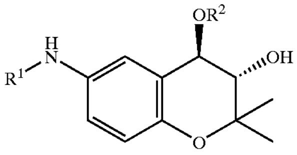
| Compound No. | $R^1$ | $R^2$ | NMR/MS Data |
|---|---|---|---|
| 5-1328 | 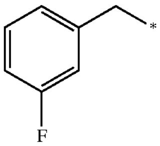 | 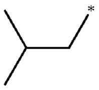 | M/S 373.47 |
| 5-1329 | 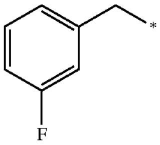 | 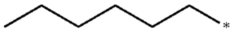 | M/S 401.52 |
| 5-1330 | 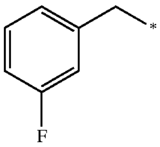 | 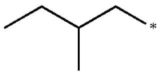 | M/S 387.49 |
| 5-1331 | 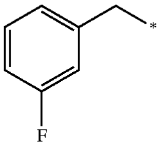 | 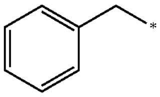 | M/S 407.48 |
| 5-1332 | 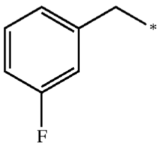 | 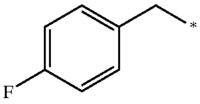 | M/S 425.47 |
| 5-1333 | 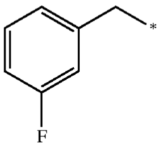 | 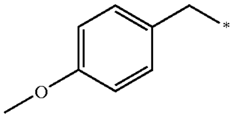 | M/S 437.51 |
| 5-1334 | 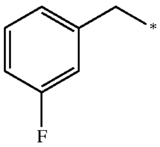 | 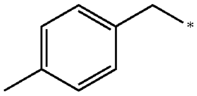 | M/S 435.54 |
| 5-1335 | 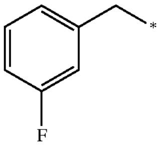 | 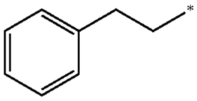 | M/S 421.51 |

TABLE 2-continued
(5)
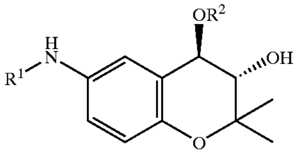
| Compound No. | $R^1$ | $R^2$ | NMR/MS Data |
|---|---|---|---|
| 5-1336 | 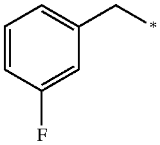 | 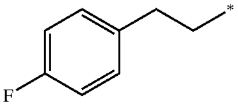 | M/S 439.50 |
| 5-1337 | 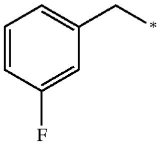 | 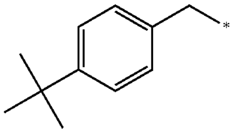 | M/S 463.59 |
| 5-1338 | 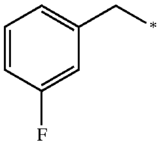 | 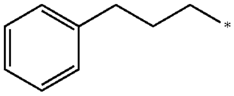 | M/S 435.54 |
| 5-1339 | 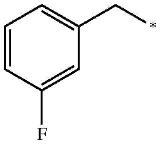 | 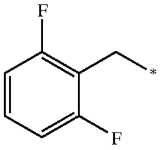 | M/S 443.47 |
| 5-1340 | 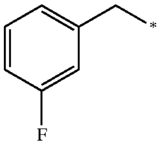 | 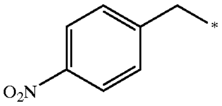 | M/S 452.48 |
| 5-1341 | 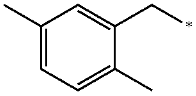 |  | M/S 341.45 |
| 5-1342 | 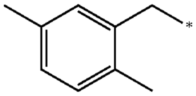 | 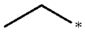 | M/S 355.48 |
| 5-1343 | 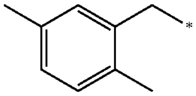 | 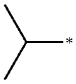 | M/S 369.50 |
| 5-1344 | 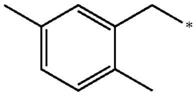 | 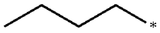 | M/S 383.53 |
| 5-1345 | 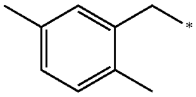 | 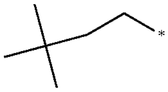 | M/S 411.58 |

TABLE 2-continued
(5)
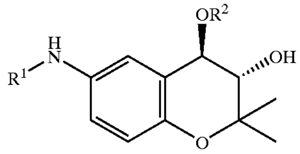
| Compound No. | $R^1$ | $R^2$ | NMR/MS Data |
|---|---|---|---|
| 5-1346 | 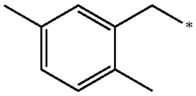 | 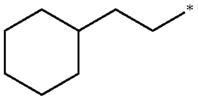 | M/S 437.62 |
| 5-1347 | 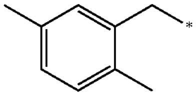 | 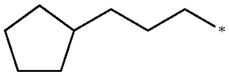 | M/S 437.62 |
| 5-1348 | 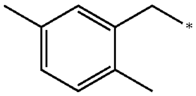 | 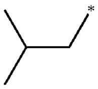 | M/S 383.53 |
| 5-1349 | 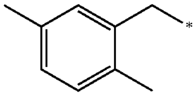 | 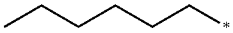 | M/S 411.58 |
| 5-1350 | 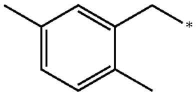 | 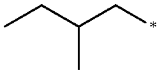 | M/S 397.56 |
| 5-1351 | 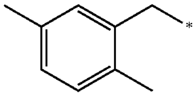 | 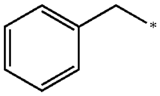 | M/S 417.55 |
| 5-1352 | 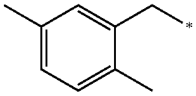 | 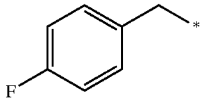 | M/S 435.54 |
| 5-1353 | 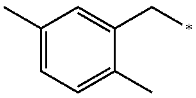 | 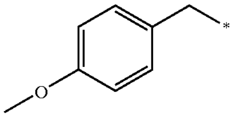 | M/S 447.57 |
| 5-1354 | 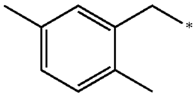 | 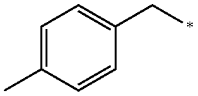 | M/S 445.60 |
| 5-1355 | 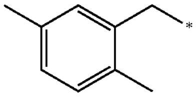 | 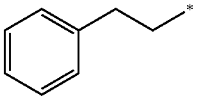 | M/S 431.58 |
| 5-1356 | 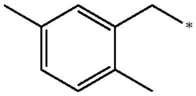 | 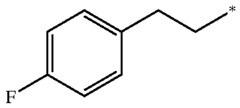 | M/S 449.57 |

TABLE 2-continued
(5)
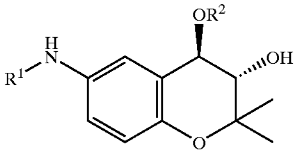
| Compound No. | $R^1$ | $R^2$ | NMR/MS Data |
|---|---|---|---|
| 5-1357 | 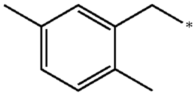 | 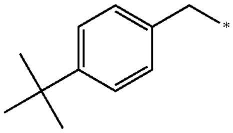 | M/S 473.66 |
| 5-1358 | 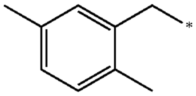 | 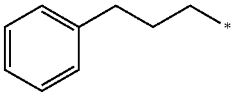 | M/S 445.60 |
| 5-1359 | 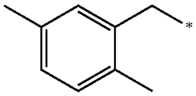 | 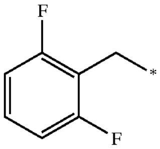 | M/S 453.53 |
| 5-1360 | 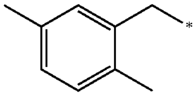 | 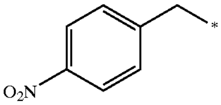 | M/S 462.55 |
| 5-1361 | 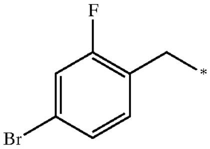 |  | M/S 410.28 |
| 5-1362 | 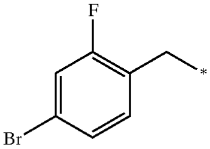 | 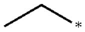 | M/S 424.31 |
| 5-1363 | 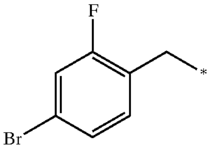 | 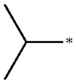 | M/S 438.34 |
| 5-1364 | 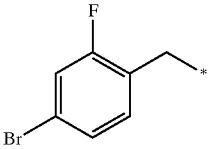 | 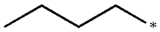 | M/S 452.36 |
| 5-1365 | 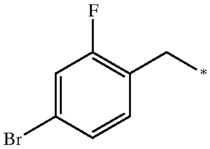 | 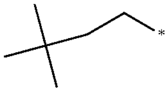 | M/S 480.42 |

TABLE 2-continued
(5)
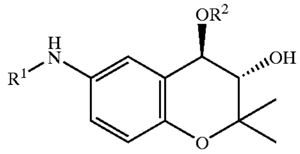
| Compound No. | $R^1$ | $R^2$ | NMR/MS Data |
|---|---|---|---|
| 5-1366 | 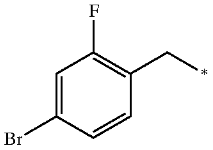 | 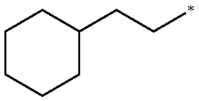 | M/S 506.46 |
| 5-1367 | 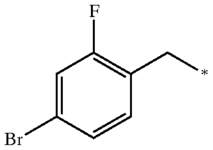 | 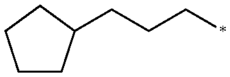 | M/S 506.46 |
| 5-1368 | 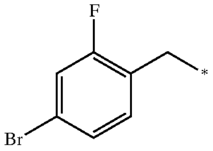 | 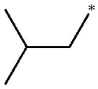 | M/S 452.36 |
| 5-1369 | 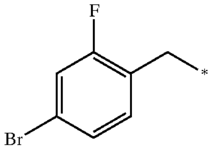 | 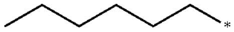 | M/S 480.42 |
| 5-1370 | 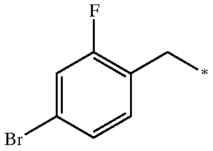 | 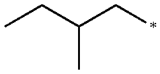 | M/S 466.39 |
| 5-1371 | 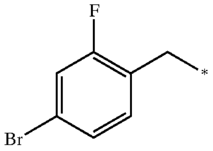 | 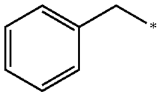 | M/S 486.38 |
| 5-1372 | 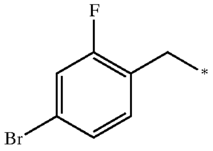 | 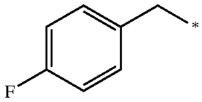 | M/S 504.37 |
| 5-1373 | 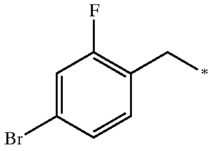 | 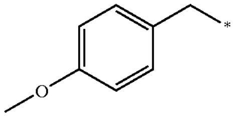 | M/S 516.41 |

TABLE 2-continued
(5)
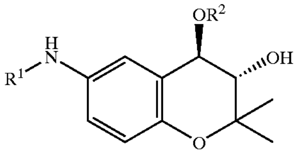
| Compound No. | $R^1$ | $R^2$ | NMR/MS Data |
| --- | --- | --- | --- |
| 5-1374 | 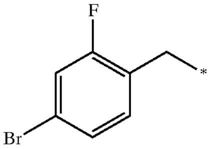 | 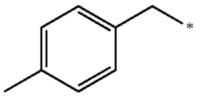 | M/S 514.43 |
| 5-1375 | 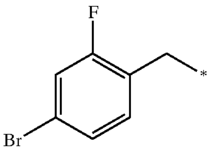 | 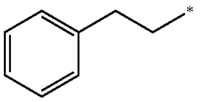 | M/S 500.41 |
| 5-1376 | 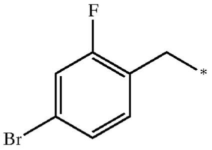 | 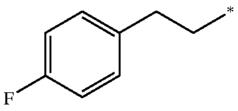 | M/S 518.40 |
| 5-1377 | 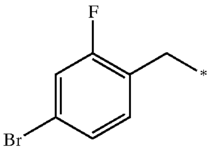 | 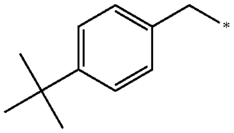 | M/S 542.49 |
| 5-1378 | 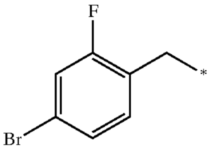 | 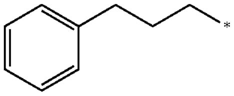 | M/S 514.43 |
| 5-1379 | 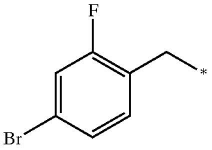 | 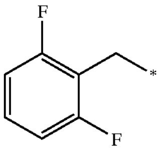 | M/S 522.36 |
| 5-1380 | 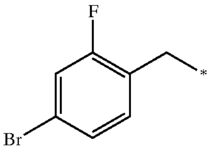 | 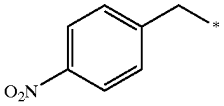 | M/S 531.38 |
| 5-1381 | 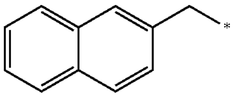 |  | M/S 363.46 |
| 5-1382 | 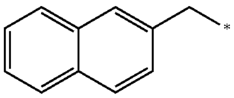 | 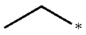 | M/S 377.48 |

TABLE 2-continued
(5)
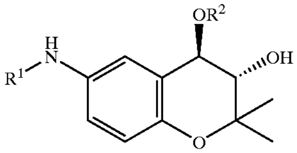
| Compound No. | $R^1$ | $R^2$ | NMR/MS Data |
|---|---|---|---|
| 5-1383 | 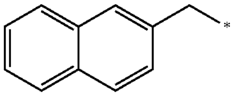 | 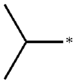 | M/S 391.51 |
| 5-1384 | 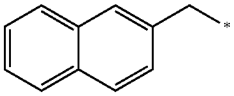 | 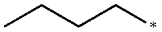 | M/S 405.54 |
| 5-1385 | 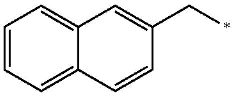 | 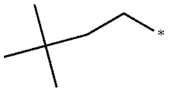 | M/S 433.59 |
| 5-1386 | 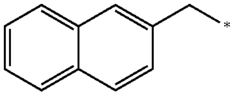 | 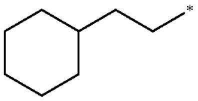 | M/S 459.63 |
| 5-1387 | 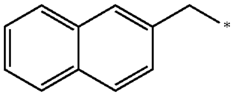 | 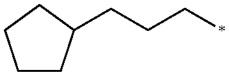 | M/S 459.63 |
| 5-1388 | 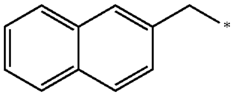 | 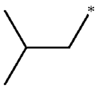 | M/S 405.54 |
| 5-1389 | 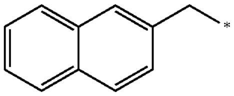 | 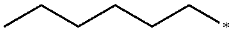 | M/S 433.59 |
| 5-1390 | 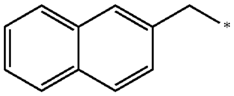 | 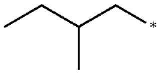 | M/S 419.56 |
| 5-1391 | 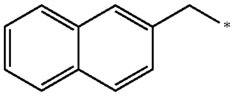 | 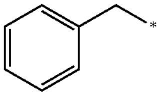 | M/S 439.55 |
| 5-1392 | 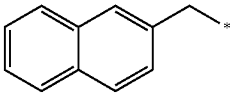 | 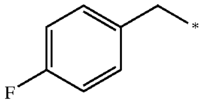 | M/S 457.54 |
| 5-1393 | 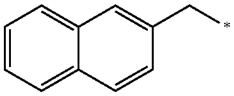 | 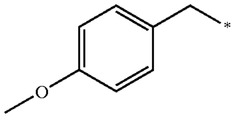 | M/S 469.58 |
| 5-1394 | 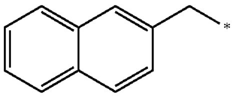 | 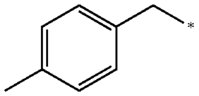 | M/S 453.58 |

TABLE 2-continued
(5)
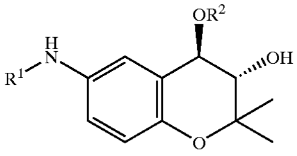
| Compound No. | $R^1$ | $R^2$ | NMR/MS Data |
| --- | --- | --- | --- |
| 5-1395 | 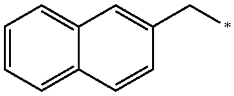 | 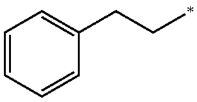 | M/S 453.58 |
| 5-1396 | 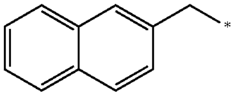 | 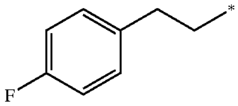 | M/S 471.57 |
| 5-1397 | 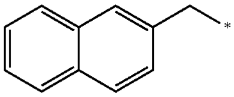 | 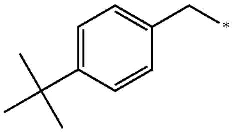 | M/S 495.66 |
| 5-1398 | 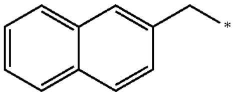 | 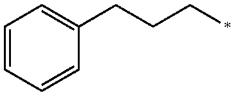 | M/S 467.61 |
| 5-1399 | 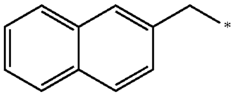 | 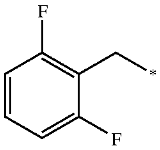 | M/S 475.54 |
| 5-1400 | 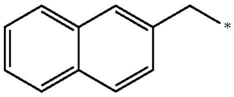 | 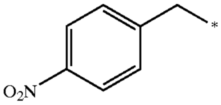 | M/S 484.55 |
| 5-1401 | 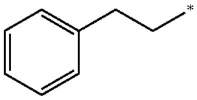 |  | M/S 327.42 |
| 5-1402 | 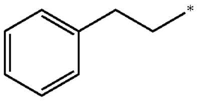 | 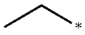 | M/S 341.45 |
| 5-1403 | 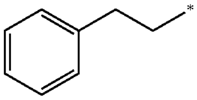 | 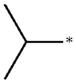 | M/S 355.48 |
| 5-1404 | 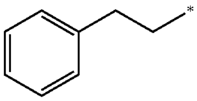 | 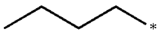 | M/S 369.50 |
| 5-1405 | 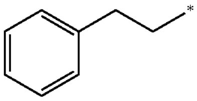 | 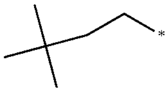 | M/S 397.56 |

TABLE 2-continued
(5)
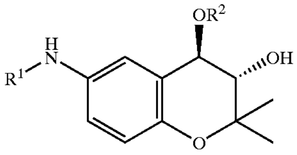
| Compound No. | $R^1$ | $R^2$ | NMR/MS Data |
|---|---|---|---|
| 5-1406 | 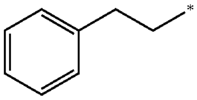 | 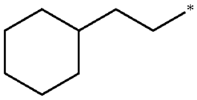 | M/S 423.60 |
| 5-1407 | 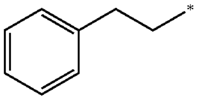 | 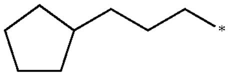 | M/S 423.60 |
| 5-1408 | 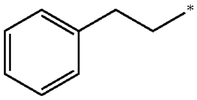 | 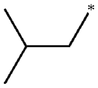 | M/S 369.50 |
| 5-1409 | 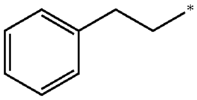 | 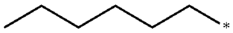 | M/S 397.56 |
| 5-1410 | 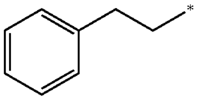 | 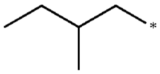 | M/S 383.53 |
| 5-1411 | 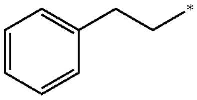 | 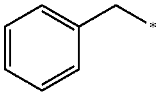 | M/S 403.52 |
| 5-1412 | 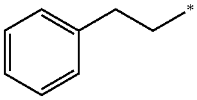 | 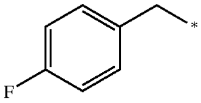 | M/S 421.51 |
| 5-1413 | 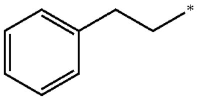 | 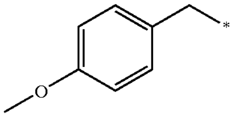 | M/S 433.55 |
| 5-1414 | 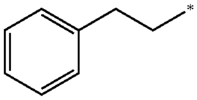 | 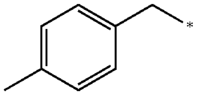 | M/S 417.55 |
| 5-1415 | 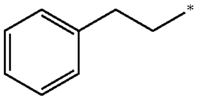 | 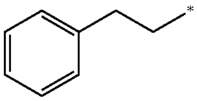 | M/S 417.55 |
| 5-1416 | 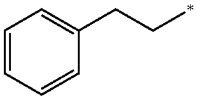 | 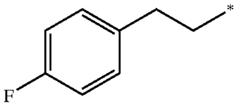 | M/S 435.54 |

TABLE 2-continued (5)

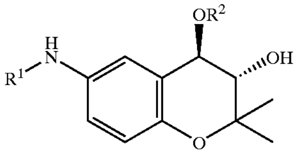

| Compound No. | $R^1$ | $R^2$ | NMR/MS Data |
|---|---|---|---|
| 5-1417 | 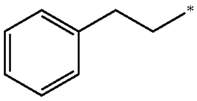 | 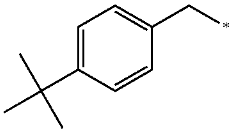 | M/S 459.63 |
| 5-1418 | 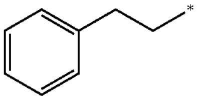 | 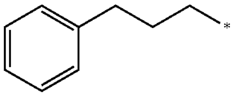 | M/S 431.58 |
| 5-1419 | 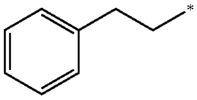 | 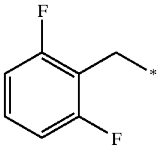 | M/S 439.50 |
| 5-1420 | 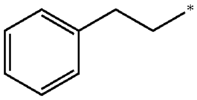 | 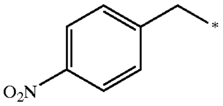 | M/S 448.52 |
| 5-1421 | 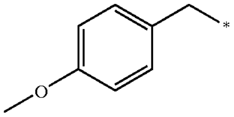 |  | $^1$H NMR(300MHz, $CDCl_3$) δ 7.27(d, 2H, J=8.6Hz), 6.87(d, 2H, J=8.6Hz), 6.67(d, 1H, J=8.7Hz), 6.64(d, 1H, J=2.8Hz), 6.53(dd, 1H, J=8.7Hz, J=2.8Hz), 4.31(d, 1H, J=7.3Hz), 3.81(d, 1H, J=7.3Hz), 3.80(s, 3H), 3.43(s, 3H), 1.43(s, 3H), 1.24(s, 3H); M/S 343.42 |
| 5-1422 | 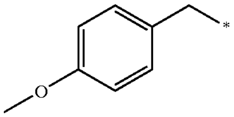 | 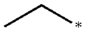 | $^1$H NMR(300MHz, $CDCl_3$) δ 7.29(d, 2H, J=8.6Hz), 6.87(d, 2H, J=8.6Hz), 6.67(d, 1H, J=8.7Hz), 6.64(d, 1H, J=2.8Hz), 6.56(dd, 1H, J=8.7Hz, J=2.8Hz), 4.33(d, 1H, J=8.4Hz), 3.20(d, 1H, J=7.3Hz), 3.80(d, 3H), 3.78(d, 1H, J=8.4Hz), 3.66(m, 2H), 1.43(s, 3H), 1.24(s, 3H), 1.22(s, 3H); M/S 357.45 |
| 5-1423 | 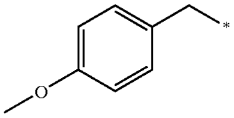 | 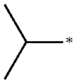 | $^1$H NMR(300MHz, $CDCl_3$) δ 7.28(d, 2H, J=8.6Hz), 6.85(d, 2H, J=8.6Hz), 6.65(br, 2H), 6.75(s, 1H), 4.26(d, 1H, J=6.6Hz), 4.19(s, 2H), 3.98(m, 1H), 3.78(s, 3H), 3.66(d, 1H, J=6.6Hz), 1.40~1.23(m, 12H); M/S 371.48 |
| 5-1424 | 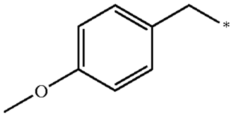 | 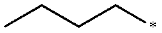 | $^1$H NMR(300MHz, $CDCl_3$) δ 7.27(d, 2H, J=8.6Hz), 6.83(d, 2H, J=8.6Hz), 6.70(m, 3H), 4.28(d, 1H, J=7.1Hz), 4.20(s, 2H), 3.77(s, 3H), 3.76(d, 1H, J=7.1Hz), 3.61(t, 2H, J=6.6Hz), 1.58(m, 2H), 1.38(m, 2H), 1.42(s, 3H), 1.25(s, 3H), 0.93(d, 3H, J=7.3Hz); M/S 385.50 |
| 5-1425 | 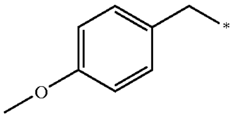 | 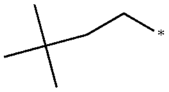 | M/S 413.56 |
| 5-1426 | 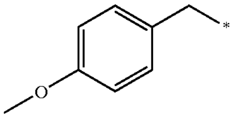 | 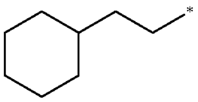 | $^1$H NMR(300MHz, $CDCl_3$) δ 7.28(d, 2H, J=8.6Hz), 6.83(d, 2H, J=8.6Hz), 6.77(m, 3H), 4.28(d, 1H, J=7.1Hz), 4.19(s, 2H), 3.78(d, 1H, J=7.1Hz), 3.78(s, 3H), 3.66(t, 2H, J=6.7Hz), 1.48(s, 3H), 1.26(s, 3H), 1.72~0.90(m, 13H); M/S 439.60 |

TABLE 2-continued
(5)
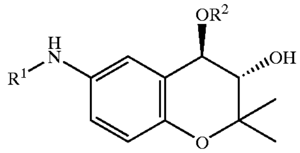
| Compound No. | $R^1$ | $R^2$ | NMR/MS Data |
|---|---|---|---|
| 5-1427 | 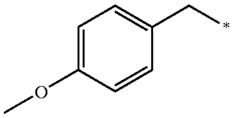 | 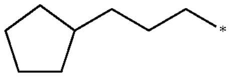 | M/S 439.60 |
| 5-1428 | 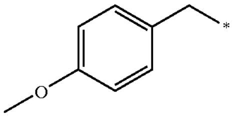 | 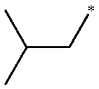 | M/S 385.50 |
| 5-1429 | 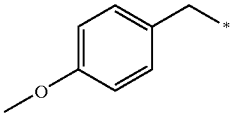 | 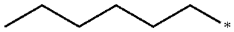 | M/S 413.56 |
| 5-1430 | 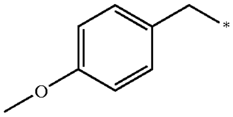 | 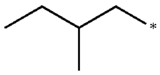 | M/S 399.53 |
| 5-1431 | 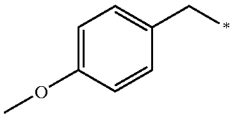 | 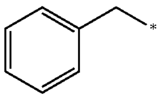 | $^1$H NMR(300MHz, $CDCl_3$) δ 7.38~7.24(m, 7H), 6.83(d, 2H, J=8.7Hz), 6.72~6.64(m, 3H), 4.68(s, 2H), 4.45(d, 1H, J=7.1Hz), 4.15(s, 2H), 3.85(d, 1H, J=7.1Hz), 3.76(s, 2H), 1.43(s, 3H), 1.25(s, 3H); M/S 419.52 |
| 5-1432 | 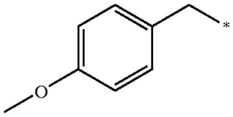 | 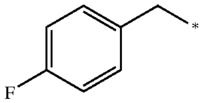 | M/S 437.51 |
| 5-1433 | 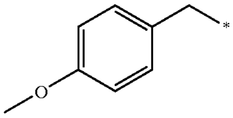 | 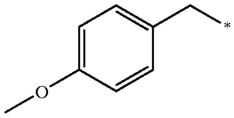 | M/S 449.55 |
| 5-1434 | 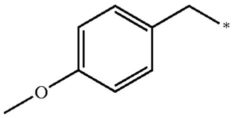 | 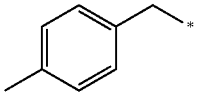 | M/S 433.55 |
| 5-1435 | 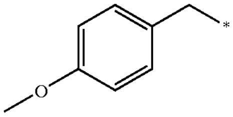 | 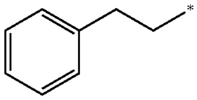 | $^1$H NMR(300 MHZ, $CDCl_3$) δ 7.27(m, 6H), 7.17(t, 1H, J=7.2Hz), 6.88(d, 2H, J=8.7Hz), 6.52(dd, 1H, J=8.7Hz, J=2.8Hz), 6.38(d, 1H, J=2.8Hz), 4.30(d, 1H, J=7.8Hz), 4.12(s, 2H), 3.83(m, 2H), 3.79(s, 3H), 3.67(d, 1H, J=7.8Hz), 2.89(t, 2H, J=6.5Hz), 1.36(s, 3H), 1.17(s, 3H); M/S 433.55 |
| 5-1436 | 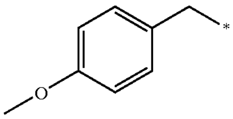 | 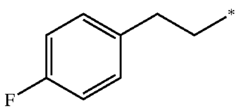 | M/S 451.54 |

TABLE 2-continued
(5)
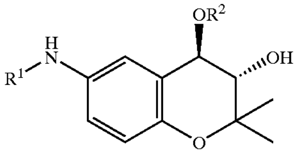
| Compound No. | $R^1$ | $R^2$ | NMR/MS Data |
|---|---|---|---|
| 5-1437 | 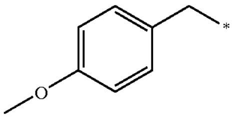 | 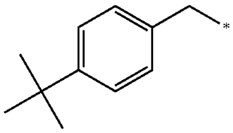 | M/S 475.63 |
| 5-1438 | 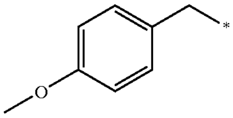 | 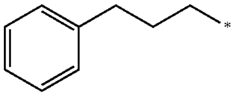 | M/S 447.57 |
| 5-1439 | 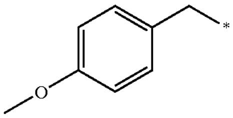 | 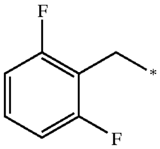 | M/S 455.50 |
| 5-1440 | 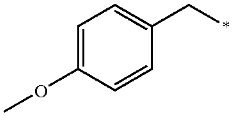 | 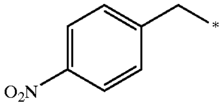 | M/S 464.52 |
| 5-1441 | 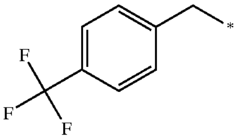 |  | M/S 381.39 |
| 5-1442 | 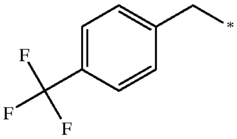 | 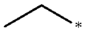 | M/S 395.42 |
| 5-1443 | 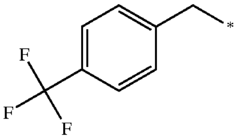 | 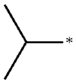 | M/S 409.45 |
| 5-1444 | 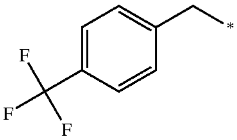 | 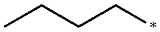 | M/S 423.47 |
| 5-1445 | 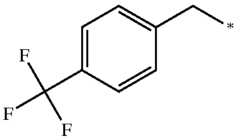 | 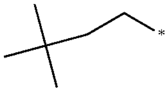 | M/S 451.53 |

TABLE 2-continued
(5)
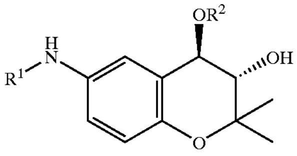
| Compound No. | $R^1$ | $R^2$ | NMR/MS Data |
| --- | --- | --- | --- |
| 5-1446 | 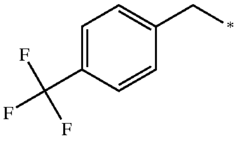 | 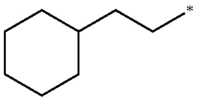 | M/S 477.57 |
| 5-1447 | 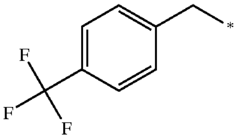 | 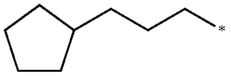 | M/S 477.57 |
| 5-1448 | 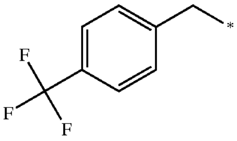 | 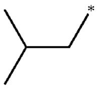 | M/S 423.47 |
| 5-1449 | 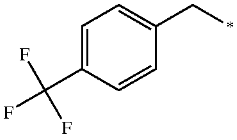 | 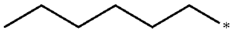 | M/S 451.53 |
| 5-1450 | 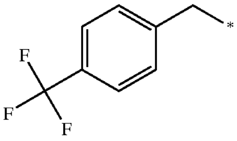 | 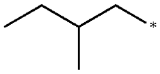 | M/S 437.50 |
| 5-1451 | 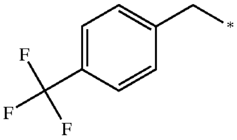 | 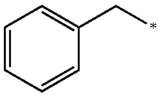 | M/S 457.49 |
| 5-1452 | 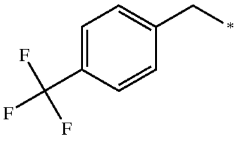 | 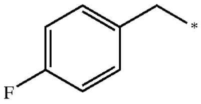 | M/S 475.48 |
| 5-1453 | 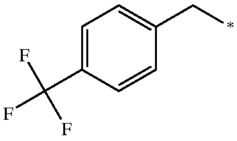 | 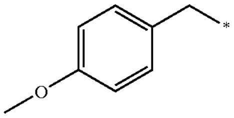 | M/S 487.52 |
| 5-1454 | 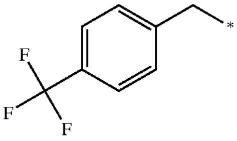 | 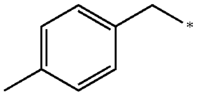 | M/S 471.52 |

TABLE 2-continued
(5)
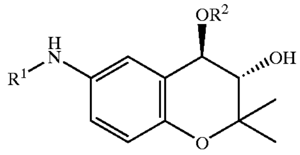
| Compound No. | $R^1$ | $R^2$ | NMR/MS Data |
|---|---|---|---|
| 5-1455 | 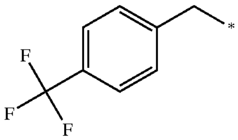 | 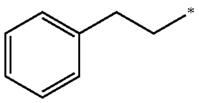 | M/S 471.52 |
| 5-1456 | 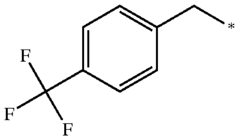 | 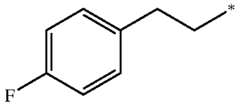 | M/S 489.51 |
| 5-1457 | 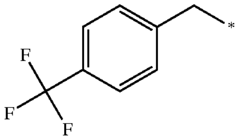 | 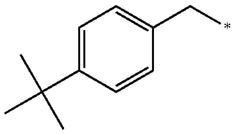 | M/S 513.60 |
| 5-1458 | 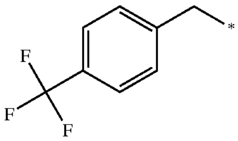 | 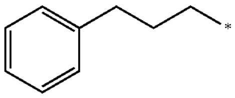 | M/S 485.55 |
| 5-1459 | 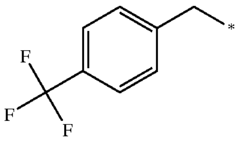 | 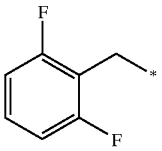 | M/S 493.47 |
| 5-1460 | 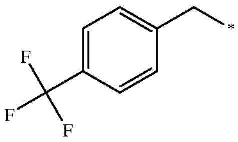 | 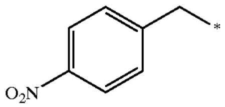 | M/S 502.49 |
| 5-1461 | 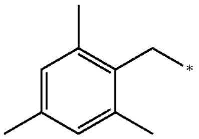 |  | M/S 355.48 |
| 5-1462 | 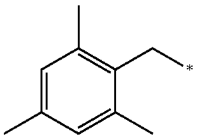 | 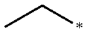 | M/S 369.50 |
| 5-1463 | 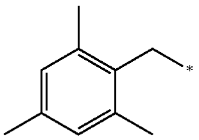 | 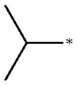 | M/S 383.53 |

TABLE 2-continued
(5)
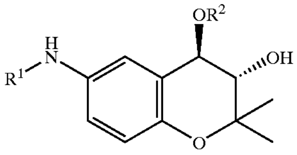
| Compound No. | $R^1$ | $R^2$ | NMR/MS Data |
|---|---|---|---|
| 5-1464 | 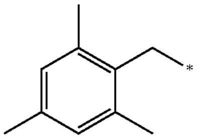 | 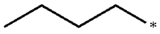 | M/S 397.56 |
| 5-1465 | 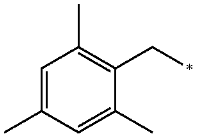 | 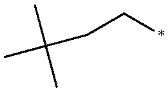 | M/S 425.61 |
| 5-1466 | 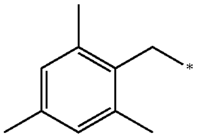 | 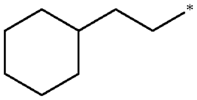 | M/S 451.65 |
| 5-1467 | 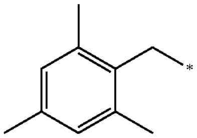 | 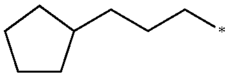 | M/S 451.65 |
| 5-1468 | 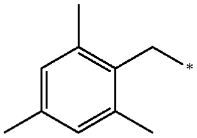 | 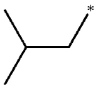 | M/S 397.56 |
| 5-1469 | 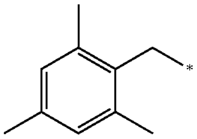 | 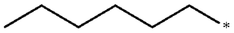 | M/S 425.61 |
| 5-1470 | 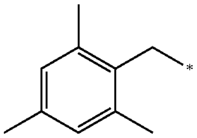 | 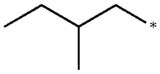 | M/S 411.58 |
| 5-1471 | 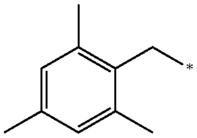 | 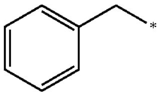 | M/S 431.58 |
| 5-1472 | 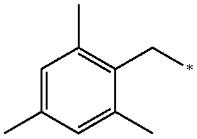 | 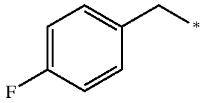 | M/S 449.57 |

TABLE 2-continued
(5)
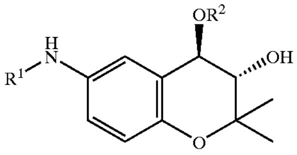
| Compound No. | $R^1$ | $R^2$ | NMR/MS Data |
|---|---|---|---|
| 5-1473 | 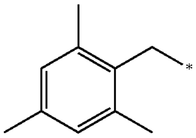 | 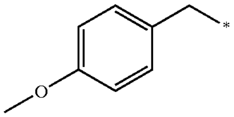 | M/S 461.60 |
| 5-1474 | 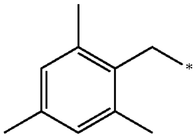 | 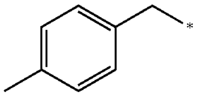 | M/S 445.60 |
| 5-1475 | 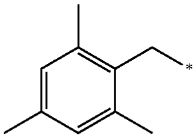 | 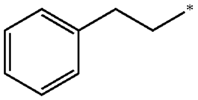 | M/S 445.60 |
| 5-1476 | 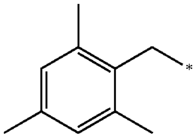 | 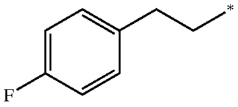 | M/S 449.57 |
| 5-1477 | 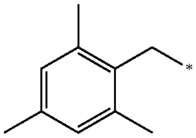 | 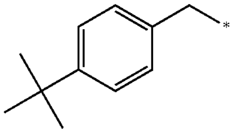 | M/S 487.68 |
| 5-1478 | 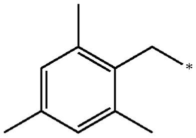 | 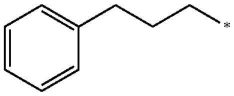 | M/S 459.63 |
| 5-1479 | 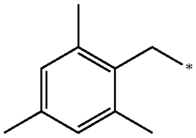 | 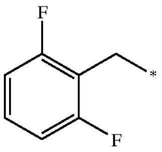 | M/S 467.56 |
| 5-1480 | 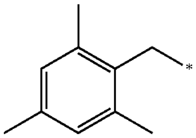 | 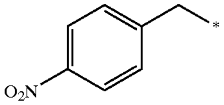 | M/S 476.57 |

EXAMPLE III

Synthesis of 2,2-dimethyl-3-acetylester-4-methoxy-6-methylamino Benzopyran (III-1) N-methylation of Olefin Resin (Formula 1)

(1)

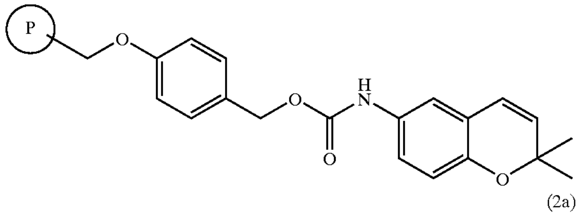

(2a)

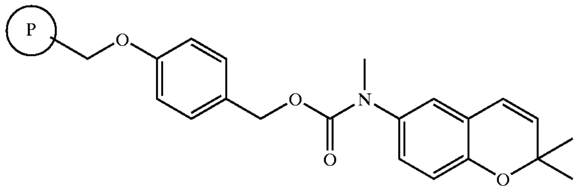

Carbamate resin having benzopyran structure of the formula (1) (200.00 mg, 0.11 mmol) was added to dimethylsulfoxide (DMSO; 3 ml) and agitated for 10 min at room temperature, followed by adding 1 M lithium t-butoxide solution (LiOtBu)(0.36 ml, 0.36 mmol) and agitating for 20 min at the same temperature. To the mixture, iodomethane (MeI; 0.051 ml, 0.36 mmol) was added and agitated to proceed with a reaction for 15 hr at 35° C. Upon completion of the reaction, the reactant mixture was filtered and washed repeatedly with DMF, MC, MC/MeOH and MeOH, thereby yielding N-4-methyl substituted carbamate resin of the formula (2a) as light brown-colored solid (ATR-FTIR: N-methylation carbamate, 1700 $cm^{-1}$)

(III-2) Addition of Hydroxy Methoxy to N-methyl-substituted Olefin Resin (Formula 2a)

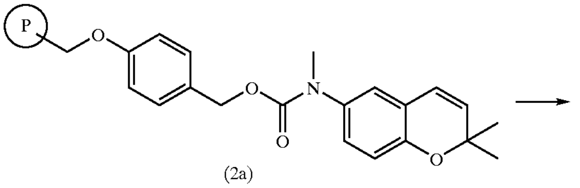

(2a)

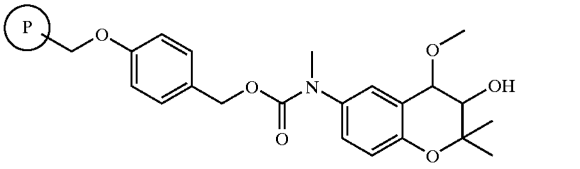

(3a)

N-methyl-substituted carbamate resin (200 mg, 0.12 mmol) of the formula (2a) was added to the mixed solution of dichloromethane (3 ml) and methanol (3 ml) and agitated for 30 min, after which metachloroperbenzoic acid (m-CPBA, 103 mg, 0.60 mmol) was added at room temperature and agitated to proceed with a reaction for 12 hr at room temperature. After completion of the reaction, the reactant mixture was filtered and washed repeatedly with DMF, MC, MC/MeOH and MeOH, thereby yielding the resin of the formula (3a) as a light yellow solid.

(111-3) Esterification of N-methyl-substituted Hydroxyl Methoxy Resin (Formula 3a)

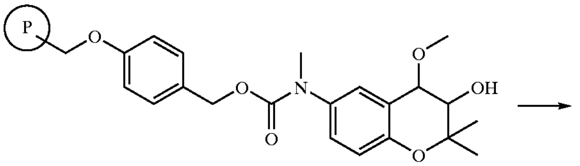

(3a)

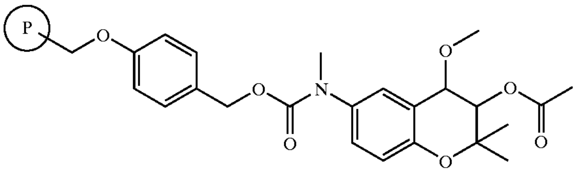

(4a)

2,2-dimethyl-3-hydroxy-4-methoxy-6-methyl amino benzopyran resin (200 mg, 0.12 mmol) linked to a carbamate linker represented by the formula (3a) was added to a solution of dichloromethane (3 ml) and agitated for 10 min at room temperature, followed by adding pyridine (0.136 ml, 1.68 mmol) and agitating for 30 min to proceed a reaction. To the mixture, acetyl chloride (0.119 ml, 1.68 mmol) and 4-dimethylaminopyridine (0.0137 g, 0.112 mmol) were added and allowed reaction for 12 hr at room temperature. After completion of the reaction, the reactant mixture was filtered and washed repeatedly with DMF, MC, MC/MeOH and MeOH, thereby yielding the resin of the formula (4a) as a light brown solid.

(III-4) Departure Reaction of N-methyl-substituted Ester Methoxy Resin (Formula 4a)

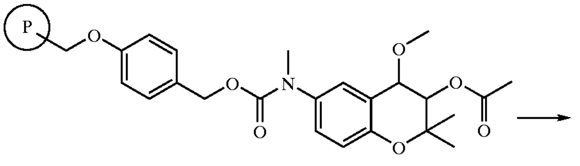

(4a)

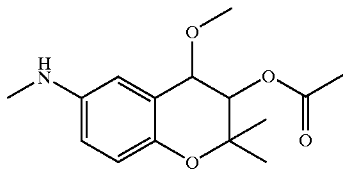

(5-1481)

The resin (200 mg) of the formula (4a) was added to a solution of dichloromethane (4 ml) and agitated, followed by addition of trifluoroacetic acid (TFA, 1 ml) and agitation for 3 hr at room temperature. After completion of the reaction, the reactant mixture was filtered and the filtrate was washed repeatedly with dichloromethane and methyl alcohol. The filtrates were combined and concentrated. To the concentrates, ethylacetate (3 ml) was added, filtered thorough strong anion exchange resin (SAX) and washed repeatedly with ethylacetate to remove residual TFA. Following concentration of the filtrate under reduced pressure, the concentrate was purified with silica gel column chromatography in the presence of hexane/ethylacetate (4/1, v/v), giving the compound of the formula (5-1481) as light-yellow oil (17.42 mg, yield=51.97%; 4 step overall yield from resin 1; loading capacity of resin 1=0.55 mmol/g).

The 2,2-dimethyl-3-ester-4-alkoxy-6-alkyl amino benzopyran derivatives synthesized according to the method of parallel synthesis on the solid-phase as Example III are summarized in Table 3.

In construction of the library in Table 3, the following precursors were employed to preparing combinations of each substituent: for example, $R^1$ precursor includes MeI, EtI, BnBr, 4-MeO-BnCl, 4-Fe-BnBr and 4-Me-BnBr; $R^2$ precursor includes MeOH, EtOH, $^i$PrOH, $^i$BuOH, BnOH, PhEtOH and $^c$HexEtOH; $R^3$ precursor includes acetyl chloride, t-butylacetyl chloride, cyclohexanecarbonyl chloride, 3,3-dimethylacryloyl chloride, benzoyl chloride, p-toluyl chloride, 4-anisoyl chloride, 4-fluorobenzoyl chloride, 2-thiopencarbonyl chloride and 2-furoyl chloride.

TABLE 3
| Compound No. | NMR/MS Data |
| --- | --- |
| 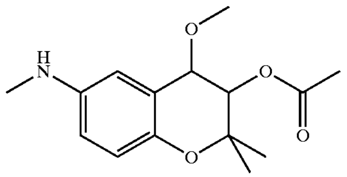 5-1481 | $^1$H NMR(200MHz, $CDCl_3$) δ 7.26~6.56(m, 3H), 5.23(d, 1H, J=5.3Hz), 4.30(d, 1H, J=5.3Hz), 3.45(s, 3H), 2.82(s, 3H), 2.12(s, 3H), 1.35(s, 3H), 1.29(s, 3H); MS, m/z: 279.3 |
| 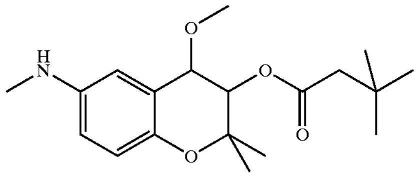 5-1482 | $^1$H NMR(200MHz, $CDCl_3$) δ 6.74~6.55(m, 3H), 5.24(d, 1H, (J=6.0Hz), 4.35(d, 1H, J=6.0Hz), 3.41(s, 3H), 2.80(s, 3H), 2.27(s, 2H), 1.36(s, 3H), 1.29(s, 3H), 1.05(s, 9H); MS, m/z: 335.4 |
| 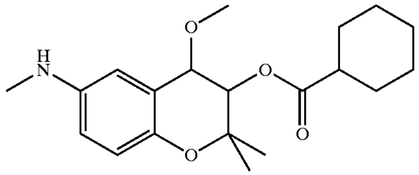 5-1483 | $^1$H NMR(200MHz, $CDCl_3$) δ 6.74(m, 3H), 5.23(d, 1H, J=5.8 Hz), 4.29(d, 1H, J=5.8Hz), 3.44(s, 3H), 2.81(s, 3H), 2.35(m, 1H), 1.93~1.26(m, 10H), 1.34(s, 3H), 1.29(s, 3H); MS, m/z: 347.4 |
| 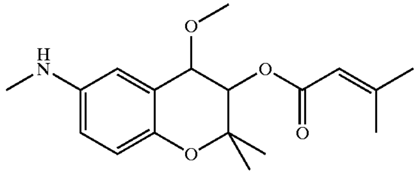 5-1484 | $^1$H NMR(200MHz, $CDCl_3$) δ 6.75~6.58(m, 3H), 5.72(m, 1H), 5.26(d, 1H, J=5.3Hz), 4.31(d, 1H, J=5.3Hz), 3.48(s, 3H), 2.82(s, 3H), 2.18(s, 3H), 1.90(s, 3H), 1.36(s, 3H), 1.30(s, 3H); MS, m/z: 319.4 |

TABLE 3-continued
| Compound No. | NMR/MS Data | |
|---|---|---|
| 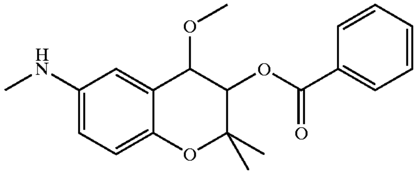 5-1485 | $^1H$ NMR(200MHz, $CDCl_3$) δ 8.05(d, 1H, J=7.1Hz), 7.58–7.40(m, 3H), 6.79~6.61(m, 3H), 5.48(d, 1H, J=5.5Hz), 4.46(d, 1H, J=5.5Hz), 3.52(s, 3H), 2.82(s, 3H), 1.41 (s, 3H), 1.39(s, 3H); MS, m/z: 341.4 | |
| 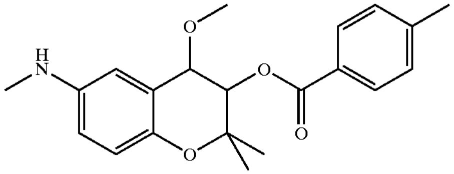 5-1486 | $^1H$ NMR(200MHz, $CDCl_3$) δ 8.07~7.78(m, 2H), 7.27~7.21(m, 2H), 6.87~6.59(m, 3H), 5.46(d, 1H, J=5.6Hz), 4.44(d, 1H, J=5.6Hz), 3.52(s, 3H), 2.83(s, 3H), 2.41(s, 3H), 1.49–1.13(m, 6H); MS, m/z: 355.4 | |
| 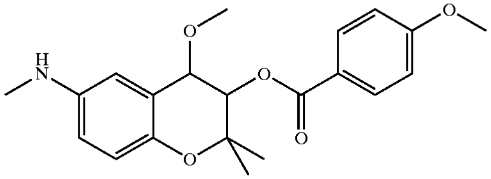 5-1487 | MS, m/z: 371.4 | |
| 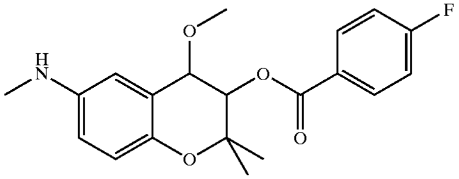 5-1488 | | MS, m/z:359.4 |
| 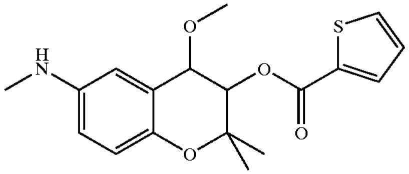 5-1489 | $^1H$ NMR(200MHz, $CDCl_3$) δ 7.83(m, 1H), 7.58(m, 1H), 7.14(m, 1H), 6.74(d, 1H, J=8.5Hz), 6.63~6.51(m, 3H), 5.42(d, 1H, J=6.0Hz), 4.50(d, 1H, J=6.0Hz), 3.49(s, 3H), 2.81(s, 3H), 1.40(s, 3H), 1.36(s, 3H); MS, m/z: 347.4 | |

TABLE 3-continued
| Compound No. | NMR/MS Data |
|---|---|
| 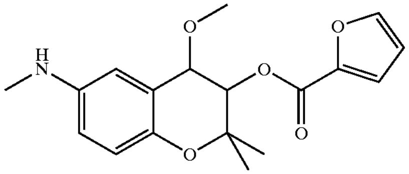 5-1490 | $^1H$ NMR(200MHz, $CDCl_3$) δ 7.60(m, 1H), 7.22(m, 1H), 6.74(d, 1H, J=8.3Hz), 6.62~6.46(m, 3H), 5.43(d, 1H, J=5.8Hz), 4.47(d, 1H, J=5.8Hz), 3.48(s, 3H), 2.81(s, 3H), 1.40(s, 3H), 1.35(s, 3H); MS, m/z: 331.3 |
| 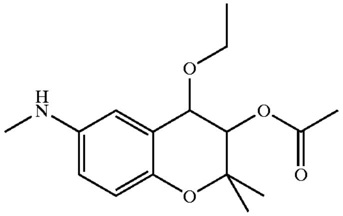 5-1491 | $^1H$ NMR(200MHz, $CDCl_3$) δ 6.73~6.53(m, 3H), 5.19(d, 1H, J=5.2Hz), 4.33(d, 1H, J=5.2Hz), 3.70(q, 2H, J=7.0Hz), 2.81 (s, 3H), 2.11 (s, 3H), 1.35(s, 3H), 1.29(s, 3H), 1.23(t, 3H, J=6.9Hz); MS, m/z: 293.3 |
| 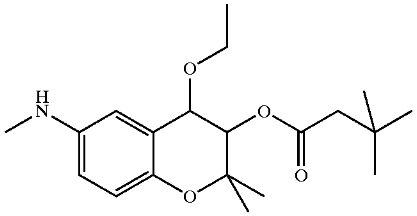 5-1492 | $^1H$ NMR(200MHz, $CDCl_3$) δ 6.73~6.52(m, 3H), 5.21(d, 1H, J=5.7Hz), 4.38(d, 1H, J=5.7Hz), 3.66(q, 2H, J=6.9Hz), 2.80(s, 3H), 2.26(s, 3H), 1.36(s, 3H), 1.29(s, 3H), 1.21(t, 3H, J=6.9Hz), 1.04(s, 9H); MS, m/z: 349.4 |
| 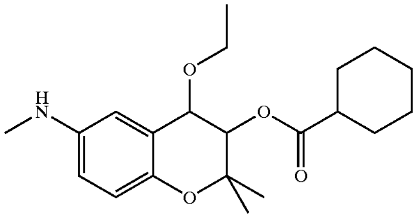 5-1493 | $^1H$ NMR(200MHz, $CDCl_3$) δ 6.73~6.54(m, 3H), 5.19(d, 1H, J=5.6Hz), 4.33(d, 1H, J=5.6Hz), 3.67(q, 2H, J=6.9Hz), 2.80(s, 3H), 2.36(m, 1H), 1.90~0.88(m, 10H), 1.34(s, 3H), 1.28(s, 3H), 1.22(t, 3H, J=6.9Hz); MS, m/z: 361.4 |

TABLE 3-continued
| Compound No. | NMR/MS Data |
|---|---|
| 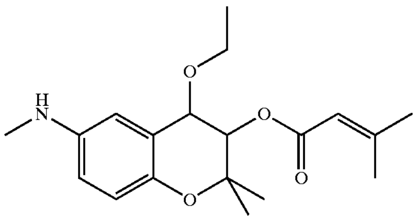 5-1494 | $^1$H NMR(200MHz, $CDCl_3$) δ 6.73~6.54(m, 3H), 5.71(d, 1H, J=1.4Hz), 5.21(d, 1H, J=5.1Hz), 4.33(d, 1H, J=5.1Hz), 3.72(m, 2H), 2.80(s, 3H), 2.17(s, 3H), 1.89(s, 3H), 1.36(s, 3H), 1.30(s, 3H), 1.28~1.26(m, 3H); MS, m/z: 333.4 |
| 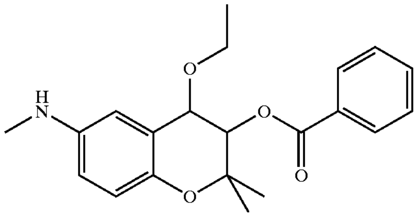 5-1495 | $^1$H NMR(200MHz, $CDCl_3$) δ 8.07~8.03(m, 2H), 7.90~7.40(m, 3H), 6.85~6.51(m, 3H), 5.44(d, 1H, J=5.2Hz), 4.59(d, 1H, J=5.2Hz), 3.77(m, 2H), 2.81 (s, 3H), 1.41 (s, 3H), 1.39(s, 3H), 1.23(t, 3H, J=6.9Hz); MS, m/z: 355.4 |
| 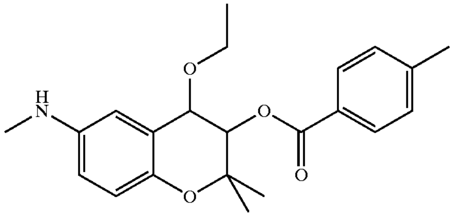 5-1496 | $^1$H NMR(200MHz, $CDCl_3$) δ 7.93(d, 2H, J=8.1Hz), 7.21(m, 2H), 6.84~6.51(m, 3H), 5.42(d, 1H, J=5.1Hz), 4.48(d, 1H, J=5.1Hz), 3.77(m, 2H), 2.81(s, 3H), 2.40(s, 3H), 1.40(s, 3H), 1.38(s, 3H), 1.22(t, 3H, J=6.9Hz); MS, m/z: 369.4 |
| 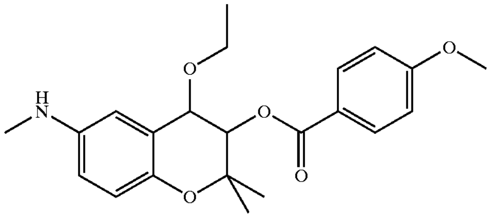 5-1497 | $^1$H NMR(200MHz, $CDCl_3$) δ 7.99(d, 2H, J=9.1Hz), 6.90(d, 2H, J=9.1Hz), 6.74~6.64(m, 3H), 5.40(d, 1H, J=5.0Hz), 4.42(d, 1H, J=5.0Hz), 3.85(s, 3H), 3.76(m, 2H), 2.82(s, 3H), 1.41(s, 3H), 1.38(s, 3H), 1.23(m, 3H); MS. m/z: 371.4 |

TABLE 3-continued
| Compound No. | NMR/MS Data |
|---|---|
| 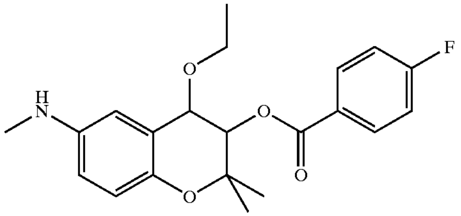 5-1498 | $^1H$ NMR(200MHz, $CDCl_3$) δ 8.09~8.02(m, 2H), 7.17~7.06(m, 2H), 6.78~6.62(m, 3H), 5.41(d, 1H, J=5.2Hz), 4.46(d, 1H, J=5.2Hz), 3.75(m, 2H), 2.82(s, 3H), 1.41 (s, 3H), 1.38(s, 3H), 1.23(m, 3H); MS, m/z: 373.4 |
| 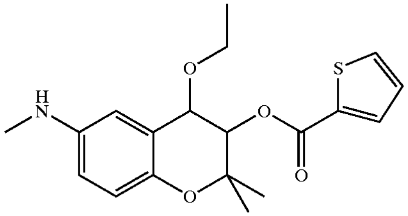 5-1499 | MS, m/z: 361.4 |
| 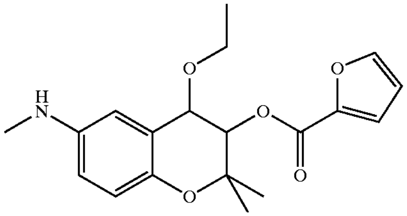 5-1500 | MS, m/z: 345.4 |
| 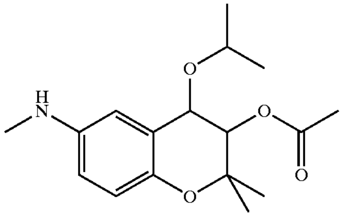 5-1501 | $^1H$ NMR(200MHz, $CDCl_3$) δ 6.90~6.79(m, 3H), 5.04(d, 1H, J=4.0Hz), 4.24(d, 1H, J=4.0Hz), 4.06(m, 1H, 2.86(s, 3H), 2.08(s, 3H), 1.50~1.20(m, 6H); MS, m/z: 307.3 |
| 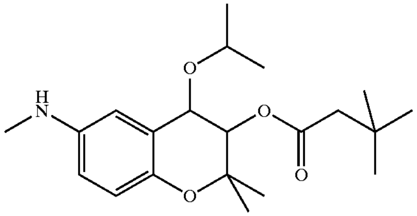 5-1502 | $^1H$ NMR(200MHz, $CDCl_3$) δ 6.75~6.72(m, 3H), 5.02(d, 1H, J=3.6Hz), 4.21(d, 1H, J=3.6Hz), 4.10(m, 1H), 2.82(s, 3H), 2.22(s, 2H), 1.50~1.12(m, 15H); MS, m/z: 363.5 |

TABLE 3-continued
| Compound No. | NMR/MS Data |
| --- | --- |
| 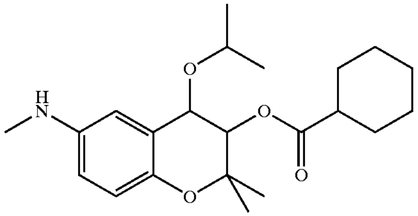 5-1503 | $^1$H NMR(200MHz, $CDCl_3$) δ 6.81~6.68(m, 3H), 5.04(d, 1H, J=3.9Hz), 4.20(d, 1H, J=3.9Hz), 4.06(m, 1H), 2.81(s, 3H), 2.32(m, 1H), 1.88~1.19(m, 22H); MS, m/z: 375.5 |
| 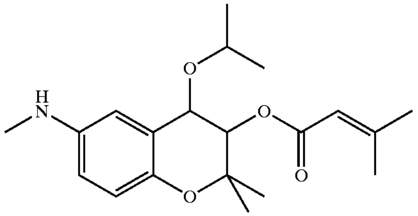 5-1504 | MS, m/z: 347.4 |
| 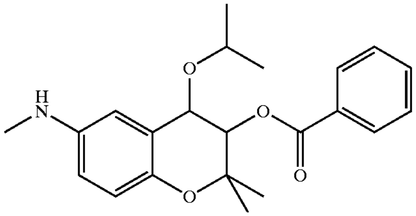 5-1505 | MS, m/z: 369.4 |
| 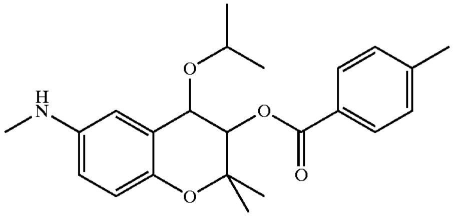 5-1506 | MS, m/z: 383.4 |
| 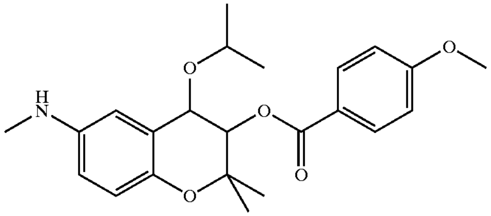 5-1507 | $^1$H NMR(200MHz, $CDCl_3$) δ 7.97(d, 2H, J=9.0Hz), 6.92~6.70(m, 5H), 5.27(d, 1H, J=4.1Hz), 4.38(1H, J=4.1Hz), 4.11(m, 1H), 4.38(s, 3H), 2.83(s, 3H), 1.42~1.21(m, 12H); MS, m/z: 399.4 |

TABLE 3-continued
| Compound No. | NMR/MS Data |
| --- | --- |
| 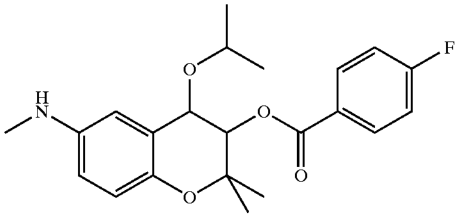 5-1508 | MS, m/z: 387.4 |
| 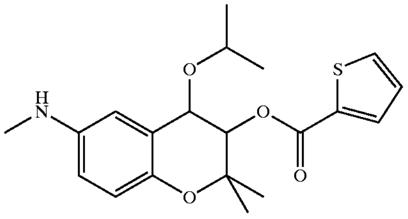 5-1509 | MS, m/z: 375.4 |
| 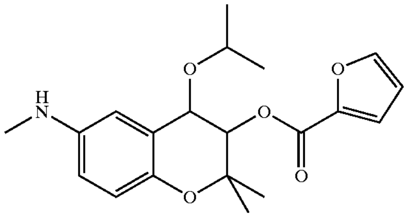 5-1510 | $^1$H NMR(200MHz, $CDCl_3$) δ 7.58(m, 1H), 7.17(m, 1H), 6.77~6.62(m, 3H), 6.47(m, 1H), 5.24(d, 1H, J=4.4Hz), 4.39(d, 1H, J=4.4Hz), 4.10(m, 1H), 2.81(s, 3H), 1.41~1.18(m, 12H); MS, m/z: 359.4 |
| 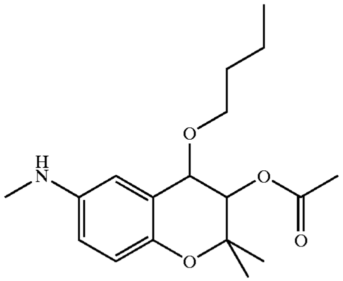 5-1511 | $^1$H NMR(200MHz, $CDCl_3$) δ 6.75~6.59(m, 3H), 5.19(d, 1H, J=5.1Hz), 4.30(d, 1H, J=5.1Hz), 3.66(m, 2H), 2.81(s, 3H), 2.10(s, 3H), 1.59(m, 2H), 1.56(m, 2H), 1.35(s, 3H), 1.30(s, 3H), 0.92(t, 3H, J=7.2Hz): MS, m/z: 321.4 |

TABLE 3-continued
| Compound No. | NMR/MS Data | Compound No. | NMR/MS Data |
| --- | --- | --- | --- |
| 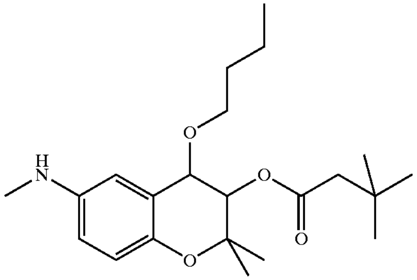 5-1512 | MS, m/z: 377.5 | 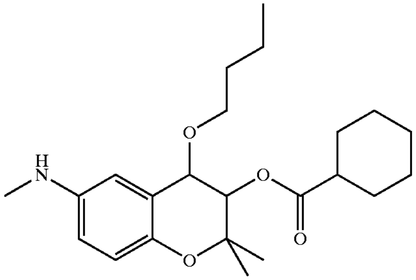 5-1513 | MS, m/z: 389.5 |
| 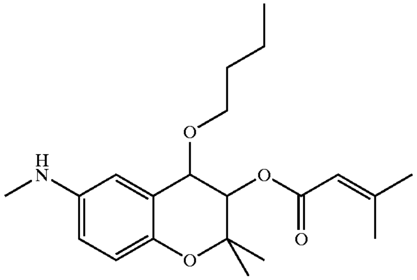 5-1514 | $^1H$ NMR(200MHz, $CDCl_3$) δ 7.16~6.77(m, 3H), 5.70(m, 1H), 5.21(d, 1H, J=4.7Hz), 4.28(d, 1H, J=4.7Hz), 3.70(m, 2H), 2.88(s, 3H), 2.17(s, 3H), 1.89(s, 3H), 1.58(m, 2H), 1.44(m, 2H), 1.37(s, 3H), 1.32(s, 3H), 0.91(t, 3H, J=7.2Hz); MS, m/z: 361.4 | | |
| 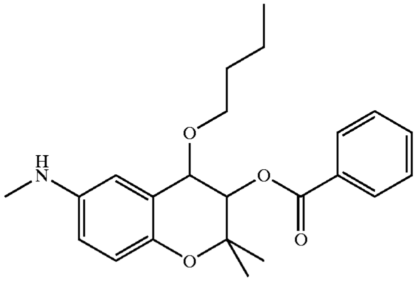 5-1515 | MS, m/z: 393.4 | 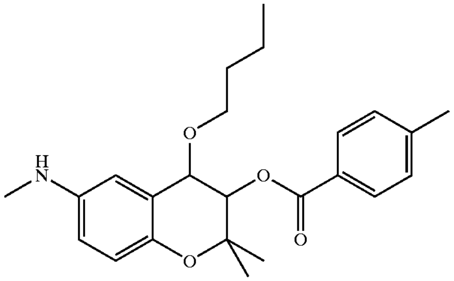 5-1516 | MS, m/z: 397.5 |

TABLE 3-continued
| Compound No. | NMR/MS Data |
|---|---|
| 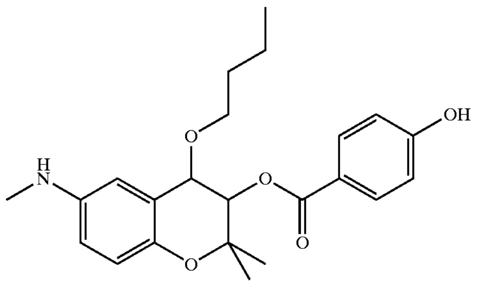 5-1517 | $^1$H NMR(200MHz, $CDCl_3$) δ 7.99(d, 2H, J=9.0Hz), 6.90(d, 2H, J=9.0Hz), 6.79~6.63(m, 3H), 5.40(d, 1H, J=4.9Hz), 4.44(d, 1H, J=4.9Hz), 3.86(s, 3H), 3.68(m, 2H), 2.82(s, 3H), 1.70(m, 2H), 1.50(m, 2H), 1.41(s, 3H), 1.38(s, 3H), 0.95(m, 3H); MS, m/z: 399.4 |
| 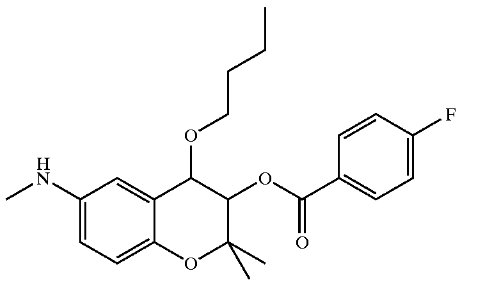 5-1518 | MS, m/z; 401.4 |
| 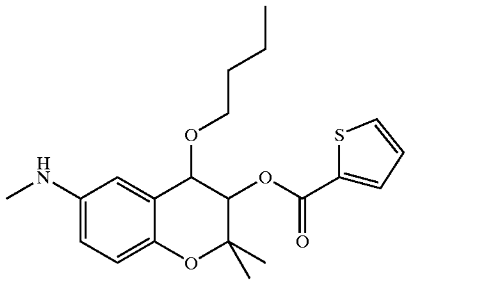 5-1519 | $^1$H NMR(200MHz, $CDCl_3$) δ 7.82(m, 1H), 7.57(m, 1H), 7.11(m, 1H), 6.77~6.59(m, 3H), 5.37(d, 1H, J=5.7Hz), 4.49(d, 1H, J=5.7Hz), 3.72(t, 2H, J=6.4Hz), 2.82(s, 3H), 1.58(m, 2H), 1.43(m, 2H), 1.41 (s, 3H), 1.37(s, 3H), 0.88(t, 3H, J=7.2Hz); MS, m/z: 389.5 |

TABLE 3-continued
| Compound No. | NMR/MS Data |
|---|---|
| 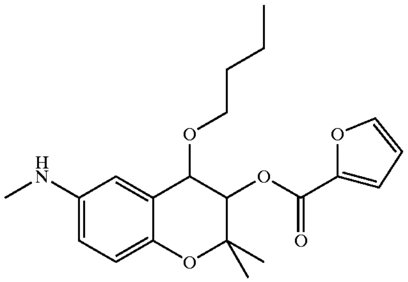 5-1520 | $^1$H NMR(200MHz, $CDCl_3$) δ 7.60(m, 1H), 7.20(m, 1H), 6.74(d, 1H, J=8.5Hz), 6.64~6.58(m, 2H), 6.50(m, 1H), 5.39(d, 1H, J=5.4Hz), 4.46(d, 1H, J=5.4Hz), 3.71(t, 2H, J=6.3Hz), 2.82(s, 3H), 1.66~1.43(m, 4H), 1.40(s, 3H), 1.36(s, 3H), 0.89(t, 3H, J=7.2Hz); MS, m/z: 373.4 |
| 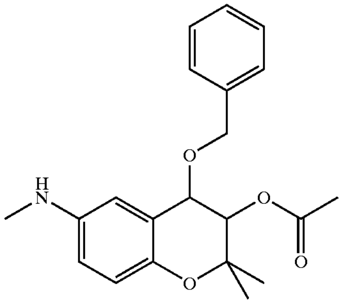 5-1521 | $^1$H NMR(200MHz, $CDCl_3$) δ 7.39~7.26(m, 5H), 6.92~6.76(m, 3H), 5.27(d, 1H, J=4.3Hz), 4.75(s, 2H), 4.40(d, 1H, J=4.4Hz), 2.81 (s, 3H), 2.09(s, 3H), 1.40(s, 3H), 1.35(s, 3H); MS, m/z: 355.4 |
| 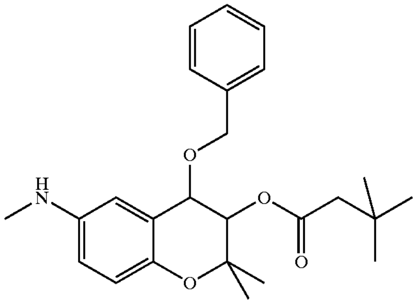 5-1522 | $^1$H NMR(200MHz, $CDCl_3$) δ 7.38~7.25(m, 5H), 7.10~6.80(m, 3H), 5.28(d, 1H, J=4.0Hz), 4.75(s, 2H), 4.38(d, 1H, J=4.0 Hz), 2.84(s, 3H), 2.23(s, 2H), 1.44~1.20(m, 6H), 1.00(s, 9H); MS, m/z: 411.5 |

TABLE 3-continued
| Compound No. | NMR/MS Data |
| --- | --- |
| 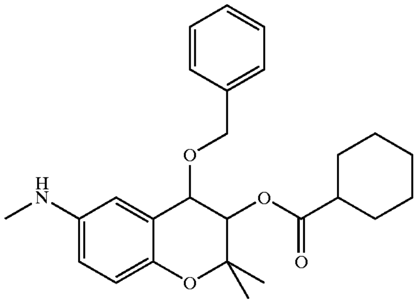 5-1523 | $^1H$ NMR(200MHz, $CDCl_3$) δ 7.40~7.26(m, 5H), 6.78~6.73(m, 3H), 5.29(d, 1H, J=4.6Hz), 4.72(s, 2H), 4.39(d, 1H, J=4.6 Hz), 2.79(s, 3H), 2.34(m, 1H), 1.89~1.25(m, 11H), 1.38(s, 3H), 1.33(s, 3H); MS, m/z: 423.5 |
| 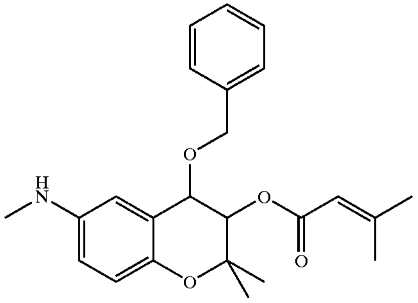 5-1524 | MS, m/z: 395.5 |
| 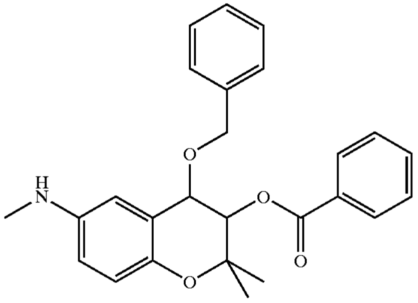 5-1525 | MS, m/z: 417.5 |
| 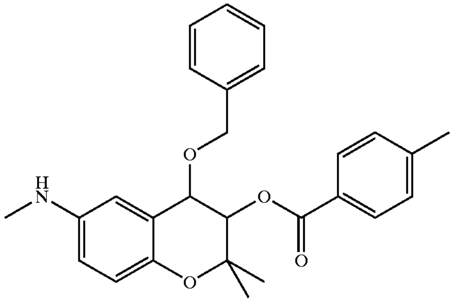 5-1526 | MS, m/z: 431.5 |
| 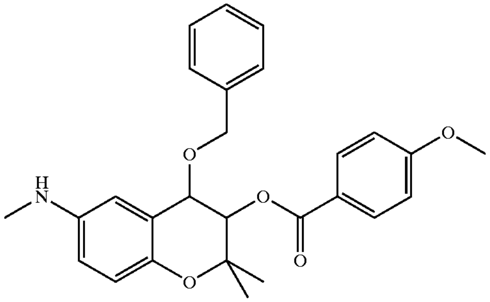 5-1527 | MS, m/z: 447.5 |

TABLE 3-continued
| Compound No. | NMR/MS Data |
|---|---|
| 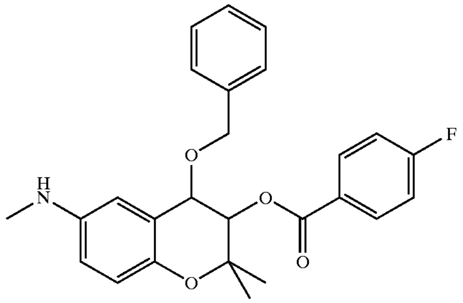 5-1528 | $^1H$ NMR(200MHz, $CDCl_3$) δ 8.04(m, 2H), 7.41~7.26(m, 5H), 7.10(m, 2H), 6.77~6.56(m, 3H), 5.49(d, 1H, J=4.4Hz), 4.80(s, 2H), 4.56(d, 1H, J=4.4Hz), 2.77(s, 3H), 1.45(s, 3H), 1.41(s, 3H); MS, m/z: 435.5 |
| 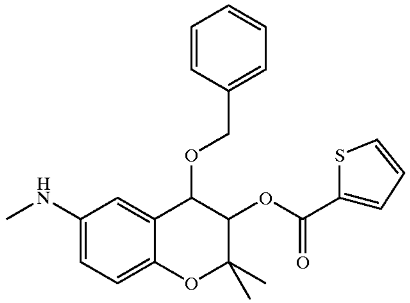 5-1529 | $^1H$ NMR(200MHz, $CDCl_3$) δ 7.83(m, 1H), 7.58(m, 1H), 7.36(m, 5H), 7.27(m, 1H), 6.77~6.25(m, 3H), 5.46(d, 1H, J=4.4Hz), 4.79(s, 2H), 4.61 (d, 1H, J=4.4Hz), 2.78(s, 3H), 1.44(s, 3H), 1.40(s, 3H); MS, m/z: 423.5 |
| 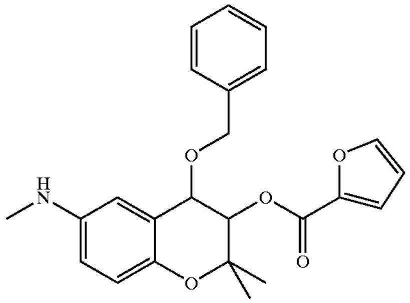 5-1530 | $^1H$ NMR(200MHz, $CDCl_3$) δ 7.60(m, 1H), 7.42~7.26(m, 5H), 7.18(d, 1H, J=3.5Hz), 6.79~6.63(m, 3H), 6.51~6.48(m, 1H), 5.47(d, 1H, J=5.0Hz), 4.78(s, 2H), 4.58(d, 1H, J=4.0Hz), 2.76(s, 3H), 1.44(s, 3H), 1.39(s, 3H); MS, m/z: 407.4 |

TABLE 3-continued
| Compound No. | NMR/MS Data |
| --- | --- |
| 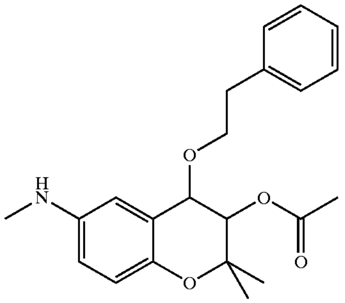 5-1531 | $^{1}$H NMR(200MHz, $CDCl_3$) δ 7.30~7.20(m, 5H), 6.70(d, 1H, J=8.7Hz), 6.56(dd, 1H, J=8.7Hz, J=2.6Hz), 6.39(d, 1H, J=6.7Hz), 2.91 (t, 2H, J=6.7Hz), 2.76(s, 3H), 2.08(s, 3H), 1.27(s, 6H); MS, m/z: 369.4 J = 2.6 Hz), 5.16(d, 1H, J = 5.3 Hz), 4.32(d, 1H, J = 5.3 Hz), 3.89(t, 2H, |
| 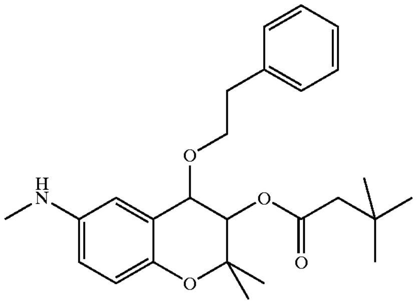 5-1532 | $^{1}$H NMR(200MHz, $CDCl_3$) δ 7.89~7.20(m, 5H), 6.72~6.07(m, 3H), 5.17(d, 1H, J=5.5Hz), 4.36(d, 1H, J=5.5Hz), 3.85(t, 2H, J=6.7Hz), 2.89(t, 2H, J=6.7Hz), 2.75(s, 3H), 2.17(s, 2H), 1.29(s, 3H), 1.27(s, 3H), 1.04(s, 9H); MS, m/z: 425.5 |
| 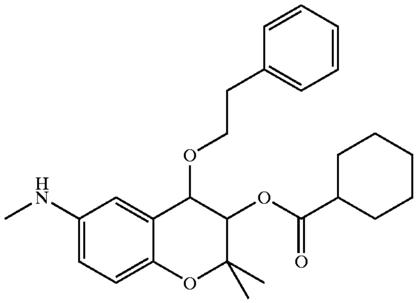 5-1533 | $^{1}$H NMR(200MHz, $CDCl_3$) δ 7.29~7.19(m, 5H), 6.71~6.37(m, 3H), 5.17(d, 1H, J=5.5Hz), 4.32(d, 1H, J=5.5Hz), 3.86(t, 2H, J=6.7Hz), 2.89(t, 2H, J=6.7Hz), 2.75(s, 3H), 2.33(m, 1H), 1.90~1.26(m, 17H); MS, m/z: 437.5 |

TABLE 3-continued
| Compound No. | NMR/MS Data |
| --- | --- |
| 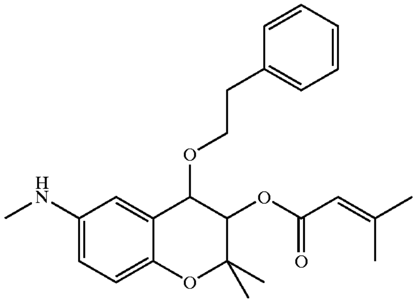 5-1534 | MS, m/z: 409.5 |
| 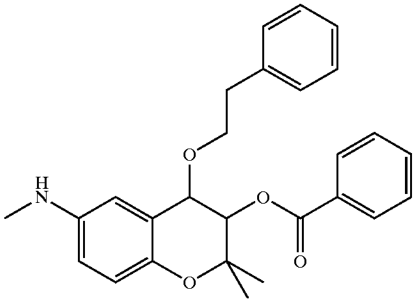 5-1535 | MS, m/z: 431.5 |
| 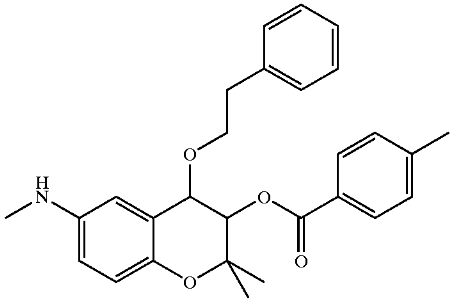 5-1536 | MS, m/z: 445.5 |
| 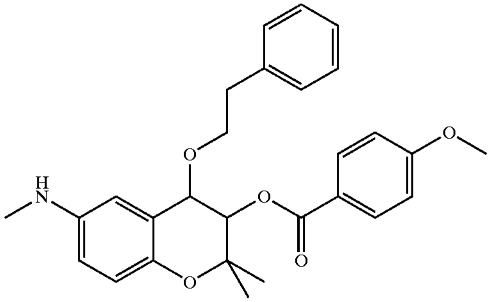 5-1537 | $^1H$ NMR(200MHz, $CDCl_3$) δ 8.01~7.96(m, 2H), 7.27~7.20(m, 5H), 6.93~6.51 (m, 5H), 5.37(d, 1H, J=5.0Hz), 4.43(d, 1H, J=5.0Hz), 3.96(m, 2H), 3.86(s, 3H), 2.90(m, 2H), 2.77(s, 3H), 1.37~1.30(m, 6H); MS, m/z: 461.5 |

TABLE 3-continued
| Compound No. | NMR/MS Data |
| --- | --- |
| 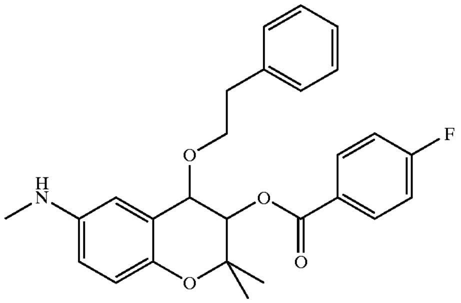 5-1538 | $^1$H NMR(200MHz, $CDCl_3$) δ 8.15~8.01(m, 2H), 7.28~7.24(m, 5H), 7.24~7.02(m, 2H), 6.79~6.24(m, 3H), 5.37(d, 1H, J=5.1 HZ), 4.45(d, 1H, J=5.1Hz), 3.95(t, 2H, J=6.8Hz), 2.90(t, 2H, J=6.8Hz), 2.75(s, 3H), 1.34(s, 3H), 1.31(s, 3H); MS, m/z: 437.5 |
| 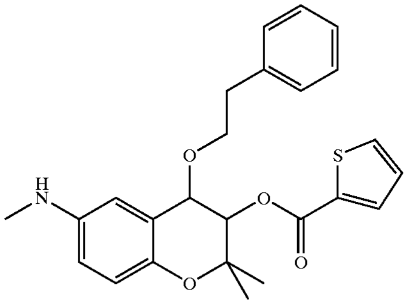 5-1539 | $^1$H NMR(200MHz, $CDCl_3$) δ 7.82(m, 1H). 7.57(m, 1H), 7.27~7.15(m, 5H), 7.09(m, 1H), 6.78~6.34(m, 3H), 5.35(d, 1H, J=5.9Hz), 4.50(d, 1H, J=5.9Hz), 3.94(t, 2H, J=6.7Hz), 2.90(t, 2H, J=6.7Hz), 2.74(s, 3H), 1.33(s, 6H); MS, m/z: 437.5 |
| 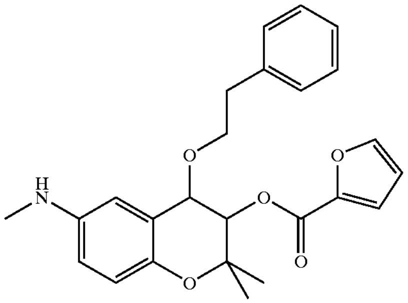 5-1540 | $^1$H NMR(200MHz, $CDCl_3$) δ 7.60(m, 1H), 7.26~7.18(m, 6H), 6.73~6.27(m, 4H), 5.36(d, 1H, J=5.7Hz), 4.48(d, 1H, J=5.7 Hz), 3.93(t, 2H, J=6.8Hz), 2.90(t, 2H, J=6.8Hz), 2.74(s, 3H), s, 6H); MS, m/z: 421 .5 |

TABLE 3-continued
| Compound No. | NMR/MS Data |
| --- | --- |
| 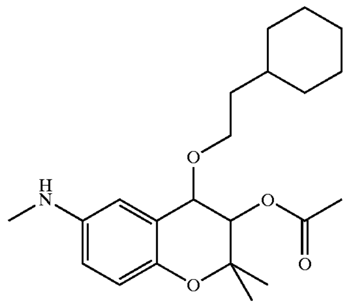 5-1541 | $^1$H NMR(200MHz, $CDCl_3$) δ 7.19~6.75(m, 3H), 5.14(d, 1H, J=4.5Hz), 4.23(d, 1H, J=4.5Hz), 3.71(m, 2H), 2.86(s, 3H), 2.07(s, 3H), 1.64~0.86(m, 13H), 1.33(s, 3H), 1.29(s, 3H); MS, m/z 375.5 |
| 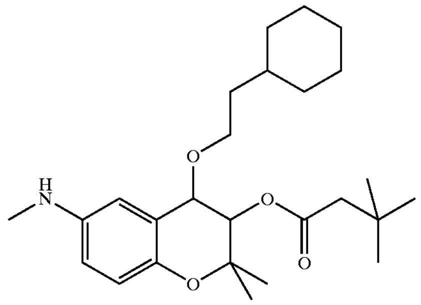 5-1542 | MS, m/z: 431.6 |
| 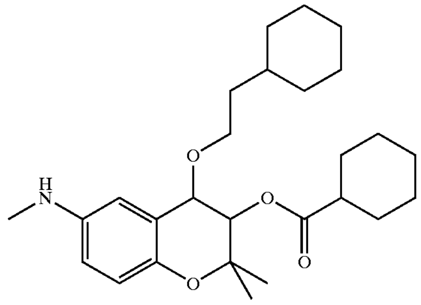 5-1543 | $^1$H NMR(200MHz, $CDCl_3$) δ 7.07~6.56(m, 3H), 5.15(d, 1H, J=4.9Hz), 4.22(d, 1H, J=4.9Hz), 3.69(m, 2H), 2.86(s, 3H), 2.30(m, 1H), 1.87~0.86(m, 13H), 1.32(s, 3H), 1.28(s, 3H); MS, m/z: 443.6 |

TABLE 3-continued
| Compound No. | NMR/MS Data | Compound No. | NMR/MS Data |
|---|---|---|---|
| 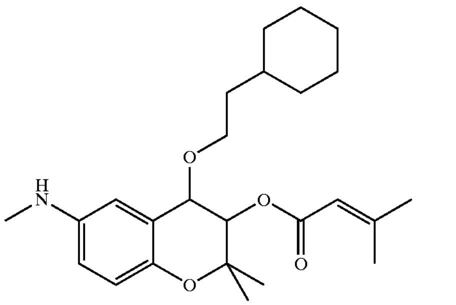 5-1544 | MS, m/z: 415.5 | 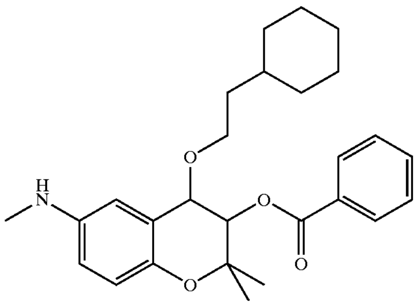 5-1545 | MS, m/z 437.5 |
| 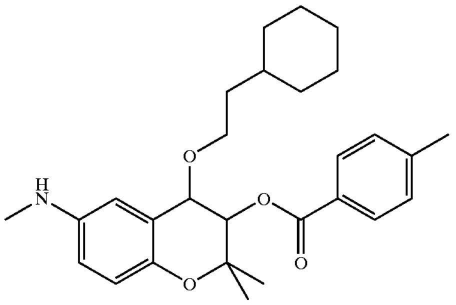 5-1546 | MS, m/z: 451.6 | 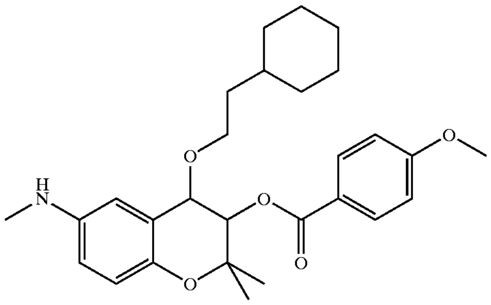 5-1547 | MS, m/z 467.6 |
| 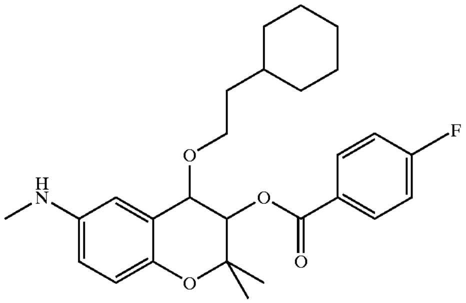 5-1548 | $^1$H NMR(200MHz, $CDCl_3$) δ 8.01(m, 2H), 7.27~6.84(m, 5H), 5.73(d, 1H, J=4.1Hz), 4.38(d, 1H, J=4.1Hz), 3.75(m, 2H), 2.89(s, 3H), 1.79~1.12(m, 19H); MS, m/z: 455.5 | | |

TABLE 3-continued
| Compound No. | NMR/MS Data |
|---|---|
| 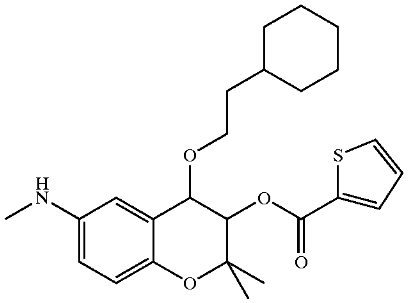 5-1549 | MS, m/z: 443.6 |
| 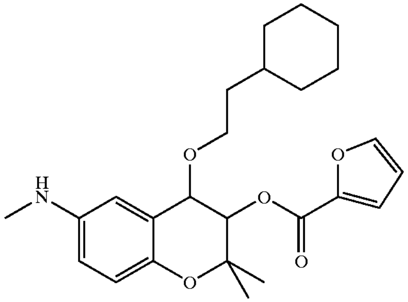 5-1550 | $^1$H NMR(200MHz, $CDCl_3$) δ 7.56(m, 1H), 7.13(m, 1H), 6.70(d, 1H, J=8.1Hz), 6.57~6.46(m, 3H), 5.36(d, 1H, J=5.5Hz), 4.43(d, 1H, J=5.5Hz), 3.68(m, 2H), 2.78(s, 3H), 1.62~0.86(m, 13H), 1.37(s, 3H), 1.33(s, 3H); MS, m/z: 427.5 |
| 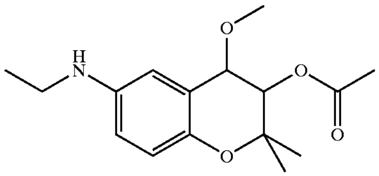 5-1551 | $^1$H NMR(200MHz, $CDCl_3$) δ 6.72~6.54(m, 3H), 5.22(d, 1H, J=5.5Hz), 4.30(d, 1H, J=5.5Hz), 3.43(s, 3H), 3.10(q, 2H, J=7.1Hz), 2.11(s, 3H), 1.34(s, 3H), 1.28(s, 3H), 1.20(m, 3H); MS, m/z: 293.3 |

TABLE 3-continued
| Compound No. | NMR/MS Data |
|---|---|
| 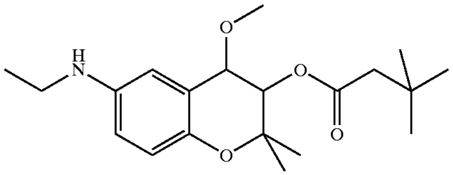 5-1552 | $^1$H NMR(200MHz, $CDCl_3$) δ 6.76~6.69(m, 3H), 5.24(d, 1H, J=5.7Hz), 4.33(d, 1H, J=5.9Hz), 3.41(s, 3H), 3.14(q, 2H, J=7.1Hz), 2.26(s, 2H), 1.36(s, 3H), 1.29(s, 3H), 1.24(m, 3H), 1.04(s, 9H); MS, m/z: 349.4 |
| 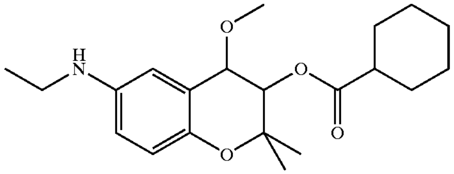 5-1553 | $^1$H NMR(200MHz, $CDCl_3$) δ 6.74~6.61(m, 3H), 5.22(d, 1H, J=5.6Hz), 4.28(d, 1H, J=5.6Hz), 3.43(s, 3H), 3.13(q, 2H, J=7.1Hz), 2.36(m, 1H), 2.00~1.21(br, 10Hz), 1.33(s, 3H), 1.28(s, 3H), 1.24(m, 3H); MS, m/z: 361.4 |
| 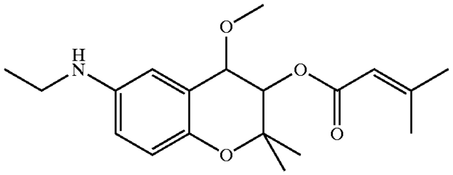 5-1554 | $^1$H NMR(200MHz, $CDCl_3$) δ 6.97~6.74(m, 3H), 5.71(d, 1H, J=1.5Hz), 5.24(d, 1H, J=5.0Hz), 4.26(d, 1H, J=5.0Hz), 3.49(s, 3H), 3.18(q, 2H, J=7.1Hz), 2.18(s, 3H), 1.89(s, 3H), 1.35(s, 3H), 1.31(s, 3H), 1.25(m, 3H); MS, m/z: 333.4 |
| 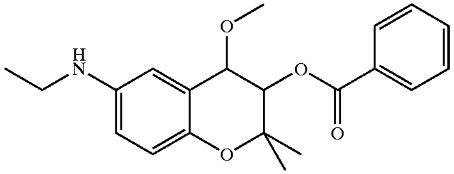 5-1555 | $^1$H NMR(200MHz, $CDCl_3$) δ 8.08~8.03(m, 2H), 7.58~7.53(m, 1H), 7.48~7.26(m, 2H), 6.82~6.75(m, 3H0, 5.47(d, 1H, J=5.5 Hz), 4.44(d, 1H, J=5.5Hz), 3.51(s, 3H), 3.15(q, 2H, J=7.2Hz), 1.41 (s, 3H), 1.39(s, 3H), 1.25(t, 3H, J=7.2Hz); MS, m/z: 355.4 |

TABLE 3-continued
| Compound No. | NMR/MS Data |
|---|---|
| 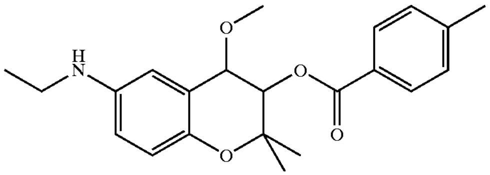 5-1556 | $^1H$ NMR(200MHz, $CDCl_3$) δ 7.03(d, 2H, J=7.6Hz), 7.23(d, 2H, J=7.6Hz), 6.82~6.75(m, 3H), 5.46(d, 1H, J=5.5Hz), 4.43(d, 1H, J=5.5Hz), 3.51(s, 3H), 3.15(q, 2H, J=7.2Hz), 2.41(s, 3H), 40(s, 3H), 1.38(s, 3H), 1.25(t, 3H, J=7.1Hz); MS, m/z: 369.4 |
| 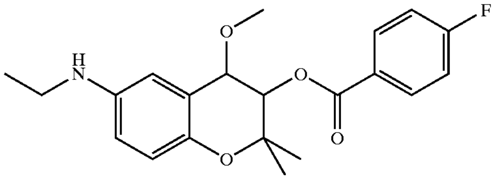 5-1558 | $^1H$ NMR(200MHz, $CDCl_3$) δ 8.10~8.03(m, 2H), 7.25~7.06(m, 2H), 6.78~6.64(m, 3H), 5.45(d, 1H, J=5.4Hz), 4.43(d, 1H, J=5.4Hz), 3.50(s, 3H), 3.13(q, 2H, J=7.1Hz), 1.40(s, 3H), 1.37(s, 3H), 1.24(t, 3H, J=7.1Hz); MS, m/z: 373.4 |
| 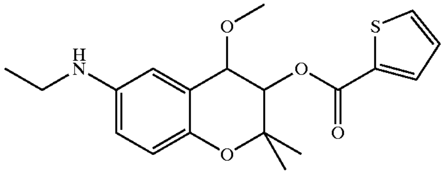 5-1559 | $^1H$ NMR(200MHz, $CDCl_3$) δ 7.85~7.82(m, 1H), 7.60~7.57(m, 1H), 7.13~7.09(m, 1H), 6.73(d, 1H, J=10.5 6.54(m, 2H), 5.42(d, 1H, J=6.2Hz), 4.50(d, 1H, J=6.2Hz), 3.47(s, 3H), 3.12(q, 2H, J=7.1Hz), 1.40(s, 3H), 1.36(s, 3H), 1.24(t, 3H, J=7.0Hz), ; MS, m/z: 361.4 |
| 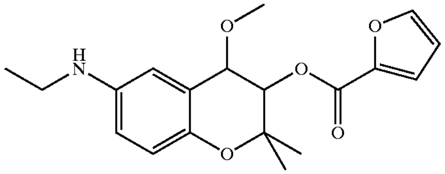 5-1560 | $^1H$ NMR(200MHz, $CDCl_3$) δ 7.60~7.56(m, 1H), 7.26~7.17(m, 1H), 6.75~6.47(m, 4H), 5.43(d, 1H, J=5.9Hz), 4.47(d, 1H, J=5.9Hz), 3.46(s, 3H), 3.07(q, 2H, J=7.2Hz), 1 .39(s, 3H), 1.35(s, 3H). 1.23(t, 3H, J=7.1Hz); MS, m/z: 345.4 |

TABLE 3-continued
| Compound No. | NMR/MS Data |
|---|---|
| 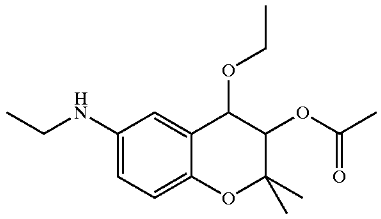 5-1561 | MS, m/z: 307.3 |
| 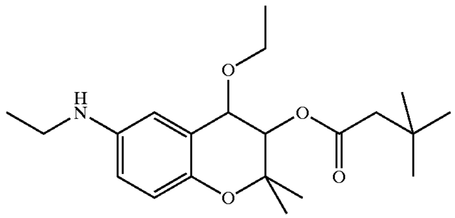 5-1562 | $^{1}$H NMR(200MHz, $CDCl_3$) δ 6.72~6.62(m, 3H), 5.21(d, 1H, J=5.7Hz), 4.37(d, 1H, J=5.7Hz), 3.65(q, 2H, J=7.1Hz), 3.12(q, 2H, J=7.1Hz), 2.26(s, 2H), 1.36(s, 3H), 1.29(s, 3H), 1.21(m, 3H), 1.04(s, 9H); MS, m/z: 307.3 |
| 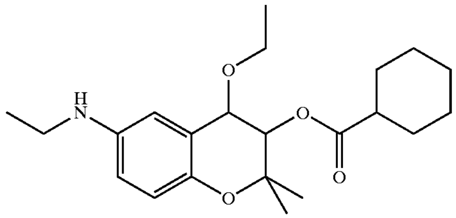 5-1563 | $^{1}$H NMR(200MHz, $CDCl_3$) δ 6.69(d, 1H, J=8.5Hz), 6.62~6.55(m, 2H), 5.19(d, 1H, J=5.7Hz), 4.32(d, 1H, J=5.7Hz), 3.65(q, 2H, J=7.1Hz), 3.10(q, 2H, J=7.1Hz), 2.35(m, 1H), 1.74~1.17(m, 16H), 1.33(s, 3H), 1.28(s, 3H); MS, m/z: 375.5 |
| 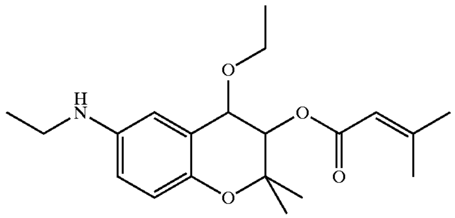 5-1564 | MS, m/z 347,4 |

TABLE 3-continued

| Compound No. | NMR/MS Data |
|---|---|
| 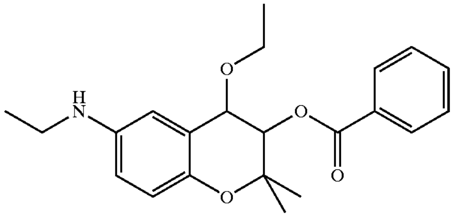 5-1565 | $^{1}H$ NMR(200MHz, $CDCl_3$) δ 8.07~8.03(m, 2H), 7.57~7.39(m, 3H), 6.78~6.61(m, 3H), 5.449d, 1H, J=5.4Hz), 4.48(d, 1H, J=5.4Hz), 3.76(q, 2H, J=7.1Hz), 3.13(q, 2H, J=7.1Hz), 1.41(s, 3H), 1.39(s, 3H), 1.28~1.19(m, 6H); MS, m/z: 369.4 |
| 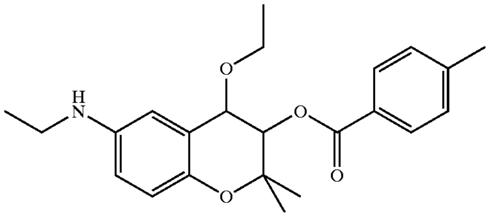 5-1566 | $^{1}H$ NMR(200MHz, $CDCl_3$) δ 7.93(d, 1H, J=8.1Hz), 7.23(d, 1H, J=8.0Hz), 6.78~6.68(m, 3H), 5.42(d, 1H, J=5.4Hz), 4.47(d, 1H, J=5.4Hz), 3.76(q, 2H, J=6.9Hz), 3.12(q, 2H, J=7.1Hz), 2.40(s, 3H), 1.40(s, 3H), 1.38(s, 3H), 1.29~1.18(m, 6H); MS, m/z: 383.4 |
| 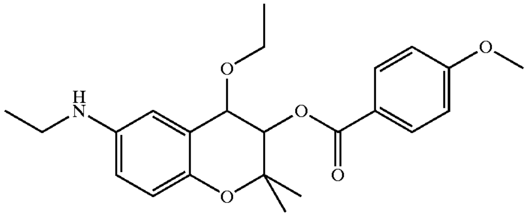 5-1567 | $^{1}H$ NMR(200MHz, $CDCl_3$) δ 8.00(d, 2H, J=9.0Hz), 6.90(d, 2H, J=9.0Hz), 6.76~6.71 (m, 3H), 5.41(d, 1H, J=5.4Hz), 4.46(d, 1H, J=5.4Hz), 3.85(s, 3H), 3.76(q, 2H, J=6.9Hz), 3.14(q, 2H, J=7.1Hz) 1.40(s, 3H), 1.38(s, 3H), 1.29~1.18(m, 6H); MS, m/z: 399.4 |
| 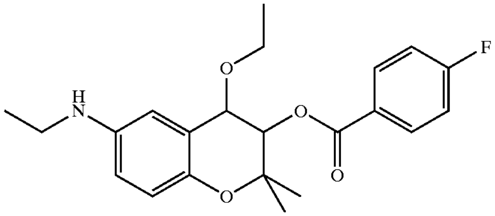 5-1568 | $^{1}H$ NMR(200MHz, $CDCl_3$) δ 8.09~8.02(m, 2H), 7.15~7.069 m, 2H), 6.74(d, 1H, J=8.5Hz), 6.64~6.58(m, 2H), 5.42(d, 1H, J=5.3Hz), 4.46(d, 1H, J=5.3Hz), 3.71(q, 2H, J=7.1Hz), 3.12(q, 2H, J=7.1Hz), 1.41(s, 3H), 1.37(s, 3H), 1.28~1.19(m, 6H); MS, m/z: 387.4 |

TABLE 3-continued
| Compound No. | NMR/MS Data |
| --- | --- |
| 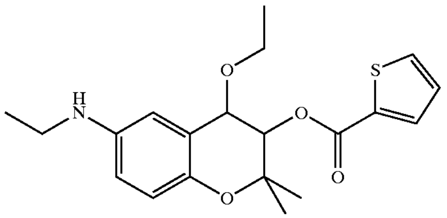 5-1569 | $^1H$ NMR(200MHz, $CDCl_3$) δ 7.84~7.81(m, 1H), 7.60~7.56(m, 1H), 7.13~7.08(m, 1H), 6.75~6.57(m, 3H), 5.37(d, 1H, J=5.9 Hz), 4.51(d, 1H, J=5.9Hz), 3.74(q, 2H, J=6.9Hz), 3.12(q, 2H, J=7.1Hz), 1.40(s, 3H), 1.36(s, 3H), 1.28~1.15(m, 6H); MS, m/z: 375.4 |
| 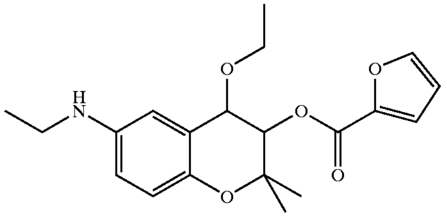 5-1570 | $^1H$ NMR(200MHz, $CDCl_3$) δ 7.60(m, 1H0, 7.20~7.18(m, 1H), 6.72(d, 1H, J=8.5Hz), 6.66~6.49(m, 2H), 5.39(d, 1H, J=5.7 Hz), 4.49(d, 1H, J=5.7Hz), 3.72(q, 2H, J=6.9Hz), 3.12(q, 2H, J=7.1Hz), 1.40(s, 3H), 1.35(s, 3H), 1.28~1.18(m, 6H); MS, m/z: 359.4 |
| 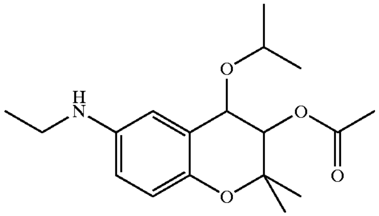 5-1571 | MS, m/z: 321.4 |
| 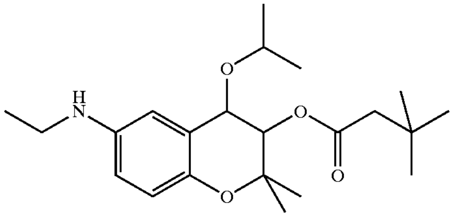 5-1572 | MS, m/z: 377.5 |

TABLE 3-continued
| Compound No. | NMR/MS Data | Compound No. | NMR/MS Data |
|---|---|---|---|
| 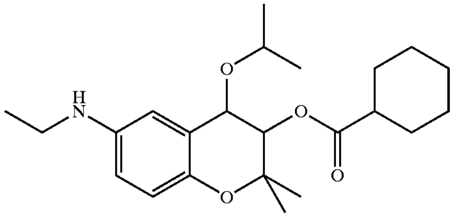 5-1573 | MS, m/z: 389.5 | 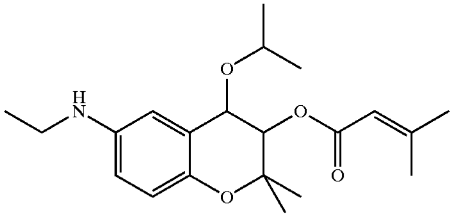 5-1572 | MS, m/z: 361.4 |
| 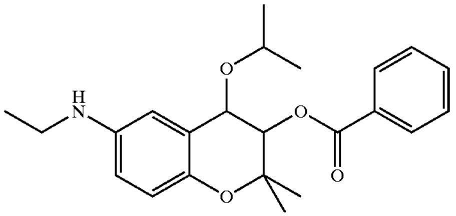 5-1575 | MS, m/z: 383.4 | 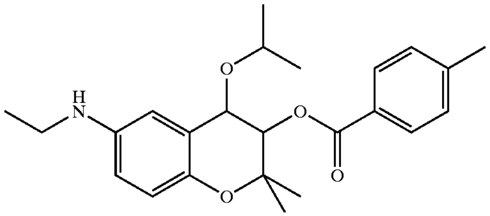 5-1576 | MS, m/z: 397.5 |
| 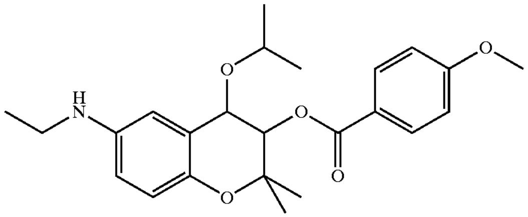 5-1577 | MS, m/z: 413.5 | 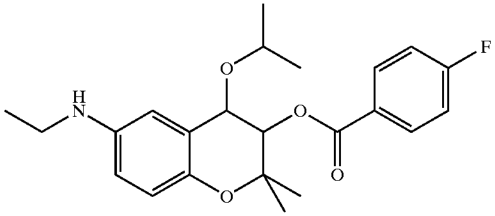 5-1578 | MS, m/z: 401.3 |
| 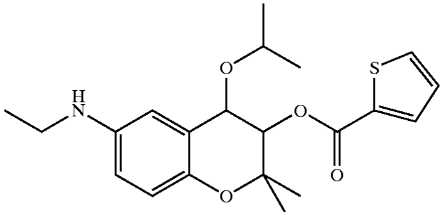 5-1579 | MS, m/z: 389.5 | 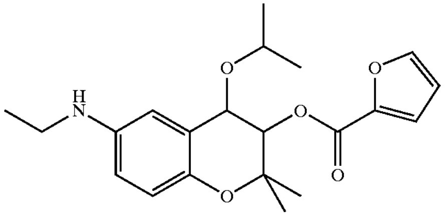 5-1580 | MS, m/z: 373.4 |

TABLE 3-continued
| Compound No. | NMR/MS Data |
| --- | --- |
| 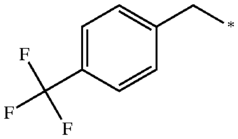 | $^1H$ NMR(200MHz, $CDCl_3$) δ 6.69(d, 1H, J=8.3Hz), 6.57~6.52(m, 2H), 5.19(d, 1H, J=5.1Hz), 4.30(d, 1H, J=5.1Hz), 3.64(m, 2H), 3.11(q, 2H, J=7.1Hz), 2.10(s, 3H), 1.55(m, 2H), 1.42(m, 2H), 1.35(s, 3H), 1.29(s, 3H); MS, m/z: 335.4 |
| 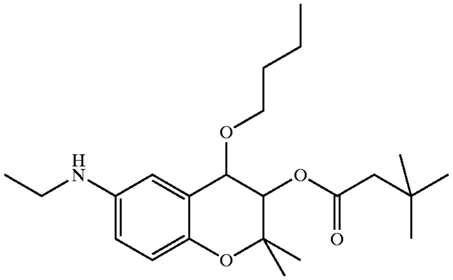 5-1582 | MS, m/z: 391.5 |
| 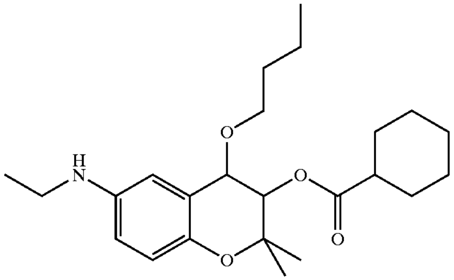 5-1583 | MS, m/z: 403.5 |
| 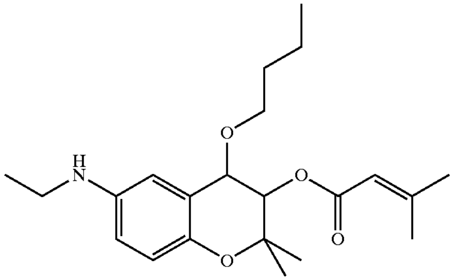 5-1584 | $^1H$ NMR(200MHz, $CDCl_3$) δ 6.72~6.52(m, 3H), 5.71(d, 1H, J=1.2Hz), 5.21(d, 1H, J=5.2Hz), 3.68(m, 2H), 2.17(s, 3H), 1.89(s, 3H), 1.54(m, 2H), 1.42(m, 2H), 1.35(s, 3H), 1.30(s, 3H), 1.24(t, 3H, J=7.1Hz), 0.91(t, 3H, J=7.2Hz); MS, m/z: 375.5 |

TABLE 3-continued
| Compound No. | NMR/MS Data |
|---|---|
| 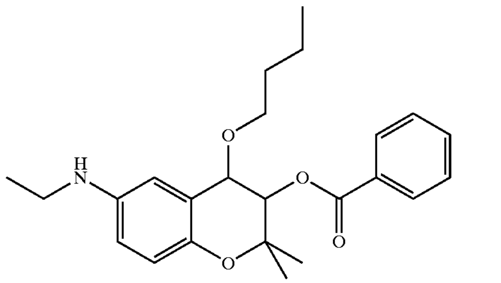 5-1585 | $^{1}H$ NMR(200MHz, $CDCl_3$) δ 8.07~8.02(m, 2H), 7.57~7.26(m, 3H), 6.77~6.59(m, 3H), 5.43(d, 1H, J=5.3Hz), 4.45(d, 1H, J=5.3Hz), 3.72(m, 2H), 3.10(m, 2H), 1.54(m, 2H), 1.45(m, 2H), 1.41 (s, 3H), 1.39(s, 3H), 1.24(m, 3H), 0.88(t, 3H, J=7.2 Hz); MS, m/z: 397.5 |
| 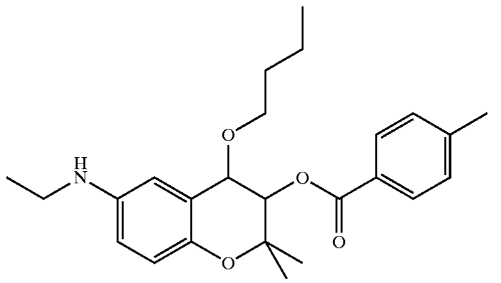 5-1586 | $^{1}H$ NMR(200MHz, $CDCl_3$) δ 7.93(d, 2H, J=8.6Hz), 7.25~7.20(m, 2H), 6.74(d, 1H, J=8.5Hz), 6.65~6.63(m, 2H), 5.42(d, 1H, J=5.3Hz), 4.44(d, 1H, J=5.3Hz), 3.72(q, 2H, J=7.1Hz), 2.40(s, 3H), 1.55(m, 2H), 1.43~1.28(m, 2H), 1.40(s, 3H), 1.37(s, 3H), 1.24(t, 3H, J=7.1Hz), 0.88(t, 3H, J=7.2Hz); MS, m/z: 411.5 |
| 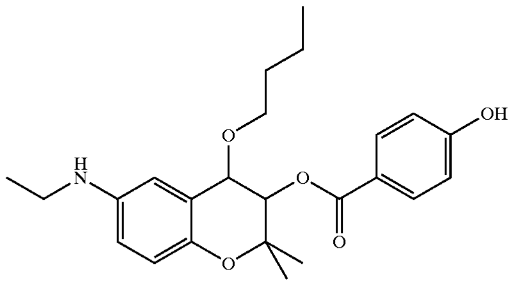 5-1587 | $^{1}H$ NMR(200MHz, $CDCl_3$) δ 7.99(d, 2H, J=8.2Hz), 6.90(d, 2H, J=8.2Hz), 5.40(d, 1H, J=4.5Hz), 4.42(d, 1H, J=4.5Hz), 3.85(s, 3H-), 3.71(m, 2H), 3.11(m, 2H), 1.57~1.35(m, 4H), 1.40(s, 3H), 1.37(s, 3H), 1.24(m, 3H), 0.88(t, 3H, J=7.1Hz); MS, m/z: 413.5 |

TABLE 3-continued
| Compound No. | NMR/MS Data |
|---|---|
| 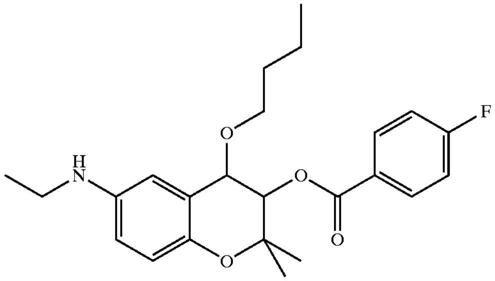 5-1588 | MS, m/z: 415.5 |
| 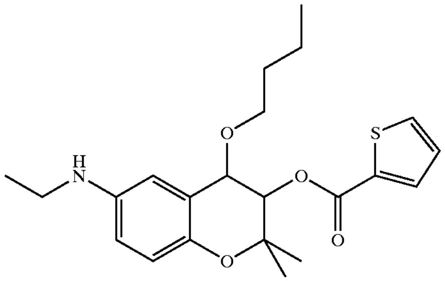 5-1589 | $^1$H NMR(200MHz, $CDCl_3$) δ 7.84~7.81(m, 1H), 7.59~7.56(m, 1H), 7.13~7.08(m, 1H), 6.72(d, 1H, J=8.5Hz), 6.64~6.54(m, 2H), 5.37(d, 1H, J=6.0Hz), 4.48(d, 1H, J=6.0Hz), 3.70(t, 2H, J=6.4Hz), 3.11(q, 2H, J=7.1Hz), 1.61~1.46(m, 2H), 1.43~1.32(m, 2H), 1.40(s, 3H), 1.36(s, 3H), 1.24(t, 3H, J=7.1Hz), 0.88(t, 3H, J=7.1Hz); MS, m/z: 403.5 |
| 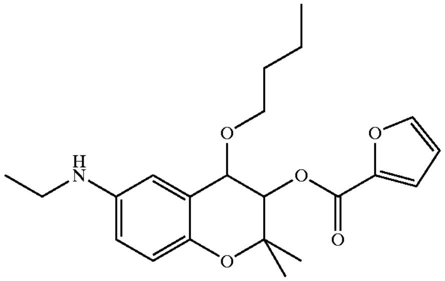 5-1590 | $^1$H NMR(200MHz, $CDCl_3$) δ 7.59(m, 1H), 7.20~7.18(m, 2H), 6.72(d, 1H, J=8.5Hz), 6.62~6.49(m, 3H), 5.39(d, 1H, J=5.6 Hz), 4.45(d, 1H, J=5.6Hz), 3.69(t, 2H, J=6.9Hz), 3.10(q, 2H, J=7.2Hz), 1.55(m,.2H), 1.51~1.35(m, 2H), 1.39(s, 3H), 1.35(s, 3H), 1.24(t, 3H, J=7.1Hz), 0.88(t, 3H, J=7.2Hz); MS, m/z: 387.4 |

TABLE 3-continued
| Compound No. | NMR/MS Data |
| --- | --- |
| 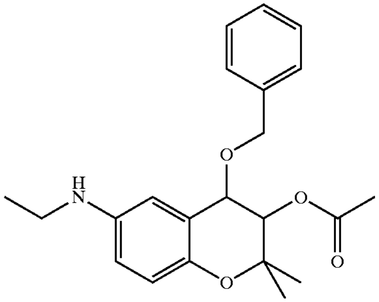 5-1591 | $^1H$ NMR(200MHz, $CDCl_3$) δ 7.42~7.24(m, 5H), 6.73~6.47(m, 3H), 5.27(d, 1H, J=4.7Hz), 4.72(s, 2H), 4.42(d, 1H, J=4.7 Hz), 3.05(q, 2H, J=7.1Hz), 2.10(s, 3H), 1.39(s, 3H), 1.33(s, 3H), 1.22(t, 3H, J=7.1Hz); MS, m/z: 369.4 |
| 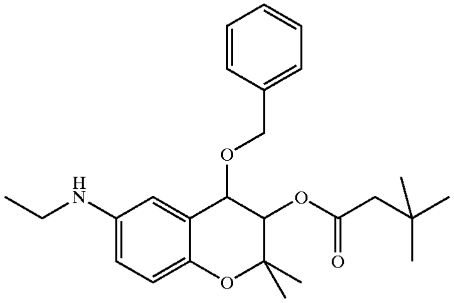 5-1592 | $^1H$ NMR(200MHz, $CDCl_3$) δ 7.42~7.28(m, 5H), 6.70(d, 1H, J=8.5Hz), 6.57~6.43(m, 2H), 5.29(d, 1H, J=5.0Hz), 4.70(s, 2H), 4.44(d, 1H, J=5.0Hz), 3.04(q, 2H, J=7.1Hz), 2.25(s, 2H), 1.40(s, 3H), 1.33(s, 3H), 1.21(t ,3H, J=7.1Hz), 1.02(s, 9H); MS, m/z: 425.5 |
| 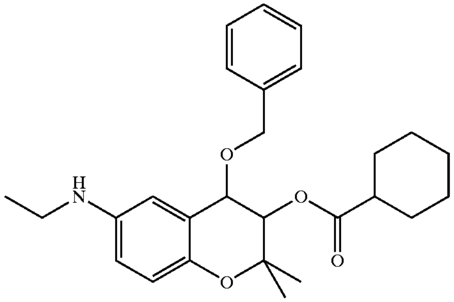 5-1593 | $^1H$ NMR(200MHz, $CDCl_3$) δ 7.41~7.26(m, 5H), 6.70(d, 1H, J=8.5Hz), 6.57~6.47(m, 2H), 5.29(d, 1H, J=5.1Hz), 4.70(s, 2H), 4.41(d, 1H, J=5.1Hz), 3.05(q, 2H, J=7.1Hz), 2.35(m, 1H), 2.00~1.18(m, 10H), 1.38(s, 3H), 1.32(s, 3H), 1.21(m, 3H); MS, m/z: 437.5 |

TABLE 3-continued
| Compound No. | NMR/MS Data |
| --- | --- |
| 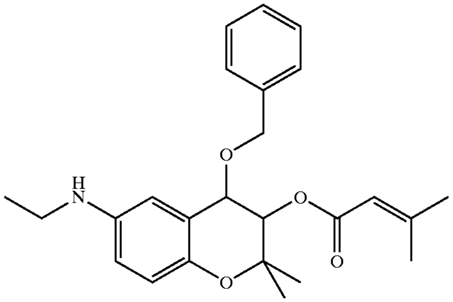 5-1594 | MS, m/z: 409.5 |
| 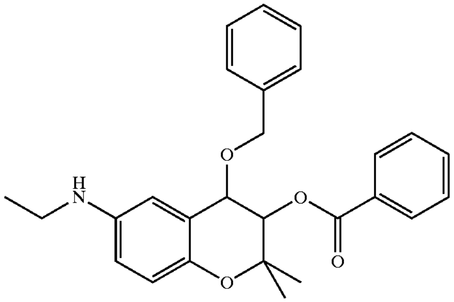 5-1595 | MS, m/z: 431.5 |
| 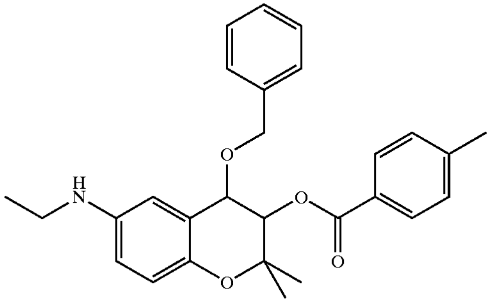 5-1596 | MS, m/zL 445.5 |
| 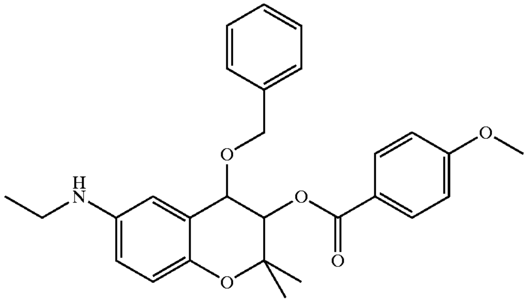 5-1597 | $^1H$ NMR(200MHz, $CDCl_3$) δ 8.01(d, 2H, J=8.9Hz), 7.40~7.27(m,SH), 6.90(d, 2H, J=8.9Hz), 6.75(d, 1H, J=8.6Hz), 6.64~6.28(m, 2H), 5.49(d, 1H, J=4.9Hz), 4.79(s, 2H), 4.56(d, 1H, J=4.9Hz), 3.85(s, 3H), 3.05(q, 2H, J=7.0Hz), 1.44(s, 3H), 1.40(s, 3H), 1.21(m, 3H); MS, m/z: 461.5 |

TABLE 3-continued
| Compound No. | NMR/MS Data |
| --- | --- |
| 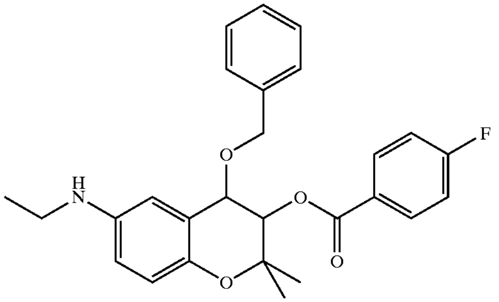 5-1598 | MS, m/z: 449.5 |
| 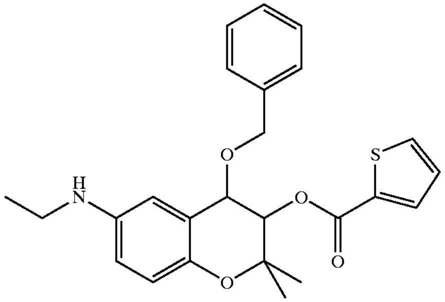 5-1599 | $^1$H NMR(200MHz, $CDCl_3$) δ 7.84~7.82(m, 1H), 7.60(m, 1H), 7.40~7.26(m, 5H), 6.73(d ,1H, J=8.3Hz), 6.59~6.51(m, 2H), 5.47(d, 1H, J=5.3Hz), 4.77(s, 2H), 4.62(d, 1H, J=5.3Hz), 3.03(q, 2H, J=7.1Hz), 1.44(s, 3H), 1.39(s, 3H), 1.21(t, 3H, J=7.1Hz); MS, m/z: 437.5 |
| 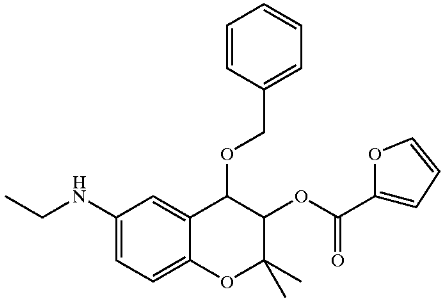 5-1600 | $^1$H NMR(200MHz, $CDCl_3$) δ 7.60~7.59(m, 1H), 7.41~7.18(m, 6H), 6.73(d, 1H, J=8.5Hz), 6.59~6.45(m, 3H), 5.47(d, 1H, J=5.1Hz), 4.77(s, 2H), 4.58(d, 1H, J=5.0Hz), 3.10~3.02(m, 2H), 1.43(s, 3H), 1.39(s, 3H), 1.21(m, 3H); MS, m/z: 421.5 |

TABLE 3-continued
| Compound No. | NMR/MS Data |
|---|---|
| 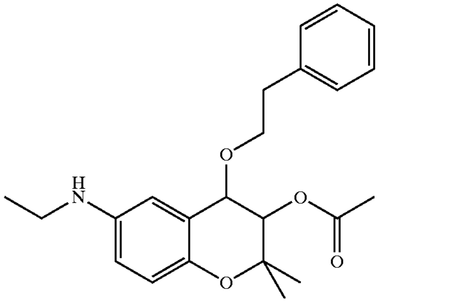 5-1601 | MS, m/z: 383.4 |
| 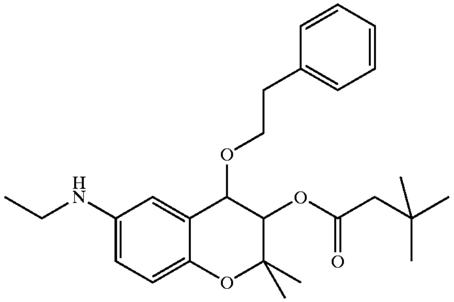 5-1602 | MS, m/z: 439.6 |
| 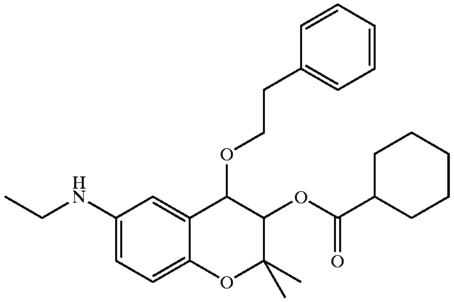 5-1603 | MS, m/z: 451.6 |
| 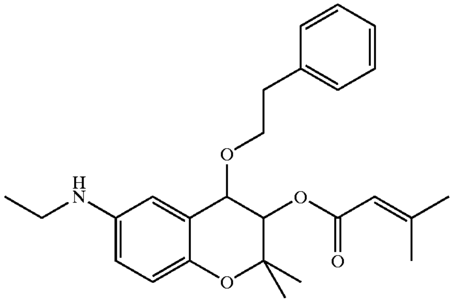 5-1604 | MS, m/z: 423.5 |
| 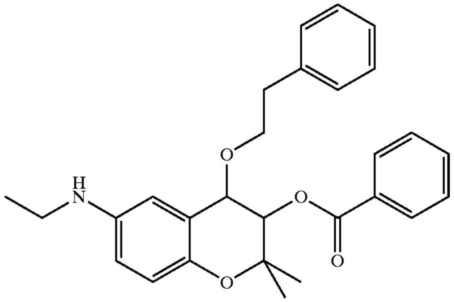 5-1605 | MS, m/z: 445.4 |
| 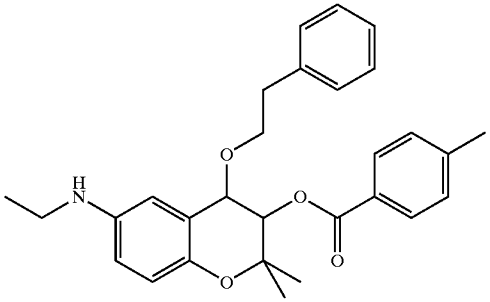 5-1606 | MS, m/z: 459.5 |

TABLE 3-continued
| Compound No. | NMR/MS Data | Compound No. | NMR/MS Data |
|---|---|---|---|
| 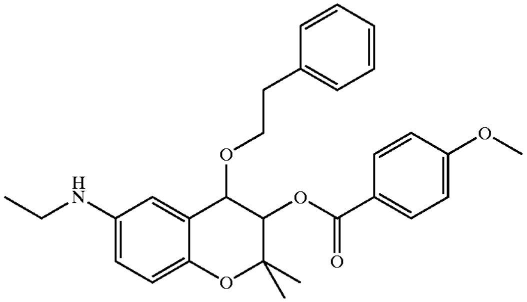 5-1607 | MS, m/z: 475.5 | 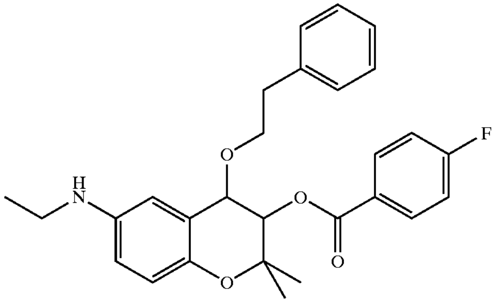 5-1608 | MS, m/z: 463.5 |
| 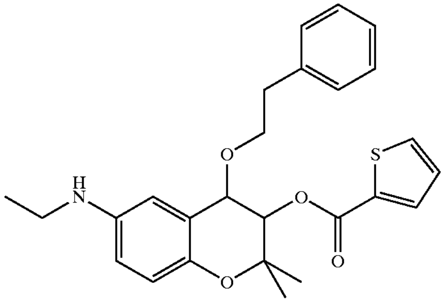 5-1609 | MS, m/z: 451.5 | 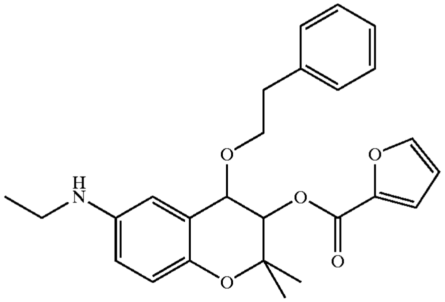 5-1610 | MS, m/z: 435.5 |
| 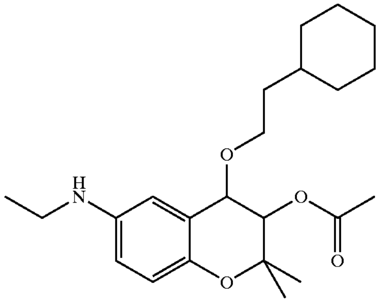 5-1611 | MS, m/z: 389.5 | 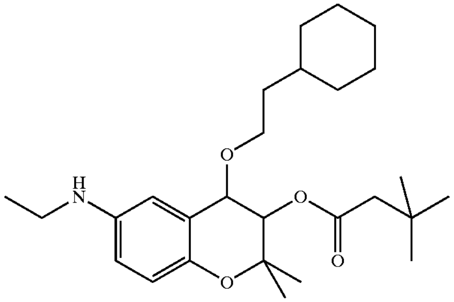 5-1612 | MS, m/z: 445.6 |

TABLE 3-continued
| Compound No. | NMR/MS Data |
| --- | --- |
| 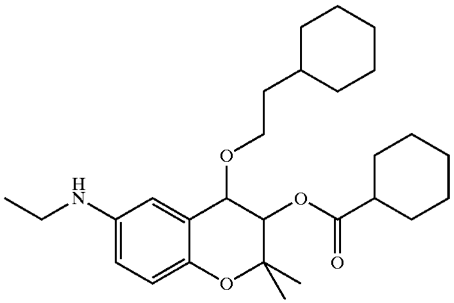 5-1613 | MS, m/z: 457.6 |
| 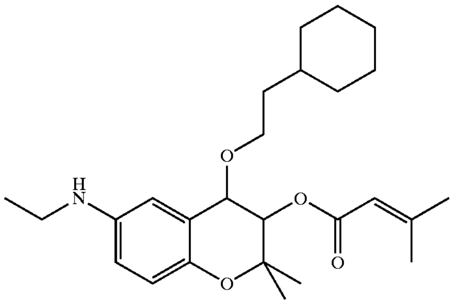 5-1614 | MS, m/z: 429.6 |
| 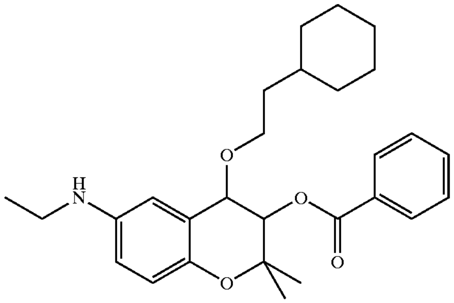 5-1615 | MS, m/z: 451.6 |
| 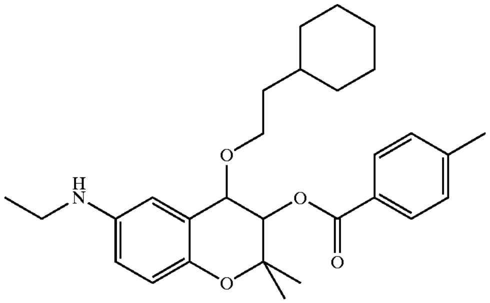 5-1616 | MS, m/z: 465.6 |
| 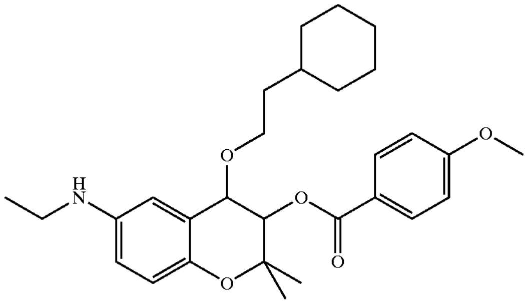 5-1617 | MS, m/z: 481.6 |
| 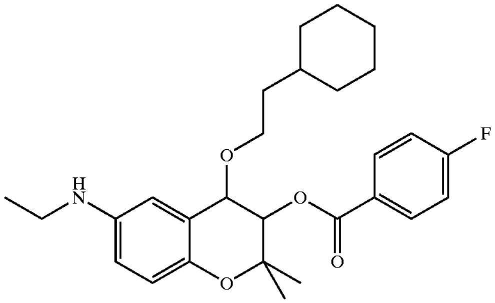 5-1618 | MS, m/z: 469.6 |

TABLE 3-continued
| Compound No. | | NMR/MS Data |
|---|---|---|
| 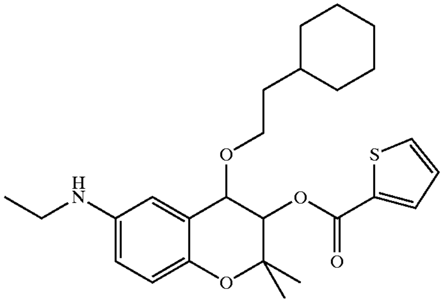 | 5-1619 | MS, m/z: 457.6 |
| 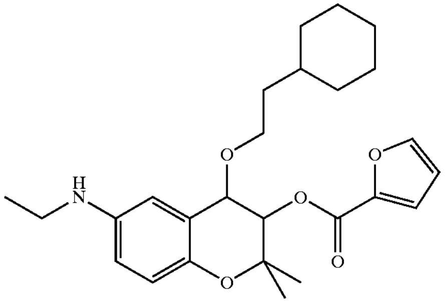 | 5-1620 | MS, m/z: 441.5 |
| 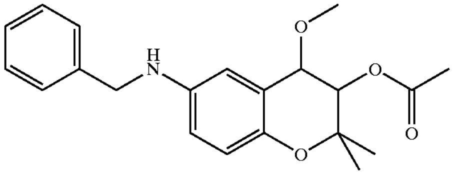 | 5-1621 | $^{1}$H NMR(200MHz, $CDCl_3$) δ 7.25~7.37(m, 5H), 6.59~6.70(m, 3H), 5.18(d, 1H, J=5.09Hz), 4.28(d, 1H, J=5.09 Hz), 4.27(s, 2H), 3.56~3.60(m, 2H), 2.10(s, 3H), 2.03~2.09(m, 1H), 1.38~1.50(m, 2H), 1.35(s, 3H), 1.29(s, 3H), 1.26~1.35(m, 2H), 0.91(t, 3H, J=7.12Hz) MS, m/z: 355.4 |
| 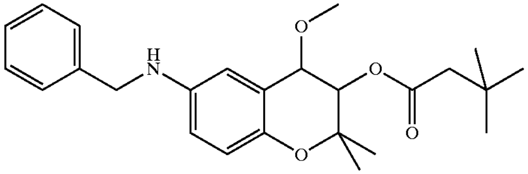 | 5-1622 | MS, m/z: 411.5 |
| 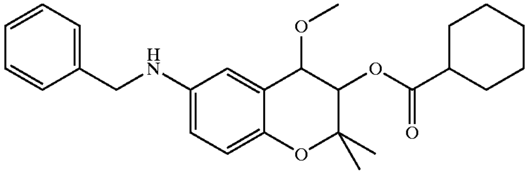 | 5-1623 | $^{1}$H NMR(200MHz, $CDCl_3$) δ 7.23~7.40(m, 5H), 6.54~6.71(m, 3H), 5.18(d, 1H, J=5.49Hz), 4.28(d, 1H, J=5.49 Hz), 4.27(s, 2H), 3.52~3.61(m, 2H), 2.29~2.34(m, 1H), 1.30~1.89(m, 14H), 1.33(s, 3H), 1.27(s, 3H), 0.90(t, 3H, J=7.12Hz); MS, m/z: 423.5 |

TABLE 3-continued
| Compound No. | | NMR/MS Data |
|---|---|---|
| 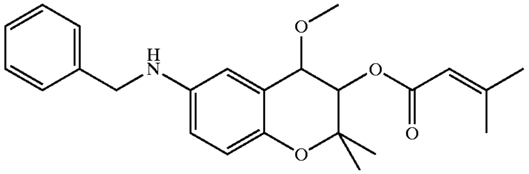 | 5-1624 | MS, m/z: 395.5 |
| 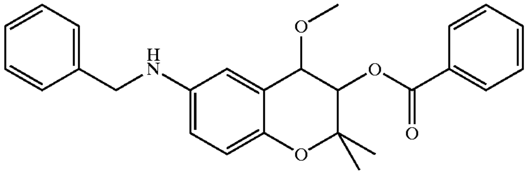 | 5-1625 | MS, m/z: 417.5 |
| 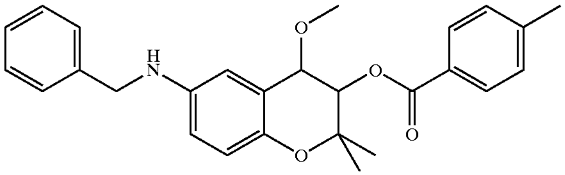 | 5-1626 | MS, m/z: 431.5 |
| 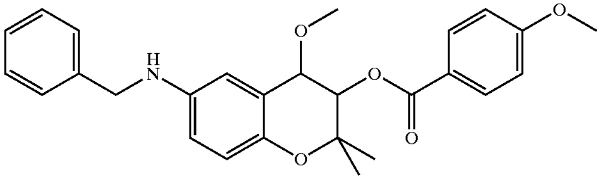 | 5-1627 | MS, m/z: 447.5 |
| 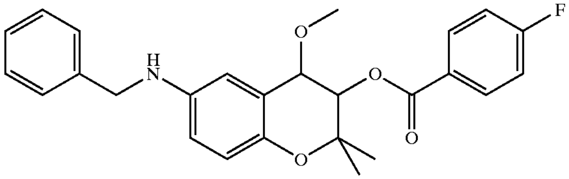 | 5-1628 | MS, m/z: 435.5 |
| 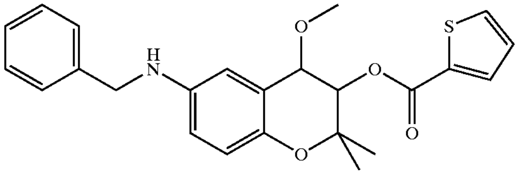 | 5-1629 | MS, m/z: 423.5 |
| 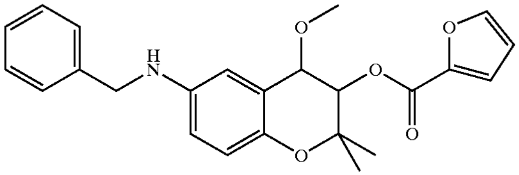 | 5-1630 | MS, m/z: 407.4 |
| 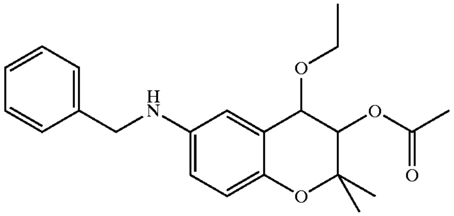 | 5-1631 | MS, m/z: 369.4 |

TABLE 3-continued
| Compound No. | | NMR/MS Data |
|---|---|---|
| 5-1632 | 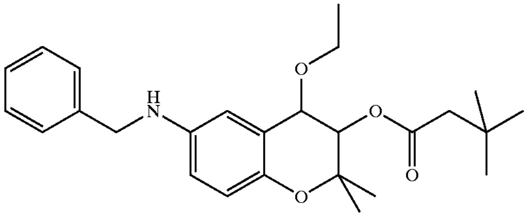 | MS, m/z: 425.5 |
| 5-1633 | 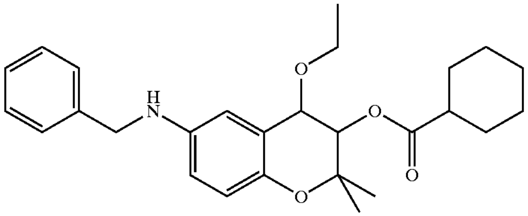 | MS, m/z: 437.5 |
| 5-1634 | 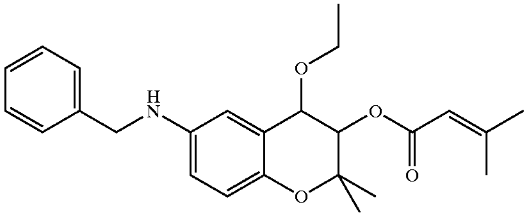 | MS, m/z: 409.5 |
| 5-1635 | 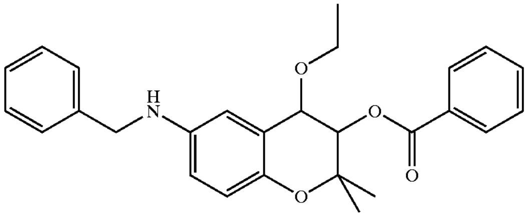 | MS, m/z: 431.5 |
| 5-1636 | 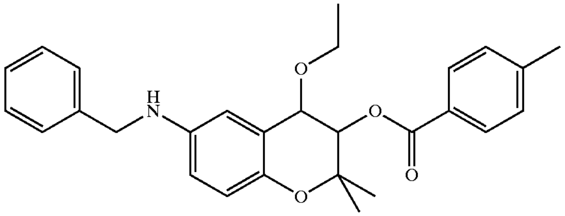 | MS, m/z: 445.5 |
| 5-1637 | 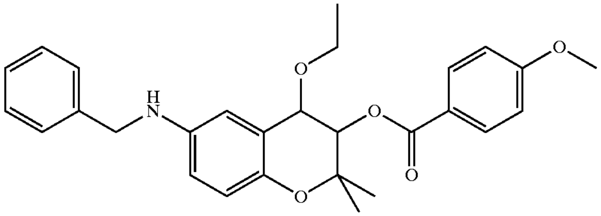 | MS, m/z: 461.5 |
| 5-1638 | 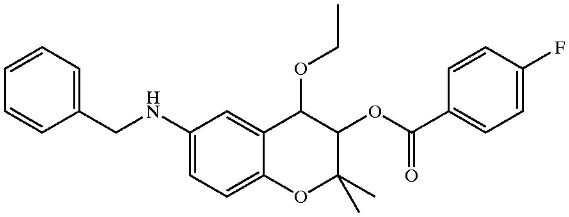 | MS, m/z: 449.5 |
| 5-1639 | 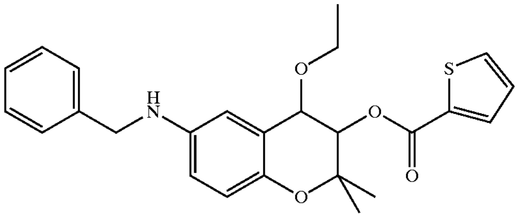 | MS, m/z: 437.5 |

TABLE 3-continued
| Compound No. | NMR/MS Data | Compound No. | NMR/MS Data |
|---|---|---|---|
| 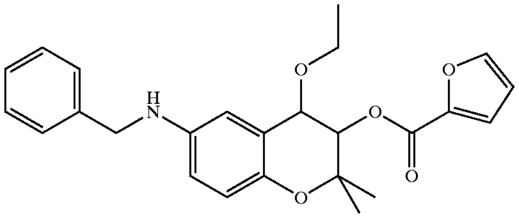 5-1640 | MS, m/z: 421.5 | 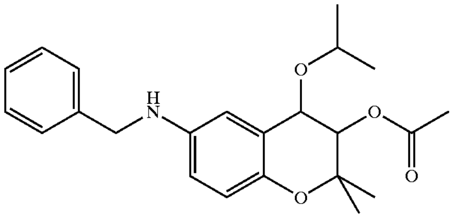 5-1641 | MS, m/z: 383.4 |
| 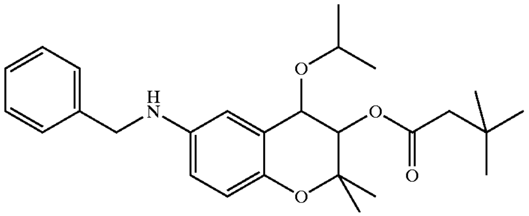 5-1642 | MS, m/z: 439.6 | 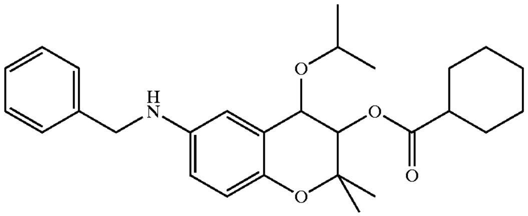 5-1643 | MS, m/z: 451.6 |
| 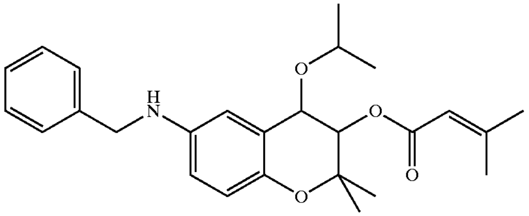 5-1644 | MS, m/z: 423.5 | 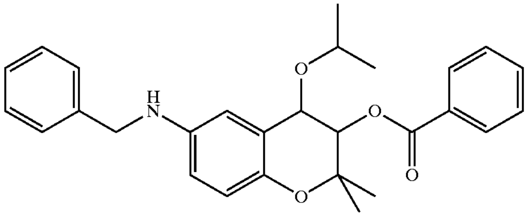 5-1645 | MS, m/z: 445.5 |
| 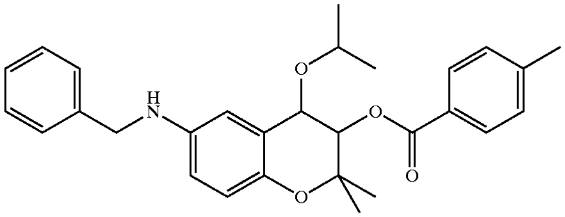 5-1646 | MS, m/z: 495.5 | 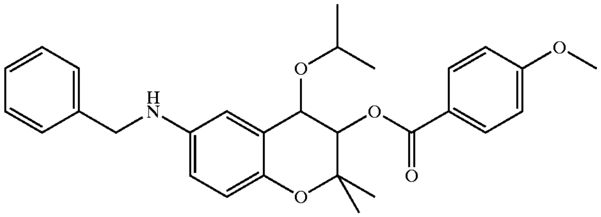 5-1647 | MS, m/z: 475.5 |

TABLE 3-continued
| Compound No. | NMR/MS Data |
|---|---|
| 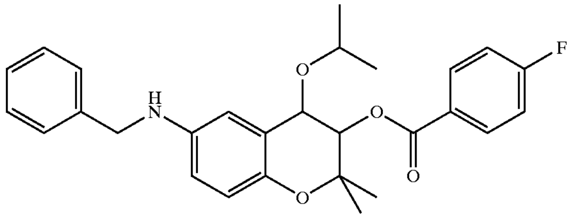 5-1648 | MS, m/z: 463.5 |
| 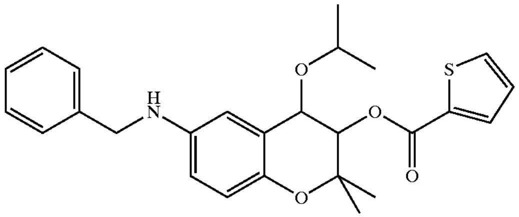 5-1649 | MS, m/z: 451.5 |
| 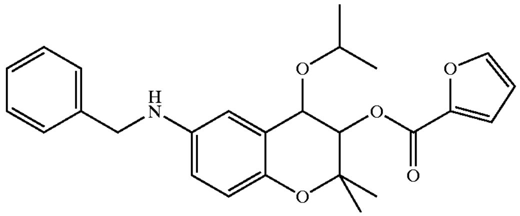 5-1650 | MS, m/z: 435.5 |
| 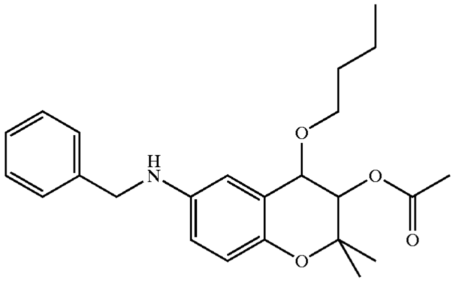 5-1651 | MS, m/z: 397.5 |
| 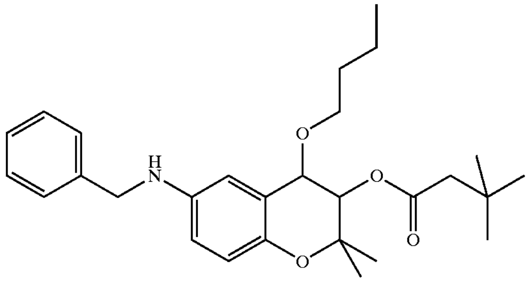 5-1652 | MS, m/z: 453.6 |
| 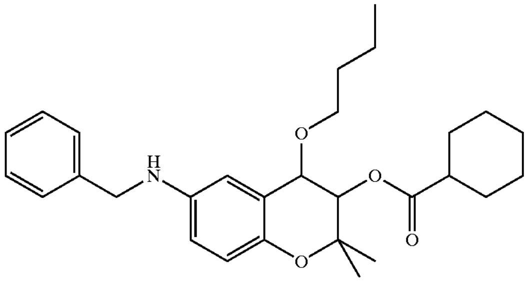 5-1653 | MS, m/z: 465.5 |

TABLE 3-continued
| Compound No. | NMR/MS Data |
|---|---|
| 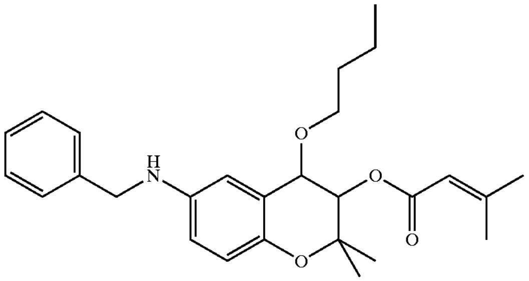 5-1654 | MS, m/z: 427.5 |
| 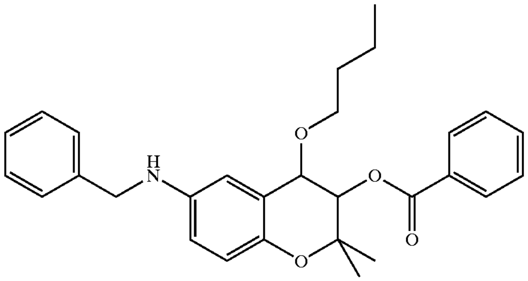 5-1655 | MS, m/z: 459.5 |
| 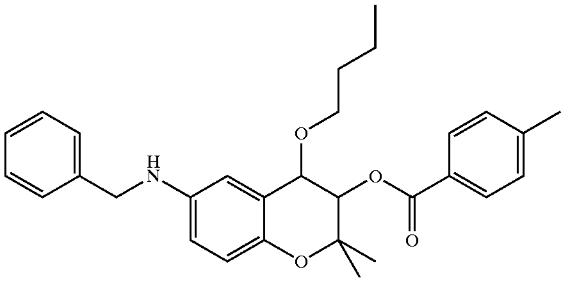 5-1656 | MS, m/z: 473.6 |
| 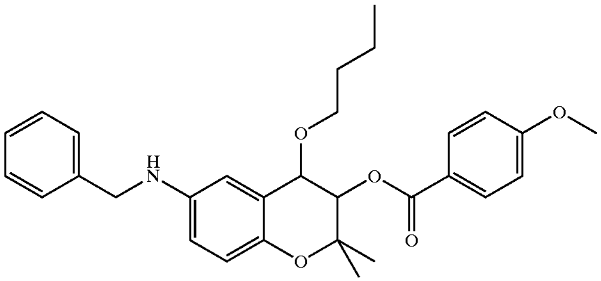 5-1657 | MS, m/z: 489.6 |
| 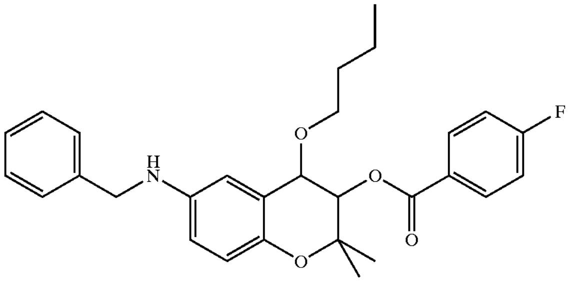 5-1658 | MS, m/z: 477.5 |
| 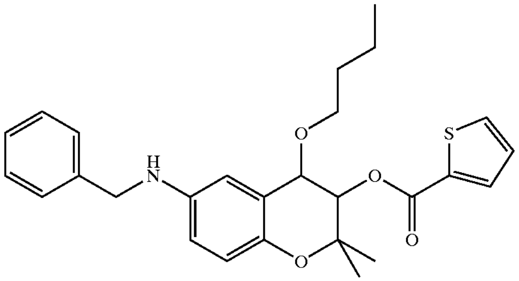 5-1659 | MS, m/z: 465.6 |

TABLE 3-continued
| Compound No. | NMR/MS Data |
| --- | --- |
| 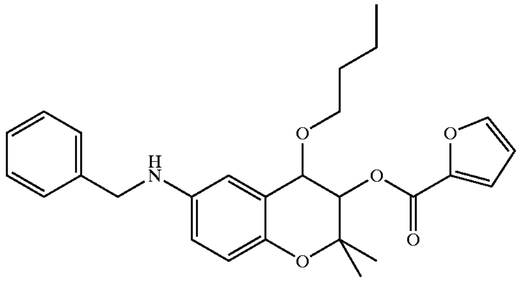 5-1660 | MS, m/z: 449.5 |
| 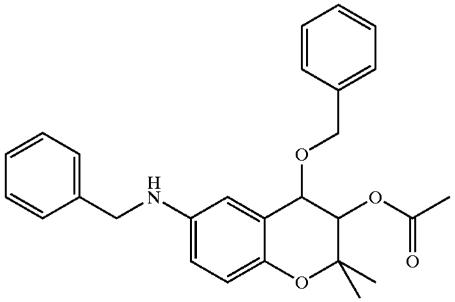 5-1661 | MS, m/z: 431.5 |
| 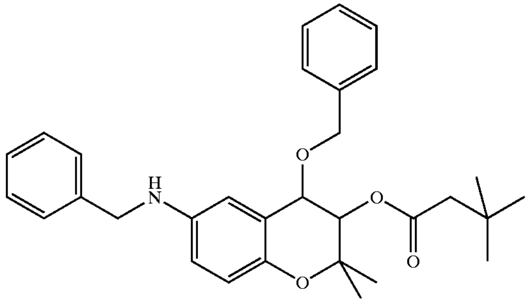 5-1662 | MS, m/z: 487.6 |
| 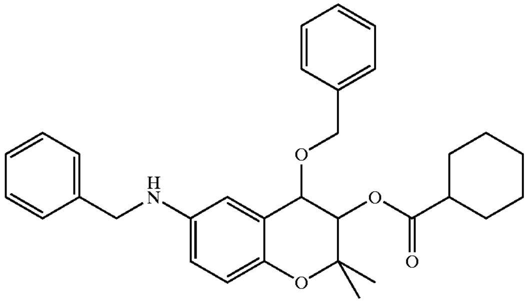 5-1663 | MS, m/z: 499.6 |
| 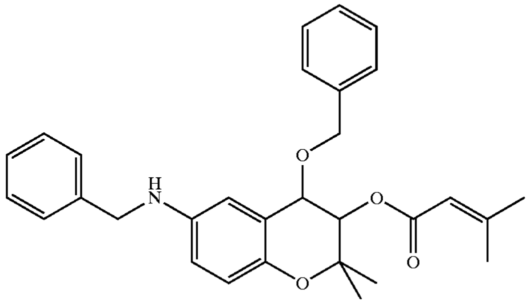 5-1664 | MS, m/z: 471.6 |
| 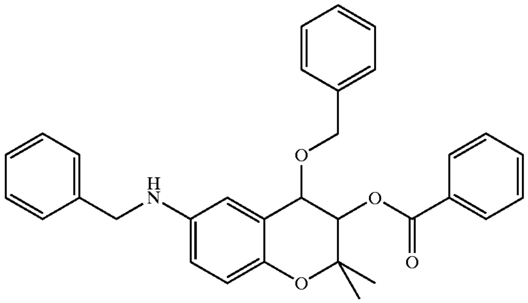 5-1665 | MS, m/z: 493.6 |

TABLE 3-continued
| Compound No. | NMR/MS Data | Compound No. | NMR/MS Data |
|---|---|---|---|
| 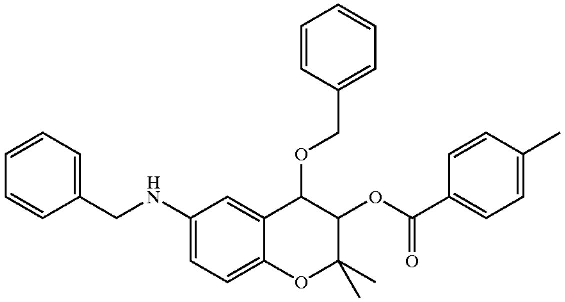 5-1666 | MS, m/z: 507.6 | 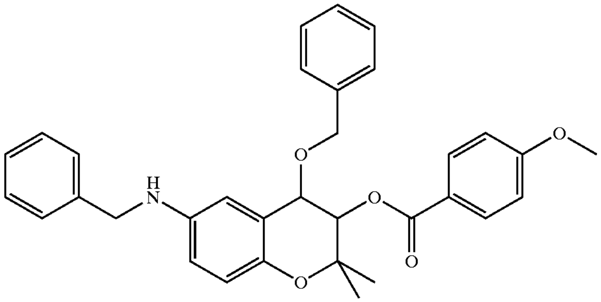 5-1667 | MS, m/z: 523.6 |
| 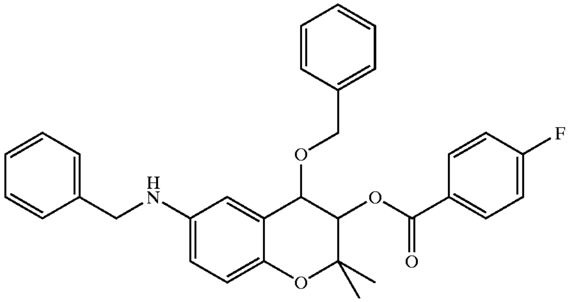 5-1668 | MS, m/z: 511.6 | 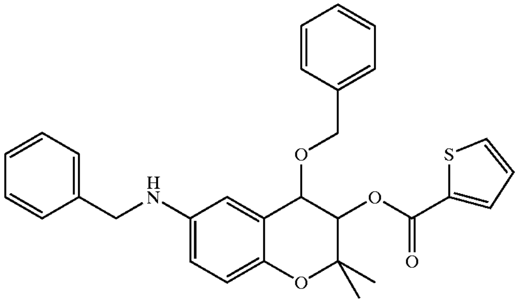 5-1669 | MS, m/z: 499.6 |
| 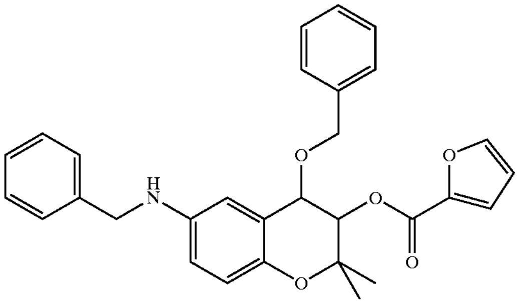 5-1670 | MS, m/z: 483.5 | 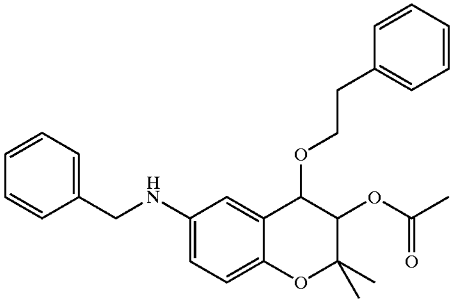 5-1671 | MS, m/z: 445.5 |

TABLE 3-continued
| Compound No. | | NMR/MS Data |
|---|---|---|
| 5-1672 | 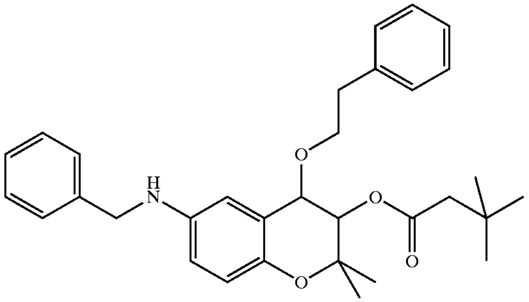 | MS, m/z: 501.6 |
| 5-1673 | 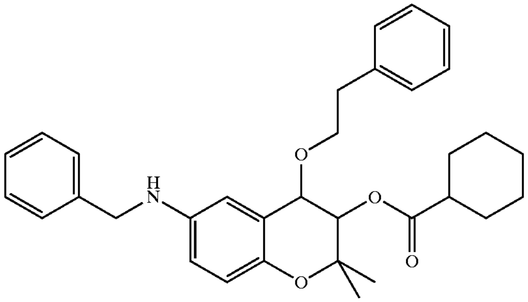 | MS, m/z: 513.68 |
| 5-1674 | 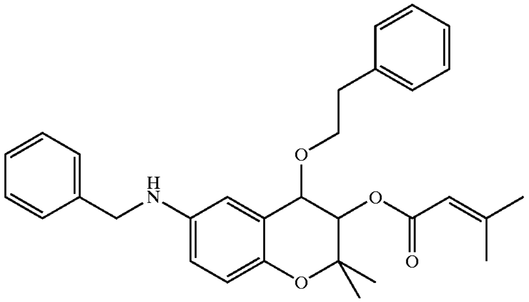 | MS, m/z: 485.6 |
| 5-1675 | 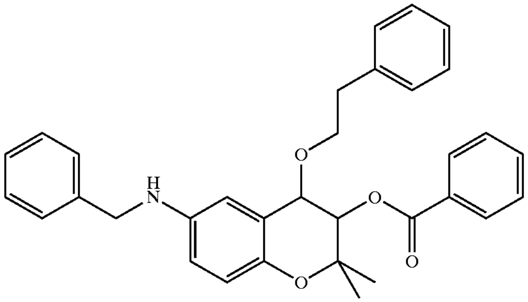 | MS, m/z: 507.6 |
| 5-1676 | 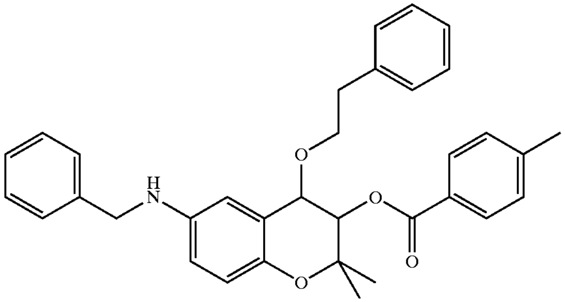 | MS, m/z: 521.6 |
| 5-1677 | 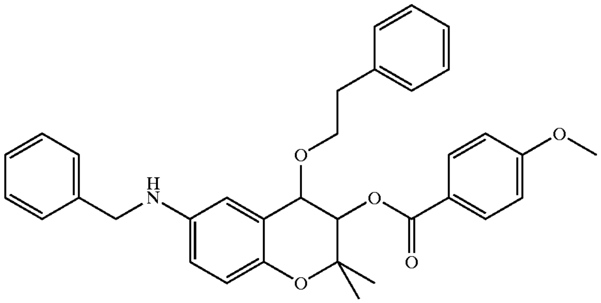 | MS, m/z: 537.6 |

TABLE 3-continued
| Compound No. | NMR/MS Data |
|---|---|
| 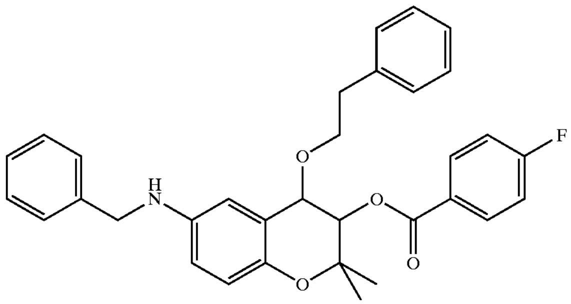 5-1678 | MS, m/z: 525.6 |
| 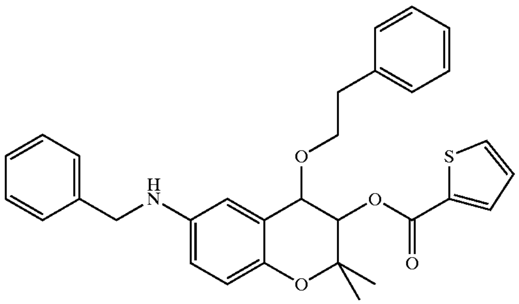 5-1679 | MS, m/z: 513.6 |
| 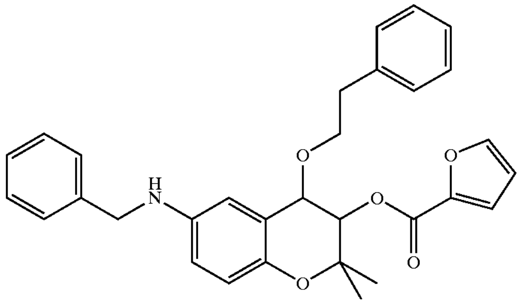 5-1680 | MS, m/z: 497.6 |
| 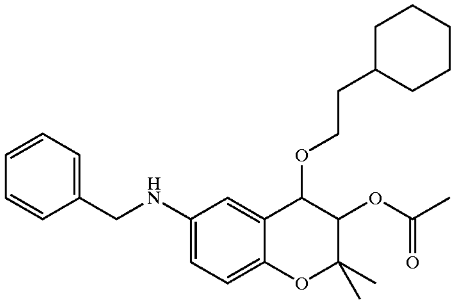 5-1681 | MS, m/z: 451.6 |
| 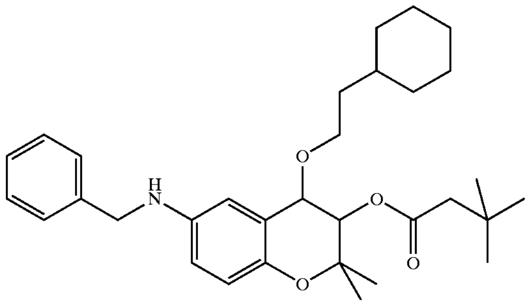 5-1682 | MS, m/z: 507.7 |
| 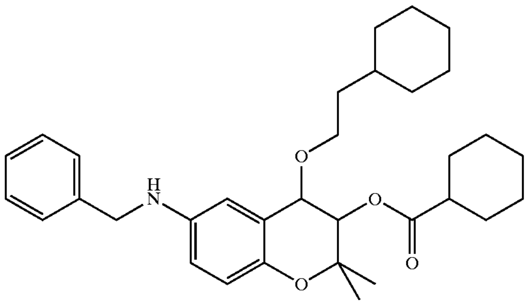 5-1683 | MS, m/z: 519.7 |

TABLE 3-continued
| Compound No. | NMR/MS Data |
| --- | --- |
| 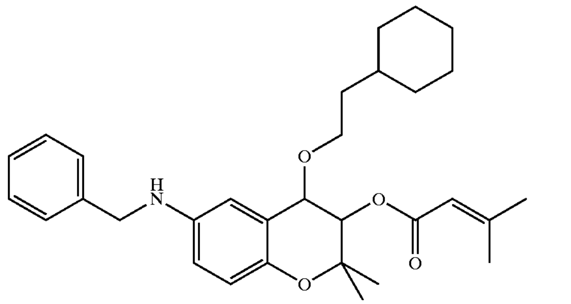 5-1684 | MS, m/z: 491.6 |
| 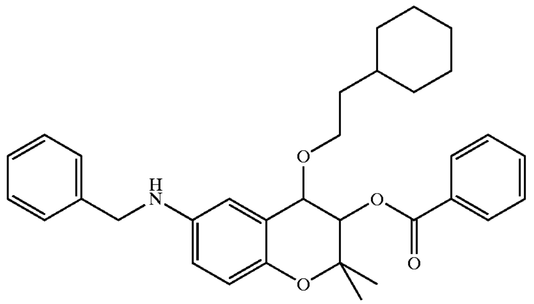 5-1685 | MS, m/z: 513.6 |
| 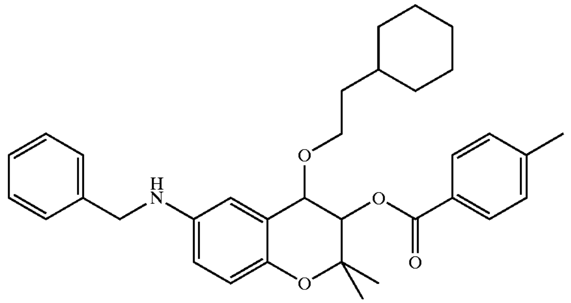 5-1686 | MS, m/z: 527.7 |
| 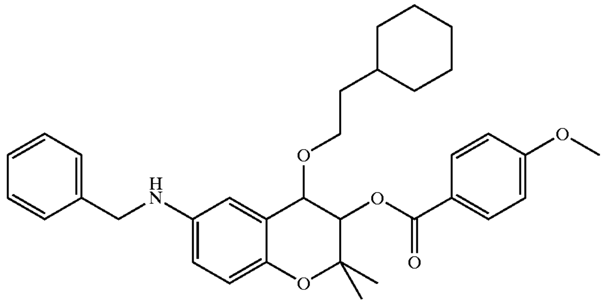 5-1687 | MS, m/z: 543.7 |
| 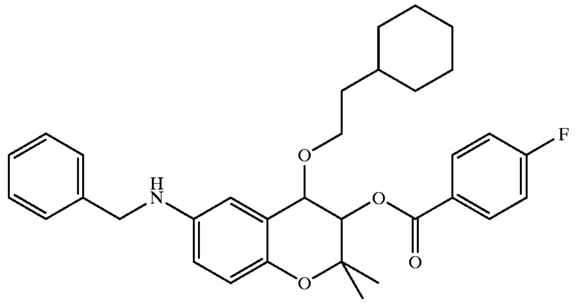 5-1688 | MS, m/z: 531.6 |
| 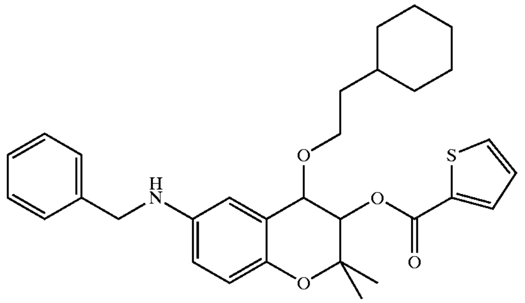 5-1689 | MS, m/z: 519.7 |

TABLE 3-continued
| Compound No. | | NMR/MS Data |
|---|---|---|
| 5-1690 | 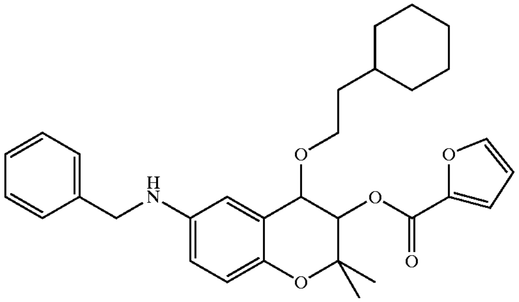 | MS, m/z: 503.6 |
| 5-1691 | 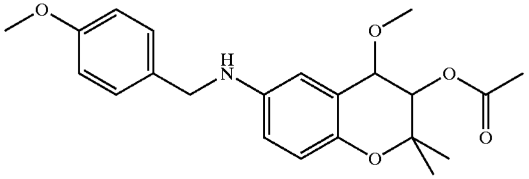 | $^1$H NMR(200MHz, $CDCl_3$) δ 7.28(d, 2H, J=8.5Hz), 6.86(d, 2H, J=8.5Hz), 6.72~6.55(m, 3H), 5.22(d, 1H, J=5.7Hz), 4.29(d, 1H, J=5.7Hz), 4.19(s, 2H), 3.79(s, 3H), 3.40(s, 3H), 2.11(s, 3H), 1.34(s, 3H), 1.28(s, 3H); MS, m/z: 385.4 |
| 5-1692 | 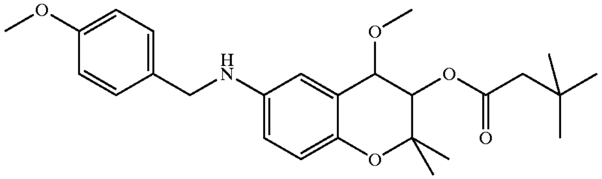 | $^1$H NMR(200MHz, $CDCl_3$) δ 7.27(m, 2H), 6.87(d, 2H, J=8.7Hz), 6.70(d, 1H, J=8.5Hz), 6.62~6.50(m, 2H), 5.24(d, 1H, J=6.0Hz), 4.34(d, 1H, J=6.0Hz), 4.20(s, 2H), 3.80(s, 3H), 3.37(s, 3H), 2.27(s, 3H), 1.36(s, 3H), 1.29(s, 3H), 1.05(s, 9H); MS, m/z: 441.5 |
| 5-1693 | 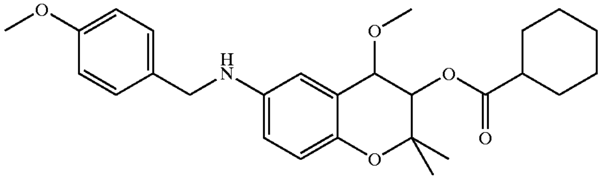 | $^1$H NMR(200MHz, $CDCl_3$) δ 7.28(d, 2H, J=9.0Hz), 6.86(d, 2H, J=9.0Hz), 6.84~6.60(m, 3H), 5.22(d, 1H, J=5.7Hz), 4.30(d, 1H, J=5.7Hz), 4.19(s, 3H), 3.79(s, 3H), 3.38(s, 1.28(s, 3H); MS, m/z: 453.5 |

TABLE 3-continued
| Compound No. | NMR/MS Data |
|---|---|
| 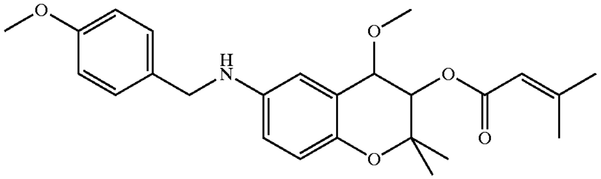 5-1694 | $^1$H NMR(200MHz, $CDCl_3$) δ 7.28(d, 2H, J=9.0Hz), 6.86(d, 2H, J=9.0Hz), 6.72~6.56(m, 3H), 5.71 (d, 1H, J=1.2Hz), 5.25(d, 1H, J=5.3Hz), 4.29(d, 1H, J=5.3Hz), 4.19(s, 2H), 3.79(s, 3H), 3.44(s, 3H), 2.18(s, 3H), 1.89(s, 3H), 1.35(s, 3H), 1.29(s, 3H); MS, m/z: 425.5 |
| 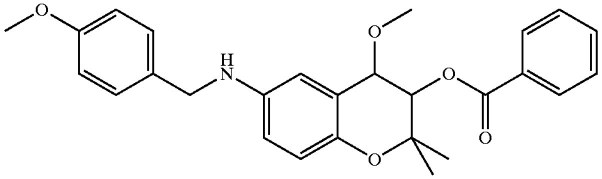 5-1695 | $^1$H NMR(200MHz, $CDCl_3$) δ 8.05(d, 2H, J=8.3Hz), 7.61~7.19(m, 5H), 6.89~6.57(m, 5H), 5.48(d, 1H, J=5.7Hz), 4.45(d, H, J=5.7Hz), 4.20(s, 2H), 3.79(s, 3H), 3.47(s, 3H), 1.41(s, 3H), 1.38(s, 3H); MS, m/z: 447.5 |
| 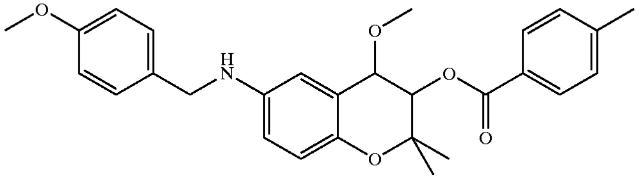 5-1696 | $^1$H NMR(200MHz, $CDCl_3$) δ 7.94(d, 2H, J=8.3Hz), 7.31~7.21(m, 4H), 6.89~6.62(m, 5H), 5.46(d, 1H, J=5.6Hz), 4.44(d, 1H, J=5.6Hz), 4.20(s, 2H), 3.80(s, 3H), 3.47(s, 3H), 2.41(s, 3H), 1.40(s, 3H), 1.38(s, 3H); MS, m/z: 461.5 |
| 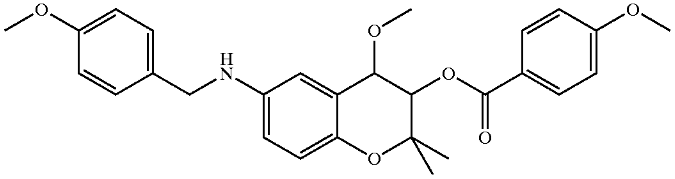 5-1697 | $^1$H NMR(200MHz, $CDCl_3$) δ 7.99(d, 2H, J=9.0Hz), 6.94~6.64(m, 5H), 5.43(d, 1H, J=5.5Hz), 4.41 (d, 1H, J=5.5Hz), 4.19(s, 2H), 3.86(s, 3H), 3.78(s, 3H), 3.47(s, 3H), 1.39(s, 3H), 1.37(s, 3H); MS, m/z: 477.5 |

TABLE 3-continued
| Compound No. | NMR/MS Data |
|---|---|
| 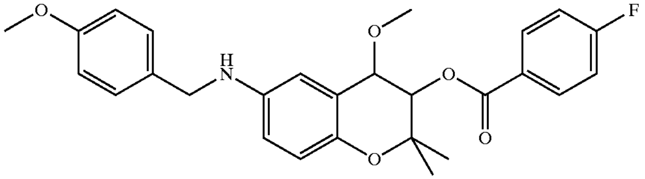 5-1698 | $^1$H NMR(200MHz, $CDCl_3$) δ 8.10~8.03(m, 2H), 7.31 7.25(m, 2H), 7.15~7.07(m, 2H), 6.87(d, 2H, J=8.8Hz), 6.75(d, 1H, 8.5Hz), 5.45(d, 1H, J=5.4Hz), 4.44(d, 1H, J=5.4Hz), 4.20(s, 2H), 3.80(s, 3H), 3.46(s, 3H), 1.41(s, 3H), 1.38(s, 3H); MS, m/z: 465.5 |
| 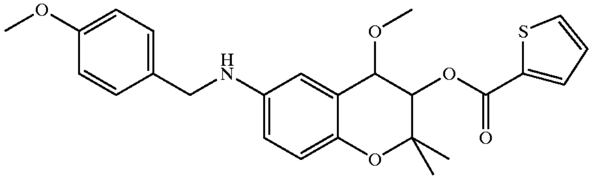 5-1699 | MS, m/z: 453.5 |
| 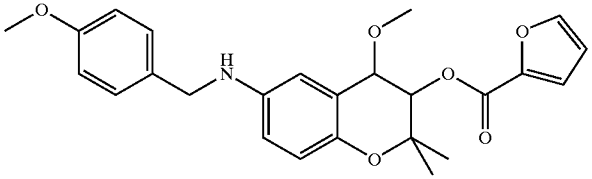 5-1700 | MS, m/z: 437.5 |
| 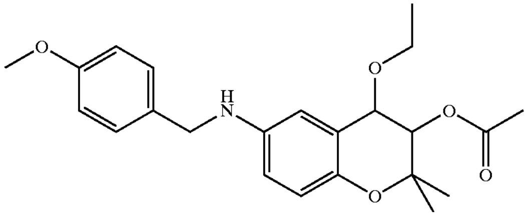 5-1701 | $^1$H NMR(200MHz, $CDCl_3$) δ 7.31~7.25(m, 2H), 6.91~6.85(m, 2H), 6.72~6.59(m, 3H), 5.18(d, 1H, J=5.4Hz), 4.31(d, 1H, J=5.4Hz), 4.20(s, 2H), 3.80(s, 3H), 3.70~3.59(m, 2H), 2.10(s, 3H), 1.35(s, 3H), 1.29(s, 3H), 1.18(t, 3H, J=7.1Hz); MS, m/z: 399.4 |
| 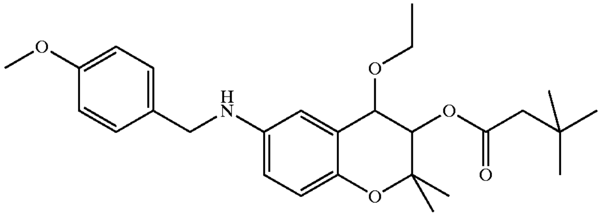 5-1702 | $^1$H NMR(200MHz, $CDCl_3$) δ 7.28(d, 2H, J=8.6Hz), 6.87(d, 2H, J 32 8.6Hz), 6.72~6.58(m, 3H), 5.20(d, 1H, J=5.8Hz), 4.36(d, 1H, J=5.8Hz), 4.20(s, 2H), 3.80(s, 3H), 3.60(q, 2H, J=6.9Hz), 2.26(s, 2H), 1.36(s, 3H), 1.29(s, 3H), 1.17(t, 3H, J=6.9Hz), 1.04(s, 9H); MS, m/z: 455.6 |

TABLE 3-continued
| Compound No. | NMR/MS Data |
|---|---|
| 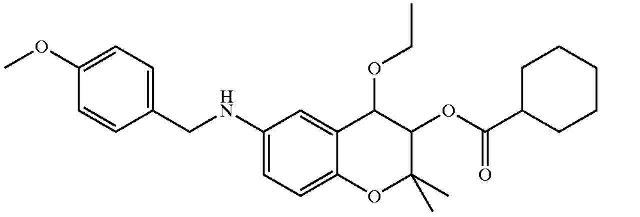 5-1703 | $^1$H NMR(200MHz, $CDCl_3$) δ 7.29(d, 2H, J=8.4Hz), 6.87(d, 2H, J=8.5Hz), 6.72~6.55(m, 3H), 5.19(d, 1H, J=5.7Hz), 4.32(d, 1H, J=5.7Hz), 4.20(s, 2H), 3.80(s, 3H), 3.62(q, 2H, J=6.9Hz), 2.35(m, 1H), 1.90~1.22(m, 13H), 1.34(s, 3H), 1.28(s, 3H), 1.17(t, 3H, J=6.9Hz); MS, m/z: 467.6 |
| 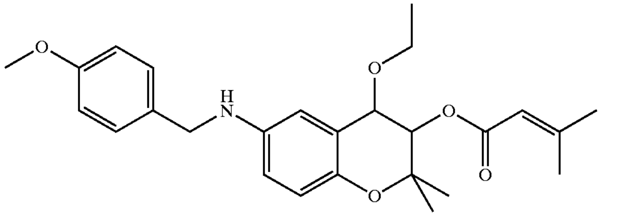 5-1704 | $^1$H NMR(200MHz, $CDCl_3$) δ 7.29(d, 2H, J=8.5Hz), 6.87(d, 2H, J=8.5Hz), 6.72~6.54(m, 3H), 5.72(d, 1H, J=1.2Hz), 5.21(d, 1H, J=5.2Hz), 4.32(d, 1H, J=5.2Hz), 4.19(s, 2H), 3.80(s, 3H), 3.67(m, 2H), 2.17(s, 3H), 1.89(s, 3H), 1.36(s, 3H), 1.30(s, 3H), 1.18(m, 3H): MS, m/z: 439.5 |
| 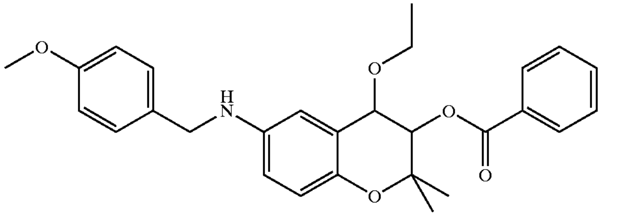 5-1705 | $^1$H NMR(200MHz, $CDCl_3$) δ 8.08~8.03(m, 2H), 7.58~7.26(m, 5H), 6.87(d, 2H, J=8.5Hz), 6.74(d, 2H, J=8.5Hz), 6.64~6.57(m, 3H), 5.43(d, 1H, J=5.4Hz), 4.47(d, 1H, J=5.4Hz), 4.20(s, 2H), 3.80(s, 3H), 3.77~3.67(m, 2H), 1.41(s, 3H), 1.38(s, 3H), 1.18(t, 3H, J=6.9Hz); MS, m/z:461.5 |
| 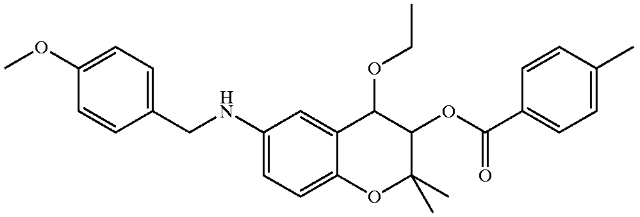 5-1706 | MS, m/z: 475.5 |

TABLE 3-continued
| Compound No. | NMR/MS Data |
| --- | --- |
| 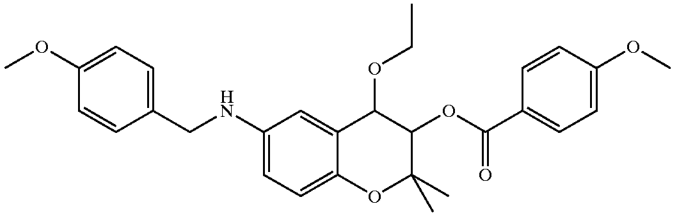 5-1707 | $^1$H NMR(200MHz, $CDCl_3$) δ 7.99(d, 2H, J=9.0Hz), 7.29(d, 2H, J=9.0Hz), 6.93~6.80(m, 4H), 6.77~6.49(m, 3H), 5.49(d, 1H, J=5.2Hz), 4.45(d, 1H, J=5.2Hz), 4.20(s, 2H), 3.85(s, 3H), 3.79(s, 3H), 3.76(m, 2H), 1.40(s, 3H), 1.37(s, 3H), 1.18(t, 3H, J=7.0Hz); MS, m/z: 491.5 |
| 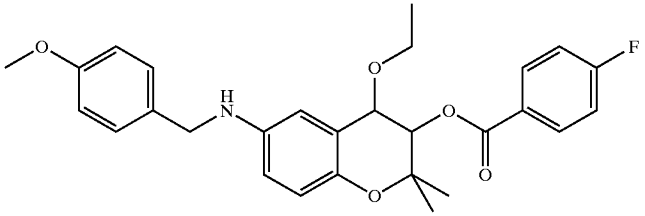 5-1708 | MS, m/z: 479.5 |
| 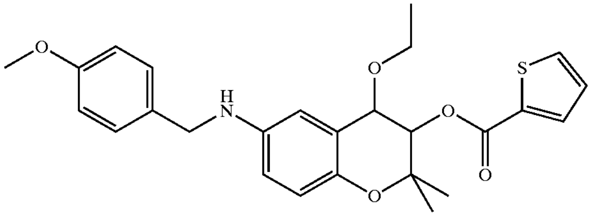 5-1709 | MS, m/z: 467.5 |
| 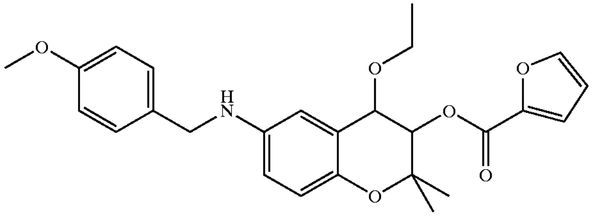 5-1710 | MS, m/z: 451.5 |
| 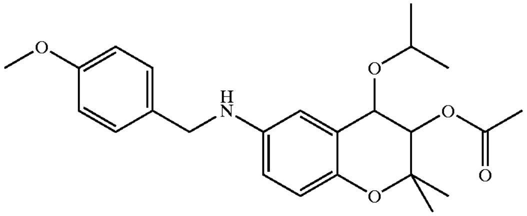 5-1711 | MS, m/z: 413.5 |
| 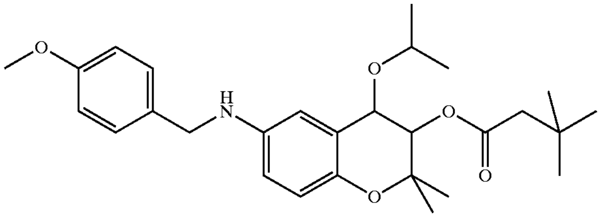 5-1712 | MS, m/z: 469.6 |
| 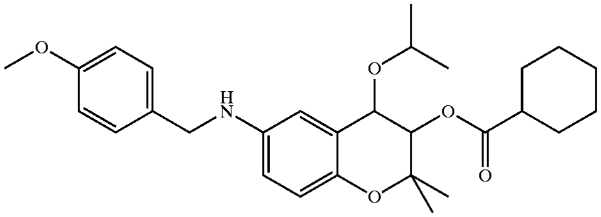 5-1713 | MS, m/z: 481.6 |

TABLE 3-continued
| Compound No. | | NMR/MS Data |
|---|---|---|
| 5-1714 | 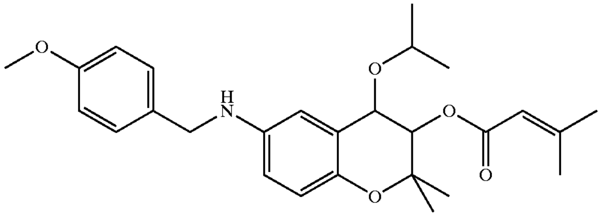 | MS, m/z: 453.5 |
| 5-1715 | 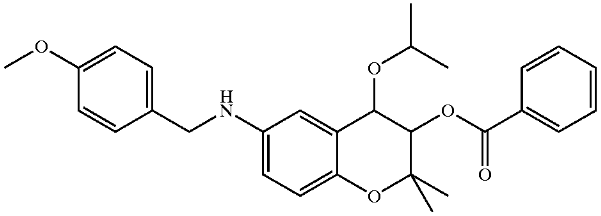 | MS, m/z: 475.5 |
| 5-1716 | 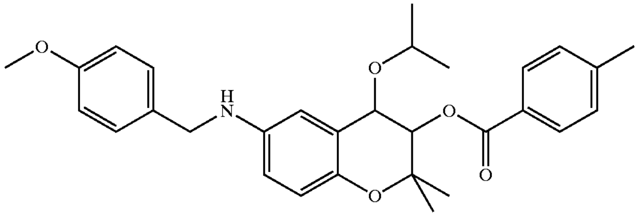 | MS, m/z: 489.6 |
| 5-1717 | 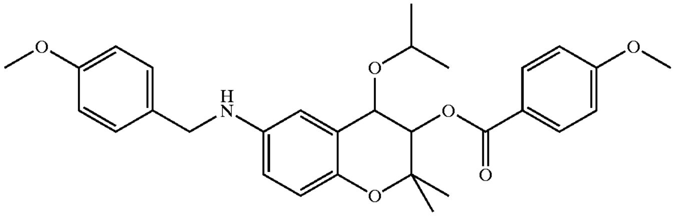 | MS, m/z: 505.6 |
| 5-1718 | 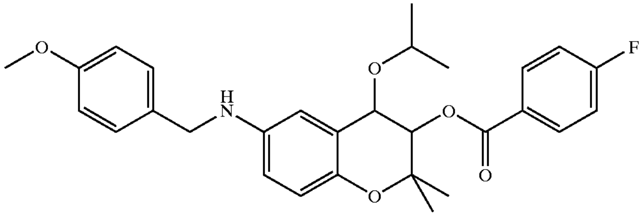 | MS, m/z: 493.5 |
| 5-1719 | 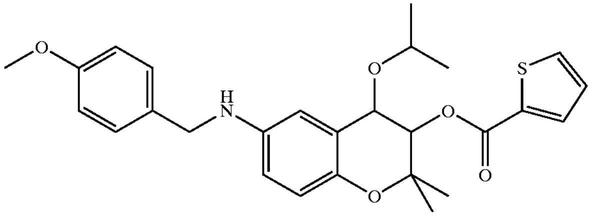 | MS, m/z: 481.6 |
| 5-1720 | 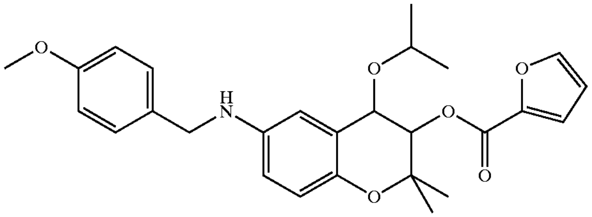 | MS, m/z: 465.5 |

TABLE 3-continued
| Compound No. | NMR/MS Data |
|---|---|
| 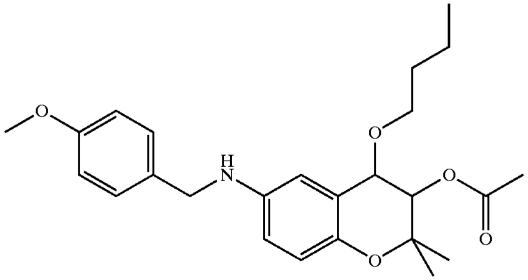 5-1721 | $^1$H NMR(200MHz, $CDCl_3$) δ 7.39(d, 2H, J=8.7Hz), 6.88(d, 2H, J=8.7Hz0, 6.83~6.55(m, 3H), 5.18(d, 1H, J=5.2Hz), 4.28(d, 1H, J=5.2Hz), 4.19(s, 2H), 3.80(s, 3H), 3.75~ 1.38(m, 2H), 1.35(s, 3H), 1.29(s, 3H), 0.91 (t, 3H); MS, m/z: 427.5 |
| 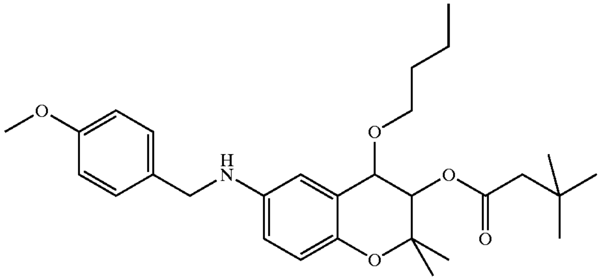 5-1722 | $^1$H NMR(200MHz, $CDCl_3$) δ 7.28(d, 2H, J=9.0Hz), 6.86(d, 2H, J=8.6Hz), 6.72~6.60(m, 3H), 5.19(d, 1H, J=5.4Hz), 2H, J=6.3Hz), 2.25(s, 3H), 1.53~1.42(m, 4H), 1.36(s, 3H), 1.29(s, 3H), 1.04(s, 9H), 0.93(m, 3H); MS, m/z: 483.6 |
| 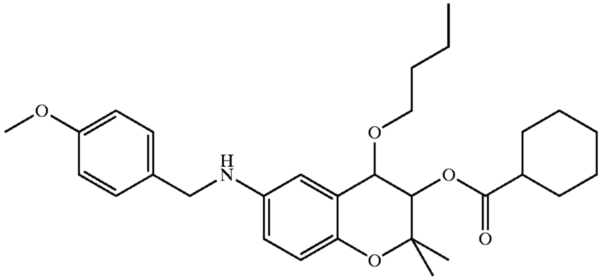 5-1723 | $^1$H NMR(200MHz, $CDCl_3$) δ 7.29(d, 2H, J=8.7Hz), 6.87(d, 2H, J=8.7Hz), 6.72~6.60(m, 3H), 5.18(d, 1H, J=5.5Hz), 4.28(d, 1H, J=5.5Hz), 4.19(s, 2H), 3.79(s, 3H), 3.58~ 3.57(m, 2H), 2.30(m, 1H), 2.0~1.20(m, 14H), 1.33(s, 3H), 1.28(s, 3H), 0.90(t, 3H, J=7.2Hz); MS, m/z: 495.6 |

TABLE 3-continued
| Compound No. | NMR/MS Data |
|---|---|
| 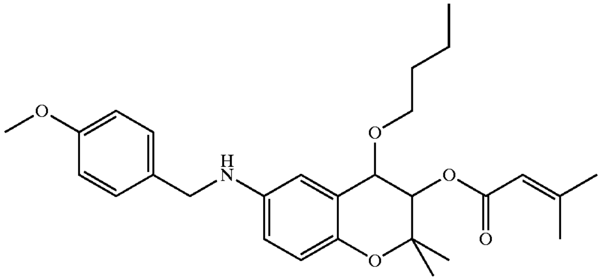 5-1724 | $^1$H NMR(200MHz, $CDCl_3$) δ 7.28(d, 2H, J=8.7Hz), 6.86(d, 2H, J=8.7Hz), 6.72~6.60(m, 3H), 5.70(d, 1H, J=1.2Hz), 5.20(d, 1H, J=5.0Hz), 4.28(d, 1H, J=5.0Hz), 4.19(s, 2H), 3.79(s, 3H), 3.68~3.55(m, 2H), 2.17(s, 3H), 1.89(s, 3H), 1.62~1.45(m, 2H), 1.42~1.26(m, 2H), 1.35(s, 3H), 1.29(s, 3H), 0.90(t, 3H, J=7.2Hz); MS, m/z: 467.6 |
| 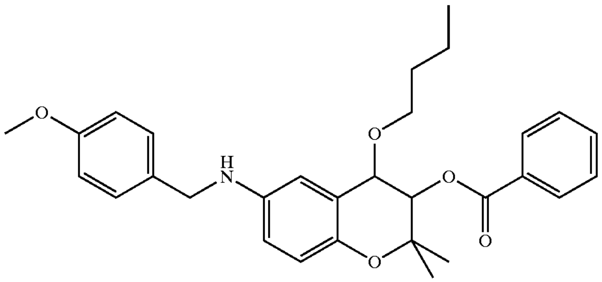 5-1725 | $^1$H NMR(200MHz, $CDCl_3$) δ 8.04(d, 2H, J=8.7Hz), 7.57~7.25(m, 6H), 6.88~6.61(m, 5H), 5.43(d, 1H, J=5.2Hz), 4.43(d, 1H, J=5.2Hz), 4.20(s, 2H), 3.79(s, 3H), 3.72~3.65(m, 2H), 1.54~1.26(m, 4H), 1.41(s, 3H), 1.39(s, 3H), 0.87(t, 3H, J=7.2Hz); MS, m/z: 489.6 |
| 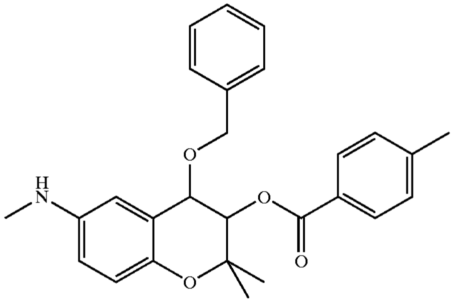 5-1526 | MS, m/z: 503.6 |
| 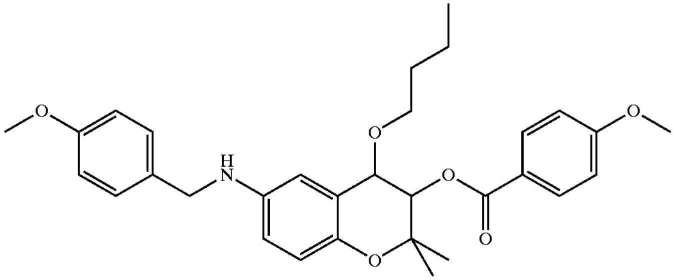 5-1727 | MS, m/z: 519.6 |

TABLE 3-continued
| Compound No. | NMR/MS Data |
|---|---|
| 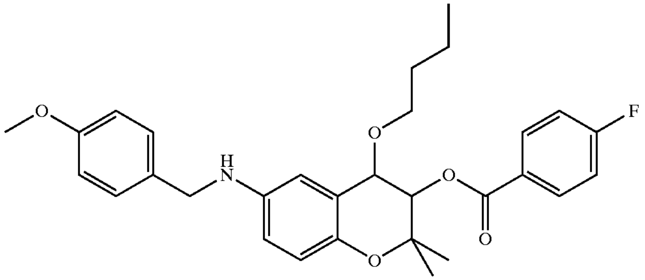<br>5-1728 | $^1$H NMR(200MHz, $CDCl_3$) δ 8.08~8.01 (m, 2H), 7.30~7.14(m, 2H), 7.10~7.05(m, 2H), 6.87~6.73(m, 5H), 5.39(d, 1H, J=5.1Hz), 4.40(d, 1H, J=5.1Hz), 4.19(s, 2H), 3.78(s, 3H), 3.66(m, 2H), 1.57~1.25(m, 4H), 1.40(s, 3H), 1.37(s, 3H), 0.87(t, 3H, J=7.2Hz); MS, m/z: 507.6 |
| 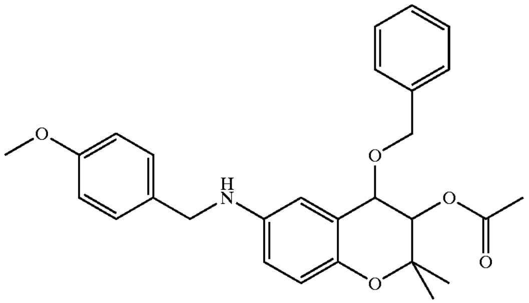<br>5-1731 | $^1$H NMR(200MHz, $CDCl_3$) δ 7.38~7.23(m, 7H), 6.88~6.53(m, 5H), 5.28(d, 1H, J=4.7Hz), 4.69(s, 2H), 4.41(d, 1H, J=4.7Hz), 4.13(s, 2H), 3.79(s, 3H), 2.10(s, 3H), 1.39(s, 3H), 1.33(s, 3H); MS, m/z: 461.5 |
| 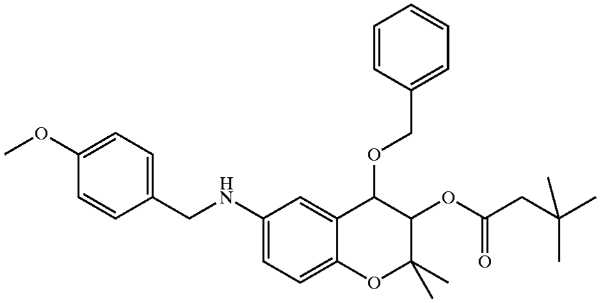<br>5-1732 | $^1$H NMR(200MHz, $CDCl_3$) δ 7.38~7.23(m, 7H), 6.85(d, 2H, J=8.5Hz), 6.79~6.56(m, 3H), 5.29(d, 1H, J=4.9Hz), 4.67(s, 2H), 4.41(d, 1H, J=4.9Hz), 4.12(s, 2H), 3.78(s, 3H), 2.25(s, 2H), 1.40(s, 3H), 1.33(s, 3H), 1.02(s, 9H); MS, m/z: 517.6 |

TABLE 3-continued
| Compound No. | NMR/MS Data |
|---|---|
| 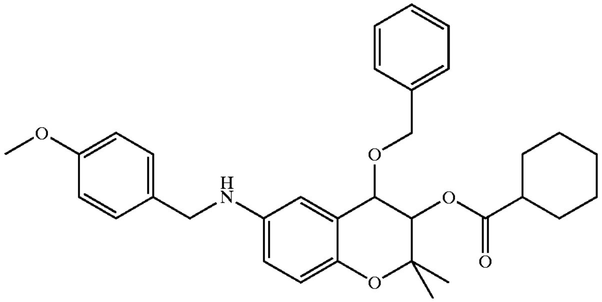 5-1733 | $^{1}$H NMR(200MHz, $CDCl_3$) δ 7.38~7.18(m, 7H), 6.85(d, 2H, J=8.5Hz), 6.79~6.58(m, 3H), 5.29(d, 1H, J=4.9Hz), 4.66(s, 2H), 4.40(d, 1H, J=4.9Hz), 4.13(s, 2H), 3.78(s, 3H), 2.34(m, 1H), 2.00~1.20(m, 10H), 1.37(s, 3H), 1.32(s, 3H); MS, m/z: 529.6 |
| 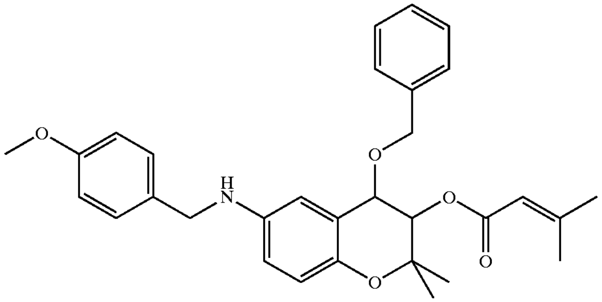 5-1734 | $^{1}$H NMR(200MHz, $CDCl_3$) δ 7.38~7.18(m, 7H), 6.88~6.52(m, 5H), 5.71(d, 1H, J=1.4Hz), 5.32(d, 1H, J=4.6Hz), 4.72(s, 2H), 4.42(d, 1H, J=4.6Hz), 4.12(s, 2H), 3.17(s, 3H), 2.19(s, 3H), 1.89(s, 3H), 1.40(s, 3H), 1.33(s, 3H); MS, m/z: 501.6 |
| 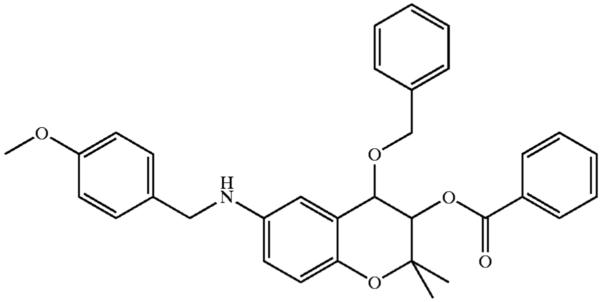 5-1735 | $^{1}$H NMR(200MHz, $CDCl_3$) δ 8.08~7.98(m, 2H), 7.58~7.19(m, 10H), 6.87~6.58(m, 5H), 5.52(d, 1H, J=4.7Hz), 4.76(s, 2H), 4.57(d, 1H, J=4.7Hz), 4.13(s, 2H), 3.77(s, 3H), 1.45(3, 3H), 1.42(3, 3H); MS, m/z: 523.6 |

TABLE 3-continued
| Compound No. | | NMR/MS Data |
|---|---|---|
| 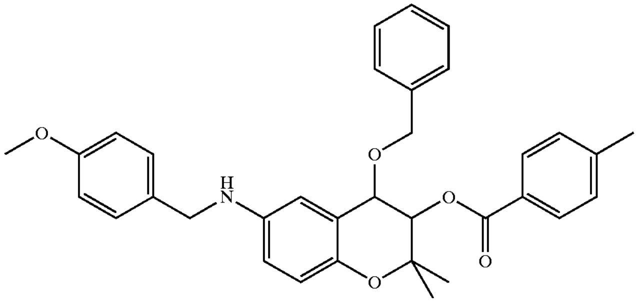 5-1736 | | $^1H$ NMR(200MHz, $CDCl_3$) δ 7.94(d, 2H, J=8.3Hz), 7.33~7.19(m, 9H), 6.89~6.73(m, 3H), 6.61~6.52(m, 2H), 5.52(d, 1H, J=4.8Hz), 4.75(s, 2H), 4.47(d, 1H, J=4.8Hz), 4.13(s, 2H), 3.79(s, 3H), 2.41(s, 3H), 1.44(s, 3H), 1.41(s, 3H); MS, m/z: 537.6 |
| 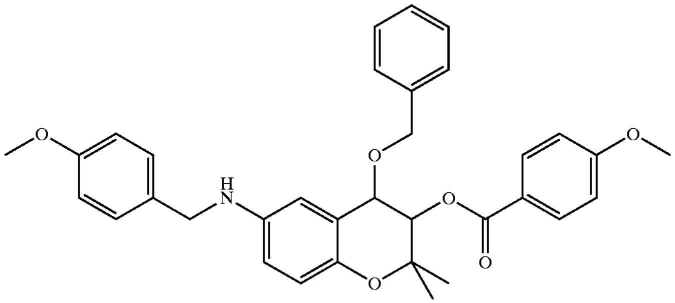 5-1737 | MS, m/z: 553.6 | |
| 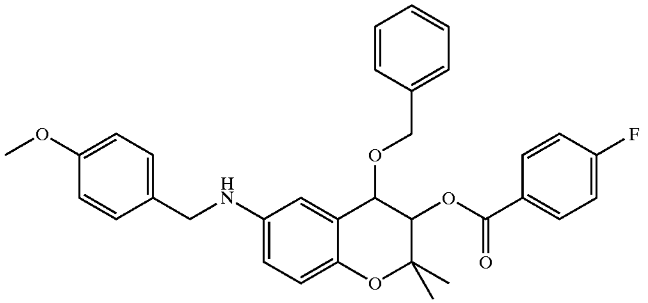 5-1738 | MS, m/z: 541.6 | |
| 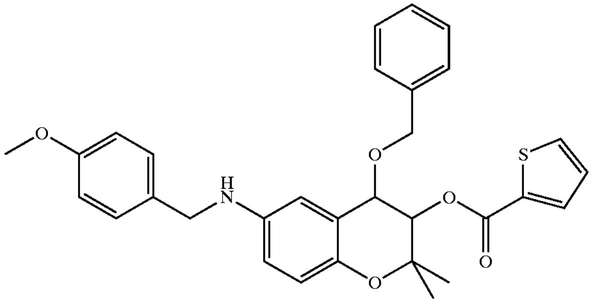 5-1739 | MS, m/z: 529.6 | |
| 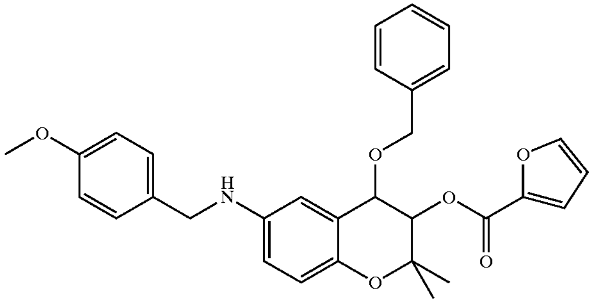 5-1740 | MS, m/z: 513.6 | |

TABLE 3-continued
| Compound No. | | NMR/MS Data |
|---|---|---|
| 5-1741 | 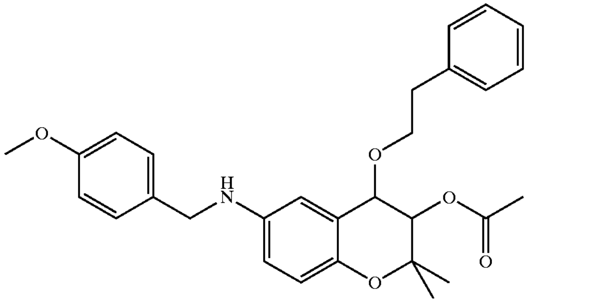 | MS, m/z: 475.5 |
| 5-1742 | 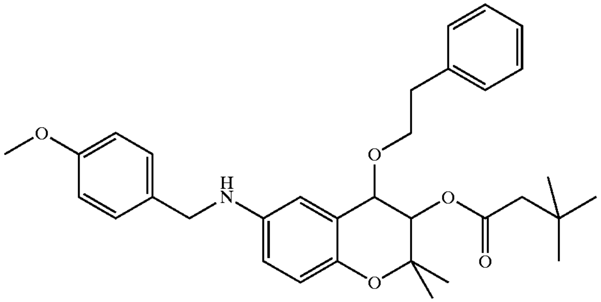 | MS, m/z: 531.7 |
| 5-1743 | 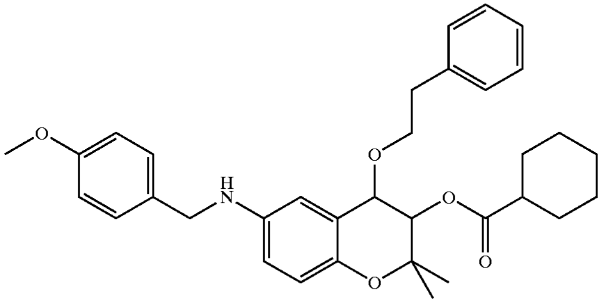 | MS, m/z: 543.7 |
| 5-1744 | 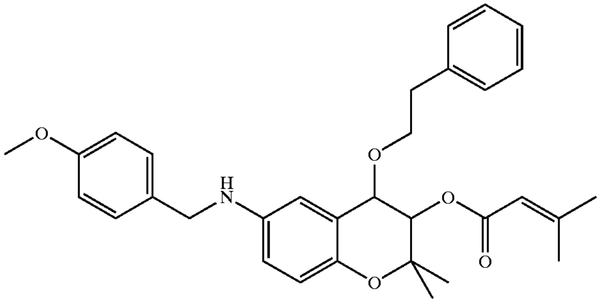 | MS, m/z: 515.6 |
| 5-1745 | 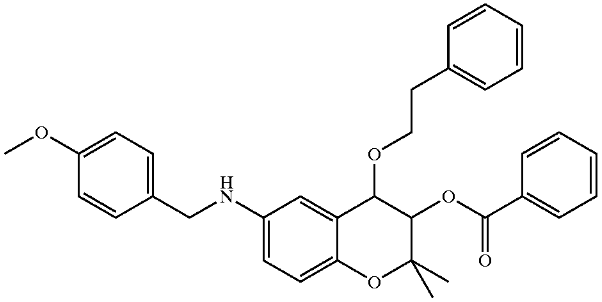 | MS, m/z: 537.6 |
| 5-1746 | 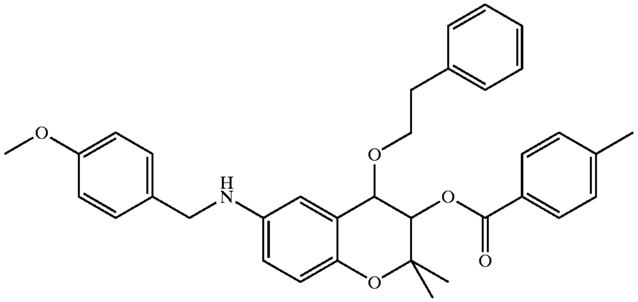 | MS, m/z: 551.6 |

TABLE 3-continued
| Compound No. | NMR/MS Data |
|---|---|
| 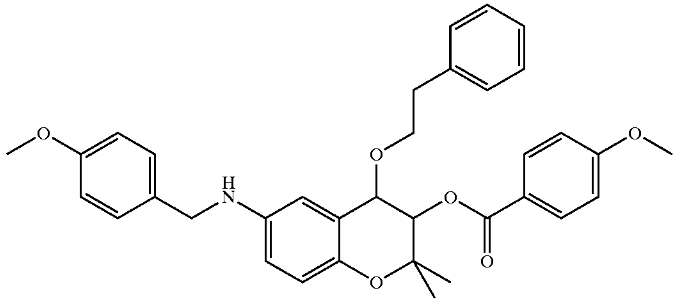 5-1747 | MS, m/z: 567.6 |
| 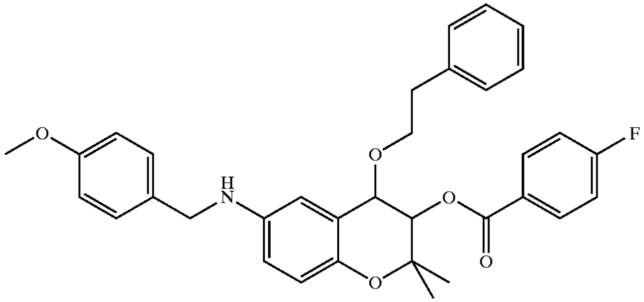 5-1748 | MS, m/z: 555.6 |
| 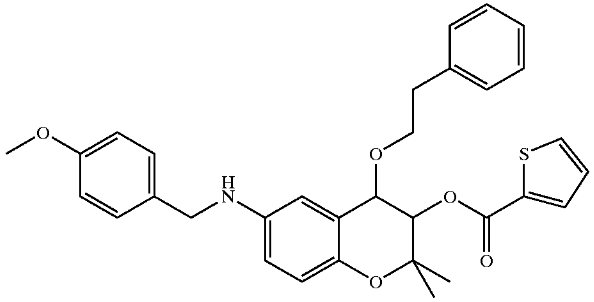 5-1749 | MS, m/z: 543.6 |
| 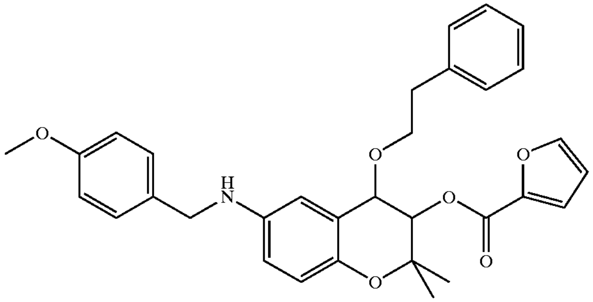 5-1750 | MS, m/z: 527.6 |
| 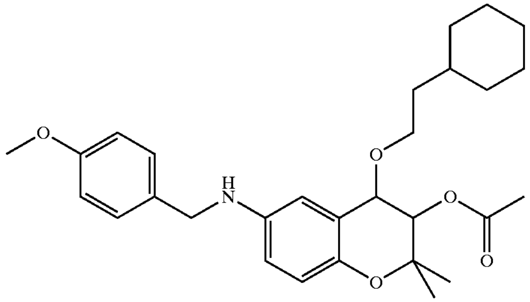 5-1751 | MS, m/z: 481.6 |
| 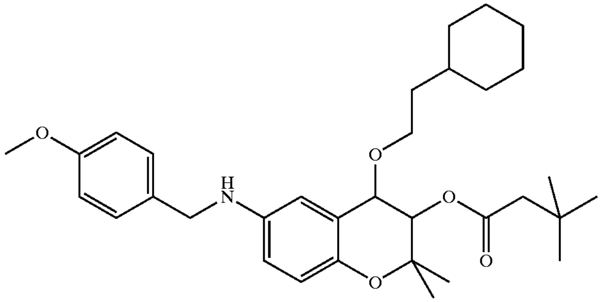 5-1752 | MS, m/z: 537.7 |

TABLE 3-continued
| Compound No. | | NMR/MS Data |
|---|---|---|
| 5-1753 | 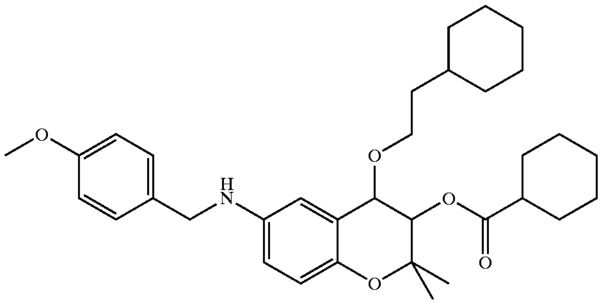 | MS, m/z: 549.7 |
| 5-1754 | 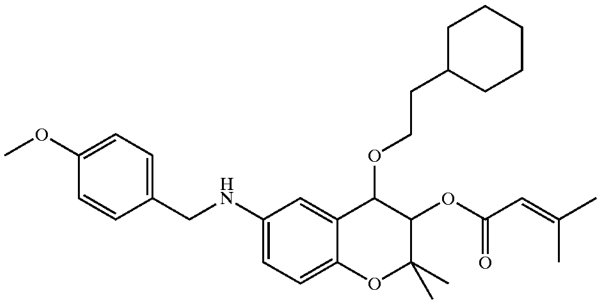 | MS, m/z: 521.7 |
| 5-1755 | 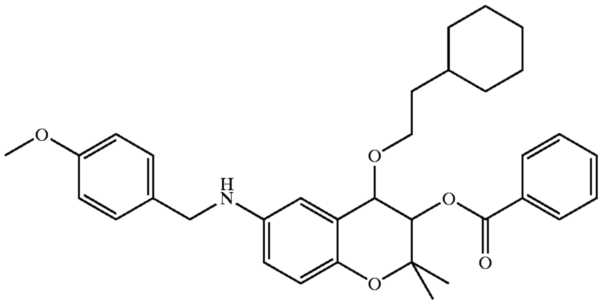 | MS, m/z: 543.7 |
| 5-1756 | 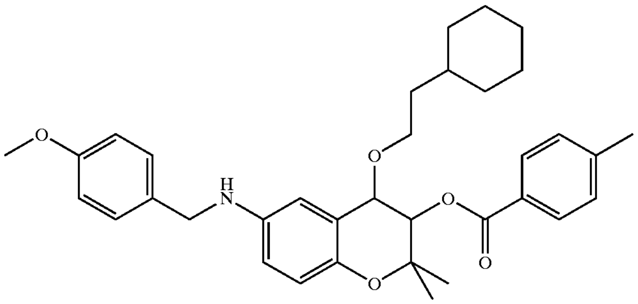 | MS, m/z: 557.7 |
| 5-1757 | 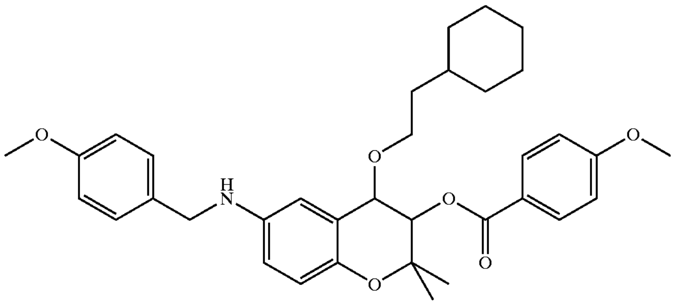 | MS, m/z: 573.7 |
| 5-1758 | 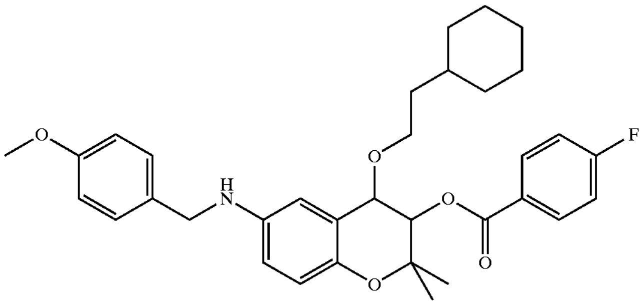 | MS, m/z: 561.7 |

TABLE 3-continued
| Compound No. | NMR/MS Data |
|---|---|
| 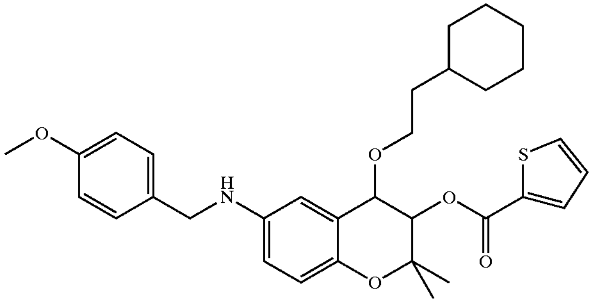 5-1759 | MS, m/z: 549.7 |
| 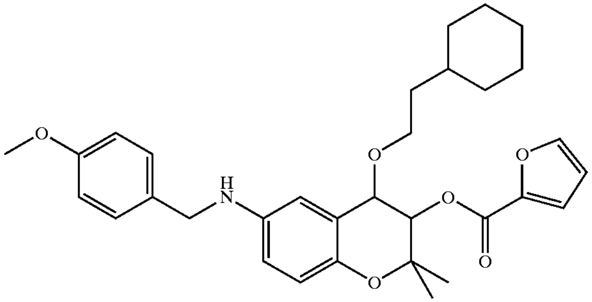 5-1760 | MS, m/z: 533.6 |
| 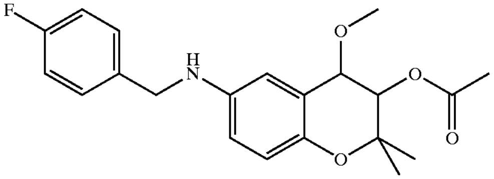 5-1761 | $^1$H NMR(200MHz, $CDCl_3$) δ 7.26~7.37(m, 2H), 6.97~7.06(m, 2H), 6.53~6.68(m, 3H), 5.22(d, 1H, J=5.70Hz), 4.28(d, 1H, J=5.70Hz), 4.24(s, 2H), 3.40(s, 3H), 2.11(s, 3H), 1.34(s, 3h), 1.26(s, 3H); MS, m/z: 373.4 |
| 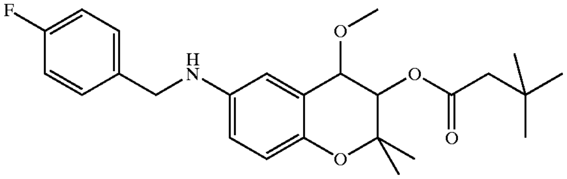 5-1762 | $^1$H NMR(200MHz, $CDCl_3$) δ 7.26~7.36(m, 2H), 6.97~7.05(m, 2H), 6.55~6.72(m, 3H), 5.23(d, 1H, J=6.10Hz), 5.32(d, 1H, J=6.10), 4.24(s, 2H), 3.35(3, 3H), 2.26(s, 2H), 1.36(s, 3H), 1.28(s, 3H), 1.04(s, 9H); MS, m/z: 429.5 |
| 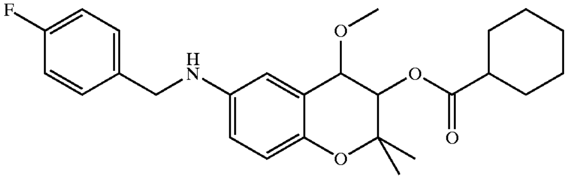 5-1763 | $^1$H NMR(200MHz, $CDCl_3$) δ 7.26~7.37(m, 2H), 6.97~7.06(m, 2H), 6.53~6.72(m, 5.21(d, 1H J=5.90Hz), 4.27(d, 1H, J=5.90Hz), 4.24(s, 2H), 3.37(s, 3H), 2.31~2.41(m, 1H), 1.37~1.92(m, 10H), 1.33(s, 3H), 1.28(s, 3H); MS, m/z: 441.5 |

TABLE 3-continued
| Compound No. | | NMR/MS Data |
|---|---|---|
| 5-1764 | 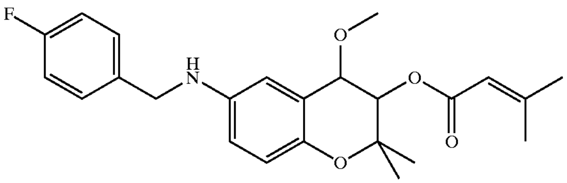 | MS, m/z: 413.4 |
| 5-1765 | 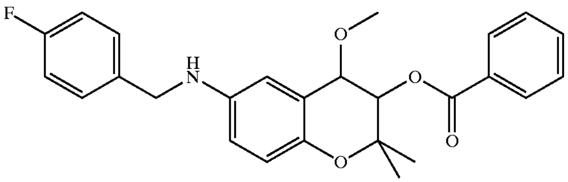 | $^1H$ NMR(200MHz, $CDCl_3$) δ 7.30~7.58(m, 7H), 6.97~7.05(m, 2H), 6.58~6.77(m, 3H), 5.46(d, 1H, J=5.49Hz), 4.44(d, 1H, J=5.49), 4.25(s, 2H), 3.46(s, 3H), 1.40(s, 3H), 1.38(s, 3H) MS, m/z: 435.5 |
| 5-1766 | 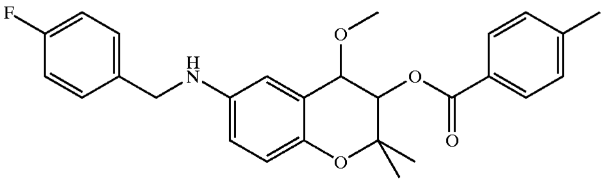 | $^1H$ NMR(200MHz, $CDCl_3$) δ 7.93(d, 2H, J=8.34Hz), 7.21~7.37(m, 4H), 6.96~7.05(m, 2H), 6.59~6.77(m, 3H), 5.44(d, 1H, J=5.49Hz), 4.42(d, 1H, J=5.49Hz), 4.25(s, 2H), 3.45(s, 3H), 2.41(s, 3H), 1.39(s, 3H), 1.37(s, 3H); MS, m/z: 449.5 |
| 5-1767 | 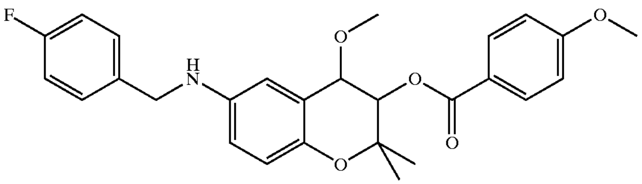 | $^1H$ NMR(200MHz, $CDCl_3$) δ 7.98~8.02(m, 2H), 7.30~7.37(m, 2H), 6.88~7.05(m, 4H), 6.59~6.77(m, 3H), 5.44(d, 1H, J=5.49Hz), 4.41(d, 1H, J=5.49Hz), 4.25(s, 2H), 3.86(s, 3H), 3.46(s, 3H), 1.39(s, 3H), 1.37(s, 3H); MS, m/z: 465.5 |

TABLE 3-continued
| Compound No. | NMR/MS Data |
|---|---|
| 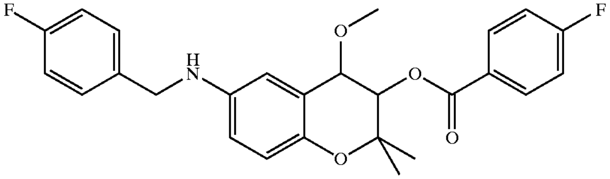 5-1768 | $^1$H NMR(200MHz, $CDCl_3$) δ 8.03~8.10(m, 2H), 7.26~7.37(m, 2H), 6.97~7.25(m, 4H), 6.58~6.77(m, 3H), 5.45(d, 1H, J=5.49Hz), 4.42(d, 1H, J=5.49Hz), 4.25(s, 2H), 3.45(s, 3H), 1.40(s, 3H), 1.37(s, 3H); MS, m/z: 453.4 |
| 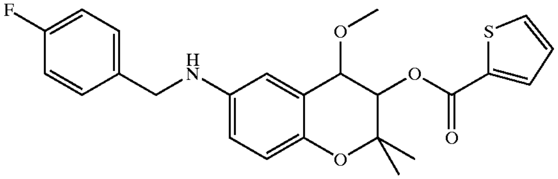 5-1769 | $^1$H NMR(200MHz, $CDCl_3$) δ 7.82~7.85(m, 1H), 7.57~7.60(m, 1H), 7.26~7.37(m, 2H), 6.97~7.13(m, 3H), 6.55~6.75(m, 3H), 5.40(d, 1H, J=6.10Hz), 4.48(d, 1H, J=6.30 Hz), 4.25(s, 2H), 3.44(s, 3H), 1.40(s, 3H), 1.36(s, 3H); MS, m/z: 441.5 |
| 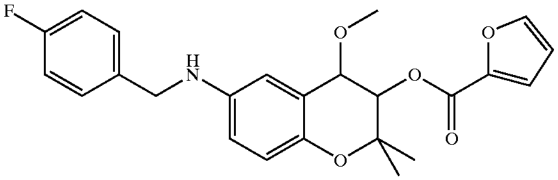 5-1770 | $^1$H NMR(200MHz, $CDCl_3$) δ 7.59~7.60(m, 1H), 7.19~7.37(m, 3H), 6.97~7.05(m, 2H), 6.49~6.75(m, 4H), 5.42(d, 1H, J=5.90Hz), 4.45(d, 1H, J=5.90Hz), 4.24(s, 2H), 3.42(s, 3H), 1.39(s, 3H), 1.35(s, 3H) MS, m/z: 425.4 |
| 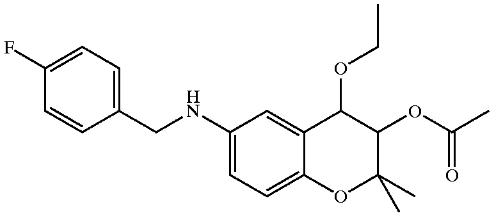 5-1771 | $^1$H NMR(200MHz, $CDCl_3$) δ 7.26~7.36(m, 2H), 6.96~7.17(m, 2H), 6.59~6.73(m, 3H), 5.17(d, 1H, J=5.29Hz), 4.29(d, 1H, J=5.29Hz), 4.24(s, 2H), 3.63(q, 2H, 6.92Hz), 2.10(s, 3H), 1.34(s, 3H), 1.29(s, 3H), 1.17(t, 3H, J=7.12 Hz) MS, m/z: 387.4 |

TABLE 3-continued
| Compound No. | NMR/MS Data | Compound No. | NMR/MS Data |
|---|---|---|---|
| 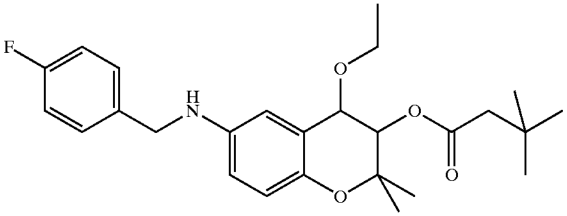 5-1772 | -$^1$H NMR(200MHz, $CDCl_3$) δ 7.11~7.36(m, 4H), 6.80~1H, J=4.88Hz), 3.64(q, 2H, 6.92Hz), 1.36(s, 3H), 1.32(s, 3H), 1.18(t, 3H, J=6.92Hz), 1.01(s, 9H) MS, m/z: 443.5 | | |
| 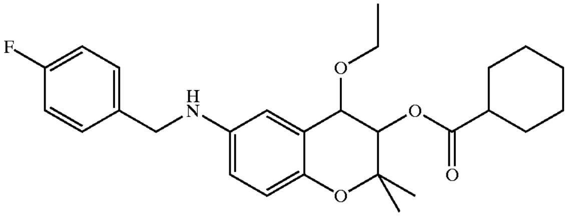 5-1773 | MS, m/z: 455.5 | 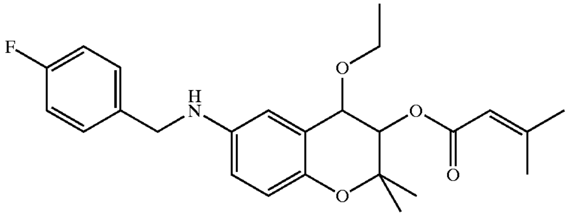 5-1774 | MS, m/z: 427.5 |
| 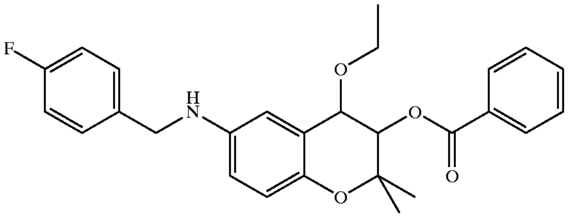 5-1775 | MS, m/z: 449.5 | 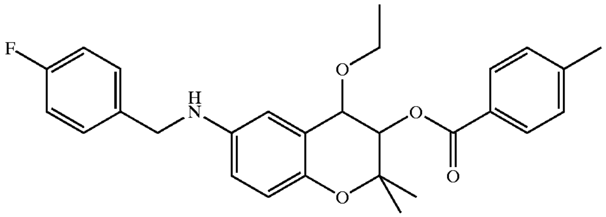 5-1776 | MS, m/z: 463.5 |
| 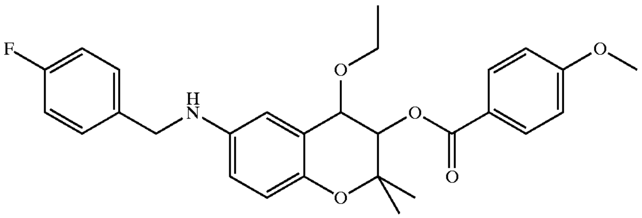 5-1777 | MS, m/z: 479.5 | 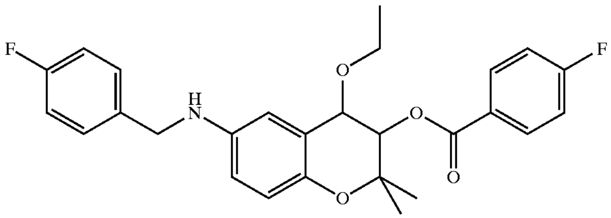 5-1778 | MS, m/z: 467.5 |

TABLE 3-continued
| Compound No. | NMR/MS Data |
| --- | --- |
| 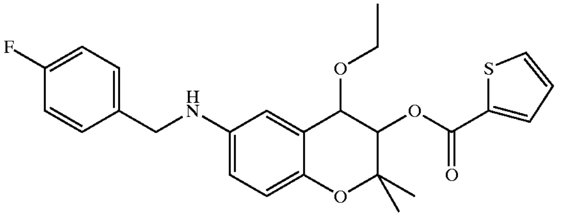 5-1779 | MS, m/z: 455.5 |
| 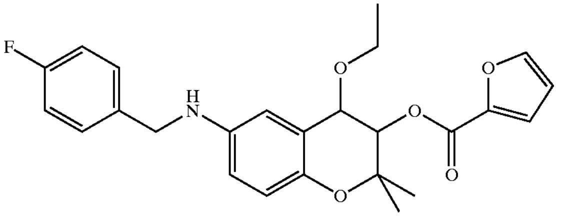 5-1780 | $^1$H NMR(200MHz, $CDCl_3$) δ 7.59~7.60(m, 1H), 7.18~7.56(m, 3H), 6.92~7.16(m, 2H), 6.63~6.88(m, 3H), 6.45~6.52(m, 1H), 5.37(d, 1H, J=5.70Hz), 4.45(d, 1H, J=5.70 Hz), 4.24(s, 2H), 3.68(q, 2H, J=6.92Hz), 1.39(s, 3H), 1.35(s, 3H), 1.16~1.26(m, 3H); MS, m/z: 439.4 |
| 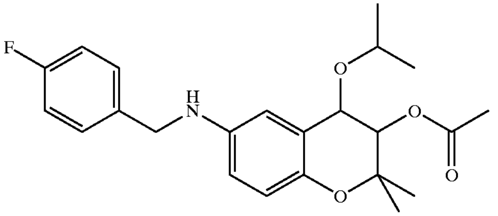 5-1781 | MS, m/z: 401.4 |
| 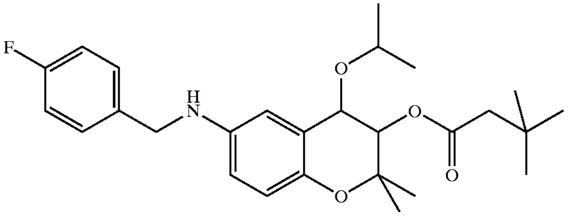 5-1782 | MS, m/z: 457.5 |
| 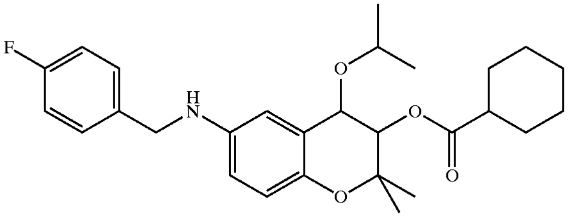 5-1783 | MS, m/z: 469.6 |
| 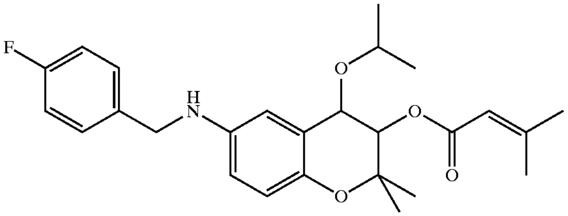 5-1784 | MS, m/z: 441.5 |

TABLE 3-continued
| Compound No. | NMR/MS Data |
| --- | --- |
| 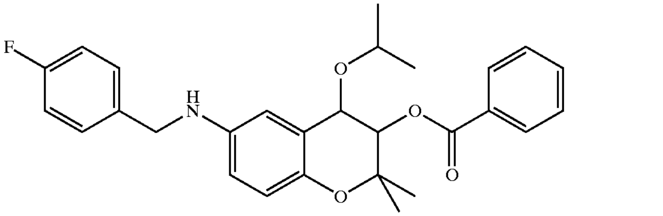 5-1785 | MS, m/z: 463.5 |
| 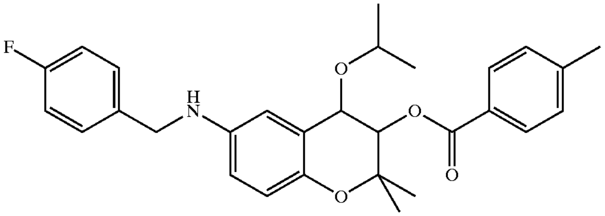 5-1786 | MS, m/z: 477.5 |
| 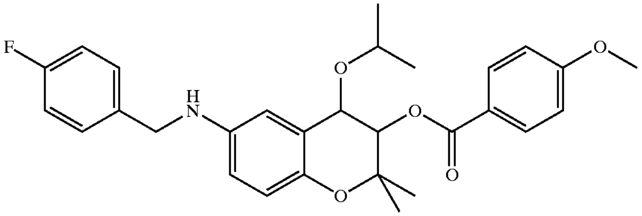 5-1787 | MS, m/z: 493.5 |
| 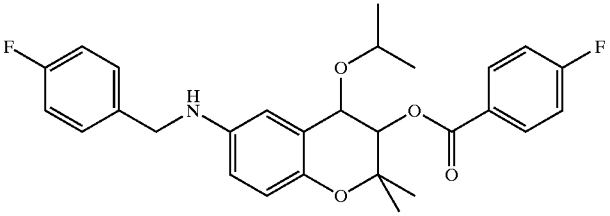 5-1788 | MS, m/z: 481.5 |
| 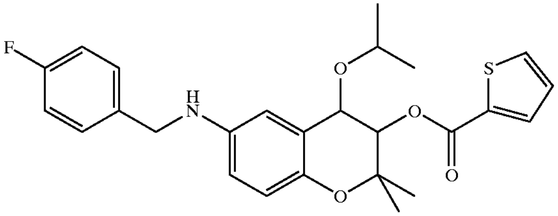 5-1789 | MS, m/z: 469.5 |
| 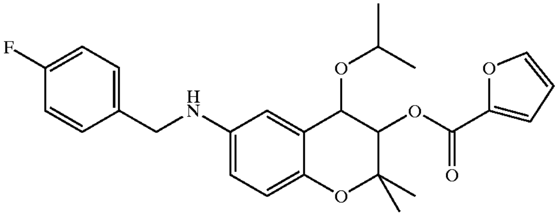 5-1790 | MS, m/z: 453.5 |

TABLE 3-continued
| Compound No. | NMR/MS Data |
| --- | --- |
| 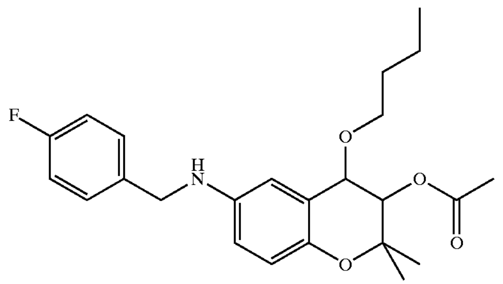 5-1791 | MS, m/z: 415.5 |
| 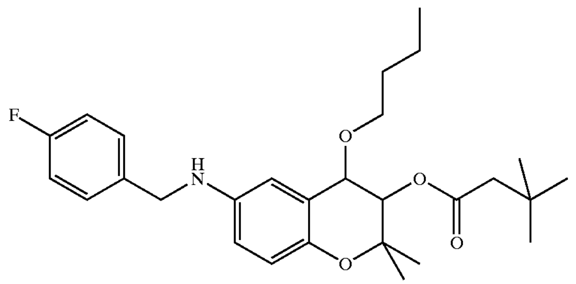 5-1792 | $^1$H NMR(200MHz, $CDCl_3$) δ 7.30~7.37(m, 2H), 6.96~7.05(m, 2H), 6.59~6.67(m, 3H), 5.18(d, 1H, J=5.29Hz), 4.30(d, 1H, J=5.29Hz), 4.24(s, 2H), 3.55(t, 2H, J=6.31 Hz), 2.24(s, 2H), 1.40~1.54(m, 4H), 1.35(s, 3H), 1.28(s, 3H), 1.03(s, 9H), 0.90~0.93(m, 3H); MS, m/z: 471.6 |
| 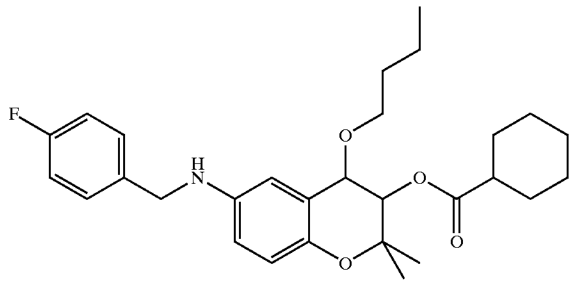 5-1793 | MS, m/z: 483.6 |

TABLE 3-continued
| Compound No. | NMR/MS Data |
|---|---|
| 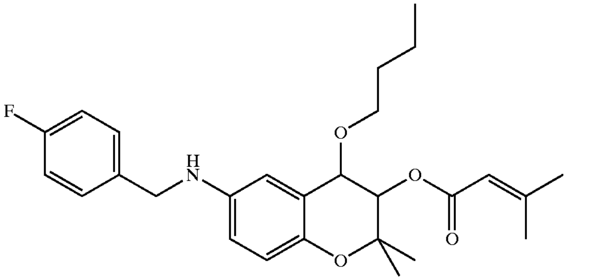 5-1794 | $^1$H NMR(200MHz, $CDCl_3$) δ 7.30~7.37(m, 2H), 6.96~7.05(m, 2H), 6.63~6.68(m, 3H), 5.70(d, 1H, J=1.20Hz), 5.20(d, 1H, J=5.09Hz), 4.26(d, 1H, J=5.09Hz), 4.24(s, 2H), 3.61~3.64(m, 2H), 2.16(d, 3H, J=1.02Hz), 1.88(d, 3H, J=1.42Hz), 1.35(s, 3H), 1.29(s, 3H), 0.90(t, 3H, J=6.90Hz); MS, m/z: 455.5 |
| 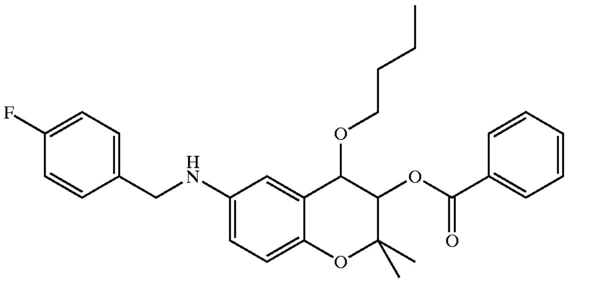 5-1795 | $^1$H NMR(200MHz, $CDCl_3$) δ 8.04(d, 2H, J=8.34Hz), 7.30~7.57(m, 5H), 6.96~7.04(m, 3H), 6.59~6.76(m, 3H), 5.41(d, 1H, J=5.09Hz), 4.41(d, 1H, J=5.09Hz), 4.24(s, 2H), 3.63~3.70(m, 2H), 1.31~1.59(m, 4H), 1.40(s, 3H), 1.38(s, 3H), 0.86(t, 3H, J=7.12Hz); MS, m/z: 477.5 |
| 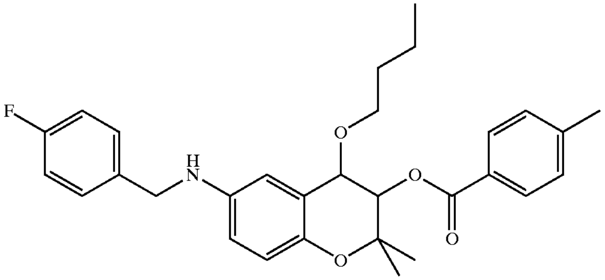 5-1796 | $^1$H NMR(200MHz, $CDCl_3$) δ 7.93(d, 2H, J=8.14Hz), 7.20~7.37(m, 4H), 6.96~7.05(m, 2H), 6.58~6.76(m, 3H), 5.40(d, 1H, 5.09Hz), 4.41 (d, 1H, J=5.09Hz), 4.24(s, 2H), 3.62~3.68(m, 2H), 2.40(s, 3H), 1.22~1.55(m, 4H), 1.39(s, 3H), 1.37(s, 3H), 0.86(t, 3H, J=7.33Hz); MS, m/z: 491.6 |

TABLE 3-continued
| Compound No. | NMR/MS Data |
| --- | --- |
| 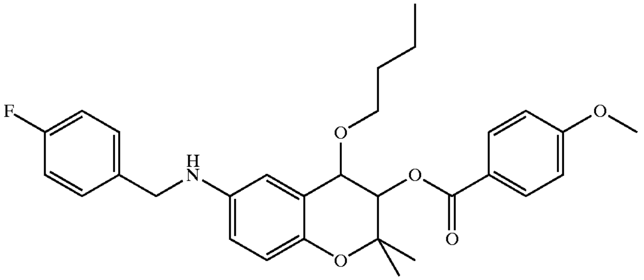 5-1797 | $^1$H NMR(200MHz, $CDCl_3$) δ 7.98(d, 2H, J=8.95Hz), 7.26~7.92(m, 2H), 6.86~7.05(m, 4H), 6.57~6.76(m, 3H), 5.39(d, 1H, J=5.09Hz), 4.40(d, 1H, J=5.09Hz), 4.24(s, 2H), 3.85(s 3H), 3.62~3.83(m, 2H), 1.22~1.56(m, 4H), 1.39(s, 3H), 1.37(s, 3H), 0.90(t, 3H, J=4.27Hz); MS, m/z: 507.6 |
| 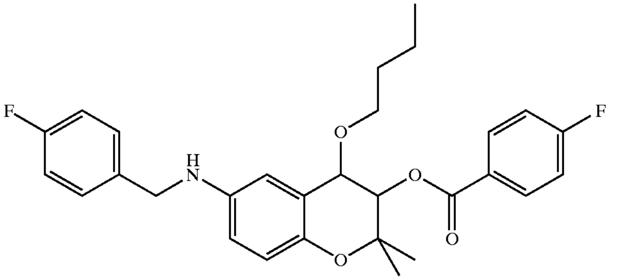 5-1798 | MS, m/z: 495.5 |
| 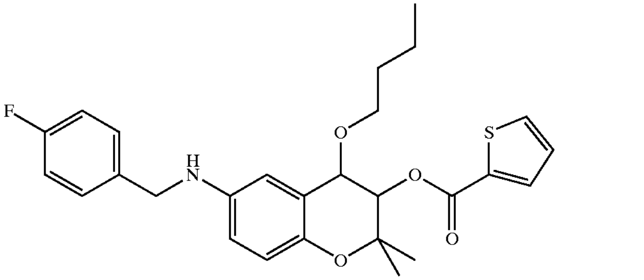 5-1799 | $^1$H NMR(200MHz, $CDCl_3$) δ 7.82(dd, 1H, J=1.02Hz, J=3.87Hz), 7.57(dd, 1H, J=1.02Hz, J=3.87Hz), 7.26~7.37(m, 2H), 6.97~7.13(m, 3H), 6.55~6.74(m, 3H), 5.36(d, 1H, J=5.70Hz), 4.45(d, 1H, J=5.70Hz), 4.24(s, 2H), 3.65(t, 2H, J=6.10Hz), 1.22~1.55(m, 4H), 1.40(s, 3H), 1.36(s, 3H), 0.86(t, 3H, J=7.12Hz); MS, m/z: 483.6 |

TABLE 3-continued
| Compound No. | NMR/MS Data |
| --- | --- |
| 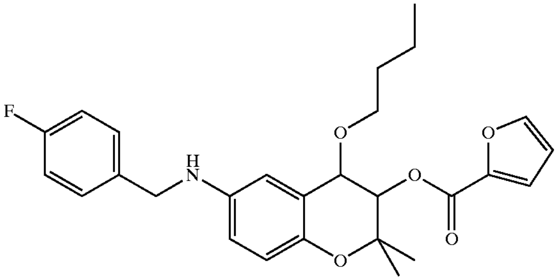 5-1800 | $^1$H NMR(200MHz, $CDCl_3$) δ 7.59(d, 1H, J=1.02Hz), 7.30~7.37(m, 2H), 7.18(d, 1H, J=3.46Hz), 6.97~7.05(m, 2H), 6.54~6.74(m, 3H), 6.49~6.51(m, 1H), 5.37(d, 1H, J=5.49 Hz), 4.42(d, 1H, J=5.49Hz), 4.24(s, 2H), 3.64(t, 2H, J=6.31Hz), 1.22~1.55(m, 4H), 1.39(s, 3H), 1.35(s, 3H), 0.87(t, 3H, J=7.32Hz); MS, m/z: 467.5 |
| 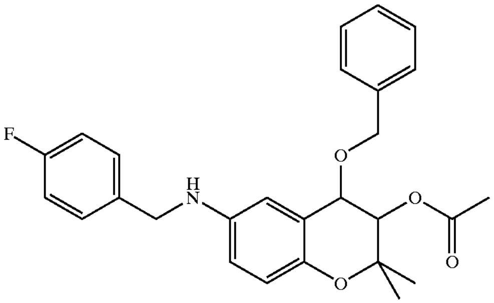 5-1801 | MS, m/z: 449.5 |
| 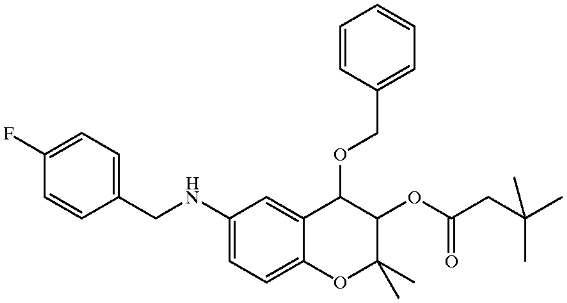 5-1802 | $^1$H NMR(200MHz, $CDCl_3$) δ 7.26~7.32(m, 7H), 6.95~7.04(m, 2H), 6.47~6.72(m, 3H), 5.28(d, 1H, J=4.68Hz), 4.17(s, 2H), 4.40(d, 1H, J=4.68Hz), 4.17(s, 2H), 2.24(s, 2H), 1.39(s, 3H), 1.33(s, 3H), 1.01 (s, 9H); MS, m/z: 505.6 |

TABLE 3-continued
| Compound No. | NMR/MS Data |
| --- | --- |
| 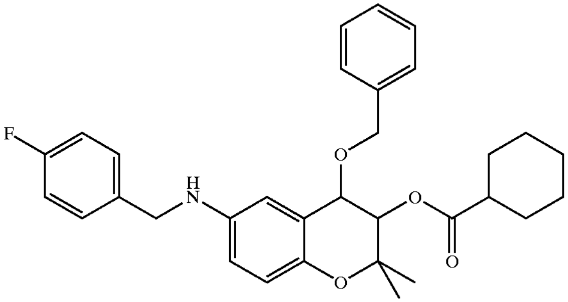 5-1803 | MS, m/z: 517.6 |
| 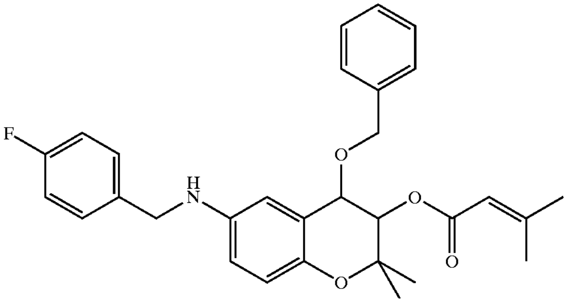 5-1804 | MS, m/z: 489.5 |
| 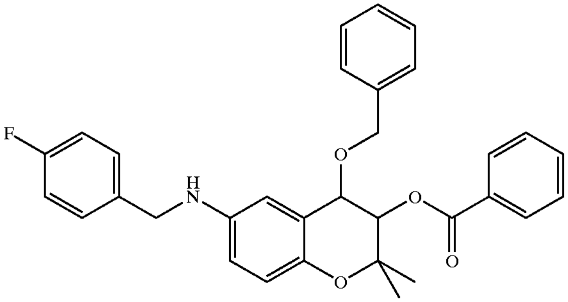 5-1805 | MS, m/z: 511.6 |
| 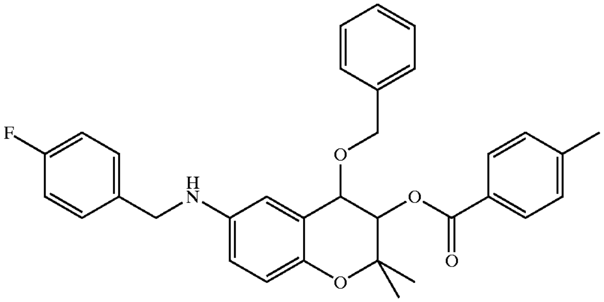 5-1806 | $^1$H NMR(200MHz, $CDCl_3$) δ 7.93(d, 2H, J=7.94Hz), 7.21~7.86(m, 9H), 6.96~7.04(m, 2H), 6.49~6.76(m, 3H), 5.51(d, 1H, J=4.88Hz), 4.75(s, 2H), 4.56(d, 1H, J=4.88 Hz), 4.17(s, 2H), 2.41(s, 2H), 2.41(s, 3H), 1.43(s, 3H), 1.40(s, 3H); MS, m/z: 525.6 |

TABLE 3-continued
| Compound No. | | NMR/MS Data |
|---|---|---|
| 5-1807 | 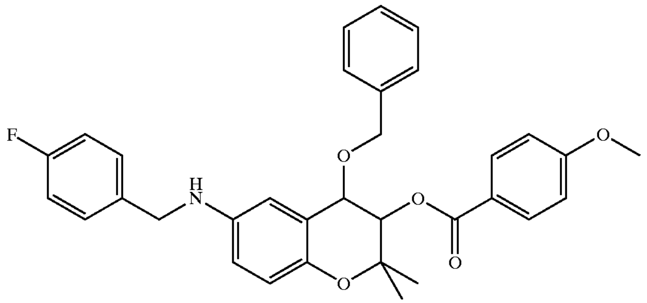 | $^1H$ NMR(200MHz, $CDCl_3$) δ 8.00(d, 2H, J=8.75Hz), 7.26~7.29(m, 7H), 6.88~7.04(m, 4H), 6.51~6.76(m, 3H), J=4.88Hz), 4.75(s, 2H), 4.50(d, 1H, J=4.88 Hz), 4.17(s, 2H), 3.85(s, 3H), 1.43(s, 3H), 1.40(s, 3H); MS, m/z: 541.6 |
| 5-1808 | 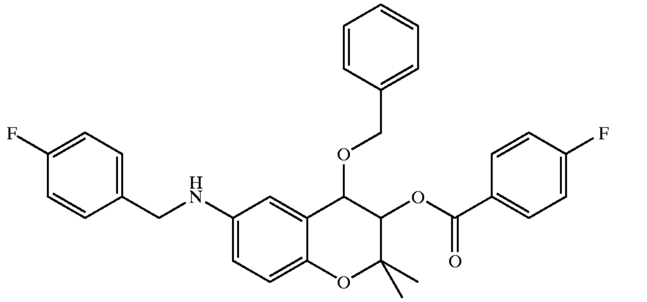 | $^1H$ NMR(200MHz, $CDCl_3$) δ , 8.02~8.09(m, 2H), 7.27~7.35(m, 7H), 7.00~7.15(m, 4H), 6.49~6.77(m, 3H), 5.50(d, 1H, J=4.68Hz), 4.75(s, 2H), 4.55(d, 1H, J=4.68 Hz), 4.17(s, 2H), 1.44(s, 3H), 1.41(s, 3H); MS, m/z: 529.5 |
| 5-1809 | 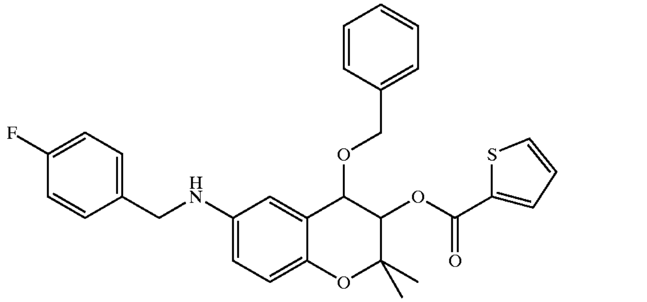 | $^1H$ NMR(200MHz, $CDCl_3$) δ 7.82~7.84(m, 1H), 7.57~7.60(m, 1H), 7.26~7.33(m, 7H), 6.96~7.13(m, 3H), 5.46(d, 1H, J=5.29Hz), 4.73(s, 2H), 4.60(d, 1H, J=5.29 Hz), 4.17(s, 2H), 1.43(s, 3H), 1.39(s, 3H); MS, m/z: 517.6 |

TABLE 3-continued
| Compound No. | NMR/MS Data |
| --- | --- |
| 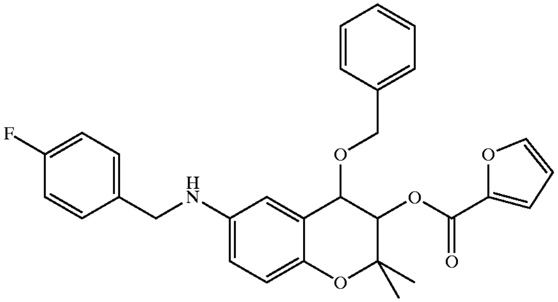 5-1810 | $^{1}H$ NMR(200MHz, $CDCl_3$) δ 7.59~7.60(m, 1H), 7.20~7.35(m, 7H), 7.18~7.20(m, 1H), 6.96~7.05(m, 2H), 6.49~6.75(m, 4H), 5.47(d, 1H, J=5.09Hz), 4.73(s, 2H), 4.56(d, 1H, J=5.09Hz), 4.17(s, 2H), 1.43(s, 3H), 1.38(s, 3H); MS, m/z: 501.5 |
| 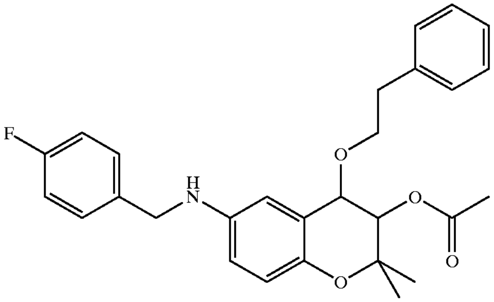 5-1811 | MS, m/z: 463.5 |
| 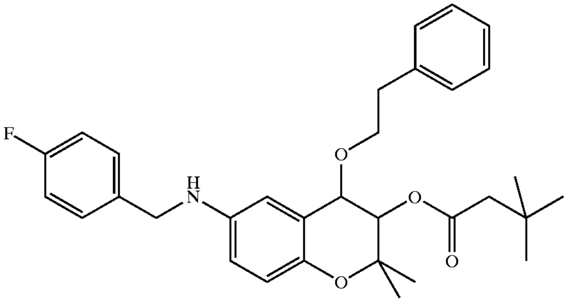 5-1812 | MS, m/z: 519.6 |
| 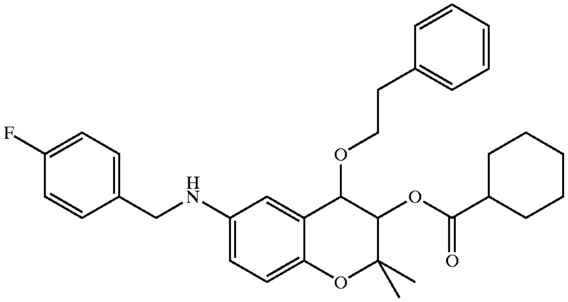 5-1813 | MS, m/z: 531.6 |
| 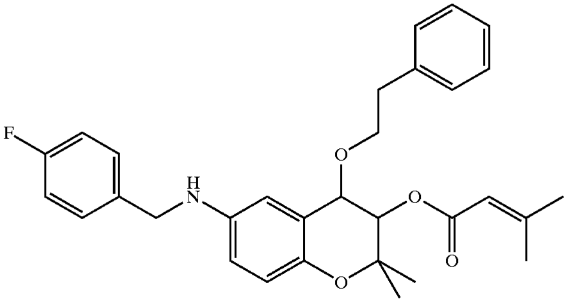 5-1814 | MS, m/z: 503.6 |

TABLE 3-continued
| Compound No. | NMR/MS Data |
| --- | --- |
| 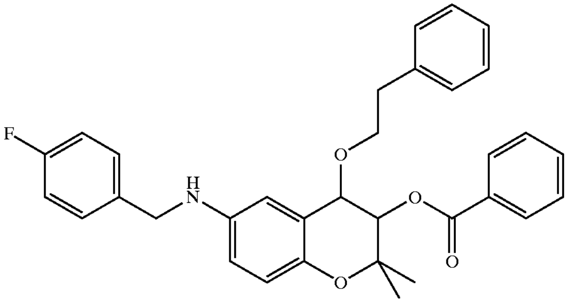 5-1815 | MS, m/z: 525.6 |
| 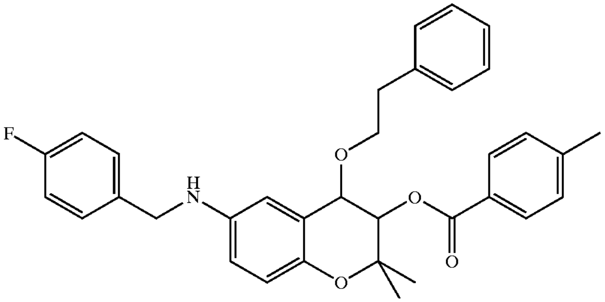 5-1816 | MS, m/z: 539.6 |
| 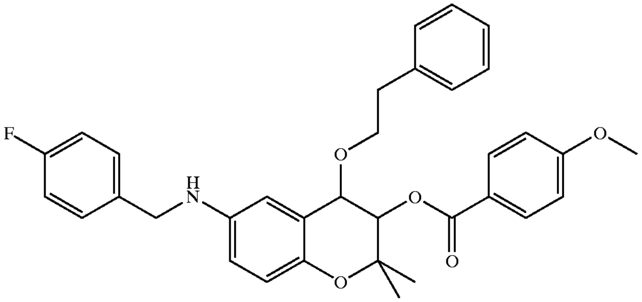 5-1817 | MS, m/z: 555.6 |
| 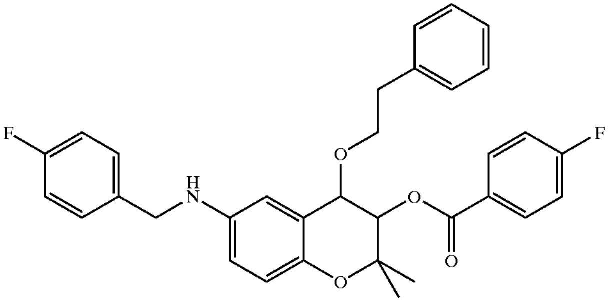 5-1818 | MS, m/z: 543.6 |
| 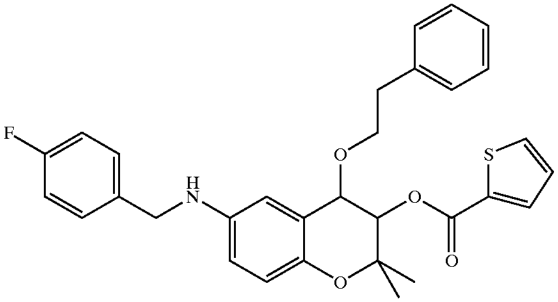 5-1819 | MS, m/z: 531.6 |
| 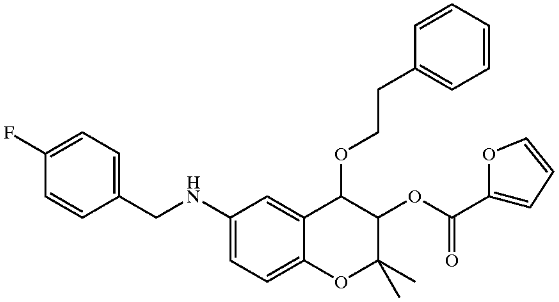 5-1820 | MS, m/z: 515.5 |

TABLE 3-continued
| Compound No. | | NMR/MS Data |
|---|---|---|
| 5-1821 | 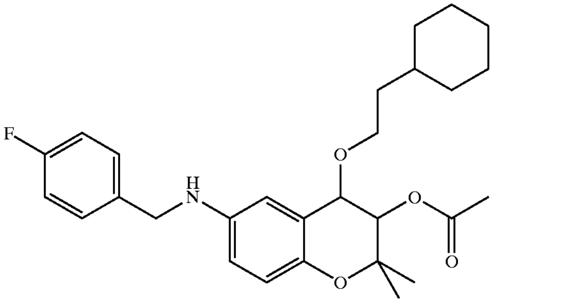 | MS, m/z: 469.9 |
| 5-1822 | 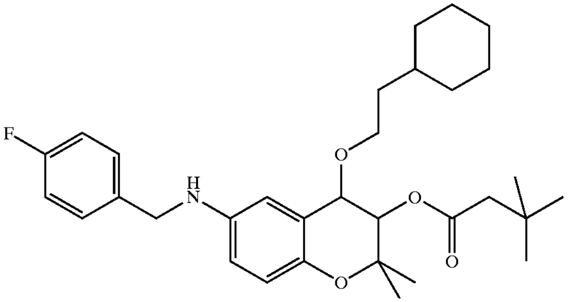 | MS, m/z: 525.7 |
| 5-1823 | 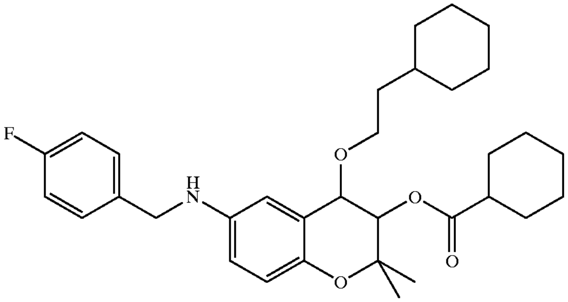 | MS, m/z: 537.7 |
| 5-1824 | 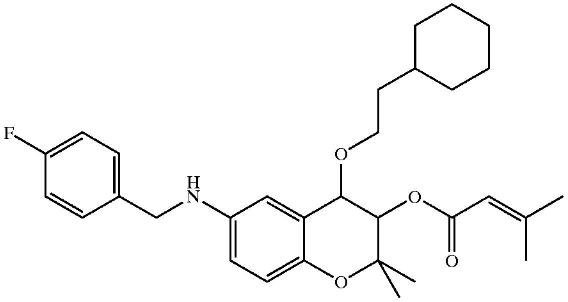 | MS, m/z: 509.6 |
| 5-1825 | 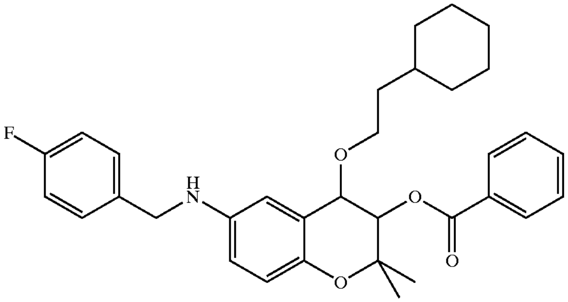 | MS, m/z: 531.6 |
| 5-1776 | 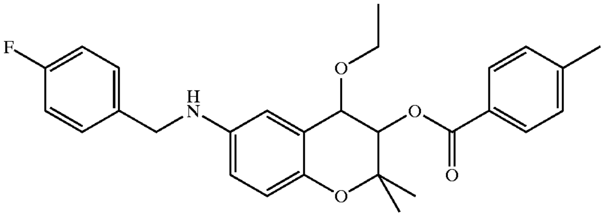 | MS, m/z: 545.7 |

TABLE 3-continued
| Compound No. | | NMR/MS Data |
| --- | --- | --- |
| 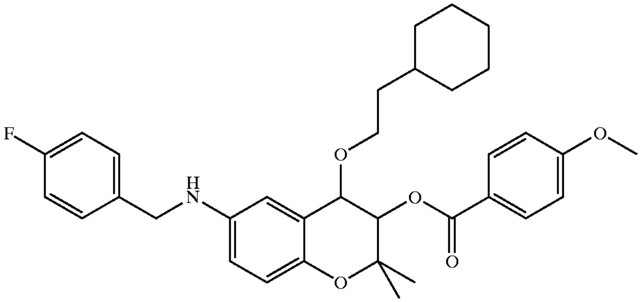 5-1827 | | MS, m/z: 561.7 |
| 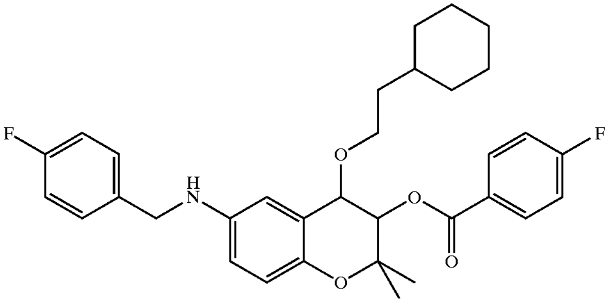 5-1828 | | MS, m/z: 549.6 |
| 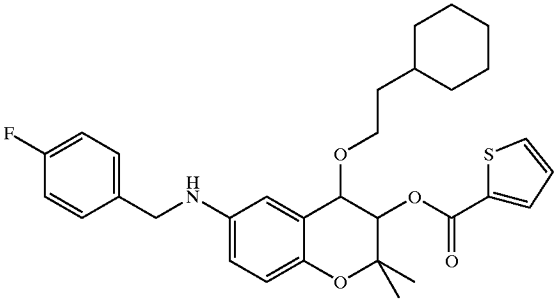 5-1829 | | MS, m/z: 537.7 |
| 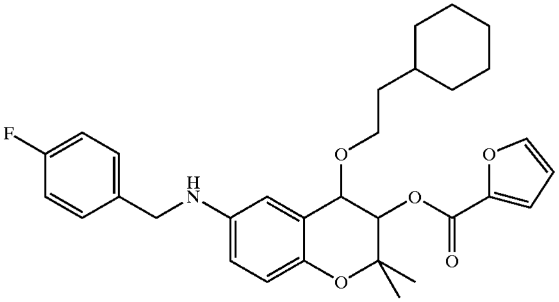 5-1830 | | MS, m/z: 521.6 |
| 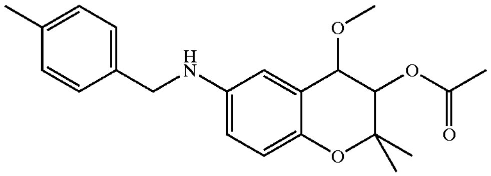 5-1831 | | $^1H$ NMR(200MHz, $CDCl_3$) δ 7.12~7.26(m, 4H), 6.59~6.73(m, 3H), 5.22(d, 1H, J=5.49Hz), 4.28(d, 1H, J=5.49 Hz), 4.22(s, 2H), 3.40(s, 3H), 2.33(s, 3H), 2.11(s, 3H), 1.35(s, 3H), 1.29(s, 3H); MS, m/z: 369.4 |

TABLE 3-continued
| Compound No. | NMR/MS Data |
| --- | --- |
| 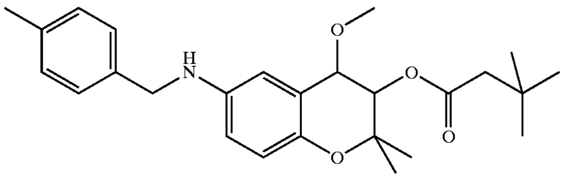 5-1832 | $^1$H NMR(200MHz, $CDCl_3$) δ 7.12~7.27(m, 4H), 6.57~6.73(m, 3H), 5.24(d, 1H, J=10Hz), 4.33(d, 1H, J=6.10 Hz), 4.22(s, 2H), 3.36(s, 3H), 2.33(s, 3H), 2.27(s, 2H), 1.36(s, 3H), 1.29(s, 3H), 1.05(s, 9H); MS, m/z: 425.5 |
| 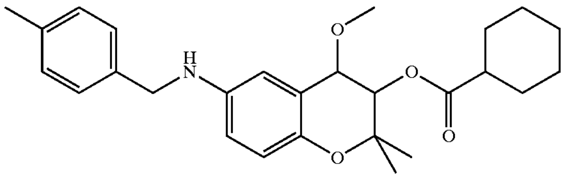 5-1833 | $^1$H NMR(200MHz, $CDCl_3$) δ 7.12~7.28(m, 4H), 6.56~6.73(m, 3H), 5.22(d, 1H, J=5.9Hz), 4.29(d, 1H, J=5.9Hz), 4.22(s, 2H), 3.39(s, 3H), 2.98~2.37(m, 1H), 1.28~1.93(m, 10H), 1.34(s, 3H), 1.28(s, 3H); MS, m/z: 437.5 |
| 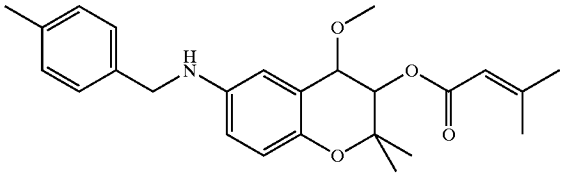 5-1834 | $^1$H NMR(200MHz, $CDCl_3$) δ 7.12~7.27(m, 4H), 6.58~216.73(m, 3H), 5.72~5.73(m, 1H), 5.25(d, 1H, J=5.49Hz), 4.29(d, 1H, J=5.49Hz), 4.22(s, 2H), 3.43(s, 3H), 2.33(s, 3H), 2.18(d, 3H, J=1.20Hz), 1.90(d, 3H, J=1.20Hz), 1.36(s, 3H), 1.30(s, 3H); MS, m/z: 409.5 |
| 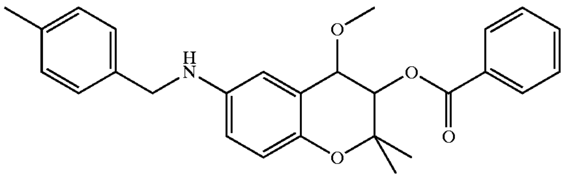 5-1835 | $^1$H NMR(200MHz, $CDCl_3$) δ 8.04~8.09(m, 2H), 7.41~7.58(m, 3H), 7.07~7.37(m, 4H), 6.61~6.78(m, 3H), 5.48(d, 1H, J=5.70), 4.45(d, 1H, J=5.70Hz), 4.23(s, 2H), 3.47(s, 3H), 2.33(s, 3H), 1.42(s, 3H), 1.39(s, 3H); MS, m/z: 431.5 |

TABLE 3-continued
| Compound No. | NMR/MS Data |
|---|---|
| 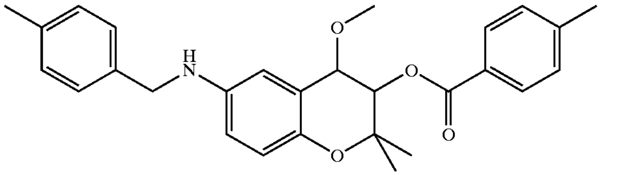 5-1836 | $^1$H NMR(200MHz, $CDCl_3$) δ 7.94(d, 2H, J=8.34Hz), 7.12~7.28(m, 6H), 6.60~6.77(m, 3H), 5.46(d, 1H, J=5.70Hz), 4.44(d, 1H, J=5.70Hz), 4.23(s, 2H), 3.46(s, 3H), 2.41(s, 3H), 2.33(s, 3H), 1.40(s, 3H), 1.38(s, 3H); MS, m/z: 445.5 |
| 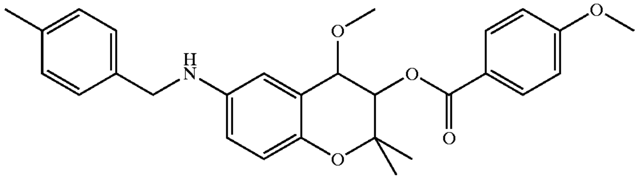 5-1837 | $^1$H NMR(200MHz, $CDCl_3$) δ 8.00(dd, 2H, J=2.04Hz, J=6.92Hz), 7.11~7.26(m, 4H), 6.89~6.85(m, 2H), 6.65~6.77(m, 3H), 5.43(d, 1H, J=5.49Hz), 4.41(d, 1H, J=5.49 Hz), 4.22(s, 2H), 3.86(s, 3H), 3.46(s, 3H), 2.32(s, 3H), 1.40(s, 3H), 1.37(s, 3H); MS, m/z: 461.5 |
| 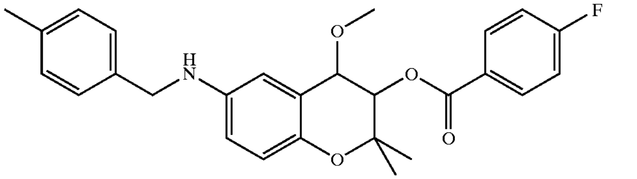 5-1838 | $^1$H NMR(200MHz, $CDCl_3$) δ 8.03~8.10(m, 2H), 7.07~7.28(m, 6H), 6.59~6.77(m, 3H), 5.45(d, 1H, J=5.48Hz), 4.43(d, 1H, J=5.49Hz), 4.23(s, 2H), 3.46(s, 3H), 2.33(s, 3H), 1.41(s, 3H), 1.38(s, 3H); MS, m/z: 449.5 |
| 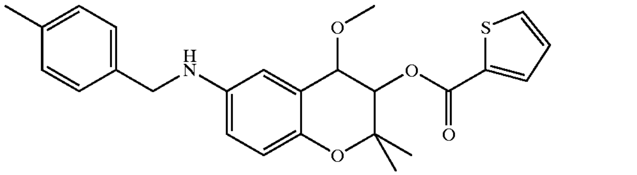 5-1839 | $^1$H NMR(200MHz, $CDCl_3$) δ 7.84(dd, 1H, J=1.22Hz, J=3.87Hz), 7.58(dd, 1H, J=1.22Hz, J=3.87Hz), 7.09~7.28(m, 5H), 6.58~6.76(m, 3H), 5.41(d, 1H, J=6.31Hz), 4.49(d, 1H, J=6.31Hz), 4.23(s, 2H), 3.44(s, 3H), 2.33(s, 3H), 1.41(s, 3H), 1.36(s, 3H); MS, m/z: 437.5 |

TABLE 3-continued
| Compound No. | NMR/MS Data |
| --- | --- |
| 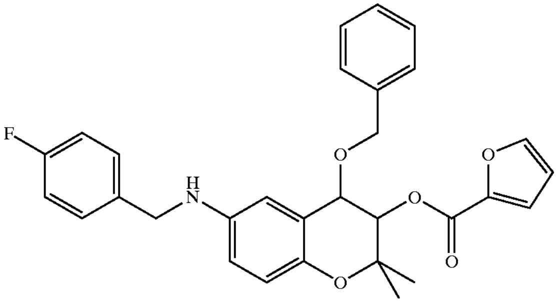 5-1810 | $^1$H NMR(200MHz, $CDCl_3$) δ 7.60(dd, 1H, J=0.81Hz, J=1.83Hz), 7.12~7.27(m, 5H), 6.58~6.75(m, 3H), 6.51 (dd, 1H, J=1.83Hz, J=3.46Hz), 5.42(d, 1H, J=6.10 Hz), 4.46(d, 1H, J=6.10Hz), 4.22(s, 2H), 3.43(s, 3H), 2.33(s, 3H), 1.40(s, 3H), 1.35(s, 3H); MS, m/z: 421.5 |
| 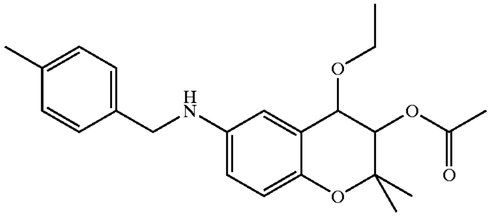 5-1841 | MS, m/z: 383.4 |
| 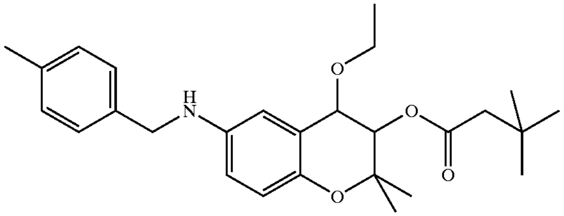 5-1842 | MS, m/z: 439.6 |
| 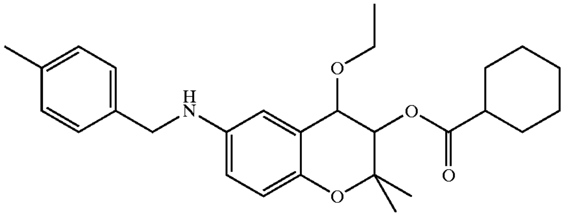 5-1843 | MS, m/z: 351.6 |
| 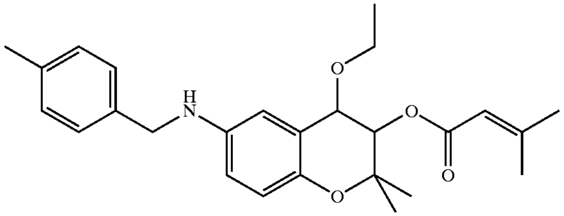 5-1844 | MS, m/z: 423.5 |

TABLE 3-continued
| Compound No. | NMR/MS Data | Compound No. | NMR/MS Data |
|---|---|---|---|
| 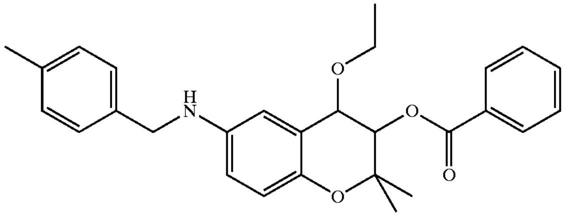 5-1845 | MS, m/z: 445.4 | 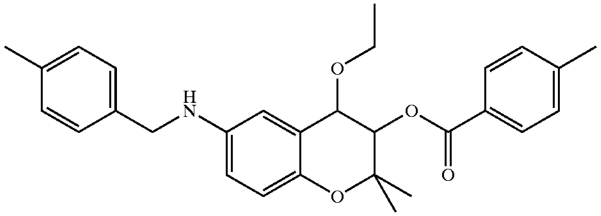 5-1846 | MS, m/z: 459.5 |
| 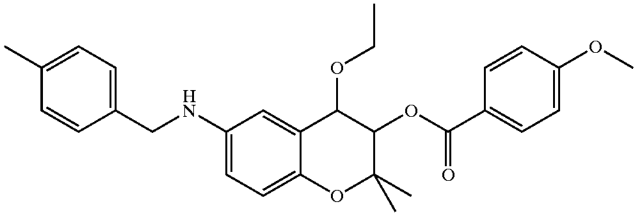 5-1847 | MS, m/z: 451.5 | 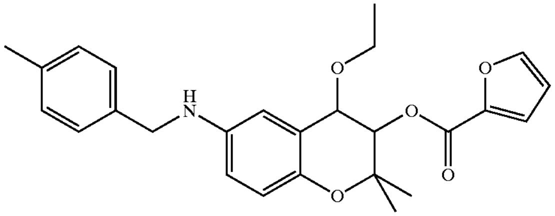 5-1850 | MS, m/z: 463.5 |
| 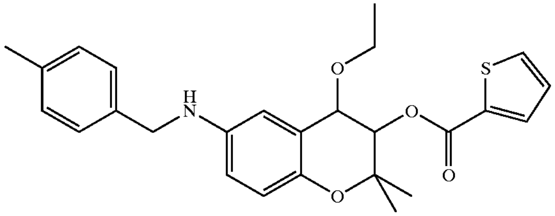 5-1849 | MS, m/z: 451.5 | 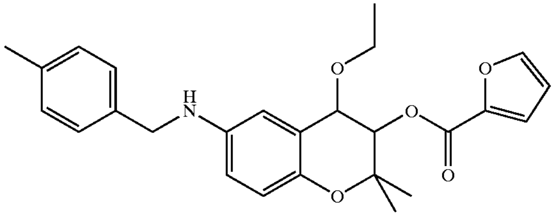 5-1850 | MS, m/z: 435.5 |
| 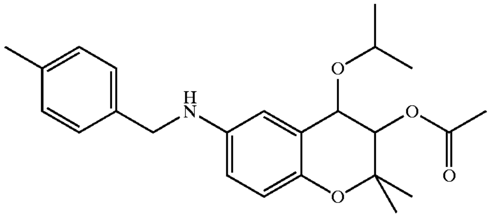 5-1851 | MS, m/z: 397.5 | 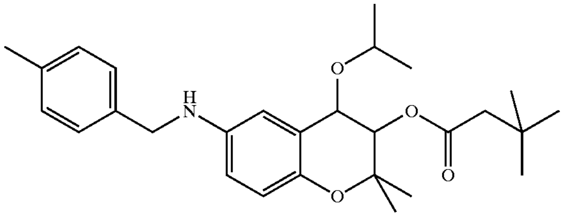 5-1852 | MS, m/z: 453.6 |

TABLE 3-continued
| Compound No. | NMR/MS Data | Compound No. | NMR/MS Data |
|---|---|---|---|
| 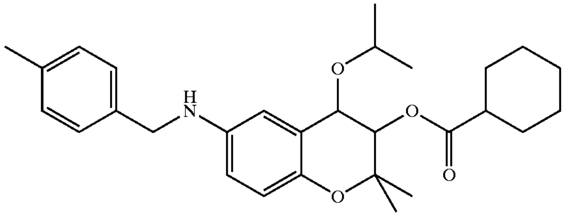 5-1853 | MS, m/z: 465.6 | 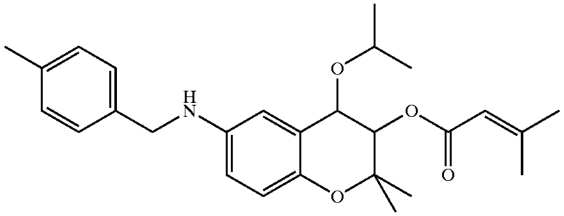 5-1854 | MS, m/z: 437.5 |
| 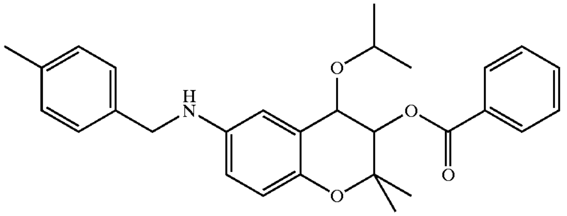 5-1855 | MS, m/z: 459.5 | 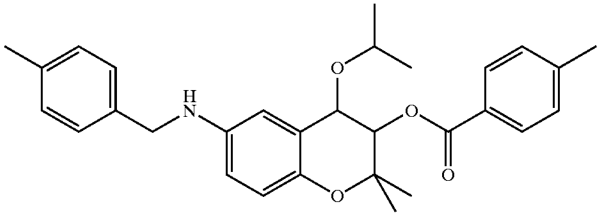 5-1856 | MS, m/z: 473.6 |
| 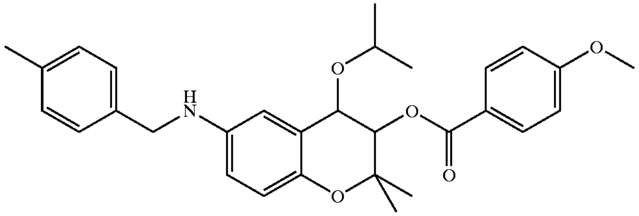 5-1857 | MS, m/z: 489.6 | 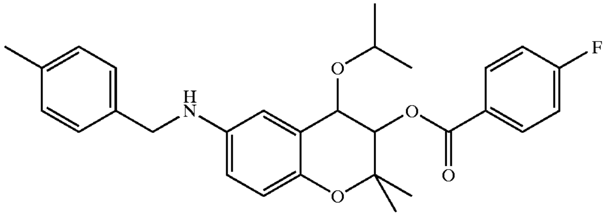 5-1858 | MS, m/z: 477.5 |
| 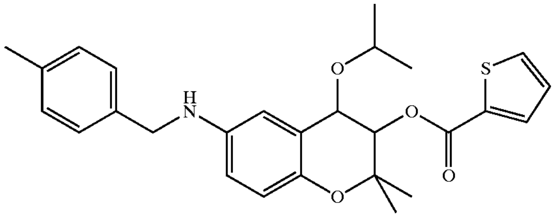 5-1859 | MS, m/z: 465.6 | 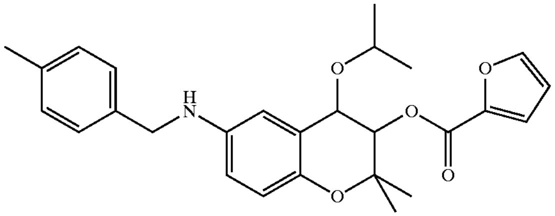 5-1860 | MS, m/z: 449.5 |

TABLE 3-continued
| Compound No. | NMR/MS Data |
| --- | --- |
| 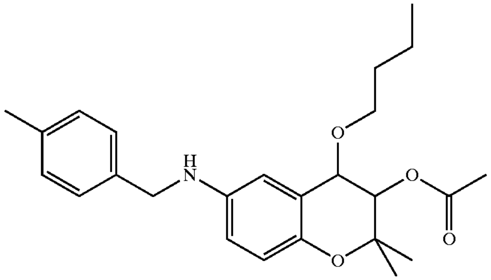 5-1861 | MS, m/z: 411.5 |
| 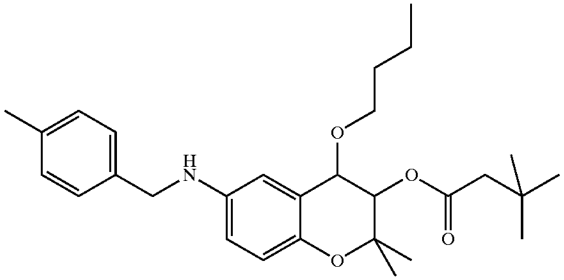 5-1862 | MS, m/z: 467.6 |
| 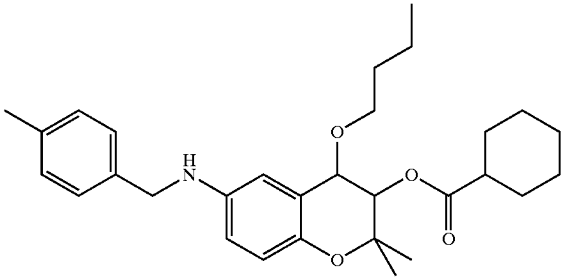 5-1863 | MS, m/z: 479.6 |
| 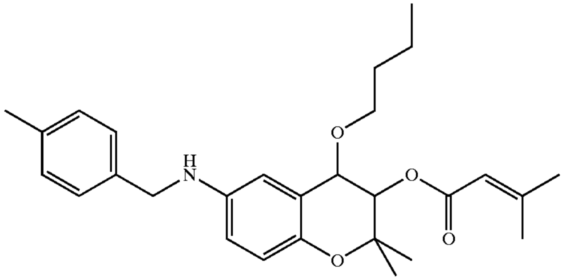 5-1864 | $^1$H NMR(200MHz, $CDCl_3$) δ 7.16~7.26(m, 4H), 7.06~7.09(m, 2H), 6.71~6.98(m, 3H), 5.68(d, 1H, J=1.42Hz), 5.19(d, 1H, J=4.68Hz), 4.22(d, 1H, J=4.68Hz), 4.17(s, 2H), 3.59~3.68(m, 2H), 2.26(s, 3H), 2.17(s, 3H), 1.89(s, 3H), 1.35(s, 3H), 1.30(s, 3H), 1.19~1.59(m, 4H), 0.90(t, 3H, J=7.32Hz); MS, m/z: 451.6 |

TABLE 3-continued
| Compound No. | NMR/MS Data |
| --- | --- |
| 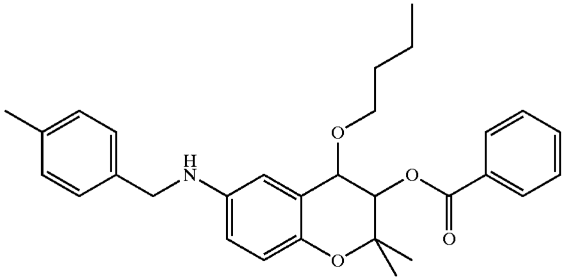 5-1865 | $^1$H NMR(200MHz, $CDCl_3$) δ 8.01~8.05(m, 2H), 7.26~7.57(m, 3H), 7.07~7.23(m, 4H), 6.77~6.83(m, 3H), 5.41(d, 1H, J=4.55Hz), 4.40(d, 1H, J=4.55Hz), 4.20(s, 2H), 3.21~3.70(s, 2H), 2.28(s, 3H), 1.40(s, 3H), 1.38(s, 3H), 1.19~1.57(m, 4H), 0.86(t, 3H, J=7.32Hz); MS, m/z: 473.6 |
| 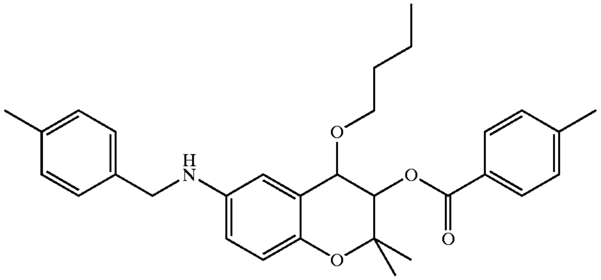 5-1866 | MS, m/z: 487.6 |
| 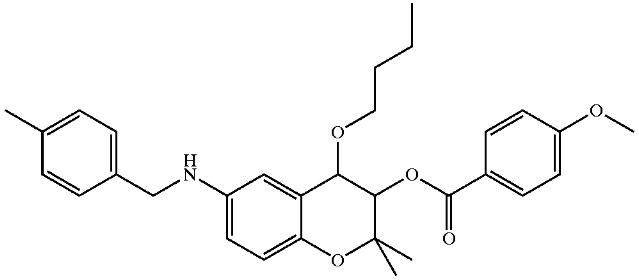 5-1867 | $^1$H NMR(200MHz, $CDCl_3$) δ 7.93~7.98(m, 2H), 6.98~7.26(m, 6H), 6.79~6.97(m, 3H), 5.35(d, 1H, J=4.68Hz), 4.30(d, 1H, J=4.68Hz), 4.16(s, 2H), 3.84(s, 3H), 3.65~3.76(m, 2H), 2.17(s, 3H), 1.39(s, 3H), 1.37(s, 3H), 1.19~1.52(m, 4H), 0.86(t, 3H, J=7.12Hz); MS, m/z: 503.6 |

TABLE 3-continued
| Compound No. | NMR/MS Data |
|---|---|
| 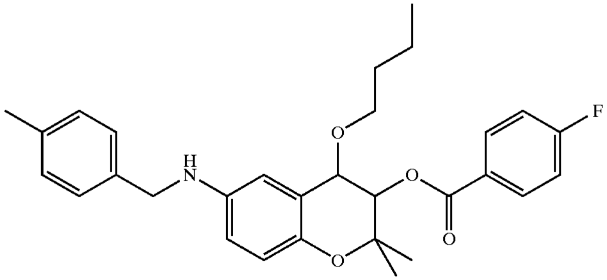 5-1868 | $^1$H NMR(200MHz, $CDCl_3$) δ 8.00~8.07(m, 2H), 7.06~7.25(m, 6H), 6.78~6.87(m, 3H), 5.38(d, 1H, J=4.88Hz), 4.37(d, 1H, J=4.88Hz), 4.18(s, 2H), 3.62~3.70(m, 2H), 2.27(s, 3H), 1.40(s, 3H), 1.37(s, 3H), 1.19~1.56(m, 4H), 0.87(t, 3H, J=7.12Hz); MS, m/z: 491.6 |
| 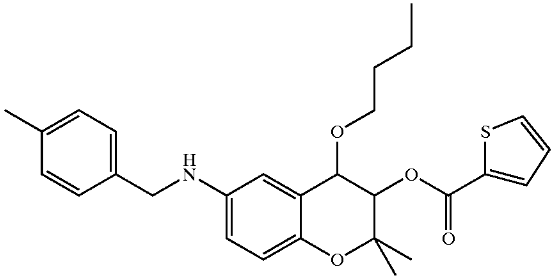 5-1869 | $^1$H NMR(200MHz, $CDCl_3$) δ 7.81 (dd, 1H, J=1.42Hz, J=3.87Hz), 7.57(dd, 1H, J=1.42Hz, J=3.87Hz), 7.08~7.26(m, 5H), 6.72~7.06(m, 3H), 5.33(d, 1H, J=5.49Hz), 4.40(d, 1H, J=5.49Hz), 4.18(s, 2H), 3.66(t, 2H, J=6.31 Hz), 2.26(s, 3H), 1.39)s, 3H), 1.36(s, 3H), 1.19~1.56(m, 4H), 0.82(t, 3H, J=7.12Hz); MS, m/z: 479.6 |
| 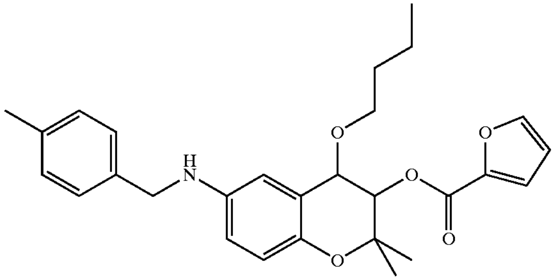 5-1870 | $^1$H NMR(200MHz, $CDCl_3$) δ 7.58(s, 1H), 7.01~7.18(m, 7H), 6.75~6.80(m, 1H), 6.49~6.51(m, 1H), 5.33(d, 1H, J=5.09Hz), 4.33(d, 1H, J=5.09Hz), 4.16(s, 2H), 3.65(t, 2H, J=6.71Hz), 2.21(s, 3H), 1.38(s, 3H), 1.35(s, 3H), 1.18~1.56(m, 4H), 0.87(t, 3H, J=7.12Hz); MS, m/z: 463.5 |

TABLE 3-continued
| Compound No. | | NMR/MS Data |
|---|---|---|
| 5-1871 | 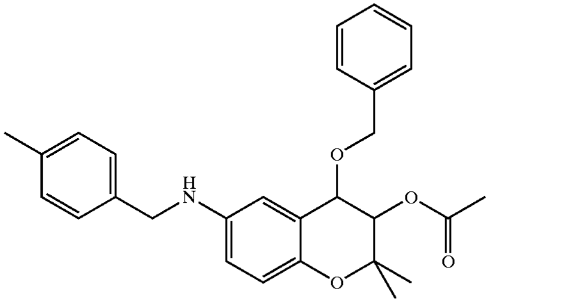 | MS, m/z: 445.5 |
| 5-1872 | 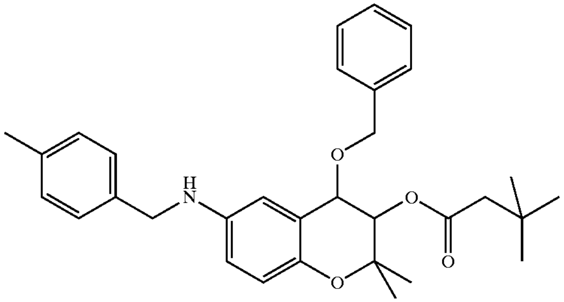 | MS, m/z: 501.6 |
| 5-1873 | 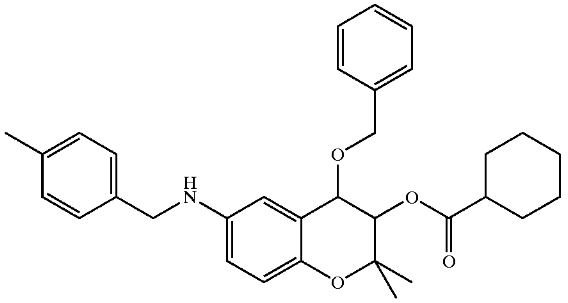 | MS, m/z: 513.6 |
| 5-1874 | 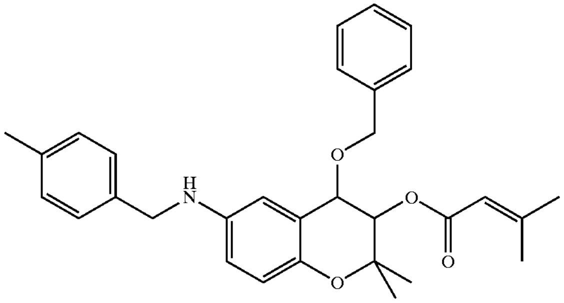 | MS, m/z: 485.6 |
| 5-1875 | 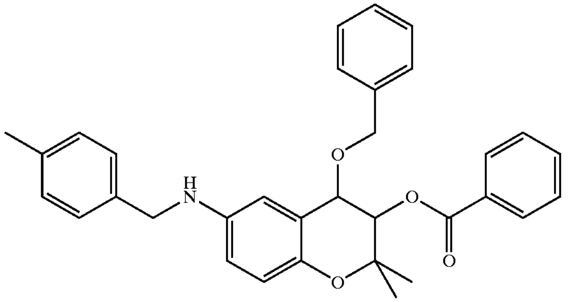 | MS, m/z: 507.6 |
| 5-1876 | 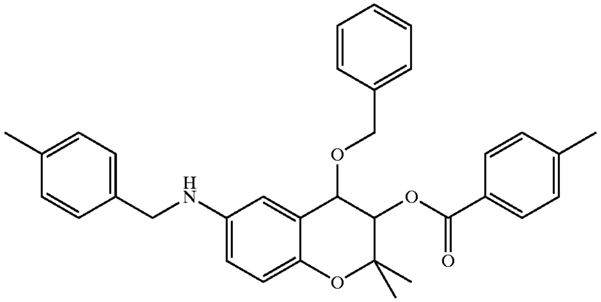 | MS, m/z: 521.6 |

TABLE 3-continued
| Compound No. | | NMR/MS Data |
|---|---|---|
| 5-1877 | 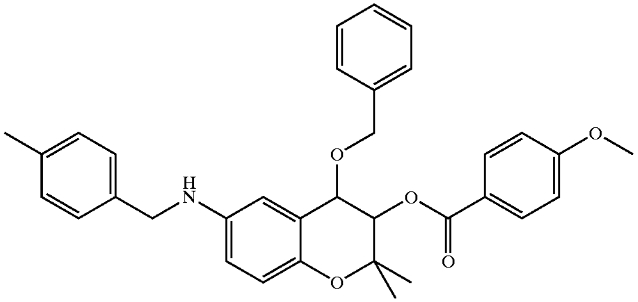 | MS, m/z: 537.6 |
| 5-1878 | 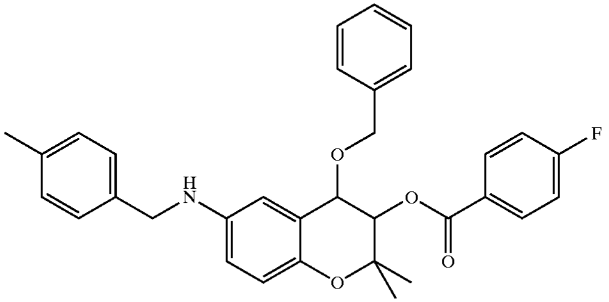 | MS, m/z: 525.6 |
| 5-1879 | 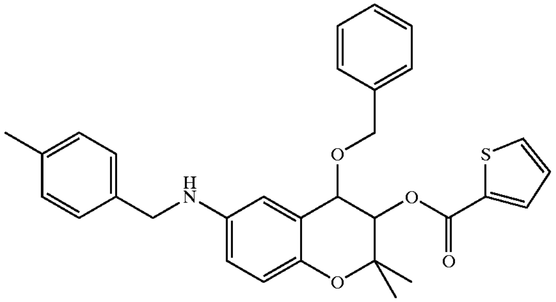 | MS, m/z: 513.6 |
| 5-1880 | 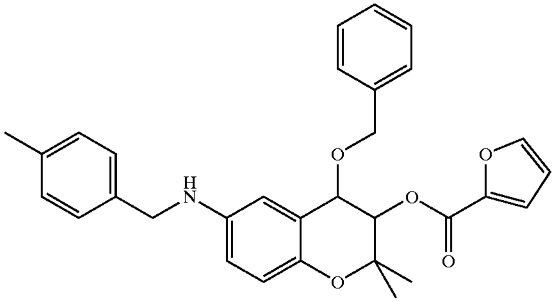 | MS, m/z: 497.6 |
| 5-1881 | 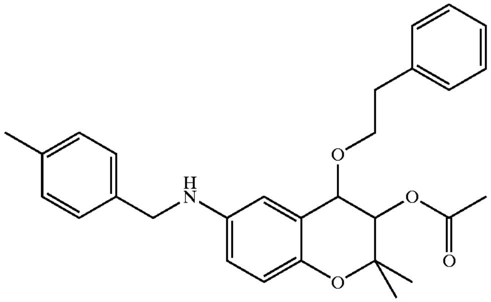 | MS, m/z: 459.5 |
| 5-1882 | 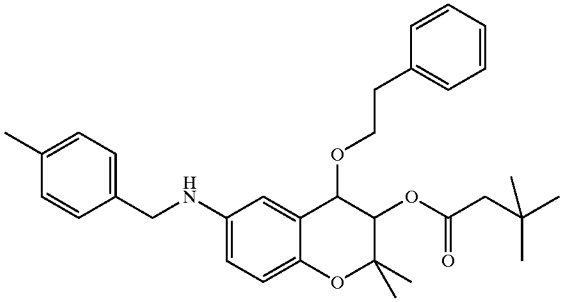 | MS, m/z: 515.7 |

TABLE 3-continued
| Compound No. | NMR/MS Data | Compound No. | NMR/MS Data |
|---|---|---|---|
| 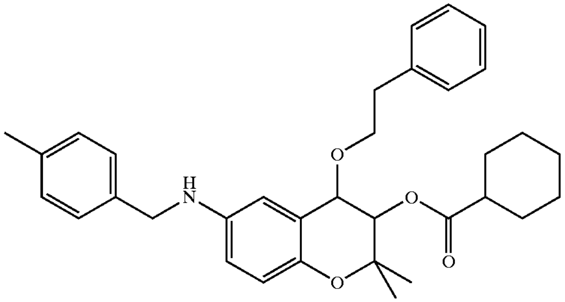 5-1883 | MS, m/z: 527.7 | 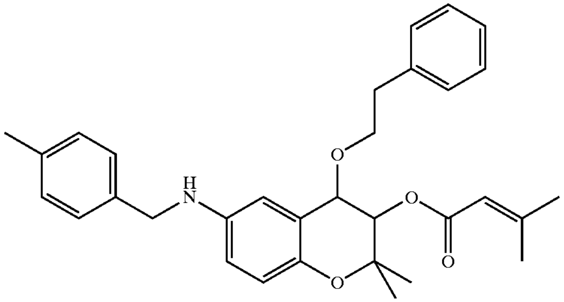 5-1884 | MS, m/z: 499.6 |
| 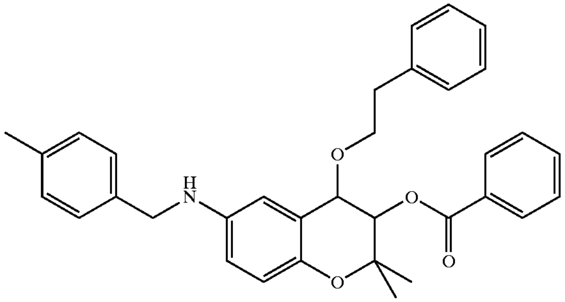 5-1885 | MS, m/z: 521.6 | 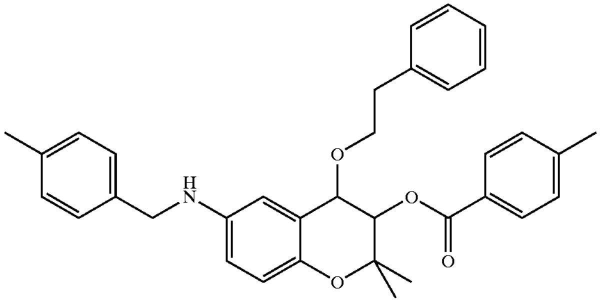 5-1886 | MS, m/z: 535.6 |
| 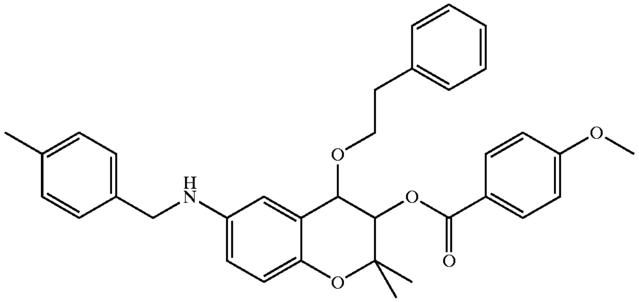 5-1887 | MS, m/z: 551.6 | 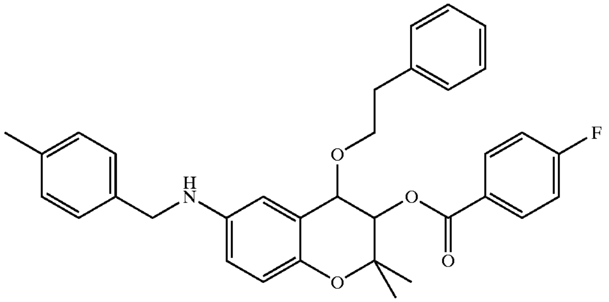 5-1888 | MS, m/z: 539.6 |

TABLE 3-continued
| Compound No. | | NMR/MS Data |
|---|---|---|
| 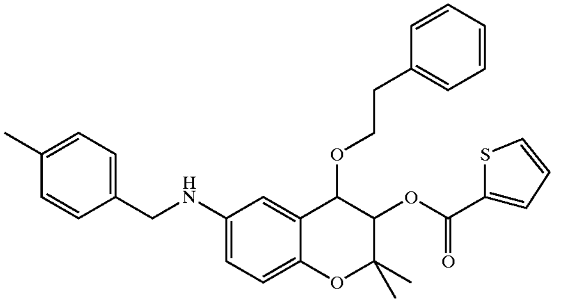 | 5-1889 | MS, m/z: 527.6 |
| 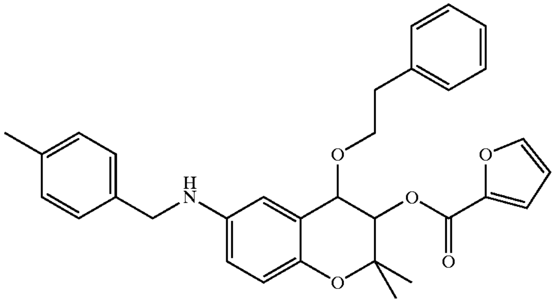 | 5-1890 | MS, m/z: 511.6 |
| 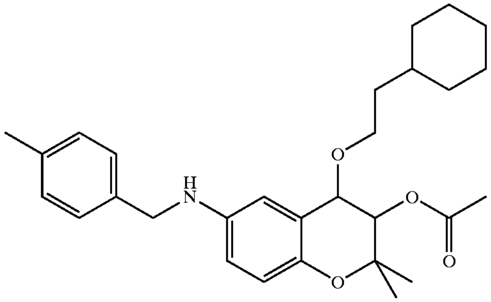 | 5-1891 | MS, m/z: 465.6 |
| 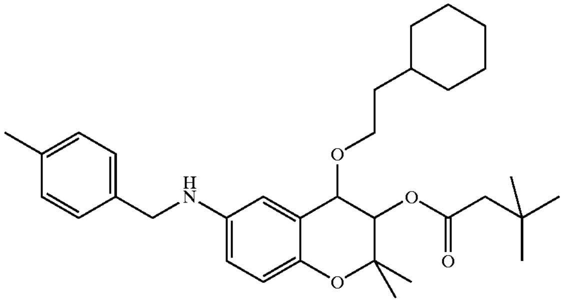 | 5-1892 | MS, m/z: 521.7 |
| 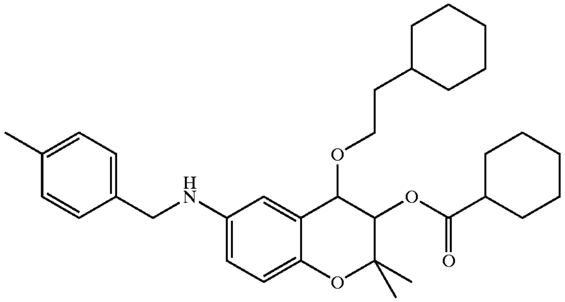 | 5-1893 | MS, m/z: 533.7 |
| 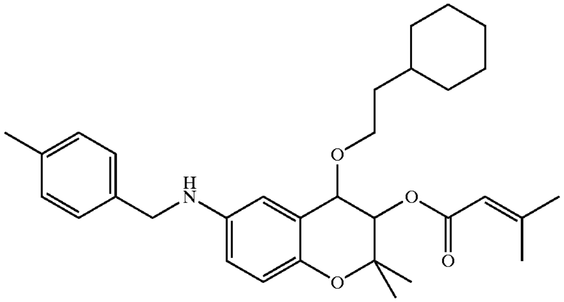 | 5-1894 | MS, m/z: 505.7 |

TABLE 3-continued
| Compound No. | | NMR/MS Data |
|---|---|---|
| 5-1895 | 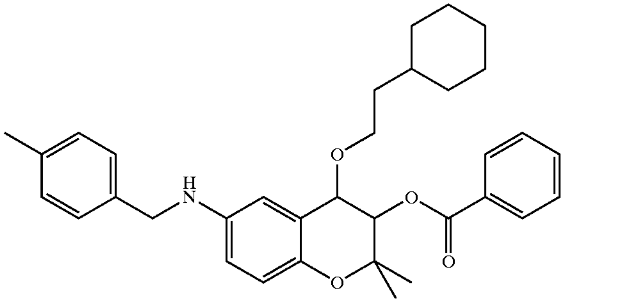 | MS, m/z: 527.7 |
| 5-1896 | 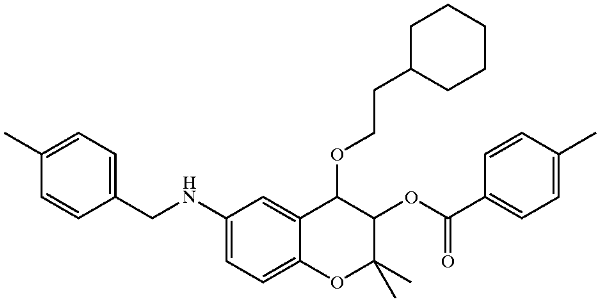 | MS, m/z: 541.7 |
| 5-1897 | 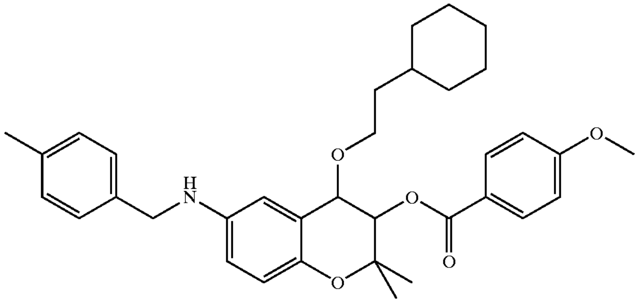 | MS, m/z: 557.7 |
| 5-1898 | 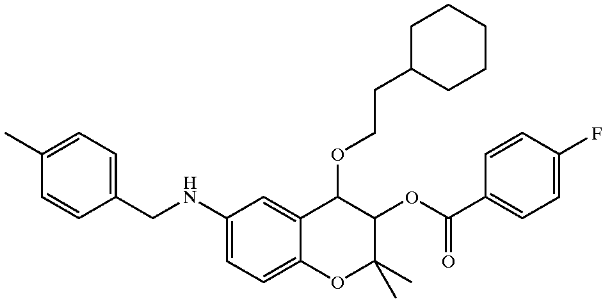 | MS, m/z: 545.7 |
| 5-1899 | 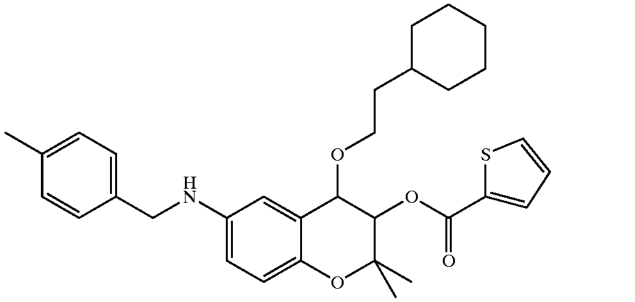 | MS, m/z: 533.7 |
| 5-1900 | 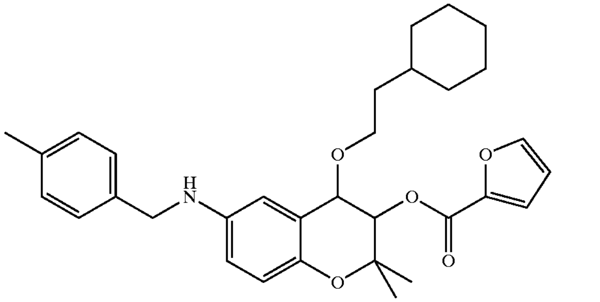 | MS, m/z: 517.6 |

The following specific formulations comprising the compound of this invention as an active ingredient are intended to be illustrative of the invention and should not be construed as limiting the scope of the invention.

FORMULATION EXAMPLE 1

Tablet (Direct Pressure)

5.0 mg of active ingredient were sieved, and 14.1 mg of lactose, 0.8 mg of crosspovidone USNF and 0.1 mg of magnesium stearate were mixed and then pressured to prepare tablets.

FORMULATION EXAMPLE 2

Tablet (Wet Granulation)

5.0 mg of active ingredient was sieved, and 16.0 mg of lactose and 4.0 mg of starch were mixed. 0.3 mg of polysorbate 80 in purified water was added to the mixture and the resultant was treated to form fine granules. After drying, the fine granules were sieved and 2.7 mg of colloidal silicone dioxide and 2.0 mg of magnesium stearate were mixed. The fine granules were pressured to prepare tablets.

FORMULATION EXAMPLE 3

Powder and Capsule 5.0 mg of active ingredient was sieved, and 14.8 mg of lactose, 10.0 mg of polyvinyl pyrrolidone and 0.2 mg of magnesium stearate were mixed. The mixture was introduced into No. 5 gelatin capsule by use of a suitable device.

FORMULATION EXAMPLE 4

Injections 100 mg of active ingredient, 180 mg of mannitol, 26 mg of $Na_2HPO_4 \cdot 12H_2O$ and 2974 mg of distilled water were employed to produce injections.

The inhibitory effect of the present compounds on lipid peroxidation induced by iron was evaluated as follows:

EXPERIMENTAL EXAMPLE

Inhibitory Effect on Lipid Peroxiation

Rat brain was homogenized in Krebs buffer (15 mM HEPES, 10 mM glucose, 140 mM NaCl, 3.6 mM KCl, 1.5 mM $CaCl_2$, 1.4 mM $KH_2PO_4$ and 0.7 mM MgCl, pH 7.4) and centrifuged at 12,000 rpm to obtain the supernatant serving as a raw material of lipid. To the brain homogenates, $FeCl^2$ was added to give a final concentration of 400 $\mu$M and allowed to stand for 30 min at 37° C. for promoting oxidation. Each of the compounds to be tested was added to give a concentration of 12.5 $\mu$M and a control group was solely added with dimethylsulfoxide (DMSO).

When iron is added to brain homogenates, oxidation is promoted to increase the amount of malondialdehyde (MDA) as lipid peroxidation product. Therefore, in this Example, the level of lipid peroxidation was evaluated according to MDA measurement method. In general MDA measurement, the test sample is reacted with TBA (2-thiobarbituric acid) and the absorbance at 530 nm was measured. However, since such process includes a boiling step, it is unsuitable for dealing with test samples in large quantity. Therefore, in this Example, N-methyl-2-phenylindole was used as a color developing reagent in place of TBA so as to avoid boiling step. Two molecules of N-methyl-2-phenylindole are reacted with one molecule of MDA to form chromophore that shows its maximum absorption at 586 nm (absorption measurement with Bioxytech LPO-586 Kit). The inhibitory effect on lipid peroxidation of test compounds was evaluated by calculating the decreased level of MDA in percentage based on the amount of MDA in the control group. For the test compounds showing more than 80% inhibitory effect, the concentration-lipid peroxidation inhibition curves were plotted with reference to the decrease rate of MDA amount based on the amount of MDA in the control group and their $IC_{50}$ values was calculated through least linear regression analysis. The results are summarized in Table 4.

In addition, the representative antioxidants commercialized such as Promethazine, Trolox, Probucol and N-propyl gallate were examined in terms of 50% inhibition concentration ($IC_{50}$) according to the above procedure and the results are shown in Table 4.

TABLE 4

| Compound No. | $IC_{50}$ ($\mu$M) | Compound No. | $IC_{50}$ ($\mu$M) |
|---|---|---|---|
| 5-49 | 2.85 | 5-50 | 4.90 |
| 5-51 | 5.20 | 5-52 | 0.98 |
| 5-53 | 1.80 | 5-55 | 2.61 |
| 5-57 | 4.37 | 5-63 | 2.46 |
| 5-64 | 2.57 | 5-65 | 1.13 |
| 5-67 | 6.06 | 5-68 | 1.39 |
| 5-69 | 1.42 | 5-70 | 1.15 |
| 5-71 | 1.70 | 5-72 | 7.39 |
| 5-73 | 2.85 | 5-74 | 3.60 |
| 5-77 | 2.50 | 5-78 | 1.14 |
| 5-79 | 0.79 | 5-80 | 1.08 |
| 5-97 | 5.34 | 5-98 | 5.30 |
| 5-100 | 3.89 | 5-101 | 6.03 |
| 5-103 | 5.10 | 5-104 | 4.01 |
| 5-106 | 5.51 | 5-289 | 1.32 |
| 5-290 | 3.02 | 5-292 | 3.25 |
| 5-293 | 3.68 | 5-295 | 1.29 |
| 5-296 | 5.85 | 5-298 | 6.07 |
| 5-300 | 1.36 | 5-306 | 4.12 |
| 5-307 | 3.55 | 5-308 | 4.75 |
| 5-309 | 2.90 | 5-310 | 1.10 |
| 5-311 | 1.19 | 5-312 | 4.13 |
| 5-313 | 1.44 | 5-315 | 3.43 |
| 5-318 | 5.27 | 5-464 | 3.81 |
| 5-465 | 6.41 | 5-466 | 1.20 |
| 5-467 | 3.60 | 5-468 | 4.27 |
| 5-469 | 4.38 | 5-470 | 4.15 |
| 5-471 | 4.85 | 5-472 | 3.90 |
| 5-473 | 2.72 | 5-474 | 3.45 |
| 5-476 | 1.35 | 5-477 | 3.63 |
| 5-478 | 6.21 | 5-480 | 5.55 |
| 5-485 | 2.66 | 5-486 | 0.91 |
| 5-490 | 2.24 | 5-495 | 2.04 |
| 5-510 | 9.45 | 5-511 | 0.12 |
| 5-512 | 3.60 | 5-514 | 2.39 |
| 5-519 | 4.60 | 5-562 | 6.47 |
| 5-564 | 4.33 | 5-566 | 5.73 |
| 5-1126 | 2.56 | 5-1131 | 9.38 |
| 5-1223 | 4.29 | 5-1231 | 1.00 |
| 5-1235 | 1.00 | 5-1261 | 4.7 |
| 5-1482 | 5.27 | 5-1483 | 2.39 |
| 5-1489 | 3.33 | 5-1490 | 3.04 |
| 5-1515 | 2.23 | 5-1516 | 6.34 |
| 5-1520 | 3.10 | 5-1552 | 5.43 |
| 5-1558 | 3.37 | 5-1560 | 2.31 |
| 5-1561 | 2.89 | 5-1562 | 3.03 |
| 5-1563 | 2.05 | 5-1568 | 4.09 |
| 5-1569 | 3.41 | 5-1570 | 3.03 |
| 5-1762 | 1.80 | 5-1765 | 5.13 |
| 5-1767 | 2.63 | 5-1768 | 2.73 |
| 5-1769 | 5.97 | 5-1770 | 3.11 |
| 5-1797 | 3.56 | 5-1799 | 6.01 |
| 5-1800 | 3.90 | 5-1802 | 4.12 |

TABLE 4-continued

| Compound No. | $IC_{50}$ ($\mu M$) | Compound No. | $IC_{50}$ ($\mu M$) |
|---|---|---|---|
| 5-1806 | 5.85 | 5-1808 | 3.97 |
| 5-1809 | 6.36 | 5-1810 | 4.34 |
| 5-1831 | 2.71 | 5-1832 | 1.09 |
| 5-1834 | 1.29 | 5-1835 | 1.14 |
| 5-1836 | 1.16 | 5-1837 | 4.25 |
| 5-1838 | 1.31 | 5-1839 | 1.07 |
| 5-1840 | 1.03 | | |
| Promethazine | 10.2 | Trolox | 24.6 |
| Probucol | 18.2 | N-propyl gallate | 25.0 |

As shown in Table 4, the present compounds exhibit inhibitory effect on iron-induced lipid peroxidation. Of them, several compounds showed inhibition rate of at below 2.0 $\mu$M, thus showing high inhibition potency.

As described previously, although the conventional processes perform multi-step reactions in a solution and require several treatment and purification steps after several reactions, the process of the present invention for preparing 6-amino-2,2-dimethyl-3,4,6-trisubstituted benzopyran derivative according to parallel synthesis on solid-phase makes it possible to significantly reduce the number of treatments and purification steps to a single step, thereby enabling to construct a large amount of benzopyran library in a short period of time. In particular, the present process comprises: the first step for producing N-substituted carbamate resin of the formula (2); the second step for producing 2,2-dimethyl-3-hydroxy-4-alkoxy-6-alkylamino benzopyran resin of the formula (3); the third step for producing 2,2-dimethyl-3-substituted-4-alkoxy-6-alkylamino benzopyran resin of the formula (4); and the fourth step for producing, the compound of interest of the formula (5) by use of dichloromethane solution containing TFA or an organic solvent containing an organic acid. The present process is very useful in mass production of 6-amino-2,2-dimethyl-3,4,6° trisubstituted benzopyran derivatives.

Therefore, the present invention establishes the technology for construction of 6-amino-2,2-dimethyl-3,4,6-trisubstituted benzopyran library according to parallel synthesis on solid-phase, which highlights the applicability of combinatorial chemical synthesis technology. Furthermore, the present invention permits to easily screen and optimize structure and function of the lead compound with novel structure useful in developing drugs for preventing and treating diseases of nervus craniales induced by accumulation of oxidized molecules through lipid peroxidation in nerve cells such as apoplexy and dementia, as well as inflammatory diseases such as arthritis, cardiac infarction and acute or chronic tissue injury.

What is claimed is:

1. A compound chosen from the following formula (5) and optical isomers thereof:

(5)

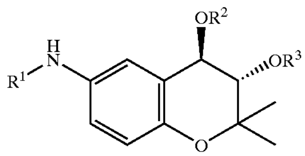

wherein $R^1$ represents a $C_1$–$C_{10}$ alkyl, allyl, benzyl or substituted benzyl, or phenethyl group; $R^2$ represents a $C_1$–$C_{10}$ alkyl, benzyl or substituted benzyl, or phenethyl group; $R^3$ represents a $C_1$–$C_{10}$ alkyl group, a $C_2$–$C_{10}$ alkenyl group, a $C_2$–$C_{10}$ alkynyl, benzyl or substituted benzyl, naphthylmethyl groups, or —C(O) $R^4$; $R^4$ represents phenyl or substituted phenyl groups or five-or seven-membered heterocyclic ring containing a heteroatom selected from the group consisting of oxygen and sulfur; and said substituted phenyl or said substituted benzyl group may be substituted with 1–4 substituents selected from the group consisting of a halogen atom, a nitro group, a $C_1$–$C_{10}$ alkyl group, a $C_1$–$C_{10}$ alkoxy group and a $C_1$–$C_{10}$ haloalkyl group.

2. A process for preparing a compound chosen from the following formula (5) and optical isomers thereof, comprising the following steps of:

(a) synthesizing an N-alkyl substituted carbamate resin of the following formula (2) by introducing an alkyl substituent selectively to a nitrogen atom of benzopyran linked to a carbamate linker represented by the following formula (1);

(b) synthesizing a 2,2-dimethyl-3-hydroxy-6-alkyl amino benzopyran resin of the following formula (3) or its optical isomers by performing epoxidation and alkoxy addition simultaneously by adding metachloroperbenzoic acid (m-CPBA) and alcohol to the compound of the following formula (2);

(c) synthesizing a 2,2-dimethyl-3-substituted-4-alkoxy-6-alkyl amino benzopyran resin of the following formula (4) or its optical isomers by introducing a substituent $R^3$ to 3-hydroxyl group of the compound of the following formula (3) or its optical isomers; and (d) synthesizing said compound by releasing said compound from the resin of the following formula (4) or its optical isomers with dichloromethane solution containing trifluoroacetic acid (TFA) or an organic solvent containing an organic acid;

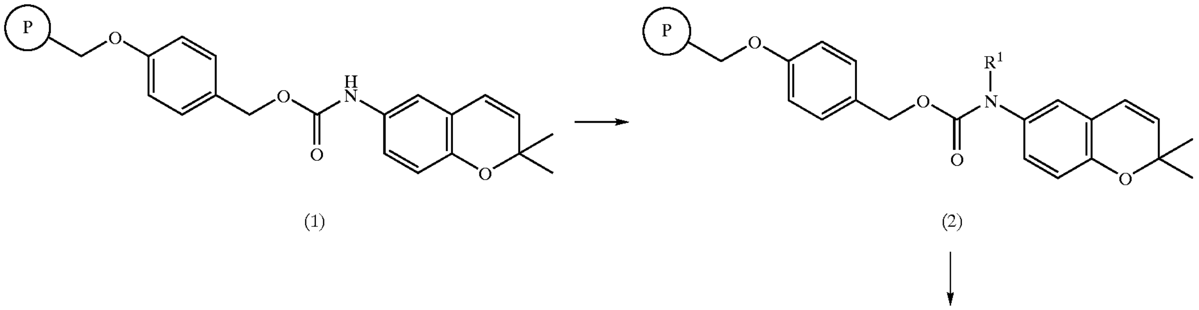

(1) (2)

-continued

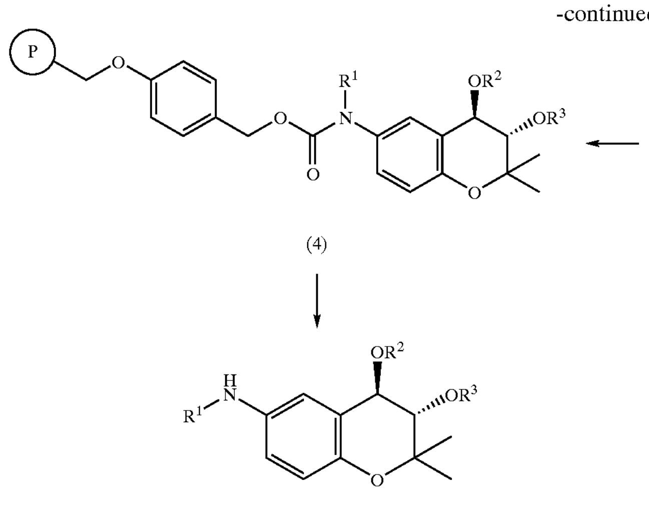

(4) (3) (5)

wherein $R_1$ represents a $C_1$–$C_{10}$ alkyl, allyl, benzyl or substituted benzyl, or phenethyl group; $R^2$ represents a $C_1$–$C_{10}$ alkyl, benzyl or substituted benzyl, or phenethyl group; $R^3$ represents a hydrogen atom, a $C_1$–$C_{10}$ alkyl group, a $C_2$–$C_{10}$ alkenyl group, a $C_2$–$C_{10}$ alkynyl, benzyl or substituted benzyl, naphthylmethyl groups, or —C(O)$R^4$; $R^4$ represents a $C_1$–$C_{10}$ alkyl, phenyl or substituted phenyl groups or five-or seven-membered heterocyclic ring containing a heteroatom selected from the group consisting of oxygen and sulfur, said substituted phenyl or said substituted benzyl group may be substituted with 1–4 substituents selected from the group consisting of a halogen atom, a nitro group, a $C_1$–$C_{10}$ alkyl group, a $C_1$–$C_{10}$ alkoxy group and a $C_1$–$C_{10}$ haloalkyl group; and

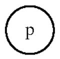

is a polymeric solid support selected from the group consisting of polystyrene-divinylbenzene, methacrylic acid-dimethylacrylamide and hydroxylmethacrylic acid.

3. A pharmaceutical composition, which comprises (a) at least one pharmaceutically acceptable component chosen from carriers, additives, vehicles, and diluents, and (b) a pharmaceutically effective amount of a compound chosen from the following formula (5) and optical isomers thereof:

(5)

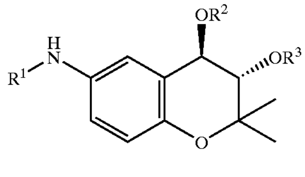

wherein the pharmaceutical composition is pharmaceutically acceptable;

the said compound is an active ingredient of the pharmaceutical composition; $R^1$ represents a $C_1$–$C_{10}$ alkyl, allyl, benzyl or substituted benzyl, or phenethyl group; $R^2$ represents a $C_1$–$C_{10}$ alkyl, benzyl or substituted benzyl, or phenethyl group; $R^3$ represents a $C_1$–$C_{10}$ alkyl group, a $C_2$–$C_{10}$ alkenyl group, a $C_2$–$C_{10}$ alkynyl, benzyl or substituted benzyl, naphthylmethyl groups, or —C(O)$R^4$; $R^4$ represents phenyl or substituted phenyl groups or five-or seven-membered heterocyclic ring containing a heteroatom selected from the group consisting of oxygen and sulfur; and said substituted phenyl or said substituted benzyl group may be substituted with 1–4 substituents selected from the group consisting of a halogen atom, a nitro group, a $C_1$–$C_{10}$ alkyl group, a $C_1$–$C_{10}$ alkoxy group and a $C_1$–$C_{10}$ haloalkyl group.

4. A pharmaceutical composition for inhibiting lipid peroxidation, which comprises (a) at least one pharmaceutically acceptable component chosen from carriers, additives, vehicles, and diluents, and (b) a pharmaceutically effective amount of a compound chosen from the following formula (5) and optical isomers thereof:

(5)

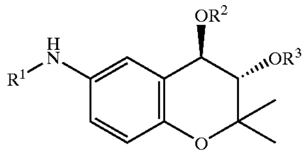

wherein the pharmaceutical composition is pharmaceutically acceptable; said compound is an active ingredient of the pharmaceutical composition; $R^1$ represents a $C_1$–$C_{10}$ alkyl, allyl, benzyl or substituted benzyl, or phenethyl group; $R^2$ represents a $C_1$–$C_{10}$ alkyl, benzyl or substituted benzyl, or phenethyl group; $R^3$ represents a $C_1$–$C_{10}$ alkyl group, a $C_2$–$C_{10}$ alkenyl group, a $C_2$–$C_{10}$ alkynyl, benzyl or substituted benzyl, naphthylmethyl groups, or —C(O)$R^4$; $R^4$ represents phenyl or substituted phenyl groups or five-or seven-membered heterocyclic ring containing a heteroatom selected from the group consisting of oxygen and sulfur; and said substituted phenyl or said substituted benzyl group may be substituted with 1–4 substituents selected from the group consisting of a halogen atom, a nitro group, a $C_1$–$C_{10}$ alkyl group, a $C_1$–$C_{10}$ alkoxy group and a $C_1$–$C_{10}$ haloalkyl group.

* * * * *